US010654834B2

(12) United States Patent
Huang et al.

(10) Patent No.: US 10,654,834 B2
(45) Date of Patent: May 19, 2020

(54) NON-SYSTEMIC TGR5 AGONISTS

(71) Applicant: Venenum Biodesign, LLC, Lawrence Township, NJ (US)

(72) Inventors: Chia-Yu Huang, Princeton Junction, NJ (US); Brian F. McGuinness, Plainsboro, NJ (US); Xiaoqing Xu, Monmouth Junction, NJ (US); Steven G. Kultgen, Hamilton, NJ (US); Ellen Sieber McMaster, Langhorne, PA (US); James R. Beasley, Doylestown, PA (US)

(73) Assignee: Venenum Biodesign, LLC, Hamilton, NJ (US)

( * ) Notice: Subject to any disclaimer, the term of this patent is extended or adjusted under 35 U.S.C. 154(b) by 11 days.

(21) Appl. No.: 16/311,185

(22) PCT Filed: Jun. 29, 2017

(86) PCT No.: PCT/US2017/039998
§ 371 (c)(1),
(2) Date: Dec. 19, 2018

(87) PCT Pub. No.: WO2018/005794
PCT Pub. Date: Jan. 4, 2018

(65) Prior Publication Data

US 2019/0330191 A1 Oct. 31, 2019

Related U.S. Application Data

(60) Provisional application No. 62/357,427, filed on Jul. 1, 2016.

(51) Int. Cl.

| | |
|---|---|
| *C07D 403/04* | (2006.01) |
| *A61P 3/10* | (2006.01) |
| *C07D 401/04* | (2006.01) |
| *C07D 401/14* | (2006.01) |
| *C07D 405/14* | (2006.01) |
| *C07D 409/14* | (2006.01) |
| *A61K 45/06* | (2006.01) |

(52) U.S. Cl.
CPC .............. *C07D 403/04* (2013.01); *A61P 3/10* (2018.01); *C07D 401/04* (2013.01); *C07D 401/14* (2013.01); *C07D 405/14* (2013.01); *C07D 409/14* (2013.01); *A61K 45/06* (2013.01)

(58) Field of Classification Search
CPC .................................................... C07D 403/04
USPC ...................................................... 514/210.2
See application file for complete search history.

(56) References Cited

U.S. PATENT DOCUMENTS 8,114,862 B2 * 2/2012 Pellicciari .................. C07J 9/00
514/182

* cited by examiner

*Primary Examiner* — Kahsay Habte
(74) *Attorney, Agent, or Firm* — Arnold Braun; Terence Bogie

(57) ABSTRACT

The present invention relates to tricyclic compounds of formula (I) and formula (II), or a pharmaceutically acceptable salt thereof. The present tricyclic compounds are useful non-systemic TGR5 agonists that can be used to treat diabetic diseases in human. The present invention provides a pharmaceutical composition containing tricyclic compounds of formula (I) and formula (II) and a method of making as well as a method of using same in treating patients inflicted with metabolic disorders by administering same. The compounds of the present invention may be used in combination with additional anti-diabetic drugs.

20 Claims, 25 Drawing Sheets

NON-SYSTEMIC TGR5 AGONISTS

This application claims the benefit of International Application No. PCT/US2017/039998, filed Jun. 29, 2017, which claims the benefit of U.S. Provisional Application Ser. No. 62/357,427, filed on Jul. 1, 2016. The entire teachings of the referenced applications are herein incorporated by reference in their entirety.

FIELD OF THE INVENTION

The present invention relates to novel compounds and pharmaceutically acceptable salts thereof that are useful as non-systemic TGR5 agonists. The present invention also relates to compositions containing such compounds, process of preparing and methods of use thereof.

BACKGROUND OF THE INVENTION

TGR5 (also known as G protein-coupled bile acid receptor 1 (GPBAR1), M-BAR, or BG-371) is a receptor present on L-cells within the gastrointestinal compartment in humans. Upon binding of bile acids, TGR5 causes the release of glucagon-like peptide-1 (GLP-1) which in turn stimulates insulin secretion and suppresses glucagon secretion (Katsuma et al., *Biochem. Biophys. Res. Commun.*, 2005, 329 (1), 386-390). Therapeutic attempts have been made to elevate GLP-1 in the blood to improve glycemic control. One approach involves the use of dipeptidyl peptidase-4 (DPP-4) inhibitors to slow down GLP-1 degradation. Another approach employs GLP-1 analogs that mimic the natural GLP-1. Yet another approach utilizes TGR5 agonists to stimulate the TGR5 receptor and trigger its signal cascades within the L-cells for glucose control.

Multiple TGR5 modulators with diverse structural features have been reported. U.S. Pat. No. 8,114,862 discloses a series of 23-substituted bile acids that mimic natural bile acids as TGR5 modulators. WO2013/164838 discloses TGR5 agonists containing 1, 2, 4-triazole with a linker containing sulfur and their use in treating diabetes, obesity and related disorders. WO2009/026241 discloses TGR5 modulators having a structure of pyrimidin-4-one that is fused with a 5 or 6-membered heterocyclic or heteroaryl group. WO2012/082947 discloses pyrazolyl based TGR5 agonists. WO2011/071565 discloses TGR5 agonists that are imidazole derivatives. WO2012/149236 discloses bicyclic heteroaryl compounds that are TGR5 agonists. WO2013/134527 discloses polycyclic alkaloids as TGR5 agonists. WO2004/067008 discloses TGR5 agonists containing benzodiazepine-2-one. WO2013/096771 discloses TGR5 agonists containing tetrahydroquinoxaline and their use in treating type 2 diabetes mellitus. WO2013/096771 further discloses some TGR5 compounds that are substantially non-bioavailable in the blood stream.

There has been a concern for an increased risk of pancreatitis in type 2 diabetes patients treated with GLP-1-based therapies (Singh et al., *JAMA Intern. Med.,* 2013, 173 (7), 534-539). Subsequent clinical studies, however, do not seem to support this contention (Butler et al., *Diabetes,* 2013, 62 (7), 2595-2604). It remains to be determined if systemic delivery of a TGR5 agonist may attribute to the pancreatitis.

Phillips et al. disclosed trifluoromethyl(pyrimidin-2-yl) azetidine-2-carboxamides as potent, orally bioavailable TGR5 agonists (*J. Med. Chem.,* 2014, 57(8), 3263-3282). The lead Compound (45h) represents a potent and selective TGR5 agonist that has high plasma exposure (i.e., high $C_{max}$ value). The authors reported glycemic effect of Compound 45h was lost upon chronic dosing. Phillips et al. questioned toxicological and therapeutic issues that may limit the utility of these systemic TGR5 agonists for treatment of metabolic disease.

There is a continuing need in developing a non-systemic TGR5 agonist, one that is restricted in the gastrointestinal compartment and has clinical safety and efficacy profiles suitable for oral administration in treating metabolic disorders.

SUMMARY OF THE INVENTION

The present invention provides novel compounds represented by formula (I):

(I)

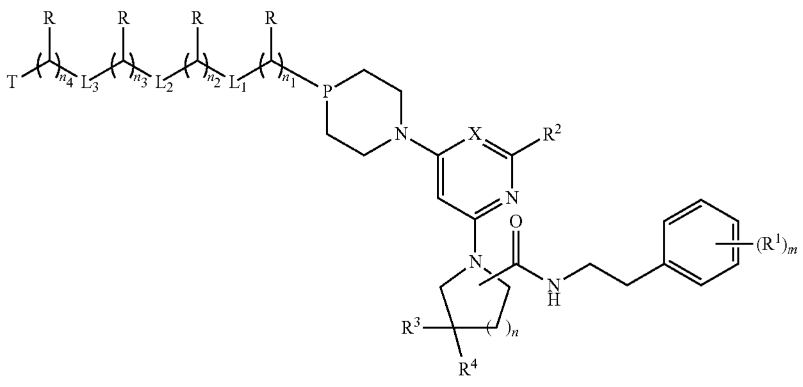

and formula (II):

(II)

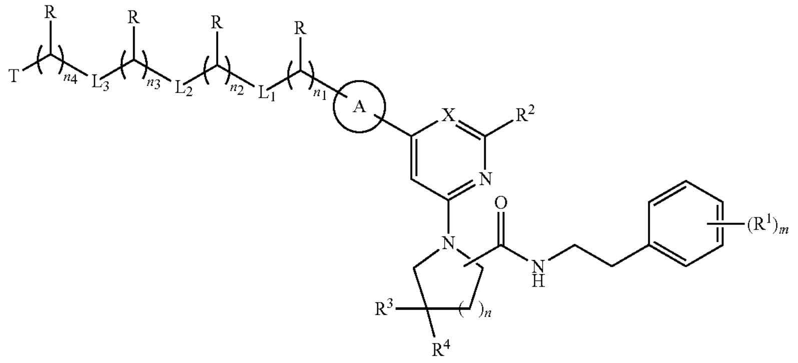

and pharmaceutically acceptable salts thereof.

The present heterocyclic compounds are useful non-systemic TGR5 agonists to treat metabolic disorders including diabetes and obesity. The present invention provides a pharmaceutical composition containing such compounds as well as a process of making them and a method of administering same to treat patients suffering from metabolic disorders. The present compounds may be used in combination with other anti-diabetic drugs.

DETAILED DESCRIPTION OF THE INVENTION

Definitions

Figure 1:
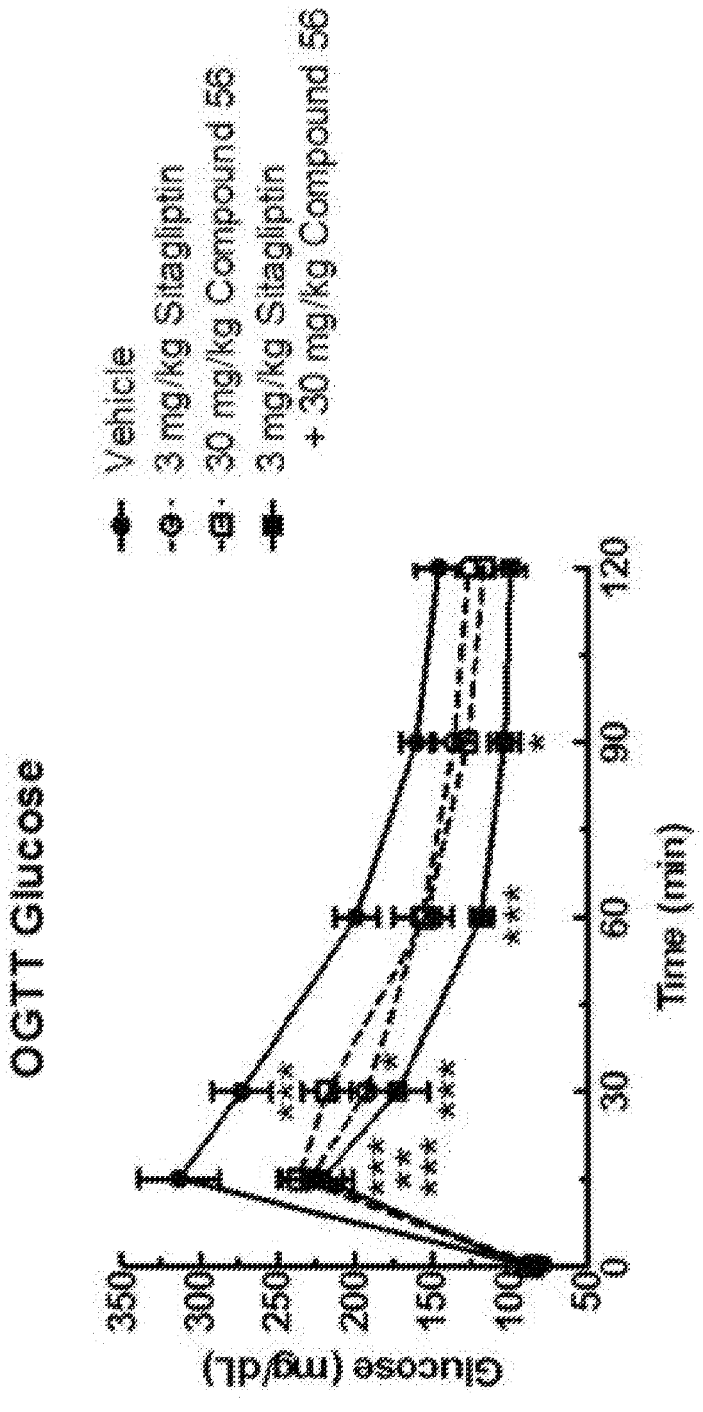
FIG. 1 depicts the plasma glucose level in an Oral Glucose Tolerance Test (OGTT) in C57BL/6NT mice treated with vehicle, sitagliptin (3 mg/kg), Compound 56 (30 mg/kg), or Compound 56 (30 mg/kg)+sitagliptin (3 mg/kg).

As used herein, number ranges where provided (e.g., 1-6) refer to each and every number in that range as a discrete embodiment.

As used herein, the term "alkyl" refers to a saturated carbon chain up to 10 carbons that may be linear, branched or a combination thereof. Exemplary alkyl includes methyl, ethyl, n-propyl, isopropyl, n-butyl, sec- and tert-butyl, pentyl, hexyl, and the like. $C_{1-6}$alkyl refers to a saturated carbon chain that may be linear, branched or a combination thereof which contains one to six carbon atoms.

As used herein, the term "alkenyl" refers a carbon chain up to 10 carbons that contains at least one carbon-carbon double bond, and that may be linear, branched or a combination thereof. Exemplary alkenyl includes vinyl, allyl, isopropenyl, pentneyl, hexenyl, heptenyl, 1-propenyl, 2-butenyl, 2-methyl-2-butenyl, and the like.

As used herein, the term "alkynyl" refers a carbon chain up to 10 carbons that contains at least one carbon-carbon triple bond, and that may be linear, branched or a combination thereof. Exemplary alkynyl includes ethynyl, propargyl, 3-methyl-1-pentynyl, 2-heptynyl, and the like.

As used herein, the term "alkoxy" refers to an alkyl up to 10 carbons linked to the parent structure through an oxygen. Exemplary alkoxy includes methoxy, ethoxy, propoxy, isopropoxy, butoxy, and the like.

As used herein, the term "cycloalkyl" refers to a monocyclic, bicyclic, tricyclic or bridged saturated hydrocarbon ring system containing 3-14 carbons. Exemplary cycloalkyl includes cyclopropyl, cyclobutyl, cyclopentyl, cyclohexyl, cycloheptyl, decahydronaphthyl and the like.

As used herein, the term "cycloalkenyl" refers a monocyclic, bicyclic, tricyclic or bridged non-aromatic hydrocarbon ring system containing 3-14 carbons and at least one double bond. Exemplary cycloalkenyl includes cyclopropenyl, cyclobutenyl, cyclopentenyl, cyclohexenyl, cycloheptenyl, and the like.

As used herein, the term "heterocycloalkyl" refers to a monocyclic, bicyclic, tricyclic, or bridged saturated hydrocarbon ring system containing 2-14 carbons and 1, 2, 3, 4, or 5 heteroatoms selected from oxygen ("0"), sulfur ("S") and nitrogen ("N") atoms. Exemplary heterocycloalkyl includes aziridinyl, azetidinyl, tetrahydrofuranyl, dioxanyl, oxanyl, morpholinyl, dithianyl, thiomorpholinyl, piperazinyl, piperidinyl, 1,3-dioxolanyl, imidazolidinyl, pyrrolidinyl, pyrazolidinyl, tetrahydropyranyl, and the like.

As used herein, the term "aryl" refers to a monocyclic, bicyclic, or tricyclic hydrocarbon ring system containing 5-14 carbon atoms, wherein at least one of the rings is aromatic. Aryl includes a ring system in which an aromatic ring is fused to a non-aromatic ring, such as a cycloalkyl or a cycloalkenyl ring. Exemplary aryl includes phenyl, naphthyl, indanyl, benzocyclobutanyl, tetrahydronaphthy, and the like.

As used herein, the term "heteroaryl" refers to a monocyclic, bicyclic or tricyclic hydrocarbon ring system containing 5-14 carbon atoms and containing 1, 2, 3, 4, or 5 heteroatoms selected from oxygen ("O"), sulfur ("S") and nitrogen ("N") atoms, wherein at least one of the heteroatoms containing rings is aromatic. "Heteroaryl" also refers to a ring system in which an aromatic heteroatom containing ring is fused to a non-aromatic ring such as a cycloalkyl, cycloalkenyl or heterocycloalkyl ring, and refers to a ring system in which an aryl is fused to a non-aromatic heteroatom containing ring, such as a heterocycloalkyl ring. Exemplary heteroaryl includes pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, oxo-dihydroqunoline, indolyl, oxindole, isoquinolyl, dibenzofuranyl, 1,3-benzodioxolyl, dihydroisoindolyl, dihydrobenzodioxinyl, dihydroindolyl, isoindolinyl, and the like.

As used herein, the term "halogen" refers to fluorine, chlorine, bromine, and iodine.

As used herein, the term "floating bond", when used in connection with a substituent depicted in a formula (e.g., —(R)), refers to that substituent (e.g., R) permitted on any available carbon or nitrogen atom in the ring to which the substituent is attached, unless expressly depicted or described.

As used herein, the term that a certain group "is optionally substituted" refers to any group having that particular component thereof can be further substituted. For example, "alkyl group is optionally further substituted with" refers any group possessing an alkyl component can be further substituted thereof. The term includes "mono-", "di-" or "tri-" substitutions.

As used herein, the term "ortho," "meta" and "para" (abbreviated as "o-," "m-," and "p-") refers to the position of two identical or different substituents relative to each other in a benzene ring. For example, ortho substitution refers to two substituents that are located in the 1, 2 positions of a benzene ring; meta substitution refers to two substituents that are located in the 1, 3 positions of a benzene ring; para substitution refers to two substituents that are located in the 1, 4 positions of a benzene ring.

When any variable (e.g., $R^1$, $R^2$) occurs more than one time in any substituent, its definition on each occurrence is independent of its definition at every other occurrence. Also combinations of substituents and/or variables are permissible only if such combinations result in stable compounds, and conform to well-known principles of chemical structure connectivity and stability. A squiggly line "∿" across a bond in a substituent variable represents the points of attachment.

As used herein, the term "pharmaceutically acceptable" refers to compositions, polymers, solvates, and dosage forms which are, within the scope of sound medical judgment, suitable for use in contact with the tissues of human beings and animals without causing excessive toxicity, irritation, allergic response, or other problem or complication, commensurate with a reasonable risk and benefit ratio.

As used herein, the term "pharmaceutically acceptable salt" refers to a derivative of a compound of the present invention wherein the parent compound is modified by making acid or base salts thereof. It includes inorganic or organic acid salts of basic residues such as amines; and inorganic or organic basic salts of acidic residues such as carboxylic acids. Exemplary pharmaceutically acceptable salt includes acetate, bicarbonate, bisulfate, formate, hydrochloride, sulfate, phosphate, and the like.

As used herein, the term "pharmaceutical composition" refers to a composition comprising a compound of the present invention together with a pharmaceutically acceptable carrier.

As used herein, the term "pharmaceutically acceptable carrier" refers to a pharmaceutically acceptable excipient that is not injurious to a patient. Exemplary pharmaceutically acceptable carrier includes starch, cellulose, gelatin, talc, glycol, polyol, ester, agar, buffering agents, alginic acid, and the like that are employed in pharmaceutical formulations.

As used herein, the term "administering" or "administration" refers to providing a compound, a pharmaceutically acceptable salt, solvate, or prodrug thereof to a human subject in need of treatment by oral administration.

As used herein, the term "mammal" refers to animal species that has the distinguished features by the presence of sweat glands, including those that are specialized to produce milk to nourish the young. Exemplary mammal includes human, mouse, rat, dog and the like.

As used herein, the term "treating" or "treatment" refers to an intervention (e.g., the administration of an agent to a subject) which cures, ameliorates or lessons the symptoms of a disease or removes (or lessens the impacts of) its cause(s).

As used herein, the term "therapeutically effective amount" refers to an amount of a compound of the present invention which, as compared to a corresponding human subject who has not received such an amount, results in improved treatment, prevention, or amelioration of metabolic disorders. The amount will depend on the particular condition, co-administrated compounds if any, and the characteristics of the human subject, such as general health, other diseases, age, sex, genotype, body weight, and tolerance to drugs. Those skilled in the art will be able to determine appropriate dosages depending on these and other factors.

As used herein, the term "combination" refers to a compound of the present invention and an additional therapeutic agent useful for the treatment of metabolic disorders. Exemplary therapeutic agent includes insulin, GLP-1 mimics, DPP-4 inhibitors, and the like. DPP-4 inhibitors include but not limited to alogliptin, linagliptin, saxagliptin, sitagliptin, anagliptin, teneligliptin, trelagliptin, vildagliptin, gemigliptin, omarigliptin, evogliptin, and dutogliptin.

As used herein, the term "metabolic disorder" refers to a disorder that disrupts the normal process of converting food to energy on a cellular level (i.e., metabolism that involves the processing or transporting proteins (amino acids), carbohydrates (sugars and starches), or lipids (fatty acids). Such disorder is usually due to a hormone or enzyme deficiency.

As used herein, the term "TGR5-related metabolic disorder" refers to a metabolic disorder that is resulted from a deficiency in TGR5 signaling. Exemplary TGR5-related metabolic disorders include, but not limited to pre-diabetes, type-2 diabetes/glucose homeostasis, obesity, fibrosing cholangitis, inflammatory diseases such as colitis, digestive disease such as pancreatitis and cancer. Such metabolic disorders are understood to be treatable with a TGR5 agonist.

As used herein, the term "diabetic," "diabetes" or "diabetes mellitus" are used interchangeably in this application to refer to a group of metabolic disorders characterized by hyperglycemia resulting from defects in insulin secretion, insulin action or both. The term "type 2 diabetes (formerly adult-onset diabetes)" refers to a condition in which a human is clinically diagnosed with any of the three tests: (i) having a fasting plasma blood glucose level of 126° mg/dL or greater on two separate occasions; (ii) an oral glucose tolerance of 200 mg/dL or greater; or (iii) an A1C (hemoglobin A1c test) of 6.5% or greater.

As used herein, the term "pre-diabetic" or "pre-diabetes" refers to a condition in which blood glucose levels are higher than normal, but not high enough to be classified as diabetes. Pre-diabetes in human is clinically diagnosed with any of the three tests: (i) having a fasting plasma blood glucose level between 100 and 125 mg/dL ("impaired fasting glucose"); (ii) an oral glucose tolerance between 140 and 199 mg/dL ("impaired glucose tolerance"); or (iii) an A1C of 5.7-6.4 percent.

As used herein, the term "obesity" refers to an adult human who has a body mass index ("BMI") of 30 or higher.

As used herein, the term "non-systemic" refers to minimized systemic exposure of a compound after ingestion. For purposes of this application, "non-systemic" and "low plasma exposure" are used interchangeably and refer to $C_{max}$ of <200 ng/mL.

As used herein, the term "non-absorbed" refers to a compound that is restricted to the gut compartment and acts within the intestinal lumen without reaching the systemic circulation.

As used herein, the term "bioavailability" or "systemic availability" refers to the extent to which a compound that is taken up by a specific tissue or organ after administration; the proportion of the dose of a drug that reaches the systemic circulation intact after administration by a route other than intravenous. Bioavailability is distinct from its chemical potency.

As used herein, the term "$EC_{50}$" refers to the concentration of a compound which induces a response halfway between the baseline and maximum after a specified exposure time and is used as a measure of compound potency. It represents the concentration of a compound where 50% of its maximal effect is observed.

As used herein, the term "pharmacokinetics" (PK) refers to how the body affects a specific drug after administration through the mechanisms of absorption and distribution, as well as the chemical changes of the substance, and the effects and routes of excretion of the metabolites of the drug. Measured PK metrics include: $C_{max}$ (peak plasma concentration of a drug after administration), $t_{max}$ (time to reach $C_{max}$), area under the curve ("AUC" the integral of the concentration-time curve), bioavailability, and the like.

The present invention relates to novel heteroyclic compounds and pharmaceutically acceptable salts thereof that are useful in the treatment of type-2 diabetes and obesity. These compounds are non-systemic TGR5 agonists. The present invention also relates to pharmaceutical compositions containing such compounds, process of making and methods of using such compounds in treating metabolic disorders.

In one aspect, the present invention provides a compound of formula (I):

-continued

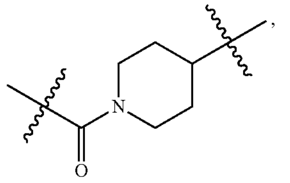

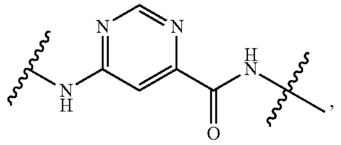

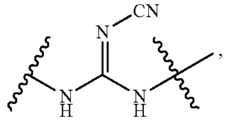

(I)

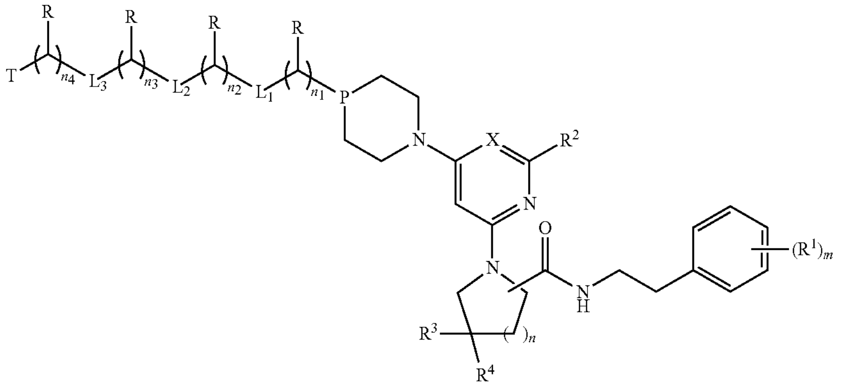

or a pharmaceutically acceptable salt thereof, wherein:

each $R^1$ is independently CN, $C_{1-6}$alkyl, pyridyl, or $C_{1-6}$alkoxy, wherein alkyl group is optionally further substituted with 1-4 halogen;

m is 0, 1, 2, or 3;

$R^2$ is $C_{1-6}$alkyl or H, wherein alkyl group is optionally further substituted with 1-4 halogen;

X is CH or N;

P is CH or N;

$L_1$, $L_2$ and $L_3$ are each independently absent,

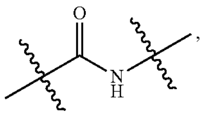

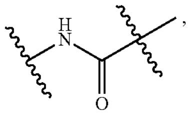

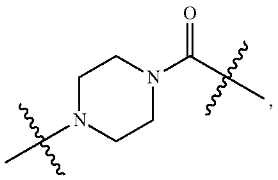

-continued

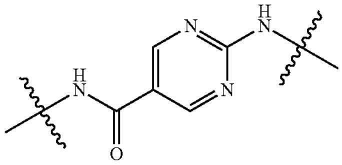

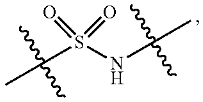

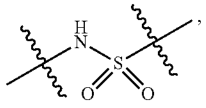

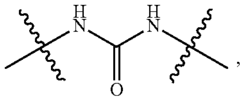

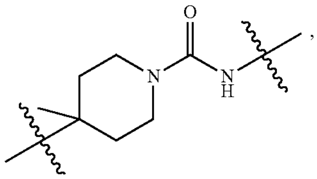

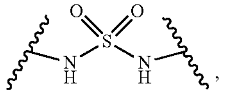

-continued

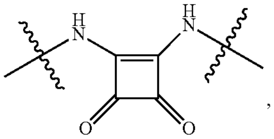 , 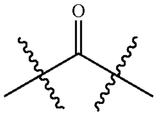 ,

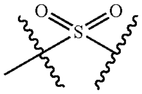 , 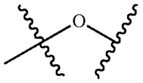 , 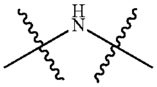 ,

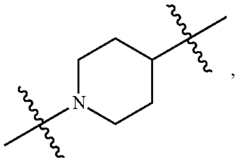 , or 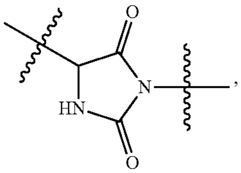 , wherein N is optionally further mono- or di-substituted with $C_{1-3}$alkyl;

$n_1$, $n_2$, $n_3$ and $n_4$ are each independently 0, 1, 2, 3, 4 or 5, and when $L_1$ is absent, $n_2$ is 0, when $L_2$ is absent, $n_3$ is 0, when $L_3$ is absent, $n_4$ is 0, with the proviso that when $L_1$, $L_2$ and $L_3$ are all absent, $n_1$ cannot be 0;

each R is independently H, OH, $NH_2$, COOH, $C_{1-6}$alkylCOOH, $COOC_{1-6}$alkyl, $C_{1-6}$alkylOH or $C_{1-6}$alkyl-NHC(NH)$NH_2$;

T is

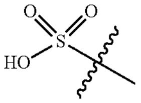 , 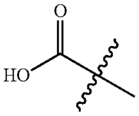 , 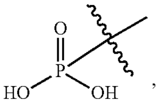 ,

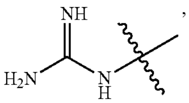 , 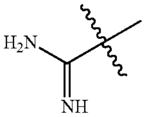 ,

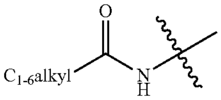 , 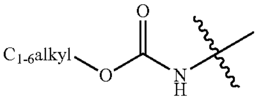 ,

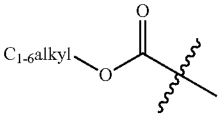 , 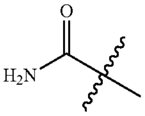 ,

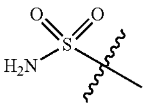 , 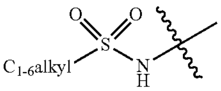 ,

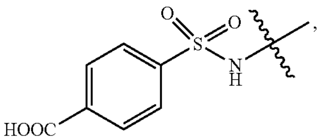 ,

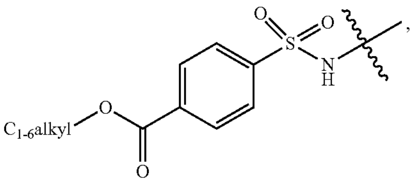 ,

-continued

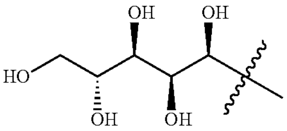 , 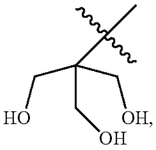

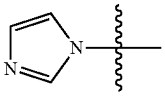 , 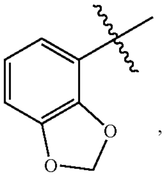 ,

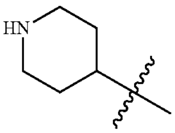 , 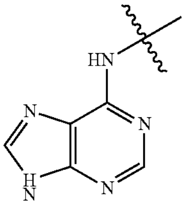 ,

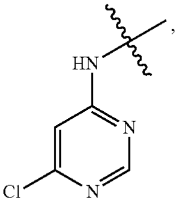 , 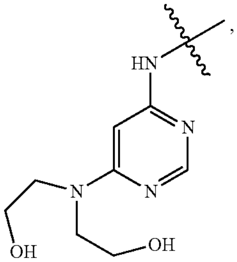 ,

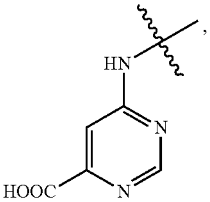 ,

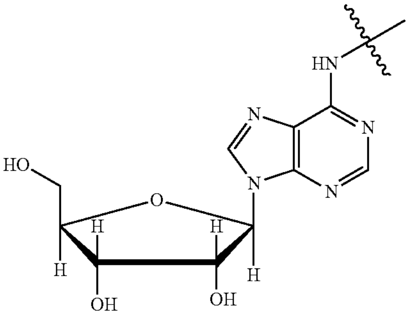 ,

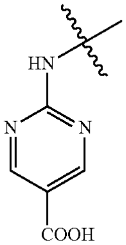 , 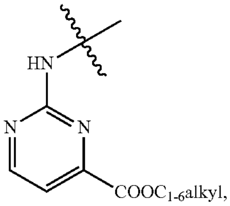

CN, OH, $NH_2$, or $OCH_3$, wherein N is optionally further mono-, di-, or tri-substituted with $C_{1-3}$alkyl;

$R^3$ and $R^4$ are each independently H, OH, halogen, $N(CH_3)_2$ or $NH_2$; and n is 0, 1 or 2.

As used herein, the symbol ∿∿∿ when drawn through a bond refers to the point of attachment of a functional group to the parent molecule. When the functional group has two symbols ∿∿∿ present, it means the functional group has two points of attachment. For purpose of the present application, the left-hand point of attachment of the functional group is attached to the left-hand side of the parent molecule. While the right-hand point of attachment of the functional group is attached to the right-hand side of the parent molecule. For example, the left-hand side of $L_1$ is attached to $(CHR)_{n2}$ of the parent molecule, while the right-hand side of the $L_1$ is attached to $(CHR)_{n1}$ of the parent molecule.

In one embodiment, $L_3$ is absent, and $L_1$ and $L_2$ are each independently

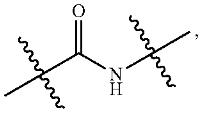, 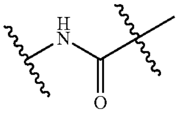,

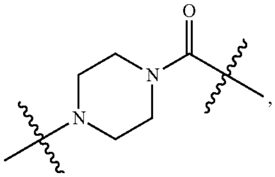,

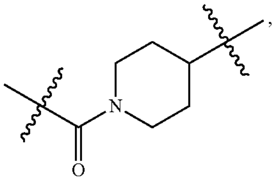,

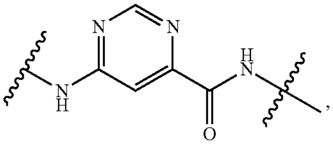,

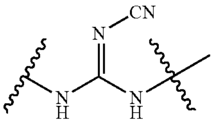,

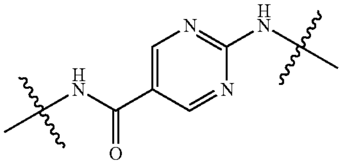,

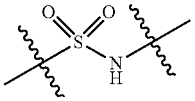, 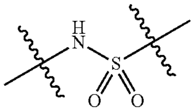,

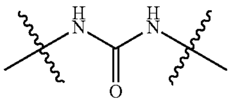,

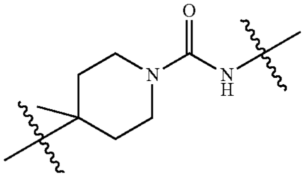,

-continued

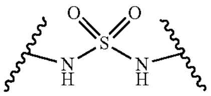,

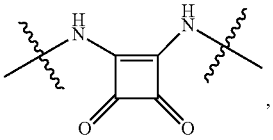, 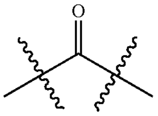,

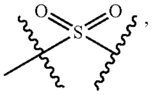, 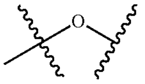, 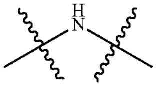,

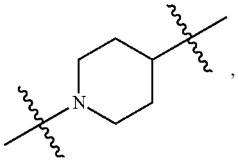, or 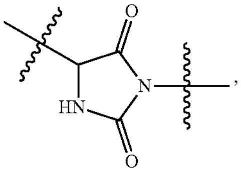, wherein N is optionally further mono- or di-substituted with $C_{1-3}$alkyl.

In one preferred embodiment, when $L_3$ is absent, $L_1$ and $L_2$ are each independently

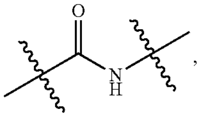, 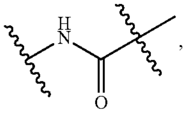,

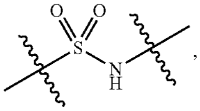, 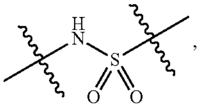,

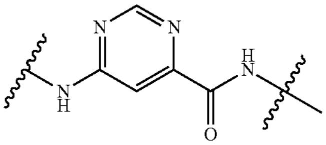,

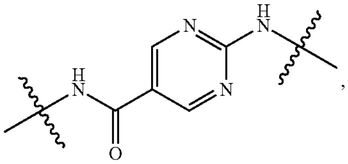,

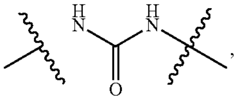, or 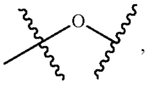, wherein N is optionally further substituted with $C_{1-3}$alkyl.

In one preferred embodiment, when $L_3$ is absent, $L_1$ and $L_2$ are each independently

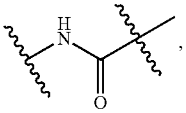, 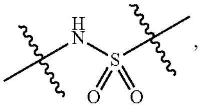,

-continued

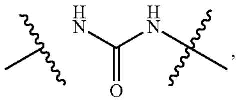

or

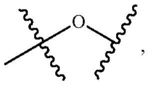

wherein N is optionally further substituted with $C_{1-3}$alkyl.

In one embodiment, $L_2$ and $L_3$ are absent, and $L_1$ is

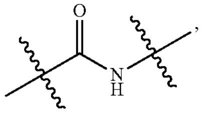

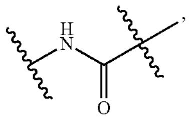

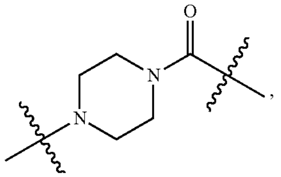

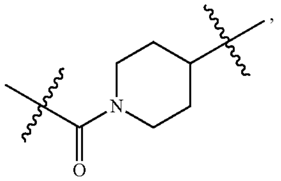

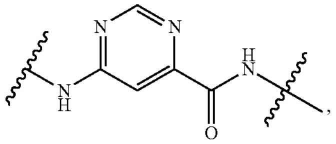

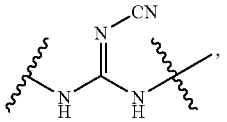

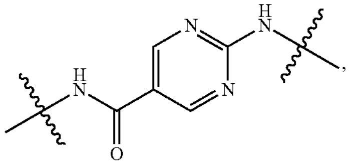

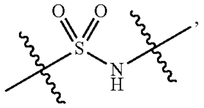

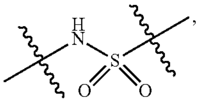

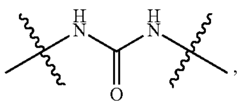

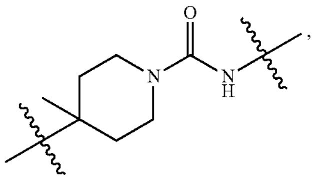

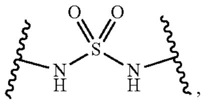

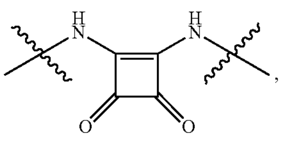

-continued

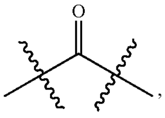

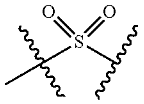

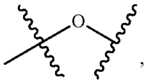

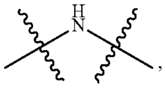

or

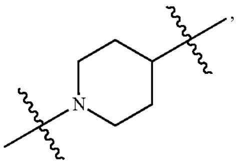

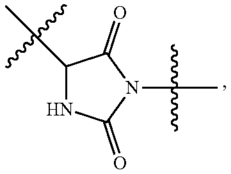

wherein N is optionally further mono- or di-substituted with $C_{1-3}$alkyl.

In one preferred embodiment, when $L_2$ and $L_3$ are absent, $L_1$ is

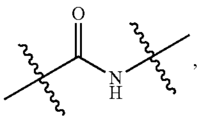

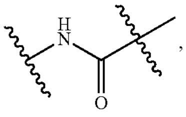

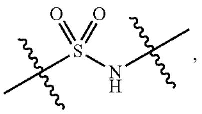

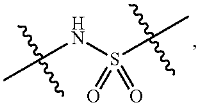

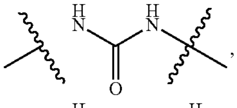

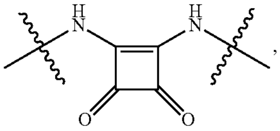

or

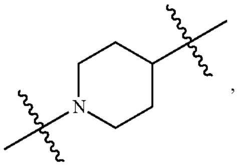

wherein N is optionally further substituted with $C_{1-3}$alkyl.

In one preferred embodiment, when $L_2$ and $L_3$ are absent, $L_1$ is

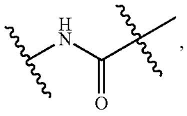

or

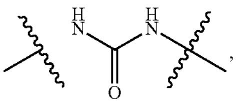

wherein N is optionally further substituted with $C_{1-3}$alkyl.

In one embodiment, $n_1$, $n_2$, $n_3$ and $n_4$ are each independently 0, 1, 2, 3 or 4.

In one preferred embodiment, $n_1$, $n_2$, $n_3$ and $n_4$ are each independently 0, 1, 2 or 3.

In one embodiment, each R is independently H, $NH_2$, COOH or $C_{1-6}$alkylNHC(NH)ONH$_2$.

In one preferred embodiment, each R is independently H, $NH_2$ or COOH.

In one embodiment, T is

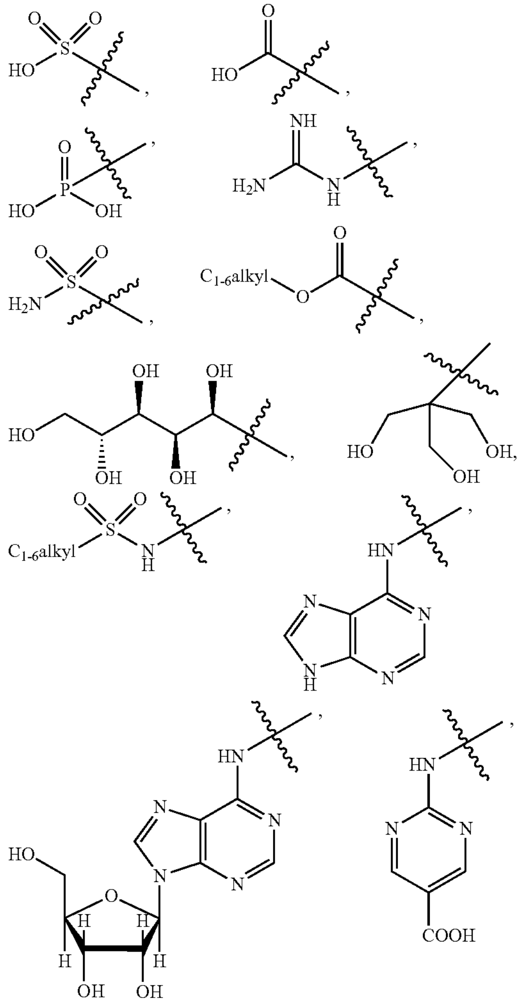

or $NH_2$, wherein N is optionally further mono-, di-, or tri-substituted with $C_{1-3}$alkyl.

In one preferred embodiment, T is

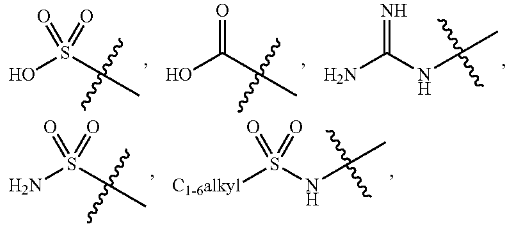

-continued

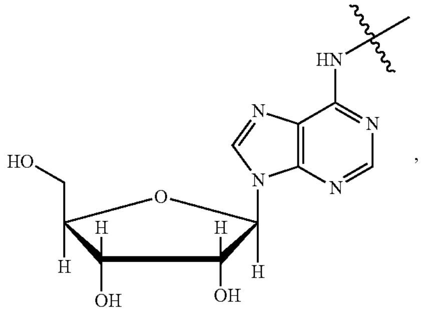

or $NH_2$, wherein N is optionally further mono-, di-, or tri-substituted with $C_{1-3}$ alkyl.

In one embodiment, n is 0. In one preferred embodiment, phenethylcarboxamide is substituted in the two position of N in the azetidinyl ring. In one preferred embodiment, phenethylcarboxamide is substituted in the two position of N in the azetidinyl ring with S configuration.

In one embodiment, n is 1. In one preferred embodiment, phenethylcarboxamide is substituted in the two position of N in the pyrrolidinyl ring. In one preferred embodiment, phenethylcarboxamide is substituted in the two position of N in the pyrrolidinyl ring with S configuration.

In one embodiment, n is 2. In one preferred embodiment, phenethylcarboxamide is substituted in the three position of N in the piperidinyl ring. In one preferred embodiment, phenethylcarboxamide is substituted in the three position of N in the piperidinyl ring with R configuration.

In one embodiment, P is CH. In one embodiment, P is N.

In one embodiment, X is N. In one embodiment, X is CH.

In one embodiment, $R^2$ is $C_{1-6}$alkyl, wherein alkyl group is optionally further substituted with 1-4 halogen. In one preferred embodiment, $R^2$ is $CH_3$. In one preferred embodiment, $R^2$ is $CF_3$.

In one embodiment, $R^1$ is each independently CN or $C_{1-6}$alkyl, wherein alkyl group is optionally further substituted with 1-4 halogen.

In one preferred embodiment, $R^1$ is CN. In one preferred embodiment, $R^1$ is $CF_3$. In one preferred embodiment, the CN or $CF_3$ substitution occurs on the para position of phenethyl ring.

In one embodiment, $R^1$ is $C_{1-2}$alkoxy. In one preferred embodiment, $R^1$ is $OCH_3$.

In one embodiment, m is 1 or 2. In one preferred embodiment, m is 1.

In one embodiment, $R^3$ and $R^4$ are each independently H, OH, F, or $NH_2$. In one preferred embodiment, $R^3$ and $R^4$ are each independently H or OH. In one preferred embodiment, $R^3$ and $R^4$ are each independently H.

In one preferred embodiment, the present invention provides a compound selected from:

1) (S)—N-(4-cyanophenethyl)-1-(6-(4-(hydroxymethyl)piperidin-1-yl)-2-(trifluoromethyl)pyrimidin-4-yl)pyrrolidine-2-carboxamide;

2) (S)-1-(6-(4-(hydroxymethyl)piperidin-1-yl)-2-(trifluoromethyl)pyrimidin-4-yl)-N-(4-(trifluoromethyl)-phenethyl)pyrrolidine-2-carboxamide;

3) (S)-1-(6-(4-(2-(dimethylamino)ethyl)piperidin-1-yl)-2-(trifluoromethyl)pyrimidin-4-yl)-N-(4-(trifluoromethyl) phenethyl)-pyrrolidine-2-carboxamide;

4) (S)-tert-butyl (2-(1-(2-(trifluoromethyl)-6-(2-((4-(trifluoromethyl)phenethyl) carbamoyl)pyrrolidin-1-yl)pyrimidin-4-yl)piperidin-4-yl)ethyl)carbamate;

5) (S)-1-(6-(4-(2-hydroxyethyl)piperidin-1-yl)-2-(trifluoromethyl)pyrimidin-4-yl)-N-(4-(trifluoromethyl)phenethyl)-pyrrolidine-2-carboxamide;
6) (S)-1-(6-(4-(methoxymethyl)piperidin-1-yl)-2-(trifluoromethyl)pyrimidin-4-yl)-N-(4-(trifluoromethyl)phenethyl)-pyrrolidine-2-carboxamide;
7) (S)-4-(1-(2-(trifluoromethyl)-6-(2-((4-(trifluoromethyl) phenethyl) carbamoyl) pyrrolidin-1-yl)pyrimidin-4-yl)piperidin-4-yl)butanoic acid;
8) (S)-1-(6-(4-(2-cyanoethyl)piperazin-1-yl)-2-(trifluoromethyl)pyrimidin-4-yl)-N-(4-(trifluoromethyl)-phenethyl) pyrrolidine-2-carboxamide;
9) (S)-1-(6-(4-(2-cyanoethyl)piperidin-1-yl)-2-(trifluoromethyl)pyrimidin-4-yl)-N-(4-(trifluoromethyl)phenethyl)-pyrrolidine-2-carboxamide;
10) (S)-tert-butyl ((1-(6-(2-((4-cyanophenethyl)carbamoyl) pyrrolidin-1-yl)-2-(trifluoromethyl)pyrimidin-4-yl)piperidin-4-yl)methyl)carbamate;
11) (S)-tert-butyl (2-(1-(6-(2-((4-cyanophenethyl)carbamoyl)pyrrolidin-1-yl)-2-(trifluoromethyl)pyrimidin-4-yl) piperidin-4-yl)ethyl)carbamate;
12) (S)—N-(4-cyanophenethyl)-1-(6-(4-((dimethylamino) methyl)piperidin-1-yl)-2-(trifluoromethyl)pyrimidin-4-yl)pyrrolidine-2-carboxamide;
13) (S)-tert-butyl ((1-(6-(2-((4-cyanophenethyl)carbamoyl) pyrrolidin-1-yl)-2-(trifluoromethyl)pyrimidin-4-yl)piperidin-4-yl)methyl) (methyl)carbamate;
14) (S)—N-(4-cyanophenethyl)-1-(6-(4-(2-(dimethylamino)ethyl)piperidin-1-yl)-2-(trifluoromethyl)pyrimidin-4-yl)pyrrolidine-2-carboxamide;
15) (S)—N-(4-cyanophenethyl)-1-(6-(4-(2-hydroxyethyl) piperidin-1-yl)-2-(trifluoromethyl)pyrimidin-4-yl)pyrrolidine-2-carboxamide;
16) (S)—N-(4-cyanophenethyl)-1-(6-(4-(3-hydroxypropyl) piperidin-1-yl)-2-(trifluoromethyl)pyrimidin-4-yl)pyrrolidine-2-carboxamide;
17) (S)—N-(4-cyanophenethyl)-1-(6-(4-(methoxymethyl) piperidin-1-yl)-2-(trifluoromethyl)pyrimidin-4-yl)pyrrolidine-2-carboxamide;
18) (S)—N-(4-cyanophenethyl)-1-(6-(4-(2-methoxyethyl) piperidin-1-yl)-2-(trifluoromethyl)pyrimidin-4-yl)pyrrolidine-2-carboxamide;
19) (S)-2-(1-(6-(2-((4-cyanophenethyl)carbamoyl)pyrrolidin-1-yl)-2-(trifluoromethyl)pyrimidin-4-yl)piperidin-4-yl)acetic acid;
20) (S)-3-(1-(6-(2-((4-cyanophenethyl)carbamoyl)pyrrolidin-1-yl)-2-(trifluoromethyl)pyrimidin-4-yl)piperidin-4-yl)propanoic acid;
21) (S)-4-(1-(6-(2-((4-cyanophenethyl)carbamoyl)pyrrolidin-1-yl)-2-(trifluoromethyl)pyrimidin-4-yl)piperidin-4-yl)butanoic acid;
22) (S)—N-(4-cyanophenethyl)-1-(6-(4-(2-(dimethylamino)ethyl)piperazin-1-yl)-2-(trifluoromethyl)pyrimidin-4-yl)pyrrolidine-2-carboxamide;
23) (S)—N-(4-cyanophenethyl)-1-(6-(4-(2-hydroxyethyl) piperazin-1-yl)-2-(trifluoromethyl)pyrimidin-4-yl)pyrrolidine-2-carboxamide;
24) (S)-1-(6-(4-(2-cyanoethyl)piperazin-1-yl)-2-(trifluoromethyl)pyrimidin-4-yl)-N-(4-cyanophenethyl)pyrrolidine-2-carboxamide;
25) (S)-1-(6-(4-(2-cyanoethyl)piperidin-1-yl)-2-(trifluoromethyl)pyrimidin-4-yl)-N-(4-cyanophenethyl)pyrrolidine-2-carboxamide;
26) (S)-4-(1-(6-(2-((2-methoxy-4-(trifluoromethyl)phenethyl) carbamoyl)pyrrolidin-1-yl)-2-(trifluoromethyl)-pyrimidin-4-yl)piperidin-4-yl)butanoic acid;
27) (S)-4-(1-(6-(2-((2,4-dichlorophenethyl)carbamoyl)pyrrolidin-1-yl)pyrimidin-4-yl)piperidin-4-yl)butanoic acid;
28) (S)—N-(4-cyanophenethyl)-1-(6-(4-(hydroxymethyl) piperidin-1-yl)-2-methylpyrimidin-4-yl)pyrrolidine-2-carboxamide;
29) (S)—N-(4-cyanophenethyl)-1-(4-(4-(hydroxymethyl) piperidin-1-yl)-6-(trifluoromethyl)pyridine-2-yl)pyrrolidine-2-carboxamide;
30) (S)-1-(6-(4-(aminomethyl)piperidin-1-yl)-2-(trifluoromethyl)pyrimidin-4-yl)-N-(4-cyanophenethyl)pyrrolidine-2-carboxamide;
31) (S)—N-(4-cyanophenethyl)-1-(6-(3-oxopiperazin-1-yl)-2-(trifluoromethyl) pyrimidin-4-yl)pyrrolidine-2-carboxamide;
32) (S)-1-(6-(4-(2-aminoethyl)piperidin-1-yl)-2-(trifluoromethyl)pyrimidin-4-yl)-N-(4-cyanophenethyl)pyrrolidine-2-carboxamide;
33) (S)-1-(6-(4-(acetamidomethyl)piperidin-1-yl)-2-(trifluoromethyl)pyrimidin-4-yl)-N-(4-cyanophenethyl)pyrrolidine-2-carboxamide;
34) (S)—N-(4-cyanophenethyl)-1-(6-(4-((N-methyl acetamido)methyl) piperidin-1-yl)-2-(trifluoromethyl)pyrimidin-4-yl)pyrrolidine-2-carboxamide;
35) (S)-ethyl 3-(3-(2-(1-(6-(2-((4-cyanophenethyl)carbamoyl)pyrrolidin-1-yl)-2-(trifluoromethyl)pyrimidin-4-yl) piperidin-4-yl)ethyl)ureido)propanoate;
36) (S)-2-(3-(1-(6-(2-((4-cyanophenethyl)carbamoyl)pyrrolidin-1-yl)-2-(trifluoromethyl)pyrimidin-4-yl)piperidin-4-yl)propanamido)ethanesulfonic acid;
37) (S)-2-(4-(1-(6-(2-((2-methoxy-4-(trifluoromethyl)phenethyl)carbamoyl)-pyrrolidin-1-yl)-2-(trifluoromethyl)-pyrimidin-4-yl)piperidin-4-yl) butanamido)ethanesulfonic acid;
38) (S)-2-(4-(1-(2-(trifluoromethyl)-6-(2-((4-(trifluoromethyl)phenethyl)-carbamoyl)-pyrrolidin-1-yl)-pyrimidin-4-yl)piperidin-4-yl) butanamido)ethanesulfonic acid;
39) (S)-1-(6-(4-(4-oxo-4-((2-sulfamoylethyl)amino)butyl) piperidin-1-yl)-2-(trifluoromethyl)pyrimidin-4-yl)-N-(4-(trifluoromethyl)phenethyl)-pyrrolidine-2-carboxamide;
40) (S)-3-(4-(1-(2-(trifluoromethyl)-6-(2-((4-(trifluoromethyl)phenethyl) carbamoyl)pyrrolidin-1-yl)pyrimidin-4-yl)piperidin-4-yl)butanamido)propane-1-sulfonic acid;
41) (S)-2-(4-(1-(6-(2-((4-cyanophenethyl)carbamoyl)pyrrolidin-1-yl)-2-(trifluoromethyl)pyrimidin-4-yl)-piperidin-4-yl)butanamido)ethanesulfonic acid;
42) (S)—N-(4-cyanophenethyl)-1-(6-(4-(4-oxo-4-((2-sulfamoylethyl)amino) butyl)piperidin-1-yl)-2-(trifluoromethyl)pyrimidin-4-yl)pyrrolidine-2-carboxamide;
43) (S)-3-(4-(1-(6-(2-((4-cyanophenethyl)carbamoyl)pyrrolidin-1-yl)-2-(trifluoromethyl)pyrimidin-4-yl)-piperidin-4-yl)butanamido)propane-1-sulfonic acid;
44) (S)-((4-(1-(6-(2-((4-cyanophenethyl)carbamoyl)pyrrolidin-1-yl)-2-(trifluoromethyl)pyrimidin-4-yl)piperidin-4-yl)butanamido)methyl)-phosphonic acid;
45) (S)-4-(4-(1-(6-((S)-2-((4-cyanophenethyl)carbamoyl) pyrrolidin-1-yl)-2-(trifluoromethyl)pyrimidin-4-yl)piperidin-4-yl)butanamido)-5-methoxy-N,N,N-trimethyl-5-oxopentan-1-aminium;
46) (S)-(4-(1-(6-(2-((4-cyanophenethyl)carbamoyl)pyrrolidin-1-yl)-2-(trifluoromethyl)pyrimidin-4-yl)piperidin-4-yl)butanamido)-methanesulfonic acid; 47) (S)-1-(6-(4-(4-((2-(2-(2-aminoethoxy)ethoxy)ethyl)amino)-4-oxobutyl) piperidin-1-yl)-2-(trifluoromethyl)pyrimidin-4-yl)-N-(4-cyanophenethyl)pyrrolidine-2-carboxamide;
48) (S)-1-(6-(4-(4-((2-amino-2-oxoethyl)amino)-4-oxobutyl)piperidin-1-yl)-2-(trifluoromethyl)pyrimidin-4-yl)-N-(4-cyanophenethyl)pyrrolidine-2-carboxamide;

49) (S)-methyl 2-(4-(1-(6-(2-((4-cyanophenethyl)carbamoyl)pyrrolidin-1-yl)-2-(trifluoromethyl)pyrimidin-4-yl)piperidin-4-yl)butanamido)acetate;
50) (S)-methyl 3-(4-(1-(6-(2-((4-cyanophenethyl)carbamoyl)pyrrolidin-1-yl)-2-(trifluoromethyl)pyrimidin-4-yl)piperidin-4-yl)butanamido)-propanoate;
51) (S)-methyl 2-amino-6-(4-(1-(6-((S)-2-((4-cyanophenethyl)carbamoyl)-pyrrolidin-1-yl)-2-(trifluoromethyl)-pyrimidin-4-yl)piperidin-4-yl)butanamido)hexanoate;
52) (S)-2-(4-(1-(6-((S)-2-((4-cyanophenethyl)carbamoyl)pyrrolidin-1-yl)-2-(trifluoromethyl)pyrimidin-4-yl)piperidin-4-yl)butanamido)-5-guanidinopentanoic acid;
53) (R)-2-(4-(1-(6-((S)-2-((4-cyanophenethyl)carbamoyl)pyrrolidin-1-yl)-2-(trifluoromethyl)pyrimidin-4-yl)piperidin-4-yl)butanamido)-5-guanidinopentanoic acid;
54) (S)-5-guanidino-2-(4-(1-(2-(trifluoromethyl)-6-((S)-2-((4-(trifluoromethyl)phenethyl)carbamoyl)pyrrolidin-1-yl)pyrimidin-4-yl)piperidin-4-yl)butanamido)pentanoic acid;
55) (R)-2-(4-(1-(6-((S)-2-((4-cyanophenethyl)carbamoyl)pyrrolidin-1-yl)-2-(trifluoromethyl)pyrimidin-4-yl)piperidin-4-yl)butanamido)succinic acid;
56) (S)-2-(4-(1-(6-((S)-2-((4-cyanophenethyl)carbamoyl)pyrrolidin-1-yl)-2-(trifluoromethyl)pyrimidin-4-yl)piperidin-4-yl)butanamido)-pentanedioic acid;
57) (S)-2-amino-5-oxo-5-((3-(1-(2-(trifluoromethyl)-6-((S)-2-((4-(trifluoromethyl)phenethyl)carbamoyl)pyrrolidin-1-yl)pyrimidin-4-yl)piperidin-4-yl)propyl)amino)pentanoic acid;
58) (S)-2-(3-(2-(1-(6-(2-((4-cyanophenethyl)carbamoyl)pyrrolidin-1-yl)-2-(trifluoromethyl)pyrimidin-4-yl)piperidin-4-yl)ethyl)ureido)ethanesulfonic acid;
59) (S)-(3-(2-(1-(6-(2-((4-cyanophenethyl)carbamoyl)pyrrolidin-1-yl)-2-(trifluoromethyl)pyrimidin-4-yl)piperidin-4-yl)ethyl)ureido)methanesulfonic acid;
60) (S)—N-(4-cyanophenethyl)-1-(6-(4-(2-(3-(2-sulfamoylethyl)ureido)-ethyl)piperidin-1-yl)-2-(trifluoromethyl)pyrimidin-4-yl)pyrrolidine-2-carboxamide;
61) (S)-3-(3-(2-(1-(6-(2-((4-cyanophenethyl)carbamoyl)pyrrolidin-1-yl)-2-(trifluoromethyl)pyrimidin-4-yl)piperidin-4-yl)ethyl)ureido)-propanoic acid;
62) (R)-2-(3-(2-(1-(6-((S)-2-((4-cyanophenethyl)carbamoyl)pyrrolidin-1-yl)-2-(trifluoromethyl)pyrimidin-4-yl)piperidin-4-yl)ethyl)ureido)succinic acid;
63) (S)-2-(3-(2-(1-(6-((S)-2-((4-cyanophenethyl)carbamoyl)pyrrolidin-1-yl)-2-(trifluoromethyl)pyrimidin-4-yl)piperidin-4-yl)ethyl)ureido)-5-guanidinopentanoic acid;
64) (S)—N-(2-(1-(6-(2-((4-cyanophenethyl)carbamoyl)pyrrolidin-1-yl)-2-(trifluoromethyl)pyrimidin-4-yl)piperidin-4-yl)ethyl)-4-(hydroxymethyl)-4-methylpiperidine-1-carboxamide;
65) (S)—N-(2-(1-(6-(2-((4-cyanophenethyl)-carbamoyl)pyrrolidin-1-yl)-2-(trifluoromethyl)pyrimidin-4-yl)piperidin-4-yl)ethyl)-2-(2-aminoethylsulfonamido)acetate methyl ester;
66) (S)-2-(3-(2-(1-(2-(trifluoromethyl)-6-(2-((4-(trifluoromethyl)phenethyl)-carbamoyl)pyrrolidin-1-yl)pyrimidin-4-yl)piperidin-4-yl)ethyl)ureido)-ethanesulfonic acid;
67) (S)-2-(3-(3-(1-(2-(trifluoromethyl)-6-(2-((4-(trifluoromethyl)phenethyl)-carbamoyl)-pyrrolidin-1-yl)pyrimidin-4-yl)piperidin-4-yl)propyl)ureido)-ethanesulfonic acid;
68) (S)-2-((1-(6-(2-((4-cyanophenethyl)carbamoyl)pyrrolidin-1-yl)-2-(trifluoromethyl)pyrimidin-4-yl)piperidin-4-yl)methoxy)acetic acid;
69) (S)-2-(2-((1-(6-(2-((4-cyanophenethyl)carbamoyl)pyrrolidin-1-yl)-2-(trifluoromethyl)pyrimidin-4-yl)piperidin-4-yl)methoxy)acetamido)-ethanesulfonic acid;
70) (S)-1-(6-(4-(4-((2-aminoethyl)amino)-4-oxobutyl)piperidin-1-yl)-2-(trifluoromethyl)pyrimidin-4-yl)-N-(4-(trifluoromethyl)phenethyl)pyrrolidine-2-carboxamide;
71) (S)-1-(6-(4-(4-((2-(methylsulfonamido)ethyl)amino)-4-oxobutyl)piperidin-1-yl)-2-(trifluoromethyl)pyrimidin-4-yl)-N-(4-(trifluoromethyl)phenethyl)pyrrolidine-2-carboxamide;
72) (S)-1-(6-(4-(4-((2-aminoethyl)amino)-4-oxobutyl)piperidin-1-yl)-2-(trifluoromethyl)pyrimidin-4-yl)-N-(4-cyanophenethyl)pyrrolidine-2-carboxamide;
73) (S)—N-(4-cyanophenethyl)-1-(6-(4-(4-((2-(methylsulfonamido)ethyl)amino)-4-oxobutyl)piperidin-1-yl)-2-(trifluoromethyl)pyrimidin-4-yl)pyrrolidine-2-carboxamide;
74) (S)-4-(N-(2-(4-(1-(2-(trifluoromethyl)-6-(2-((4-(trifluoromethyl)phenethyl)-carbamoyl)-pyrrolidin-1-yl)pyrimidin-4-yl)piperidin-4-yl)butanamido)ethyl)-sulfamoyl)benzoic acid;
75) (S)-1-(6-(4-(4-((2-((9H-purin-6-yl)amino)ethyl)amino)-4-oxobutyl)piperidin-1-yl)-2-(trifluoromethyl)pyrimidin-4-yl)-N-(4-(trifluoromethyl)phenethyl)pyrrolidine-2-carboxamide;
76) (2 S)-1-(6-(4-(4-((2-((9-((2R,5R)-3,4-dihydroxy-5-(hydroxymethyl)-tetrahydrofuran-2-yl)-9H-purin-6-yl)amino)ethyl)amino)-4-oxobutyl)piperidin-1-yl)-2-(trifluoromethyl)-pyrimidin-4-yl)-N-(4-(trifluoromethyl)-phenethyl)-pyrrolidine-2-carboxamide;
77) (2 S)—N-(4-cyanophenethyl)-1-(6-(4-(4-((2-((9-((2R,5R)-3,4-dihydroxy-5-(hydroxymethyl)tetrahydrofuran-2-yl)-9H-purin-6-yl)amino)ethyl)amino)-4-oxobutyl)piperidin-1-yl)-2-(trifluoromethyl)-pyrimidin-4-yl)pyrrolidine-2-carboxamide;
78) (S)-2-((2-(4-(1-(6-(2-((4-cyanophenethyl)carbamoyl)pyrrolidin-1-yl)-2-(trifluoromethyl)pyrimidin-4-yl)piperidin-4-yl)butanamido)ethyl)-amino)pyrimidine-5-carboxylic acid;
79) (S)-methyl-2-((2-(4-(1-(6-(2-((4-cyanophenethyl)carbamoyl)pyrrolidin-1-yl)-2-(trifluoromethyl)pyrimidin-4-yl)-piperidin-4-yl)butanamido)ethyl)amino)-pyrimidine-4-carboxylate;
80) N-(2-(4-(1-(6-((S)-2-((4-cyanophenethyl)carbamoyl)pyrrolidin-1-yl)-2-(trifluoromethyl)pyrimidin-4-yl)piperidin-4-yl)butanamido)ethyl)-6-(((2S,3R,4R,5R)-2,3,4,5,6-pentahydroxyhexyl)amino)-pyrimidine-4-carboxamide;
81) (S)-6-((2-(4-(1-(6-(2-((4-cyanophenethyl)carbamoyl)pyrrolidin-1-yl)-2-(trifluoromethyl)pyrimidin-4-yl)piperidin-4-yl)butanamido)ethyl)amino)-pyrimidine-4-carboxylic acid;
82) (S)-2-((2-(4-(1-(6-(2-((4-cyanophenethyl)carbamoyl)pyrrolidin-1-yl)-2-(trifluoromethyl)pyrimidin-4-yl)piperidin-4-yl)butanamido)ethyl)amino) pyrimidine-4-carboxylic acid;
83) (S)-2-(4-(1-(6-(2-((4-cyanophenethyl)carbamoyl)pyrrolidin-1-yl)-2-(trifluoromethyl)pyrimidin-4-yl)piperidin-4-yl)butanamido)acetic acid;
84) (S)-3-(4-(1-(6-(2-((4-cyanophenethyl)carbamoyl)pyrrolidin-1-yl)-2-(trifluoromethyl)pyrimidin-4-yl)-piperidin-4-yl)butanamido)-propanoic acid;
85) (S)-4-carboxy-4-(4-(1-(6-((S)-2-((4-cyanophenethyl)carbamoyl)pyrrolidin-1-yl)-2-(trifluoromethyl)pyrimidin-4-yl)piperidin-4-yl)butanamido)-N,N,N-trimethylbutan-1-aminium;
86) (S)-2-amino-6-(4-(1-(6-((S)-2-((4-cyanophenethyl)carbamoyl)pyrrolidin-1-yl)-2-(trifluoromethyl)pyrimidin-4-yl)-piperidin-4-yl)butanamido)hexanoic acid;

87) (S)—N-(2-(1-(6-(2-((4-cyanophenethyl)-carbamoyl)pyrrolidin-1-yl)-2-(trifluoromethyl)pyrimidin-4-yl)piperidin-4-yl)ethyl)-2-(2-aminoethylsulfonamido)-acetic acid;
88) (S)-2-(4-(4-(1-(6-(2-((4-cyanophenethyl)carbamoyl)pyrrolidin-1-yl)-2-(trifluoromethyl)pyrimidin-4-yl)piperidin-4-yl)butanoyl)piperazin-1-yl)acetic acid;
89) (S)—N-(4-cyanophenethyl)-1-(6-(4-(4-((3-((1,3-dihydroxy-2-(hydroxymethyl)propan-2-yl)amino)-3-oxopropyl)amino)-4-oxobutyl)piperidin-1-yl)-2-(trifluoromethyl)-pyrimidin-4-yl)pyrrolidine-2-carboxamide;
90) (S)-1-(6-(4-(4-((2-((6-chloropyrimidin-4-yl)amino)ethyl)amino)-4-oxobutyl)piperidin-1-yl)-2-(trifluoromethyl)pyrimidin-4-yl)-N-(4-cyanophenethyl)pyrrolidine-2-carboxamide;
91) (S)-1-(6-(4-(4-((2-((6-(bis(2-hydroxyethyl)amino)pyrimidin-4-yl)amino)ethyl)amino)-4-oxobutyl)piperidin-1-yl)-2-(trifluoromethyl)pyrimidin-4-yl)-N-(4-cyanophenethyl)pyrrolidine-2-carboxamide;
92) (S)-2-(2-((2-(4-(1-(6-(2-((4-cyanophenethyl)carbamoyl)pyrrolidin-1-yl)-2-(trifluoromethyl)pyrimidin-4-yl)piperidin-4-yl)butanamido)ethyl)amino)-pyrimidine-5-carboxamido)ethanesulfonic acid;
93) (S)-2-(3-(3-(2-(1-(6-(2-((4-cyanophenethyl)carbamoyl)pyrrolidin-1-yl)-2-(trifluoromethyl)pyrimidin-4-yl)piperidin-4-yl)ethyl)ureido)-propanamido)-ethanesulfonic acid;
94) (S)-2-(2-(4-(1-(2-(trifluoromethyl)-6-(2-((4-(trifluoromethyl)phenethyl)-carbamoyl)-pyrrolidin-1-yl)pyrimidin-4-yl)piperidin-4-yl)butanamido)ethyl-sulfonamido)acetic acid;
95) (S)-2-(2-(4-(1-(6-(2-((4-cyanophenethyl)carbamoyl)pyrrolidin-1-yl)-2-(trifluoromethyl)pyrimidin-4-yl)piperidin-4-yl)butanamido)-ethylsulfonamido)acetic acid;
96) (S)-1-(6-(4-(2-(2-aminoethylsulfonamido)ethyl)piperidin-1-yl)-2-(trifluoromethyl)-pyrimidin-4-yl)-N-(4-cyanophenethyl)pyrrolidine-2-carboxamide;
97) (S)-2-((2-(N-(2-(1-(6-(2-((4-cyanophenethyl)carbamoyl)pyrrolidin-1-yl)-2-(trifluoromethyl)pyrimidin-4-yl)piperidin-4-yl)ethyl)sulfamoyl)ethyl)amino)-pyrimidine-5-carboxylic acid;
98) (S)-(3-(3-(1-(6-(2-((4-cyanophenethyl)carbamoyl)pyrrolidin-1-yl)-2-(trifluoromethyl)pyrimidin-4-yl)piperidin-4-yl)propyl)ureido)methanesulfonic acid;
99) (S)-2-(3-(3-(1-(6-(2-((4-cyanophenethyl)carbamoyl)pyrrolidin-1-yl)-2-(trifluoromethyl)pyrimidin-4-yl)piperidin-4-yl)propyl)ureido)-ethanesulfonic acid;
100) (S)—N-(4-cyanophenethyl)-1-(6-(4-(3-(3-(2-sulfamoylethyl)ureido)propyl)piperidin-1-yl)-2-(trifluoromethyl)pyrimidin-4-yl)pyrrolidine-2-carboxamide;
101) (S)-2-(3-(3-(1-(6-(2-((4-cyanophenethyl)carbamoyl)pyrrolidin-1-yl)-2-(trifluoromethyl)pyrimidin-4-yl)piperidin-4-yl)propyl)ureido)acetic acid; 102) ((R)-1-(2-(1-(6-((S)-2-((4-cyanophenethyl)carbamoyl)pyrrolidin-1-yl)-2-(trifluoromethyl)pyrimidin-4-yl)piperidin-4-yl)ethyl)-2,5-dioxoimidazolidin-4-yl)methanesulfonic acid;
103) (R)-2-amino-3-((2-(1-(6-((S)-2-((4-cyanophenethyl)carbamoyl)pyrrolidin-1-yl)-2-(trifluoromethyl)pyrimidin-4-yl)piperidin-4-yl)ethyl)amino)-3-oxopropane-1-sulfonic acid;
104) (S)-2-((2-(4-(1-(6-(2-((4-cyanophenethyl)carbamoyl)pyrrolidin-1-yl)-2-(trifluoromethyl)pyrimidin-4-yl)piperidin-4-yl)butanamido)-ethyl) amino)-2-oxoethanesulfonic acid;
105) (R)-2-amino-3-((2-(N-(2-(1-(6-((S)-2-((4-cyanophenethyl)carbamoyl)-pyrrolidin-1-yl)-2-(trifluoromethyl)-pyrimidin-4-yl)piperidin-4-yl)ethyl)sulfamoyl)ethyl)amino)-3-oxopropane-1-sulfonic acid;
106) (S)—N-(4-cyanophenethyl)-1-(6-(4-(2-guanidinoethyl)piperidin-1-yl)-2-(trifluoromethyl)pyrimidin-4-yl)pyrrolidine-2-carboxamide;
107) (S)-1-(6-(4-(1-amino-1-imino-12-oxo-5,8-dioxa-2,11-diazapentadecan-15-yl)piperidin-1-yl)-2-(trifluoromethyl)-pyrimidin-4-yl)-N-(4-cyanophenethyl)-pyrrolidine-2-carboxamide;
108) (S)—N-(4-cyanophenethyl)-1-(6-(4-(4-((2-guanidinoethyl)amino)-4-oxobutyl)piperidin-1-yl)-2-(trifluoromethyl)pyrimidin-4-yl)pyrrolidine-2-carboxamide;
109) (S)-6-(4-(1-(6-((S)-2-((4-cyanophenethyl)carbamoyl)pyrrolidin-1-yl)-2-(trifluoromethyl)pyrimidin-4-yl)piperidin-4-yl)butanamido)-2-guanidinohexanoic acid;
110) (S)—N-(4-cyanophenethyl)-1-(6-(4-(2-(2-guanidinoethylsulfonamido) ethyl)piperidin-1-yl)-2-(trifluoromethyl)pyrimidin-4-yl)pyrrolidine-2-carboxamide;
111) (S)-1-(6-(4-(4-((2-guanidinoethyl)-amino)-4-oxobutyl)piperidin-1-yl)-2-(trifluoromethyl)pyrimidin-4-yl)-N-(4-(trifluoromethyl)phenethyl)pyrrolidine-2-carboxamide;
112) (S)-1-(6-(4-(3-guanidinopropyl)piperidin-1-yl)-2-(trifluoromethyl)pyrimidin-4-yl)-N-(4-(trifluoromethyl)phenethyl)-pyrrolidine-2-carboxamide;
113) (S)-2-guanidino-5-oxo-5-((3-(1-(2-(trifluoromethyl)-6-((S)-2-((4-(trifluoromethyl)phenethyl)carbamoyl)pyrrolidin-1-yl)pyrimidin-4-yl)piperidin-4-yl)propyl)amino)pentanoic acid;
114) (S)-(4-(1-(6-(2-((3,4-dichlorophenethyl)carbamoyl)pyrrolidin-1-yl)-2-(trifluoromethyl)pyrimidin-4-yl)piperidin-4-yl)butanamido)methanesulfonic acid;
115) (S)-(4-(1-(6-(2-((4-chlorophenethyl)-carbamoyl)pyrrolidin-1-yl)-2-(trifluoromethyl)pyrimidin-4-yl)-piperidin-4-yl)butanamido)-methanesulfonic acid;
116) (S)-(4-(1-(6-(2-((2,3-dichlorophenethyl)carbamoyl)pyrrolidin-1-yl)-2-(trifluoromethyl)pyrimidin-4-yl)piperidin-4-yl)butanamido)-methanesulfonic acid;
117) (S)-4-(1-(2-(2-((4-cyanophenethyl)carbamoyl)pyrrolidin-1-yl)-6-(trifluoromethyl)pyridin-4-yl)piperidin-4-yl)butanoic acid;
118) (S)-(4-(1-(2-(2-((4-cyanophenethyl)carbamoyl)pyrrolidin-1-yl)-6-(trifluoromethyl)pyridin-4-yl)piperidin-4-yl)butanamido)methanesulfonic acid;
119) (S)-2-(4-(1-(2-(2-((4-cyanophenethyl)carbamoyl)pyrrolidin-1-yl)-6-(trifluoromethyl)pyridin-4-yl)piperidin-4-yl)butanamido)ethanesulfonic acid;
120) (S)-2-(4-(1-(2-((S)-2-((4-cyanophenethyl)carbamoyl)pyrrolidin-1-yl)-6-(trifluoromethyl)pyridin-4-yl)piperidin-4-yl)butanamido)-5-guanidinopentanoic acid;
121) (S)-(3-(3-(1-(2-(2-((4-cyanophenethyl)carbamoyl)pyrrolidin-1-yl)-6-(trifluoromethyl)pyridin-4-yl)piperidin-4-yl)propyl)ureido)methanesulfonic acid;
122) (S)-2-((S)-2-(4-(1-(2-((S)-2-((4-cyanophenethyl)carbamoyl)pyrrolidin-1-yl)-6-(trifluoromethyl)pyridin-4-yl)piperidin-4-yl)butanamido)-5-guanidinopentanamido)-5-guanidinopentanoic acid;
123) (R)-2-((R)-2-(4-(1-(6-((S)-2-((4-cyanophenethyl)carbamoyl)pyrrolidin-1-yl)-2-(trifluoromethyl)pyrimidin-4-yl)piperidin-4-yl)butanamido)-5-guanidino-pentanamido)pentanedioic acid;
124) (2S,4R)—N-(4-cyanophenethyl)-4-hydroxy-1-(6-(4-(2-hydroxyethyl)piperidin-1-yl)-2-(trifluoromethyl)pyrimidin-4-yl)pyrrolidine-2-carboxamide;
125) (2S,4R)—N-(4-cyanophenethyl)-4-hydroxy-1-(6-(4-(hydroxymethyl)piperidin-1-yl)-2-(trifluoromethyl)pyrimidin-4-yl)pyrrolidine-2-carboxamide;

126) 4-(1-(6-((2S,4R)-4-hydroxy-2-((4-(trifluoromethyl)phenethyl) carbamoyl)pyrrolidin-1-yl)-2-(trifluoromethyl)pyrimidin-4-yl)piperidin-4-yl)butanoic acid;

127) (S)-tert-butyl (2-(1-(6-(2-((4-cyanophenethyl)carbamoyl)-4,4-difluoropyrrolidin-1-yl)-2-(trifluoromethyl)pyrimidin-4-yl)piperidin-4-yl)ethyl)carbamate;

128) (2S,4R)-4-hydroxy-1-(6-(4-(4-oxo-4-(((2S,3R,4R,5R)-2,3,4,5,6-pentahydroxyhexyl)-amino)butyl)-piperidin-1-yl)-2-(trifluoromethyl)-pyrimidin-4-yl)-N-(4-(trifluoromethyl)phenethyl)pyrrolidine-2-carboxamide;

129) (S)-1-(6-(4-(2-aminoethyl)piperidin-1-yl)-2-(trifluoromethyl)pyrimidin-4-yl)-N-(4-cyanophenethyl)-4,4-difluoropyrrolidine-2-carboxamide;

130) (S)-2-(3-(2-(1-(6-(2-((4-cyanophenethyl)carbamoyl)-4,4-difluoropyrrolidin-1-yl)-2-(trifluoromethyl)pyrimidin-4-yl)piperidin-4-yl)ethyl)ureido) ethanesulfonic acid;

131) (4R)-4-amino-1-(6-(4-(hydroxymethyl)piperidin-1-yl)-2-(trifluoromethyl)pyrimidin-4-yl)-N-(4-(trifluoromethyl)phenethyl)pyrrolidine-2-carboxamide;

132) (S)—N-(4-cyanophenethyl)-1-(6-(4-(hydroxymethyl)piperidin-1-yl)-2-(trifluoromethyl)pyrimidin-4-yl)azetidine-2-carboxamide;

133) (S)-1-(6-(4-(hydroxymethyl)piperidin-1-yl)-2-(trifluoromethyl)pyrimidin-4-yl)-N-(4-(trifluoromethyl)-phenethyl)azetidine-2-carboxamide;

134) (S)—N-(4-cyanophenethyl)-1-(6-(4-((dimethylamino)methyl)piperidin-1-yl)-2-(trifluoromethyl)pyrimidin-4-yl)azetidine-2-carboxamide;

135) (S)—N-(4-cyanophenethyl)-1-(6-(4-(methoxymethyl)piperidin-1-yl)-2-(trifluoromethyl)pyrimidin-4-yl)azetidine-2-carboxamide;

136) (S)—N-(4-cyanophenethyl)-1-(6-(4-(2-hydroxyethyl)piperidin-1-yl)-2-(trifluoromethyl)pyrimidin-4-yl)azetidine-2-carboxamide;

137) (S)—N-(4-cyanophenethyl)-1-(6-(4-(2-hydroxyethyl)piperazin-1-yl)-2-(trifluoromethyl)pyrimidin-4-yl)azetidine-2-carboxamide;

138) (S)—N-(4-cyanophenethyl)-1-(6-(4-(2-methoxyethyl)piperidin-1-yl)-2-(trifluoromethyl)pyrimidin-4-yl)azetidine-2-carboxamide;

139) (S)—N-(4-cyanophenethyl)-1-(6-(4-(2-(dimethylamino)ethyl)piperazin-1-yl)-2-(trifluoromethyl)pyrimidin-4-yl)azetidine-2-carboxamide;

140) (S)-3-(1-(6-(2-((4-cyanophenethyl)carbamoyl)azetidin-1-yl)-2-(trifluoromethyl)pyrimidin-4-yl)piperidin-4-yl)propanoic acid;

141) (S)—N-(4-cyanophenethyl)-1-(6-(4-(2-(dimethylamino)ethyl)piperidin-1-yl)-2-(trifluoromethyl)pyrimidin-4-yl)azetidine-2-carboxamide;

142) (S)-1-(6-(4-(2-cyanoethyl)piperazin-1-yl)-2-(trifluoromethyl)pyrimidin-4-yl)-N-(4-cyanophenethyl)azetidine-2-carboxamide;

143) (S)-1-(6-(4-(2-cyanoethyl)piperidin-1-yl)-2-(trifluoromethyl)pyrimidin-4-yl)-N-(4-cyanophenethyl)azetidine-2-carboxamide;

144) (S)-4-(1-(6-(2-((4-cyanophenethyl)carbamoyl)azetidin-1-yl)-2-(trifluoromethyl)pyrimidin-4-yl)piperidin-4-yl)butanoic acid;

145) (S)-3-(1-(2-(trifluoromethyl)-6-(2-((4-(trifluoromethyl)phenethyl) carbamoyl)azetidin-1-yl)pyrimidin-4-yl)piperidin-4-yl)propanoic acid;

146) (S)-4-(1-(2-(trifluoromethyl)-6-(2-((4-(trifluoromethyl)phenethyl) carbamoyl)azetidin-1-yl)pyrimidin-4-yl)piperidin-4-yl)butanoic acid;

147) (S)-tert-butyl ((1-(6-(2-((4-cyanophenethyl)carbamoyl)azetidin-1-yl)-2-(trifluoromethyl)pyrimidin-4-yl)piperidin-4-yl)methyl)carbamate;

148) (S)-tert-butyl (2-(1-(6-(2-((4-cyanophenethyl)carbamoyl)azetidin-1-yl)-2-(trifluoromethyl)pyrimidin-4-yl)piperidin-4-yl)ethyl)carbamate;

149) (S)-tert-butyl (2-(1-(2-(trifluoromethyl)-6-(2-((4-(trifluoromethyl)phenethyl) carbamoyl)azetidin-1-yl)pyrimidin-4-yl)piperidin-4-yl)ethyl)carbamate;

150) (S)-1-(6-(4-(hydroxymethyl)piperidin-1-yl)-2-(trifluoromethyl)pyrimidin-4-yl)-N-(2-methoxy-4-(trifluoromethyl)phenethyl)azetidine-2-carboxamide;

151) (S)-1-(6-(4-(2-hydroxyethyl)piperidin-1-yl)-2-(trifluoromethyl)pyrimidin-4-yl)-N-(2-methoxy-4-(trifluoromethyl)phenethyl)azetidine-2-carboxamide;

152) (S)-3-(1-(6-(2-((2-methoxy-4-(trifluoromethyl)phenethyl)carbamoyl)azetidin-1-yl)-2-(trifluoromethyl)pyrimidin-4-yl)piperidin-4-yl)propanoic acid;

153) (S)-4-(1-(6-(2-((2-methoxy-4-(trifluoromethyl)phenethyl)carbamoyl)azetidin-1-yl)-2-(trifluoromethyl)pyrimidin-4-yl)piperidin-4-yl)butanoic acid;

154) N-(4-cyanophenethyl)-1-(6-(4-(hydroxymethyl)piperidin-1-yl)-2-(trifluoromethyl)pyrimidin-4-yl)azetidine-2-carboxamide;

155) (S)-(1-(6-(4-aminomethylpiperidin-1-yl)-2-(trifluoromethyl)pyrimidin-4-yl)-N-(4-cyanophenethyl)azetidine-2-carboxamide hydrochloride;

156) (S)-1-(6-(4-(2-aminoethyl)piperidin-1-yl)-2-(trifluoromethyl)pyrimidin-4-yl)-N-(4-cyanophenethyl)azetidine-2-carboxamide;

157) (S)-1-(6-(4-(2-aminoethyl)piperidin-1-yl)-2-(trifluoromethyl)pyrimidin-4-yl)-N-(4-(trifluoromethyl)phenethyl)-azetidine-2-carboxamide;

158) (S)-3-(4-(1-(6-(2-((4-cyanophenethyl)carbamoyl)azetidin-1-yl)-2-(trifluoromethyl)pyrimidin-4-yl)piperidin-4-yl)butanamido)propane-1-sulfonic acid;

159) (S)-2-(4-(1-(6-(2-((4-cyanophenethyl)carbamoyl)azetidin-1-yl)-2-(trifluoromethyl)pyrimidin-4-yl)piperidin-4-yl)butanamido)ethanesulfonic acid;

160) (S)-(4-(1-(6-(2-((4-cyanophenethyl)carbamoyl)azetidin-1-yl)-2-(trifluoromethyl)pyrimidin-4-yl)piperidin-4-yl)butanamido)methanesulfonic acid;

161) (S)-2-(4-(1-(6-((S)-2-((4-cyanophenethyl)carbamoyl)azetidin-1-yl)-2-(trifluoromethyl)pyrimidin-4-yl)piperidin-4-yl)butanamido)-5-guanidinopentanoic acid;

162) (S)-2-(N-methyl-3-(1-(2-(trifluoromethyl)-6-(2-((4-(trifluoromethyl) phenethyl)carbamoyl)azetidin-1-yl)pyrimidin-4-yl)piperidin-4-yl)propanamido)ethanesulfonic acid;

163) (S)-(3-(1-(2-(trifluoromethyl)-6-(2-((4-(trifluoromethyl)phenethyl)-carbamoyl)azetidin-1-yl)pyrimidin-4-yl)piperidin-4-yl)propanamido)-methanesulfonic acid;

164) (S)-2-(3-(1-(2-(trifluoromethyl)-6-(2-((4-(trifluoromethyl)phenethyl) carbamoyl)-azetidin-1-yl)pyrimidin-4-yl)piperidin-4-yl)propanamido)ethanesulfonic acid;

165) (S)-(4-(1-(2-(trifluoromethyl)-6-(2-((4-(trifluoromethyl)phenethyl)-carbamoyl)azetidin-1-yl)pyrimidin-4-yl)piperidin-4-yl)butanamido)methanesulfonic acid;

166) (S)-di-tert-butyl 2-(4-(1-(2-(trifluoromethyl)-6-((S)-2-((4-(trifluoromethyl) phenethyl)carbamoyl)azetidin-1-yl)pyrimidin-4-yl)piperidin-4-yl)butanamido)pentanedioate;

167) (R)-di-tert-butyl 2-(4-(1-(2-(trifluoromethyl)-6-((S)-2-((4-(trifluoromethyl) phenethyl)carbamoyl)azetidin-1-yl)pyrimidin-4-yl)piperidin-4-yl)butanamido)pentanedioate;

168) (S)-5-guanidino-2-(3-(1-(2-(trifluoromethyl)-6-((S)-2-((4-(trifluoromethyl) phenethyl)carbamoyl)azetidin-1-yl)pyrimidin-4-yl)piperidin-4-yl)propanamido)pentanoic acid;

169) (S)-2-(3-(1-(6-(2((2-methoxy-4-(trifluoromethyl)phenethyl)carbamoyl) azetidin-1-yl)-2-trifluoromethyl)-pyrimidin-4-yl)piperidin-4-yl)propanamido)ethanesulfonic acid;

170) (S)—N-(4-cyanophenethyl)-1-(6-(4-(4-oxo-4-(((2R, 3S,4S,5S)-2,3,4,5,6-pentahydroxyhexyl)amino)butyl)piperidin-1-yl)-2-(trifluoromethyl)pyrimidin-4-yl)azetidine-2-carboxamide;

171) (S)—N-(4-cyanophenethyl)-1-(6-(4-(4-(((R)-2,3-dihydroxypropyl)amino)-4-oxobutyl)piperidin-1-yl)-2-(trifluoromethyl)pyrimidin-4-yl)azetidine-2-carboxamide;

172) (S)-3-(3-(1-(6-(2((4-cyanophenethyl)carbamoyl)azetidin-1-yl)-2-trifluoromethyl)pyrimidin-4-yl)propanamido) propane-1-sulfonic acid;

173) (S)-tert-butyl (2-(4-(1-(6-(2-((4-cyanophenethyl)carbamoyl)azetidin-1-yl)-2-(trifluoromethyl)pyrimidin-4-yl) piperidin-4-yl)butanamido)-ethyl)carbamate;

174) (S)-tert-butyl (4-(4-(1-(6-(2-((4-cyanophenethyl)carbamoyl)azetidin-1-yl)-2-(trifluoromethyl)pyrimidin-4-yl) piperidin-4-yl)butanamido)-butyl)carbamate;

175) (S)-tert-butyl (2-(2-(4-(1-(6-(2-((4-cyanophenethyl) carbamoyl)azetidin-1-yl)-2-(trifluoromethyl)pyrimidin-4-yl)piperidin-4-yl)butanamido)ethoxy) ethyl)carbamate;

176) (S)-ethyl 3-(3-(2-(1-(6-(2-((4-cyanophenethyl)carbamoyl)azetidin-1-yl)-2-(trifluoromethyl)pyrimidin-4-yl)piperidin-4-yl)ethyl)ureido)propanoate;

177) (S)-3-(3-(2-(1-(6-(2-((4-cyanophenethyl)carbamoyl) azetidin-1-yl)-2-(trifluoromethyl)pyrimidin-4-yl)piperidin-4-yl)ethyl)ureido)propanoic acid;

178) (S)—N-(4-cyanophenethyl)-1-(6-(4-(2-(3-(2-sulfamoylethyl)ureido) ethyl)piperidin-1-yl)-2-(trifluoromethyl)pyrimidin-4-yl)azetidine-2-carboxamide;

179) (S)-(3-(2-(1-(6-(2-((4-cyanophenethyl)carbamoyl)azetidin-1-yl)-2-(trifluoromethyl)pyrimidin-4-yl)piperidin-4-yl)ethyl)ureido)-methanesulfonic acid;

180) (S)-2-(3-(2-(1-(6-(2-((4-cyanophenethyl)carbamoyl) azetidin-1-yl)-2-(trifluoromethyl)pyrimidin-4-yl)piperidin-4-yl)ethyl)ureido)-ethanesulfonic acid;

181) (S)-tert-butyl (2-(3-(2-(1-(6-(2-((4-cyanophenethyl) carbamoyl)azetidin-1-yl)-2-(trifluoromethyl)pyrimidin-4-yl)-piperidin-4-yl)ethyl)ureido)ethyl)carbamate;

182) (S)-tert-butyl (2-(2-(3-(2-(1-(6-(2-((4-cyanophenethyl) carbamoyl)azetidin-1-yl)-2-(trifluoromethyl)pyrimidin-4-yl)piperidin-4-yl)ethyl)ureido)-ethoxy)ethyl)carbamate;

183) (S)-methyl-2-amino-6-(3-(2-(1-(6-((S)-2-((4-cyanophenethyl)carbamoyl) azetidin-1-yl)-2-(trifluoromethyl) pyrimidin-4-yl)piperidin-4-yl)ethyl)ureido)hexanoate;

184) (S)-1-(6-(4-(3-(piperidin-4-yl)propyl)piperidin-1-yl)-2-(trifluoromethyl) pyrimidin-4-yl)-N-(4-(trifluoromethyl)phenethyl)azetidine-2-carboxamide;

185) (R)-2-amino-3-oxo-3-((2-(1-(2-(trifluoromethyl)-6-((S)-2-((4-(trifluoromethyl)-phenethyl)carbamoyl)azetidin-1-yl)pyrimidin-4-yl)piperidin-4-yl)ethyl)amino)-propane-1-sulfonic acid;

186) (S)-2-oxo-2-((2-(1-(2-(trifluoromethyl)-6-(2-((4-(trifluoromethyl)phenethyl) carbamoyl)azetidin-1-yl)pyrimidin-4-yl)piperidin-4-yl)ethyl)amino)-ethanesulfonic acid;

187) (S)-2-oxo-2-(4-(3-(1-(2-(trifluoromethyl)-6-(2-((4-(trifluoromethyl)phenethyl) carbamoyl)azetidin-1-yl)pyrimidin-4-yl)piperidin-4-yl)propyl)piperidin-1-yl)ethanesulfonic acid;

188) (S)-2-(4-(3-(1-(2-(trifluoromethyl)-6-(2-((4-(trifluoromethyl)phenethyl) carbamoyl)-azetidin-1-yl)pyrimidin-4-yl)piperidin-4-yl)propyl)piperidin-1-yl)acetic acid;

189) (S)—N-(4-cyanophenethyl)-1-(6-(4-(4-((2-guanidinoethyl)amino)-4-oxobutyl)piperidin-1-yl)-2-(trifluoromethyl)pyrimidin-4-yl)azetidine-2-carboxamide;

190) (S)—N-(4-cyanophenethyl)-1-(6-(4-(4-((4-guanidinobutyl)amino)-4-oxobutyl)piperidin-1-yl)-2-(trifluoromethyl)pyrimidin-4-yl)azetidine-2-carboxamide;

191) (S)—N-(4-cyanophenethyl)-1-(6-(4-(4-((2-(2-guanidinoethoxy)-ethyl)amino)-4-oxobutyl)piperidin-1-yl)-2-(trifluoromethyl)pyrimidin-4-yl)azetidine-2-carboxamide;

192) (S)—N-(4-cyanophenethyl)-1-(6-(4-(2-guanidinoethyl)piperidin-1-yl)-2-(trifluoromethyl)pyrimidin-4-yl) azetidine-2-carboxamide;

193) (S)—N-(4-cyanophenethyl)-1-(6-(4-(2-(3-(2-guanidinoethyl)-ureido)ethyl)piperidin-1-yl)-2-(trifluoromethyl) pyrimidin-4-yl)azetidine-2-carboxamide;

194) (S)-1-(6-(4-(1-amino-1-imino-9-oxo-5-oxa-2,8,10-triazadodecan-12-yl)piperidin-1-yl)-2-(trifluoromethyl)pyrimidin-4-yl)-N-(4-cyanophenethyl)azetidine-2-carboxamide;

195) (S)-1-(6-(4-(3-(1-carbamimidoylpiperidin-4-yl)propyl) piperidin-1-yl)-2-(trifluoromethyl)pyrimidin-4-yl)-N-(4-(trifluoromethyl)phenethyl)-azetidine-2-carboxamide;

196) (S)-methyl-4-(N-(2-(2-(4-(1-(6-(2-((4-cyanophenethyl)carbamoyl)azetidin-1-yl)-2-(trifluoromethyl)pyrimidin-4-yl)piperidin-4-yl)butanamido)ethoxy)ethyl)-sulfamoyl)benzoate;

197) (S)-4-(N-(2-(2-(4-(1-(6-(2-((4-cyanophenethyl)carbamoyl)azetidin-1-yl)-2-(trifluoromethyl)pyrimidin-4-yl) piperidin-4-yl)butanamido) ethoxy) ethyl)sulfamoyl)-benzoic acid;

198) (S)—N-(4-cyanophenethyl)-1-(6-(4-(2-(3-(2-(2-(methylsulfonylamino)-ethoxy)ethyl)ureido)ethyl)piperidin-1-yl)-2-(trifluoromethyl)pyrimidin-4-yl)azetidine-2-carboxamide;

199) (S)-2-(3-(1-(2-(Trifluoromethyl)-6-((S)-2-((4-(trifluoromethyl)phenethyl) carbamoyl)azetidin-1-yl)pyrimidin-4-yl)piperidin-4-yl)propanamido) pentanedioic acid;

200) (R)-2-(4-(1-(2-(trifluoromethyl)-6-((S)-2-((4-(trifluoromethyl)-phenethyl) carbamoyl)azetidin-1-yl)pyrimidin-4-yl)piperidin-4-yl)butanamido) pentanedioic acid;

201) N-(4-cyanophenethyl)-1-(6-(4-(2-((3-hydroxypropyl) (methyl)amino)ethyl)-piperidin-1-yl)-2-(trifluoromethyl) pyrimidin-4-yl)azetidine-2-carboxamide;

202) N-(2-(1-(6-(2-((4-cyanophenethyl)carbamoyl)azetidin-1-yl)-2-(trifluoromethyl)pyrimidin-4-yl)piperidin-4-yl) ethyl)-3-hydroxy-N,N-dimethylpropan-1-aminium;

203) (S)-2-((2-((2-(1-(6-(2-((4-cyanophenethyl)carbamoyl) azetidin-1-yl)-2-(trifluoromethyl)pyrimidin-4-yl)piperidin-4-yl)ethyl)amino)-3,4-dioxocyclobut-1-en-1-yl) amino)ethanesulfonic acid;

204) (S)-((2-((2-(1-(6-(2-((4-cyanophenethyl)carbamoyl) azetidin-1-yl)-2-(trifluoromethyl)pyrimidin-4-yl)piperidin-4-yl)ethyl)amino)-3,4-dioxocyclobut-1-en-1-yl) amino)methanesulfonic acid;

205) (S)-2-((2-((2-(1-(6-(2-((4-cyanophenethyl)carbamoyl) azetidin-1-yl)-2-(trifluoromethyl)pyrimidin-4-yl)piperidin-4-yl)ethyl)amino)-3,4-dioxocyclobut-1-en-1-yl) (methyl)amino)ethanesulfonic acid;

206) (S)-tert-butyl 3-((2-((2-(1-(6-(2-((4-cyanophenethyl) carbamoyl)azetidin-1-yl)-2-(trifluoromethyl)pyrimidin-4-yl)piperidin-4-yl)ethyl)amino)-3,4-dioxocyclobut-1-en-1-yl)amino)propanoate;

207) (S)-3-((2-((2-(1-(6-(2-((4-cyanophenethyl)carbamoyl) azetidin-1-yl)-2-(trifluoromethyl)pyrimidin-4-yl)piperidin-4-yl)ethyl)amino)-3,4-dioxocyclobut-1-en-1-yl) amino)propanoic acid;

208) (S)-2-((2-((2-(1-(6-(2-((4-cyanophenethyl)carbamoyl) azetidin-1-yl)-2-(trifluoromethyl)pyrimidin-4-yl)piperidin-4-yl)ethyl)amino)-3,4-dioxocyclobut-1-en-1-yl) amino)acetic acid;

209) (R)—N-(4-cyanophenethyl)-1-(6-(4-(hydroxymethyl) piperidin-1-yl)-2-(trifluoromethyl)pyrimidin-4-yl)piperidine-3-carboxamide;

210) (R)—N-(4-cyanophenethyl)-1-(6-(4-(2-hydroxyethyl) piperidin-1-yl)-2-(trifluoromethyl)pyrimidin-4-yl)piperidine-3-carboxamide;

211) (R)—N-(4-cyanophenethyl)-1-(6-(4-(methoxymethyl) piperidin-1-yl)-2-(trifluoromethyl)pyrimidin-4-yl)piperidine-3-carboxamide;

212) (R)-1-(6-(4-(2-cyanoethyl)piperidin-1-yl)-2-(trifluoromethyl)pyrimidin-4-yl)-N-(4-cyanophenethyl)piperidine-3-carboxamide;

213) (R)-tert-butyl (2-(1-(6-(3-((4-cyanophenethyl)carbamoyl)piperidin-1-yl)-2-(trifluoromethyl)pyrimidin-4-yl)piperidin-4-yl)ethyl)carbamate;

214) (R)—N-(4-cyanophenethyl)-1-(6-(4-(2-hydroxyethyl) piperazin-1-yl)-2-(trifluoromethyl)pyrimidin-4-yl)piperidine-3-carboxamide;

215) (R)—N-(4-cyanophenethyl)-1-(6-(4-(2-(2-hydroxy ethoxy)ethyl)piperazin-1-yl)-2-(trifluoromethyl)pyrimidin-4-yl)piperidine-3-carboxamide;

216) (R)-2-(4-(6-(3-((4-cyanophenethyl)carbamoyl)piperidin-1-yl)-2-(trifluoromethyl)pyrimidin-4-yl)piperazin-1-yl)acetic acid;

217) (R)-1-(6-(4-(2-cyanoethyl)piperazin-1-yl)-2-(trifluoromethyl)pyrimidin-4-yl)-N-(4-cyanophenethyl)piperidine-3-carboxamide;

218) (R)—N-(4-cyanophenethyl)-1-(6-(4-(2-(dimethylamino)ethyl)piperazin-1-yl)-2-(trifluoromethyl)pyrimidin-4-yl)piperidine-3-carboxamide;

219) (R)-1-(6-(4-(2-(1H-imidazol-1-yl)ethyl)piperazin-1-yl)-2-(trifluoromethyl) pyrimidin-4-yl)-N-(4-cyanophenethyl)piperidine-3-carboxamide;

220) (R)-1-(6-(4-(benzo[d][1,3]dioxol-4-ylmethyl)piperazin-1-yl)-2-(trifluoromethyl)pyrimidin-4-yl)-N-(4-cyanophenethyl)piperidine-3-carboxamide;

221) (R)-1-(6-(4-(2-methoxyethyl)piperazin-1-yl)-2-(trifluoromethyl)pyrimidin-4-yl)-N-(4-(trifluoromethyl) phenethyl)piperidine-3-carboxamide;

222) (R)-1-(6-(4-(hydroxymethyl)piperidin-1-yl)-2-(trifluoromethyl)pyrimidin-4-yl)-N-(4-(trifluoromethyl)-phenethyl)piperidine-3-carboxamide;

223) (R)-4-(1-(2-(trifluoromethyl)-6-(3-((4-(trifluoromethyl)phenethyl)carbamoyl) piperidin-1-yl)pyrimidin-4-yl)piperidin-4-yl)butanoic acid;

224) (R)-1-(6-(4-hydroxymethyl)piperidin-1-yl)-2-(trifluoromethyl)pyrimidin-4-yl)-N-(2-methoxy-4-(trifluoromethyl)-phenethyl)piperidine-3-carboxamide;

225) (R)-1-(6-(4-(2-hydroxyethyl)piperidin-1-yl)-2-(trifluoromethyl)pyrimidin-4-yl)-N-(2-methoxy-4-(trifluoromethyl)-phenethyl)piperidine-3-carboxamide;

226) (R)—N-(4-cyanophenethyl)-1-(6-(4-(2-(dimethylamino)ethyl)piperazin-1-yl)-2-(trifluoromethyl)pyrimidin-4-yl)piperidine-3-carboxamide;

227) (R)-2-(4-(1-(2-(trifluoromethyl)-6-(3-((4-(trifluoromethyl)phenethyl) carbamoyl)-piperidin-1-yl)pyrimidin-4-yl)piperidin-4-yl)butanamido)ethanesulfonic acid;

228) (R)-1-(6-(4-(2-methoxyacetyl)piperazin-1-yl)-2-(trifluoromethyl)pyrimidin-4-yl)-N-(4-(trifluoromethyl) phenethyl)piperidine-3-carboxamide;

229) (R)-1-(6-(4-(2-(dimethylamino)-acetyl)piperazin-1-yl)-2-(trifluoromethyl)-pyrimidin-4-yl)-N-(4-(trifluoromethyl)phenethyl)-piperidine-3-carboxamide;

230) (R)-methyl 2-oxo-2-(4-(2-(trifluoromethyl)-6-(3-((4-(trifluoromethyl) phenethyl)-carbamoyl)piperidin-1-yl) pyrimidin-4-yl)piperazin-1-yl)acetate;

231) (R)-2-oxo-2-(4-(2-(trifluoromethyl)-6-(3-((4-(trifluoromethyl)phenethyl)-carbamoyl)piperidin-1-yl)pyrimidin-4-yl)piperazin-1-yl)acetic acid;

232) tert-butyl-((S)-3-hydroxy-1-oxo-1-(4-(2-(trifluoromethyl)-6-((R)-3-((4-(trifluoromethyl)phenethyl)carbamoyl)piperidin-1-yl)pyrimidin-4-yl)piperazin-1-yl)propan-2-yl)carbamate;

233) (R)-1-(6-(4-((S)-2-amino-3-hydroxypropanoyl)piperazin-1-yl)-2-(trifluoromethyl)pyrimidin-4-yl)-N-(4-(trifluoromethyl)phenethyl)piperidine-3-carboxamide;

234) (R)-ethyl 3-(4-(2-(trifluoromethyl)-6-(3-((4-(trifluoromethyl)phenethyl) carbamoyl)-piperidin-1-yl)pyrimidin-4-yl)piperazine-1-carboxamido)propanoate;

235) (R)-3-(4-(2-(trifluoromethyl)-6-(3-((4-(trifluoromethyl)phenethyl)carbamoyl)-piperidin-1-yl)pyrimidin-4-yl)piperazine-1-carboxamido)propanoic acid;

236) (R)-1-(6-(4-(2-aminoethyl)piperidin-1-yl)-2-(trifluoromethyl)pyrimidin-4-yl)-N-(4-cyanophenethyl)piperidine-3-carboxamide;

237) (R)-ethyl 3-(3-(2-(1-(6-(3-((4-cyanophenethyl)carbamoyl)piperidin-1-yl)-2-(trifluoromethyl)pyrimidin-4-yl)piperidin-4-yl)ethyl)ureido)propanoate;

238) (R)-3-(3-(2-(1-(6-(3-((4-cyanophenethyl)carbamoyl) piperidin-1-yl)-2-(trifluoromethyl)pyrimidin-4-yl)piperidin-4-yl)ethyl)ureido)propanoic acid;

239) (R)-1-(6-(4-(2-hydroxyacetyl)piperazin-1-yl)-2-(trifluoromethyl)pyrimidin-4-yl)-N-(4-(trifluoromethyl) phenethyl)piperidine-3-carboxamide; and 240) (R)-1-(6-(4-((2-guanidinoethyl)sulfonyl)piperazin-1-yl)-2-(trifluoromethyl)-pyrimidin-4-yl)-N-(4-(trifluoromethyl)phenethyl)piperidine-3-carboxamide, or a pharmaceutically acceptable salt thereof.

In one preferred embodiment, the present invention provides a compound selected from:

1) (S)-2-(3-(1-(6-(2-((4-cyanophenethyl)carbamoyl)pyrrolidin-1-yl)-2-(trifluoromethyl)pyrimidin-4-yl)piperidin-4-yl)propanamido)-ethanesulfonic acid;

2) (S)-3-(4-(1-(2-(trifluoromethyl)-6-(2-((4-(trifluoromethyl)phenethyl)-carbamoyl)pyrrolidin-1-yl)pyrimidin-4-yl)piperidin-4-yl)butanamido)propane-1-sulfonic acid;

3) (S)-2-(4-(1-(6-(2-((4-cyanophenethyl)carbamoyl)pyrrolidin-1-yl)-2-(trifluoromethyl)pyrimidin-4-yl)-piperidin-4-yl)butanamido)ethanesulfonic acid;

4) (S)-3-(4-(1-(6-(2-((4-cyanophenethyl)carbamoyl)pyrrolidin-1-yl)-2-(trifluoromethyl)pyrimidin-4-yl)-piperidin-4-yl)butanamido)propane-1-sulfonic acid;

5) (S)-(4-(1-(6-(2-((4-cyanophenethyl)carbamoyl)pyrrolidin-1-yl)-2-(trifluoromethyl)pyrimidin-4-yl)piperidin-4-yl)butanamido)-methanesulfonic acid;

6) (S)-5-guanidino-2-(4-(1-(2-(trifluoromethyl)-6-((S)-2-((4-(trifluoromethyl) phenethyl)carbamoyl)pyrrolidin-1-yl)pyrimidin-4-yl)piperidin-4-yl)butanamido)pentanoic acid;

7) (S)-2-(4-(1-(6-((S)-2-((4-cyanophenethyl)carbamoyl)pyrrolidin-1-yl)-2-(trifluoromethyl)pyrimidin-4-yl)piperidin-4-yl)butanamido)-pentanedioic acid;

8) (S)-2-(3-(2-(1-(6-(2-((4-cyanophenethyl)carbamoyl)pyrrolidin-1-yl)-2-(trifluoromethyl)pyrimidin-4-yl)piperidin-4-yl)ethyl)ureido)ethanesulfonic acid;

9) (S)—N-(4-cyanophenethyl)-1-(6-(4-(2-(3-(2-sulfamoylethyl)ureido)-ethyl)piperidin-1-yl)-2-(trifluoromethyl) pyrimidin-4-yl)pyrrolidine-2-carboxamide;

10) (S)-3-(3-(2-(1-(6-(2-((4-cyanophenethyl)carbamoyl)pyrrolidin-1-yl)-2-(trifluoromethyl)pyrimidin-4-yl)piperidin-4-yl)ethyl)ureido)-propanoic acid;

11) (S)—N-(2-(1-(6-(2-((4-cyanophenethyl)-carbamoyl)pyrrolidin-1-yl)-2-(trifluoromethyl)pyrimidin-4-yl)piperidin-4-yl)ethyl)-2-(2-aminoethylsulfonamido)acetate methyl ester;

12) (S)-2-(2-((2-(4-(1-(6-(2-((4-cyanophenethyl)carbamoyl)pyrrolidin-1-yl)-2-(trifluoromethyl)pyrimidin-4-yl)piperidin-4-yl)butanamido)ethyl)amino)-pyrimidine-5-carboxamido)ethanesulfonic acid;

13) (S)-2-(2-(4-(1-(2-(trifluoromethyl)-6-(2-((4-(trifluoromethyl)phenethyl)-carbamoyl)-pyrrolidin-1-yl)pyrimidin-4-yl)piperidin-4-yl)butanamido)ethyl-sulfonamido)acetic acid;

14) (S)-2-(2-(4-(1-(6-(2-((4-cyanophenethyl)carbamoyl)pyrrolidin-1-yl)-2-(trifluoromethyl)pyrimidin-4-yl)piperidin-4-yl)butanamido)-ethylsulfonamido)acetic acid;

15) (S)-2-((2-(N-(2-(1-(6-(2-((4-cyanophenethyl)carbamoyl)pyrrolidin-1-yl)-2-(trifluoromethyl)pyrimidin-4-yl)piperidin-4-yl)ethyl)sulfamoyl)ethyl)-amino)-pyrimidine-5-carboxylic acid;

16) (S)-(3-(3-(1-(6-(2-((4-cyanophenethyl)carbamoyl)pyrrolidin-1-yl)-2-(trifluoromethyl)pyrimidin-4-yl)piperidin-4-yl)propyl)ureido)-methanesulfonic acid;

17) (R)-2-amino-3-((2-(N-(2-(1-(6-((S)-2-((4-cyanophenethyl)carbamoyl)-pyrrolidin-1-yl)-2-(trifluoromethyl)-pyrimidin-4-yl)piperidin-4-yl)ethyl)sulfamoyl)ethyl)amino)-3-oxopropane-1-sulfonic acid;

18) (S)—N-(4-cyanophenethyl)-1-(6-(4-(2-(2-guanidino-ethylsulfonamido)ethyl)-piperidin-1-yl)-2-(trifluoromethyl)pyrimidin-4-yl)pyrrolidine-2-carboxamide;

19) (S)-2-guanidino-5-oxo-5-((3-(1-(2-(trifluoromethyl)-6-((S)-2-((4-(trifluoromethyl)phenethyl)carbamoyl)pyrrolidin-1-yl)pyrimidin-4-yl)piperidin-4-yl)propyl)amino)pentanoic acid;

20) (S)-2-(4-(1-(2-(2-((4-cyanophenethyl)carbamoyl)pyrrolidin-1-yl)-6-(trifluoromethyl)pyridin-4-yl)piperidin-4-yl)butanamido)ethanesulfonic acid;

21) (S)-(3-(4-(2-(2-((4-cyanophenethyl)carbamoyl)pyrrolidin-1-yl)-6-(trifluoromethyl)pyridin-4-yl)phenyl)propanamido)methanesulfonic acid;

22) (S)-3-(4-(1-(6-(2-((4-cyanophenethyl)carbamoyl)azetidin-1-yl)-2-(trifluoromethyl)pyrimidin-4-yl)piperidin-4-yl)butanamido)propane-1-sulfonic acid;

23) (S)-2-(4-(1-(6-(2-((4-cyanophenethyl)carbamoyl)azetidin-1-yl)-2-(trifluoromethyl)pyrimidin-4-yl)piperidin-4-yl)butanamido)ethanesulfonic acid;

24) (S)-(4-(1-(6-(2-((4-cyanophenethyl)carbamoyl)azetidin-1-yl)-2-(trifluoromethyl)pyrimidin-4-yl)piperidin-4-yl)butanamido)methanesulfonic acid;

25) (S)-3-(3-(2-(1-(6-(2-((4-cyanophenethyl)carbamoyl)azetidin-1-yl)-2-(trifluoromethyl)pyrimidin-4-yl)piperidin-4-yl)ethyl)ureido)propanoic acid;

26) (S)—N-(4-cyanophenethyl)-1-(6-(4-(2-(3-(2-sulfamoyl-ethyl)ureido)ethyl)-piperidin-1-yl)-2-(trifluoromethyl)pyrimidin-4-yl)azetidine-2-carboxamide;

27) (S)-2-(3-(2-(1-(6-(2-((4-cyanophenethyl)carbamoyl)azetidin-1-yl)-2-(trifluoromethyl)pyrimidin-4-yl)piperidin-4-yl)ethyl)ureido)-ethanesulfonic acid;

28) (R)-2-amino-3-oxo-3-((2-(1-(2-(trifluoromethyl)-6-((S)-2-((4-(trifluoromethyl)-phenethyl)carbamoyl)azetidin-1-yl)pyrimidin-4-yl)piperidin-4-yl)ethyl)amino)-propane-1-sulfonic acid;

29) (S)—N-(4-cyanophenethyl)-1-(6-(4-(4-((4-guanidinobutyl)amino)-4-oxobutyl)piperidin-1-yl)-2-(trifluoromethyl)pyrimidin-4-yl)azetidine-2-carboxamide;

30) (S)—N-(4-cyanophenethyl)-1-(6-(4-(2-guanidino ethyl)piperidin-1-yl)-2-(trifluoromethyl)pyrimidin-4-yl)azetidine-2-carboxamide; and 31) (S)-2-(3-(1-(2-(Trifluoromethyl)-6-((S)-2-((4-(trifluoromethyl)phenethyl)-carbamoyl)azetidin-1-yl)pyrimidin-4-yl)piperidin-4-yl)propanamido)-pentanedioic acid, or pharmaceutically acceptable salts thereof.

In another aspect, the present invention provides a compound of formula (II):

(II)

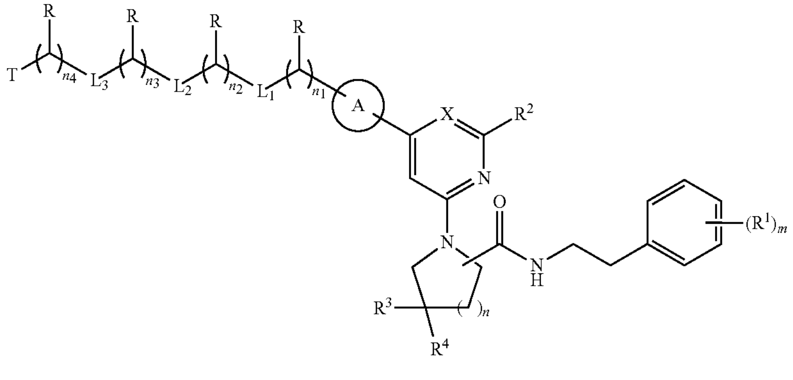

or pharmaceutically acceptable salts thereof, wherein:

each $R^1$ is independently CN, $C_{1-6}$alkyl or $C_{1-6}$alkoxy, wherein alkyl group is optionally further substituted with 1-4 halogen;

m is 0, 1, 2 or 3;

$R^2$ is $C_{1-6}$alkyl or H, wherein alkyl group is optionally further substituted with 1-4 halogen;

X is CH or N;

A is

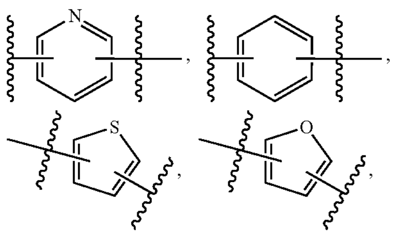

-continued

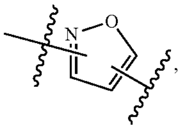, 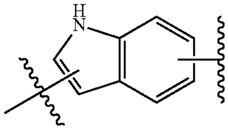, or

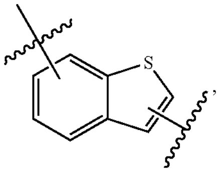, wherein each ring is optionally further substituted with $C_{1-6}$alkyl, $C_{1-6}$alkoxyl or halogen;

$L_1$, $L_2$ and $L_3$ are each independently absent,

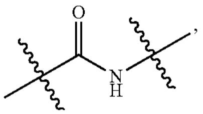, 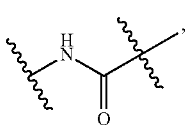,

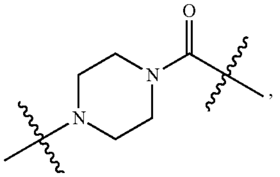,

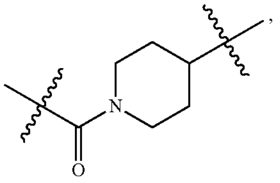,

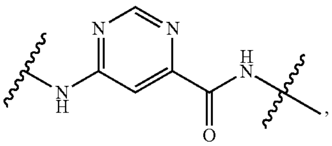,

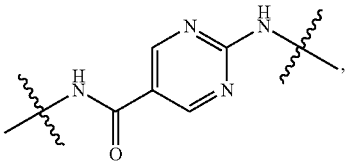,

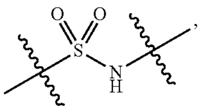, 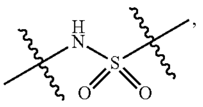,

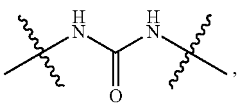,

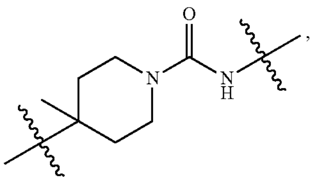,

-continued

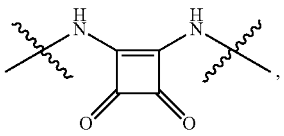, 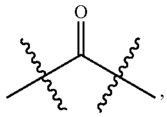,

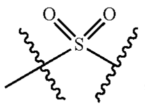, 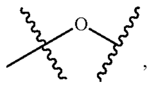, 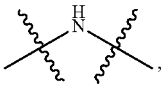,

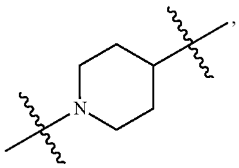, or

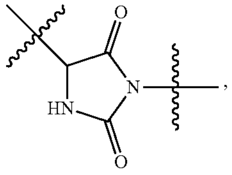, wherein N is optionally further mono- or di-substituted with $C_{1-3}$alkyl;

$n_1$, $n_2$, $n_3$ and $n_4$ are each independently 0, 1, 2, 3, 4 or 5, and when $L_1$ is absent, $n_2$ is 0, when $L_2$ is absent, $n_3$ is 0, when $L_3$ is absent, $n_4$ is 0;

each R is independently H, OH, $NH_2$, COOH, $C_{1-6}$alkylCOOH, $COOC_{1-6}$alkyl, $C_{1-6}$alkylOH or $C_{1-6}$alkyl-NHC(NH)$NH_2$;

T is

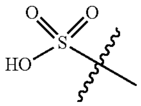, 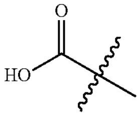, 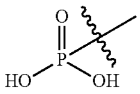,

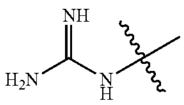, 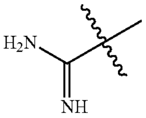,

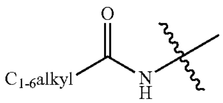, 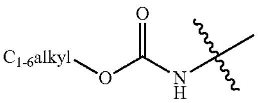,

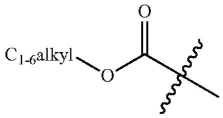, 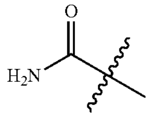,

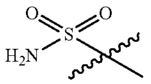, 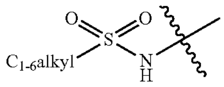,

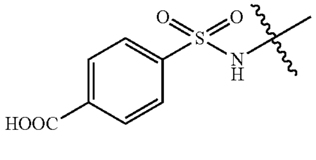,

-continued

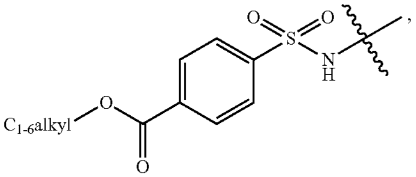

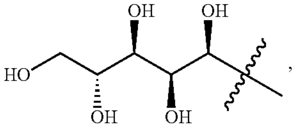 , 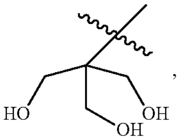 ,

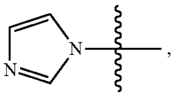 , 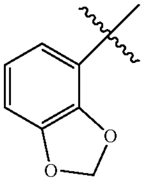 , 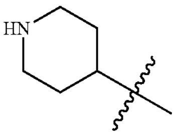 ,

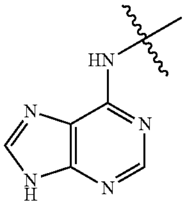 , 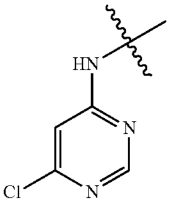 ,

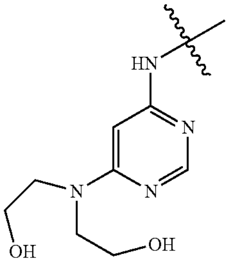 , 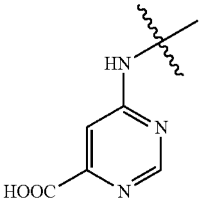 ,

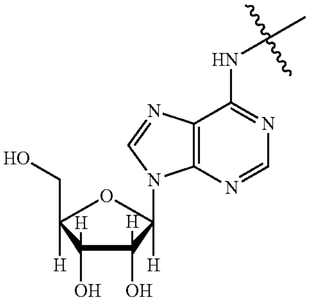 , 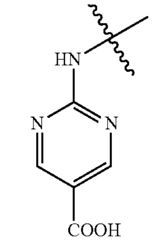 ,

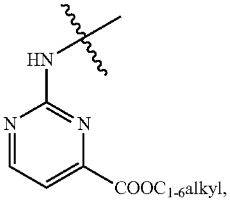 , 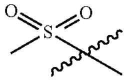

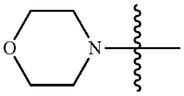 , 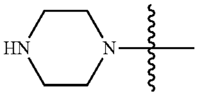 ,

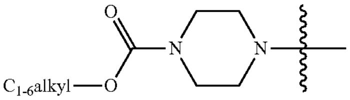 ,

-continued

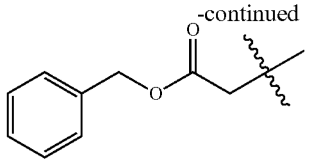 ,

CN, OH, $NH_2$, $CH_3$, $CF_3$, H or halogen, wherein N is optionally further mono-, di-, or tri-substituted with $C_{1-3}$alkyl;

$R^3$ and $R^4$ are each independently H, OH, halogen or $NH_2$; and n is 0, 1 or 2.

In one embodiment, $L_3$ is absent, and $L_1$ and $L_2$ are each independently

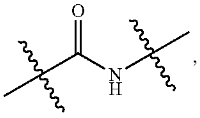 , 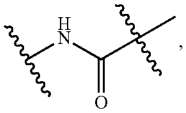 ,

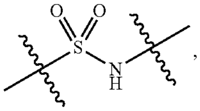 , 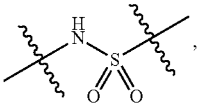 ,

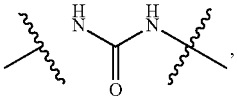 , 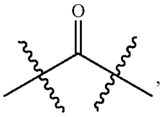 ,

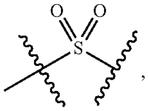 , 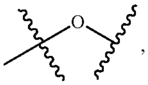 , or 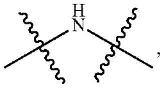 , wherein N is optionally further mono- or di-substituted with $C_{1-3}$alkyl.

In one preferred embodiment, when $L_3$ is absent, $L_1$ and $L_2$ are each independently

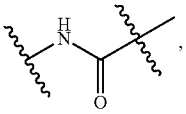 , 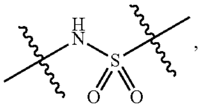 ,

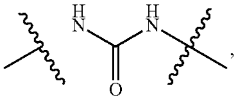 , 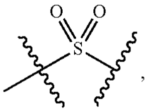 , or

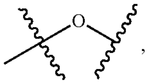 , wherein N is optionally further substituted with $C_{1-3}$alkyl.

In one embodiment, $L_2$ and $L_3$ are absent, and $L_1$ is

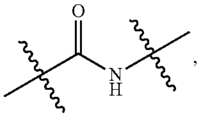 , 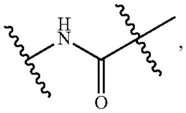 ,

-continued

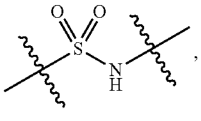, 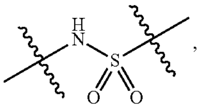,

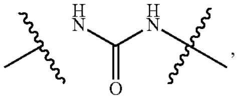, 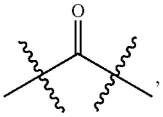,

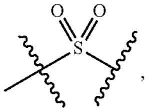, 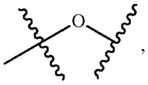, or 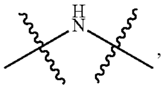, wherein N is optionally further substituted with $C_{1-3}$alkyl.

In one preferred embodiment, when $L_2$ and $L_3$ are absent, $L_1$ is

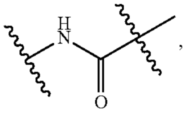, 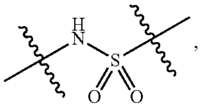,

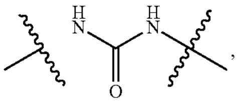, 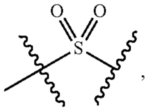, or

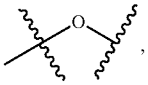, wherein N is optionally further substituted with $C_{1-3}$alkyl.

In one embodiment, $n_1$, $n_2$, $n_3$ and $n_4$ are each independently 0, 1, 2, 3 or 4.

In one preferred embodiment, $n_1$, $n_2$, $n_3$ and $n_4$ are each independently 0, 1, 2 or 3.

In one embodiment, each R is independently H, $NH_2$, COOH or $C_{1-6}$alkylNHC(NH)$NH_2$.

In one preferred embodiment, each R is independently H, $NH_2$ or COOH.

In one embodiment, T is

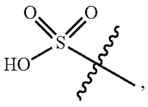, 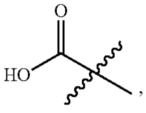,

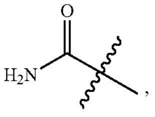, 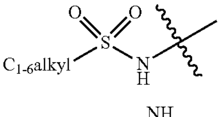,

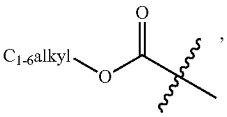, 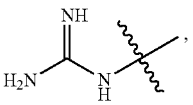,

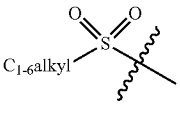, 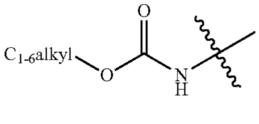,

-continued

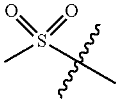, 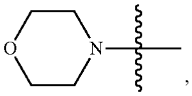,

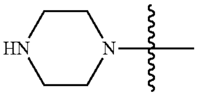,

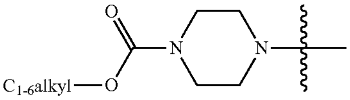,

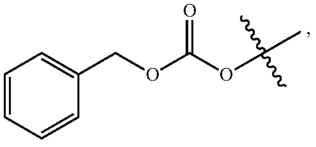,

CN, OH, $NH_2$, $CH_3$, $CF_3$, H or halogen, wherein N is optionally further mono-, di-, or tri-substituted with $C_{1-3}$alkyl.

In one embodiment, n is 0. In one preferred embodiment, phenethylcarboxamide is substituted in the two position of N in the azetidinyl ring. In one preferred embodiment, phenethylcarboxamide is substituted in the two position of N in the azetidinyl ring with S configuration.

In one embodiment, n is 1. In one preferred embodiment, phenethylcarboxamide is substituted in the two position of N in the pyrrolidinyl ring. In one preferred embodiment, phenethylcarboxamide is substituted in the two position of N in the pyrrolidinyl ring with S configuration.

In one embodiment, n is 2. In one preferred embodiment, phenethylcarboxamide is substituted in the three position of N in the piperidinyl ring. In one preferred embodiment, phenethylcarboxamide is substituted in the three position of N in the piperidinyl ring with R configuration.

In one embodiment, A is

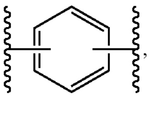, or 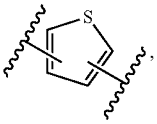, wherein each ring is optionally further substituted with $C_{1-4}$alkyl, $C_{1-4}$alkoxyl or halogen.

In one embodiment, X is CH. In one embodiment, X is N.

In one embodiment, $R^2$ is $C_{1-6}$alkyl, wherein alkyl group is optionally further substituted with 1-4 halogen. In one preferred embodiment, $R^2$ is $CF_3$.

In one embodiment, $R^1$ is each independently CN or $C_{1-6}$alkyl, wherein alkyl group is optionally further substituted with 1-4 halogen.

In one preferred embodiment, $R^1$ is CN. In one preferred embodiment, $R^1$ is $CF_3$. In one preferred embodiment, the CN or $CF_3$ substitution occurs on the para position of phenethyl.

In one embodiment, $R^1$ is $C_{1-2}$alkoxy. In one preferred embodiment, $R^1$ is $OCH_3$.

In one embodiment, m is 1 or 2. In one preferred embodiment, m is 1.

In one embodiment, $R^3$ and $R^4$ are each independently H, OH, F or $NH_2$. In one preferred embodiment, $R^3$ and $R^4$ are each independently H or OH. In one preferred embodiment, $R^3$ and $R^4$ are each independently H.

In one preferred embodiment, the present invention provides a compound selected from:

1) (S)—N-(4-cyanophenethyl)-1-(6-(5-hexylthiophene-2-yl)-2-(trifluoromethyl) pyrimidin-4-yl)pyrrolidine-2-carboxamide;
2) (S)-1-(6-(pyridin-4-yl)-2-(trifluoromethyl)pyrimidin-4-yl)-N-(4-(trifluoromethyl)phenethyl)pyrrolidine-2-carboxamide;
3) (S)—N-(4-cyanophenethyl)-1-(6-(pyridin-4-yl)-2-(trifluoromethyl)pyrimidin-4-yl)pyrrolidine-2-carboxamide;
4) (S)—N-(4-cyanophenethyl)-1-(6-(pyridin-3-yl)-2-(trifluoromethyl)pyrimidin-4-yl)pyrrolidine-2-carboxamide;
5) (S)—N-(4-cyanophenethyl)-1-(6-(p-tolyl)-2-(trifluoromethyl)pyrimidin-4-yl)pyrrolidine-2-carboxamide;
6) (S)—N-(4-cyanophenethyl)-1-(6-phenyl-2-(trifluoromethyl)pyrimidin-4-yl)pyrrolidine-2-carboxamide;
7) (S)—N-(4-cyanophenethyl)-1-(6-(4-cyanophenyl)-2-(trifluoromethyl)pyrimidin-4-yl)pyrrolidine-2-carboxamide;
8) (S)—N-(4-cyanophenethyl)-1-(6-(4-(hydroxymethyl) phenyl)-2-(trifluoromethyl) pyrimidin-4-yl)pyrrolidine-2-carboxamide;
9) (S)—N-(4-cyanophenethyl)-1-(2-(trifluoromethyl)-6-(4-(trifluoromethyl) phenyl)pyrimidin-4-yl)pyrrolidine-2-carboxamide;
10) (S)—N-(4-cyanophenethyl)-1-(6-(4-methoxyphenyl)-2-(trifluoromethyl) pyrimidin-4-yl)pyrrolidine-2-carboxamide;
11) (S)—N-(4-cyanophenethyl)-1-(6-(3,4-dimethoxyphenyl)-2-(trifluoromethyl) pyrimidin-4-yl)pyrrolidine-2-carboxamide;
12) (S)—N-(4-cyanophenethyl)-1-(6-(4-(trifluoromethoxy) phenyl)-2-(trifluoromethyl)pyrimidin-4-yl)pyrrolidine-2-carboxamide;
13) (S)—N-(4-cyanophenethyl)-1-(6-(4-ethoxyphenyl)-2-(trifluoromethyl)pyrimidin-4-yl)pyrrolidine-2-carboxamide;
14) (S)—N-(4-cyanophenethyl)-1-(6-(4-(methylsulfonyl) phenyl)-2-(trifluoromethyl) pyrimidin-4-yl)pyrrolidine-2-carboxamide;
15) (S)—N-(4-cyanophenethyl)-1-(6-(3-(methylsulfonamido)phenyl)-2-(trifluoromethyl)pyrimidin-4-yl)pyrrolidine-2-carboxamide;
16) (S)—N-(4-cyanophenethyl)-1-(6-(4-(morpholinosulfonyl)phenyl)-2-(trifluoromethyl)pyrimidin-4-yl)pyrrolidine-2-carboxamide;
17) (S)—N-(4-cyanophenethyl)-1-(6-(3-fluoropyridin-4-yl)-2-(trifluoromethyl) pyrimidin-4-yl)pyrrolidine-2-carboxamide;
18) (S)—N-(4-cyanophenethyl)-1-(6-(3,5-dimethylisoxazol-4-yl)-2-(trifluoromethyl) pyrimidin-4-yl)pyrrolidine-2-carboxamide;
19) (S)-1-(6-(1H-indol-5-yl)-2-(trifluoromethyl)pyrimidin-4-yl)-N-(4-cyanophenethyl)pyrrolidine-2-carboxamide;
20) (S)—N-(4-cyanophenethyl)-1-(6-(thiophen-3-yl)-2-(trifluoromethyl)pyrimidin-4-yl)pyrrolidine-2-carboxamide;
21) (S)—N-(4-cyanophenethyl)-1-(6-(3-methoxypyridin-4-yl)-2-(trifluoromethyl) pyrimidin-4-yl)pyrrolidine-2-carboxamide;
22) (S)—N-(4-cyanophenethyl)-1-(6-(2-methoxypyridin-4-yl)-2-(trifluoromethyl) pyrimidin-4-yl)pyrrolidine-2-carboxamide;
23) (S)-1-(6-(5-chloro-2-methoxy-pyridin-4-yl)-2-(trifluoromethyl)pyrimidin-4-yl)-N-(4-cyanophenethyl)pyrrolidine-2-carboxamide;
24) (S)—N-(4-cyanophenethyl)-1-(6-(pyridin-2-yl)-2-(trifluoromethyl)pyrimidin-4-yl)pyrrolidine-2-carboxamide;
25) (S)-1-(6-(pyridin-2-yl)-2-(trifluoromethyl)pyrimidin-4-yl)-N-(4-(trifluoromethyl)phenethyl)-pyrrolidine-2-carboxamide;
26) (S)—N-(4-cyanophenethyl)-1-(6-(furan-3-yl)-2-(trifluoromethyl)pyrimidin-4-yl)pyrrolidine-2-carboxamide;
27) (S)—N-(4-cyanophenethyl)-1-(6-(thiophen-2-yl)-2-(trifluoromethyl)pyrimidin-4-yl)pyrrolidine-2-carboxamide;
28) (S)—N-(4-cyanophenethyl)-1-(6-(5-methylfuran-2-yl)-2-(trifluoromethyl) pyrimidin-4-yl)pyrrolidine-2-carboxamide;
29) (S)—N-(4-cyanophenethyl)-1-(6-(furan-2-yl)-2-(trifluoromethyl)pyrimidin-4-yl)pyrrolidine-2-carboxamide;
30) (S)—N-(4-cyanophenethyl)-1-(6-(5-(morpholinomethyl)thiophen-2-yl)-2-(trifluoromethyl)pyrimidin-4-yl) pyrrolidine-2-carboxamide;
31) (S)—N-(4-cyanophenethyl)-1-(6-(1-methyl-1H-indol-5-yl)-2-(trifluoromethyl) pyrimidin-4-yl)pyrrolidine-2-carboxamide;
32) (S)—N-(4-cyanophenethyl)-1-(6-(5-methylthiophen-2-yl)-2-(trifluoromethyl) pyrimidin-4-yl)pyrrolidine-2-carboxamide;
33) (S)—N-(4-cyanophenethyl)-1-(6-(4-methylthiophen-2-yl)-2-(trifluoromethyl) pyrimidin-4-yl)pyrrolidine-2-carboxamide;
34) (S)—N-(4-cyanophenethyl)-1-(6-(3-methylthiophen-2-yl)-2-(trifluoromethyl) pyrimidin-4-yl)pyrrolidine-2-carboxamide;
35) (S)-1-(6-(benzo[b]thiophen-2-yl)-2-(trifluoromethyl) pyrimidin-4-yl)-N-(4-cyanophenethyl)pyrrolidine-2-carboxamide;
36) (S)-benzyl 4-(6-(2-((4-cyanophenethyl)carbamoyl)pyrrolidin-1-yl)-2-(trifluoromethyl)pyrimidin-4-yl)phenethylcarbamate;
37) (S)-tert-butyl 4-(6-(2-((4-cyanophenethyl)carbamoyl) pyrrolidin-1-yl)-2-(trifluoromethyl)pyrimidin-4-yl)benzylcarbamate;
38) (S)-tert-butyl 4-(4-(6-(2-((4-cyanophenethyl)carbamoyl)pyrrolidin-1-yl)-2-(trifluoromethyl)pyrimidin-4-yl) benzyl)piperazine-1-carboxylate;
39) (S)-tert-butyl (4-(6-(2-((4-cyanophenethyl)carbamoyl) pyrrolidin-1-yl)-2-(trifluoromethyl)pyrimidin-4-yl)phenyl)(methyl)carbamate;
40) (S)-4-(6-(2-((4-cyanophenethyl)carbamoyl)pyrrolidin-1-yl)-2-(trifluoromethyl)pyrimidin-4-yl)thiophene-2-carboxylic acid;
41) (S)—N-(4-cyanophenethyl)-1-(6-(5-(methylcarbamoyl) thiophen-3-yl)-2-(trifluoromethyl)pyrimidin-4-yl)pyrrolidine-2-carboxamide;
42) (S)-methyl 5-(6-(2-((4-cyanophenethyl)carbamoyl)pyrrolidin-1-yl)-2-(trifluoromethyl)pyrimidin-4-yl)thiophene-2-carboxylate;
43) (S)-5-(6-(2-((4-cyanophenethyl)carbamoyl)pyrrolidin-1-yl)-2-(trifluoromethyl)pyrimidin-4-yl)thiophene-2-carboxylic acid;
44) (S)—N-(4-cyanophenethyl)-1-(6-(5-(hydroxymethyl) thiophen-3-yl)-2-(trifluoromethyl)pyrimidin-4-yl)pyrrolidine-2-carboxamide;
45) (S)—N-(4-cyanophenethyl)-1-(6-(5-(hydroxymethyl) thiophen-2-yl)-2-(trifluoromethyl)pyrimidin-4-yl)pyrrolidine-2-carboxamide;
46) (S)-1-(6-(4-(2-aminoethyl)phenyl)-2-(trifluoromethyl) pyrimidin-4-yl)-N-(4-cyanophenethyl)pyrrolidine-2-carboxamide;

47) (S)-1-(6-(4-(aminomethyl)phenyl)-2-(trifluoromethyl) pyrimidin-4-yl)-N-(4-cyanophenethyl)pyrrolidine-2-carboxamide;

48) (S)—N-(4-cyanophenethyl)-1-(6-(4-(methylamino)phenyl)-2-(trifluoromethyl) pyrimidin-4-yl)pyrrolidine-2-carboxamide;

49) (S)—N-(4-cyanophenethyl)-1-(6-(4-(piperazin-1-ylmethyl)phenyl)-2-(trifluoromethyl)pyrimidin-4-yl)pyrrolidine-2-carboxamide;

50) (S)-3-(4-(6-(2-((4-cyanophenethyl)carbamoyl)pyrrolidin-1-yl)-2-(trifluoromethyl)pyrimidin-4-yl)phenyl)propanoic acid;

51) (S)-2-(3-(4-(6-(2-((4-cyanophenethyl)carbamoyl)pyrrolidin-1-yl)-2-(trifluoromethyl)pyrimidin-4-yl)phenyl)propanamido)ethanesulfonic acid;

52) (S)-2-(3-(3-(6-(2-((4-cyanophenethyl)-carbamoyl)pyrrolidin-1-yl)-2-(trifluoromethyl)pyrimidin-4-yl)phenyl)-propanamido)ethanesulfonic acid;

53) (S)-2-(3-(4-(6-(2-((4-cyanophenethyl)carbamoyl)pyrrolidin-1-yl)-2-(trifluoromethyl)pyrimidin-4-yl)benzyl) ureido)ethanesulfonic acid;

54) (S)-(3-(4-(6-(2-((4-cyanophenethyl)carbamoyl)pyrrolidin-1-yl)-2-(trifluoromethyl)pyrimidin-4-yl)benzyl) ureido)methanesulfonic acid;

55) (S)-3-(3-(4-(6-(2-((4-cyanophenethyl)carbamoyl)pyrrolidin-1-yl)-2-(trifluoromethyl)pyrimidin-4-yl)benzyl) ureido)propane-1-sulfonic acid;

56) (S)-2-(3-(4-(6-(2-((4-cyanophenethyl)carbamoyl)pyrrolidin-1-yl)-2-(trifluoromethyl)pyrimidin-4-yl)phenethyl) ureido)ethanesulfonic acid;

57) (S)-3-(3-(4-(6-(2-((4-cyanophenethyl)carbamoyl)pyrrolidin-1-yl)-2-(trifluoromethyl)pyrimidin-4-yl)phenethyl) ureido)propane-1-sulfonic acid;

58) (S)-3-(3-(4-(6-(2-((4-cyanophenethyl)carbamoyl)pyrrolidin-1-yl)-2-(trifluoromethyl)pyrimidin-4-yl)phenyl)-3-methylureido)propanoic acid;

59) (S)—N-(4-cyanophenethyl)-1-(4-(4-(hydroxymethyl) phenyl)-6-(trifluoromethyl)pyridin-2-yl)pyrrolidine-2-carboxamide;

60) (S)-3-(4-(2-(2-((4-cyanophenethyl)carbamoyl)pyrrolidin-1-yl)-6-(trifluoromethyl)pyridin-4-yl)phenyl)propanoic acid;

61) (S)-(3-(4-(2-(2-((4-cyanophenethyl)carbamoyl)pyrrolidin-1-yl)-6-(trifluoromethyl)pyridin-4-yl)phenyl)propanamido)methanesulfonic acid;

62) (S)-2-(3-(4-(2-((S)-2-((4-cyanophenethyl)carbamoyl) pyrrolidin-1-yl)-6-(trifluoromethyl)pyridin-4-yl)phenyl) propanamido)-5-guanidinopentanoic acid;

63) (S)-2-((4-(2-(2-((4-cyanophenethyl)carbamoyl)pyrrolidin-1-yl)-6-(trifluoromethyl)pyridin-4-yl)benzyl)oxy) acetic acid;

64) (S)-(2-((4-(2-(2-((4-cyanophenethyl)carbamoyl)pyrrolidin-1-yl)-6-(trifluoromethyl)pyridin-4-yl)benzyl)oxy)acetamido)methanesulfonic acid;

65) (S)—N-(4-cyanophenethyl)-1-(6-pyridin-4-yl)-2-(trifluoromethyl)pyrimidin-4-yl)azetidine-2-carboxamide;

66) (S)—N-(4-cyanophenethyl)-1-(6-(4-(hydroxymethyl) phenyl)-2-(trifluoromethyl) pyrimidin-4-yl)azetidine-2-carboxamide;

67) (S)—N-(4-cyanophenethyl)-1-(6-(pyridin-3-yl)-2-(trifluoromethyl)pyrimidin-4-yl)azetidine-2-carboxamide;

68) (S)—N-(4-cyanophenethyl)-1-(6-(pyridin-2-yl)-2-(trifluoromethyl)pyrimidin-4-yl)azetidine-2-carboxamide; and 69) N-(4-cyanophenethyl)-1-(6-(pyridin-4-yl)-2-(trifluoromethyl)pyrimidin-4-yl)azetidine-2-carboxamide, or a pharmaceutically acceptable salt thereof.

The compounds of the present invention may contain an asymmetric center and may exist as enantiomers. Where the compounds of the present invention possess two or more asymmetric centers, they may additionally exist as diastereomers. When bonds to the chiral carbon are depicted as straight lines in the formulas of the present invention, it is understood that both the (R) and (S) configurations of the chiral carbon, and hence both enantiomers and mixtures thereof, are embraced. The present invention includes all such possible stereoisomers as substantially pure resolved enantiomers, racemic mixtures, as well as mixtures of diastereomers thereof. Except where otherwise specified, the formulas encompassing compounds of the present invention are shown without a definitive stereochemistry at certain positions. The present invention may be understood to include all stereoisomers of compounds and pharmaceutically acceptable salts thereof. It is generally preferable to administer compounds of the present invention as enantiomerically pure formulations.

Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the present invention may be obtained by stereospecific synthesis using optically pure starting materials or reagents of known configuration.

The compounds of the present invention include tautomers of such compounds. Tautomers are defined as compounds that undergo rapid proton shifts from one atom of the compound to another atom of the compound. Some of the compounds described herein may exist as tautomers with different points of attachment of hydrogen. Exemplary tautomer includes a ketone and its enol form known as keto-enol tautomers.

Accordingly, the compounds within the generic structural formulas, embodiments and specific compounds described and claimed herein are intended to encompass salts, all possible stereoisomers and tautomers.

The compounds of the present invention include all suitable isotopic variations of such compounds. An isotopic variation of a compound is defined as one in which at least one atom is replaced by an atom having the same atomic number but an atomic mass different from the atomic mass usually found in nature. Exemplary isotope includes isotope of hydrogen, carbon, nitrogen and oxygen such as $^{2}H$, $^{3}H$, $^{11}C$, $^{13}C$, $^{14}C$, $^{15}N$, $^{17}O$, $^{18}O$, $^{35}S$, $^{18}F$, $^{36}Cl$, $^{123}I$ and the like. Certain isotopic variations of the compounds are useful in drug or substrate tissue distribution studies. Others may afford certain therapeutic advantages resulting from greater metabolic stability, such as increased or decreased in vivo half-life or reduced dosage requirements. Isotopic variations of the compounds of the present invention provided herein are prepared by conventional procedures using appropriate isotopic variations of suitable reagents.

In one aspect, the present invention provides a pharmaceutical composition containing a TGR5 compound described herein, method of preparation and use of same in treating metabolic diseases such as type-2 diabetic mellitus and obesity in a mammal, preferably a human.

In one embodiment, the present invention provides a pharmaceutical composition containing a compound of formula (I) for use in therapy in humans in needs thereof for diabetic diseases. In another embodiment, the present invention provides a pharmaceutical composition containing a compound of formula (II) for use in therapy for diabetic diseases.

The present composition encompasses a TGR5 compound in the form of a vehicle such as a pharmaceutically acceptable carrier. The pharmaceutical acceptable carrier comprises agents that aid optimization of solubility, absorption, flavor or texture of the composition. Pharmaceutically acceptable carriers are commonly known to a skilled artisan and include a variety of organic or inorganic carriers including starch, cellulose, gelatin, talc, glycol, polyol, ester, agar, buffering agents, alginic acid and the like that are employed in pharmaceutical formulations. Such carriers include, for solid preparations, diluents, lubricants, binders, and disintegrants, and for liquid preparations, solvents, solubilizing agents, suspending agents, isotonic agents, buffer agents, soothing agents and the like.

Suitable exemplary diluents include lactose, sucrose, D-mannitol, starch, crystalline cellulose, light silica anhydrate and the like. Suitable exemplary lubricants include magnesium stearate, calcium stearate, talc, colloidal silica and the like. Suitable exemplary binders include crystalline cellulose, sucrose, D-mannitol, dextrin, hydroxypropylcellulose, hydroxypropylmethylcellulose, polyvinylpyrrolidone and the like. Suitable exemplary disintegrants include starch, carboxymethylcellulose, calcium carboxymethylcellulose, sodium croscarmellose, sodium carboxymethylstarch and the like. Suitable exemplary solvents include injectable water, alcohol, propylene glycol, macrogol, sesame oil, corn oil, etc. Suitable exemplary solubilizing agents include polyethylene glycol, propylene glycol, D-mannitol, benzylbenzoate, ethanol, trisaminomethane, cholesterol, triethanolamine, sodium carbonate, sodium citrate and the like. Suitable exemplary suspending agents include surfactants such as stearyltriethanolamine, sodium laurylsulfate, laurylaminopropionic acid, lecithin, benzalkonium chloride, benzethonium chloride, glycerin monostearate and the like; and hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like. Suitable exemplary isotonic agent includes sodium chloride, glycerin, D-mannose and the like. Suitable exemplary buffer agents include buffer solutions of salts, such as phosphate, acetates, carbonates, citrates and the like. Suitable exemplary soothing agents include benzyl alcohol and the like. Suitable exemplary antiseptic substances include para-oxybenzoic acid esters, chlorobutanol, benzyl alcohol, phenethyl alcohol, dehydroacetic acid, sorbic acid and the like. Suitable exemplary antioxidants include sulfite salts, ascorbic acid and the like. Suitable exemplary sealers include, but are not limited to HPMC (or hypromellose), HPC, PEG and combinations thereof. In some embodiments, disintegrants are added to the formulation to help the all or part of the dosage form disintegrate after consumption, thereby releasing at least a portion of the active ingredients. Some common disintegrants include several modified cellulose derivatives, such as croscarmellose sodium and other modified starch derivatives such as sodium starch glycolate. It will also be understood by one of ordinary skill in the art that a pharmaceutical composition may contain other suitable ingredients, binders and lubricants that provide optimal dissolution profiles of dosage forms.

When the dosage form of pharmaceutical composition is a capsule, it may contain a liquid carrier. Other materials may be present as coatings or to otherwise modify the physical form of the dosage form. For instance, tablets, pills, or capsules may be coated with shellac, sugar or both. A syrup or elixir may contain sucrose as a sweetening agent and methyl and propylparabens as preservatives, a dye and flavoring, such as cherry or orange flavor. Of course, materials used in preparing any dosage form should be pharmaceutically pure and substantially non-toxic in the amounts employed.

Pharmaceutical additives such as antiseptic substances, antioxidants, coloring agents and sweeteners may also be added if necessary.

The present invention, in various embodiments, provides an oral composition suitable for human administration. The present oral composition encompasses various dosage forms. For example, the oral composition can be a tablet, coated tablet, capsule, caplet, cachet, lozenges, gel capsule, hard gelatin capsule, soft gelatin capsule, troche, dragee, dispersion, powder, granule, pill, liquid, an aqueous or non-aqueous liquid suspension, an oil-in-liquid or oil-in-water emulsion, including sustained release formulations that are known in the art. (See, e.g., Introduction to Pharmaceutical Dosage Forms, 1985, Ansel, H. C., Lea and Febiger, Philadelphia, Pa.; *Remington's Pharmaceutical Sciences,* 1995, Mack Publ. Co., Easton, Pa.)

These dosage forms can be prepared using standard procedures that are known to the art, including but not limited to encapsulating procedures. In one embodiment, the dosage form provides a low blood concentration of TGR5 agonists (TGR5 compounds) after ingestion but continues to release TGR5 compounds in the gut compartment over time to permit low pharmaceutical exposure (i.e., TGR5 compounds are restricted to the gut compartment). Preferably, the oral compositions (after ingestion) provide a plasma level of TGR5 compounds at <20 ng/mL. More preferably, the present compounds of the invention have <5 ng/mL.

In one embodiment, the present compositions are formulated into a dosage form releasing TGR5 compounds for a period of 1 to 12, typically 3 to 12 hours, more typically 6-12 hours after ingestion. Preferably, the oral pharmaceutical compositions of the present invention may be administered in single or divided doses, from one to four times a day. The oral dosage forms may be conveniently presented in unit dosage forms and prepared by any methods well known in the art of pharmacy. In another embodiment, the present composition contains a predetermined amount of a therapeutic amount of TGR5 compound effective in treating diabetic diseases.

The present formulations can be prepared by any suitable method of pharmacy which includes the step of bringing into association the therapeutic TGR5 compound compositions and a suitable carrier (which can contain one or more accessory ingredients as noted above). In general, the pharmaceutical compositions according to embodiments of the present invention are prepared by uniformly and intimately admixing the TGR5 compounds with a liquid or finely divided solid carrier, or both, and then, if necessary, shaping the resulting mixture. For example, tablets may be prepared by compressing or molding powders or granules containing the therapeutic TGR5 compounds, optionally with one or more accessory ingredients. Compressed tablets can be prepared by compressing, in a suitable machine, the therapeutic TGR5 compounds in a free-flowing form, including a powder or granules optionally mixed with a binder, lubricant, inert diluent, and/or surface active or dispersing agent (s). Molded tablets can be made by molding, in a suitable machine, the powdered compound moistened with an inert liquid binder. The tablets can optionally be coated or scored and can be formulated so as to provide slow or controlled release of the active ingredient TGR5 compounds therein.

When the pharmaceutical compositions are applied to humans, they are desirably administered via the oral route. The therapeutic effective dose of each TGR5 active compounds depends on the age or symptom of the patient to be treated. Generally, the pharmaceutical preparations may contain about 50 mg, 100 mg, 250 mg, 500 mg or 1,000 mg of the TGR5 compounds per unit dosage form and may be administered to humans or animals at a daily dose of 0.1-100 mg per kilogram of body weight. The optimal dose suitable for a particular patient can be conveniently determined (by a physician) without undue experimentation.

The pharmaceutical compositions generally are administered in a therapeutic effective amount for treatment or prophylaxis of diabetic conditions. Initial dosing in human can be accompanied by clinical monitoring of symptoms for the selected condition (e.g., blood sugar (glucose) level or HbA1c test) for administration particularly to mammals, and particularly humans, it is expected that the daily dosage level of the TGR5 compounds may be determined to maintain an optimal blood sugar level or HbA1c level.

It will be appreciated that optimum dosage will be determined by standard methods for each treatment modality and indication, taking into account the indication, its severity, route of administration, complicating conditions and the like. The physician in any event will determine the actual dosage that will be most suitable for an individual and will vary with the age, weight and response of the particular individual. The effectiveness of a selected actual dose can readily be determined, for example, by measuring clinical symptoms or standard diabetic indicia after administration of the selected dose. The above dosages are exemplary of the average case. There can, of course, be individual instances where higher or lower dosage ranges are merited, and such are within the scope of this present invention. For conditions or disease states as are treated by the present invention, maintaining consistent daily levels in a subject over an extended period of time, e.g., in a maintenance regime, can be particularly beneficial.

For purposes of the present invention, "treating" or "treatment" in the present context includes alleviating symptoms, enhancing glycemic control or insulin sensitivity, arresting, slowing, retarding or stabilizing progression of a condition or a physiological or morphological marker thereof, or improving clinical outcome, for example as measured by quality of life, incidence or severity of adverse cardiac events, time to end-stage renal disease or survival time.

Without wishing to be bound by a theory, it is discovered that the present tricyclic compounds are good TGR5 agonists and have a low plasma exposure profile (i.e., low $C_{max}$ values). Low plasma exposure refers to maintaining a plasma level of TGR5 compounds (i.e., <200 ng/mL) after administration of the compounds. Preferably, the present compounds of the invention have a $C_{max}$<20 ng/mL. More preferably, the present compounds of the invention have a $C_{max}$<5 ng/mL.

The present inventors discovered that when administered via an oral route, the present compounds are restricted to the gut compartment and thus have low bioavailability in the blood stream (i.e., the compounds do not leak into the circulation and the resulting low plasma level). Not wishing to be bound to a theory, it is speculated that one functional group (e.g., $(CHR)_{n1}$-$L_1$-$(CHR)_{n2}$-$L_2$-$(CHR)_{n3}$-$L_3$-$(CHR)_{n4}$-T) on the parent molecule may have affected the gut permeability and renders the compounds to be restricted in the gut compartment. It is possible that the functional group acts in concert with other functional groups on the parent molecules to exert this unique effect.

In one aspect, the present invention provides a combination therapy using the compounds as described herein and one or more of an additional therapeutic agent(s). The additional therapeutic agents preferably include medications commonly prescribed for diabetic treatments. Exemplary additional therapeutic agents include, but are not limited to metformin, sulfonylurea (such as gliclazide, glimepiride, and glipizide), nateglinide and repaglinide, dipeptidyl peptidase 4 (DPP-4) (such as linagliptin, saxagliptin, sitagliptin and vildagliptin), thiazolidinediones (such as glitazones or pioglitazone), acarbose, pramlintide, insulin, exenatide, liraglutide, dapagliflozin, canagliflozin and the like.

The combination therapy provides the beneficial effect from the co-action of these therapeutic agents, due to synergistic or additive effects. Therapeutic agents are preferably administered simultaneous, or carried out over a defined time interval (e.g., minutes or hours depending upon the combination selected). In one embodiment, co-administration can be accomplished, for example, by administering to the subject a single dosage form (e.g., capsule) having a fixed ratio of each therapeutic agent. In another embodiment, while TGR5 compound of the present invention is administered by oral route, the second therapeutic agent can be administered by the same route or by different routes (e.g., orally, intravenous injection, intramuscular or nasally). In one embodiment, the combined therapy composition includes an oral TGR5 compound and an injectable insulin. In another embodiment, the combined therapy composition includes an oral TGR5 compound and sitagliptin.

In one aspect, the present invention provides a composition comprising a compound of the present invention or a pharmaceutically acceptable salt, solvate or prodrug thereof.

In one aspect, the present invention relates to a method of treating diseases in a subject by administering a therapeutically effective amount of a compound of the present invention or a pharmaceutically acceptable salt, solvate or prodrug thereof.

The present inventors designed the compounds of the present invention to have favorable PK profile characteristics (e.g., low $C_{max}$). Without wishing to be bound by a theory, it is further discovered that the compounds of the present invention, when orally ingested, are not leaking into the blood stream (i.e., low $C_{max}$). The low $C_{max}$ is believed to render the present compounds superior properties of reducing side-effects (such as bile retention in gall-bladder). The compounds of the present invention are therefore superior and suitable for treating a TGR5-related metaolic disease, such as pre-diabetes, type-2 diabetes, and obesity. For purposes of this application, TGR5-related metabolic disease may also include fibrosing cholangitis, colitis, pancreatitis, cancer, and the like.

In one embodiment, the subject in need of treatment is a human. The present compounds are suitable for treating a TGR5 related metabolic disease in a human. In one embodiment, the human disorder is pre-diabetes. In a preferred embodiment, the human metabolic disorder is type-2 diabetes. In another preferred embodiment, the human metabolic disorder is obesity. In further embodiments, the TGR5-related metabolic disorder may include diabetes, insulin resistance, and pre-diabetic insulin resistance. In another embodiment, the human metabolic disorder is fibrosing cholangitis. In another embodiment, the human metabolic disorder is an inflammatory disease, preferably colitis. In another embodiment, the human metabolic disorder is a digestive disease, preferably pancreatitis. In another embodiment, the human metabolic disorder is cancer.

Without wishing to be bound by a theory, it is discovered that one functional group (e.g., $(CHR)_{n1}$-$L_1$-$(CHR)_{n2}$-$L_2$-$(CHR)_{n3}$-$L_3$-$(CHR)_{n4}$-T) attributes to the non-systemic property of the compounds. The functional group is speculated to render the compound with a low pharmacokinetic profile while surprisingly effective in exerting the glycemic control in diabetic conditions. In accordance with this unexpected finding, the present compounds have practical clinical utility and application in the treatment of TGR5-related metabolic disorders including pre-diabetes, type-2 diabetes, obesity, fibrosing cholangitis, colitis, pancreatitis, cancer, and the like.

While the present invention has been described in conjunction with the detailed description thereof, the foregoing description is intended to illustrate and not limit the scope of the present invention, which is defined by the scope of the appended claims. Other embodiments, advantages, and modifications are within the scope of the following claims. It will be understood by those skilled in the art that various changes in form and details may be made therein without departing from the scope of the present invention encompassed by the appended claims.

General Synthetic Schemes

Compounds of the present invention were prepared using the synthetic schemes described herein. The general schemes utilize various transformations such as alkylations, reductions, oxidations, displacements, and amide bond formations. During the chemical syntheses, various protecting groups may be employed and subsequently removed in order to generate the compounds of the present invention. Exemplary protecting groups and conditions for their removal are described in Greene's *Protecting Groups in Organic Synthesis* P. G. M. Nuts, T. W. Greene, Fourth Edition, Wiley, New York, 2006.

Amine protecting groups include, for example, tert-butoxy carbamate, carboxybenzyl group, and 9-fluorenylmethyl carbamate. Deprotection conditions vary depending on the protecting groups. For example, if the amine is protected as a tert-butoxy carbamate, suitable acidic conditions such as a solution of TFA in DCM or a solution of HCl in dioxane can be used to remove the protecting group. Alternatively, if the protecting group is a 9-fluorenylmethyl carbamate, suitable basic conditions such as a solution of piperidine in DMF or a solution of diethylamine in DMF can be used to remove the protecting group. Alternatively, if the amine is protected as a carboxybenzyl group, catalytic hydrogenation can be employed for its deprotection.

Carboxylic acid protecting groups include, for example, tert-butyl, benzyl, ethyl, and methyl ester. Removal of a tert-butyl ester can be completed under acid conditions such as treatment with a solution of TFA in DCM. Alternatively, the removal of a benzyl ester can be completed via hydrogenolysis using, for example, palladium on carbon under a hydrogen atmosphere. In further examples, ethyl and methyl esters can be hydrolyzed to the carboxylic acid under hydrolytic conditions such as LiOH in aqueous THF.

In the general schemes below, the syntheses of compounds sometimes require the formation of an amide bond. Coupling agents such as EDC, DIC, or HATU can be used to form the amide bond generally in a solvent such as DCM or DMF with a suitable base present such as DIEA or triethylamine as required. An additive such as HOBt, HOAt, or DMAP can also be employed during the reaction.

Specific synthetic transformations not covered in the general schemes below are described in detail in the experimental section. It is apparent to those skilled in the art that the order of steps might be adjusted depending on the compound to be produced.

General Scheme 1

Route 1-1

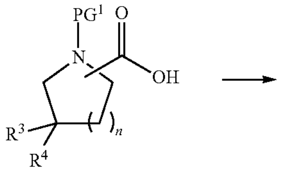

III

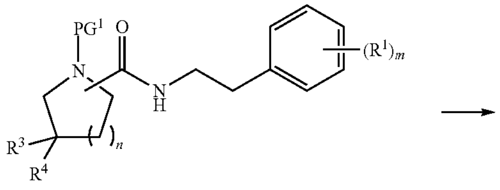

IV

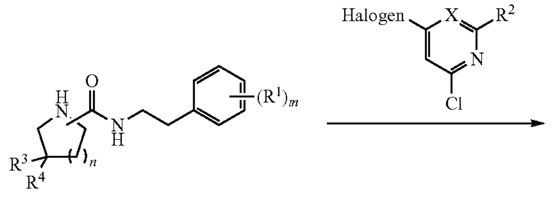

V

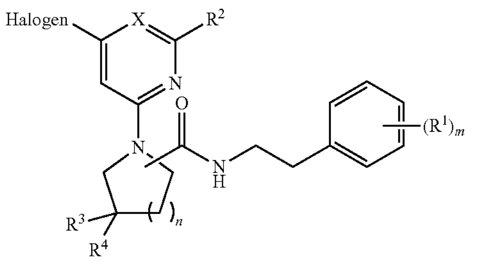

VI

Route 1-2

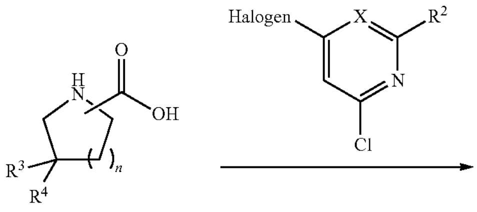

VII

-continued

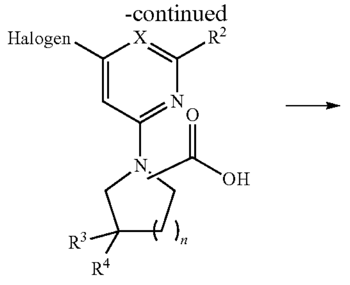

VIII

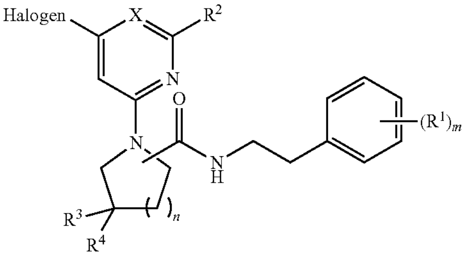

VI

Route 1-3

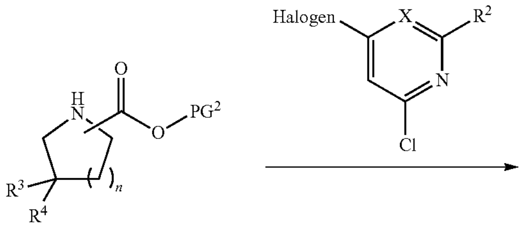

IX

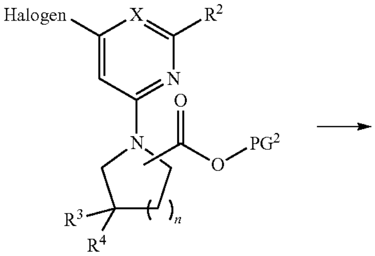

X

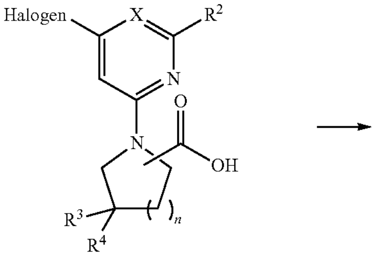

VIII

-continued

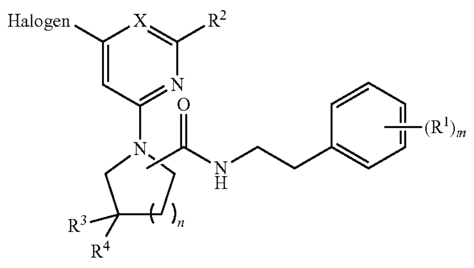

VI (PG = Protecting Group)

General Scheme 1 depicts three routes to synthesize intermediate VI. As shown in Route 1-1, a suitably protected amino acid derivative III (PG=protecting group) can be coupled with an amine to form amide derivative IV using conditions for amide bond formation known to those skilled in the art and outlined above. Deprotection of the amine protecting group of intermediate IV is carried out by methods known to those skilled in the art and outlined above. The resultant amine V can be converted to Intermediate VI by reaction with a suitable halogen-bearing heterocycle as depicted such as 4,6-dichloro-2-(trifluoromethyl)pyrimidine or 2-chloro-4-iodo-6-(trifluoromethyl)pyridine in the presence of a suitable base such as DIEA or triethylamine. Suitable solvents for this reaction include DMF, DMSO, and dioxane. Depending on the substrates, the reaction can be carried out at room temperature or up to 120° C.

Alternatively, compounds VI can be synthesized via Route 1-2. In this case, an amino acid derivative VII is reacted with a suitable halogen-bearing heterocycle such as 4,6-dichloro-2-(trifluoromethyl)pyrimidine or 2-chloro-4-iodo-6-(trifluoromethyl)pyridine in the presence of a suitable base such as DIEA or triethylamine to yield intermediate VIII. Coupling of a suitable amine to intermediate VIII generates the amide-bearing intermediate VI.

Alternatively, compounds VI can be synthesized via Route 1-3. In this route, ester derivatives IX are reacted with a suitable halogen-bearing heterocycle such as 4,6-dichloro-2-(trifluoromethyl)pyrimidine or 2-chloro-4-iodo-6-(trifluoromethyl)pyridine in the presence of a suitable base such as DIEA or triethylamine. Suitable solvents for this reaction include DMF, DMSO, and dioxane. This reaction yields protected intermediate X. Deprotection of intermediate X to carboxylic acid VIII can be carried out by various methods recognized by those skilled in the art and outlined above. Finally, the carboxylic acid derivative VIII can be converted to intermediate VI via amide formation employing a suitable coupling agent as previously described above.

General Scheme 2
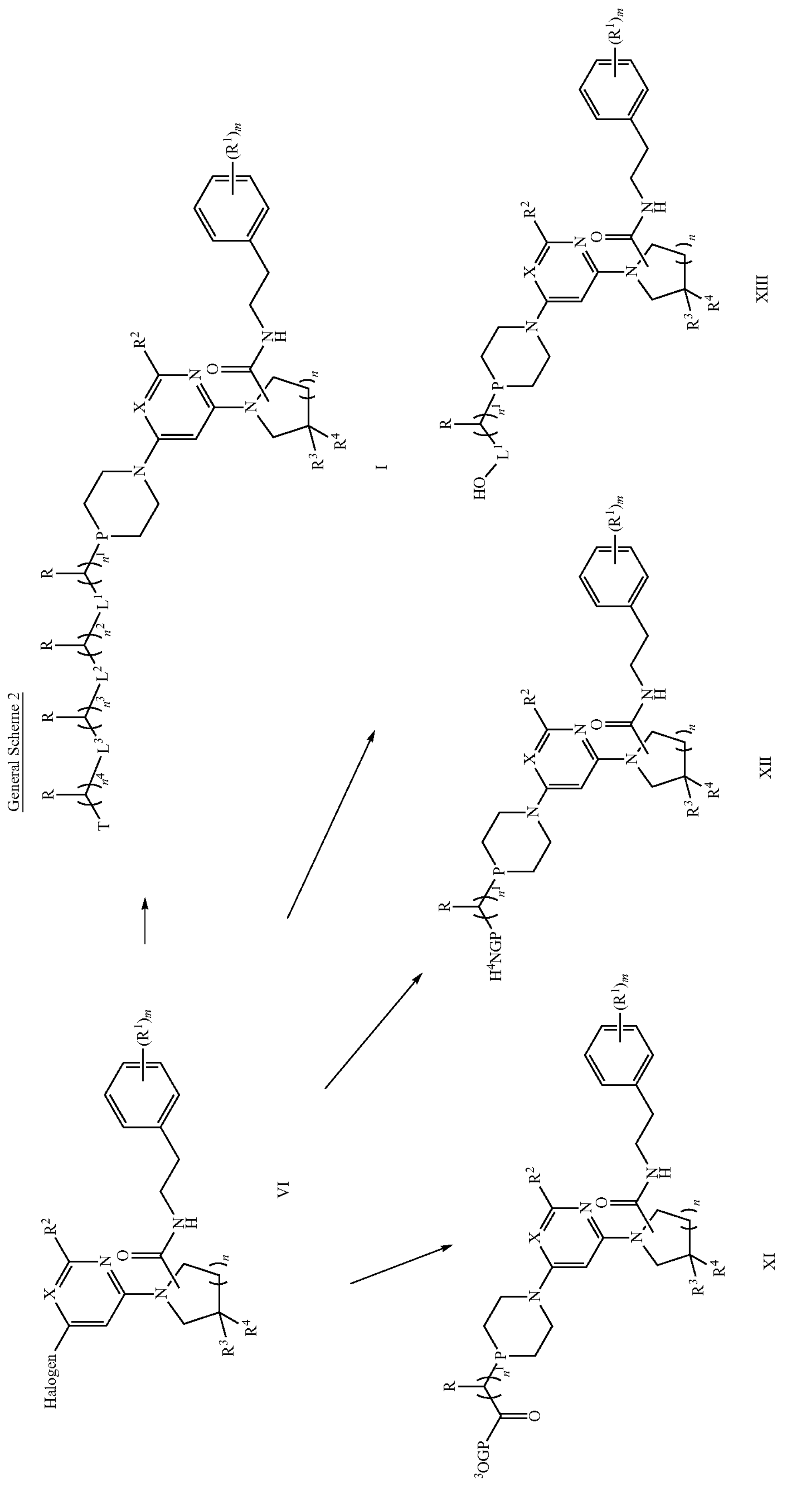
VI
I
XI
XII
XIII

As depicted in General Scheme 2, treatment of halogen-bearing compound VI with an amine in the presence of a base such as DIEA or triethylamine in a solvent such as DMSO, DMF, NMP, or the like can generate compounds I of the present invention directly. The reaction is generally heated between 80° C. to 120° C. either thermally or in a microwave oven. It is clear to those skilled in the art that protecting groups may need to be removed as described above to generate compounds I. In reactions carried out with a subset of amines, these conditions generate compounds XI, XII, and XIII which can be further reacted as described below to generate compounds of the present invention.

Buchwald/Hartwig conditions can also be employed to convert intermediate VI to compounds of the present invention I. In this case, intermediate VI is generally heated between 80° C. to 120° C. with an amine in the presence of a suitable palladium catalyst such as RuPhos precatalyst, a ligand such as RuPhos, and a suitable base such as cesium carbonate in a solvent such as toluene or the like to generate compounds I. Again, protecting groups may need to be removed as described above to generate compounds I. In reactions carried out with a subset of amines, the Buchwald/Hartwig conditions generate compounds XI, XII, and XIII which can be further reacted as described below to generate compounds of the present invention.

To simplify the remaining schemes, the following is defined:

Z =
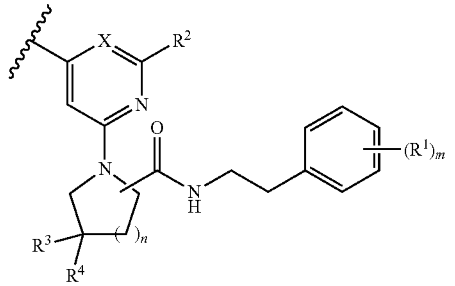

General Scheme 3

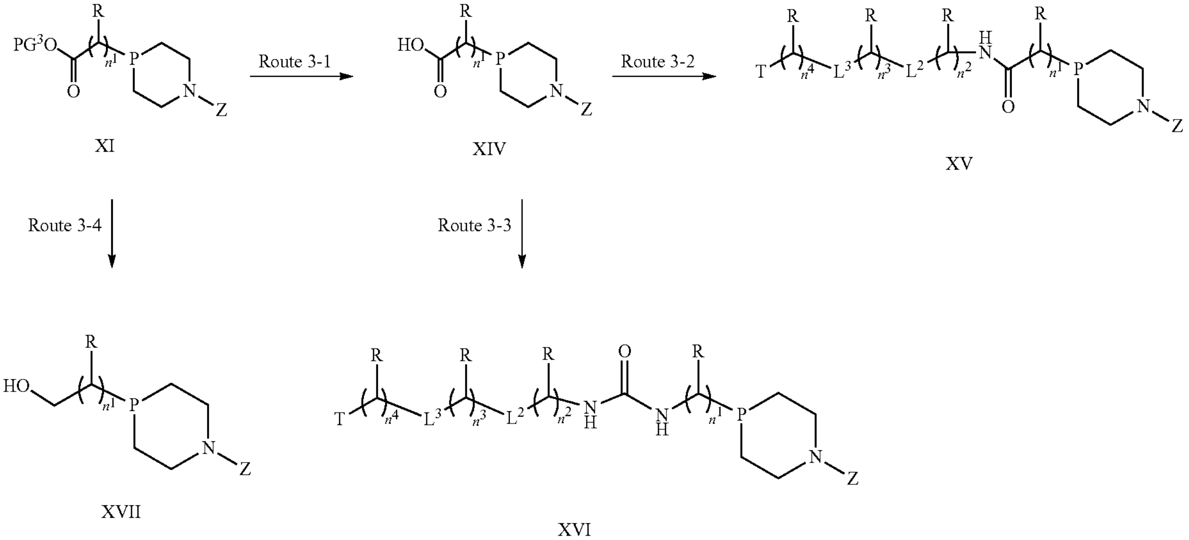

XI, XIV, XV, XVI, XVII

Some of the compounds produced by the reactions in General Scheme 2 will contain an unprotected carboxylic acid group as depicted in structure XIV. Alternatively, some compounds of the present invention produced by the reactions in General Scheme 2 can harbor a protected carboxylic acid functionality as depicted in compound XI in General Scheme 3. As shown in Route 3-1, removal of the protecting group from XI using methods described previously generates XIV, a carboxylic acid containing compound of the present invention. Various reactions of the carboxylic acid group in XIV are used to generate compounds of the present invention. For instance, as depicted in Route 3-2, carboxylic acid derivative XIV can be coupled with an amine using a suitable coupling agent as described above to generate an amide-bearing compound XV of the present invention.

Alternatively, the carboxylic acid group in XIV can undergo a Curtius rearrangement in the presence of an appropriate amine to generate a urea-bearing compound XVI of the present invention (as depicted in Route 3-3). The carboxylic acid XIV is converted into an isocyanate by treatment with diphenylphosphoryl azide while heating between 80° C. to 100° C. in a suitable solvent such as toluene. Addition of an amine to the reaction yields the urea-bearing compound XVI.

Further compounds of the present invention can be synthesized by reduction of XI when the protecting group, $PG^3$, is an appropriate ester such as a methyl ester (Route 3-4). Treatment of XI with a suitable reducing agent such as lithium aluminum hydride or sodium borohydride in a solvent such as ethanol at temperature generally from room temperature to 60° C. produces an alcohol XVII of the present invention.

General Scheme 4

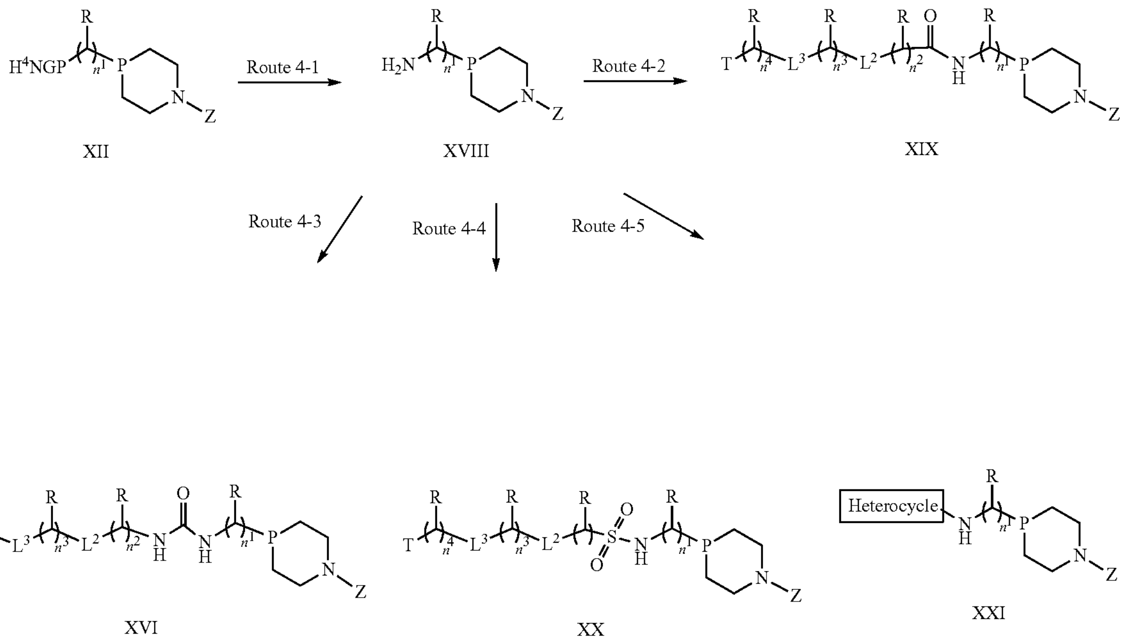

XII

XVIII

XIX

XVI

XX

XXI

Some of the compounds produced by the reactions in General Scheme 2 can contain an unprotected amine group as depicted in structure XVIII in General Scheme 4. Additionally, compounds produced by the reactions in General heating such a heterocycle with amine XVIII in the presence of a suitable base such as DIEA or triethylamine in a solvent such as DMSO, DMF, or n-butanol generates heteroaryl-bearing compounds XXI. Heating from 100° C. to 120° C. is generally employed.

General Scheme 5

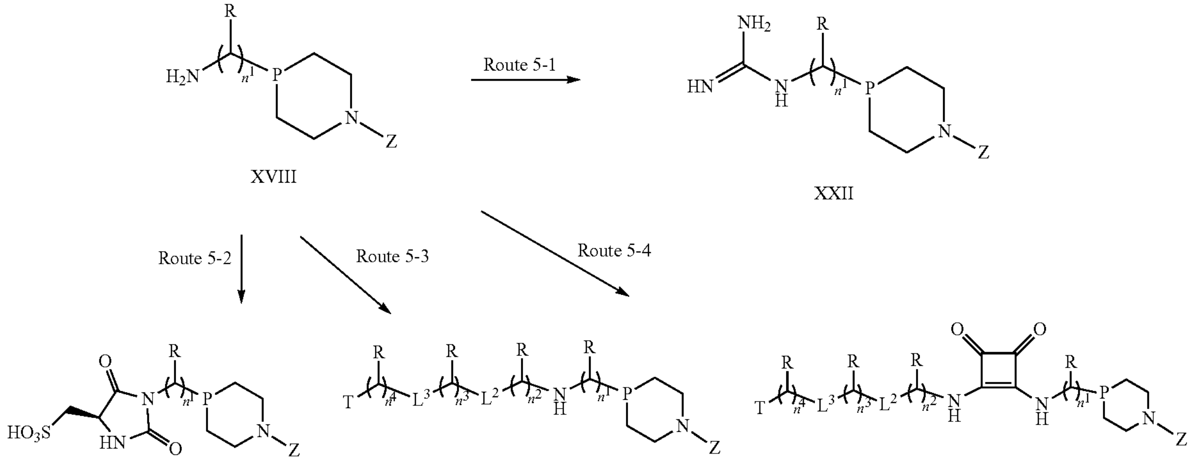

XVIII XXII XXIII XXIV XXV

Scheme 2 can harbor a protected amine functionality as depicted in compound XII of General Scheme 4. As shown in Route 4-1, removal of the protecting group yields XVIII, an amine-containing compound of the present invention. Deprotection of the amine protecting group of intermediate XII is carried out by methods known to those skilled in the art and described above.

Various reactions of the amine group in XVIII are used to generate further compounds of the present invention as shown in General Scheme 4. For instance, as depicted in Route 4-2 amine-bearing derivative XVIII can be coupled with a carboxylic acid to generate amide derivative XIX. Coupling agents as described above are employed. Alternatively, amide compounds of the present invention XIX can be synthesized by reaction of an acid chloride with amine XVIII in the presence of a suitable base such as DIEA, triethylamine, or pyridine in a solvent such as DCM.

As shown via Route 4-3, the amine derivative XVIII can also be transformed into a urea-bearing compound XVI of the present invention by conditions known to those skilled in the art. For example, treatment of XVIII with an isocyanate in a suitable solvent such as DCM or DMF will create a urea. Alternatively, treatment of compound XVIII with 1,1'-carbonyldiimidazole in the presence of a suitable base such as DIEA or triethylamine in a solvent such as DCM or DMF followed by heating in the presence of an amine will produce a urea XVI.

Further compounds of the present invention can be synthesized by converting amine-bearing derivative XVIII to a sulfonamide XX by treatment with a sulfonyl chloride in the presence of a base such as triethylamine, DIEA, or pyridine in a solvent such as DCM (Route 4-4).

Furthermore, the amine-bearing derivative XVIII can be transformed into a heterocyclic-bearing compound XXI of the present invention as depicted in Route 4-5. Heterocycles containing a halogen adjacent to nitrogen on the ring are activated to undergo displacement with amines. Therefore, As shown in General Scheme 5, the amine-bearing derivative XVIII can be transformed into a guanidine derivative XXII by treatment with 1H-pyrazole-1-carboxamidine hydrochloride in the presence of a suitable base such as DIEA or triethylamine in a solvent such as DMF with heating generally in the range of 80° C. to 120° C. (Route 5-1).

Amine XVIII can alternatively be transformed (Route 5-2) into a hydantoin-bearing compound XXIII of the present invention by treatment with 1,1'-carbonyldiimidazole in the presence of a suitable base such as DIEA or triethylamine in a solvent such as DCM or DMF followed by heating generally in the range of 80° C. to 120° C. in the presence of L-cysteic acid monohydrate.

In addition, as shown in Route 5-3, compound XVIII can be further derivatized by alkylation through the treatment with an alkyl halide in the presence of a suitable base such as potassium carbonate in a solvent such as DMF to create further amine derivatives XXIV of the present invention.

Further compounds of the present invention can be synthesized as depicted in Route 5-4. Treatment with a cyclobutenedione derivative such as 4-diethoxycyclobut-3-ene-1,2-dione with an amine in the presence of a base such as triethylamine or DIEA followed by the addition of compound XVIII generates compounds XXV of the present invention.

General Scheme 6

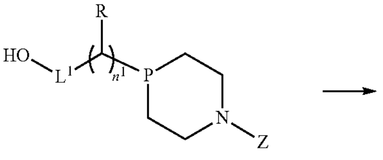

XIII

-continued

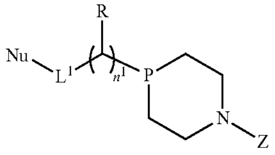

XXVI

As shown in General Scheme 6, a hydroxy-bearing compound XIII can be converted to compounds XXVI of the present invention. The hydroxyl is first activated by treatment with methanesulfonyl chloride, toluenesulfonyl chloride, or the like in the presence of a suitable base such as triethylamine or DIEA in a solvent such as DCM or DMF. The activated intermediate is then treated with a nucleophile (Nu) such as an amine or sulfite ion to generate XXVI. Reactions with an amine are generally carried out in a solvent such as ACN, DMF, or the like at temperatures ranging from room temperature to 100° C. Reactions with sodium sulfite are carried out in a mixture of an organic solvent (such as ACN) and water at temperatures ranging from room temperature to 100° C.

Subsets of compounds synthesized in General Schemes 3, 4, 5, and 6 contain functional groups that allow for further reactions. Additional compounds of the present invention are synthesized by completing further reactions on those subsets of compounds. Therefore, the starting materials in General Schemes 7, 8, and 9 are the products from the procedures carried out in General Schemes 3, 4, 5, and 6.

General Scheme 7

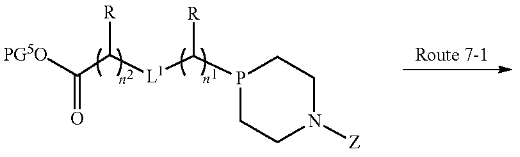

XXVII

-continued

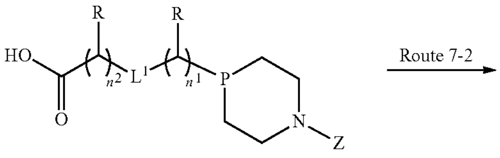

XXVIII

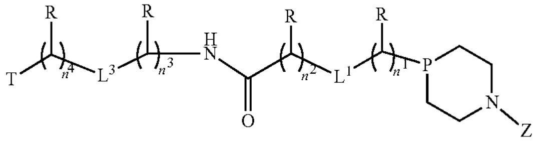

XXIX

As stated above, additional compounds of the present invention are synthesized by further reactions on the compounds produced via the procedures outlined in General Schemes 3, 4, 5, and 6. For instance, compounds XXVII of the present invention which contain a suitably protected carboxylic acid could have resulted from the reactions in general schemes 3, 4, 5, and 6. These compounds (XXVII) can be further functionalized as outlined in General Scheme 7 to produce additional compounds of the present invention. As shown in Route 7-1, removal of the protecting group from XXVII employing conditions described previously generates XXVIII, a carboxylic acid containing compound of the present invention.

As shown in Route 7-2, coupling of XXVIII with an amine (under conditions outlined above) produces compounds XXIX of the present invention.

General Scheme 8

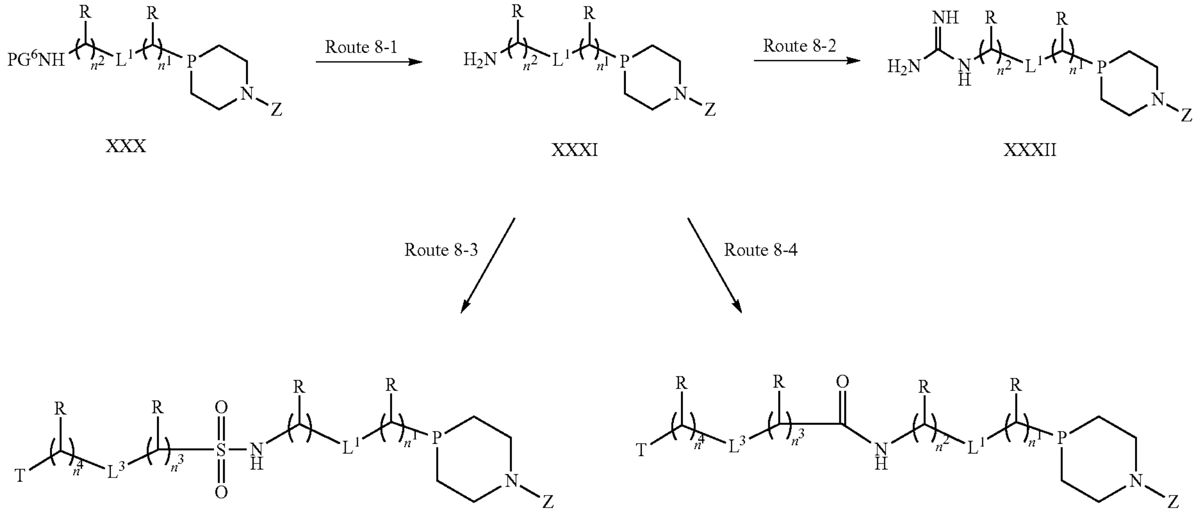

XXX

XXXI

XXXII

XXXIII

XXXIV

Compounds XXX which contain a suitably protected amine could have resulted from the reactions in general schemes 3, 4, 5, and 6. These compounds (XXX) can be further functionalized as outlined in General Scheme 8 to produce further compounds of the present invention. As shown in Route 8-1, removal of the protecting group produces XXXI, an amine-containing compound of the present invention. Deprotection of the amine protecting group of intermediate XXX is carried out by methods known to those skilled in the art and outlined above.

As shown in Route 8-2, derivative XXXI can be transformed into a guanidine-bearing compound XXXII of the present invention by treatment with 1H-pyrazole-1-carboxamidine hydrochloride in the presence of a suitable base such as DIEA or triethylamine in a solvent such as DMF with heating generally in the range of 80° C. to 120° C.

Further compounds of the present invention can be synthesized by converting amine XXXI to a sulfonamide XXXIII by treatment with a sulfonyl chloride in the presence of a base such as triethylamine, DIEA, or pyridine in a solvent such as DCM (Route 8-3).

As depicted in Route 8-4 and using previously described coupling conditions, amine XXXI can be coupled with a carboxylic acid to generate amide derivative XXXIV. Alternatively, compounds XXXIV can be synthesized by reaction of an acid chloride with amine XXXI in the presence of a suitable base such as DIEA, triethylamine, or pyridine in a solvent such as DCM.

General Scheme 9
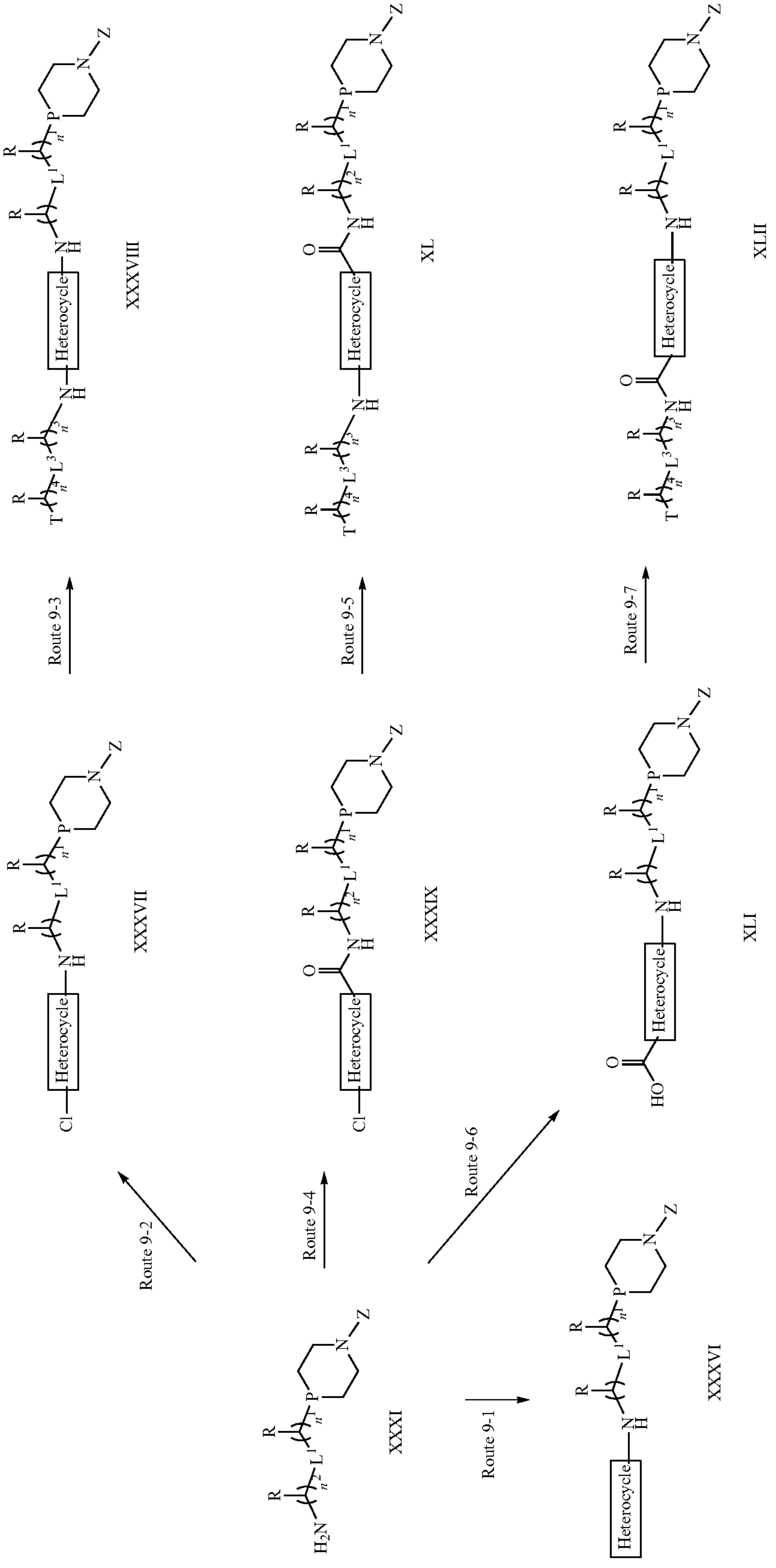
XXXI XXXVI XXXVII XXXVIII XXXIX XL XLI XLII

Reactions of the amine group of XXXI with heterocycles generate further compounds of the present invention as shown in General Scheme 9. As mentioned previously, heterocycles containing a halogen adjacent to nitrogen in the ring are activated to undergo displacement with amines. Therefore, heating such a heterocycle with amine XXXI in the presence of a suitable base such as DIEA or triethylamine in a solvent such as DMSO, DMF, or n-butanol generates compounds XXXVI of the present invention (Route 9-1). Heating between 100° C. to 120° C. is generally employed.

As shown in Route 9-2, heating amine XXXI with a suitable heterocycle containing two activated halogens in the presence of a base such as DIEA or triethylamine in a solvent such as DMSO, DMF, or n-butanol yields compounds XXXVII. Heating between 100° C. to 120° C. is generally employed. Amine displacement of the remaining halogen (Route 9-3) generates compounds XXXVIII of the present invention. The conditions employed are similar as described for the first displacement.

Compounds XXXIX of the present invention are synthesized by coupling XXXI with a halogen-bearing heterocycle functionalized with a carboxylic acid (Route 9-4). Standard amide formation conditions outlined above are employed. Displacement of the halogen of the resultant XXXIX with an amine, as shown in Route 9-5 generates compounds XL of the present invention. The reaction is carried out with heating between 100° C. to 120° C. in the presence of a suitable base such as DIEA or triethylamine in a solvent such as DMSO, DMF, or n-butanol.

Under similar conditions, XXXI can be reacted (Route 9-6) with a halogenated heterocyclic harboring a carboxylic acid moiety to generate compounds XLI. The carboxylic acid group can be further reacted by coupling to an amine to generate compounds XLII of the present invention. Coupling agents as described above can be used to complete this reaction.

General Scheme 10

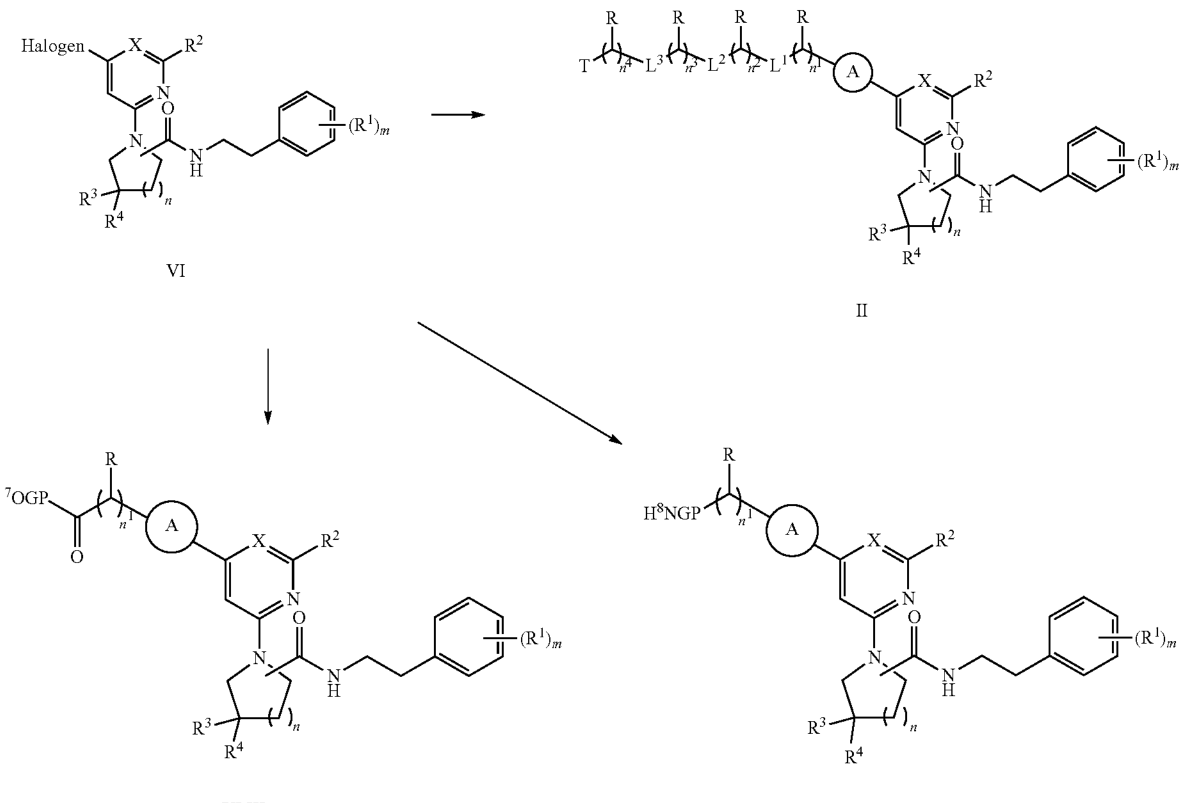

VI

II

XLIII

XLIV

Additionally, as shown in General Scheme 10, the halogen of compound VI can be reacted to form an aryl or heteroaryl compound II of the present invention by conditions known to those skilled in the art. For example, heating of VI with a aryl or heteroaryl boronic acid or boronic ester in the presence of both a palladium catalyst such as tetrakis (triphenylphosphine) palladium(0), tris(dibenzylideneacetone)dipalladium(0), [1,1'-bis(diphenylphosphino) ferrocene]dichloropalladium(II), or the like and a suitable base such as aqueous sodium carbonate or potassium carbonate in a solvent such as dioxane or DMF (Suzuki coupling conditions) will generate compounds II. Alternatively, reactions of VI with aryl or heteroaryl tin derivatives using Stille conditions could also generate compounds II. Alternatively, reactions of IV with aryl or heteroaryl zinc derivatives using Negishi conditions could also be used generate compounds II.

A subset of compounds synthesized in General Scheme 10 contains functional groups that allow for further reactions. For example, structures XLIII and XLIV contain a carboxylic acid (XIV) or amine functionality (XIX) or their respective protected counterparts. These carboxylic acids (XIV) or amines (XIX) can be further reacted using the methods outlined above in General Schemes 3, 4, 5, 7, 8, and 9 to generate further compounds II.

Some other compounds of the present invention in which $L^1$, $L^2$, and $L^3$ are present can be synthesized by subjecting the intermediates outlined above to additional reactions following the methods described in the schemes above.

EXAMPLES

The compounds of the present invention were prepared using the experimental procedures described herein. They can be made by alternate methods which are apparent to a chemist skilled in the art.

Abbreviations

ACN=acetonitrile
AIBN=2,2'-azobis(2-methylpropionitrile)
Arg=arginine
Boc=t-butoxycarbonyl
$(Boc)_2O$=di-tert-butyl dicarbonate
brine=saturated sodium chloride
t-BuOH=tert-butanol
Cbz=benzyloxycarbonyl
CDI=1,1'-carbonyldiimidazole
Conc.=concentrated
DCE=dichloroethane
DCM=dichloromethane
DIAD=diisopropyl azodicarboxylate
DIBAL=diisobutylaluminum hydride
DIC=diisopropylcarbodiimide
DIEA=diisopropylethylamine
DMAP=4-(dimethylamino)pyridine
DMF=dimethylformamide
DMSO=dimethylsulfoxide
DPPA=diphenylphosphoryl azide
EDC=1-ethyl-3-(3-dimethylaminopropyl)carbodiimide
EA=EtOAc=ethyl acetate
Fmoc=9-fluorenylmethoxycarbonyl
Glu=glutamic acid
HATU=1-[bis(dimethylamino)methylene]-1H-1,2,3-triazolo[4,5-b]pyridinium 3-oxidhexafluorophosphate
h=hours
HCl=hydrochloric acid
HOAt=1-hydroxy-7-azabenzotriazole
HOBt=N-hydroxybenzotriazole
HPLC=high performance liquid chromatography
LCMS=liquid chromatography-mass spectrometry
LDA=lithium diisopropylamide
min=minutes
MeOH=methanol
MsCl=methanesulfonyl chloride
MS-HPLC=mass-directed reverse phase semi-preparative chromatography
NBS=N-bromosuccinimide
PE=petroleum ether
PDA=photo diode array
PG=protecting group
PMC=2,2,5,7,8-pentamethylchromane-6-sulfonyl
$PPh_3$=triphenylphosphine
PS-HOBt=polystyrene bound N-hydroxybenzotriazole
Quant.=quantitative
RuPhos=2-dicyclohexylphosphino-2',6'-diisopropoxybiphenyl
RuPhos preCat=chloro-(2-dicyclohexylphosphino-2',6'-diisopropoxy-1,1'-biphenyl)[2-(2-aminoethyl)phenyl]palladium(II) methyl-t-butyl ether adduct
Sat.=saturated
TBAF=tetrabutylammonium fluoride
TBDMSCl=tert-butyldimethylsilyl chloride
TEA=triethylamine
TFA=trifluoroacetic acid
THF=tetrahydrofuran
TMSI=iodotrimethylsilane
XPhos=2-dicyclohexylphosphino-2',4',6'-triisopropylbiphenyl
XPhos G-2=chloro-(2-dicyclohexylphosphino-2',4',6'-triisopropyl-1,1'-biphenyl)[2-(2'-amino-1,1'-biphenyl)]palladium(II)

LC/MS Analysis Methods:

Method A—Compounds were analyzed on an Aquity Ultra Performance Liquid Chromatography employing an Acquity UPLC BEH C18, 1.7 μm, 2.1×50 mm column. Detection was via an Aquity PDA detector and a Waters SQD single quadrupole mass spectrometer. The aqueous acetonitrile based solvent gradient was: 0-0.1 min—Isocratic—10% of acetonitrile (0.01% TFA); 0.1-1.3 min—Linear gradient—10%-90% acetonitrile (0.01% TFA); 1.3-1.8 min—Isocratic—90% acetonitrile (0.01% TFA); 1.8-1.9 min—Linear gradient—90%-10% acetonitrile (0.01% TFA); 1.9-2.0 min—Isocratic—10% acetonitrile (0.01% TFA). Flow rate: 0.6 mL/min.

Method B—Compounds were analyzed on an Aquity Ultra Performance Liquid Chromatography employing a Acquity UPLC BEH C18, 1.7 um, 2.1×50 mm column. Detection was via an Aquity PDA detector and a Waters SQD single quadrupole mass spectrometer. The aqueous acetonitrile based solvent gradient was: 0-0.1 min—Isocratic—20% of acetonitrile (0.01% TFA); 0.1-1.3 min—Linear gradient—20%-95% acetonitrile (0.01% TFA); 1.3-1.8 min—Isocratic—95% acetonitrile (0.01% TFA); 1.8-1.9 min—Linear gradient—95%-20% acetonitrile (0.01% TFA); 1.9-2.0 min—Isocratic—20% acetonitrile (0.01% TFA). Flow rate: 0.6 mL/min.

Method C—Compounds were analyzed on a Waters 2795 AllianceHT Liquid Chromatography employing a Phenomenex Luna C18, 5 μm, 2.1×50 mm column. Detection was via a Waters 996 Photodiode Array detector and a Micromass Quattro Micro triple quadrupole mass spectrometer. The aqueous acetonitrile based solvent gradient was: 0.0-3.0 min—Linear gradient—10%-90% acetonitrile (0.01% TFA); 3.0-3.5 min—Isocratic—90% acetonitrile (0.01% TFA); 3.5-3.6 min—Linear gradient—90%-10% acetonitrile (0.01% TFA); 3.6-5.0 min—Isocratic—10% acetonitrile (0.01% TFA). Flow rate: 0.6 mL/min.

Method D—Compounds were analyzed on an Aquity Ultra Performance Liquid Chromatography employing an Acquity UPLC BEH C18, 1.7 um, 2.1×50 mm column. Detection was via an Aquity PDA detector and a Micromass Quattro Micro triple quadrupole mass spectrometer. The aqueous acetonitrile based solvent gradient was: 0-0.1 min—Isocratic—10% of acetonitrile (0.01% TFA); 0.1-1.3 min—Linear gradient—10%-90% acetonitrile (0.01% TFA); 1.3-1.8 min—Isocratic—90% acetonitrile (0.01% TFA); 1.8-1.9 min—Linear gradient—90%-10% acetonitrile (0.01% TFA); 1.9-2.0 min—Isocratic—10% acetonitrile (0.01% TFA). Flow rate: 0.6 mL/min.

NMR Spectroscopy Method:

$^1H$ NMR Spectroscopy was conducted on a Bruker 400 MHz Avance II FTNMR Spectrometer.

Preparation of Chemical Compounds:

Intermediate 1

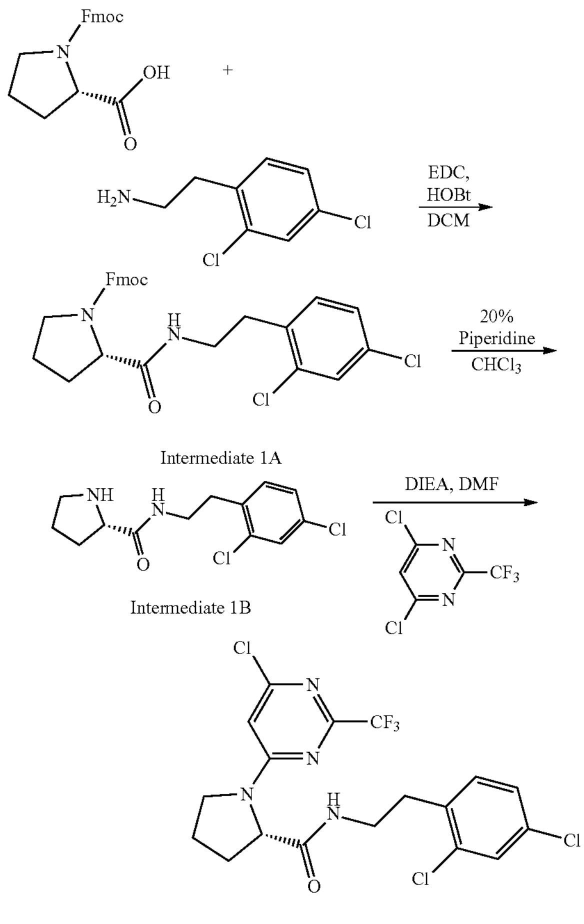

(S)-(9H-fluoren-9-yl)methyl 2-((2,4-dichlorophenethyl)carbamoyl)pyrrolidine-1-carboxylate To a solution of Fmoc-L-Proline (1.0 g, 3.0 mmol) in DCM (14 mL) were added sequentially 1-ethyl-3-(3-dimethylaminopropyl)carbodiimide (682 mg, 3.56 mmol), N-hydroxybenzotriazole (441 mg, 3.26 mmol) and 2-(2,4-dichlorophenyl)ethanamine (0.45 mL, 3.0 mmol). The reaction mixture was stirred at room temperature overnight. The reaction mixture was poured into water and extracted with DCM. The combined organic extracts were dried over sodium sulfate, filtered, and concentrated in vacuo to afford Intermediate 1A (1.5 g, 99%), which was used in the next step without further purification. LCMS (method A): m/z 509.2 $(M+H)^+$.

(S)—N-(2,4-dichlorophenethyl)pyrrolidine-2-carboxamide

A solution of Intermediate 1A (1.5 g, 3.0 mmol) in 20% piperidine/$CHCl_3$ (3 mL/12 mL) was stirred at room temperature for one hour. The solution was concentrated in vacuo, and the residue was purified by silica gel chromatography (0-5% MeOH/DCM) to afford Intermediate 1B (355 mg, 42%). LCMS (method A): m/z 287.1 $(M+H)^+$. $^1H$ NMR ($CDCl_3$) δ 7.68 (br s, 1H), 7.39 (d, 1H), 7.17 (m, 2H), 3.71 (dd, 1H), 3.50 (m, 2H), 3.01-2.91 (m, 3H), 2.82 (m, 1H), 2.15-2.09 (m, 1H), 1.90-1.83 (m, 2H), 1.70-1.65 (m, 2H).

(S)-1-(6-chloro-2-(trifluoromethyl)pyrimidin-4-yl)-N-(2,4-dichlorophenethyl)-pyrrolidine-2-carboxamide To a solution of Intermediate 1B (40 mg, 0.14 mmol) in DMF (0.3 mL) were added 4,6-dichloro-2-(trifluoromethyl)pyrimidine (30 mg, 0.14 mmol) and diisopropylethylamine (30 μL, 0.17 mmol). The reaction mixture was heated at 90° C. in a microwave for one hour. The reaction mixture was concentrated in vacuo, and the residue was purified by MS-HPLC to afford Intermediate 1 (52 mg, 79%). LCMS (method A): m/z 467.3/469.3 $(M+H)^+$. Using the method outlined above to synthesize Intermediate 1B, the following intermediates were made using the appropriate acids and amines as indicated in Table 1.

TABLE 1

| Intermediate | Structure | Acid | Amine | MS $(M + H)^+$ |
|---|---|---|---|---|
| 1C | 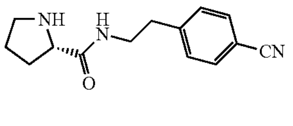 [SMILES: N#Cc1ccc(CCNC(=O)[C@@H]2CCCN2)cc1] | 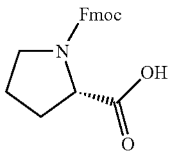 | 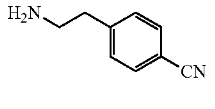 [SMILES: N#Cc1ccc(CCN)cc1] | 244.3 A |
| 1D | 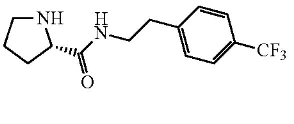 [SMILES: O=C(NCCc1ccc(C(F)(F)F)cc1)[C@@H]1CCCN1] | 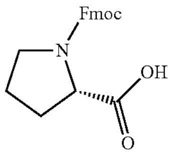 | 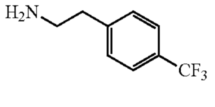 [SMILES: NCCc1ccc(C(F)(F)F)cc1] | 287.2 A |

TABLE 1-continued
| Inter-mediate | Structure | Acid | Amine | MS (M + H)+ |
|---|---|---|---|---|
| 1E | 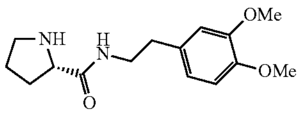 [SMILES: COc1ccc(CCNC(=O)[C@@H]2CCCN2)cc1OC] | 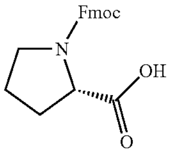 | 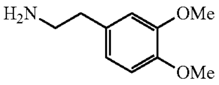 | 279.2 A |
| 1F | 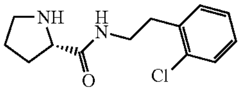 [SMILES: O=C(NCCc1ccccc1Cl)[C@@H]1CCCN1] | 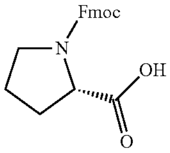 | 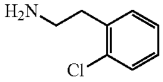 | 253.1 255.1 A |
| 1G | 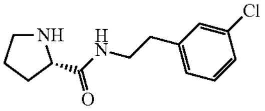 [SMILES: O=C(NCCc1cccc(Cl)c1)[C@@H]1CCCN1] | 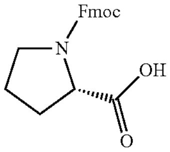 | 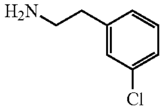 | 253.1 255.1 A |
| 1H | 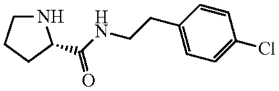 [SMILES: O=C(NCCc1ccc(Cl)cc1)[C@@H]1CCCN1] | 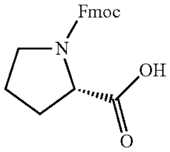 | 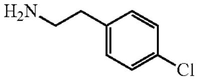 | 253.1 255.1 A |
| 1I | 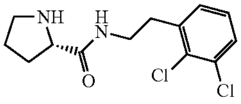 [SMILES: O=C(NCCc1cccc(Cl)c1Cl)[C@@H]1CCCN1] | 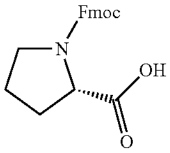 | 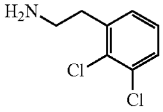 [SMILES: NCCc1cccc(Cl)c1Cl] | 287.1 288.1 289.1 A |
| 1J | 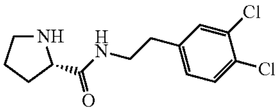 [SMILES: O=C(NCCc1ccc(Cl)c(Cl)c1)[C@@H]1CCCN1] | 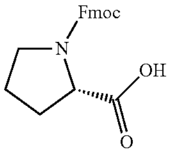 | 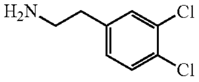 [SMILES: NCCc1ccc(Cl)c(Cl)c1] | 287.1 288.1 289.1 A |
| 1K | 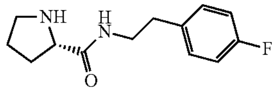 [SMILES: O=C(NCCc1ccc(F)cc1)[C@@H]1CCCN1] | 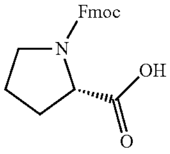 | 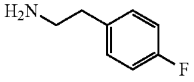 | 237.2 A |
| 1L | 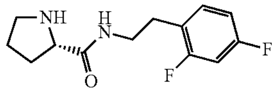 [SMILES: O=C(NCCc1ccc(F)cc1F)[C@@H]1CCCN1] | 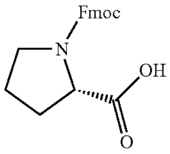 | 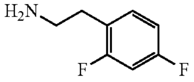 | 255.2 A |
| 1M | 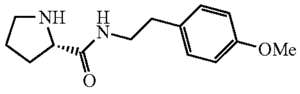 [SMILES: COc1ccc(CCNC(=O)[C@@H]2CCCN2)cc1] | 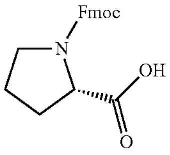 | 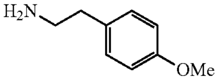 | 249.2 A |

TABLE 1-continued
| Inter-mediate | Structure | Acid | Amine | MS (M + H)+ |
|---|---|---|---|---|
| 1N | 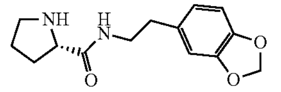 [SMILES: O=C(NCCc1ccc2c(c1)OCO2)[C@@H]1CCCN1] | 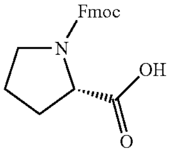 | 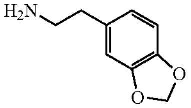 [SMILES: NCCc1ccc2c(c1)OCO2] | 263.2<br>A |
| 1O | 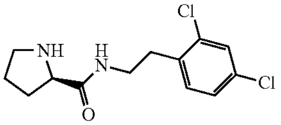 [SMILES: O=C(NCCc1ccc(Cl)cc1Cl)[C@H]1CCCN1] | 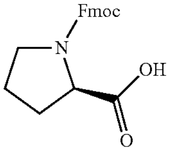 | 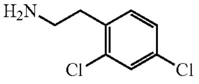 [SMILES: NCCc1ccc(Cl)cc1Cl] | 287.1<br>288.1<br>289.1<br>A |
| 1P | 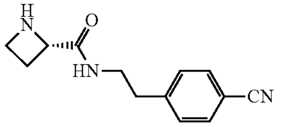 [SMILES: N#Cc1ccc(CCNC(=O)[C@@H]2CCN2)cc1] | 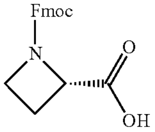 | 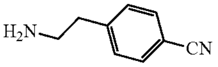 | 230.2<br>A |
| 1Q | 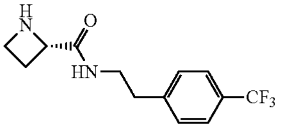 [SMILES: O=C(NCCc1ccc(C(F)(F)F)cc1)[C@@H]1CCN1] | 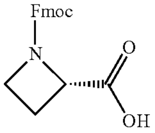 | 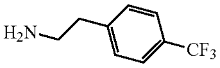 | 273.3<br>A |
| 1R | 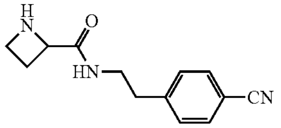 | 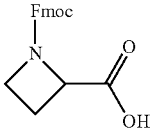 | 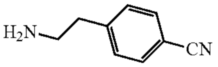 | 230.2<br>A |
| 1S | 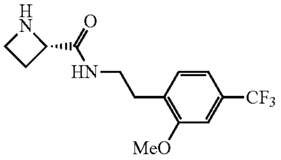 [SMILES: COc1cc(C(F)(F)F)ccc1CCNC(=O)[C@@H]1CCN1] | 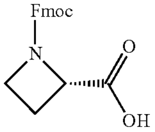 | 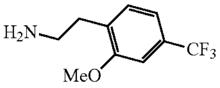<br>preparation see Intermediate 5B | 303.4<br>A |
| 1T | 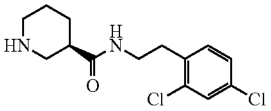 [SMILES: O=C(NCCc1ccc(Cl)cc1Cl)[C@@H]1CCCNC1] | 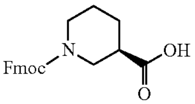 | 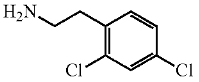 [SMILES: NCCc1ccc(Cl)cc1Cl] | 301.1<br>302.1<br>303.1<br>A |
| 1U | 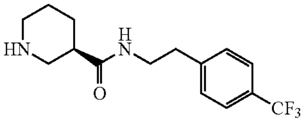 [SMILES: O=C(NCCc1ccc(C(F)(F)F)cc1)[C@@H]1CCCNC1] | 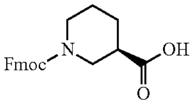 | 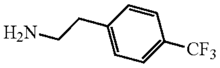 | 301.2<br>A |
| 1V | 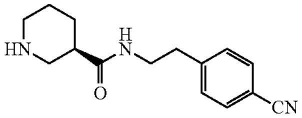 [SMILES: N#Cc1ccc(CCNC(=O)[C@@H]2CCCNC2)cc1] | 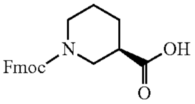 | 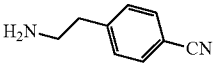 | 258.3<br>A |
| 1W | 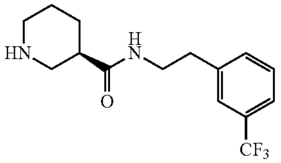 [SMILES: O=C(NCCc1cccc(C(F)(F)F)c1)[C@@H]1CCCNC1] | 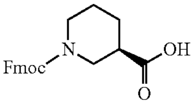 | 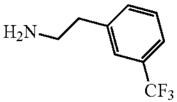 | 301.2<br>A |

TABLE 1-continued

| Inter-mediate | Structure | Acid | Amine | MS (M + H)+ |
|---|---|---|---|---|
| 1X | 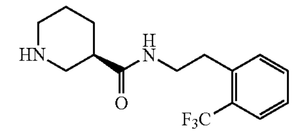 | 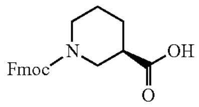 | 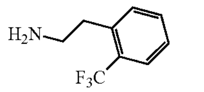 | 301.2 A |
| 1Y | 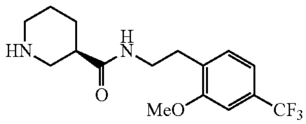 [SMILES: COc1cc(C(F)(F)F)ccc1CCNC(=O)[C@@H]1CCCNC1] | 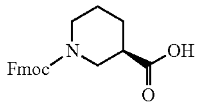 | 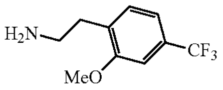 preparation see Intermediate 5B | 331.4 A |
| 1Z | 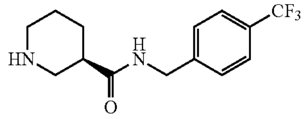 [SMILES: O=C(NCc1ccc(C(F)(F)F)cc1)[C@@H]1CCCNC1] | 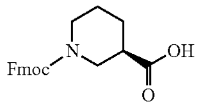 | 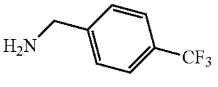 | 287.2 A |
| 1AA | 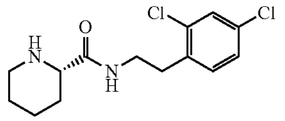 [SMILES: O=C(NCCc1ccc(Cl)cc1Cl)[C@@H]1CCCCN1] | 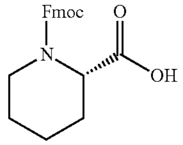 | 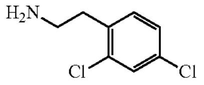 [SMILES: NCCc1ccc(Cl)cc1Cl] | 301.2 302.1 303.1 C |
| 1BB | 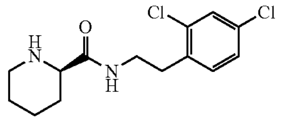 [SMILES: O=C(NCCc1ccc(Cl)cc1Cl)[C@H]1CCCCN1] | 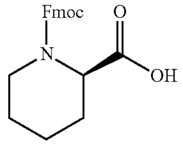 | 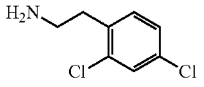 [SMILES: NCCc1ccc(Cl)cc1Cl] | 301.1 302.1 303.1 A |

Intermediate 2

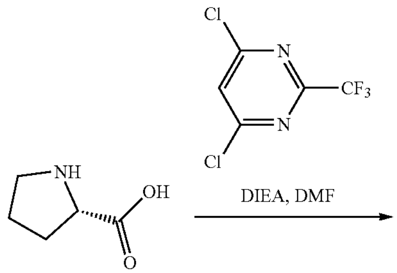

-continued

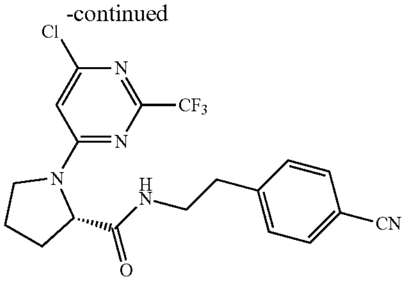

Intermediate 2

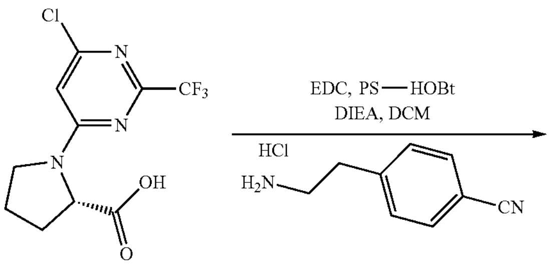

Intermediate 2A (S)-1-(6-chloro-2-(trifluoromethyl)pyrimidin-4-yl) pyrrolidine-2-carboxylic acid To a solution of L-Proline (690 mg, 6.0 mmol) in DMF (8.5 mL) were added 4,6-dichloro-2-(trifluoromethyl)pyrimidine (1.43 g, 6.60 mmol) and diisopropylethylamine (1.20 mL, 6.90 mmol). The reaction mixture was stirred at room temperature for one hour. The reaction mixture was concentrated in vacuo, and the residue was purified by silica gel chromatography (0-5% MeOH/DCM) to afford Intermediate 2A (1.2 g, 65%). LCMS (method A): m/z 296.2 $(M+H)^+$. $^1H$ NMR ($CDCl_3$) δ 6.52 (s, 1H), 6.74 (dd, 1H), 3.59 (m, 1H), 3.47 (m, 1H), 2.34-2.16 (m, 4H).

(S)-1-(6-chloro-2-(trifluoromethyl)pyrimidin-4-yl)-N-(4-cyanophenethyl)pyrrolidine-2-carboxamide To a solution of Intermediate 2A (148 mg, 0.50 mmol) in DCM (5 mL) were added sequentially 1-ethyl-3-(3-dimethylaminopropyl)carbodiimide (115 mg, 0.60 mmol), PS-HOBt resin (1.07 mmol/g) (560 mg, 0.60 mmol), 4-(2-aminoethyl)benzonitrile hydrochloride (96 mg, 0.53 mmol) and diisopropylethylamine (0.22 mL, 1.3 mmol). The reaction mixture was stirred at room temperature overnight. The resin was filtered, and washed with DCM and MeOH. The filtrate was concentrated in vacuo, and the residue was purified by silica gel chromatography (0-65% EtOAc/hexanes) to afford Intermediate 2 (116 mg, 55%). LCMS (method A): m/z 424.3 $(M+H)^+$. $^1H$ NMR ($CDCl_3$) δ 7.53 (d, 2H), 7.23 (d, 2H), 6.75 (br s, 1H), 6.48 (s, 1H), 4.61 (m, 1H), 3.56-3.49 (m, 3H), 3.39 (m, 1H), 2.86 (m, 2H), 2.38 (m, 2H), 2.15 (m, 1H), 1.98 (m, 1H).

Alternatively, Intermediate 2 can be prepared by reacting intermediate 1C with 4,6-dichloro-2-(trifluoromethyl)pyrimidine following the procedure as described for Intermediate 1, step 3.

Intermediate 3

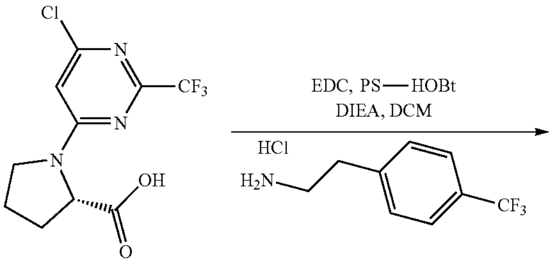

Intermediate 2A

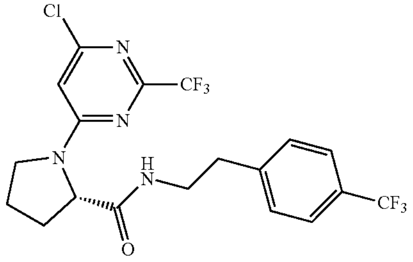

Intermediate 3

(S)-1-(6-chloro-2-(trifluoromethyl)pyrimidin-4-yl)-N-(4-(trifluoromethyl)phenethyl)-pyrrolidine-2-carboxamide Following the procedure described above for Intermediate 2, starting from intermediate 2A and using 2-(4-(trifluoromethyl)phenyl)ethanamine in step 2, Intermediate 3 was prepared. LCMS (method A): m/z 467.3 $(M+H)^+$. $^1H$ NMR ($CDCl_3$) δ 7.48 (d, 2H), 7.21 (d, 2H), 6.73 (br s, 1H), 6.45 (s, 1H), 4.61 (m, 1H), 3.59 (m, 1H), 3.49 (m, 2H), 3.32 (m, 1H), 2.85 (m, 2H), 2.37 (m, 2H), 2.14 (m, 1H), 1.97 (m, 1H).

Alternatively, Intermediate 3 can be prepared from intermediate 1D following the procedure as described for Intermediate 1, step 3.

Intermediate 4

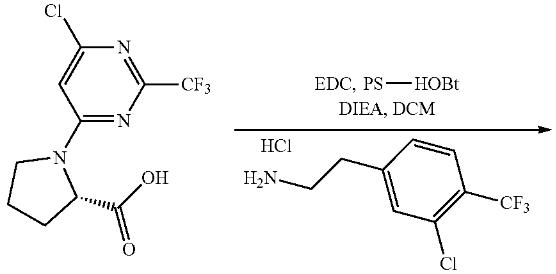

Intermediate 2A

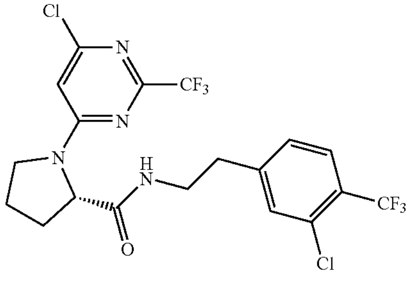

Intermediate 4

(S)-1-(6-chloro-2-(trifluoromethyl)pyrimidin-4-yl)-N-(3-chloro-4-(trifluoromethyl)-phenethyl)pyrrolidine-2-carboxamide Following the procedure described above for Intermediate 2, using 2-(3-chloro-4-(trifluoromethyl)phenyl)ethanamine in step 2, Intermediate 4 was prepared. LCMS (method D): m/z 501.0 $(M+H)^+$.

Intermediate 5

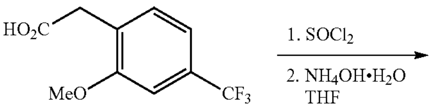

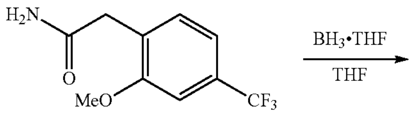

Intermediate 5A

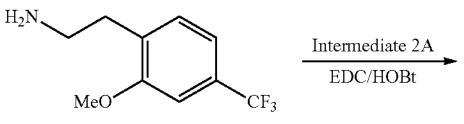

Intermediate 5B

-continued

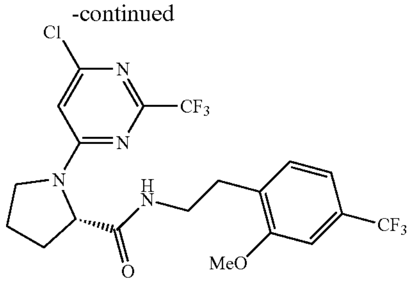

Intermediate 5

2-(2-methoxy-4-(trifluoromethyl)phenyl)acetamide 2-methoxy-4-trifluoromethyl-phenylacetic acid (1.2 g. 5.0 mmol) and thionyl chloride (2.9 mL, 40 mmol) were heated at reflux for two hours. The reaction was concentrated in vacuo, and azeotroped with anhydrous toluene (3x3 mL). The residue in THF (5 mL) was added to a solution of aqueous ammonium hydroxide (28-30%, 2.8 mL) in anhydrous THF (47 mL) at 0° C. The ice bath was then removed. The reaction was stirred vigorously for 1.5 hours, and was concentrated in vacuo. Water was added to the residue. The mixture was heated at 80° C. for 10 minutes, and then cooled to room temperature. The mixture was filtered to afford Intermediate 5A (1.03 g, 87%). LCMS (Method A): m/z 234.3 $(M+H)^+$.

2-(2-methoxy-4-(trifluoromethyl)phenyl)ethanamine

To Intermediate 5A (1.02 g, 4.37 mmol) in anhydrous THF (12 mL) was added 1M $BH_3$.THF (13.1 mL, 13.1 mmol). The solution was heated at reflux for 3.5 hours. The reaction was cooled to room temperature. After $H_2O$ (1.3 mL) and conc. HCl (5.1 mL) were added, the reaction was stirred for 30 minutes at reflux. The reaction was concentrated in vacuo to reduce the volume to ⅓ of the original amount, and 3N NaOH (12 mL) was added. The aqueous layer was extracted with ethyl ether (3x30 mL). The organic layers were dried ($Na_2SO_4$), filtered, and concentrated. The residue was purified by silica gel chromatography to afford Intermediate 5B (587 mg, 61%). LCMS (Method A): m/z 220.3 $(M+H)^+$. $^1H$ NMR ($CD_3OD$): δ 7.34-7.32 (d, 1H), 7.20-7.17 (m, 2H), 3.89 (s, 3H), 2.91-2.86 (m, 4H).

(S)-1-(6-chloro-2-(trifluoromethyl)pyrimidin-4-yl)-N-(2-methoxy-4-(trifluoromethyl)phenethyl)pyrrolidine-2-carboxamide Following the procedure described above for Intermediate 2, using HOBt instead of resin-bound HOBt, Intermediate 2A was coupled with intermediate 5B to afford Intermediate 5. LCMS (method A): m/z 497.5 $(M+H)^+$. Using the method outlined above to synthesize Intermediate 5B, the following intermediates were made using the precursors as indicated in Table 2.

TABLE 2

| Intermediate | Structure | Starting material | MS $(M + H)^+$ |
|---|---|---|---|
| 5C | 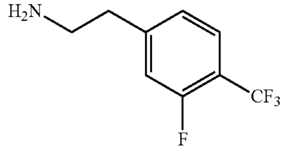 [SMILES: NCCc1ccc(C(F)(F)F)c(F)c1] | 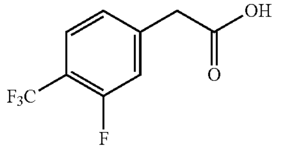 [SMILES: O=C(O)Cc1ccc(C(F)(F)F)c(F)c1] | 208.1<br>A |
| 5D | 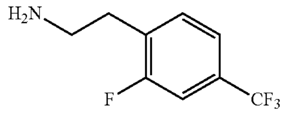 | 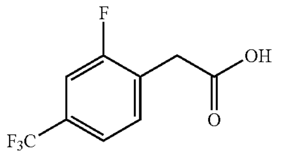 [SMILES: O=C(O)Cc1ccc(C(F)(F)F)cc1F] | 208.9<br>A |
| 5E | 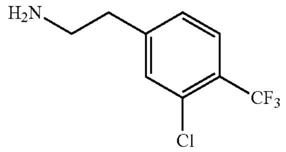 [SMILES: NCCc1ccc(C(F)(F)F)c(Cl)c1] | 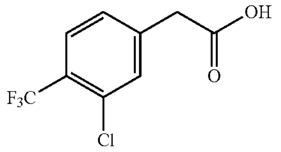 [SMILES: O=C(O)Cc1ccc(C(F)(F)F)c(Cl)c1] | 224.1<br>225.1<br>A |
| 5F | 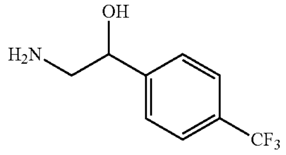 [SMILES: NCC(O)c1ccc(C(F)(F)F)cc1] | 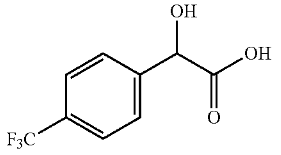 [SMILES: O=C(O)C(O)c1ccc(C(F)(F)F)cc1] | 220.1<br>A |
| 5G | 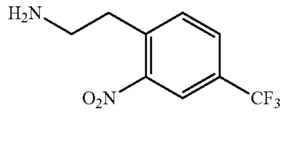 [SMILES: NCCc1ccc(C(F)(F)F)cc1[N+](=O)[O-]] | 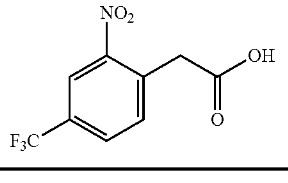 | 235.2<br>A |

Intermediate 6

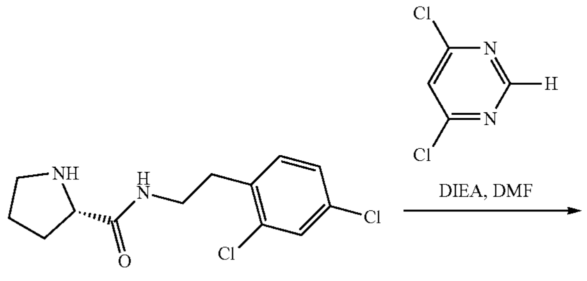

Intermediate 1B

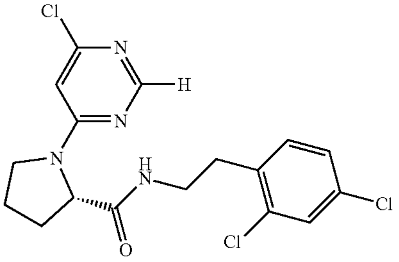

Intermediate 6

(S)-1-(6-chloropyrimidin-4-yl)-N-(2,4-dichlorophenethyl)pyrrolidine-2-carboxamide To a solution of Intermediate 1B (110 mg, 0.38 mmol) in DMF (1 mL) were added 4,6-dichloropyrimidine (80 mg, 0.54 mmol) and diisopropylethylamine (130 μL, 0.77 mmol). The reaction mixture was stirred at room temperature overnight. The reaction mixture was diluted with DCM, and washed with water and brine. The organic layer was dried ($Na_2SO_4$), filtered, and concentrated in vacuo. The residue was purified by silica gel chromatography (0-5% MeOH in DCM) to afford Intermediate 6 (129 mg, 84%). LCMS (method A): m/z 399.2 $(M+H)^+$. $^1H$ NMR ($CDCl_3$) δ 8.25 (s, 1H), 7.30 (t, 1H), 7.09 (m, 2H), 6.86 (br s, 1H), 6.36 (s, 1H), 4.60 (br s, 1H), 3.59-3.44 (m, 3H), 3.30 (br s, 1H), 2.97-2.83 (m, 2H), 2.36 (br, 1H), 2.09-1.96 (m, 3H).

Intermediate 7

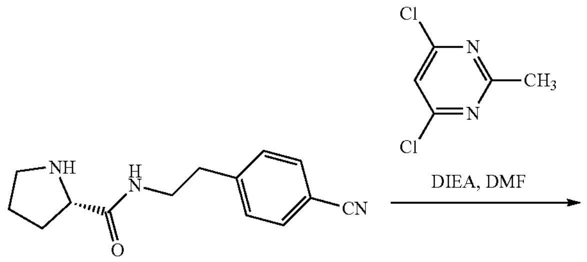

Intermediate 1C

-continued

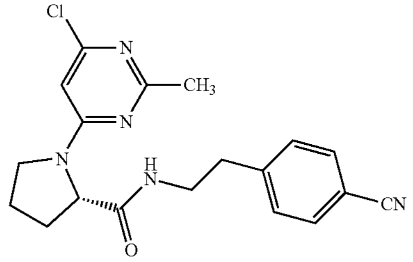

Intermediate 7

(S)-1-(6-chloro-2-methylpyrimidin-4-yl)-N-(4-cyanophenethyl)pyrrolidine-2-carboxamide Following the procedure described above for intermediate 6, intermediate 1C was reacted with 4,6-dichloro-2-methylpyrimidine by heating in a microwave for one hour at 100° C. to afford intermediate 7. LCMS (method A): m/z 421.5 $(M+H)^+$.

Intermediate 8

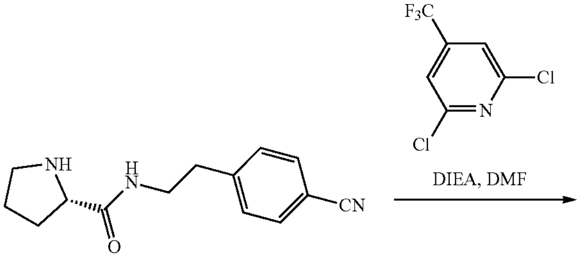

Intermediate 1C

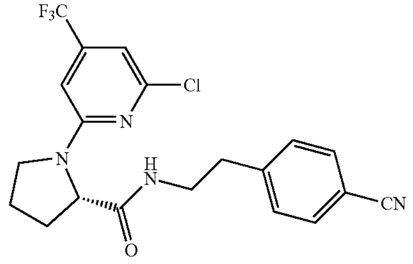

Intermediate 8

(S)-1-(6-chloro-4-(trifluoromethyl)pyridin-2-yl)-N-(4-cyanophenethyl)pyrrolidine-2-carboxamide Following the procedure described above for intermediate 6, intermediate 1C was reacted with 2,6-dichloro-4-(trifluoromethyl)pyridine by heating in a microwave for three hours at 100° C. to afford intermediate 8. LCMS (method A): m/z 423.3 $(M+H)^+$.

Intermediate 9

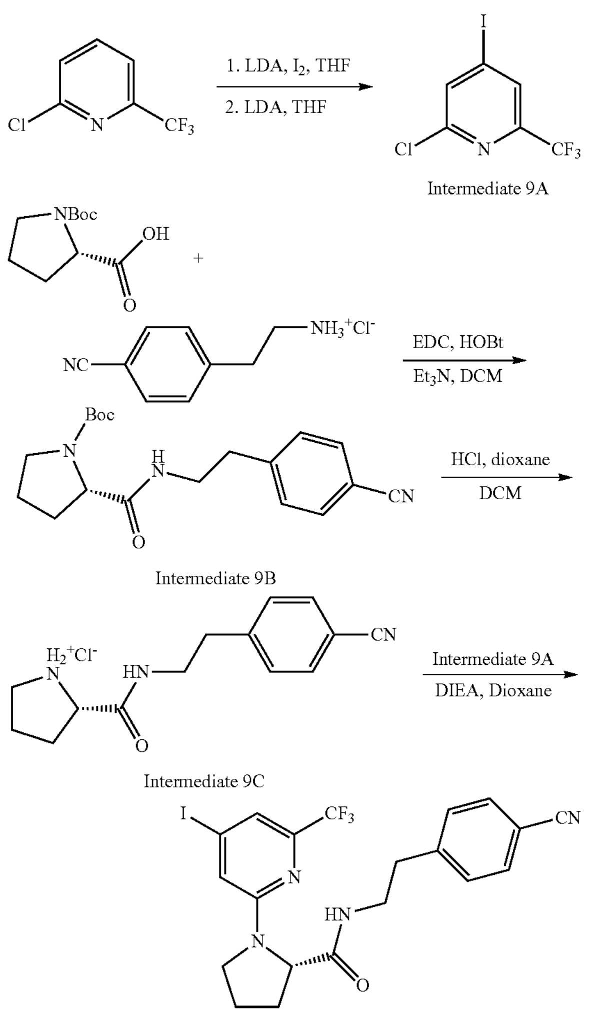

Intermediate 9

2-Chloro-4-iodo-6-(trifluoromethyl)pyridine

To a cooled (−100° C.) solution of diisopropylamine (14.5 mL, 104 mmol) in 80 mL of THF under inert atmosphere was added dropwise n-butyllithium (65 mL of a 1.6 M solution in hexanes, 104 mmol) followed by a 10 mL of THF solution of 2-chloro-6-(trifluoromethyl) pyridine (9.5 g, 52 mmol). After two hours, the temperature was raised to −78° C. and a 10 mL solution of iodine in THF (13 g, 52 mmol) was added. After 1 hour, the reaction was poured into water and extracted with DCM. The combined DCM layers were washed with brine, dried over sodium sulfate, and concentrated in vacuo to provide 14.9 g of a mixture of 6-chloro-3-iodo-2-(trifluoromethyl)pyridine and 2-chloro-4-iodo-6-(trifluoromethyl)pyridine. This crude material was resubjected to LDA as follows. To a cooled (−78° C.) solution of diisopropylamine (14.5 mL, 104 mmol) in 80 mL of THF under inert atmosphere was added dropwise n-butyllithium (65 mL of a 1.6 M solution in hexanes, 104 mmol) followed by a 30 mL solution of the preceding crude mixture in THF. After three hours, the reaction mixture was poured in water and extracted with DCM. The DCM layers were washed with brine, dried ($MgSO_4$), concentrated in vacuo, and purified via silica gel chromatography (0-20% EtOAc/hexanes) to afford Intermediate 9A as a white solid (6.9 g, 42%). $^1$H NMR ($CDCl_3$): δ 7.96 (s, 1H), 7.95 (s, 1H).

(S)-tert-butyl 2-((4-cyanophenethyl)carbamoyl)pyrrolidine-1-carboxylate

To a solution of Boc-L-proline (6.0 g, 28 mmol) in DCM (20 mL) were sequentially added EDC (5.4 g, 28 mmol), HOBt (3.8 g, 28 mmol), triethylamine (7.8 mL, 56 mmol) and 4-(2-aminoethyl)benzonitrile hydrochloride (5.1 g, 28 mmol). After stirring for 48 hours, the reaction mixture was washed with 1N HCl, saturated $NaHCO_3$ and brine, then dried ($MgSO_4$), and concentrated in vacuo to afford Intermediate 9B (9.17 g, 96%). $^1$H NMR ($CDCl_3$): δ 7.55 (d, 2H), 7.28 (d, 2H), 4.20 (bs, 1H), 3.48 (d, 2H), 3.30 (bs, 2H), 2.85 (m, 2H), 2.03 (m, 4H), 1.41 (s, 9H).

(S)—N-(4-cyanophenethyl)pyrrolidine-2-carboxamide hydrochloride

To a solution of Intermediate 9B (9.17 g, 26.7 mmol) in DCM (25 mL) was added a solution of 4N HCl/dioxane (33 mL, 130 mmol). After stirring one hour, the solvent was removed in vacuo to obtain Intermediate 9C which was carried to the next step without purification. LCMS (method A): m/z 244.3 $(M+H)^+$.

(S)—N-(4-cyanophenethyl)-1-(4-iodo-6-(trifluoromethyl)pyridin-2-yl)pyrrolidine-2-carboxamide To a solution of Intermediate 9C (13 mmol) in dioxane (25 mL) were added Intermediate 9A (4.1 g, 13 mmol) and DIEA (5.8 mL, 33 mmol). After stirring 96 hours at 95° C., the solvent was removed in vacuo, and the residue was redissolved in EtOAc, washed with brine, dried ($MgSO_4$), and concentrated in vacuo. The residue was purified via silica gel chromatography (0-100% EtOAc/hexanes) to afford Intermediate 9 (2.06 g, 30%). LCMS (method A): m/z 515.4 $(M+H)^+$. $^1$H NMR ($CDCl_3$): δ 7.37 (d, 2H), 7.23 (s, 1H), 7.07 (d, 2H), 6.91 (s, 1H), 4.46 (d, 1H), 3.40 (m, 3H), 3.22 (m, 1H), 2.74 (m, 2H), 2.11 (m, 1H), 2.03 (m, 2H), 1.08 (m, 1H).

Intermediate 10

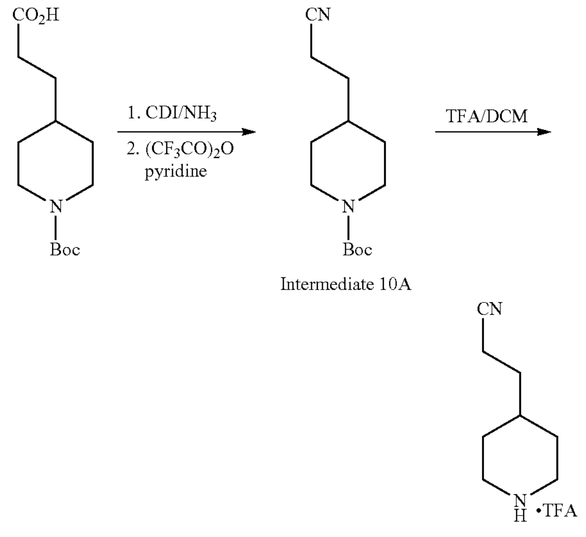

Intermediate 10 tert-butyl 4-(2-cyanoethyl)piperidine-1-carboxylate

To a stirred solution of 3-(1-(tert-butoxycarbonyl)piperidin-4-yl)propanoic acid (1.0 g, 3.9 mmol) in anhydrous THF (10 mL) under nitrogen was added carbonyldiimidazole (631 mg, 3.89 mmol). The reaction was stirred for 90 minutes, cooled to 0° C., and a solution of $NH_3$ in THF (0.40 M, 15 mL) was added. The ice bath was removed, and the mixture was stirred overnight. THF was removed under reduced pressure. The residue was dissolved in DCM (50 mL), washed with sat. $NaHCO_3$ (30 mL), and dried over sodium sulfate. The solution was filtered and concentrated in vacuo. This crude material was dissolved in anhydrous THF (20 mL) under nitrogen. Pyridine (0.940 mL, 11.7 mmol) and trifluoroacetic anhydride (3.20 mL, 23.3 mmol) were added dropwise. The mixture was stirred at room temperature overnight. After dilution with ether (100 mL), the mixture was washed with 1N HCl (50 mL), sat. $NaHCO_3$ (50 mL) and brine (50 mL). The organic layer was dried over sodium sulfate, filtered, and concentrated. The residue was purified by silica gel chromatography (0-50% EtOAc in hexanes) to afford Intermediate 10A (434 mg, 47%). $^1H$ NMR ($CDCl_3$) δ 4.12 (m, 2H), 2.70 (t, 2H), 2.39 (t, 2H), 1.85 (b, 1H), 1.69-1.59 (m, 4H), 1.45 (s, 9H), 1.11 (m, 2H).

3-(piperidin-4-yl)propanenitrile

Intermediate 10A was dissolved in DCM (3 mL), and TFA (1 mL) was added. The mixture was stirred at room temperature for 90 minutes. The solvent was removed under reduced pressure, and the residue was dried in vacuo to afford Intermediate 10 which was used in the next reaction without further purification. $^1H$ NMR ($CDCl_3$) δ 3.40 (t, 2H), 2.92 (t, 2H), 2.48 (t, 2H), 1.95 (d, 2H), 1.73-1.67 (m, 3H), 1.55-1.44 (m, 2H).

Intermediate 11

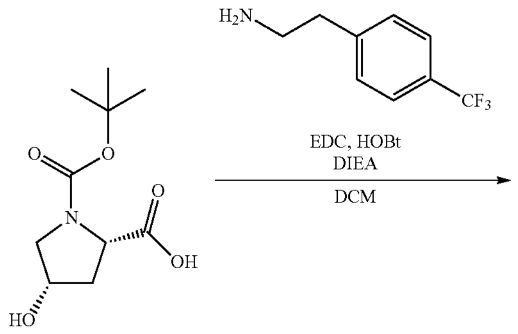

-continued

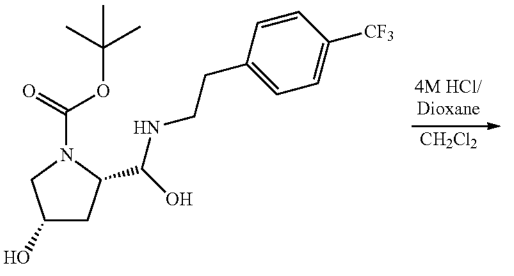

Intermediate 11A

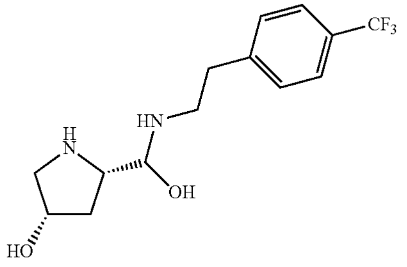

Intermediate 11

(2S,5S)-tert-butyl 2-hydroxy-5-((4-(trifluoromethyl)phenethyl)carbamoyl)-pyrrolidine-1-carboxylate Intermediate 11A was prepared from N-Boc-cis-4-hydroxy-L-proline (200 mg, 0.86 mmol) and 4-trifluoromethylphenethylamine (195 mg, 0.860 mmol) following the procedure as described for Intermediate 9, step 2. N,N-Diisopropylethylamine (0.23 mL, 1.3 mmol) was used instead of triethylamine. After work-up, the reaction mixture was purified by silica gel chromatography to afford Intermediate 11A (233 mg, 67%). LCMS (method A): m/z 303.2 $(M+H-Boc)^+$, $(M+Na)^+$425.3. $^1H$ NMR ($CDCl_3$): δ 7.57-7.55 (m, 2H), 7.34-7.32 (m, 2H), 7.14 (b, 1H), 5.06-5.03 (m, 1H), 4.39-4.32 (m, 2H), 3.63-3.40 (m, 4H), 2.89 (t, 2H), 2.34-2.28 (m, 1H), 2.14-2.07 (m, 1H), 1.55-1.38 (m, 9H).

(2S,5S)-5-hydroxy-N-(4-(trifluoromethyl)phenethyl)pyrrolidine-2-carboxamide hydrochloride Following the procedure as described in Intermediate 9, step 3, Intermediate 11A (233 mg, 0.58 mmol) was converted to Intermediate 11 (198 mg, quant.). LCMS (Method C): m/z 303.3 $(M+H)^+$. $^1H$ NMR ($CD_3OD$): δ 8.41 (m, 1H), 7.61-7.59 (m, 2H), 7.45-7.43 (m, 2H), 4.51-4.49 (m, 1H), 4.26-4.22 (m, 1H), 3.66-3.45 (m, 2H), 3.38-3.28 (m, 2H), 2.93 (t, 2H), 2.56-2.49 (m, 1H), 2.06-2.02 (m, 1H). Using the method outlined above to synthesize Intermediate 11, the following intermediates were made using the appropriate acids and amines as indicated in Table 3.

TABLE 3

| Inter-mediate | Structure | Starting Material | Amine | MS (M + H)$^+$ |
|---|---|---|---|---|
| 11B | 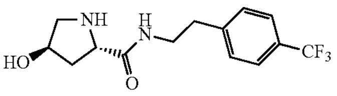 [SMILES: O=C(NCCc1ccc(C(F)(F)F)cc1)[C@@H]1C[C@@H](O)CN1] | 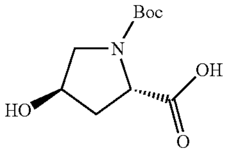 [SMILES: CC(C)(C)OC(=O)N1C[C@H](O)C[C@H]1C(=O)O] | 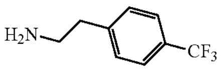 | 303.2 A |
| 11C | 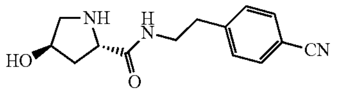 [SMILES: N#Cc1ccc(CCNC(=O)[C@@H]2C[C@@H](O)CN2)cc1] | 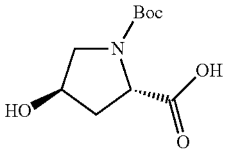 | 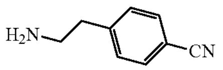 | 260.1 A |
| 11D | 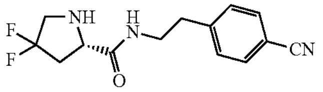 [SMILES: N#Cc1ccc(CCNC(=O)[C@@H]2CC(F)(F)CN2)cc1] | 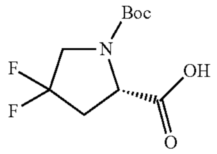 [SMILES: CC(C)(C)OC(=O)N1CC(F)(F)C[C@H]1C(=O)O] | 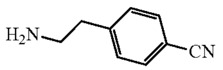 [SMILES: N#Cc1ccc(CCN)cc1] | 280.3 A |

Intermediate 12

(S)-1-(6-chloro-2-(trifluoromethyl)pyrimidin-4-yl)-N-(4-cyanophenethyl)azetidine-2-carboxamide

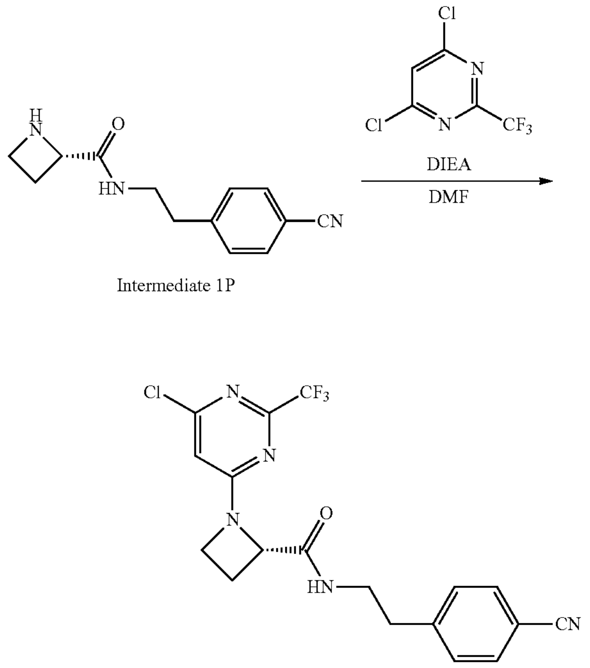

Intermediate 1P

Intermediate 12

To a solution of Intermediate 1P (120 mg, 0.54 mmol) in DMF (3.0 mL) were added N,N-diisopropylethylamine (103 μL, 0.590 mmol) and 4,6-dichloro-2-(trifluoromethyl)-pyrimidine (86 μL, 0.57 mmol). The solution was heated in a microwave at 90° C. for one hour, and was then partitioned between DCM and $H_2O$. The aqueous layer was extracted with DCM (2×), and the combined organic layers were washed with brine, dried ($Na_2SO_4$), filtered and concentrated in vacuo. The residue was purified by silica gel chromatography to afford Intermediate 12 (191 mg, 86%). LCMS (Method A): m/z 410.2 (M+H)$^+$. $^1$H NMR ($CDCl_3$): δ 7.66-7.52 (m, 3H), 7.27-7.25 (m, 2H), 6.35 (s, 1H), 4.94-4.86 (m, 1H), 4.12-4.07 (m, 1H), 4.01-3.95 (m, 1H), 3.61-3.52 (m, 2H), 2.99-2.83 (m, 3H), 2.64-2.55 (m, 1H). Using the method outlined above to synthesize Intermediate 12, the following intermediates were made using the precursors as indicated in Table 4.

TABLE 4

| Intermediate | Structure | Precursor | MS $(M + H)^+$ |
|---|---|---|---|
| 12A | 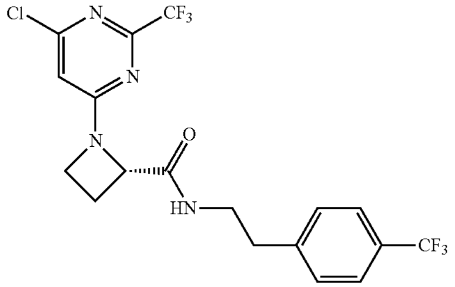 [SMILES: O=C(NCCc1ccc(C(F)(F)F)cc1)[C@@H]1CCN1c1cc(Cl)nc(C(F)(F)F)n1] | Intermediate 1Q | 453.2 A |
| 12B | 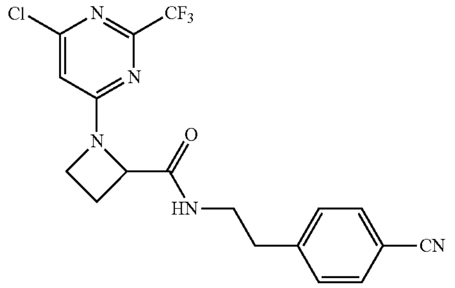 [SMILES: N#Cc1ccc(CCNC(=O)C2CCN2c2cc(Cl)nc(C(F)(F)F)n2)cc1] | Intermediate 1R | 410.2 A |
| 12C | 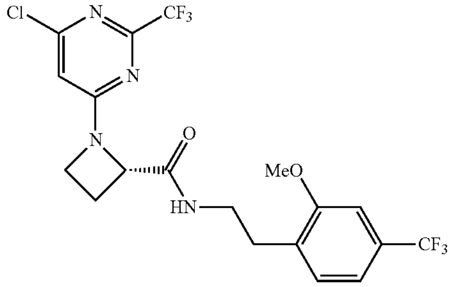 [SMILES: COc1cc(C(F)(F)F)ccc1CCNC(=O)[C@@H]1CCN1c1cc(Cl)nc(C(F)(F)F)n1] | Intermediate 1S | 483.4 A |

Intermediate 13

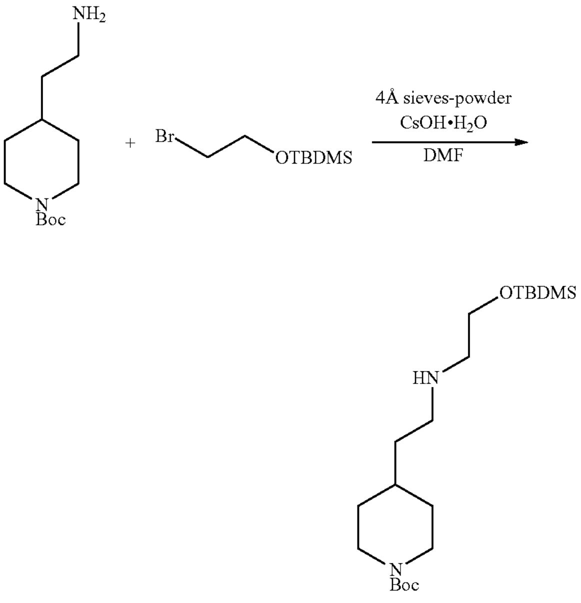

Intermediate 13 tert-butyl 4-(2-((2-tert-butyldimethlsilyl)oxy)ethyl) amino)ethyl)piperidine-1-carboxylate To a suspension of activated molecular sieves in DMF (2.2 mL) was added $CsOH.H_2O$ (74 mg, 0.44 mmol), and the mixture was stirred vigorously for 10 minutes. tert-Butyl 4-(2-aminoethyl)piperidine-1-carboxylate (99 μL, 0.44 mmol) was added, and the mixture was stirred for 30 minutes. Then (2-bromoethoxy)(tert-butyl)dimethylsilane (93 μL, 0.53 mmol) was added, and the mixture was stirred at room temperature overnight. The reaction was filtered, washed with EtOAc, and partitioned between EtOAc and 1N NaOH. The aqueous layer was extracted with EtOAc (3×). The combined organic layers were washed with brine, dried ($Na_2SO_4$), filtered and concentrated in vacuo. The residue was purified by silica gel chromatography to afford Intermediate 13 (72.6 mg, 43%). LCMS: m/z 387.6 $(M+H)^+$. $^1H$ NMR ($CDCl_3$): δ 3.99 (br, 2H), 3.67 (t, 2H), 2.68-2.59 (m, 6H), 1.76-1.54 (m, 5H), 1.10-1.09 (3H), 0.84 (s, 9H), 0.01 (s, 6H).

Intermediate 14

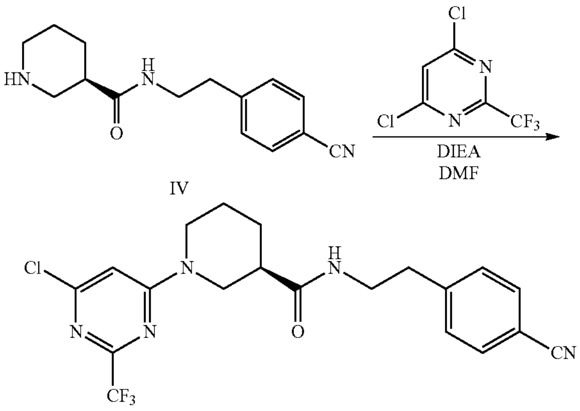

IV

Intermediate 14

(R)-1-(6-chloro-2-(trifluoromethyl)pyrimidin-4-yl)-N-(4-cyanophenethyl)piperidine-3-carboxamide Following the procedure as described for Intermediate 12, Intermediate 1V (85 mg, 0.33 mmol) was converted to Intermediate 14 (57 mg, 39%). LCMS (Method A): m/z 438.3 $(M+H)^+$. $^1H$ NMR ($CDCl_3$): δ 7.58 (m, 2H), 7.27 (d, 2H), 6.58 (s, 1H), 5.94 (br s, 1H), 4.13 (br s, 1H), 3.63-3.49 (m, 3H), 3.24 (br, 1H), 2.94-2.83 (m, 2H), 2.34 (m, 1H), 2.07-1.70 (m, 3H), 1.55 (m, 2H).

Alternatively, Intermediate 14 can be prepared using a method similar to what was used for Intermediate 2, as shown in the scheme shown below:

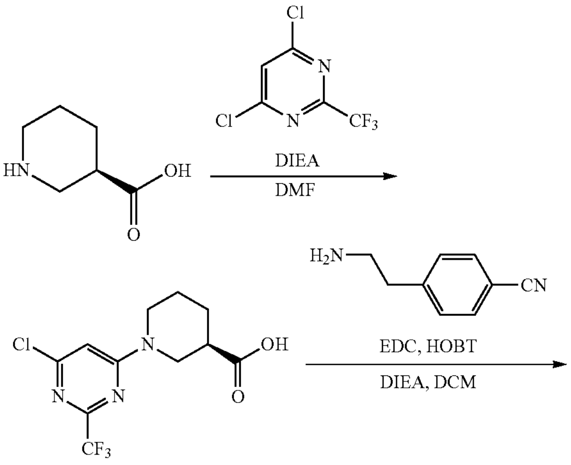

Intermediate 14A

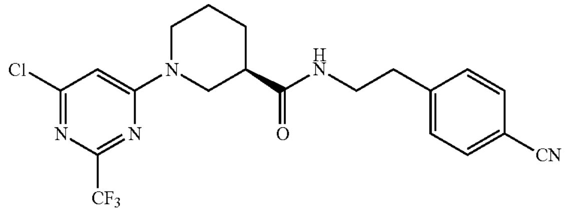

Intermediate 14

Using the method outlined above to synthesize Intermediate 14, the following intermediates were made using the precursors as indicated in Table 5.

TABLE 5

| Inter-mediate | Structure | Precursor | MS $(M+H)^+$ |
|---|---|---|---|
| 14B | 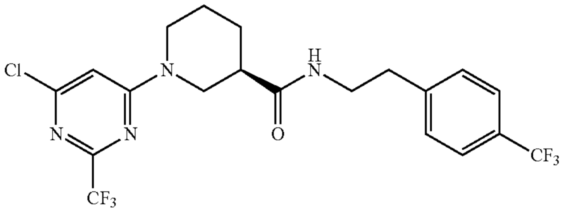 [SMILES: O=C(NCCc1ccc(C(F)(F)F)cc1)[C@@H]1CCCN(c2cc(Cl)nc(C(F)(F)F)n2)C1] | Intermediate 1U | 480.1 A |
| 14C | 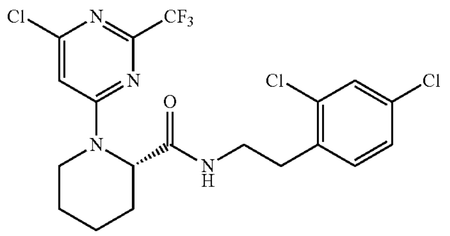 [SMILES: O=C(NCCc1ccc(Cl)cc1Cl)[C@@H]1CCCCN1c1cc(Cl)nc(C(F)(F)F)n1] | Intermediate 1AA | 481.2 A |
| 14D | 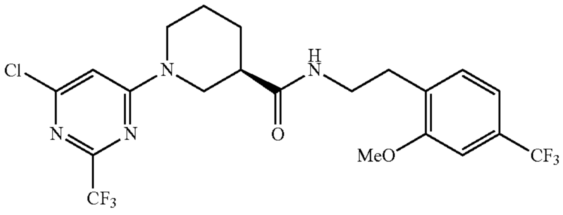 [SMILES: COc1cc(C(F)(F)F)ccc1CCNC(=O)[C@@H]1CCCN(c2cc(Cl)nc(C(F)(F)F)n2)C1] | Intermediate 1Y | 511.4 A |

Intermediate 15

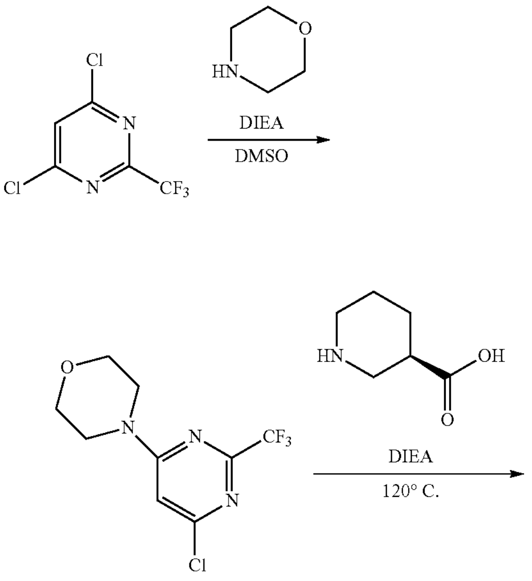

Intermediate 15A

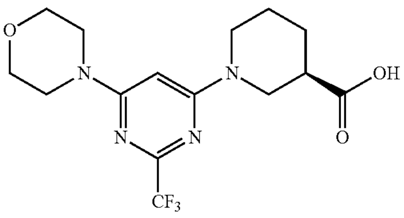

Intermediate 15

4-(6-chloro-2-(trifluoromethyl)pyrimidin-4-yl)morpholine

A mixture of 4,6-Dichloro-2-(trifluoromethyl)pyrimidine (70 μL, 0.46 mmol), morpholine (38 μL, 0.44 mmol) and diisopropylethylamine (80 μL, 0.46 mmol) in DMSO (0.5 mL) was stirred at room temperature for one hour to afford Intermediate 15A. LCMS (method A): m/z 268.1 $(M+H)^+$. The reaction mixture was used directly in the next reaction.

(R)-1-(6morpholino-2-(trifluoromethyl)pyrimidin-4-yl)piperidine-3-carboxylic acid To a reaction mixture of 15A were (R)-piperidine-3-carboxylic acid (100 mg, 0.77 mmol) and diisopropylethylamine (134 μL, 0.77 mmol), and the reaction was heated at 120° C. in a microwave for four hours. The reaction mixture was purified directly by MS-HPLC to afford Intermediate 15 (69 mg, 42%). LCMS (method A): m/z 361.2 $(M+H)^+$. $^1H$ NMR ($CD_3OD$): δ 5.90 (s, 1H), 4.40 (d, 1H), 4.14 (d, 1H), 3.72 (t, 4H), 3.58 (t, 4H), 3.29-3.09 (m, 2H), 2.50 (m, 1H), 2.09 (m, 1H), 1.77 (m, 2H), 3 (m, 1H). Using the method outlined above to synthesize Intermediate 15, the following intermediate was made from Intermediate 15A and the reagent as indicated in Table 6.

TABLE 6

| Inter-mediate | Structure | Reagent | MS $(M + H)^+$ |
|---|---|---|---|
| 15B | 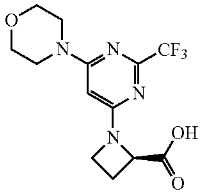 [SMILES: O=C(O)[C@H]1CCN1c1cc(N2CCOCC2)nc(C(F)(F)F)n1] | 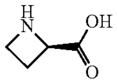 | 333.2 A |

Intermediate 16

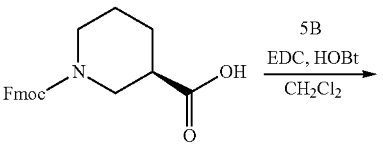

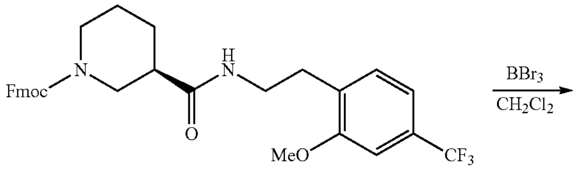

Intermediate 16A

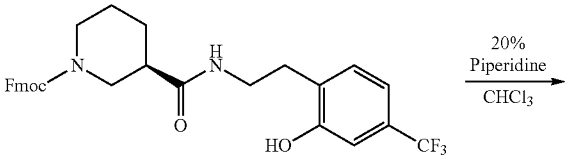

Intermediate 16B

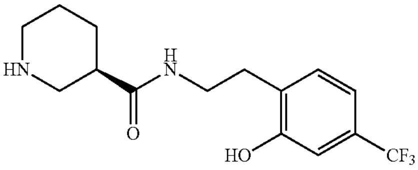

Intermediate 16

(R)-(9H-fluoren-9-yl)methyl 3-((2-methoxy-4-(trifluoromethyl)phenethyl)-carbamoyl)piperidine-1-carboxylate Following the procedure as described in Intermediate 1, step 1, (R)-1-(((9H-fluoren-9-yl)methoxy)carbonyl)piperidine-3-carboxylic acid (160 mg, 0.45 mmol) was coupled with Intermediate 5B (110 mg, 0.50 mmol) to afford Intermediate 16A (124 mg, 50%). LCMS (method A): m/z 553.5 $(M+H)^+$.

(R)-(9H-fluoren-9-yl)methyl 3-((2-hydroxy-4-(trifluoromethyl)phenethyl) carbamoyl)piperidine-1-carboxylate To a solution of Intermediate 16A (145 mg, 0.260 mmol) in DCM (5 mL) at −78° C., $BBr_3$ (250 μL, 2.6 mol) was added dropwise. The reaction was stirred for one hour at −78° C., and then at room temperature for three hours. The reaction was cooled to 0° C. and quenched with $NaHCO_3$. The mixture was extracted with DCM (3×). The combined organic layers were washed with brine, dried ($Na_2SO_4$), filtered, and concentrated. The residue was purified by silica gel chromatography to afford Intermediate 16B (116 mg, 82%). LCMS (method A): m/z 539.5 $(M+H)^+$.

(R)—N-(2-hydroxy-4-(trifluoromethyl)phenethyl) piperidine-3-carboxamide

Following the procedure as described in Intermediate 1, step 2, Intermediate 16B (152 mg, 0.18 mmol) was converted to Intermediate 16 (65.2 mg, 73%). LCMS (method A): m/z 317.4 $(M+H)^+$. $^1H$ NMR ($CD_3OD$): δ 7.21-7.19 (d, 1H), 7.01-6.99 (m, 2H), 3.42 (t, 2H), 2.97-2.89 (m, 2H), 2.84 (t, 2H), 2.70-2.64 (m, 1H), 2.59-2.52 (m, 1H), 2.32-2.25 (m, 1H), 1.85-1.81 (m, 1H), 1.70-1.44 (m, 3H).

Intemediate 17

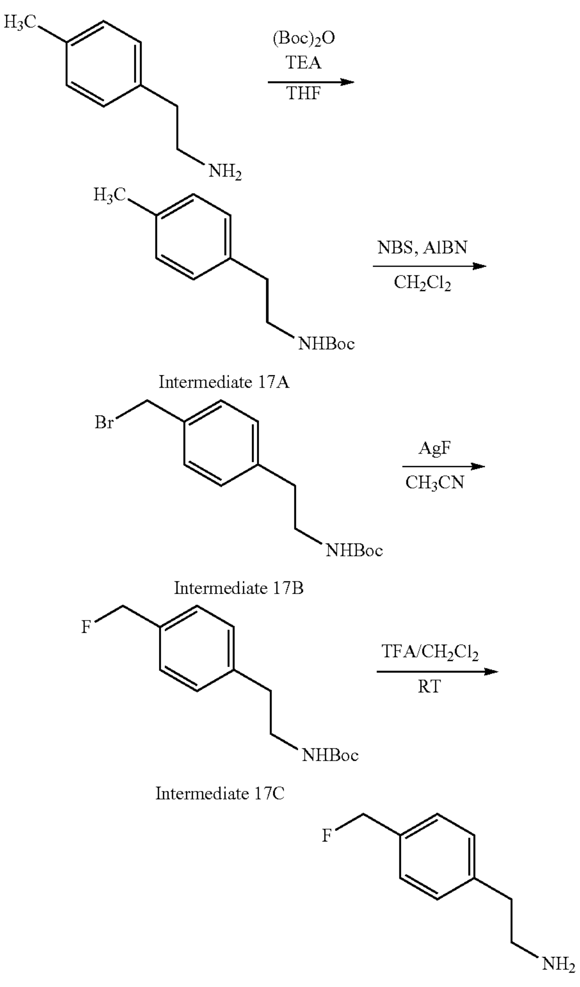

Intermediate 17A

Intermediate 17B

Intermediate 17C

Intermediate 17 tert-butyl 4-methylphenethylcarbamate

To a solution of 2-(p-tolyl)ethanamine (250 mg, 1.85 mmol) in anhydrous THF (8.5 mL) at 0° C. were added triethylamine (187 mg, 1.85 mmol) and di-tert-butyl dicarbonate (404 mg, 1.85 mmol). The reaction was stirred at 0° C. for 15 minutes, and concentrated in vacuo. The residue was diluted with EtOAc (50 mL), and washed with 0.5 N HCl (20 mL) and $H_2O$ (20 mL). The organic layer was dried ($Na_2SO_4$), filtered, and concentrated in vacuo. The residue was purified by silica gel chromatography to afford Intermediate 17A (397 mg, 91%). LCMS (method A): m/z 236.3 $(M+H)^+$.

tert-butyl 4-(bromomethyl)phenethylcarbamate

To a solution of Intermediate 17A (59.3 mg, 2.52 mmol) in DCM (84 mL) were added recrystallized N-bromosuccinimide (417 mg, 2.34 mmol) and AIBN (91 mg, 0.55 mmol). The reaction was heated for 50 minutes at 50° C., and then cooled to room temperature. The mixture was concentrated in vacuo. The residue was purified by silica gel chromatography to afford Intermediate 17B (120 mg, 15%). $^1H$ NMR ($CDCl_3$): δ 7.35-7.33 (m, 2H), 7.18-7.16 (m, 2H), 4.53 (b, 1H), 4.49 (s, 2H), 3.40-3.35 (m, 2H), 2.79 (t, 2H), 1.40 (s, 9H).

tert-butyl 4-(fluoromethyl)phenethylcarbamate

To a solution of Intermediate 17B (97 mg, 0.31 mmol) in anhydrous $CH_3CN$ (4.4 mL) in a pre-dried flask was added AgF (165 mg, 1.30 mmol). The reaction was heated to 65° C. for 2.5 hours. The reaction was cooled to room temperature, and concentrated in vacuo. The residue was purified by silica gel chromatography to afford Intermediate 17C (72 mg, 92%). $^1H$ NMR ($CDCl_3$): δ 7.34-7.32 (dd, 2H), 7.24-7.22 (m, 2H), 5.41 (s, 1H), 5.29 (s, 1H), 4.52 (b, 1H), 3.41-3.36 (m, 2H), 2.82 (t, 2H), 1.43 (s, 9H).

2-(4-(fluoromethyl)phenyl)ethanamine trifluoroacetate

Following the procedure as described in Intermediate 10, step 2, Intermediate 17C (94 mg, 0.37 mmol) was converted to Intermediate 17 (125 mg, 88%). LCMS (method A): m/z 154.2 $(M+H)^+$. $^1H$ NMR ($CD_3OD/CDCl_3$): δ 7.41-7.39 (m, 2H), 7.32-7.30 (m, 2H), 5.36 (s, 2H), 3.19-3.15 (m, 2H), 3.02-2.98 (m, 2H).

Intermediate 18

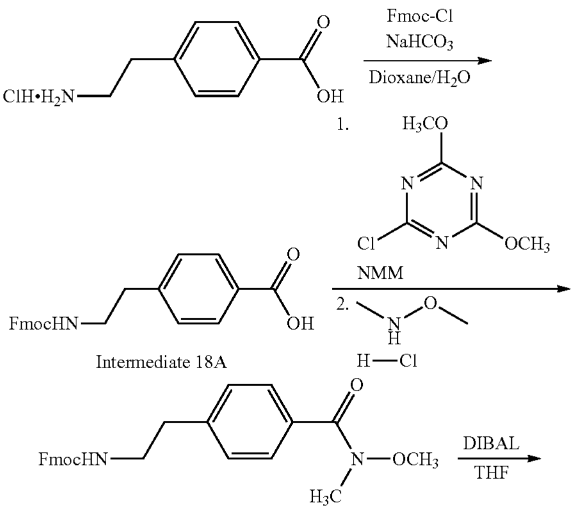

Intermediate 18A

Intermediate 18B

-continued

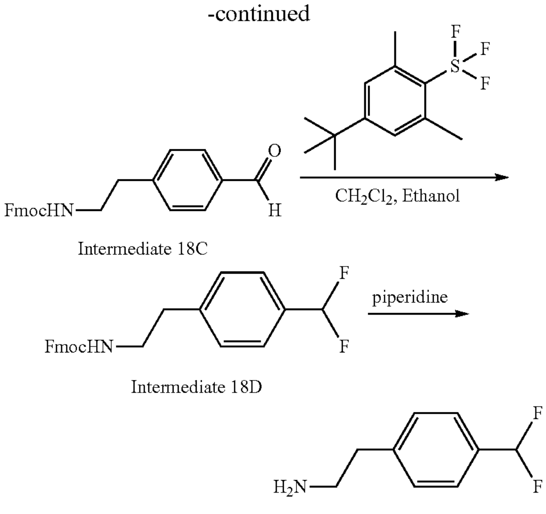

Intermediate 18C

Intermediate 18D

Intermediate 18

4-(2-((((9H-fluoren-9-yl)methoxy)carbonyl)amino)ethyl)benzoic acid

A mixture of 4-(2 aminoethyl)benzoic acid (1.0 g, 5.0 mmol) and $NaHCO_3$ (1.0 g, 12 mmol) in $H_2O$ (10 mL) (pre-cooled at 0° C.) was slowly added to a mixture of Fmoc-Cl (1.9 g, 7.4 mmol) in dioxane (20 mL) at 0° C. After 45 minutes at 0° C., the reaction was acidified to pH 1 with 1 N HCl, and extracted with EtOAc (3×75 mL). The combined organic layers were dried ($Na_2SO_4$), filtered, and concentrated in vacuo. The residue was purified by silica gel chromatography to afford Intermediate 18A (715 mg, 37%). LCMS (method A): m/z 388.4 $(M+H)^+$.

(9H-fluoren-9-yl)methyl 4-(methoxy(methyl)carbamoyl)phenethylcarbamate

To a solution of Intermediate 18A (387 mg, 1.00 mmol) in THF (3 mL) at room temperature were added 2-chloro-4,6-dimethoxy-1,3,5-triazine (210 mg, 1.2 mmol) and N-methylmorpholine (NMM, 0.33 mL, 3.0 mmol). The reaction was stirred for one hour, and N,O-dimethylhydroxylamine. HCl (98 mg, 1.0 mmol) was added. The reaction was stirred overnight at room temperature. The reaction was quenched with $H_2O$ (4 mL), and extracted with DCM. The combined organic layers were dried ($Na_2SO_4$), filtered, and concentrated in vacuo. The residue was purified by silica gel chromatography to afford Intermediate 18B (306 mg, 71%). LCMS (method A): m/z 431.4 $(M+H)^+$.

(9H-fluoren-9-yl)methyl 4-formylphenethylcarbamate

To a solution of Intermediate 18B (300 mg, 0.70 mmol) in anhydrous THF (7 mL) at −78° C. was added DIBAL (1M in hexanes, 3.5 mL, 3.5 mmol) dropwise. After one hour the reaction was quenched with saturated citric acid. The cold bath was removed and the reaction was poured into brine (45 mL), and extracted with DCM (2×60 mL). The combined organic layer was dried ($Na_2SO_4$), filtered, and concentrated in vacuo. The residue was purified by silica gel chromatography to afford Intermediate 18C (195 mg, 75%). LCMS (method A): m/z 372.4 $(M+H)^+$.

(9H-fluoren-9-yl)methyl 4-(difluoromethyl)phenethylcarbamate

To a solution of 4-tert-butyl-2-6-dimethylphenylsulfur trifluoride (298 mg, 1.19 mmol) in anhydrous DCM (1.5 mL) in a polyfluor vessel were added Intermediate 18C (250 mg, 0.68 mmol) and EtOH (16 μL, 0.27 mmol). After stirring 24 hours at room temperature, the reaction was pipetted into aqueous ammonia (28-30%, 3.5 mL) at 0° C. The mixture was stirred for one hour at room temperature. The organic layer was washed with $H_2O$, dried ($MgSO_4$), filtered, and concentrated in vacuo. The residue was purified by silica gel chromatography to afford Intermediate 18D (124 mg, 74%). LCMS (method A): m/z 394.4 $(M+H)^+$.

2-(4-(difluoromethyl)phenyl)ethanamine

Following the procedure as described in Intermediate 1, step 2, Intermediate 18D (124 mg, 0.320 mmol) was converted to Intermediate 18 (16 mg, 29%). LCMS (method A): m/z 172.3 $(M+H)^+$. $^1H$ NMR ($CD_3OD$): δ 7.49-7.47 (m, 2H), 7.36-7.34 (m, 2H), 6.72 (t, 1H), 2.95-2.92 (m, 2H), 2.86-2.82 (m, 2H).

Intermediate 19

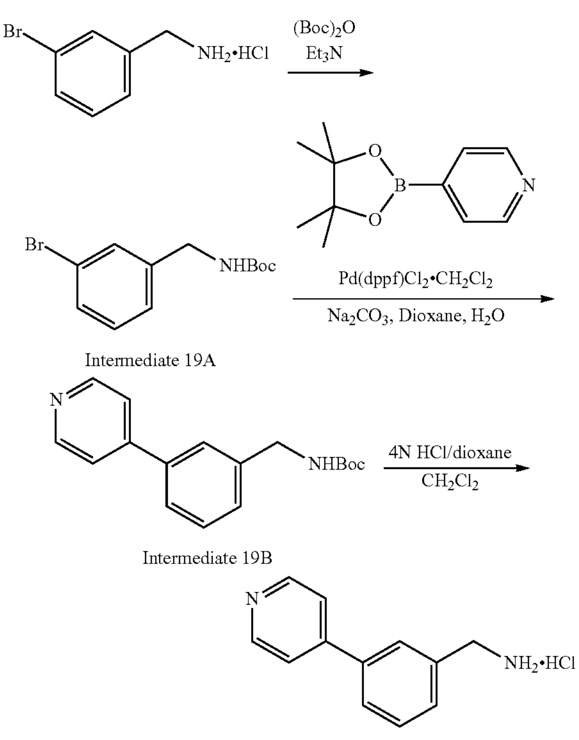

Intermediate 19A

Intermediate 19B

Intermediate 19 tert-butyl 3-bromobenzylcarbamate

To a solution of (3-bromophenyl)methanamine hydrochloride (5.0 g, 23 mmol) and di-tert-butyl dicarbonate (5.0 g, 24 mmol) in DCM (50 mL) was added triethylamine (3.2 mL, 23 mmol). The reaction was stirred overnight at room temperature. The mixture was washed with $H_2O$, and the organic layer was dried ($Na_2SO_4$), filtered, and concentrated to afford Intermediate 19A (6.5 g, quant.). $^1H$ NMR ($CDCl_3$): δ 7.43 (br s, 1H), 7.41-4.38 (m, 1H), 7.21-7.17 (m, 2H), 4.88 (br s, 1H), 4.30-4.29 (m, 2H), 1.47 (s, 9H).

tert-butyl 3-(pyridin-4-yl)benzylcarbamate

Intermediate 19A (504 mg, 1.77 mmol), 4-(4,4,5,5-tetramethyl-1,3,2-dioxaborolan-2-yl)pyridine (726 mg, 3.54 mmol), and sodium carbonate (375 mg, 3.54 mmol) were combined in dioxane (8 mL) and $H_2O$ (2 mL), and purged with nitrogen for 5 minutes. Pd(dppf)$Cl_2$. $CH_2Cl_2$ (145 mg, 0.180 mmol) was added, and the reaction was heated to 80° C. for three hours. The reaction was cooled to room temperature, and washed with $H_2O$. The solvent was removed in vacuo and the residue was purified by silica gel chromatography to afford Intermediate 19B (388 mg, 77%). LCMS (method A): m/z 285.2. $^1$H NMR ($CDCl_3$): δ 8.67-8.66 (dd, 2H), 7.55-7.36 (m, 6H), 4.92-4.91 (br s, 1H), 4.41-4.40 (m, 2H), 1.48 (s, 9H).

(3-(pyridin-4-yl)phenyl)methanamine hydrochloride

Following the procedure described in Intermediate 9, step 3, Intermediate 19B (388 mg, 1.36 mmol) was treated with 4N HCl/dioxane (3.4 mL, 13.6 mmol) to afford Intermediate 19 (360 mg, quant.). LCMS (method A): m/z 185.1 $(M+H)^+$. $^1$H NMR ($CD_3OD$): δ 8.94-8.92 (m, 2H), 8.48-8.46 (m, 2H), 8.18 (s, 1H), 8.08-8.05 (m, 1H), 7.78-7.71 (m, 2H), 4.29 (s, 2H).

Intermediate 20

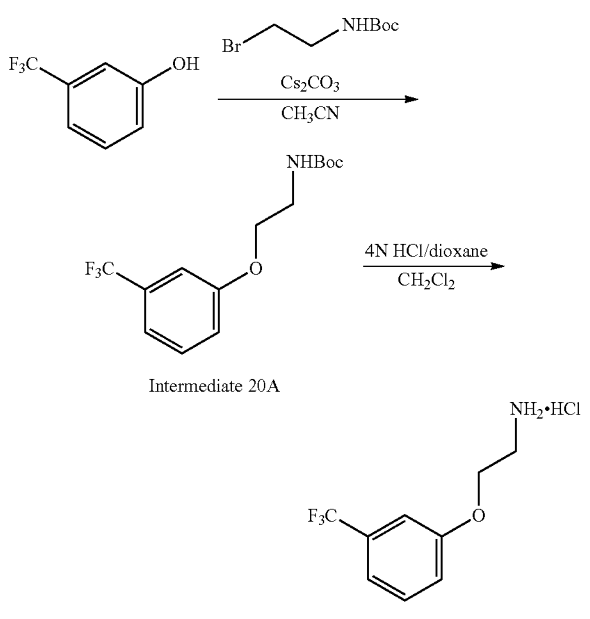

Intermediate 20A

Intermediate 20 tert-butyl (2-(3-(trifluoromethyl)phenoxy)ethyl)carbamate

To a solution of 3-(trifluoromethyl)phenol (0.15 mL, 1.20 mmol) in $CH_3CN$ (6.2 mL) were added tert-butyl (2-bromoethyl)carbamate (415 mg, 1.85 mmol) and cesium carbonate (721 mg, 2.21 mmol). The reaction was stirred at room temperature for four hours. The reaction was partitioned between EtOAc and $H_2O$, and the aqueous layer was extracted (2×25 mL) with EtOAc. The combined organic layers were washed with brine, dried ($Na_2SO_4$), filtered, and concentrated in vacuo. The residue was purified by silica gel chromatography to afford Intermediate 20A (198 mg, 53%). LCMS (method A): m/z 206.2 $(M-Boc)^+$. $^1$H NMR ($CDCl_3$): δ 7.41-7.37 (m, 1H), 7.23-7.21 (m, 1H), 7.17 (s, 1H), 7.08-7.05 (m, 1H), 4.96 (b, 1H), 4.06 (t, 2H), 3.58-3.54 (m, 2H), 1.46 (s, 9H).

2-(3-(trifluoromethyl)phenoxy)ethanamine hydrochloride

Following the procedure as described in Intermediate 9, step 3, Intermediate 20A (196 mg, 0.64 mmol) was converted to Intermediate 20 (149 mg, 96%). LCMS (method A): m/z 206.2 $(M+H)^+$. $^1$H NMR ($CD_3OD$): δ 7.53-7.50 (m, 1H), 7.32-7.26 (m, 3H), 4.29 (t, 2H), 3.39 (t, 2H). Using the method outlined above to synthesize Intermediate 20, the following intermediates were made using starting materials as indicated in Table 7.

TABLE 7

| Intermediate | Structure | Alcohol | MS $(M + H)^+$ |
|---|---|---|---|
| 20B | 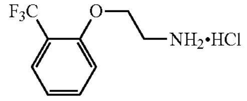 | 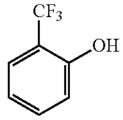 [SMILES: Oc1ccccc1C(F)(F)F] | 206.2 A |
| 20C | 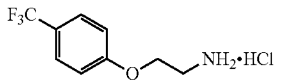 | 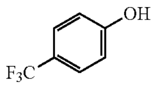 | 206.2 A |

Intermediate 21

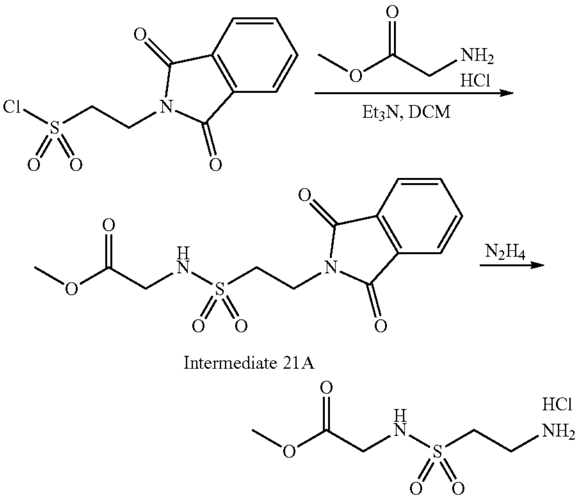

Intermediate 21A

Intermediate 21

Methyl 2-(2-(1,3-dioxoisoindolin-2-yl)ethylsulfonamido)acetate

To a solution of methyl 2-aminoacetate hydrochloride (25 mg, 0.20 mmol) and triethylamine (69 μL, 0.49 mmol) in DCM (1 mL) was added 2-(1,3-dioxoisoindolin-2-yl)ethanesulfonyl chloride (45 mg, 0.16 mmol). The reaction mixture was stirred at room temperature for three hours. The reaction mixture was concentrated in vacuo, and the residual was purified by silica gel chromatography (0-10% MeOH/DCM) to afford Intermediate 21A (37 mg, 70%). LCMS (method A): m/z 327.2 $(M+H)^+$. $^1H$ NMR ($CDCl_3$) δ 7.87-7.84 (m, 2H), 7.76-7.72 (m, 2H), 5.56 (t, 1H), 4.33 (t, 2H), 4.04 (d, 2H), 3.77 (s, 3H), 3.45 (t, 2H).

Methyl 2-(2-aminoethylsulfonamido)acetate hydrochloride

To a solution of Intermediate 21A (701 mg, 2.15 mmol) in MeOH (4 mL) was added hydrazine monohydrate (104 μL, 2.15 mmol). The reaction mixture was stirred at room temperature overnight. Concentrated hydrochloric acid (1.5 mL) was added, and the white solid was removed by filtration. The filtrate was evaporated to afford Intermediate 21 (720 mg). LCMS (method A): m/z 197.1 $(M+H)^+$. This compound was used directly in the next step without further purification.

Intemediate 22

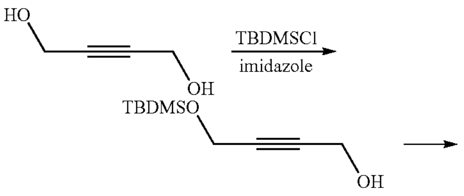

Intermediate 22A

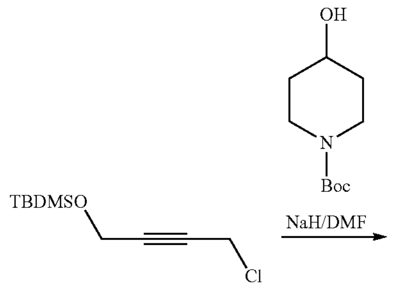

Intermediate 22B

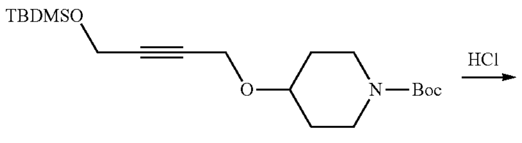

Intermediate 22C

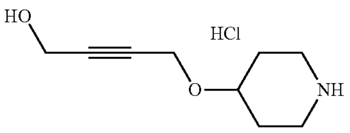

Intermediate 22

4-((tert-butyldimethylsilyl)oxy)but-2-yn-1-ol

To a solution of but-2-yne-1,4-diol (50 g, 580 mmol) in dry DMF (250 mL) were added TBDMSCl (22.0 g, 145 mmol), followed by imidazole (20 g, 290 mmol) in small portions at room temperature under $N_2$. The reaction mixture was stirred at room temperature overnight. Water was added and the mixture was extracted with EtOAc. The combined organic layers were washed with water and brine, dried ($Na_2SO_4$), filtered, and concentrated in vacuo. The residue was purified by silica gel chromatography (5-20% EtOAc/PE) to afford Intermediate 22A (20 g, 69%). $^1H$ NMR ($CDCl_3$) δ 4.5-4.3 (m, 4H), 0.9 (s, 9H), 0.2-0.1 (s, 6H).

tert-butyl((4-chlorobut-2-yn-1-yl)oxy)dimethylsilane

To a solution of Intermediate 22A (20 g, 100 mmol) in ether (250 mL) were added $CBr_4$ (65 g, 200 mmol) and $PPh_3$ (52 g, 200 mmol) under $N_2$. The reaction mixture was stirred at room temperature for four hours. The mixture was filtered, and the solid was washed with ether. The filtrates were concentrated in vacuo to provide a crude oil which was purified by silica gel chromatography (100% PE-5% EtOAc/PE) to afford Intermediate 22B (10 g, 38%). $^1H$ NMR ($CDCl_3$) δ 4.4-4.3 (s, 2H), 4.0-3.9 (s, 2H), 0.9 (s, 9H), 0.2-0.1 (s, 6H).

tert-butyl 4-((4-((tert-butyldimethylsilyl)oxy)but-2-yn-1-yl)oxy)piperidine-1-carboxylate To a solution of tert-butyl 4-hydroxypiperidine-1-carboxylate (18 g, 87 mmol) in DMF (150 mL) was added NaH (3.8 g, 94 mmol, 60%) in small portions at room temperature under $N_2$. The mixture was stirred at room temperature for one hour. A solution of Intermediate 22B (19 g, 73 mmol) in DMF (50 mL) was added drop wise at 0° C. The mixture was stirred at room temperature for three hours, and water was added. The mixture was extracted with EtOAc. The combined organic layers were washed with water and brine, dried ($Na_2SO_4$), filtered, and concentrated in vacuo. The residue was purified by silica gel chromatography (2% EtOAc/PE-10% EtOAc/PE) to afford Intermediate 22C (3 g, 11%). LCMS (method A): m/z 406.4 $(M+H)^+$. $^1H$ NMR ($CDCl_3$) δ 4.4-4.3 (s, 2H), 4.3-4.2 (s, 2H), 3.9-3.6 (m, 3H), 3.2-3.0 (m, 2H), 1.9-1.8 (m, 2H), 1.5-1.4 (s, 9H), 0.9 (s, 9H), 0.2-0.1 (s, 6H).

4-(piperidin-4-yloxy)but-2-yn-1-ol

A solution of Intermediate 22C (6 g, 15.6 mmol) in 6 N HCl/EtOH (80 mL, 1/1) was stirred at room temperature overnight. The organic solvent was removed in vacuo, and the residue was washed with DCM. The aqueous layer was concentrated in vacuo to afford Intermediate 22 (3.1 g, 96%). LCMS (method A): m/z 170.1 $(M+H)^+$. $^1H$ NMR ($D_2O$) δ 4.4-4.2 (d, 4H), 4.0-3.9 (m, 1H), 3.5-3.3 (m 2H), 3.2-3.0 (m, 2H), 2.2-2.0 (m, 2H), 1.9-1.7 (m 2H).

Intermediate 23

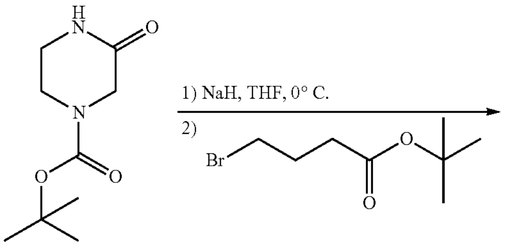

-continued

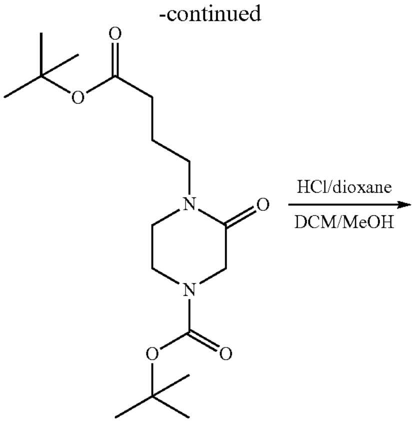

Intermediate 23A

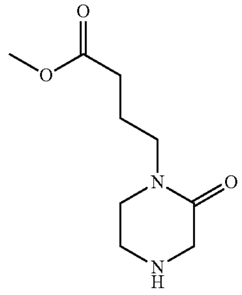

Intermediate 23 tert-butyl 4-(4-(tert-butoxy)-4-oxobutyl)-3-oxopiperazine-1-carboxylate

Under a $N_2$ atmosphere, NaH (219 mg, 5.99 mmol, 60% dispersion in mineral oil) was added to a stirring suspension of tert-butyl 3-oxopiperazine-1-carboxylate (1 g, 4.99 mmol) in THF (20 mL) at 0° C. and stirred for five minutes. Ethyl 4-bromobutanoate (1.33 g, 5.99 mmol) was added at 0° C. The reaction was stirred overnight. The reaction was quenched with several drops of methanol, diluted with ethyl acetate, and washed with $H_2O$, brine, and dried over magnesium sulfate. The organic layer was concentrated in vacuo which provided the crude material as a clear oil. The crude oil was purified by flash chromatography with ethyl acetate in hexanes as the eluent to afford Intermediate 23A (364 mg, 21%) as a clear oil. LCMS (method A): m/z 343.4 $(M+H)^+$. $^1H$ NMR ($CDCl_3$): δ 4.06 (s, 2H), 3.63 (t, 2H), 3.42 (t, 2H), 3.36 (t, 2H), 2.26 (t, 2H), 1.84 (quin, 2H), 1.46 (s, 9H), 1.44 (s, 9H).

methyl-4-(2-oxopiperazin-1-yl)butanoate

Following the procedure similar to Intermediate 9, step 3 but using DCM/MeOH (4/1, 10 mL) as solvent, Intermediate 23A (346 mg, 1.01 mmol) was converted to Intermediate 23 (224 mg, 99%) which was used directly without purification. LCMS (method A): m/z 201.2 $(M+H)^+$. $^1H$ NMR ($CDCl_3$): δ 3.93 (br s, 2H), 3.73 (br s, 2H), 3.68 (s, 3H), 3.56 (br s, 2H), 3.48 (br s, 2H), 2.39 (t, 2H), 1.92-1.89 (m, 2H).

Example 1

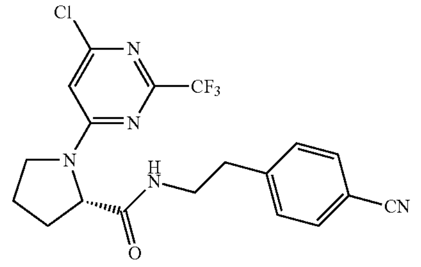

Intermediate 2

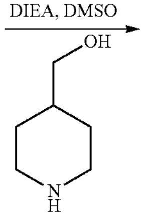

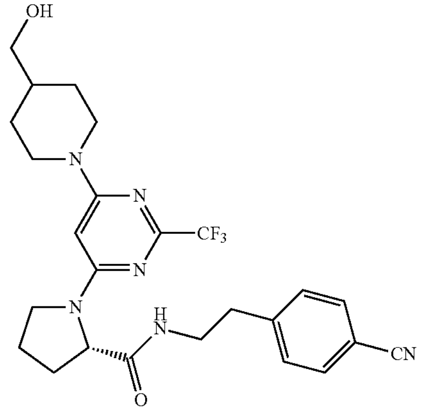

Compound 1

(S)—N-(4-cyanophenethyl)-1-(6-(4-(hydroxymethyl)piperidin-1-yl)-2-(trifluoromethyl)pyrimidin-4-yl)pyrrolidine-2-carboxamide To a solution of Intermediate 2 (120 mg, 0.28 mmol) in DMSO (1 mL) were added piperidin-4-yl methanol (58 mg, 0.84 mmol) and diisopropylethylamine (120 μL, 0.70 mmol). The solution was heated in a microwave at 90° C. for one hour. The reaction was poured into DCM (20 mL), and washed with water (10 mL). The organic layer was dried ($Na_2SO_4$), filtered, and concentrated in vacuo. The residue was purified by silica gel chromatography (0-3% MeOH/DCM) to afford Compound 1 (134 mg, 94%). LCMS (method A): m/z 503.4 $(M+H)^+$. $^1H$ NMR ($CDCl_3$) δ 7.42 (d, 2H), 7.15 (d, 2H), 5.33 (s, 1H), 4.61 (br s, 1H), 4.43 (br, 2H), 3.58 (m, 2H), 3.54 (m, 2H), 3.22 (br, 1H), 2.96-2.82 (m, 3H), 2.76 (m, 1H), 2.44 (br, 1H), 2.18 (br, 1H), 2.07 (m, 1H), 1.84 (br, 4H), 1.51 (m, 1H), 1.32 (m, 2H). Using the method described above for Example 1 and substituting the appropriate intermediates and reagents, the following compounds were prepared as indicated in Table 8.

TABLE 8

| No | Structure | Inter-mediate | Reagent | MS (M + H)$^+$ |
|---|---|---|---|---|
| 2 | 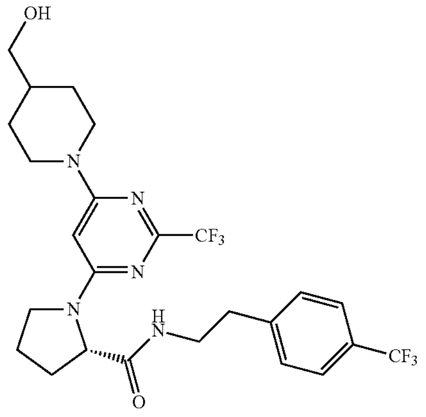 (S)-1-(6-(4-(hydroxymethyl)piperidin-1-yl)-2-(trifluoromethyl)pyrimidin-4-yl)-N-(4-(trifluoromethyl)-phenethyl)pyrrolidine-2-carboxamide | Intermediate 3 | 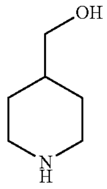 | 546.4 A |
| 3 | 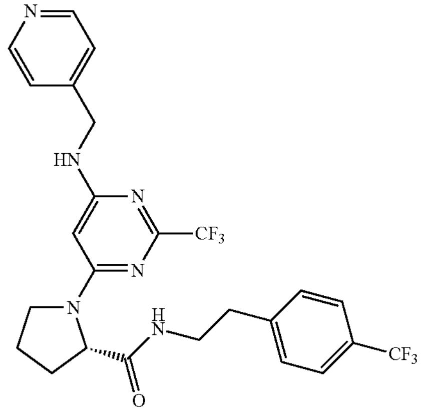 (S)-1-(6-((pyridin-4-ylmethyl)amino)-2-(trifluoromethyl)pyrimidin-4-yl)-N-(4-(trifluoromethyl)-phenethyl)pyrrolidine-2-carboxamide | Intermediate 3 | 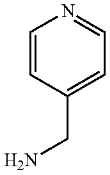 | 539.4 A |
| 4 | 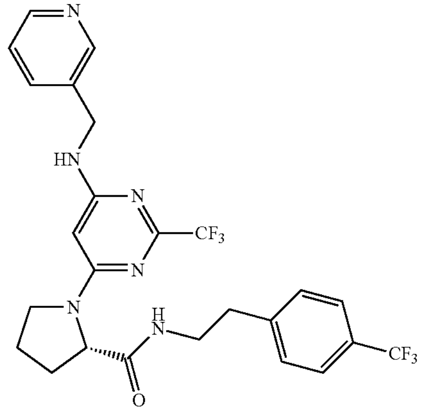 (S)-1-(6-((pyridin-3-ylmethyl)amino)-2-(trifluoromethyl)pyrimidin-4-yl)-N-(4-(trifluoromethyl)phenethyl) pyrrolidine-2-carboxamide | Intermediate 3 | 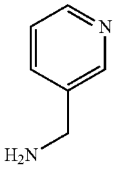 | 539.4 A |

TABLE 8-continued

| No | Structure | Intermediate | Reagent | MS (M + H)$^+$ |
|---|---|---|---|---|
| 5 | 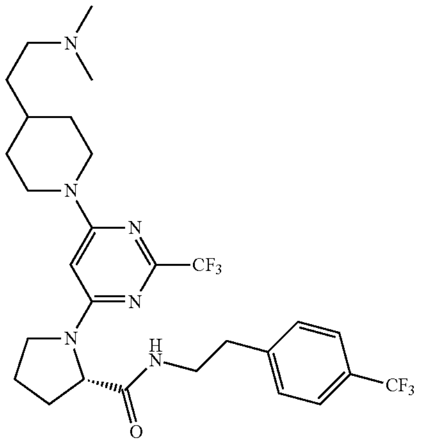 (S)-1-(6-(4-(2-(dimethylamino)ethyl)piperidin-1-yl)-2-(trifluoromethyl)pyrimidin-4-yl)-N-(4-(trifluoromethyl)phenethyl)-pyrrolidine-2-carboxamide | Intermediate 3 | 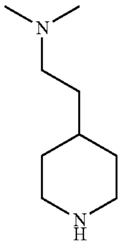 | 587.7 A |
| 6 | 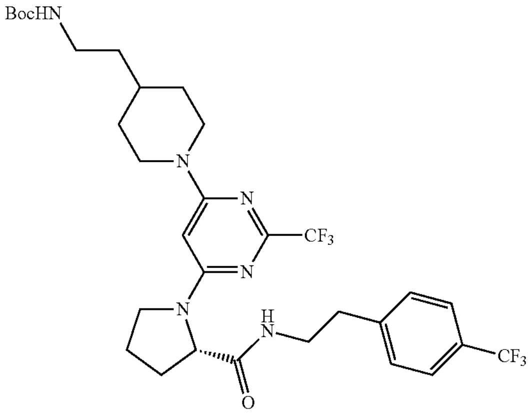 (S)-tert-butyl (2-(1-(2-(trifluoromethyl)-6-(2-((4-(trifluoromethyl)phenethyl)carbamoy)pyrrolidin-1-yl)pyrimidin-4-yl)piperidin-4-yl)ethyl)carbamate | Intermediate 3 | 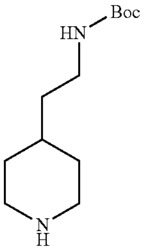 [SMILES: CC(C)(C)OC(=O)NCCC1CCNCC1] | 659.3 A |
| 7 | 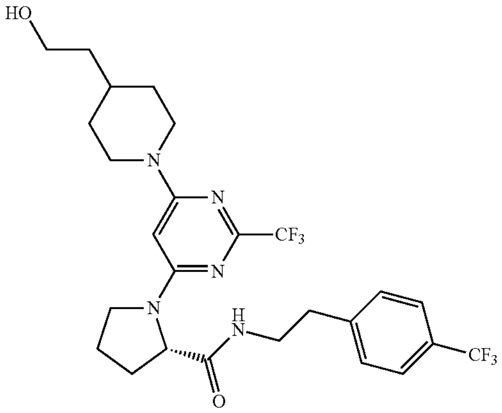 (S)-1-(6-(4-(2-hydroxyethyl)piperidin-1-yl)-2-(trifluoromethyl)pyrimidin-4-yl)-N-(4-(trifluoromethyl) phenethyl)-pyrrolidine-2-carboxamide | Intermediate 3 | 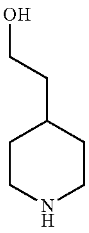 | 560.5 A |

TABLE 8-continued

| No | Structure | Intermediate | Reagent | MS (M + H)+ |
|---|---|---|---|---|
| 8 | 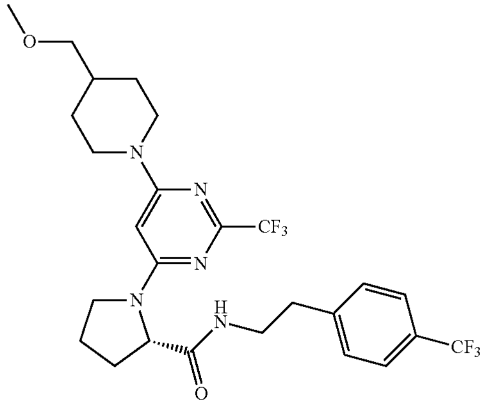 (S)-1-(6-(4-(methoxymethyl)piperidin-1-yl)-2-(trifluoromethyl)pyrimidin-4-yl)-N-(4-(trifluoromethyl) phenethyl)-pyrrolidine-2-carboxamide | Intermediate 3 | 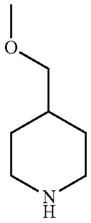 | 560.5 A |
| 9 | 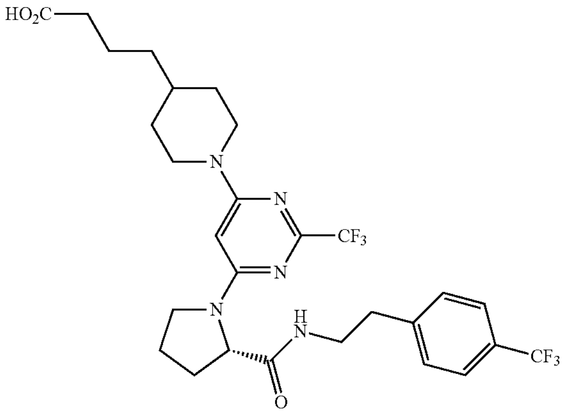 (S)-4-(1-(2-(trifluoromethyl)-6-(2-((4-(trifluoromethyl) phenethyl)carbamo)pyrrolidin-1-yl)pyrimidin-4-yl)piperidin-4-yl)butanoic acid | Intermediate 3 | 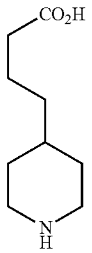 | 602.6 A |
| 10 | 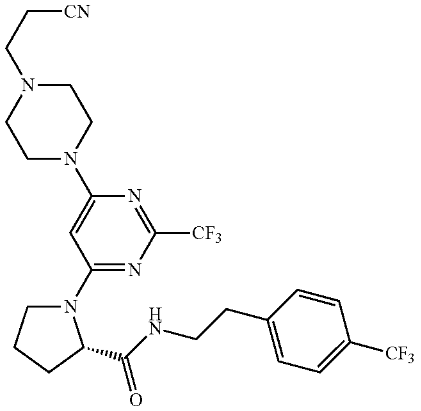 (S)-1-(6-(4-(2-cyanoethyl)piperazin-1-yl)-2-(trifluoromethyl)pyrimidin-4-yl)-N-(4-(trifluoromethyl)-phenethyl)pyrrolidine-2-carboxamide | Intermediate 3 | 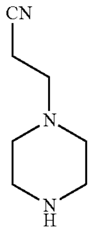 | 570.6 A |

TABLE 8-continued

| No | Structure | Inter-mediate | Reagent | MS (M + H)+ |
|---|---|---|---|---|
| 11 | 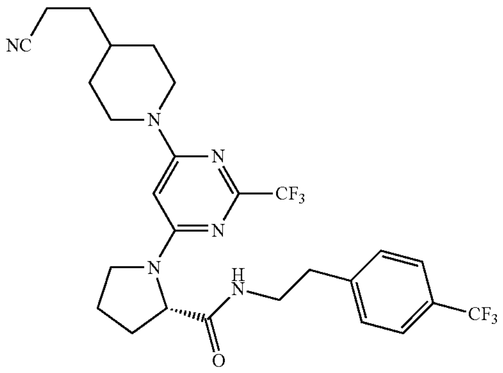 (S)-1-(6-(4-(2-cyanoethyl)piperidin-1-yl)-2-(trifluoromethyl)pyrimidin-4-yl)-N-(4-(trifluoromethyl)phenethyl)-pyrrolidine-2-carboxamide | Intermediate 3 | Intermediate 10 | 569.3 A |
| 12 | 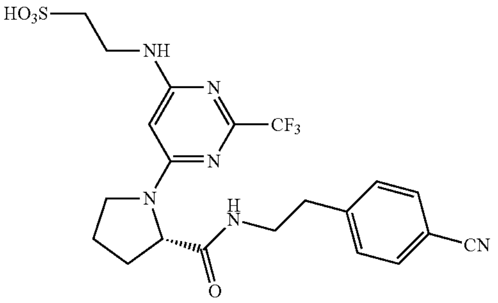 (S)-2-((6-(2-((4-cyanophenethyl)carbamoyl)pyrrolidin-1-yl)-2-(trifluoromethyl)pyrimidin-4-yl)amino)ethanesulfonic acid | Intermediate 2 | 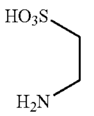 | 513.5 A |
| 13 | 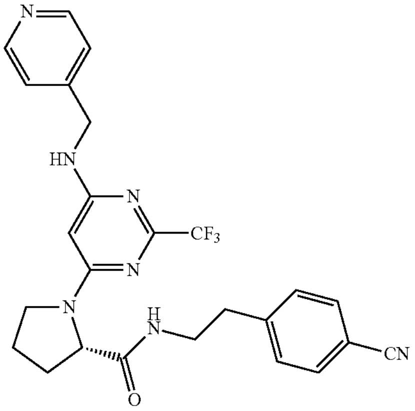 (S)-N-(4-cyanophenethyl)-1-(6-((pyridin-4-ylmethyl)amino)-2-(trifluoromethyl)pyrimidin-4-yl)pyrrolidine-2-carboxamide | Intermediate 2 | 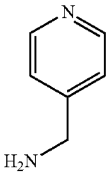 | 496.3 A |

TABLE 8-continued

| No | Structure | Inter-mediate | Reagent | MS $(M + H)^+$ |
|---|---|---|---|---|
| 14 | 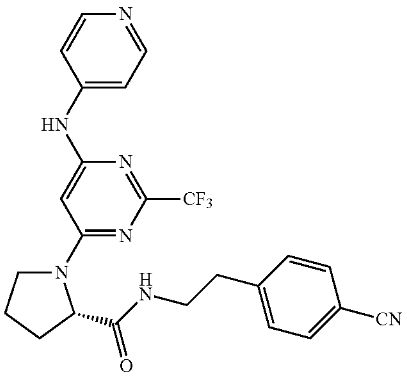<br>(S)-N-(4-cyanophenethyl)-1-(6-(pyridin-4-ylamino)-2-(trifluoromethyl)pyrimidin-4-yl)pyrrolidine-2-carboxamide | Intermediate 2 | 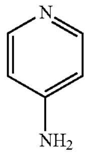 | 482.3 A |
| 15 | 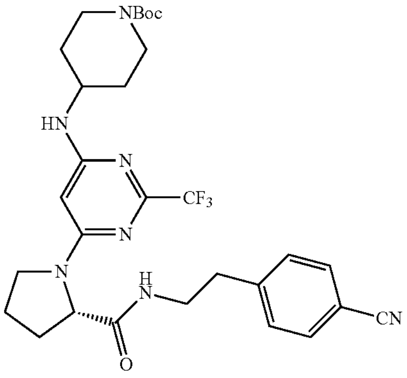<br>(S)-tert-butyl 4-((6-(2-((4-cyanophenethyl)carbamoyl)pyrrolidin-1-yl)-2-(trifluoromethyl)pyrimidin-4-yl)amino)piperidine-1-carboxylate | Intermediate 2 | 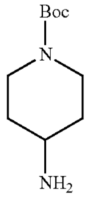 [SMILES: CC(C)(C)OC(=O)N1CCC(N)CC1] | 588.4 A |
| 16 | 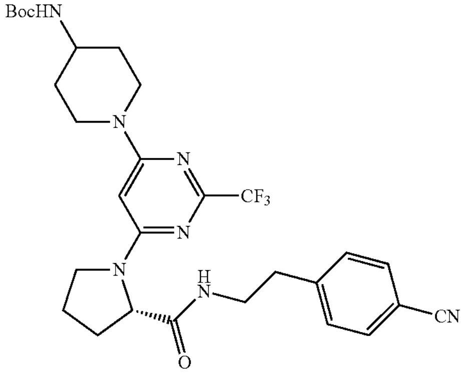<br>(S)-tert-butyl (1-(6-(2-((4-cyanophenethyl)carbamoyl)pyrrolidin-1-yl)-2-(trifluoromethyl)pyrimidin-4-yl)piperidin-4-yl)carbamate | Intermediate 2 | 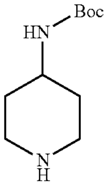 | 588.4 A |

TABLE 8-continued

| No | Structure | Inter-mediate | Reagent | MS (M + H)$^+$ |
|---|---|---|---|---|
| 17 | 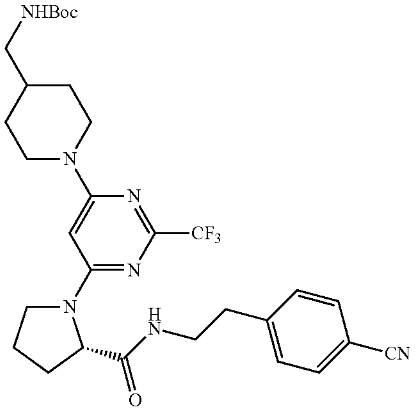 (S)-tert-butyl ((1-(6-(2-((4-cyanophenethyl)carbamoyl)pyrrolidin-1-yl)-2-(trifluoromethyl)pyrimidin-4-yl)piperidin-4-yl)methyl)carbamate | Intermediate 2 | 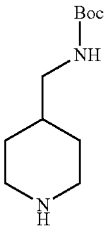 | 602.4 A |
| 18 | 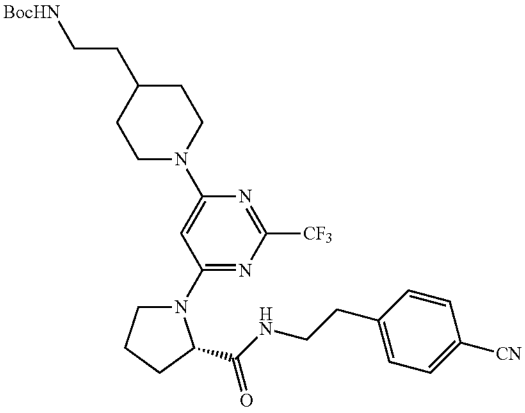 (S)-tert-butyl (2-(1-(6-(2-((4-cyanophenethyl)carbamoyl) pyrrolidin-1-yl)-2-(trifluoromethyl)pyrimidin-4-yl) piperidin-4-yl)ethyl)carbamate | Intermediate 2 | 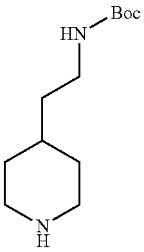 [SMILES: CC(C)(C)OC(=O)NCCC1CCNCC1] | 616.5 A |
| 19 | 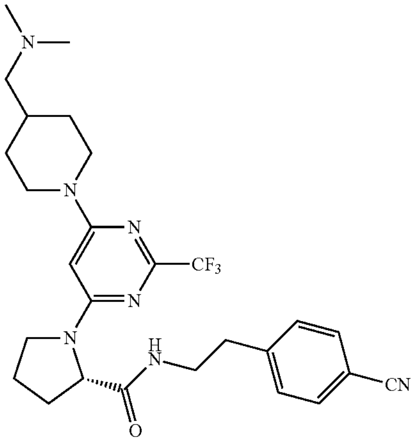 (S)-N-(4-cyanophenethyl)-1-(6-(4-((dimethylamino)methyl)piperidin-1-yl)-2-(trifluoromethyl)pyrimidin-4-yl)pyrrolidine-2-carboxamide | Intermediate 2 | 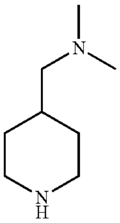 | 530.4 A |

TABLE 8-continued

| No | Structure | Inter-mediate | Reagent | MS (M + H)+ |
|---|---|---|---|---|
| 20 | 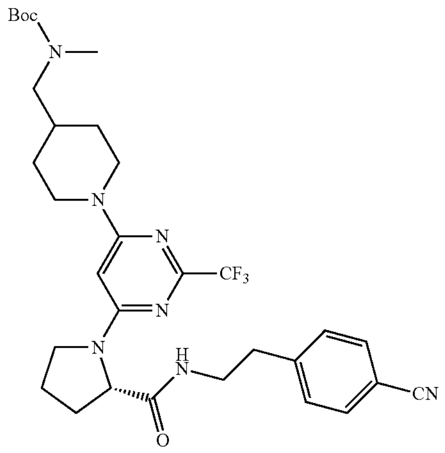 (S)-tert-butyl ((1-(6-(2-((4-cyanophenethyl)carbamoyl)pyrrolidin-1-yl)-2-(trifluoromethyl)pyrimidin-4-yl)piperidin-4-yl)methyl)(methyl)carbamate | Intermediate 2 | 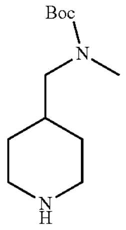 [SMILES: CN(CC1CCNCC1)C(=O)OC(C)(C)C] | 616.5 A |
| 21 | 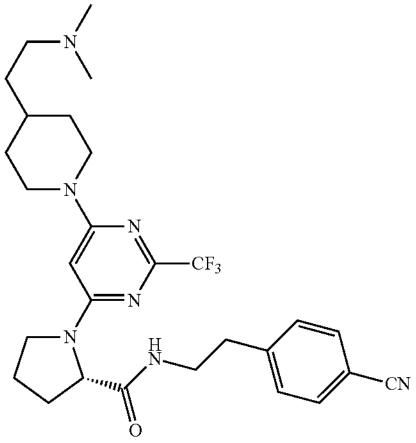 (S)-N-(4-cyanophenethyl)-1-(6-(4-(2-(dimethylamino)ethyl)piperidin-1-yl)-2-(trifluoromethyl)pyrimidin-4-yl)pyrrolidine-2-carboxamide | Intermediate 2 | 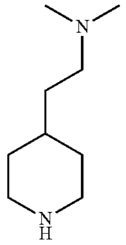 | 544.7 A |
| 22 | 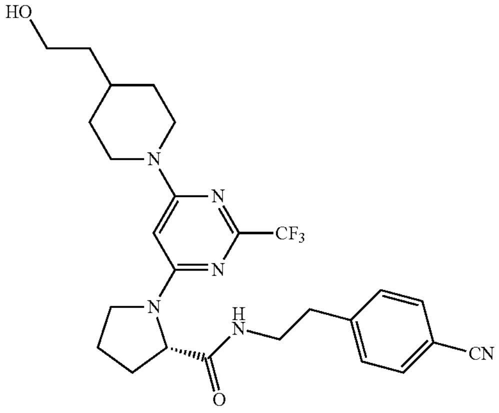 (S)-N-(4-cyanophenethyl)-1-(6-(4-(2-hydroxyethyl)piperidin-1-yl)-2-(trifluoromethyl)pyrimidin-4-yl)pyrrolidine-2-carboxamide | Intermediate 2 | 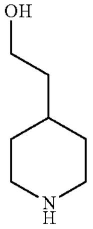 | 517.5 A |

TABLE 8-continued

| No | Structure | Inter-mediate | Reagent | MS (M + H)+ |
|---|---|---|---|---|
| 23 | 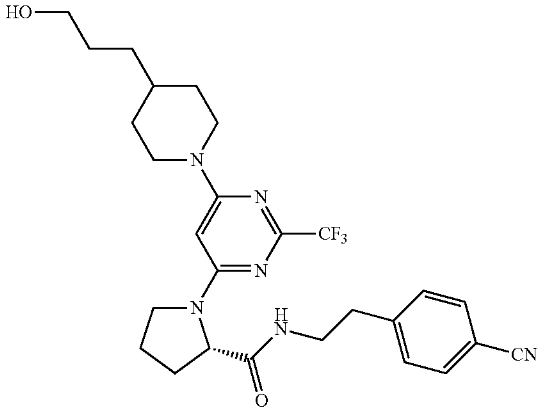<br>(S)-N-(4-cyanophenethyl)-1-(6-(4-(3-hydroxypropyl)piperidin-1-yl)-2-(trifluoromethyl) pyrimidin-4-yl)pyrrolidine-2-carboxamide | Intermediate 2 | 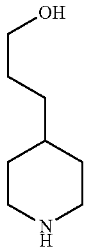 | 531.6 A |
| 24 | 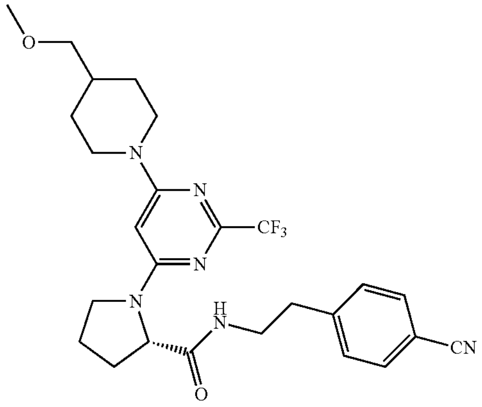<br>(S)-N-(4-cyanophenethyl)-1-(6-(4-(methoxymethyl)piperidin-1-yl)-2-(trifluoromethyl)pyrimidin-4-yl)pyrrolidine-2-carboxamide | Intermediate 2 | 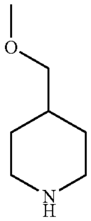 | 517.5 A |
| 25 | 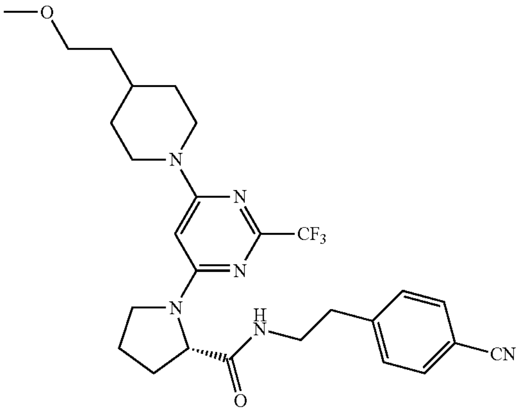<br>(S)-N-(4-cyanophenethyl)-1-(6-(4-(2-methoxyethyl)piperidin-1-yl)-2-(trifluoromethyl)pyrimidin-4-yl)pyrrolidine-2-carboxamide | Intermediate 2 | 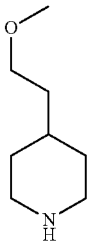 | 531.6 A |

TABLE 8-continued

| No | Structure | Inter-mediate | Reagent | MS (M + H)$^+$ |
|---|---|---|---|---|
| 26 | 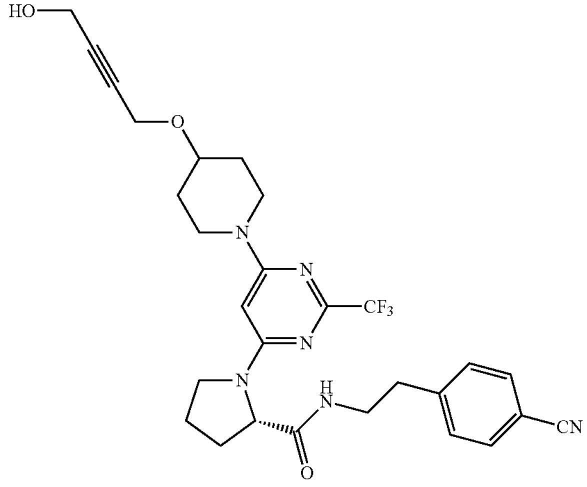<br>(S)-N-(4-cyanophenethyl)-1-(6-(4-((4-hydroxybut-2-yn-1-yl)oxy)-piperidin-1-yl)-2-(trifluoromethyl)-pyrimidin-4-yl)pyrrolidine-2-carboxamide | Intermediate 2 | Intermediate 22 | 557.4 A |
| 27 | 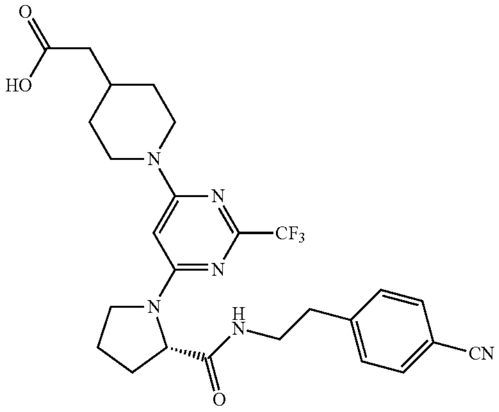<br>(S)-2-(1-(6-(2-((4-cyanophenethyl) carbamoyl)pyrrolidin-1-yl)-2-(trifluoromethyl) pyrimidin-4-yl)piperidin-4-yl)acetic acid | Intermediate 2 | 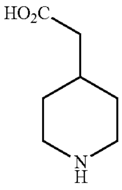 | 531.5 A |
| 28 | 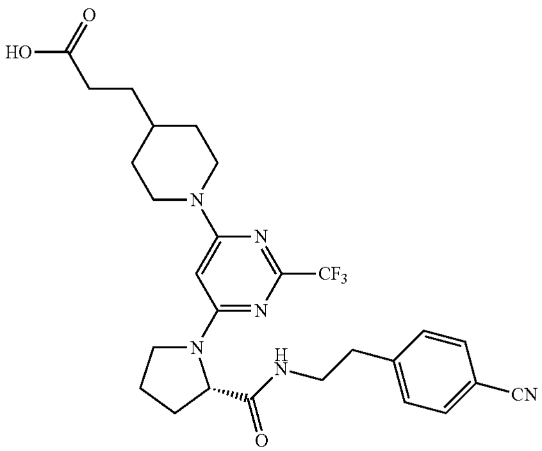<br>(S)-3-(1-(6-(2-((4-cyanophenethyl)carbamoyl) pyrrolidin-1-yl)-2-(trifluoromethyl)pyrimidin-4-yl)piperidin-4-yl)propanoic acid | Intermediate 2 | 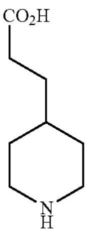 | 545.5 A |

TABLE 8-continued

| No | Structure | Inter-mediate | Reagent | MS (M + H)+ |
|---|---|---|---|---|
| 29 | 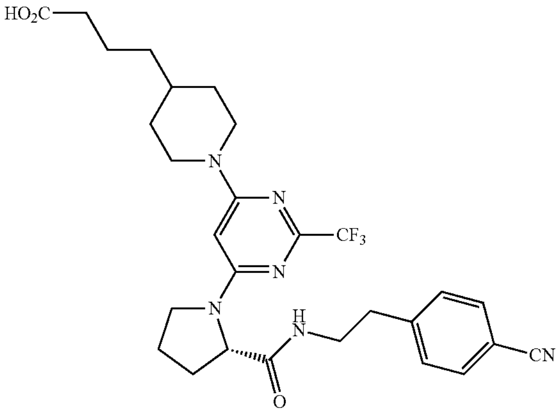 (S)-4-(1-(6-(2-((4-cyanophenethyl)carbamoyl) pyrrolidin-1-yl)-2-(trifluoromethyl)pyrimidin-4-yl)piperidin-4-yl)butanoic acid | Intermediate 2 | 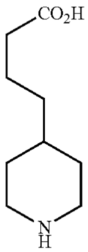 | 559.6 A |
| 30 | 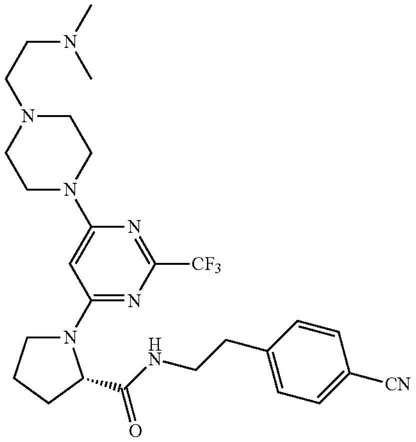 (S)-N-(4-cyanophenethyl)-1-(6-(4-(2-(dimethylamino)ethyl)piperazin-1-yl)-2-(trifluoromethyl)pyrimidin-4-yl) pyrrolidine-2-carboxamide | Intermediate 2 | 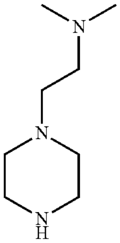 | 545.6 A |
| 31 | 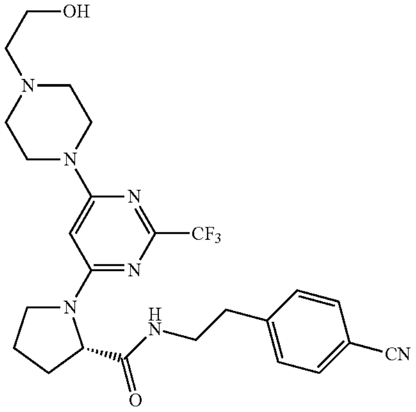 (S)-N-(4-cyanophenethyl)-1-(6-(4-(2-hydroxyethyl)piperazin-1-yl)-2-(trifluoromethyl)pyrimidin-4-yl) pyrrolidine-2-carboxamide | Intermediate 2 | 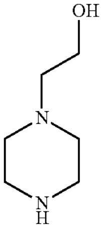 | 518.6 A |

TABLE 8-continued

| No | Structure | Inter-mediate | Reagent | MS (M + H)$^+$ |
|---|---|---|---|---|
| 32 | 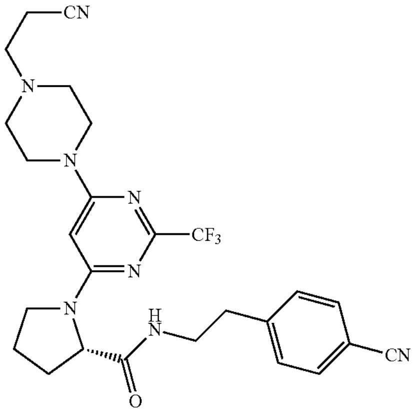<br>(S)-1-(6-(4-(2-cyanoethyl) piperazin-1-yl)-2-(trifluoromethyl) pyrimidin-4-yl)-N-(4-cyanophenethyl) pyrrolidine-2-carboxamide | Intermediate 2 | 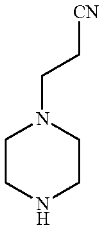 | 527.6 A |
| 33 | 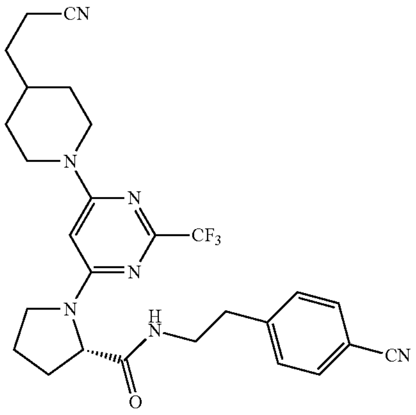<br>(S)-1-(6-(4-(2-cyanoethyl) piperidin-1-yl)-2-(trifluoromethyl) pyrimidin-4-yl)-N-(4-cyanophenethyl) pyrrolidine-2-carboxamide | Intermediate 2 | Intermediate 10 | 512.6 A |
| 34 | 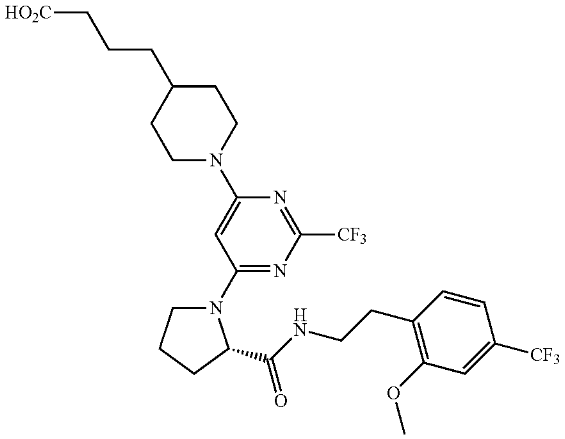<br>(S)-4-(1-(6-(2-((2-methoxy-4-(trifluoromethyl) phenethyl)carbamoy)pyrrolidin-1-yl)-2-(trifluoromethyl)-pyrimidin-4-yl)piperidin-4-yl)butanoic acid | Intermediate 5 | 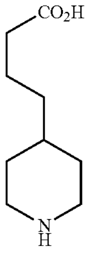 | 632.7 A |

TABLE 8-continued
| No | Structure | Inter-mediate | Reagent | MS (M + H)$^+$ |
|---|---|---|---|---|
| 35 | 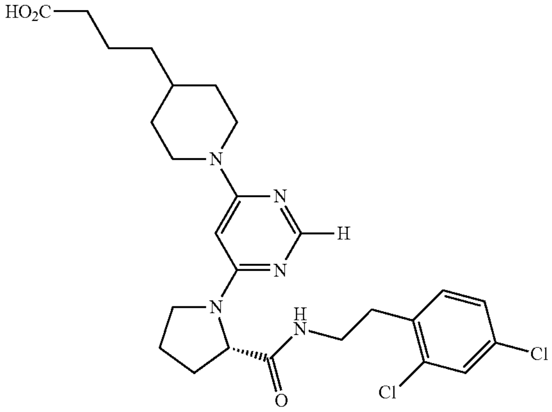<br>(S)-4-(1-(6-(2-((2,4-dichlorophenethyl)carbamoyl)pyrrolidin-1-yl)pyrimidin-4-yl)piperidin-4-yl)butanoic acid | Intermediate 6 | 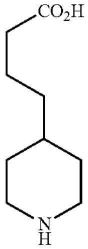 | 534.5<br>536.5<br>A |
| 36 | 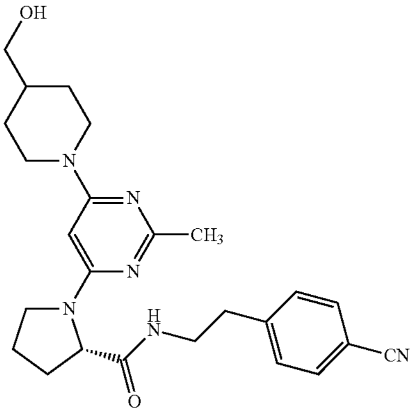<br>(S)-N-(4-cyanophenethyl)-1-(6-(4-(hydroxymethyl)piperidin-1-yl)-2-methylpyrimidin-4-yl)pyrrolidine-2-carboxamide | Intermediate 7 | 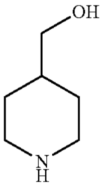 | 449.6<br>A |

TABLE 8-continued
| No | Structure | Inter-mediate | Reagent | MS (M + H)$^+$ |
|---|---|---|---|---|
| 37 | 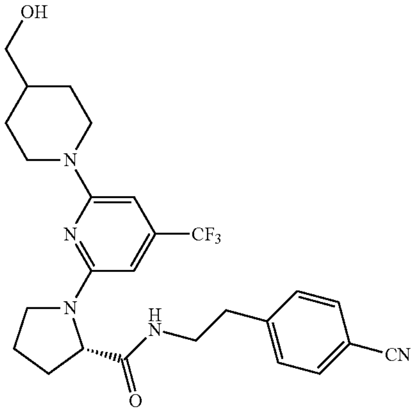 (S)-N-(4-cyanophenethyl)-1-(6-(4-(hydroxymethyl)piperidin-1-yl)-4-(trifluoromethyl)pyridin-2-yl) pyrrolidine-2-carboxamide | Intermediate 8 | 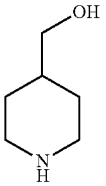 | 502.6 A |
| 38 | 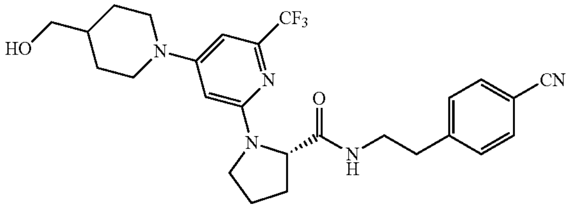 (S)-N-(4-cyanophenethyl)-1-(4-(4-(hydroxymethyl) piperidin-1-yl)-6-(trifluoromethyl)pyridine-2-yl) pyrrolidine-2-carboxamide | Intermediate 9 | 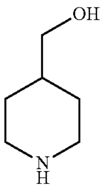 | 502.6 A |
Example 2
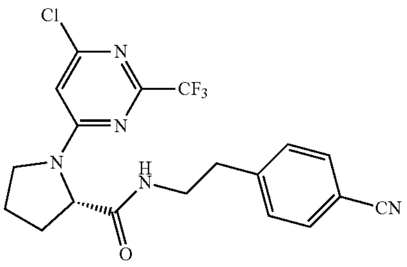
Intermediate 2
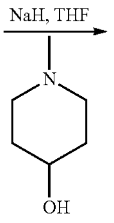
-continued
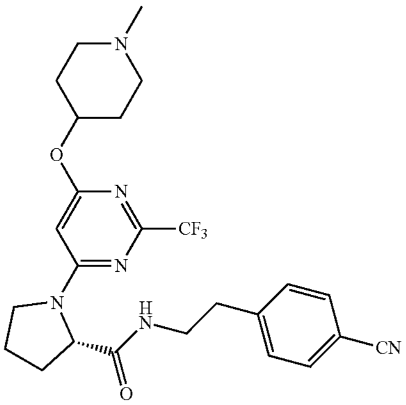
Compound 39

(S)—N-(4-cyanophenethyl)-1-(6-((1-methylpiperidin-4-yl)oxy)-2-(trifluoromethyl)pyrimidin-4-yl)pyrrolidine-2-carboxamide To a solution of 1-methylpiperidin-4-ol (35 mg, 0.30 mmol) in THF (0.5 mL) at 0° C. was added 60% NaH (12 mg, 0.30 mmol). After the mixture was stirred for 20 minutes, a solution of Intermediate 2 (42 mg, 0.10 mmol) in THF (0.5 mL) was added.

Then the ice bath was removed, and the reaction mixture was stirred at room temperature for two hours. The reaction was quenched by water (0.1 mL), and concentrated. The residue was purified directly by MS-HPLC to afford Compound 39 (18 mg, 35%). LCMS (method A): m/z 503.4 $(M+H)^+$. $^1H$ NMR ($CDCl_3$) δ 8.50 (s, 1H), 77.44 (d, 2H), 7.17 (d, 2H), 5.72 (d, 1H), 5.31 (m, 1H), 4.60 (br, 1H), 3.60 (m, 1H), 3.40 (m, 2H), 3.24 (br, 1H), 3.03 (br, 2H), 2.92-2.77 (m, 4H), 2.40 (br, 1H), 2.25 (m, 3H), 2.11-1.88 (m, 4H). Using the method described above for Example 2 and substituting the appropriate intermediates and reagents, the following compounds were prepared as indicated in Table 9.

TABLE 9

| No | Structure | Intermediate | Reagent | MS $(M + H)^+$ |
|---|---|---|---|---|
| 40 | 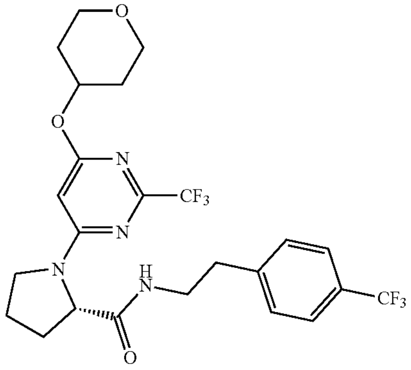 [SMILES: O=C(NCCc1ccc(C(F)(F)F)cc1)[C@@H]1CCCN1c1cc(OC2CCOCC2)nc(C(F)(F)F)n1] (S)-1-(6-((tetrahydro-2H-pyran-4-yl)oxy)-2-(trifluoromethyl)pyrimidin-4-yl)-N-(4-(trifluoromethyl)phenethyl)pyrrolidine-2-carboxamide | Intermediate 3 | 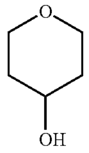 | 533.4 A |
| 41 | 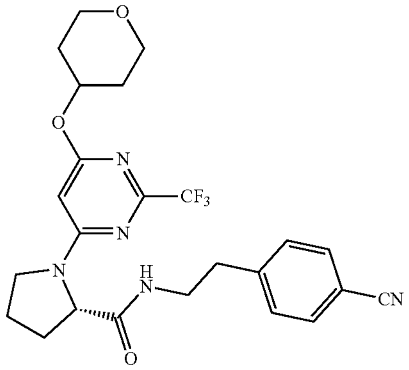 (S)-N-(4-cyanophenethyl)-1-(6-((tetrahydro-2H-pyran-4-yl)oxy)-2-(trifluoromethyl)pyrimidin-4-yl)pyrrolidine-2-carboxamide | Intermediate 2 | 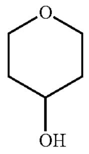 | 490.4 A |
| 42 | 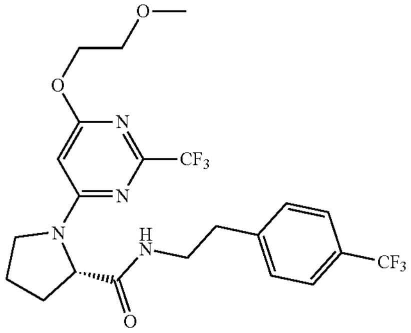 [SMILES: COCCOc1cc(N2CCC[C@H]2C(=O)NCCc2ccc(C(F)(F)F)cc2)nc(C(F)(F)F)n1] | Intermediate 3 | 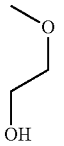 | 507.4 A |

TABLE 9-continued

| No | Structure | Inter-mediate | Reagent | MS (M + H)+ |
|---|---|---|---|---|
| | (S)-1-(6-(2-methoxyethoxy)-2-(trifluoromethyl)pyrimidin-4-yl)-N-(4-(trifluoromethyl)phenethyl)pyrrolidine-2-carboxamide | | | |
| 43 | 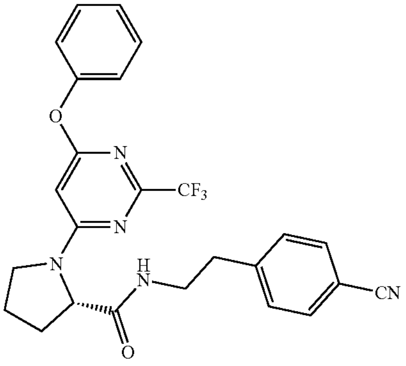 [SMILES: N#Cc1ccc(CCNC(=O)[C@@H]2CCCN2c2cc(Oc3ccccc3)nc(C(F)(F)F)n2)cc1]<br>(S)-N-(4-cyanophenethyl)-1-(6-phenoxy-2-(trifluoromethyl)pyrimidin-4-yl)pyrrolidine-2-carboxamide | Inter-mediate 2 | 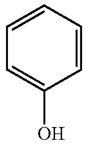 | 482.3 A |
| 44 | 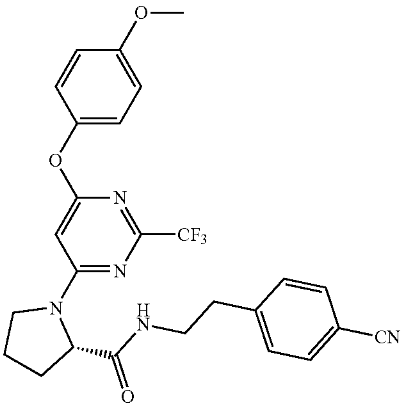 [SMILES: COc1ccc(Oc2cc(N3CCC[C@H]3C(=O)NCCc3ccc(C#N)cc3)nc(C(F)(F)F)n2)cc1]<br>(S)-N-(4-cyanophenethyl)-1-(6-(4-methoxyphenoxy)-2-(trifluoromethyl)pyrimidin-4-yl)pyrrolidine-2-carboxamide | Inter-mediate 2 | 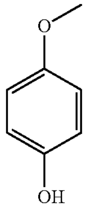 | 512.3 A |
| 45 | 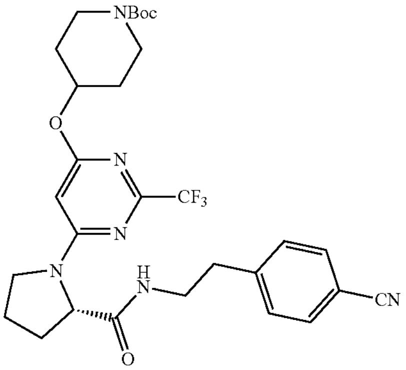 [SMILES: CC(C)(C)OC(=O)N1CCC(Oc2cc(N3CCC[C@H]3C(=O)NCCc3ccc(C#N)cc3)nc(C(F)(F)F)n2)CC1]<br>(S)-tert-butyl 4-((6-(2-((4-cyanophenethyl)carbamoyl)pyrrolidin-1-yl)-2-(trifluoromethyl)pyrimidin-4-yl)oxy)piperidine-1-carboxylate | Inter-mediate 2 | 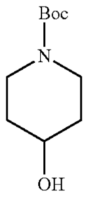 [SMILES: CC(C)(C)OC(=O)N1CCC(O)CC1] | 533.3 (loss of t-Butyl) A |

Example 3

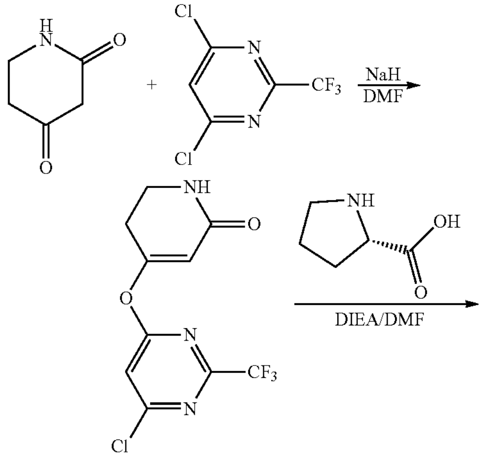

Compound 3A

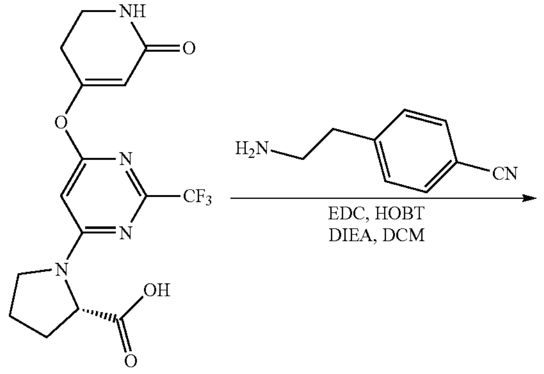

Compound 3B

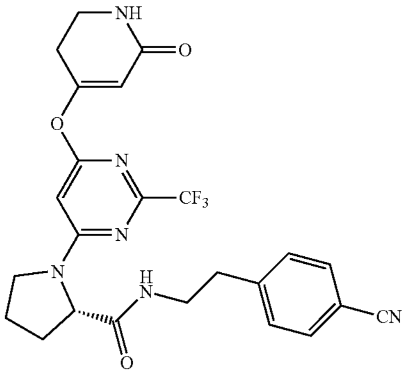

Compound 46

4-((6-chloro-2-(trifluoromethyl)pyrimidin-4-yl)oxy)-5,6-dihydropyridin-2(1H)-one Following procedure as described in Example 2, and replacing THF with DMF, piperidine-2,4-dione (249 mg, 2.20 mmol) was converted to Compound 3A. The crude material was purified by silica gel chromatography (0-90% EA/hexane) to afford Compound 3A (375 mg, 64%). LCMS (method A): m/z 294.3 $(M+H)^+$. $^1H$ NMR ($CDCl_3$): δ 7.14 (s, 1H), 5.97 (br s, 1H), 5.83 (s, 1H), 3.60 (t, 2H), 2.72 (m, 2H).

(S)-1-(6-((6-oxo-1,2,3,6-tetrahydropyridin-4-yl)oxy)-2-(trifluoromethyl)pyrimidin-4-yl)pyrrolidine-2-carboxylic acid To a solution of Compound 3A (367 mg, 1.25 mmol) in DMF (6 mL) were added L-Proline (432 mg, 3.75 mmol) and diisopropylethylamine (0.55 mL, 3.13 mmol). The solution was heated in a microwave at 90° C. for one hour, and concentrated in vacuo. The residue was purified by column chromatography (reverse phase C18 column, 0-50% acetonitrile/water containing 0.25% formic acid) to afford Compound 3B (265 mg, 57%). LCMS (method A): m/z 501.6 $(M+H)^+$.

(S)—N-(4-cyanophenethyl)-1-(6-((6-oxo-1,2,3,6-tetrahydropyridin-4-yl)oxy)-2-(trifluoromethyl)pyrimidin-4-yl)pyrrolidine-2-carboxamide Using a similar procedure as described in preparation of Intermediate 1, step 1, Compound 3B (130 mg, 0.35 mmol) was subjected to similar coupling conditions and purified by column chromatography (reverse phase C18 column, 0-75% acetonitrile/water containing 0.25% formic acid) to afford Compound 46 (140 mg, 80%). LCMS (method A): m/z 373.3 $(M+H)^+$. $^1H$ NMR ($CDCl_3$): δ 7.51 (d, 2H), 7.23 (d, 2H), 6.93 (br s, 1H), 5.99 (br s, 1H), 5.79 (s, 1H), 5.62 (s, 1H), 4.64 (m, 1H), 3.58-3.45 (m, 5H), 3.31 (m, 1H), 2.91-2.82 (m, 2H), 2.74-2.69 (m, 2H), 2.33 (m, 2H), 2.12 (m, 1H), 1.98 (m, 1H).

Example 4

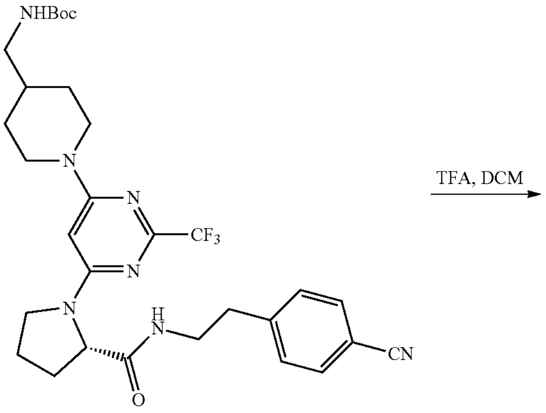

Compound 17

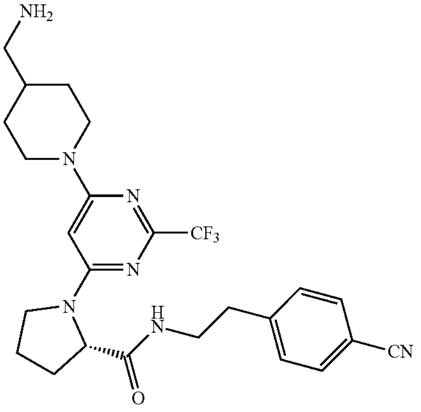

Compound 47

(S)-1-(6-(4-(aminomethyl)piperidin-1-yl)-2-(trifluoromethyl)pyrimidin-4-yl)-N-(4-cyanophenethyl) pyrrolidine-2-carboxamide To a solution of Compound 17 (98 mg, 0.16 mmol) in DCM (1.3 mL) was added trifluoroacetic acid (0.7 mL). The reaction mixture was stirred at room temperature for one hour and concentrated in vacuo. The residue was purified by MS-HPLC. To product containing fractions was added ~10 drops of 3N methanolic HCl. These fractions were concentrated in vacuo to afford Compound 47 as the HCl salt (50 mg, 61%) which can be used in the next reaction without further purification. LCMS (method A): m/z 502.4 $(M+H)^+$. $^1H$ NMR ($CD_3OD$) δ 7.55 (d, 2H), 7.34 (d, 2H), 5.50 (s, 1H), 4.52-4.43 (m, 3H), 3.61 (br, 1H), 3.52-3.40 (m, 3H), 2.99 (t, 2H), 2.90-2.84 (m, 4H), 2.20 (t, 1H), 2.06-1.99 (m, 4H), 1.90 (d, 2H), 1.30 (m, 2H). Using the procedure described above for Example 4, the following compounds were prepared from precursors as indicated in Table 10.

TABLE 10

| No | Structure | Pre-cursor | MS $(M + H)^+$ |
|---|---|---|---|
| 48 | 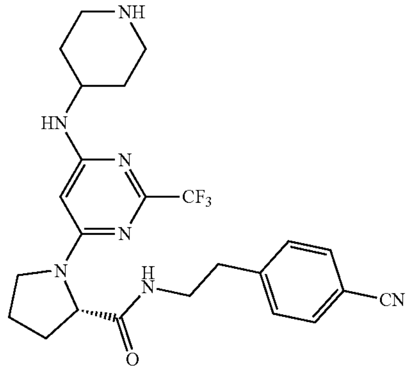 [SMILES: N#Cc1ccc(CCNC(=O)[C@@H]2CCCN2c2cc(NC3CCNCC3)nc(C(F)(F)F)n2)cc1] (S)-N-(4-cyanophenethyl)-1-(6-(piperidin-4-ylamino)-2-(trifluoromethyl)pyrimidin-4-yl)pyrrolidine-2-carboxamide | 15 | 488.4 A |
| 49 | 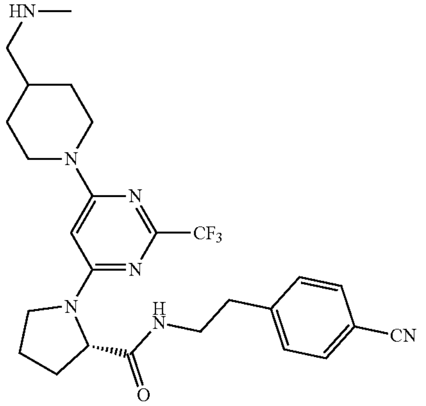 [SMILES: CNCC1CCN(c2cc(N3CCC[C@H]3C(=O)NCCc3ccc(C#N)cc3)nc(C(F)(F)F)n2)CC1] (S)-N-(4-cyanophenethyl)-1-(6-(3-oxopiperazin-1-yl)-2-(trifluoromethyl)pyrimidin-4-yl)pyrrolidine-2-carboxamide | 20 | 516.5 A |

TABLE 10-continued
| No | Structure | Pre-cursor | MS (M + H)$^+$ |
|---|---|---|---|
| 50 | 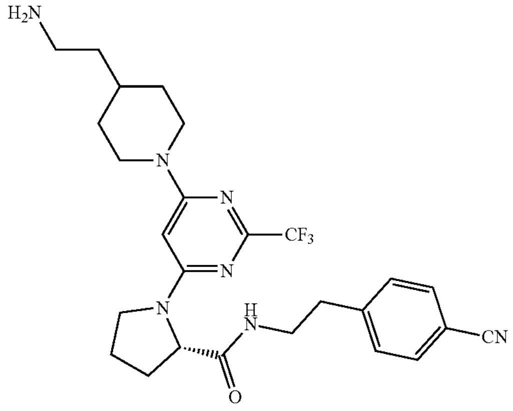 [SMILES: N#Cc1ccc(CCNC(=O)[C@@H]2CCCN2c2cc(N3CCC(CCN)CC3)nc(C(F)(F)F)n2)cc1] (S)-1-(6-(4-(2-aminoethyl)piperidin-1-yl)-2-(trifluoromethyl)pyrimidin-4-yl)-N-(4-cyanophenethyl)pyrrolidine-2-carboxamide | 18 | 516.5 A |
| 51 | 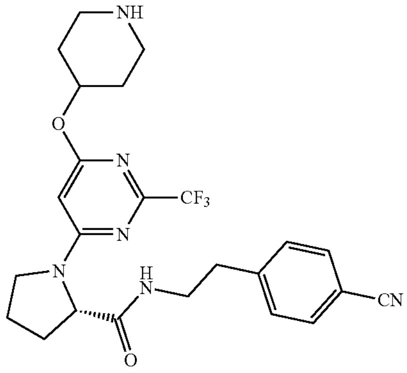 [SMILES: N#Cc1ccc(CCNC(=O)[C@@H]2CCCN2c2cc(OC3CCNCC3)nc(C(F)(F)F)n2)cc1] (S)-N-(4-cyanophenethyl)-1-(6-(piperidin-4-yloxy)-2-(trifluoromethyl)pyrimidin-4-yl)pyrrolidine-2-carboxamide | 45 | 489.4 A |
Example 5
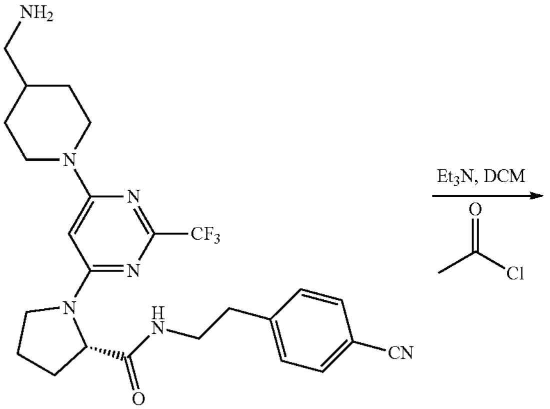
Compound 47
-continued
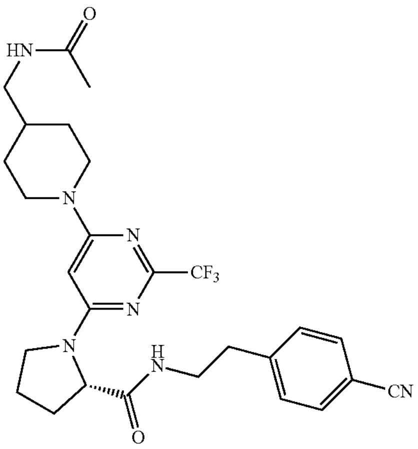
Compound 52

(S)-1-(6-(4-(acetamidomethyl)piperidin-1-yl)-2-(trifluoromethyl)pyrimidin-4-yl)-N-(4-cyanophenethyl) pyrrolidine-2-carboxamide To a solution of crude Compound 47 (110 mg, 0.22 mmol) in DCM (1 mL) were added acetyl chloride (17 μL, 0.24 mmol) and triethylamine (0.09 mL, 0.66 mmol). The reaction mixture was stirred at room temperature for 90 minutes, and then quenched with a small amount of MeOH, and concentrated in vacuo. The residue was purified by MS-HPLC to afford Compound 52 (61 mg, 51%). LCMS (method A): m/z 544.5 $(M+H)^+$. $^1H$ NMR ($CDCl_3$) δ 7.63 (br s, 1H), 7.40 (d, 2H), 7.14 (d, 2H), 6.08 (br s, 1H), 5.82 (br s, 1H), 5.34 (s, 1H), 4.61 (br, 1H), 4.41 (t, 2H), 3.59 (m, 1H), 3.40 (m, 2H), 3.19 (m, 3H), 2.89 (m, 3H), 2.77 (m, 1H), 2.41 (m, 1H), 2.17 (m, 1H), 2.06 (m, 1H), 2.00 (s, 3H), 1.83 (m, 4H), 1.25 (m, 2H). Using the procedure described above for Example 5, the following compounds were prepared from precursors as indicated in Table 11.

TABLE 11

| No | Structure | Pre-cursor | MS $(M + H)^+$ |
|---|---|---|---|
| 53 | 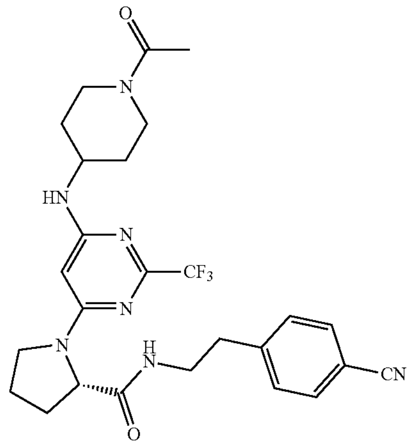 [SMILES: CC(=O)N1CCC(Nc2cc(N3CCC[C@H]3C(=O)NCCc3ccc(C#N)cc3)nc(C(F)(F)F)n2)CC1] (S)-1-(6-((1-acetylpiperidin-4-yl)amino)-2-(trifluoromethyl)pyrimidin-4-yl)-N-(4-cyanophenethyl)pyrrolidine-2-carboxamide | 48 | 530.4 A |
| 54 | 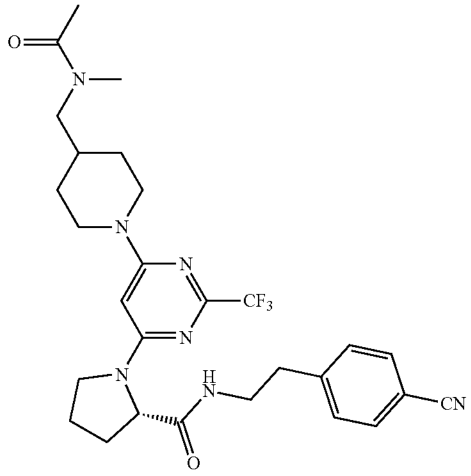 [SMILES: CC(=O)N(C)CC1CCN(c2cc(N3CCC[C@H]3C(=O)NCCc3ccc(C#N)cc3)nc(C(F)(F)F)n2)CC1] (S)-N-(4-cyanophenethyl)-1-(6-(4-((N-methylacetamido)methyl)piperidin-1-yl)-2-(trifluoromethyl)pyrimidin-4-yl)pyrrolidine-2-carboxamide | 49 | 558.5 A |

Example 6

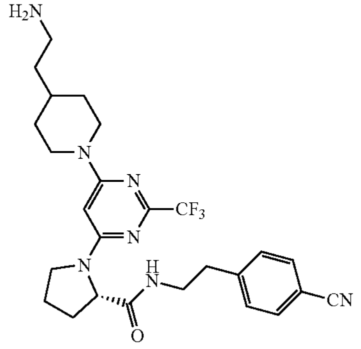

Compound 50

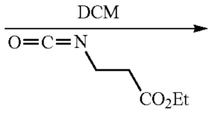

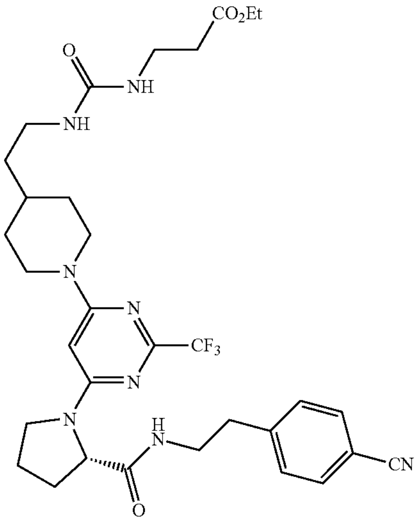

Compound 55

(S)-ethyl 3-(3-(2-(1-(6-(2-((4-cyanophenethyl)carbamoyl)pyrrolidin-1-yl)-2-(trifluoromethyl)pyrimidin-4-yl)piperidin-4-yl)ethyl)ureido)propanoate To a solution of Compound 50 (250 mg, 0.49 mmol) in DCM (5 mL) was added ethyl 3-isocyanatopropanoate (130 μL, 0.97 mmol). The reaction mixture was stirred at room temperature overnight, and concentrated in vacuo. The residue was purified by silica gel chromatography (0-5% MeOH/DCM) to afford Compound 55 (288 mg, 90%). LCMS (method A) m/z 659.3 $(M+H)^+$. $^1$H NMR ($CDCl_3$) δ 7.70 (br s, 1H), 7.41 (d, 2H), 7.15 (d, 2H), 5.34 (s, 1H), 5.31 (s, 2H), 4.99 (t, 1H), 4.62 (br s, 1H), 4.36 (m, 2H), 4.13 (q, 2H), 3.57 (m, 1H), 3.48-3.37 (m, 4H), 3.22 (m, 3H), 2.92-2.84 (m, 3H), 2.78 (m, 1H), 2.53 (m, 2H), 2.43 (m, 1H), 2.18 (br, 1H), 1.83-1.70 (m, 3H), 1.64 (br, 1H), 1.47 (m, 2H), 1.28-1.23 (m, 4H).

Example 7

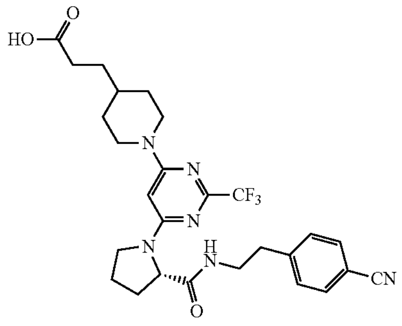

Compound 28

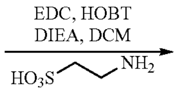

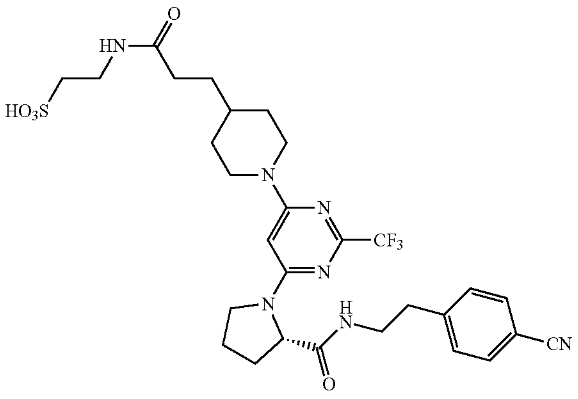

Compound 56

(S)-2-(3-(1-(6-(2-((4-cyanophenethyl)carbamoyl)pyrrolidin-1-yl)-2-(trifluoromethyl)pyrimidin-4-yl)piperidin-4-yl)propanamido)ethanesulfonic acid To a solution of Compound 28 (530 mg, 0.97 mmol) in DCM (7 mL) were added sequentially 1-ethyl-3-(3-dimethylaminopropyl)carbodiimide (224 mg, 1.17 mmol), N—S hydroxybenzotriazole (145 mg, 1.07 mmol), taurine (128 mg, 1.02 mmol) and diisopropylethylamine (0.43 mL, 2.5 mmol). The reaction mixture was stirred at room temperature overnight, and the solvent was evaporated in vacuo. The residue was purified by column chromatography (reverse phase C-18 column, 0-42% aceonitrile/water containing 0.25% formic acid) and then further purified by MS-HPLC to afford Compound 56 (270 mg, 43%). LCMS (method A): m/z 652.6 $(M+H)^+$. $^1$H NMR ($CD_3OD$) δ 7.59 (d, 2H), 7.37 (d, 2H), 4.49 (br s, 1H), 4.37 (t, 2H), 3.62 (t, 3H), 3.50-3.34 (m, 3H), 3.00-2.83 (m, 6H), 2.30 (m, 2H), 2.18 (m, 1H), 2.01 (m, 3H), 1.82 (d, 2H), 1.60 (t, 3H), 1.18 (m, 2H). Using the procedure described above for Example 7, the following compounds were prepared from precursors and reagents as indicated in Table 12.

TABLE 12

| No | Structure | Pre-cursor | Reagent | MS (M + H)$^+$ |
|---|---|---|---|---|
| 57 | 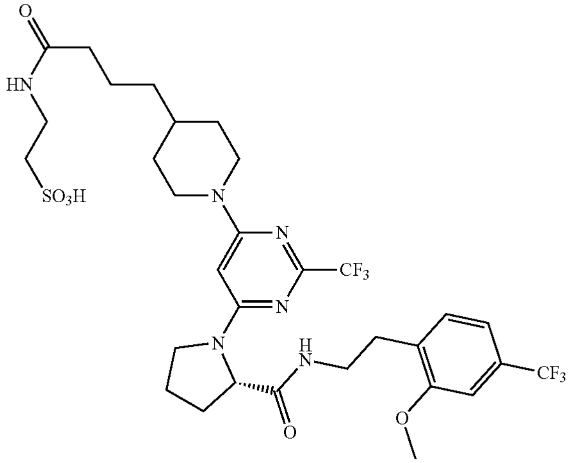 [SMILES: COc1cc(C(F)(F)F)ccc1CCNC(=O)[C@@H]1CCCN1c1cc(N2CCC(CCCC(=O)NCCS(=O)(=O)O)CC2)nc(C(F)(F)F)n1]<br>(S)-2-(4-(1-(6-(2-((2-methoxy-4-(trifluoromethyl)phenethyl)carbamoyl)-pyrrolidin-1-yl)-2-(trifluoromethyl)-pyrimidin-4-yl)piperidin-4-yl)butanamido)ethanesulfonic acid | 34 | 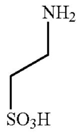 | 739.7 A |
| 58 | 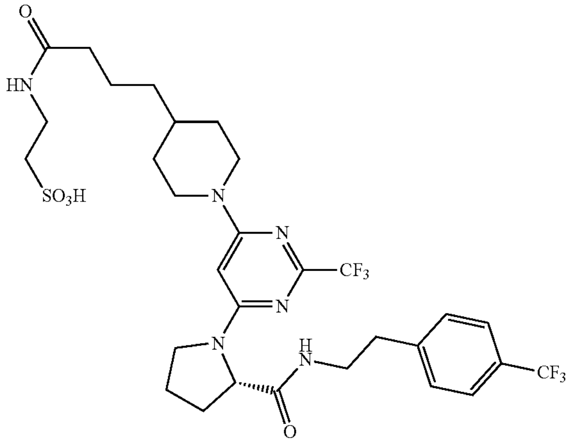 [SMILES: O=C(CCCC1CCN(c2cc(N3CCC[C@H]3C(=O)NCCc3ccc(C(F)(F)F)cc3)nc(C(F)(F)F)n2)CC1)NCCS(=O)(=O)O]<br>(S)-2-(4-(1-(2-(trifluoromethyl)-6-(2-((4-(trifluoromethyl)phenethyl)-carbamoyl)-pyrrolidin-1-yl)-pyrimidin-4-yl)piperidin-4-yl)butanamido)ethanesulfonic acid | 9 | 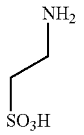 | 709.7 A |
| 59 | 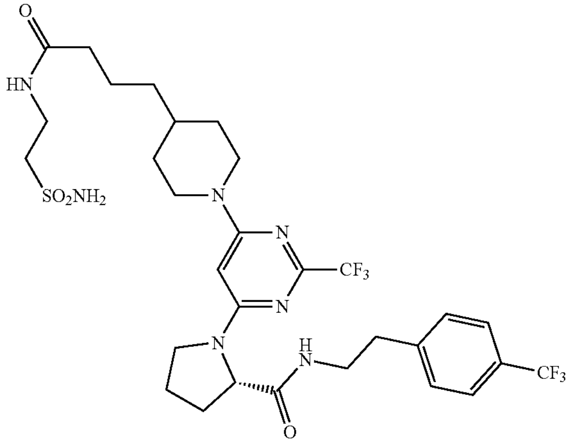 [SMILES: NS(=O)(=O)CCNC(=O)CCCC1CCN(c2cc(N3CCC[C@H]3C(=O)NCCc3ccc(C(F)(F)F)cc3)nc(C(F)(F)F)n2)CC1]<br>(S)-1-(6-(4-(4-oxo-4-((2-sulfamoylethyl)amino)butyl)piperidin-1-yl)-2-(trifluoromethyl)pyrimidin-4-yl)-N-(4-(trifluoromethyl)phenethyl)-pyrrolidine-2-carboxamide | 9 | 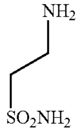 | 708.6 A |

TABLE 12-continued

| No | Structure | Pre-cursor | Reagent | MS $(M + H)^+$ |
|---|---|---|---|---|
| 60 | 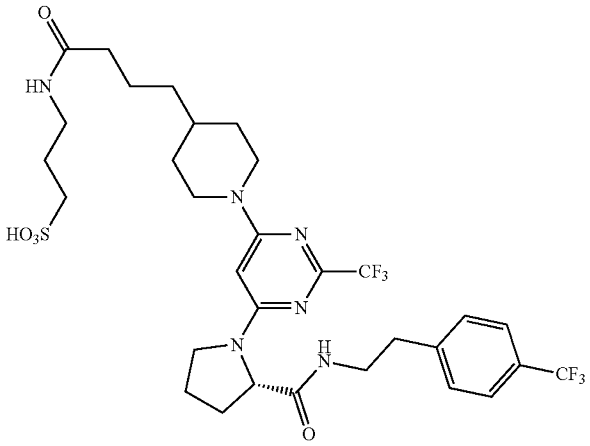 [SMILES: O=C(CCCC1CCN(c2cc(N3CCC[C@H]3C(=O)NCCc3ccc(C(F)(F)F)cc3)nc(C(F)(F)F)n2)CC1)NCCCS(=O)(=O)O]<br>(S)-3-(4-(1-(2-(trifluoromethyl)-6-(2-((4-(trifluoromethyl)phenethyl)carbamoyl)pyrrolidin-1-yl)pyrimidin-4-yl)piperidin-4-yl)butanamido)propane-1-sulfonic acid | 9 | 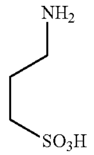 | 723.3 A |
| 61 | 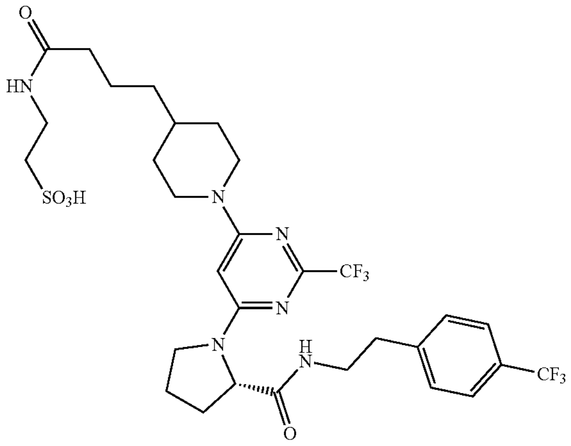 [SMILES: O=C(CCCC1CCN(c2cc(N3CCC[C@H]3C(=O)NCCc3ccc(C(F)(F)F)cc3)nc(C(F)(F)F)n2)CC1)NCCS(=O)(=O)O]<br>(S)-2-(4-(1-(6-(2-((4-cyanophenethyl)carbamoyl)pyrrolidin-1-yl)-2-(trifluoromethyl)pyrimidin-4-yl)-piperidin-4-yl)butanamido)ethanesulfonic acid | 29 | 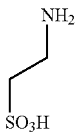 | 666.7 A |
| 62 | 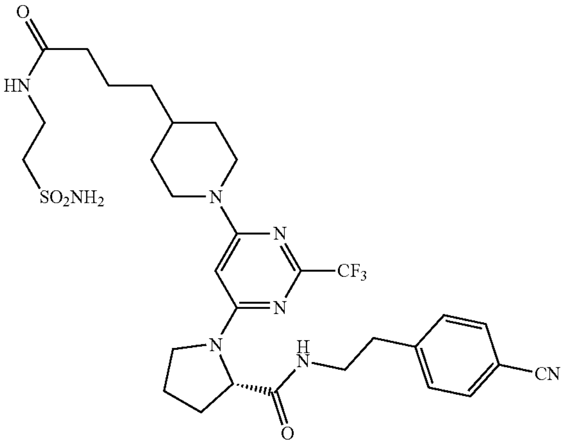 [SMILES: N#Cc1ccc(CCNC(=O)[C@@H]2CCCN2c2cc(N3CCC(CCCC(=O)NCCS(N)(=O)=O)CC3)nc(C(F)(F)F)n2)cc1]<br>(S)-N-(4-cyanophenethyl)-1-(6-(4-(4-oxo-4-((2-sulfamoylethyl)amino)butyl)piperidin-1-yl)-2- | 29 | 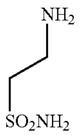 | 665.7 A |

TABLE 12-continued

| No | Structure | Pre-cursor | Reagent | MS (M + H)$^+$ |
|---|---|---|---|---|
| | (trifluoromethyl)pyrimidin-4-yl)pyrrolidine-2-carboxamide | | | |
| 63 | 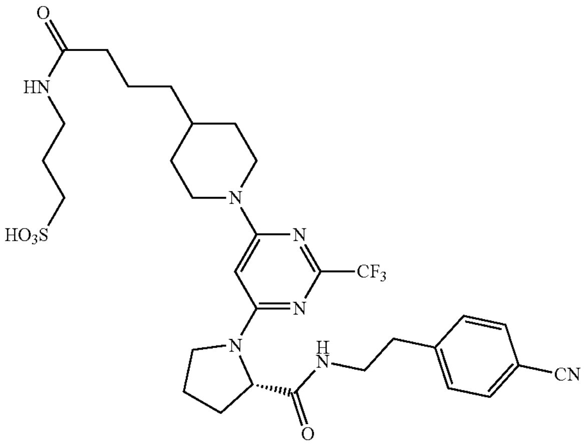<br>(S)-3-(4-(1-(6-(2-((4-cyanophenethyl)carbamoyl)pyrrolidin-1-yl)-2-(trifluoromethyl)pyrimidin-4-yl)-piperidin-4-yl)butanamido)propane-1-sulfonic acid | 29 | 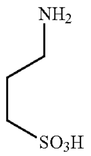 | 680.7 A |
| 64 | 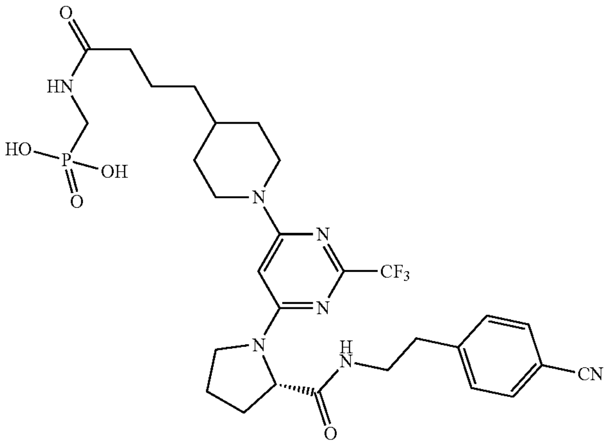 [SMILES: N#Cc1ccc(CCNC(=O)[C@@H]2CCCN2c2cc(N3CCC(CCCC(=O)NCP(=O)(O)O)CC3)nc(C(F)(F)F)n2)cc1]<br>(S)-((4-(1-(6-(2-((4-cyanophenethyl)carbamoyl)pyrrolidin-1-yl)-2-(trifluoromethyl)pyrimidin-4-yl)piperidin-4-yl)butanamido)methyl)-phosphonic acid | 29 | 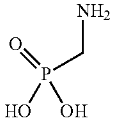 | 652.6 A |
| 65 | 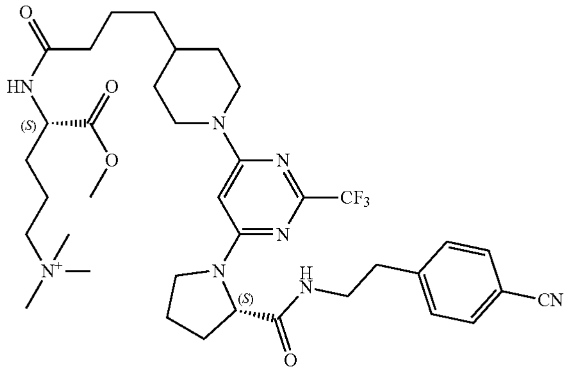<br>(S)-4-(4-(1-(6-((S)-2-((4-cyanophenethyl)carbamoyl)pyrrolidin-1-yl)-2-(trifluoromethyl)pyrimidin-4-yl)piperidin-4-yl)butanamido)-5-methoxy-N,N,N-trimethyl-5-oxopentan-1-aminium | 29 | 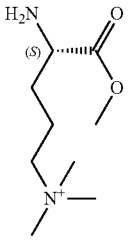 | 729.8 (M$^+$) A |

TABLE 12-continued

| No | Structure | Pre-cursor | Reagent | MS (M + H)$^+$ |
|---|---|---|---|---|
| 66 | 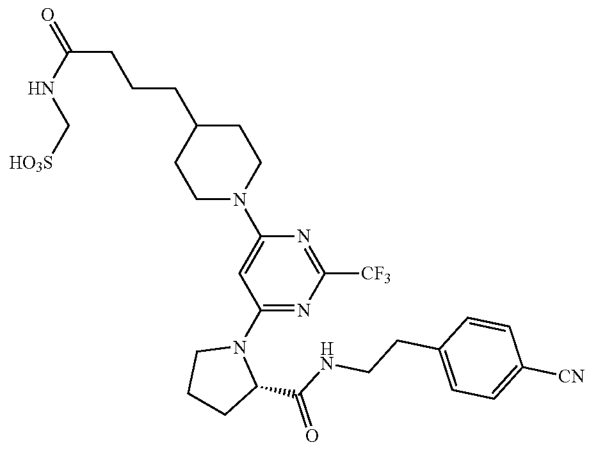 [SMILES: N#Cc1ccc(CCNC(=O)[C@@H]2CCCN2c2cc(N3CCC(CCCC(=O)NCS(=O)(=O)O)CC3)nc(C(F)(F)F)n2)cc1] (S)-(4-(1-(6-(2-((4-cyanophenethyl)carbamoyl)pyrrolidin-1-yl)-2-(trifluoromethyl)pyrimidin-4-yl)piperidin-4-yl)butanamido)-methanesulfonic acid | 29 | 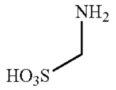 | 652.5 A |
| 67 | 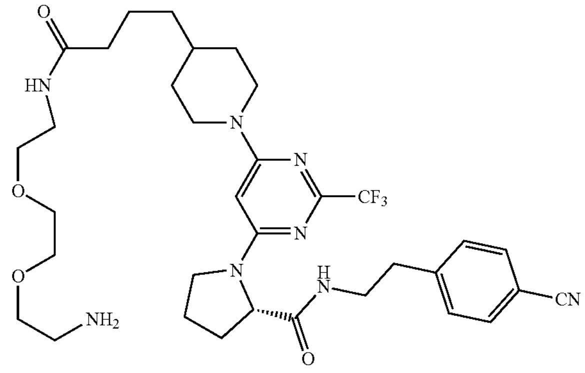 [SMILES: N#Cc1ccc(CCNC(=O)[C@@H]2CCCN2c2cc(N3CCC(CCCC(=O)NCCOCCOCCN)CC3)nc(C(F)(F)F)n2)cc1] (S)-1-(6-(4-(4-((2-(2-(2-aminoethoxy)ethoxy)ethyl)amino)-4-oxobutyl)piperidin-1-yl)-2-(trifluoromethyl)pyrimidin-4-yl)-N-(4-cyanophenethyl)pyrrolidine-2-carboxamide | 29 | 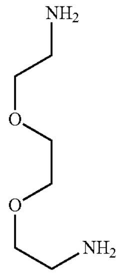 | 689.6 A |
| 68 | 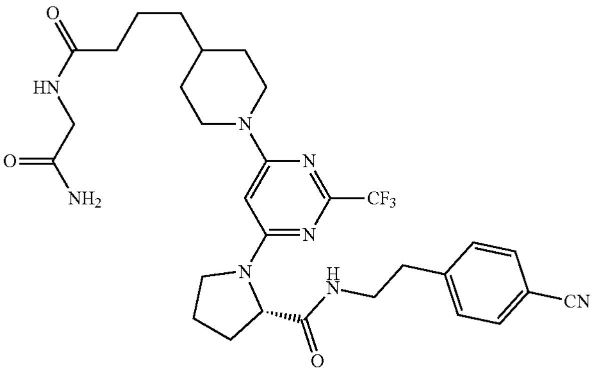 [SMILES: N#Cc1ccc(CCNC(=O)[C@@H]2CCCN2c2cc(N3CCC(CCCC(=O)NCC(N)=O)CC3)nc(C(F)(F)F)n2)cc1] (S)-1-(6-(4-(4-((2-amino-2-oxoethyl)amino)-4-oxobutyl)piperidin-1-yl)-2-(trifluoromethyl)pyrimidin-4-yl)-N-(4-cyanophenethyl)pyrrolidine-2-carboxamide | 29 | 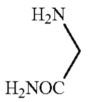 | 615.5 |

TABLE 12-continued

| No | Structure | Pre-cursor | Reagent | MS (M + H)+ |
|---|---|---|---|---|
| 69 | 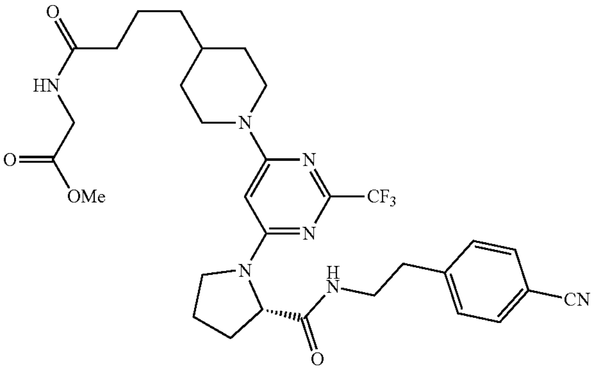 [SMILES: COC(=O)CNC(=O)CCCC1CCN(c2cc(N3CCC[C@H]3C(=O)NCCc3ccc(C#N)cc3)nc(C(F)(F)F)n2)CC1]<br>(S)-methyl 2-(4-(1-(6-(2-((4-cyanophenethyl)carbamoyl)pyrrolidin-1-yl)-2-(trifluoromethyl)pyrimidin-4-yl)piperidin-4-yl)butanamido)acetate | 29 | 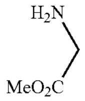 | 630.5 |
| 70 | 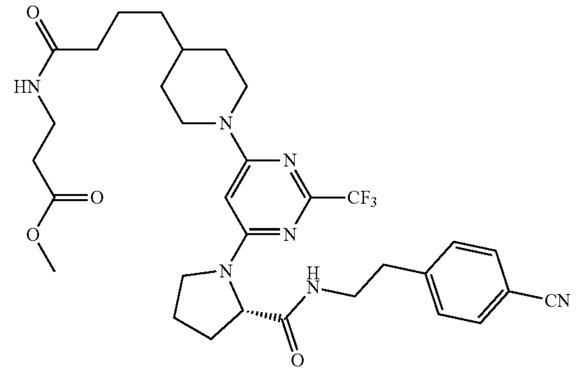 [SMILES: COC(=O)CCNC(=O)CCCC1CCN(c2cc(N3CCC[C@H]3C(=O)NCCc3ccc(C#N)cc3)nc(C(F)(F)F)n2)CC1]<br>(S)-methyl 3-(4-(1-(6-(2-((4-cyanophenethyl)carbamoyl)pyrrolidin-1-yl)-2-(trifluoromethyl)pyrimidin-4-yl)piperidin-4-yl)butanamido)-propanoate | 29 | 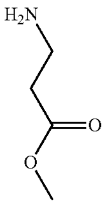 | 644.6 A |
| 71 | 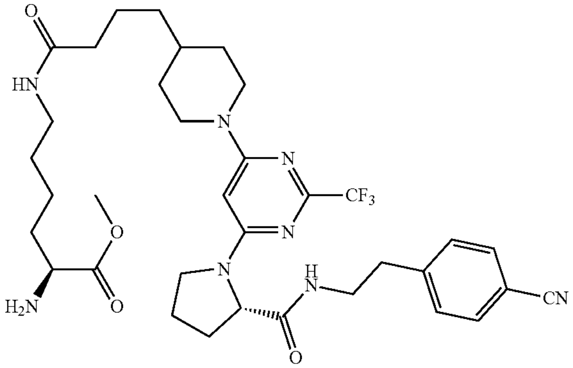 [SMILES: COC(=O)[C@@H](N)CCCCNC(=O)CCCC1CCN(c2cc(N3CCC[C@H]3C(=O)NCCc3ccc(C#N)cc3)nc(C(F)(F)F)n2)CC1]<br>(S)-methyl 2-amino-6-(4-(1-(6-((S)-2-((4-cyanophenethyl)carbamoyl)-pyrrolidin-1-yl)-2-(trifluoromethyl)-pyrimidin-4-yl)piperidin-4-yl)butanamido)hexanoate | 29 | Coupling with<br>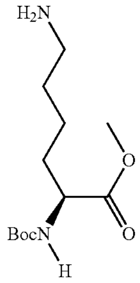<br>followed by de-protection with TFA as in Example 4 | 701.7 A |

TABLE 12-continued

| No | Structure | Pre-cursor | Reagent | MS (M + H)$^+$ |
|---|---|---|---|---|
| 72 | 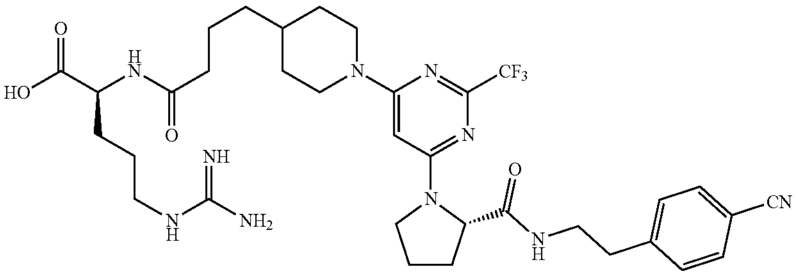 [SMILES: N#Cc1ccc(CCNC(=O)[C@@H]2CCCN2c2cc(N3CCC(CCCC(=O)N[C@@H](CCCNC(=N)N)C(=O)O)CC3)nc(C(F)(F)F)n2)cc1] (S)-2-(4-(1-(6-((S)-2-((4-cyanophenethyl)carbamoyl)pyrrolidin-1-yl)-2-(trifluoromethyl)pyrimidin-4-yl)piperidin-4-yl)butanamido)-5-guanidinopentanoic acid | 29 | Coupling with 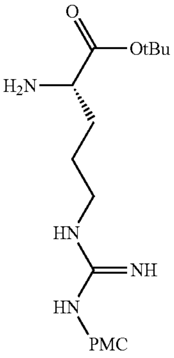 followed by de-protection with TFA as in Example 4 | 715.7 A |
| 73 | 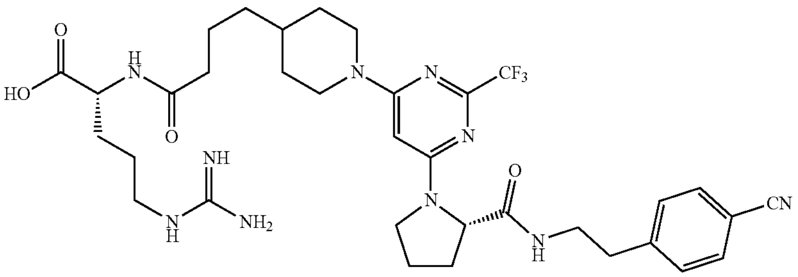 [SMILES: N#Cc1ccc(CCNC(=O)[C@@H]2CCCN2c2cc(N3CCC(CCCC(=O)N[C@H](CCCNC(=N)N)C(=O)O)CC3)nc(C(F)(F)F)n2)cc1] (R)-2-(4-(1-(6-((S)-2-((4-cyanophenethyl)carbamoyl)pyrrolidin-1-yl)-2-(trifluoromethyl)pyrimidin-4-yl)piperidin-4-yl)butanamido)-5-guanidinopentanoic acid | 29 | Coupling with 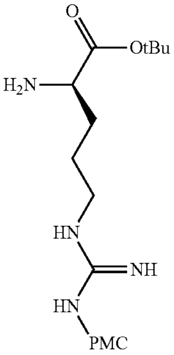 followed by de-protection with TFA as in Example 4 | 715.6 A |
| 74 | 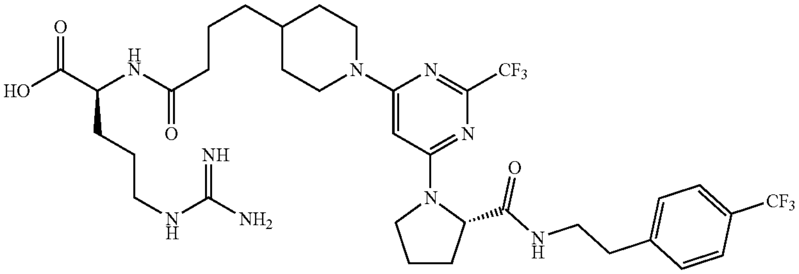 [SMILES: N=C(N)NCCC[C@H](NC(=O)CCCC1CCN(c2cc(N3CCC[C@H]3C(=O)NCCc3ccc(C(F)(F)F)cc3)nc(C(F)(F)F)n2)CC1)C(=O)O] (S)-5-guanidino-2-(4-(1-(2-(trifluoromethyl)-6-((S)-2-((4-(trifluoromethyl)phenethyl)carbamoyl)pyrrolidin-1-yl)pyrimidin-4-yl)piperidin-4-yl)butanamido)pentanoic acid | 9 | Coupling with 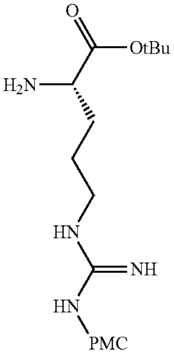 followed by de-protection with TFA as in Example 4 | 758.5 A |

TABLE 12-continued

| No | Structure | Pre-cursor | Reagent | MS (M + H)$^+$ |
|---|---|---|---|---|
| 75 | 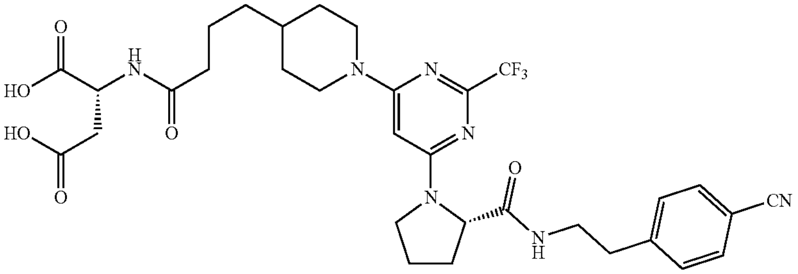 [SMILES: N#Cc1ccc(CCNC(=O)[C@@H]2CCCN2c2cc(N3CCC(CCCC(=O)N[C@H](CC(=O)O)C(=O)O)CC3)nc(C(F)(F)F)n2)cc1] (R)-2-(4-(1-(6-((S)-2-((4-cyanophenethyl)carbamoyl)pyrrolidin-1-yl)-2-(trifluoromethyl)pyrimidin-4-yl)piperidin-4-yl)butanamido)succinic acid | 29 | Coupling with 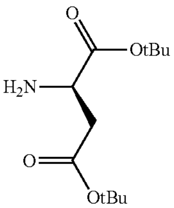 followed by de-protection with TFA as in Example 4 | 674.5 A |
| 76 | 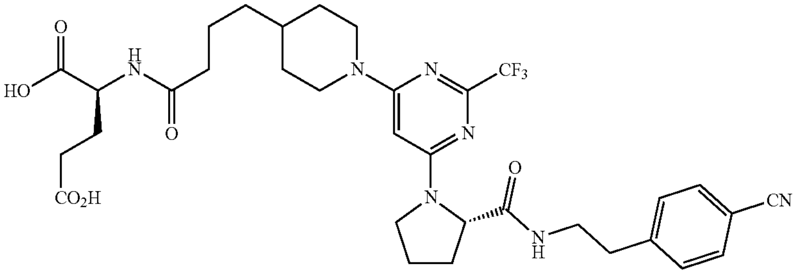 [SMILES: N#Cc1ccc(CCNC(=O)[C@@H]2CCCN2c2cc(N3CCC(CCCC(=O)N[C@@H](CCC(=O)O)C(=O)O)CC3)nc(C(F)(F)F)n2)cc1] (S)-2-(4-(1-(6-((S)-2-((4-cyanophenethyl)carbamoyl)pyrrolidin-1-yl)-2-(trifluoromethyl)pyrimidin-4-yl)piperidin-4-yl)butanamido)-pentanedioic acid | 29 | Coupling with 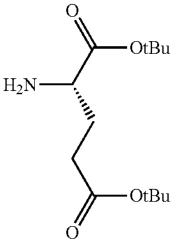 followed by de-protection with TFA as in Example 4 | 688.5 A |

Example 8

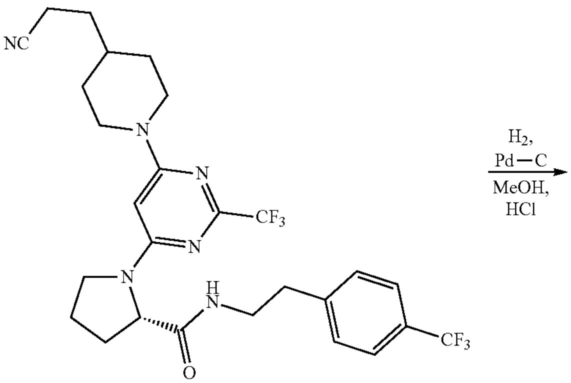

Compound 11

-continued

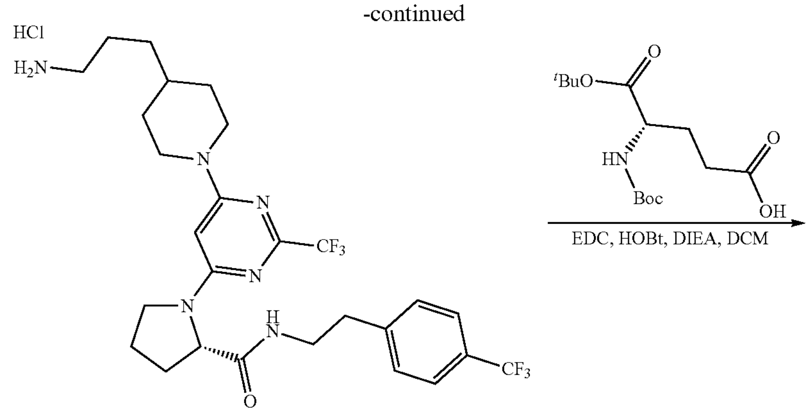

Compound 8A

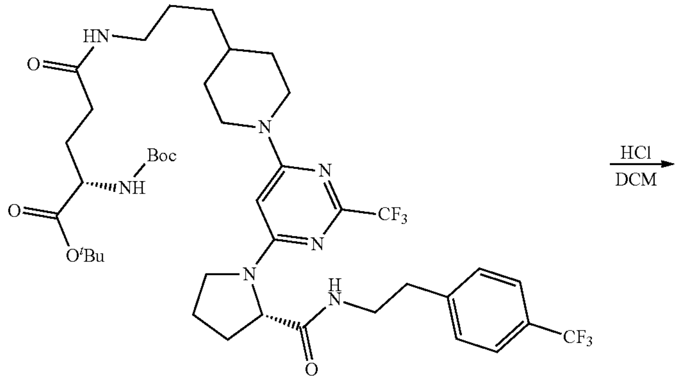

Compound 8B

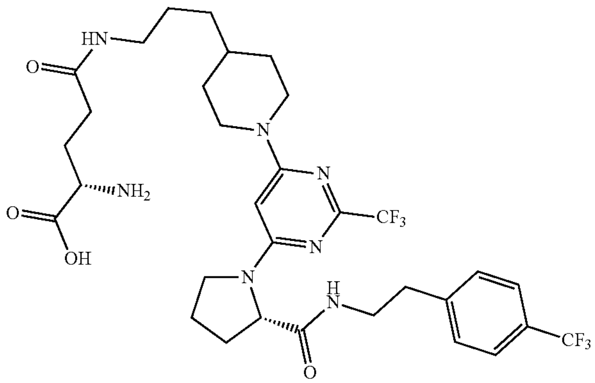

Compound 77

(S)-1-(6-(4-(3-aminopropyl)piperidin-1-yl)-2-(trifluoromethyl)pyrimidin-4-yl)-N-(4-(trifluoromethyl)phenethyl)pyrrolidine-2-carboxamide hydrochloride To a solution of Compound 11 (140 mg, 0.25 mmol) and concentrated hydrochloric acid (82 μL, 0.98 mmol) in MeOH (5 mL) was added palladium (10% on carbon, 5.0 mg, 0.25 mmol). The reaction mixture was degassed and stirred under $H_2$ (1 atm) at room temperature for six days. The reaction was filtered through a CELITE pad.

The solvent was removed under reduced pressure to give Compound 8A (142 mg, 95%) which was used directly in next step without purification. LCMS (method A): m/z 573.3 $(M+H)^+$.

(S)-tert-butyl 2-((tert-butoxycarbonyl)amino)-5-oxo-5-((3-(1-(2-(trifluoromethyl)-6-((S)-2-((4-(trifluoromethyl)phenethyl)carbamoyl)pyrrolidin-1-yl)pyrimidin-4-yl)piperidin-4-yl)propyl)amino)pentanoate Using the procedure as described in example 7, Compound 8A (71 mg, 0.12 mmol) was converted to Compound 8B (50 mg, 50%). LCMS (method A): m/z 858.5 $(M+H)^+$.

(S)-2-amino-5-oxo-5-((3-(1-(2-(trifluoromethyl)-6-((S)-2-((4-(trifluoromethyl)phenethyl)carbamoyl)pyrrolidin-1-yl)pyrimidin-4-yl)piperidin-4-yl)propyl)amino)pentanoic acid Using the procedure as described in Intermediate 9, step 3, Compound 8B (50 mg, 0.058 mmol) was deprotected to provide a crude product which was purified by MS-HPLC to afford Compound 77. LCMS (method A): m/z 702.2 $(M+H)^+$. $^1H$ NMR ($CD_3OD$) δ 7.49 (d, 2H), 7.32 (d, 2H), 5.58 (br s, 1H), 4.44-4.38 (m, 3H), 3.59 (t, 2H), 3.50-3.47 (m, 1H), 3.40-3.31 (m, 2H), 3.17 (t, 2H), 2.88-2.81 (m, 4H), 2.41 (t, 2H), 2.20-2.06 (m, 3H), 2.00-1.97 (m, 3H), 1.78 (d, 2H), 1.59-1.51 (m, 3H), 1.31-1.26 (m, 2H), 1.18-1.09 (m, 2H).

Example 9

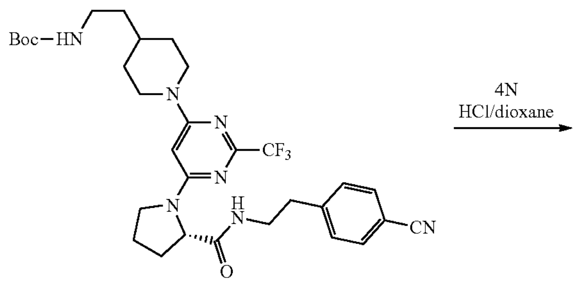

Compound 18

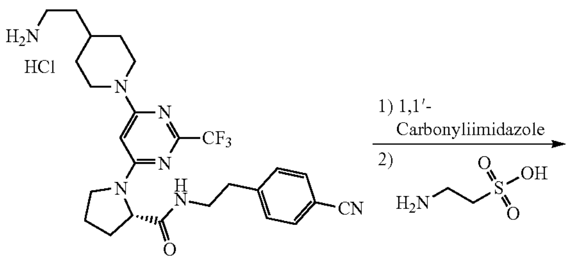

Compound 9A

-continued

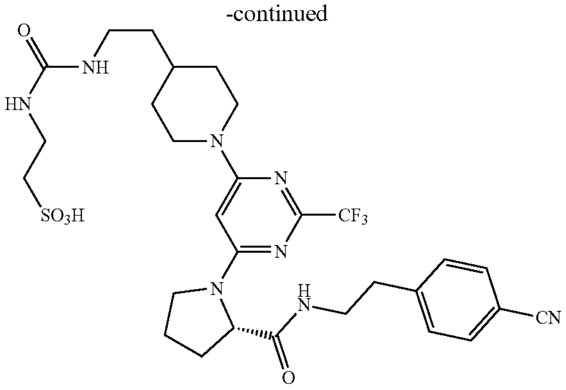

Compound 78

(S)-1-(6-(4-(2-aminoethyl)piperidin-1-yl)-2-(trifluoromethyl)pyrimidin-4-yl)-N-(4-cyano phenethyl) pyrrolidine-2-carboxamide hydrochloride Compound 18 was converted to Compound 9A following the procedure as described in Intermediate 9, step 3. LCMS (method A): m/z 516.3 $(M+H)^+$. $^1H$ NMR ($CD_3OD$): δ 7.91 (b, 1H), 7.54-7.52 (dd, 2H), 7.32-7.30 (dd, 2H), 5.59 (b, 1H), 4.49-4.39 (m, 3H), 3.67-3.31 (m, 6H), 3.01-2.80 (m, 6H), 2.15-2.00 (m, 4H), 1.83-1.59 (m, 5H), 1.28-1.19 (m, 2H).

(S)-2-(3-(2-(1-(6-(2-((4-cyanophenethyl)carbamoyl) pyrrolidin-1-yl)-2-(trifluoromethyl)pyrimidin-4-yl) piperidin-4-yl)ethyl)ureido)ethanesulfonic acid To Compound 9A (96 mg, 0.17 mmol) in DCM (1 mL) was added N,N-diisopropylethylamine (97 μL, 0.56 mmol). Once in solution, 1,1'-carbonyldiimidazole (42 mg, 0.26 mmol) was added and the reaction was stirred at room temperature for one hour. To the reaction mixture were added solid taurine (371 mg, 2.96 mmol), N,N-diisopropylethylamine (181 μL, 1.02 mmol) and DMF (0.5 mL) to aid in solubilizing the taurine. The reaction was heated in a microwave for five hours at 90° C. The reaction was concentrated in vacuo, and purified by column chromatography (reverse phase C-18 column, 0-100% acetonitrile/water containing 0.25% formic acid), followed by MS-HPLC to afford Compound 78 (44 mg, 38%). LCMS (Method D): m/z 667.1 $(M+H)^+$. $^1H$ NMR ($CD_3OD$): δ 7.56-7.54 (dd, 2H), 7.33-7.31 (dd, 2H), 5.60 (b, 1H), 4.48-4.36 (m, 3H), 3.61-3.58 (m, 3H), 3.51-3.37 (m, 3H), 3.25 (t, 2H), 3.00-2.79 (m, 6H), 2.18-2.11 (m, 1H), 2.02-1.99 (m, 3H), 1.84-1.81 (m, 2H), 1.71-1.65 (M, 1H), 1.53-1.48 (m, 2H), 1.24-1.15 (m, 2H). Using the procedure described above for Example 9, the following compounds were prepared from precursors and reagents as indicated in Table 13.

TABLE 13

| No | Structure | Pre-cursor | Reagent in step 2 | MS (M + H)$^+$ |
|---|---|---|---|---|
| 79 | 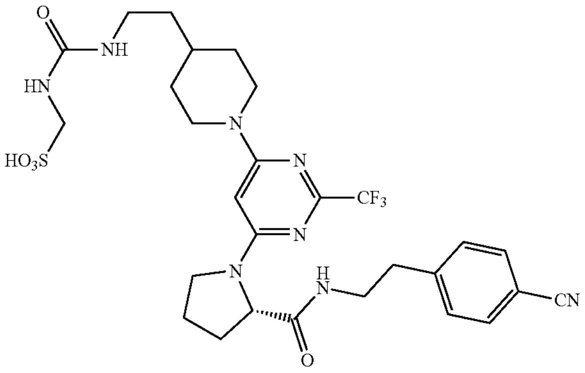 [SMILES: N#Cc1ccc(CCNC(=O)[C@@H]2CCCN2c2cc(N3CCC(CCNC(=O)NCS(=O)(=O)O)CC3)nc(C(F)(F)F)n2)cc1]<br>(S)-(3-(2-(1-(6-(2-((4-cyanophenethyl)carbamoyl)pyrrolidin-1-yl)-2-(trifluoromethyl)pyrimidin-4-yl)piperidin-4-yl)ethyl)ureido)methanesulfonic acid | 18 | 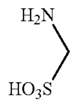 | 653.5 A |
| 80 | 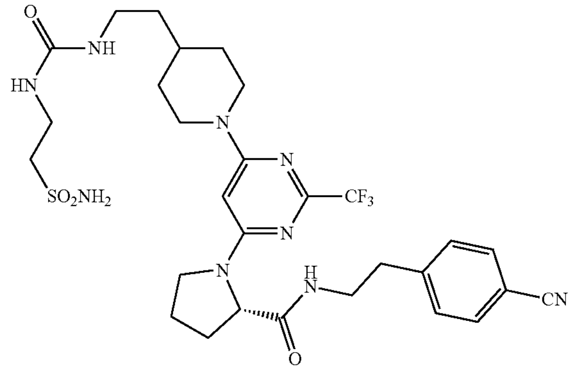 [SMILES: N#Cc1ccc(CCNC(=O)[C@@H]2CCCN2c2cc(N3CCC(CCNC(=O)NCCS(N)(=O)=O)CC3)nc(C(F)(F)F)n2)cc1]<br>(S)-N-(4-cyanophenethyl)-1-(6-(4-(2-(3-(2-sulfamoylethyl)ureido)-ethyl)piperidin-1-yl)-2-(trifluoromethyl)pyrimidin-4-yl)pyrrolidine-2-carboxamide | 18 | 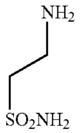 | 663.3 A |
| 81 | 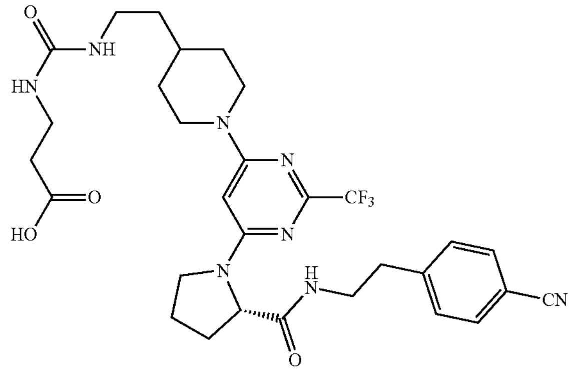 [SMILES: N#Cc1ccc(CCNC(=O)[C@@H]2CCCN2c2cc(N3CCC(CCNC(=O)NCCC(=O)O)CC3)nc(C(F)(F)F)n2)cc1]<br>(S)-3-(3-(2-(1-(6-(2-((4-cyanophenethyl)carbamoyl)pyrrolidin-1-yl)-2-(trifluoromethyl)pyrimidin-4-yl)piperidin-4-yl)ethyl)ureido)-propanoic acid | 18 | 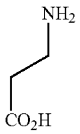 | 631.3 A |

TABLE 13-continued

| No | Structure | Pre-cursor | Reagent in step 2 | MS (M + H)+ |
|---|---|---|---|---|
| 82 | 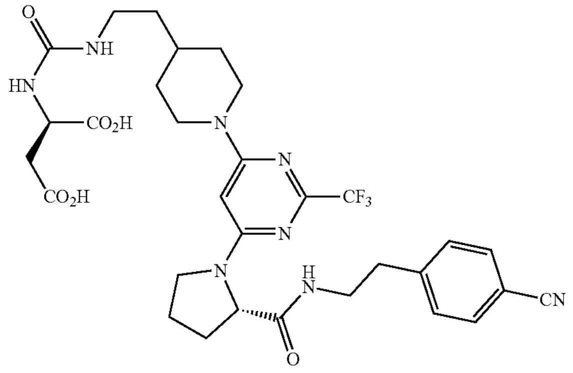 [SMILES: N#Cc1ccc(CCNC(=O)[C@@H]2CCCN2c2cc(N3CCC(CCNC(=O)N[C@H](CC(=O)O)C(=O)O)CC3)nc(C(F)(F)F)n2)cc1] (R)-2-(3-(2-(1-(6-((S)-2-((4-cyanophenethyl)carbamoyl)pyrrolidin-1-yl)-2-(trifluoromethyl)pyrimidin-4-yl)piperidin-4-yl)ethyl)ureido)succinic acid | 18 | 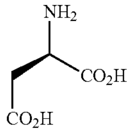 | 675.5 A |
| 83 | 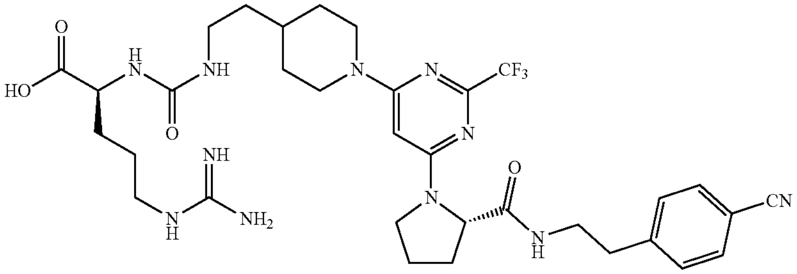 [SMILES: N#Cc1ccc(CCNC(=O)[C@@H]2CCCN2c2cc(N3CCC(CCNC(=O)N[C@@H](CCCNC(=N)N)C(=O)O)CC3)nc(C(F)(F)F)n2)cc1] (S)-2-(3-(2-(1-(6-((S)-2-((4-cyanophenethyl)carbamoyl)pyrrolidin-1-yl)-2-(trifluoromethyl)pyrimidin-4-yl)piperidin-4-yl)ethyl)ureido)-5-guanidinopentanoic acid | 18 | react with 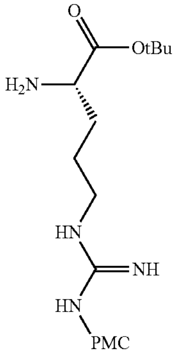 followed by de-protection with TFA as in Example 5 | 716.6 A |
| 84 | 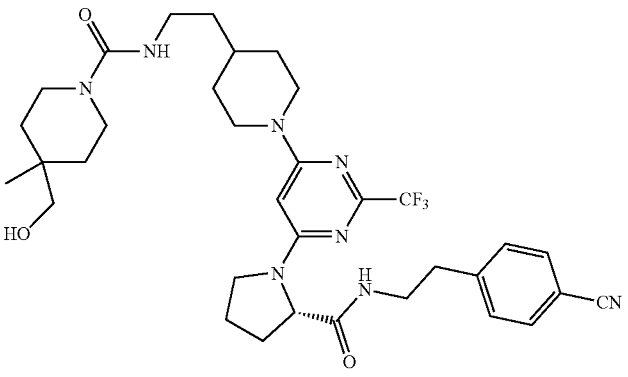 [SMILES: CC1(CO)CCN(C(=O)NCCC2CCN(c3cc(N4CCC[C@H]4C(=O)NCCc4ccc(C#N)cc4)nc(C(F)(F)F)n3)CC2)CC1] (S)-N-(2-(1-(6-(2-((4-cyanophenethyl)carbamoyl)pyrrolidin-1-yl)-2-(trifluoromethyl)pyrimidin-4-yl)piperidin-4-yl)ethyl)-4-(hydroxymethyl)-4-methylpiperidine-1-carboxamide | 18 | 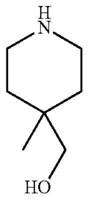 | 671.6 A |

TABLE 13-continued

| No | Structure | Pre-cursor | Reagent in step 2 | MS (M + H)+ |
|---|---|---|---|---|
| 85 | 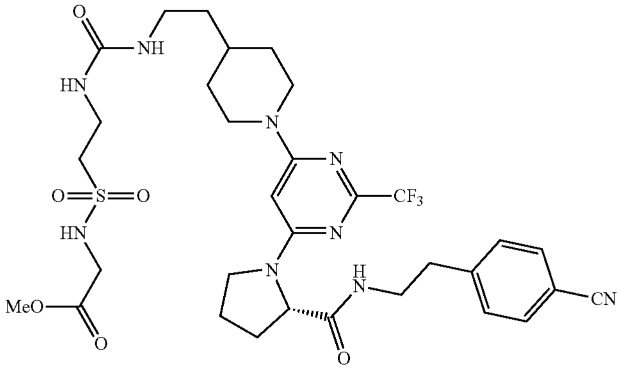 [SMILES: COC(=O)CNS(=O)(=O)CCNC(=O)NCCC1CCN(c2cc(N3CCC[C@H]3C(=O)NCCc3ccc(C#N)cc3)nc(C(F)(F)F)n2)CC1]<br>(S)-N-(2-(1-(6-(2-((4-cyanophenethyl)-carbamoyl)pyrrolidin-1-yl)-2-(trifluoromethyl)pyrimidin-4-yl)piperidin-4-yl)ethyl)-2-(2-aminoethylsulfonamido)acetate methyl ester | 18 | Inter-mediate 21 | 738.6 |
| 86 | 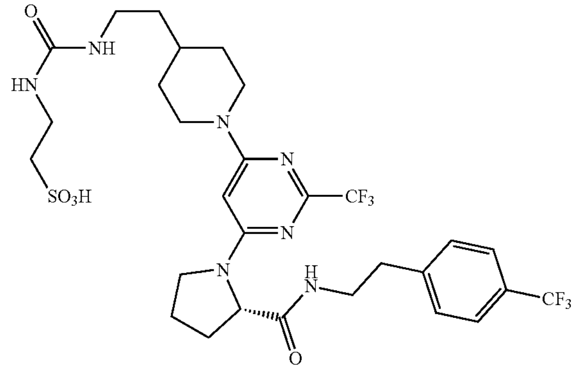 [SMILES: O=C(NCCC1CCN(c2cc(N3CCC[C@H]3C(=O)NCCc3ccc(C(F)(F)F)cc3)nc(C(F)(F)F)n2)CC1)NCCS(=O)(=O)O]<br>(S)-2-(3-(2-(1-(2-(trifluoromethyl)-6-(2-((4-(trifluoromethyl)phenethyl)-carbamoyl)pyrrolidin-1-yl)pyrimidin-4-yl)piperidin-4-yl)ethyl)ureido)-ethanesulfonic acid | 6 | 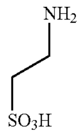 | 710.3 A |
| 87 | 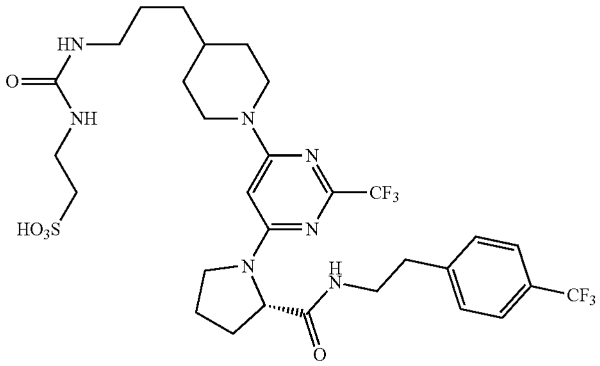 [SMILES: O=C(NCCCC1CCN(c2cc(N3CCC[C@H]3C(=O)NCCc3ccc(C(F)(F)F)cc3)nc(C(F)(F)F)n2)CC1)NCCS(=O)(=O)O]<br>(S)-2-(3-(3-(1-(2-(trifluoromethyl)-6-(2-((4-(trifluoromethyl)phenethyl)-carbamoyl)-pyrrolidin-1-yl)pyrimidin-4-yl)piperidin-4-yl)propyl)ureido)-ethanesulfonic acid | Com-pound 8A And step 2 In Example 9 | 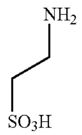 | 724.3 A |

Example 10

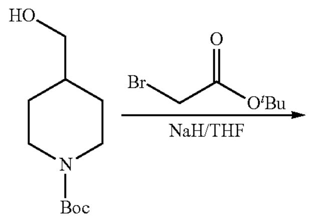

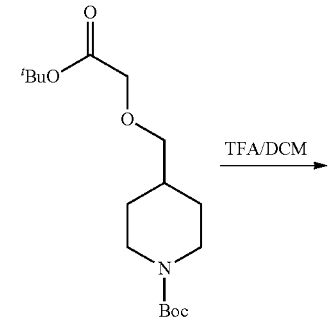

Compound 10A

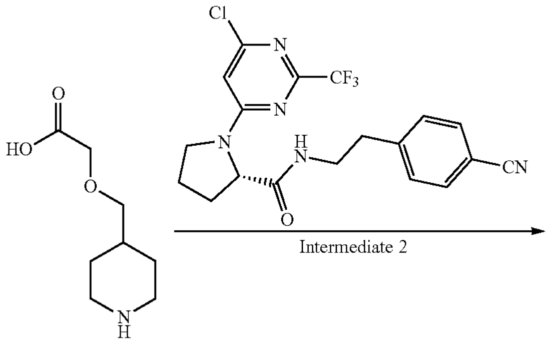

Compound 10B

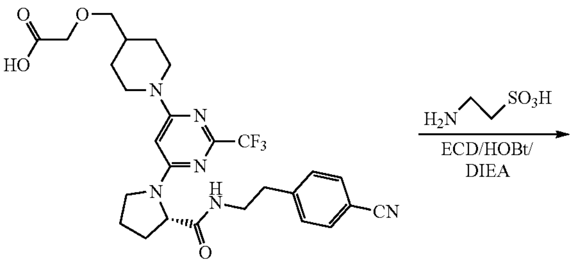

Compound 78

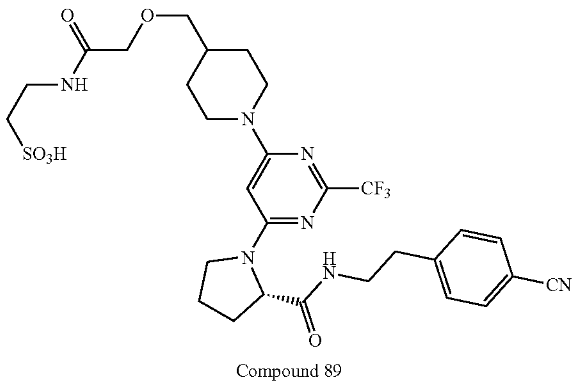

Compound 89 tert-butyl 4-((2-(tert-butoxy)-2-oxoethoxy)methyl) piperidine-1-carboxylate

Sodium hydride (480 mg, 60% suspension in mineral oil, 20 mmol) in anhydrous THF (5 mL) was cooled to 0° C. under nitrogen with stirring. A solution of N-Boc-4-hydroxymethylpiperidine (2.2 g, 10 mmol) in anhydrous THF (5 mL) was added drop wise. The mixture was stirred at 0° C. for 30 min, and t-butyl bromoacetate was added drop wise. The mixture was stirred at 0° C. for 1 hour, then at room temperature overnight. The reaction was quenched with a small amount of MeOH and the solvent was removed in vacuo. The residue was partitioned between water (30 mL) and DCM (60 mL). The aqueous layer was washed once with DCM (60 mL). The combined organic layers were dried over $Na_2SO_4$, filtered, and concentrated. The residue was purified by silica gel chromatography (0-100% EA in hexanes) to afford Compound 10A (338 mg). LCMS (method A): m/z 232.3 $(M+H)^+$. $^1H$ NMR ($CDCl_3$) δ 4.11 (br, 2H), 3.94 (s, 2H), 3.36 (d, 2H), 2.70 (m, 2H), 1.78 (m, 1H), 1.74 (m, 2H), 1.20-1.14 (m, 2H).

2-(piperidin-4-ylmethoxy)acetic acid

Compound 10A (338 mg, 1 mmol) was dissolved in DCM (6 mL), and TFA (2 mL) was added. The mixture was stirred at room temperature for five hours. Solvent was removed in vacuo. The residue was pumped under high vacuum to afford crude Compound 10B which was used in the next reaction without further purification. LCMS (method A): m/z 174.3 $(M+H)^+$. $^1H$ NMR ($CDCl_3$) δ 4.08 (s, 2H), 3.47-3.36 (m, 5H), 2.94 (m, 2H), 1.99 (m, 3H), 1.56 (m, 2H).

(S)-2-((1-(6-(2-((4-cyanophenethyl)carbamoyl)pyrrolidin-1-yl)-2-(trifluoromethyl) pyrimidin-4-yl) piperidin-4-yl)methoxy)acetic acid Intermediate 2 (360 mg, 0.86 mmol) was dissolved in DMSO (3 mL). DIEA (0.60 mL, 3.44 mmol) and crude Compound 10B were added and the mixture was heated at 120° C. in a microwave for three hours. The mixture was diluted with DCM (100 mL), and washed with water (15 mL) and brine (15 mL). The combined organic layers were dried ($Na_2SO_4$), filtered, and concentrated. The residue was purified by silica gel chromatography (0-10% MeOH in DCM) to afford Compound 88 (68 mg). LCMS (method A): m/z 561.6 $(M+H)^+$. $^1H$ NMR ($CDCl_3$) δ 7.75 (br s, 1H), 7.42 (d, 2H), 7.15 (d, 2H), 5.33 (s, 1H), 4.61 (br s, 1H), 4.42 (br s, 2H), 4.13 (s, 2H), 3.58 (m, 1H), 3.46-3.36 (m, 4H), 3.22 (m, 1H), 2.96-2.73 (m, 4H), 2.43 (m, 1H), 2.18 (m, 1H), 1.99 (m, 1H), 1.89-1.84 (m, 3H), 1.30 (m, 2H).

(S)-2-(2-((1-(6-(2-((4-cyanophenethyl)carbamoyl) pyrrolidin-1-yl)-2-(trifluoromethyl) pyrimidin-4-yl) piperidin-4-yl)methoxy)acetamido)-ethanesulfonic acid Using the procedure described above in Example 7, Compound 88 (43 mg) was converted to Compound 89 (17 mg). LCMS (method A): m/z 668.5 $(M+H)^+$. $^1H$ NMR ($CD_3OD$) δ 7.57 (d, 2H), 7.35 (d, 2H), 4.53 (br s, 1H), 4.36 (m, 2H), 3.94 (s, 2H), 3.66 (m, 3H), 3.53-3.40 (m, 5H), 3.05-2.86 (m, 6H), 2.23 (br, 1H), 2.03 (br, 4H), 1.86 (d, 2H), 1.43-1.37 (m, 2H).

Example 11

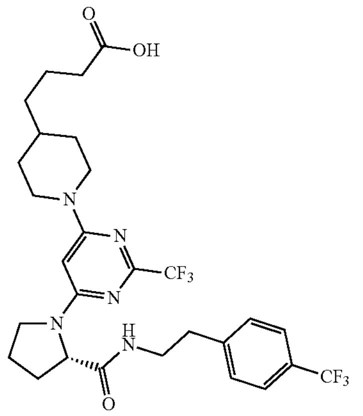

Compound 9

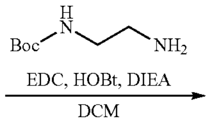

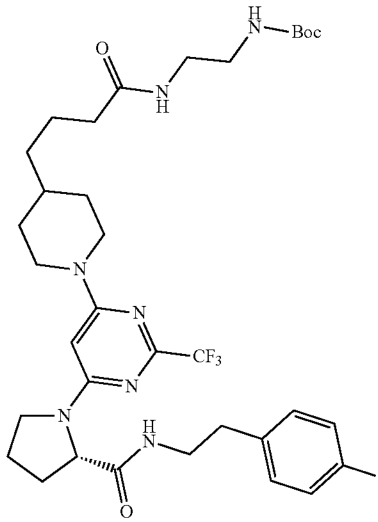

Compound 11A

HCl in
Dioxane
DCM

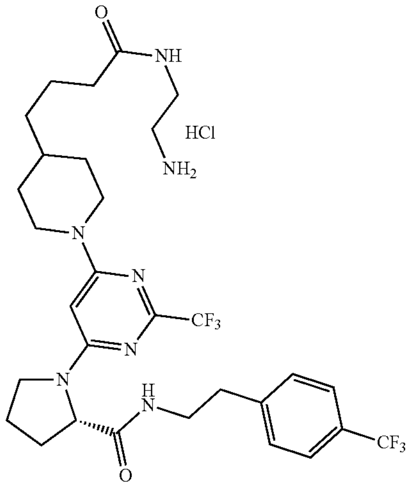

Compound 90

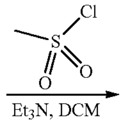

-continued

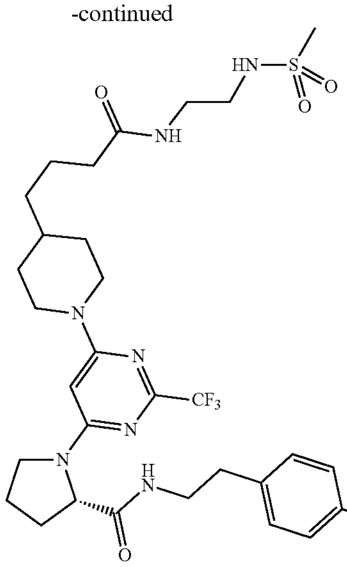

Compound 91

(S)-tert-butyl (2-(4-(1-(2-(trifluoromethyl)-6-(2-((4-(trifluoromethyl)phenethyl) carbamoyl)pyrrolidin-1-yl)pyrimidin-4-yl)piperidin-4-yl)butanamido)ethyl) carbamate Using the procedure described above in Example 10, Compound 9 (100 mg, 0.17 mmol) was converted to Compound 11A (104 mg, 84%). LCMS (method A): m/z 744.7 $(M+H)^+$.

(S)-1-(6-(4-(4-((2-aminoethyl)amino)-4-oxobutyl) piperidin-1-yl)-2-(trifluoromethyl) pyrimidin-4-yl)-N-(4-(trifluoromethyl)phenethyl)pyrrolidine-2-carboxamide hydrochloride Using the procedure described in Intermediate 9, step 3, Compound 11A (99 mg, 0.13 mmol) was converted to Compound 90. LCMS (method A): m/z 644.7 $(M+H)^+$. $^1$H NMR ($CD_3OD$) δ 7.50 (d, 2H), 7.34 (d, 2H), 4.51 (br, 1H), 4.38 (t, 1H), 3.62 (br, 1H), 3.53-3.36 (m, 5H), 3.05 (t, 2H), 2.95-2.84 (m, 4H), 2.27-2.17 (m, 3H), 2.00 (br, 3H), 1.82 (d, 2H), 1.72-1.55 (m, 3H), 1.33-1.27 (m, 2H), 1.20-1.12 (m, 2H).

(S)-1-(6-(4-(4-((2-(methylsulfonamido)ethyl)amino)-4-oxobutyl)piperidin-1-yl)-2-(trifluoromethyl)pyrimidin-4-yl)-N-(4-(trifluoromethyl)phenethyl)pyrrolidine-2-carboxamide To a mixture of Compound 90 (70 mg, 0.10 mmol) and triethylamine (86 μL, 0.62 mmol) in DCM (1 mL) was added methanesulfonyl chloride (27 μL, 0.33 mmol). The reaction mixture was stirred at room temperature for two hours. The mixture was washed with 10% citric acid, sat. $Na_2CO_3$ and brine. The solvent was removed under reduced pressure to give a crude product which was purified by MS-HPLC to afford Compound 91. LCMS (method A): m/z 722.7 $(M+H)^+$. $^1$H NMR ($CDCl_3$) δ 7.40 (d, 2H), 7.16 (d, 2H), 6.08 (t, 1H), 5.07 (t, 1H), 4.60 (br s, 1H), 4.34 (br s, 2H), 3.59-3.51 (m, 1H), 3.46-3.31 (m, 4H), 3.30-3.15 (m, 3H), 2.96 (s, 3H), 2.89-2.72 (m, 4H), 2.42 (br, 1H), 2.23-2.08 (m, 3H), 2.07-2.01 (m, 1H), 1.92-1.77 (m, 3H), 1.72-1.64 (m, 4H), 1.58-1.51 (m, 1H), 1.32-1.26 (m, 2H), 1.21-1.11 (m, 2H). Using the procedure described above for Example 11, the following compounds were prepared from precursors and reagents as indicated in Table 14.

TABLE 14

| No | Structure | Pre-cursor | Reagent | MS (M + H)+ |
| --- | --- | --- | --- | --- |
| 92 | 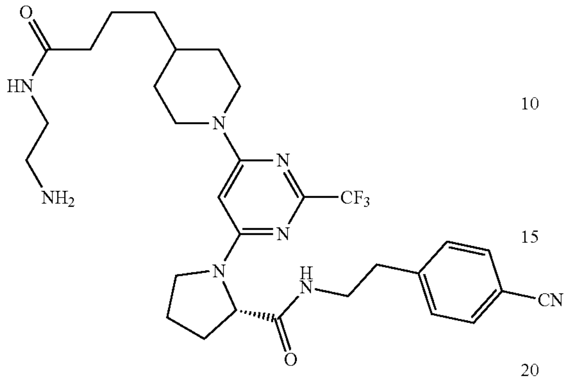<br>(S)-1-(6-(4-(4-((2-aminoethyl)amino)-4-oxobutyl)piperidin-1-yl)-2-(trifluoromethyl)pyrimidin-4-yl)-N-(4-cyanophenethyl)pyrrolidine-2-carboxamide | 29 | 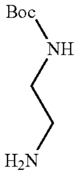<br>Same as Example 11, Step 1 Step 2 | 601.6 A |
| 93 | 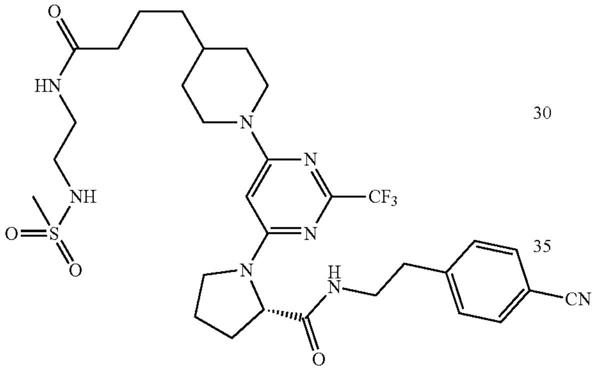 [SMILES: CS(=O)(=O)NCCNC(=O)CCCC1CCN(c2cc(N3CCC[C@H]3C(=O)NCCc3ccc(C#N)cc3)nc(C(F)(F)F)n2)CC1]<br>(S)-N-(4-cyanophenethyl)-1-(6-(4-(4-((2-(methylsulfonamido)ethylamino)-4-oxobutyl)piperidin-1-yl)-2-(trifluoromethyl)pyrimidin-4-yl)pyrrolidine-2-carboxamide | 92 | 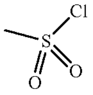 | 679.5 A |
| 94 | 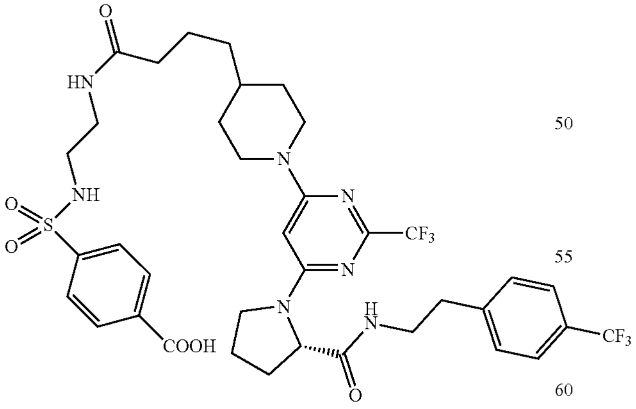 [SMILES: O=C(CCCC1CCN(c2cc(N3CCC[C@H]3C(=O)NCCc3ccc(C(F)(F)F)cc3)nc(C(F)(F)F)n2)CC1)NCCNS(=O)(=O)c1ccc(C(=O)O)cc1]<br>(S)-4-(N-(2-(4-(1-(2-(trifluoromethyl)-6-(2-((4-(trifluoromethyl)phenethyl)-carbamoyl)-pyrrolidin-1-yl)pyrimidin-4-yl)piperidin-4-yl)butanamido)ethyl)-sulfamoyl)benzoic acid | 90 | 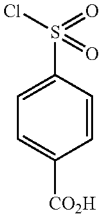 | 828.6 A |

Example 12

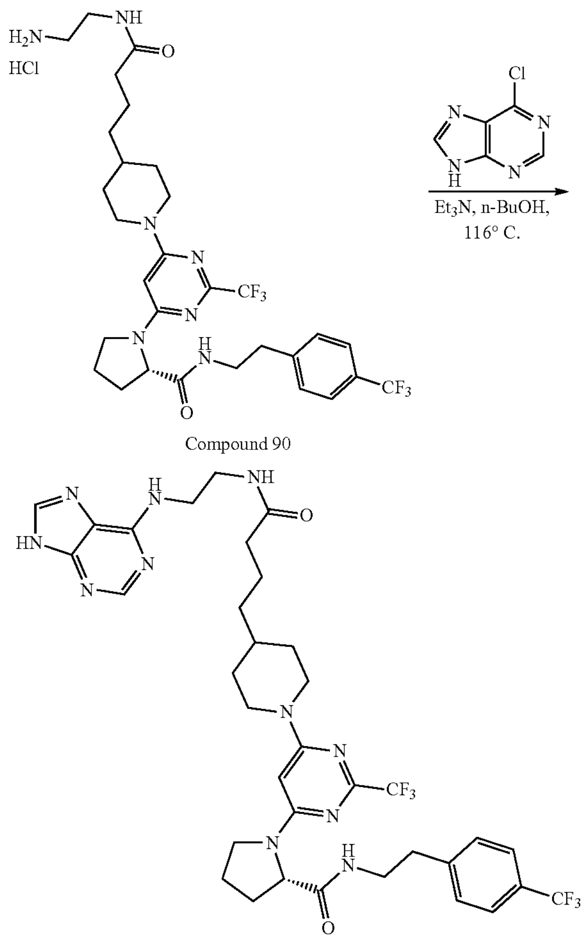

Compound 90

Compound 95

(S)-1-(6-(4-(4-((2-((9H-purin-6-yl)amino)ethyl)amino)-4-oxobutyl)piperidin-1-yl)-2-(trifluoromethyl)pyrimidin-4-yl)-N-(4-(trifluoromethyl)phenethyl)pyrrolidine-2-carboxamide To a solution of Compound 90 (100 mg, 0.15 mmol) and 6-chloro-9H-purine (38 mg, 0.25 mmol) in n-BuOH (4 mL) was added triethylamine (82 μL, 0.59 mmol). The reaction mixture was stirred at 116° C. for four hours and the solvent was removed in vacuo to give a crude product which was purified by MS-HPLC to afford Compound 95 (56 mg, 46%). LCMS (method A): m/z 762.6 $(M+H)^+$. $^1$H NMR ($CDCl_3$) δ 8.39 (s, 1H), 7.93 (s, 1H), 7.43 (br s, 1H), 7.42 (d, 2H), 7.17 (d, 2H), 6.82 (br s, 1H), 6.71 (br s, 1H), 5.28 (s, 1H), 4.58 (br s, 1H), 4.30-4.20 (m, 2H), 3.86 (br, 2H), 3.60-3.53 (m, 3H), 3.50-3.36 (m, 2H), 3.25 (br, 1H), 2.89-2.73 (m, 4H), 2.37 (br, 1H), 2.15 (t, 3H), 2.05 (br, 1H), 1.92 (br, 1H), 1.63-1.57 (m, 4H), 1.42 (br, 1H), 1.20-1.15 (m, 2H), 1.08-0.92 (m, 2H). Using the procedure described above for Example 12, the following compounds were prepared from precursors and reagents as indicated in Table 15.

TABLE 15

| No | Structure | Pre-cursor | Reagent | MS (M + H)+ |
|---|---|---|---|---|
| 96 | 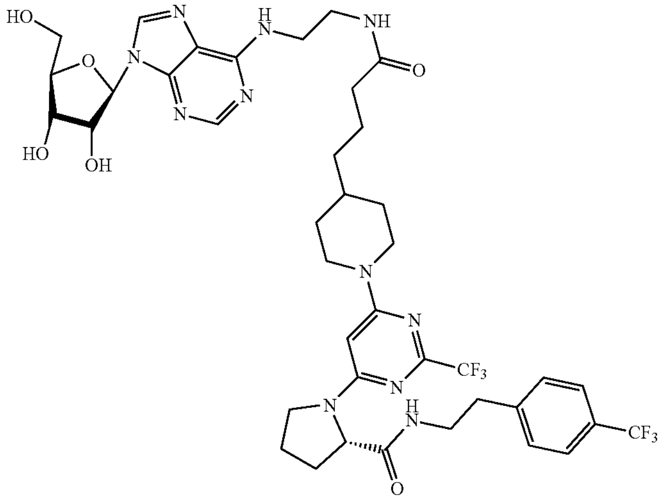 (2S)-1-(6-(4-(4-((2-((9-((2R,5R)-3,4-dihydroxy-5-(hydroxymethyl)-tetrahydrofuran-2-yl)-9H-purin-6-yl)amino)ethyl)amino)-4-oxobutyl)piperidin-1-yl)-2-(trifluoromethyl)-pyrimidin-4-yl)-N-(4-(trifluoromethyl)-phenethyl)-pyrrolidine-2-carboxamide | 90 | 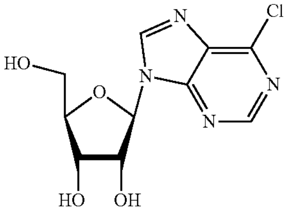 | 894.4 A |
| 97 | 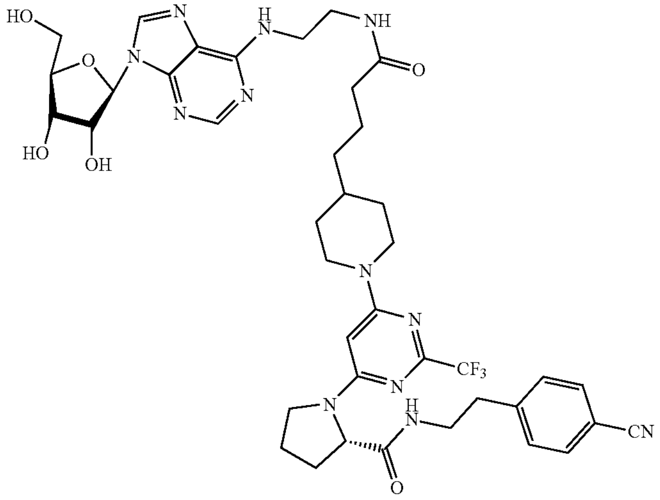 (2S)-N-(4-cyanophenethyl)-1-(6-(4-(4-((2-((9-((2R,5R)-3,4-dihydroxy-5-(hydroxymethyl)tetrahydrofuran-2-yl)-9H-purin-6-yl)amino)ethyl)amino)-4-oxobutyl)piperidin-1-yl)-2-(trifluoromethyl)-pyrimidin-4-yl)pyrrolidine-2-carboximide | 92 | 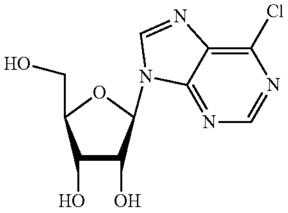 | 851.4 A |

Example 13

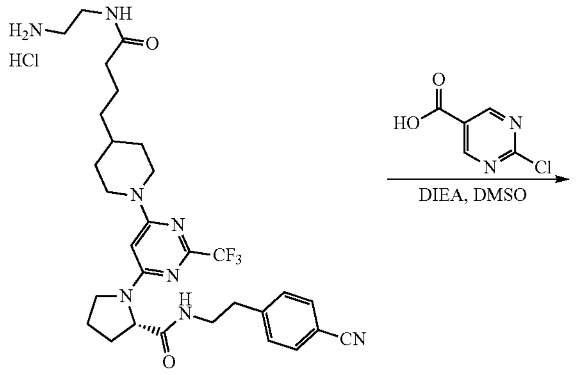

Compound 92

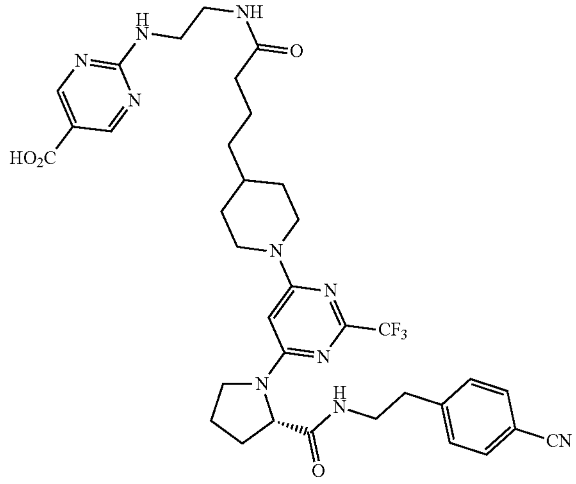

Compound 98

(S)-2-((2-(4-(1-(6-(2-((4-cyanophenethyl)carbamoyl) pyrrolidin-1-yl)-2-(trifluoromethyl)pyrimidin-4-yl) piperidin-4-yl)butanamido)ethyl)-amino)pyrimidine-5-carboxylic acid To a solution of Compound 92 (48 mg, 0.08 mmol) and 2-chloropyrimidine-5-carboxylic acid (36 mg, 0.23 mmol) in DMSO (1 mL) was added diisopropylethylamine (33 μL, 0.19 mmol). The solution mixture was heated in a microwave at 120° C. for one hour. The reaction was purified by MS-HPLC to afford Compound 98 (22 mg, 40%). LCMS (method A): m/z 723.4 $(M+H)^+$. $^1$H NMR ($CD_3OD$) δ 8.77 (d, 2H), 7.53 (d, 2H), 7.30 (d, 2H), 5.56 (br s, 1H), 4.50-4.34 (m, 3H), 3.57 (t, 3H), 3.49-3.39 (m, 4H), 2.88-2.79 (m, 4H), 2.16 (t, 3H), 2.05-1.99 (m, 3H), 1.74 (d, 2H), 1.63-1.48 (m, 3H), 1.30-1.21 (m, 3H), 1.16-1.06 (m, 2H). Using the procedure described above for Example 13, the following compound was prepared from compound 91 and the reagent as indicated in Table 16.

TABLE 16
| No | Structure | Reagent | MS (M + H)+ |
|---|---|---|---|
| 99 | 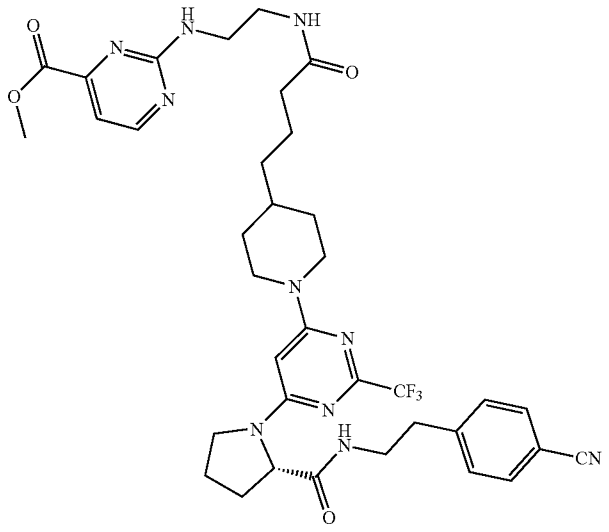 [SMILES: COC(=O)c1ccnc(NCCNC(=O)CCCC2CCN(c3cc(N4CCC[C@H]4C(=O)NCCc4ccc(C#N)cc4)nc(C(F)(F)F)n3)CC2)n1] (S)-methyl 2-((2-(4-(1-(6-(2-((4-cyanophenethyl)carbamoyl)pyrrolidin-1-yl)-2-(trifluoromethyl)pyrimidin-4-yl)-piperidin-4-yl)butanamido)ethyl)amino)-pyrimidine-4-carboxylate | 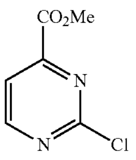 | 737.4 A |
Example 14
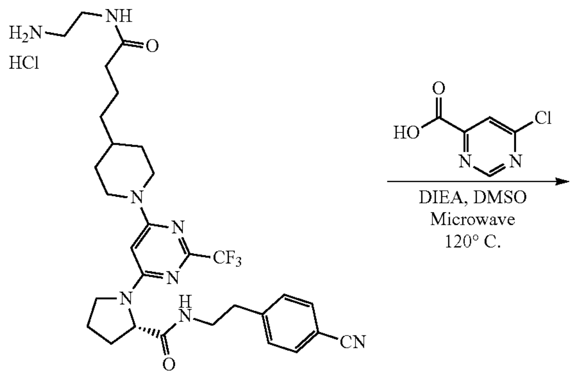
Compound 92

-continued

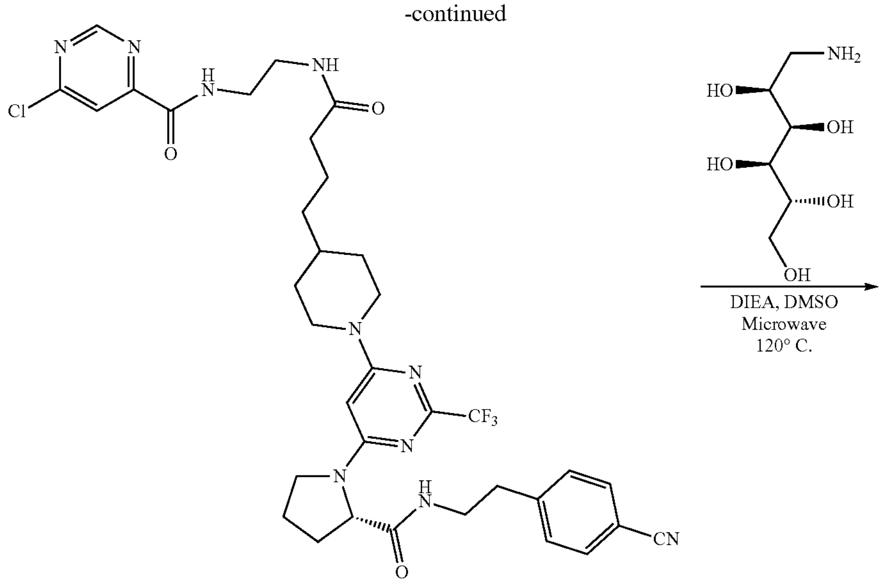

Compound 14A

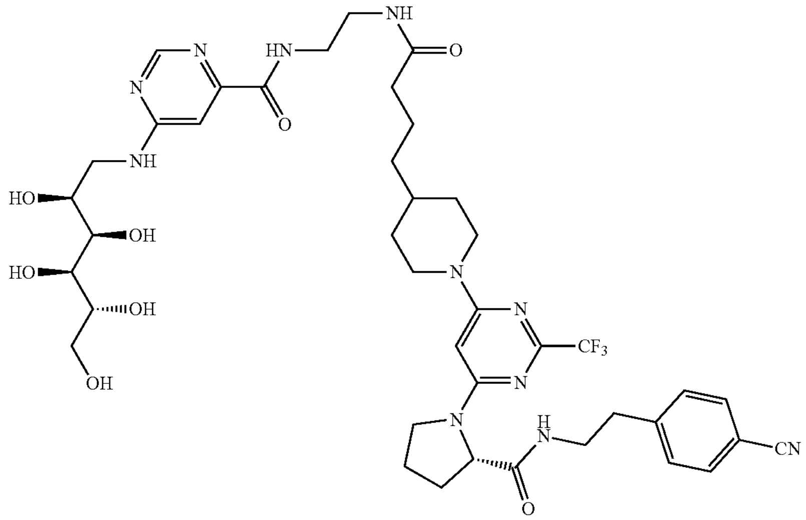

Compound 100

(S)-2-((2-(4-(1-(6-(2-((4-cyanophenethyl)carbamoyl)pyrrolidin-1-yl)-2-(trifluoromethyl)pyrimidin-4-yl)piperidin-4-yl)butanamido)ethyl)amino)-pyrimidine-5-carboxylic acid To a solution of Compound 92 (48 mg, 0.07 mmol) and 6-chloropyrimidine-4-carboxylic acid (34 mg, 0.21 mmol) in DMSO (1 mL) was added DIEA (31 μL, 0.18 mmol). The solution mixture was heated in a microwave at 120° C. for one hour. The reaction was purified directly by MS-HPLC to afford Compound 14A (10 mg, 19%). LCMS (method A): m/z 741.3 $(M+H)^+$. $^1H$ NMR (DMSO) δ 9.20 (d, 1H), 9.12 (t, 1H), 8.23 (s, 1H), 7.96-7.82 (m, 2H), 7.68 (d, 2H), 7.35 (d, 2H), 5.67 (br s, 1H), 4.40-4.10 (m, 3H), 3.52 (br, 1H), 3.40-3.20 (m, 7H), 2.82-2.74 (m, 4H), 2.03 (t, 3H), 1.92-1.78 (m, 3H), 1.67 (d, 2H), 1.54-1.41 (m, 3H), 1.19-1.10 (m, 2H), 1.03-0.89 (m, 2H).

N-(2-(4-(1-(6-((S)-2-((4-cyanophenethyl)carbamoyl)pyrrolidin-1-yl)-2-(trifluoromethyl)pyrimidin-4-yl)piperidin-4-yl)butanamido)ethyl)-6-(((2S,3R,4R,5R)-2,3,4,5,6-pentahydroxyhexyl)amino)-pyrimidine-4-carboxamide Using the procedure in step 1 above, Compound 14A was reacted with (2R,3R,4R,5S)-6-aminohexane-1,2,3,4,5-pentaol to afford Compound 100. LCMS (method A): m/z 886.4 $(M+H)^+$.

Example 15

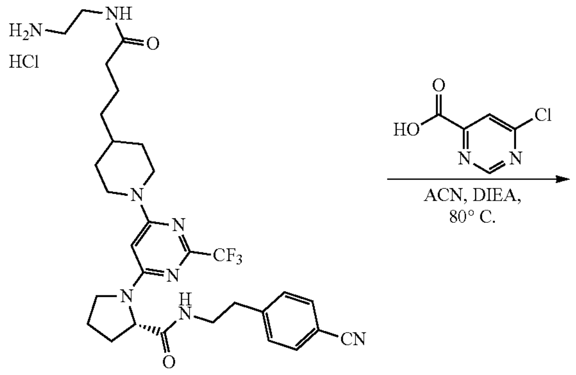

Compound 92

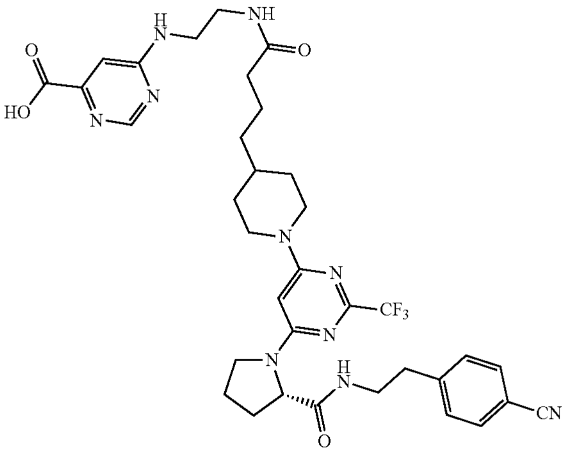

Compound 101

(S)-6-((2-(4-(1-(6-(2-((4-cyanophenethyl)carbamoyl) pyrrolidin-1-yl)-2-(trifluoromethyl)pyrimidin-4-yl) piperidin-4-yl)butanamido)ethyl)amino)-pyrimidine-4-carboxylic acid 6-chloropyrimidine-4-carboxylic acid (21 mg, 0.130 mmol) was added to a stirring suspension of Compound 92 (100 mg, 0.157 mmol) and diisopropylethylamine (0.113 mL, 0.650 mmol) in acetonitrile (3 mL). The mixture was heated overnight at 80° C. Several drops of water were added to the crude reaction mixture, and the resulting solution was purified by reverse phase chromatography using acetonitrile with 0.25% formic acid in water with 0.25% formic acid as the eluent. The impure product was triturated with hot acetonitrile to afford Compound 101 (18 mg, 15%) as a brown solid. LCMS (method A): m/z 723.6 $(M+H)^+$. $^1H$ NMR ($CD_3OD$) δ 8.54 (s, 1H), 7.53 (d, 2H), 7.30 (d, 2H), 7.11 (s, H), 5.57 (br s, 1H), 4.52-4.32 (m, 3H), 3.71 (t, 2H), 3.59 (br s, 1H), 3.51-3.38 (m, 5H), 2.91-2.80 (m, 4H), 2.20-2.13 (m, 3H) 2.05-1.96 (m, 3H), 1.79-1.71 (m, 2H), 1.65-1.49 (m, 3H), 1.30-1.21 (m, 2H), 1.18-1.08 (m, 2H).

Example 16

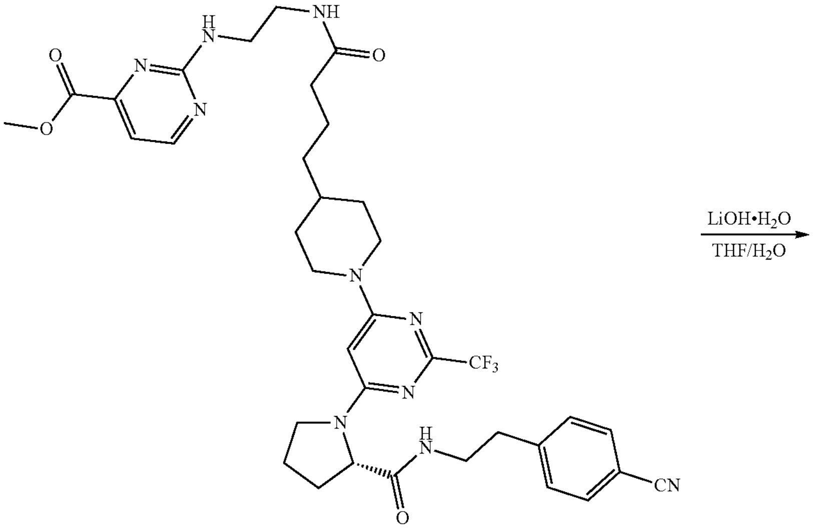

Compound 99

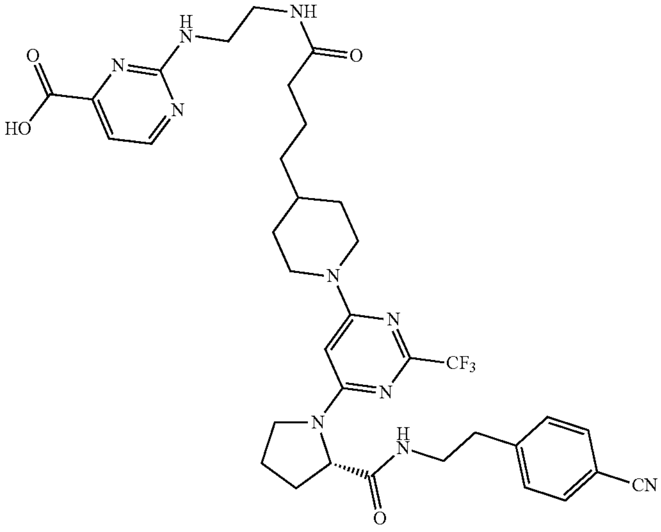

Compound 102

(S)-2-((2-(4-(1-(6-(2-((4-cyanophenethyl)carbamoyl) pyrrolidin-1-yl)-2-(trifluoromethyl)pyrimidin-4-yl) piperidin-4-yl)butanamido)ethyl)amino) pyrimidine-4-carboxylic acid To a solution of Compound 99 (32 mg, 0.043 mmol) in THF (0.5 mL)/$H_2O$ (0.25 mL) was added lithium hydroxide monohydrate (9 mg, 0.22 mmol). The reaction mixture was stirred at room temperature for two hours. The solvent was removed in vacuo to provide a crude product which was purified by MS-HPLC to afford Compound 102 (22 mg, 70%). LCMS (method A): m/z 723.3 $(M+H)^+$. $^1H$ NMR ($CD_3OD$) δ 7.47 (br s, 1H), 7.53 (d, 2H), 7.30 (d, 2H), 7.15 (d, 1H), 5.56 (br s, 1H), 4.50-4.34 (m, 3H), 3.60-3.55 (m, 3H), 3.49-3.39 (m, 5H), 2.86-2.79 (m, 4H), 2.16 (t, 3H), 2.05-1.98 (m, 3H), 1.73 (d, 2H), 1.63-1.47 (m, 3H), 1.25-1.20 (m, 2H), 1.11-1.04 (m, 2H). Using the procedure described above for Example 16, the following compounds were prepared from the precursors as indicated in Table 17.

TABLE 17

| No | Structure | Pre-cursor | MS (M + H)+ |
| --- | --- | --- | --- |
| 103 | 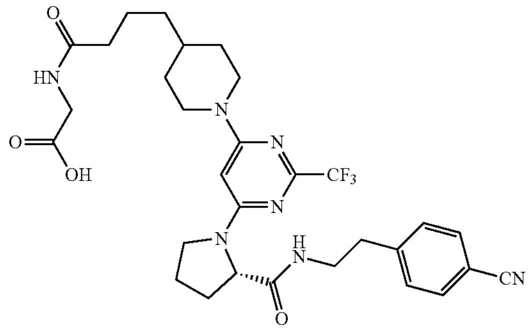 [SMILES: N#Cc1ccc(CCNC(=O)[C@@H]2CCCN2c2cc(N3CCC(CCCC(=O)NCC(=O)O)CC3)nc(C(F)(F)F)n2)cc1] (S)-2-(4-(1-(6-(2-((4-cyanophenethyl)carbamoyl)pyrrolidin-1-yl)-2-(trifluoromethyl)pyrimidin-4-yl)piperidin-4-yl)butanamido)acetic acid | 69 | 616.5 A |
| 104 | 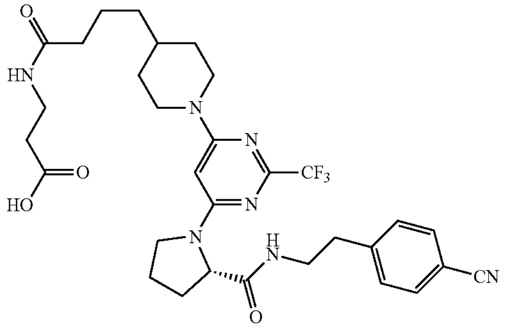 [SMILES: N#Cc1ccc(CCNC(=O)[C@@H]2CCCN2c2cc(N3CCC(CCCC(=O)NCCC(=O)O)CC3)nc(C(F)(F)F)n2)cc1] (S)-3-(4-(1-(6-(2-((4-cyanophenethyl)carbamoyl)pyrrolidin-1-yl)-2-(trifluoromethyl)pyrimidin-4-yl)-piperidin-4-yl)butanamido)-propanoic acid | 70 | 630.6 A |
| 105 | 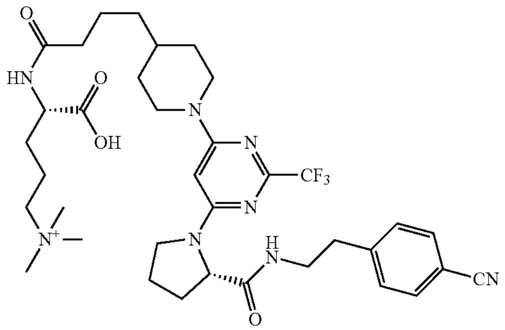 [SMILES: C[N+](C)(C)CCC[C@H](NC(=O)CCCC1CCN(c2cc(N3CCC[C@H]3C(=O)NCCc3ccc(C#N)cc3)nc(C(F)(F)F)n2)CC1)C(=O)O] (S)-4-carboxy-4-(4-(1-(6-((S)-2-((4-cyanophenethyl)carbamoyl)pyrrolidin-1-yl)-2-(trifluoromethyl)pyrimidin-4-yl)piperidin-4-yl)butanamido)-N,N,N-trimethylbutan-1-aminium | 65 | 715.6 A |

TABLE 17-continued
| No | Structure | Pre-cursor | MS (M + H)$^+$ |
|---|---|---|---|
| 106 | 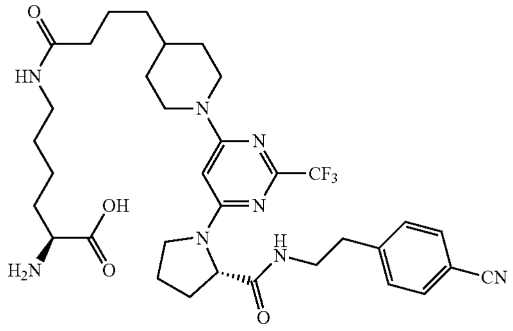 [SMILES: N#Cc1ccc(CCNC(=O)[C@@H]2CCCN2c2cc(N3CCC(CCCC(=O)NCCCC[C@H](N)C(=O)O)CC3)nc(C(F)(F)F)n2)cc1] (S)-2-amino-6-(4-(1-(6-((S)-2-((4-cyanophenethyl)carbamoyl)pyrrolidin-1-yl)-2-(trifluoromethyl)pyrimidin-4-yl)-piperidin-4-yl)butanamido)-hexanoic acid | 71 | 687.6 A |
| 107 | 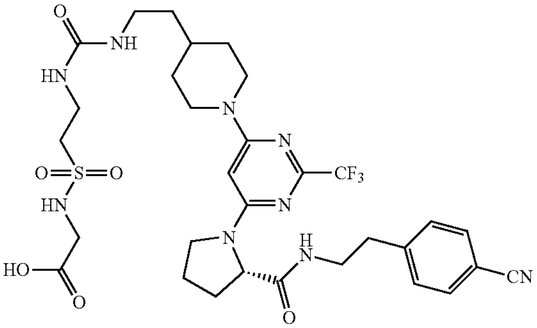 [SMILES: N#Cc1ccc(CCNC(=O)[C@@H]2CCCN2c2cc(N3CCC(CCNC(=O)NCCS(=O)(=O)NCC(=O)O)CC3)nc(C(F)(F)F)n2)cc1] (S)-N-(2-(1-(6-(2-((4-cyanophenethyl)-carbamoyl)pyrrolidin-1-yl)-2-(trifluoromethyl)pyrimidin-4-yl)piperidin 4-yl)ethyl)-2-(2-aminoethylsulfonamido)-acetic acid | 85 | 724.5 |
Example 17
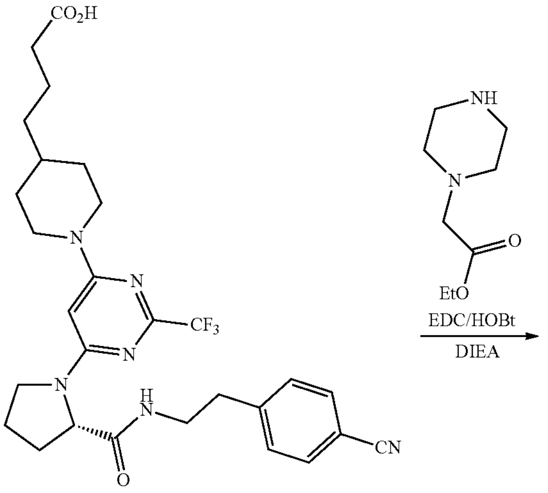
Compound 29

-continued

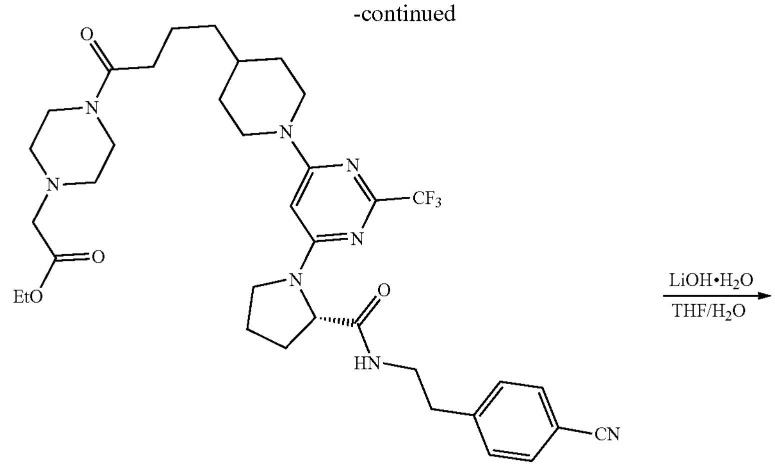

Compound 17A

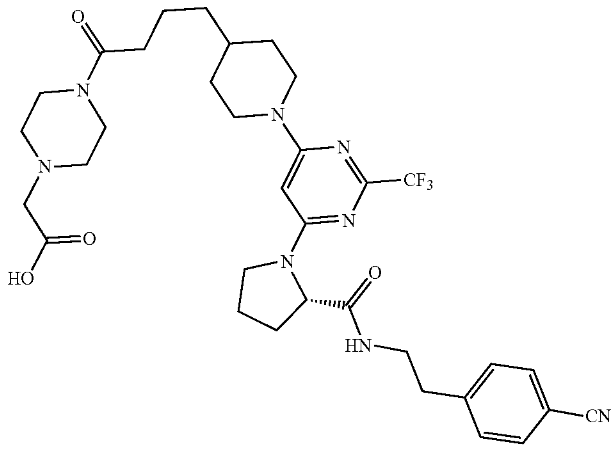

Compound 108

(S)-ethyl 2-(4-(4-(1-(6-(2-((4-cyanophenethyl)carbamoyl)pyrrolidin-1-yl)-2-(trifluoromethyl)pyrimidin-4-yl)piperidin-4-yl)butanoyl)piperazin-1-yl)acetate Using the procedure as described in Example 7, Compound 29 (62 mg, 0.11 mmol) was converted to Compound 17A, which was used directly in the next step.

(S)-2-(4-(4-(1-(6-(2-((4-cyanophenethyl)carbamoyl)pyrrolidin-1-yl)-2-(trifluoromethyl)pyrimidin-4-yl)piperidin-4-yl)butanoyl)piperazin-1-yl)acetic acid Using the procedure described as in Example 16, Compound 17A was converted to Compound 108 (12.6 mg). LCMS (method A): m/z 685.7 $(M+H)^+$. $^1H$ NMR ($CD_3OD$) δ 8.03 (br s, 1H), 7.53 (d, 2H), 7.30 (d, 2H), 5.56 (br s, 1H), 4.41 (m, 3H), 3.80 (m, 4H), 3.57 (s, 3H), 3.47 (m, 3H), 3.41 (m, 3H), 3.21 (m, 2H), 3.15 (m, 2H), 2.85 (m, 4H), 2.45 (t, 2H), 2.15 (b, 1H), 2.02 (b, 3H), 1.79 (d, 2H), 1.66 (m, 3H), 1.32 (m, 2H), 1.16 (m, 2H).

Example 18

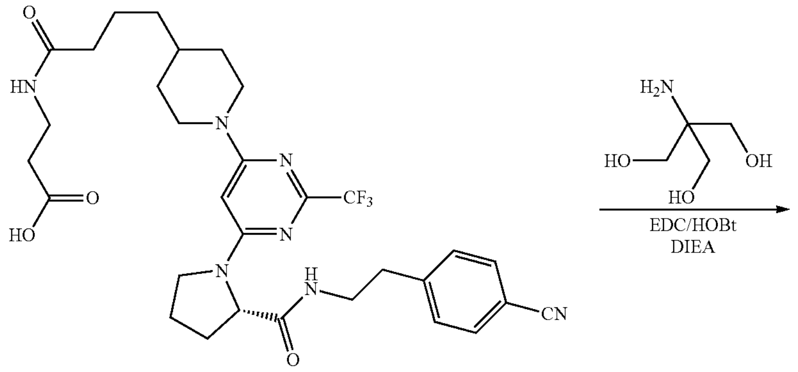

Compound 104

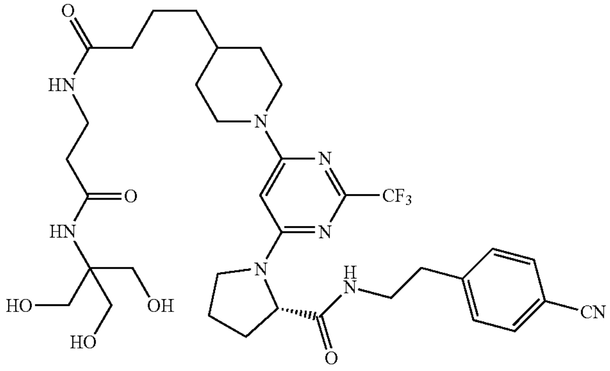

Compound 109

(S)—N-(4-cyanophenethyl)-1-(6-(4-(4-((3-((1,3-dihydroxy-2-(hydroxymethyl)propan-2-yl)amino)-3-oxopropyl)amino)-4-oxobutyl)piperidin-1-yl)-2-(trifluoromethyl)-pyrimidin-4-yl)pyrrolidine-2-carboxamide Using the procedure as described in Example 7, Compound 104 was converted to Compound 109. LCMS (method A): m/z 733.7 $(M+H)^+$. $^1H$ NMR ($CDCl_3$) δ 7.62 (br s, 1H), 7.40 (d, 2H), 7.13 (d, 2H), 6.78 (s, 1H), 6.41 (br s, 1H), 5.32 (s, 1H), 4.60 (br s, 1H), 4.36 (br s, 2H), 3.67 (s, 6H), 3.62-3.54 (m, 3H), 3.38 (m, 2H), 3.20 (br, 1H), 2.91-2.84 (m, 3H), 2.76 (m, 1H), 2.49-2.38 (m, 3H), 2.18 (m, 3H), 2.07 (m, 1H), 1.90-1.78 (m, 3H), 1.65 (m, 2H), 1.55 (br, 1H), 1.32-1.17 (m, 4H).

Example 19

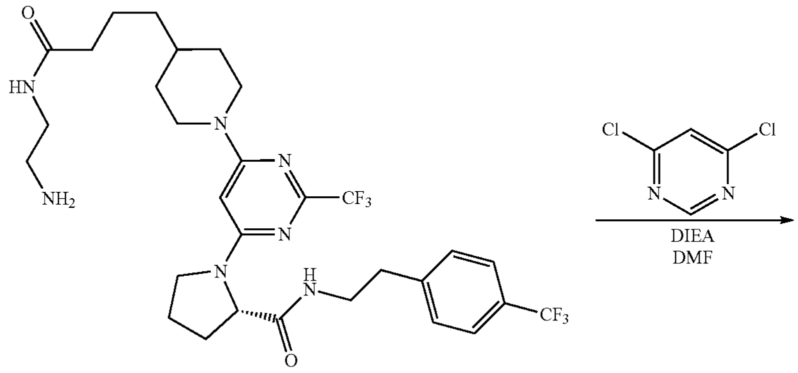

Compound 90

-continued

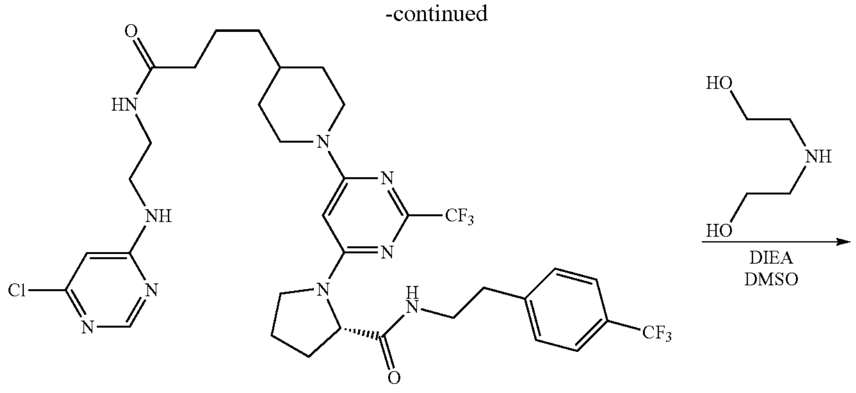

Compound 110

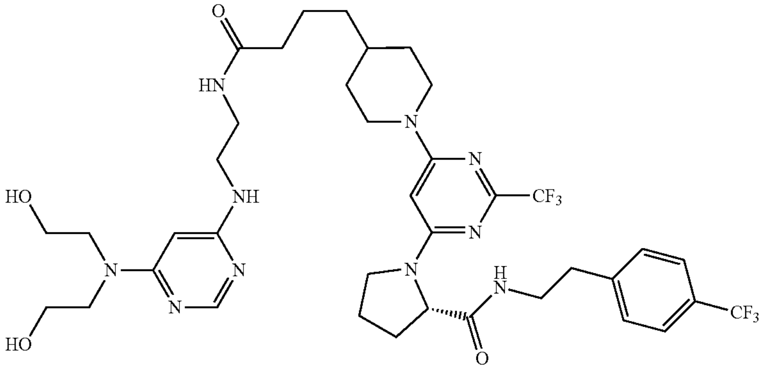

Compound 111

(S)-1-(6-(4-(4-((2-((6-chloropyrimidin-4-yl)amino) ethyl)amino)-4-oxobutyl)piperidin-1-yl)-2-(trifluoromethyl)pyrimidin-4-yl)-N-(4-cyanophenethyl) pyrrolidine-2-carboxamide Compound 90 (142 mg, 0.22 mmol) was dissolved in DMF (1 mL), and DIEA (0.11 mL, 0.65 mmol) and 4,6-dichloropyrimidine (49 mg, 0.33 mmol) were added. The mixture was stirred at room temperature overnight, diluted with DCM (50 mL), and washed with water (10 mL) and brine (10 mL). The organic layer was dried ($Na_2SO_4$), filtered and concentrated in vacuo. The residue was pumped under high vacuum and purified by silica gel chromatography (20 g, 0-5% MeOH in DCM) to afford Compound 110 (147 mg, 89%). LCMS (method A): m/z 756.6 $(M+H)^+$. $^1H$ NMR ($CDCl_3$) δ 8.32 (s, 1H), 7.60 (br s, 1H), 7.40 (d, 2H), 7.16 (d, 2H), 6.39 (s, 1H), 6.18 (br s, 1H), 6.05 (br s, 1H), 5.32 (s, 1H), 4.61 (br s, 1H), 4.34 (m, 2H), 3.57-3.38 (m, 7H), 3.23 (br, 1H), 2.17 (t, 3H), 2.05 (br, 1H), 1.80-1.49 (m, 6H), 1.30-1.05 (m, 4H).

(S)-1-(6-(4-(4-((2-((6-(bis(2-hydroxyethyl)amino) pyrimidin-4-yl)amino)ethyl)amino)-4-oxobutyl)piperidin-1-yl)-2-(trifluoromethyl)pyrimidin-4-yl)-N-(4-cyanophenethyl) pyrrolidine-2-carboxamide Compound 110 (60 mg, 0.08 mmol) was dissolved in DMSO (1 mL) and diethanolamine (0.03 mL, 0.32 mmol) and DIEA (0.06 mL, 0.32 mmol) were added. The reaction was heated at 180° C. in a microwave for three hours. The mixture was purified by MS-HPLC to afford Compound 111 (12 mg, 19%). LCMS (method A): m/z 825.7 $(M+H)^+$. $^1H$ NMR ($CDCl_3$) δ 8.32 (s, 1H), 7.98 (s, 1H), 7.40 (d, 2H), 7.16 (d, 2H), 6.77 (br s, 1H), 6.05 (s, 1H), 5.95 (br s, 3H), 5.33 (s, 1H), 4.60 (br s, 1H), 4.34 (m, 2H), 3.85-3.59 (m, 7H), 3.55 (m, 2H), 3.48-3.23 (m, 7H), 2.89-2.73 (m, 4H), 2.41 (br, 1H), 2.24-2.03 (m, 4H), 1.87-1.53 (m, 6H), 1.29-1.10 (m, 4H).

Example 20

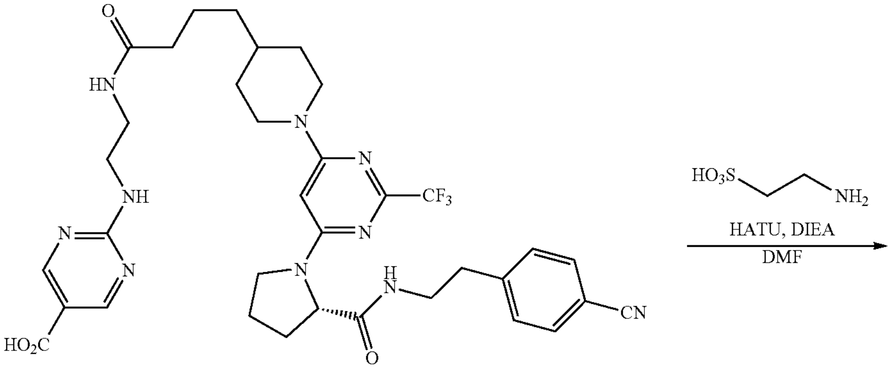

Compound 98

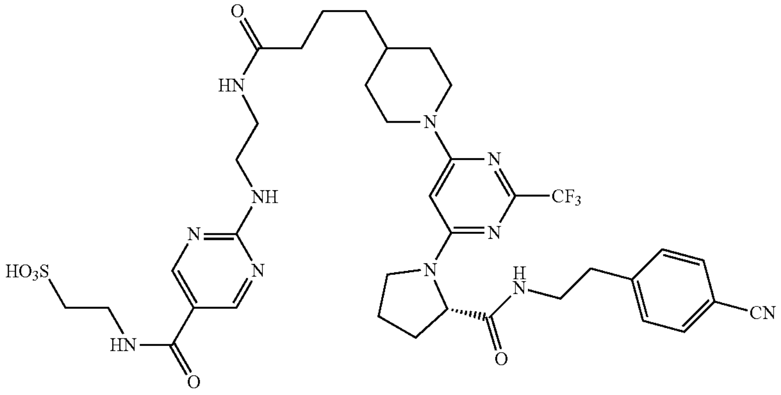

Compound 112

(S)-2-(2-((2-(4-(1-(6-(2-((4-cyanophenethyl)carbamoyl)pyrrolidin-1-yl)-2-(trifluoromethyl)pyrimidin-4-yl)piperidin-4-yl)butanamido)ethyl)amino)-pyrimidine-5-carboxamido)ethanesulfonic acid To a stirred solution of Compound 98 (50 mg, 0.07 mmol) in DMF (1 mL) were added HATU (29 mg, 0.08 mmol) and DIEA (24 μL, 0.14 mmol). Taurine (17 mg, 0.14 mmol) was added, and the reaction was stirred overnight at room temperature. The reaction was purified by reverse phase column chromatography (ISCO gold C18 column) to afford Compound 112. LCMS (method A): m/z 830.6 $(M+H)^+$. $^1H$ NMR (DMSO) δ 8.64 (br s, 1H), 8.62 (br s, 1H), 8.34 (t, 1H), 7.89 (t, 1H), 7.73 (t, 1H), 7.69 (d, 2H), 7.35 (d, 2H), 5.69 (br s, 1H), 4.91-4.01 (m, 4H), 3.53 (br s, 1H), 3.50-3.45 (m, 2H), 3.39-3.19 (m, 6H), 2.83-2.74 (m, 4H), 2.64 (t, 2H), 2.09 (br s, 1H), 2.02 (t, 2H), 1.90-1.77 (m 3H), 1.68 (d, 2H), 1.53-1.42 (m, 3H), 1.19-1.10 (m, 2H), 1.05-0.94 (m, 2H). Using the procedure described above for Example 20, the following compound was prepared from the precursor as indicated in Table 18.

TABLE 18
| No | Structure | Pre-cursor | MS (M + H)+ |
|---|---|---|---|
| 113 | 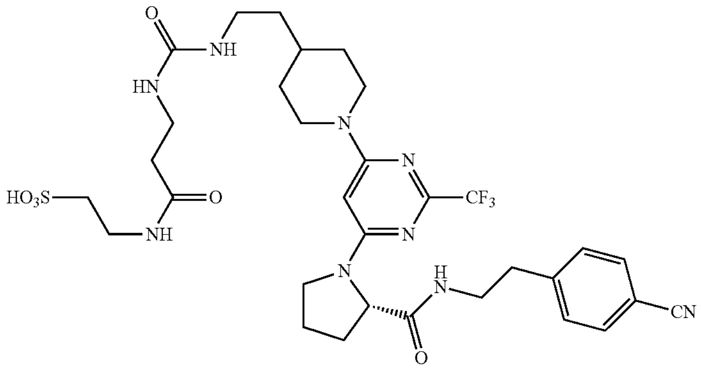 [SMILES: N#Cc1ccc(CCNC(=O)[C@@H]2CCCN2c2cc(N3CCC(CCNC(=O)NCCC(=O)NCCS(=O)(=O)O)CC3)nc(C(F)(F)F)n2)cc1] (S)-2-(3-(3-(2-(1-(6-(2-((4-cyanophenethyl)carbamoyl)pyrrolidin-1-yl)-2-(trifluromethyl)pyrimidin-4-yl)piperidin-4-yl)ethyl)ureido)-propanamido)-ethanesulfonic acid | 81 | 738.5 A |
Example 21
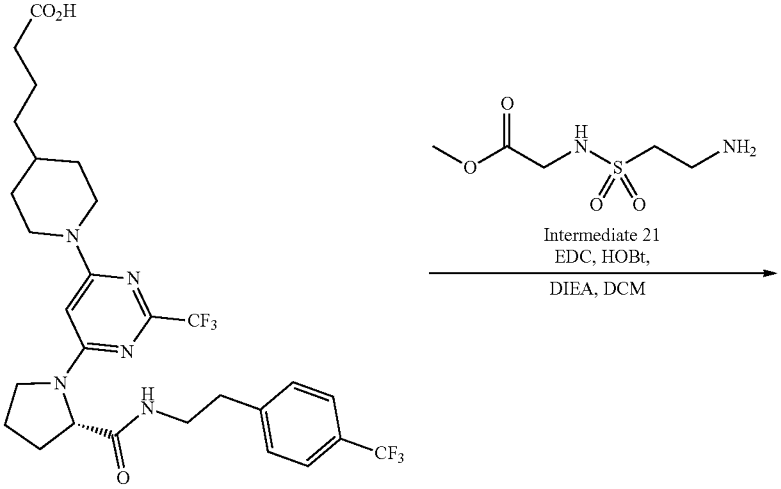
Compound 9

-continued

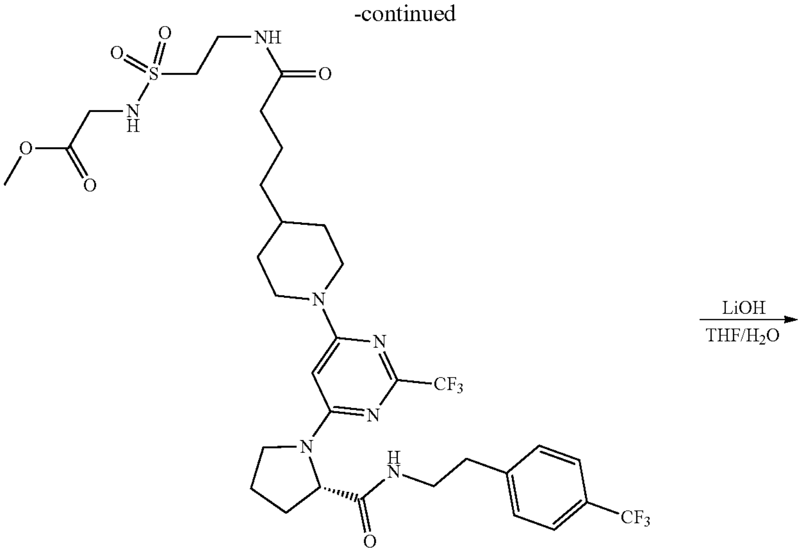

21A

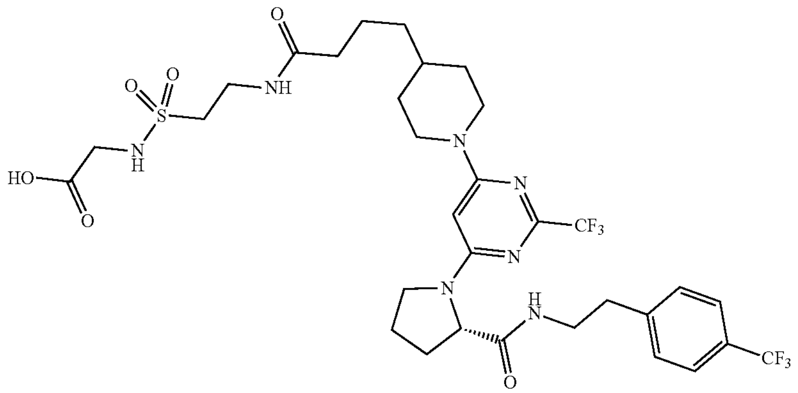

Compound 114

(S)-methyl 2-(2-(4-(1-(2-(trifluoromethyl)-6-(2-((4-(trifluoromethyl)phenethyl)carbamoyl)pyrrolidin-1-yl)pyrimidin-4-yl)piperidin-4-yl)butanamido)ethylsulfonamido)acetate Using the procedure as described in Example 7, Compound 9 (490 mg, 0.82 mmol), was reacted with Intermediate 21 (200 mg, 0.86 mmol) to afford Compound 21A (54 mg, 8%). LCMS (method A): m/z 780.4 $(M+H)^+$. $^1H$ NMR $(CDCl_3)$ δ 7.40 (d, 2H), 7.16 (d, 2H), 6.24 (t, 1H), 5.35 (t, 1H), 5.32 (s, 1H), 4.61 (br s, 1H), 4.34 (br s, 2H), 3.80 (d, 2H), 3.84-3.79 (m, 4H), 3.57-3.49 (m, 1H), 3.46-3.32 (m, 2H), 3.28-3.15 (m, 3H), 2.89-2.72 (m, 4H), 2.43 (br, 1H), 2.22-2.08 (m, 3H), 2.07-2.00 (m, 1H), 1.90-1.48 (m, 8H), 1.32-1.26 (m, 2H), 1.21-1.11 (m, 2H).

(S)-2-(2-(4-(1-(2-(trifluoromethyl)-6-(2-((4-(trifluoromethyl)phenethyl)-carbamoyl)-pyrrolidin-1-yl)pyrimidin-4-yl)piperidin-4-yl)butanamido)ethylsulfonamido)acetic acid Compound 21A was hydrolyzed using the procedure as described in Example 16 to afford Compound 114. LCMS (method A): m/z 766.3 $(M+H)^+$. $^1H$ NMR $(CD_3OD)$ δ 7.49 (d, 2H), 7.32 (d, 2H), 5.58 (br s, 1H), 4.44-4.37 (m, 3H), 3.87 (s, 2H), 3.64 (t, 2H), 3.62-3.55 (br, 1H), 3.51-3.46 (m, 1H), 3.40-3.34 (m, 1H), 3.30-3.26 (m, 3H), 2.88-2.81 (m, 4H), 2.21-2.13 (m, 3H), 2.00-1.97 (m, 3H), 1.79 (d, 2H), 1.70-1.62 (m, 2H), 1.59-1.50 (br, 1H), 1.31-1.25 (m, 2H), 1.18-1.08 (m, 2H). Using the procedure described above for Example 21, the following compound was prepared from the precursor as indicated in Table 19.

TABLE 19
| No | Structure | Pre-cursor | MS (M + H)+ |
|---|---|---|---|
| 115 | 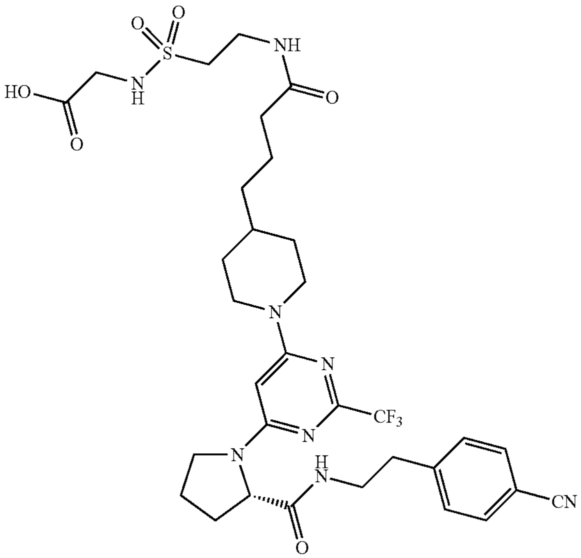 [SMILES: N#Cc1ccc(CCNC(=O)[C@@H]2CCCN2c2cc(N3CCC(CCCC(=O)NCCS(=O)(=O)NCC(=O)O)CC3)nc(C(F)(F)F)n2)cc1] (S)-2-(2-(4-(1-(6-(2-((4-cyanophenethyl)carbamoyl)pyrrolidin-1-yl)-2-(trifluoromethyl)pyrimidin-4-yl)piperidin-4-yl)butanamido)-ethylsulfonamido)acetic acid | 29 | 723.3 A |
Example 22
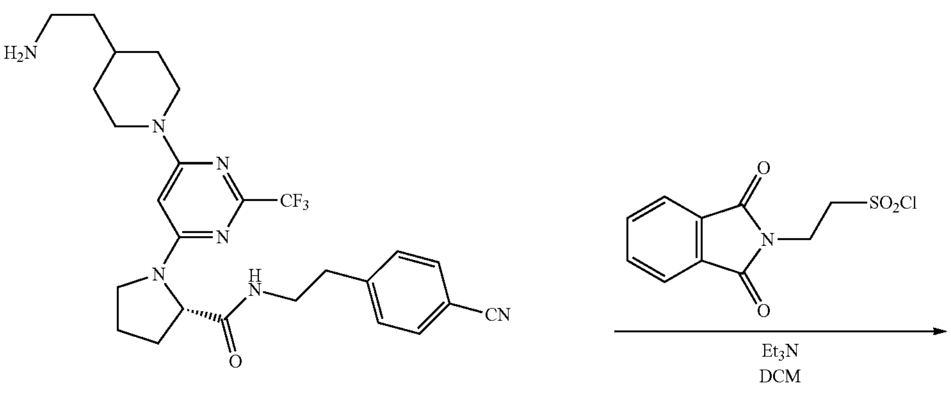
Compound 50

-continued

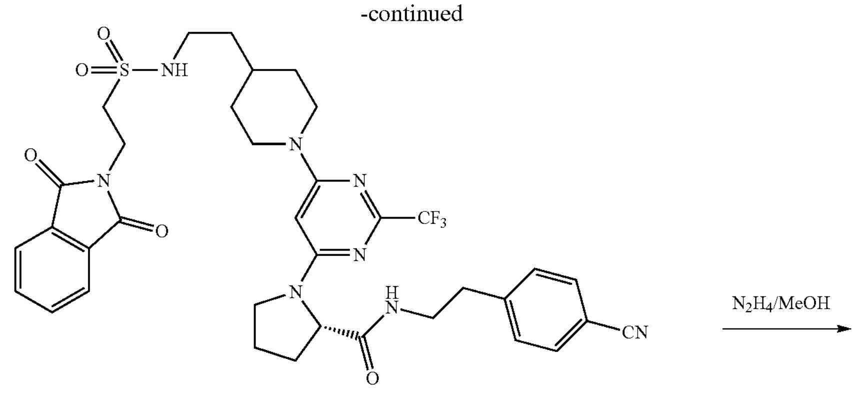

Compound 22A

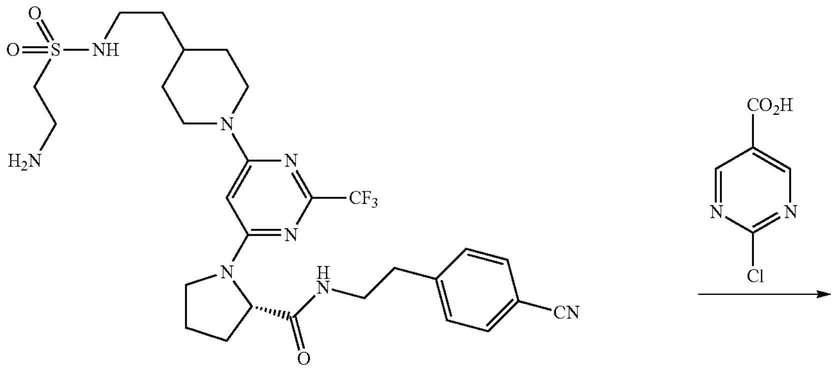

Compound 116

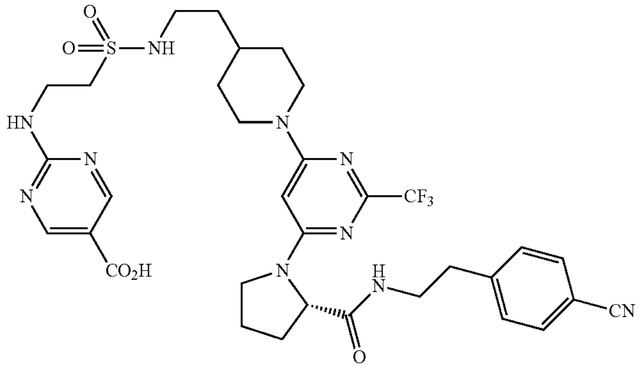

Compound 117

(S)—N-(4-cyanophenethyl)-1-(6-(4-(2-(2-(1,3-dioxoisoindolin-2-yl)ethylsulfonamido)-ethyl)piperidin-1-yl)-2-(trifluoromethyl)pyrimidin-4-yl)pyrrolidine-2-carboxamide Using the procedure as described in Intermediate 21, step 1, Compound 50 (250 mg, 0.49 mmol) was converted to Compound 22A (271 mg, 74%). LCMS (method A): m/z 753.3 $(M+H)^+$. $^1H$ NMR ($CDCl_3$) δ 7.87 (m, 2H), 7.75 (m, 2H), 7.41 (d, 2H), 7.14 (d, 2H), 5.30 (s, 1H), 4.85 (m, 1H), 4.61 (br s, 1H), 4.38 (m, 2H), 4.12 (m, 2H), 3.59 (m, 1H), 3.43-3.35 (m, 4H), 3.22 (m, 3H), 2.94-2.84 (m, 3H), 2.77 (m, 1H), 2.44 (br, 1H), 2.18 (br, 1H), 2.06 (m, 1H), 1.83-1.72 (m, 4H), 1.57 (m, 2H), 1.27-1.20 (m, 2H).

(S)-1-(6-(4-(2-(2-aminoethylsulfonamido)ethyl)piperidin-1-yl)-2-(trifluoromethyl)-pyrimidin-4-yl)-N-(4-cyanophenethyl)pyrrolidine-2-carboxamide Compound 22A (90 mg, 0.12 mmol) was deprotected using the procedure as described in Intermediate 21, step 2 to afford Compound 116 (41 mg, 55%). LCMS (method A): m/z 623.3 $(M+H)^+$. $^1H$ NMR ($CDCl_3$) δ 8.40 (s, 1H), 7.57 (br s, 1H), 7.36 (d, 2H), 7.11 (s, 2H), 6.93 (br s, 4H), 5.31 (s, 1H), 4.58 (br s, 1H), 4.37 (br s, 2H), 3.62 (m, 1H), 3.48-3.35 (m, 6H), 3.24-3.14 (m, 3H), 2.91-2.73 (m, 4H), 2.41 (br, 1H), 2.18 (br, 1H), 2.04 (br, 1H), 1.81-1.54 (m, 6H), 1.20 (m, 2H).

(S)-2-((2-(N-(2-(1-(6-(2-((4-cyanophenethyl)carbamoyl)pyrrolidin-1-yl)-2-(trifluoromethyl)pyrimidin-4-yl)piperidin-4-yl)ethyl)sulfamoyl)ethyl)amino)-pyrimidine-5-carboxylic acid Using the procedure as described in Example 13, Compound 116 (80 mg, 0.13 mmol) was converted to Compound 117 (47 mg). LCMS (method A): m/z 745.3 $(M+H)^+$. $^1H$ NMR ($CD_3OD$) δ 8.86-8.78 (m, 2H), 8.03 (s, 1H), 7.52 (d, 2H), 7.30 (d, 2H), 5.55 (br s, 1H), 4.45-4.36 (m 3H), 3.87 (t, 2H), 3.58 (m, 1H), 3.46-3.35 (m, 2H), 3.12 (t, 2H), 2.92-2.82 (m, 4H), 2.15-2.03 (m, 4H), 1.82-1.72 (m, 3H), 1.51 (m, 2H), 1.29-1.17 (m, 3H), 0.89 (m, 1H).

Example 23

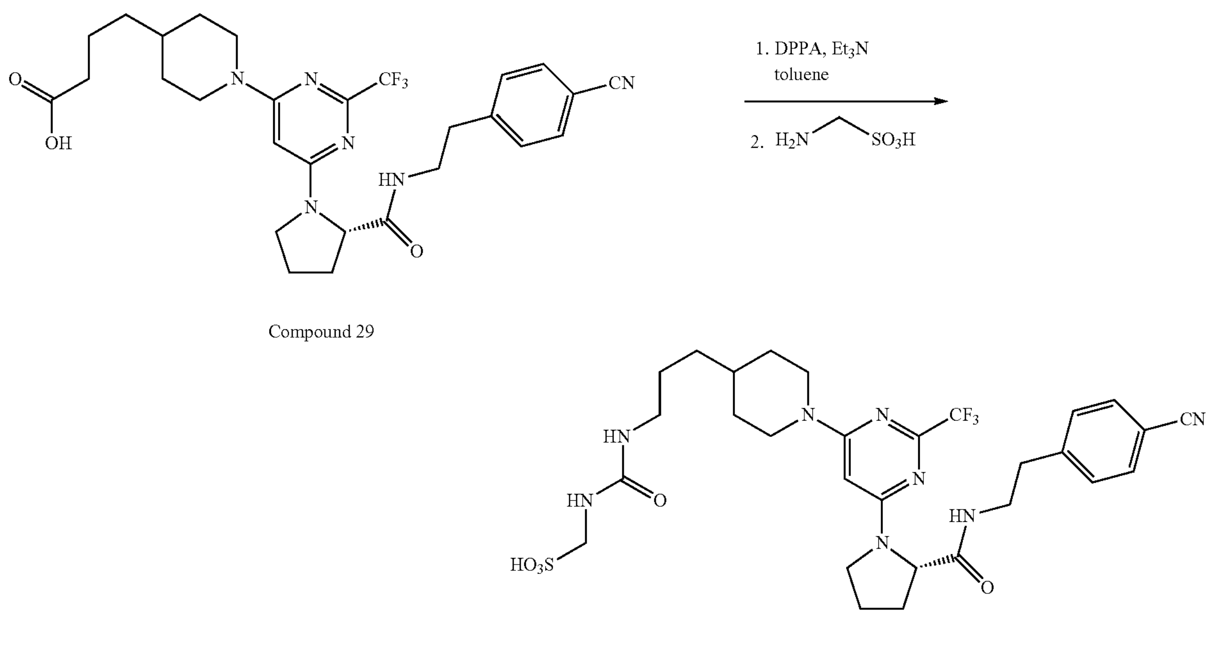

Compound 29

Compound 118

(S)-(3-(3-(1-(6-(2-((4-cyanophenethyl)carbamoyl)pyrrolidin-1-yl)-2-(trifluoromethyl)pyrimidin-4-yl)piperidin-4-yl)propyl)ureido)methanesulfonic acid To a solution of Compound 29 (120 mg, 0.23 mmol) in toluene (2 mL) were added triethylamine (105 mL, 0.750 mmol) and DPPA (39 μL, 0.18 mmol). The mixture was heated to 90° C. for two hours. Aminomethanesulfonic acid (33 mg, 0.30 mmol) was added. The reaction was heated at 90° C. After 18 hours, the reaction was concentrated in vacuo, and purified via medium pressure reverse phase chromatography (C-18 column, 0-30% acetonitrile/water containing 0.25% formic acid) to afford Compound 118 (29 mg, 29%). LCMS (method A): m/z 667.3 $(M+H)^+$. $^1H$ NMR ($CD_3OD$, 400 MHz) δ 7.55 (d, 2H), 7.33 (d, 2H), 4.50 (bs, 1H), 4.36 (m, 4H), 3.62 (bs, 1H), 3.39 (m, 3H), 3.18 (m, 2H), 2.87 (m, 4H), 2.19 (m, 1H), 2.01 (m, 3H), 1.81 (d, 2H), 1.57 (m, 3H), 1.31 (m, 2H), 1.19 (m, 2H). Using the procedure described above for Example 23, the following compounds were prepared from Compound 39 and reagents as indicated in Table 20.

TABLE 20

| No | Structure | Reagent | MS (M + H)+ |
|---|---|---|---|
| 119 | 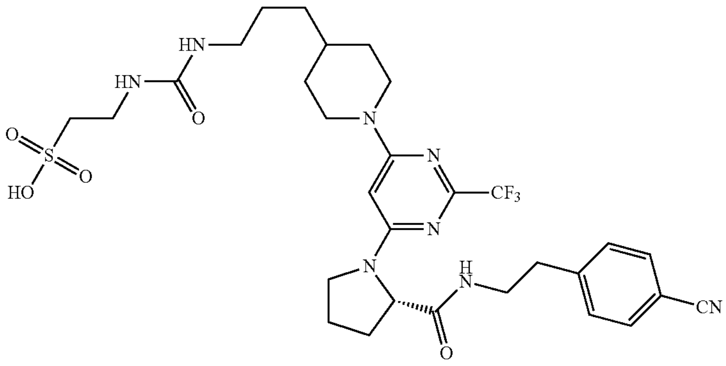 [SMILES: N#Cc1ccc(CCNC(=O)[C@@H]2CCCN2c2cc(N3CCC(CCCNC(=O)NCCS(=O)(=O)O)CC3)nc(C(F)(F)F)n2)cc1] (S)-2-(3-(3-(1-(6-(2-((4-cyanophenethyl)carbamoyl)pyrrolidin-1-yl)-2-(trifluoromethyl)pyrimidin-4-yl)piperidin-4-yl)propyl)ureido)-ethanesulfonic acid | 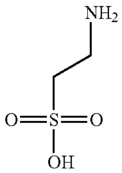 | 681.4 A |
| 120 | 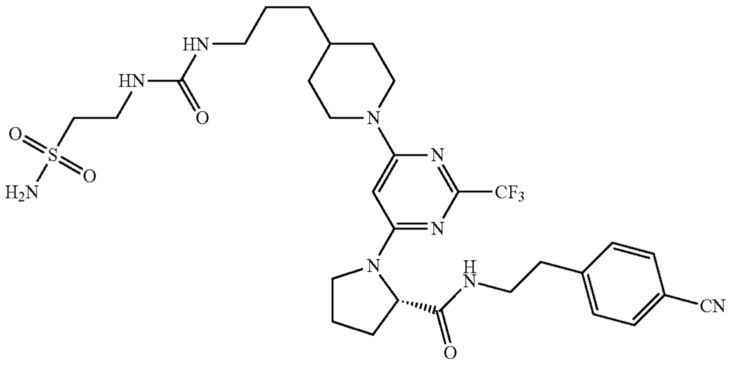 [SMILES: N#Cc1ccc(CCNC(=O)[C@@H]2CCCN2c2cc(N3CCC(CCCNC(=O)NCCS(N)(=O)=O)CC3)nc(C(F)(F)F)n2)cc1] (S)-N-(4-cyanophenethyl)-1-(6-(4-(3-(3-(2-sulfamoylethyl)ureido)propyl)piperidin-1-yl)-2-(trifluoromethyl)pyrimidin-4-yl)pyrrolidine-2-carboxamide | 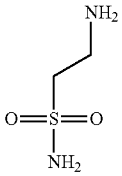 | 680.5 A |
| 121 | 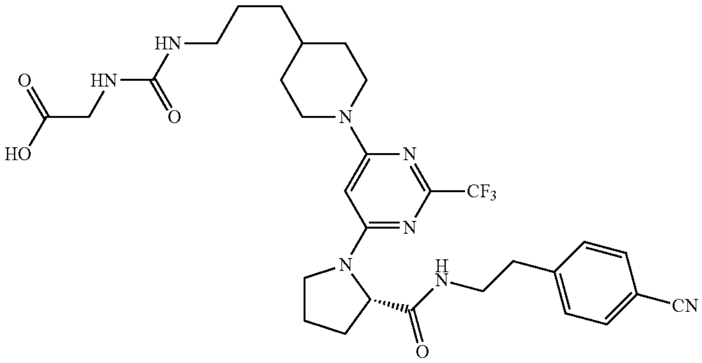 [SMILES: N#Cc1ccc(CCNC(=O)[C@@H]2CCCN2c2cc(N3CCC(CCCNC(=O)NCC(=O)O)CC3)nc(C(F)(F)F)n2)cc1] (S)-2-(3-(3-(1-(6-(2-((4-cyanophenethyl)carbamoyl)pyrrolidin-1-yl)-2-(trifluoromethyl)pyrimidin-4-yl)piperidin-4-yl)propyl)ureido)acetic acid | 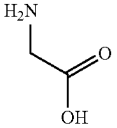 | 631.6 A |

Example 24

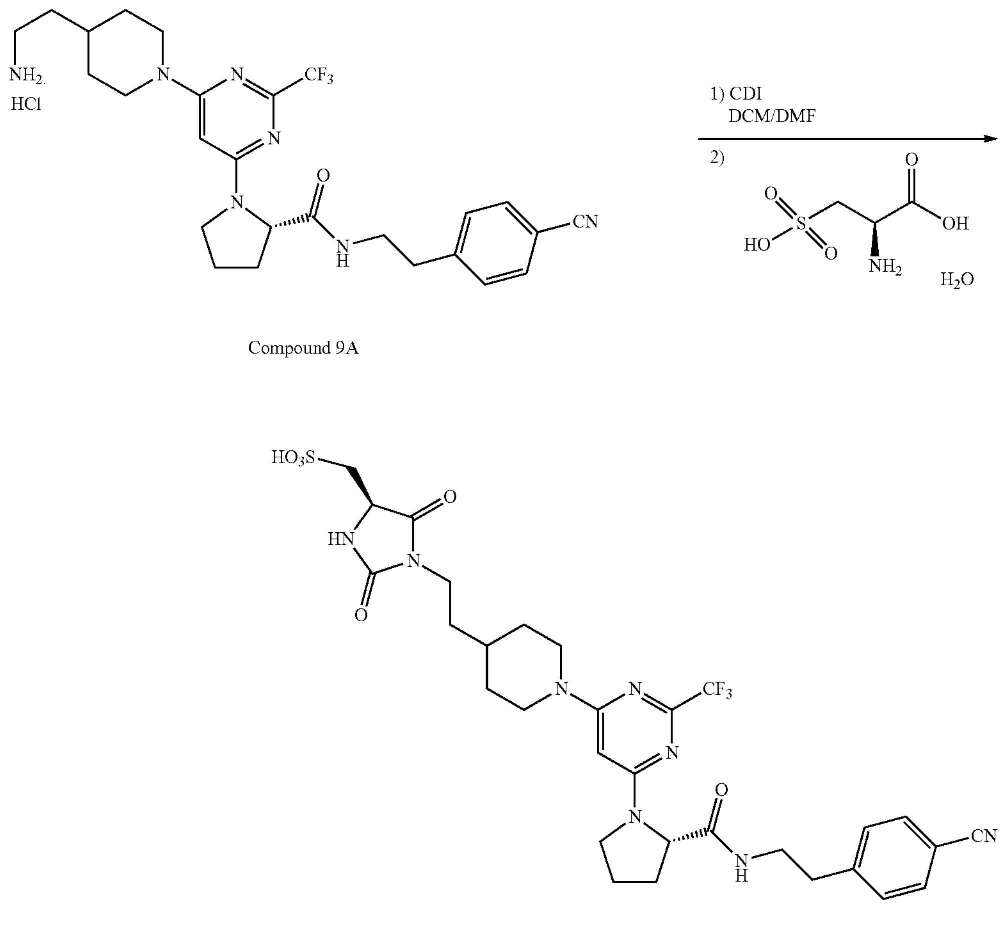

Compound 9A

Compound 122

((R)-1-(2-(1-(6-((S)-2-((4-cyanophenethyl)carbamoyl)pyrrolidin-1-yl)-2-(trifluoromethyl)pyrimidin-4-yl)piperidin-4-yl)ethyl)-2,5-dioxoimidazolidin-4-yl) methanesulfonic acid To Compound 9A (99 mg, 0.18 mmol) in DCM (1 mL)/DMF (1.5 mL) was added DIEA (345 μL, 2.00 mmol). Once in solution, 1,1'-carbonyldiimidazole (219 mg, 1.35 mmol) was added and the reaction was stirred at room temperature overnight. L-cysteic acid monohydrate (135 mg, 0.720 mmol) and DIEA (314) were added and the reaction was heated in a microwave for one hour at 90° C. The reaction was filtered (Acrodisc syringe filter) and concentrated in vacuo. The residue was purified by column chromatography (reverse phase C-18 column, 0-100% acetonitrile/water containing 0.25% formic acid), followed by MS-HPLC to afford Compound 122 (8 mg). LCMS (Method D): m/z 693.1 $(M+H)^+$. $^1H$ NMR ($CD_3OD$) δ 7.58-7.56 (dd, 2H), 7.35-7.33 (dd, 2H), 4.50-4.32 (m, 4H), 3.62-3.28 (m, 6H), 3.01-2.83 (m, 5H), 2.20-2.17 (m, 1H), 2.01 (m, 3H), 1.91-1.88 (m, 2H), 1.60-1.55 (m, 3H), 1.84-1.16 (m, 2H).

Example 25
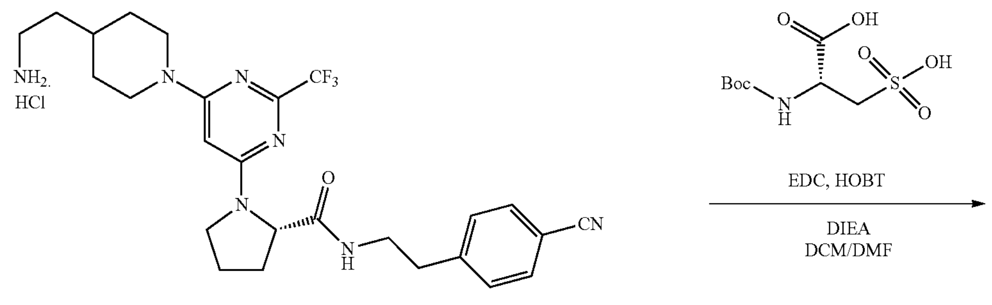
Compound 9A
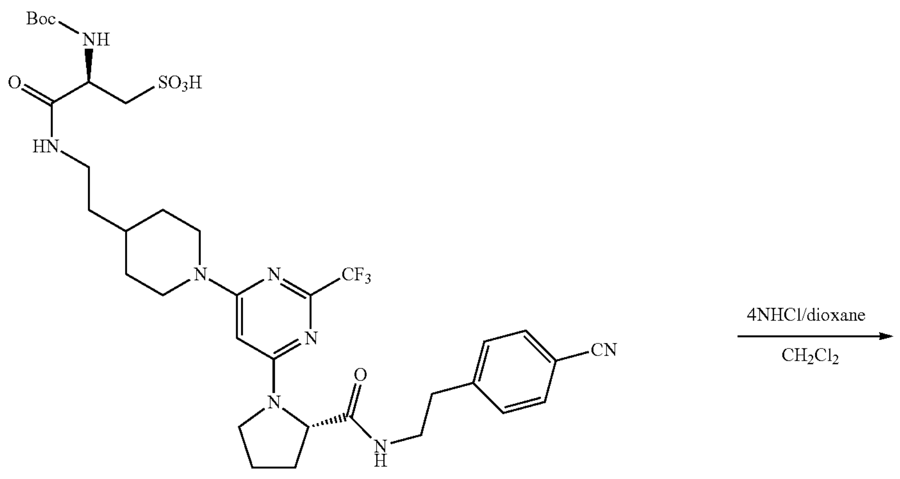
Compound 25A
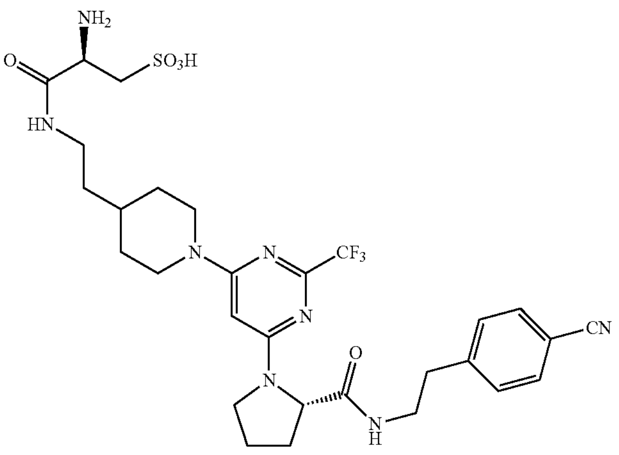
Compound 123

(R)-2-((tert-butoxycarbonyl)amino)-3-((2-(1-(6-((S)-2-((4-cyanophenethyl)carbamoyl) pyrrolidin-1-yl)-2-(trifluoromethyl)pyrimidin-4-yl)piperidin-4-yl)ethyl) amino)-3-oxopropane-1-sulfonic acid Using the procedure as described in Example 7, Compound 9A (108 mg, 0.20 mmol) was converted to Compound 25A (155 mg, quant.). LCMS (method A): m/z 767.4 $(M+H)^+$. $^1H$ NMR ($CD_3OD$) δ 7.56-7.53 (dd, 2H), 7.33-7.31 (dd, 2H), 5.58 (s, 1H), 4.44-4.36 (m, 4H), 3.76-3.10 (m, 8H), 2.91-2.81 (m, 5H), 2.15-2.00 (m, 4H), 1.87-1.68 (m, 3H), 1.49-1.34 (m, 11H), 1.2-1.08 (m, 2H).

(R)-2-amino-3-((2-(1-(6-((S)-2-((4-cyanophenethyl) carbamoyl)pyrrolidin-1-yl)-2-(trifluoromethyl)pyrimidin-4-yl)piperidin-4-yl)ethyl)amino)-3-oxopropane-1-sulfonic acid Compound 25A (150 mg, 0.20 mmol) was treated with 4N HCl/dioxane following a similar procedure as described in Intermediate 9, step 3 to afford Compound 123 (80 mg, 58%). LCMS (method A): m/z 667.3 $(M+H-)^+$. $^1H$ NMR ($CD_3OD$) δ 8.06-8.02 (m, 1H), 7.55-7.52 (m, 2H), 7.32-7.30 (m, 2H), 5.57 (b, 1H), 4.46-4.37 (m, 3H), 4.22-4.18 (m, 1H), 3.59-3.24 (m, 7H), 3.16-3.10 (m, 1H), 2.91-2.78 (m, 4H), 2.15-1.99 (m, 4H), 1.87-1.80 (m, 2H), 1.70-1.63 (m, 1H), 1.54-1.49 (m, 2H), 1.23-1.14 (m, 2H). Using the procedure described above for Example 25, the following compounds were prepared from the precursors and reagents as indicated in Table 21.

TABLE 21

| No | Structure | Pre-cursor | Acid | MS $(M + H)^+$ |
|---|---|---|---|---|
| 124 | 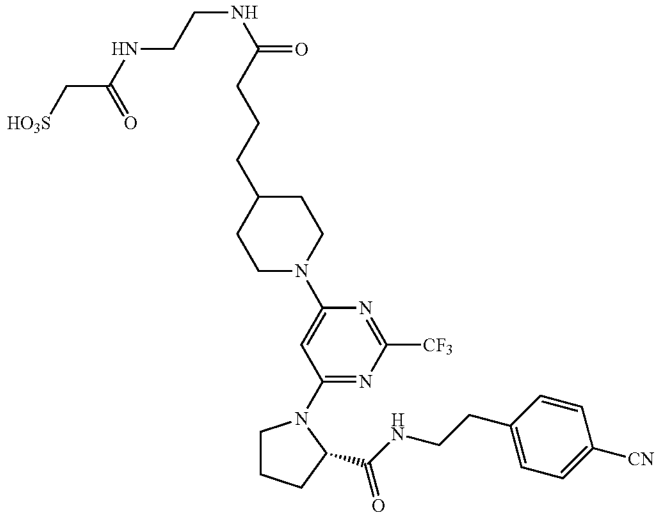 [SMILES: N#Cc1ccc(CCNC(=O)[C@@H]2CCCN2c2cc(N3CCC(CCCC(=O)NCCNC(=O)CS(=O)(=O)O)CC3)nc(C(F)(F)F)n2)cc1] (S)-2-((2-(4-(1-(6-(2-((4-cyanophenethyl)carbamoyl)pyrrolidin-1-yl)-2-(trifluoromethyl)pyrimidin-4-yl)piperidin-4-yl)butanamido)-ethyl)amino)-2-oxoethanesulfonic acid | 92 | 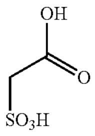 Step 1 only | 723.3 A |

TABLE 21-continued
| No | Structure | Pre-cursor | Acid | MS (M + H)+ |
|---|---|---|---|---|
| 125 | 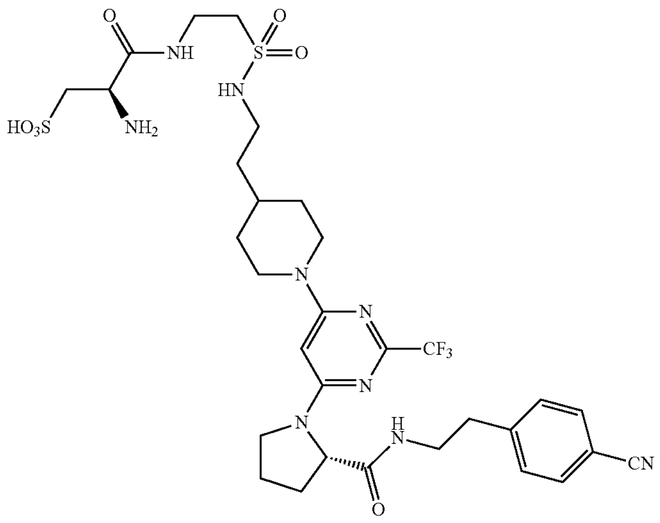 [SMILES: N#Cc1ccc(CCNC(=O)[C@@H]2CCCN2c2cc(N3CCC(CCNS(=O)(=O)CCNC(=O)[C@@H](N)CS(=O)(=O)O)CC3)nc(C(F)(F)F)n2)cc1] (R)-2-amino-3-((2-(N-(2-(1-(6-((S)-2-((4-cyanophenethyl)carbamoyl)-pyrrolidin-1-yl)-2-(trifluoromethyl)-pyrimidin-4-yl)piperidin-4-yl)ethyl)sulfamoyl)ethyl)amino)-3-oxopropane-1-sulfonic acid | 116 | 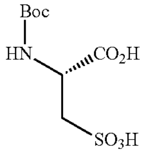 | 774.3 A |
Example 26
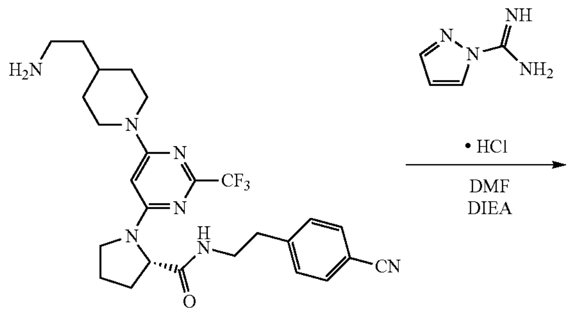
Compound 50
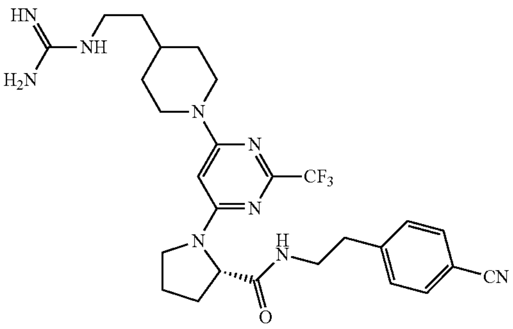
Compound 126

(S)—N-(4-cyanophenethyl)-1-(6-(4-(2-guanidino-ethyl)piperidin-1-yl)-2-(trifluoromethyl)pyrimidin-4-yl)pyrrolidine-2-carboxamide Compound 50 (TFA salt, 0.11 mmol) was dissolved in DMF (2 mL), and 1H-Pyrazole-1-carboxamidine hydrochloride (30 mg, 0.23 mmol) and DIEA (0.06 mL, 0.34 mmol) were added. The reaction mixture was heated at 90° C. in a microwave for one hour. Product was purified by MS-HPLC to afford Compound 126 (21 mg). LCMS (method A): m/z 558.6 $(M+H)^+$. $^1H$ NMR ($CDCl_3$): δ 8.58 (s, 1H), 8.52 (br s, 1H), 7.56 (br s, 2H), 7.36 (d, 2H), 7.11 (d, 2H), 5.30 (s, 1H), 4.58 (br s, 1H), 4.36 (m, 2H), 3.61 (m, 1H), 3.37-3.32 (m, 2H), 3.18 (m, 3H), 2.90-2.74 (m, 4H), 2.38 (br, 1H), 2.18 (br, 1H), 2.05 (br, 1H), 1.85-1.57 (m, 6H), 1.23-1.20 (m, 2H). Using the procedure described above for Example 26, the following compounds were prepared from the precursor as indicated in Table 22.

TABLE 22

| No | Structure | Pre-cursor | MS $(M + H)^+$ |
|---|---|---|---|
| 127 | 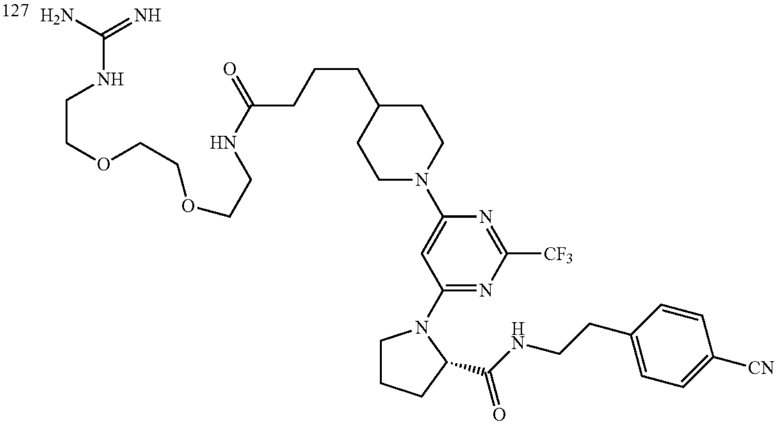<br>(S)-1-(6-(4-(1-amino-1-imino-12-oxo-5,8-dioxa-2,11-diazapentadecan-15-yl)piperidin-1-yl)-2-(trifluoromethyl)-pyrimidin-4-yl)-N-(4-cyanophenethyl)-pyrrolidine-2-carboxamide | 67 | 731.7<br>A |
| 128 | 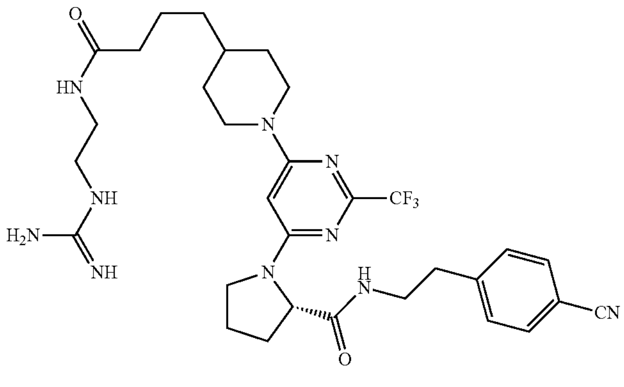 [SMILES: N#Cc1ccc(CCNC(=O)[C@@H]2CCCN2c2cc(N3CCC(CCCC(=O)NCCNC(=N)N)CC3)nc(C(F)(F)F)n2)cc1]<br>(S)-N-(4-cyanophenethyl)-1-(6-(4-(4-((2-guanidinoethyl)amino)-4-oxobutyl)piperidin-1-yl)-2-(trifluoromethyl)pyrimidin-4-yl)pyrrolidine-2-carboxamide | 92 | 643.6<br>A |

TABLE 22-continued
| No | Structure | Pre-cursor | MS (M + H)$^+$ |
|---|---|---|---|
| 129 | 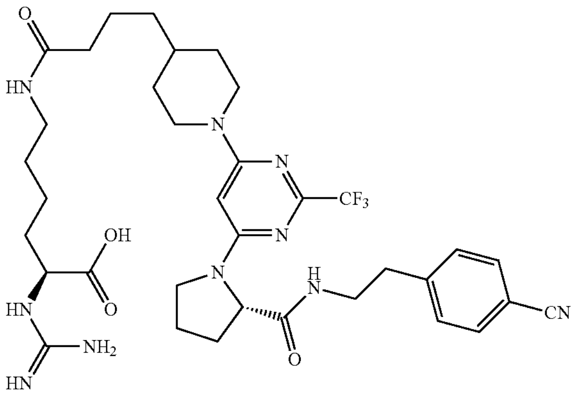 [SMILES: N#Cc1ccc(CCNC(=O)[C@@H]2CCCN2c2cc(N3CCC(CCCC(=O)NCCCC[C@H](NC(=N)N)C(=O)O)CC3)nc(C(F)(F)F)n2)cc1] (S)-6-(4-(1-(6-((S)-2-((4-cyanophenethyl)carbamoyl)pyrrolidin-1-yl)-2-(trifluoromethyl)pyrimidin-4-yl)piperidin-4-yl)butanamido)-2-guanidinohexanoic acid | 106 | 729.6 A |
| 130 | 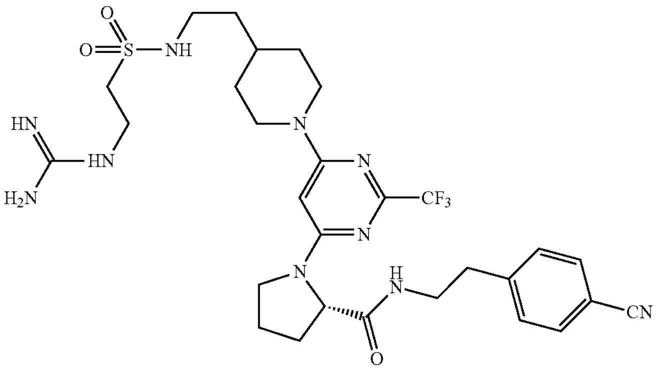 [SMILES: N#Cc1ccc(CCNC(=O)[C@@H]2CCCN2c2cc(N3CCC(CCNS(=O)(=O)CCNC(=N)N)CC3)nc(C(F)(F)F)n2)cc1] (S)-N-(4-cyanophenethyl)-1-(6-(4-(2-(2-guanidinoethylsulfonamido)ethyl) piperidin-1-yl)-2-(trifluoromethyl) pyrimidin-4-yl)pyrrolidine-2-carboxamide | 116 | 665.1 A |

TABLE 22-continued
| No | Structure | Pre-cursor | MS (M + H)+ |
| --- | --- | --- | --- |
| 131 | 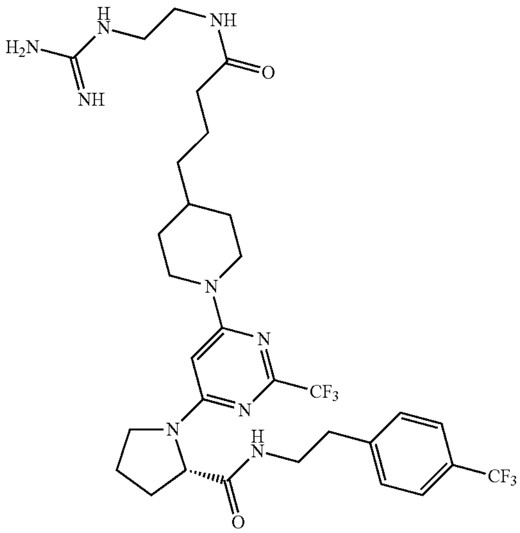 [SMILES: N=C(N)NCCNC(=O)CCCC1CCN(c2cc(N3CCC[C@H]3C(=O)NCCc3ccc(C(F)(F)F)cc3)nc(C(F)(F)F)n2)CC1] (S)-1-(6-(4-(4-((2-guanidinoethyl)-amino)-4-oxobutyl)piperidin-1-yl)-2-(trifluoromethyl)pyrimidin-4-yl)-N-(4-(trifluoromethyl)phenethyl) pyrrolidine-2-carboxamide | 90 | 686.6 A |
| 132 | 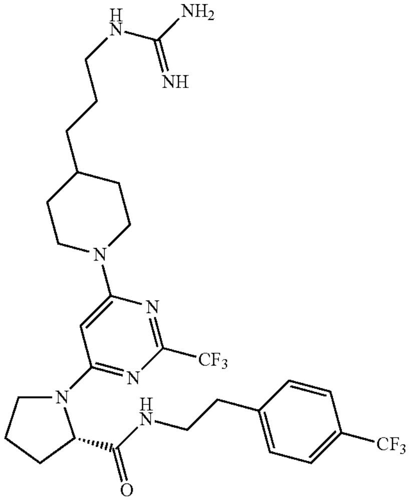 [SMILES: N=C(N)NCCCC1CCN(c2cc(N3CCC[C@H]3C(=O)NCCc3ccc(C(F)(F)F)cc3)nc(C(F)(F)F)n2)CC1] (S)-1-(6-(4-(3-guanidinopropyl)piperidin-1-yl)-2-(trifluoromethyl)pyrimidin-4-yl)-N-(4-(trifluoromethyl)phenethyl)-pyrrolidine-2-carboxamide | Com-pound 8A in Example 8 | 615.3 A |

TABLE 22-continued
| No | Structure | Pre-cursor | MS (M + H)$^+$ |
|---|---|---|---|
| 133 | 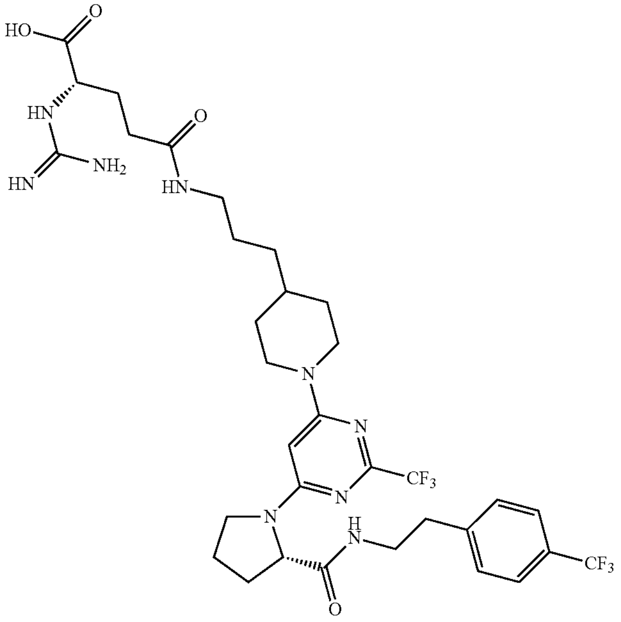 [SMILES: N=C(N)N[C@@H](CCC(=O)NCCCC1CCN(c2cc(N3CCC[C@H]3C(=O)NCCc3ccc(C(F)(F)F)cc3)nc(C(F)(F)F)n2)CC1)C(=O)O] (S)-2-guanidino-5-oxo-5-((3-(1-(2-(trifluoromethyl)-6-((S)-2-((4-(trifluoromethyl)phenethyl)carbamoyl)pyrrolidin-1-yl)pyrimidin-4-yl)piperidin-4-yl)propyl)amino)pentanoic acid | 77 | 744.3 A |
Example 27
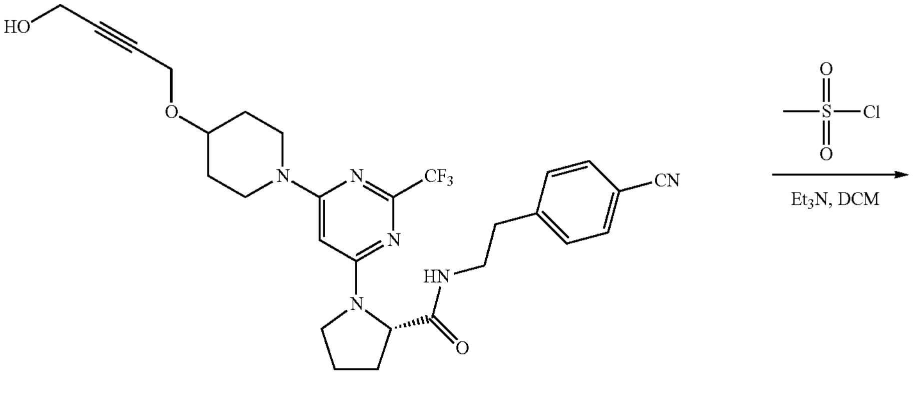
Compound 26

-continued

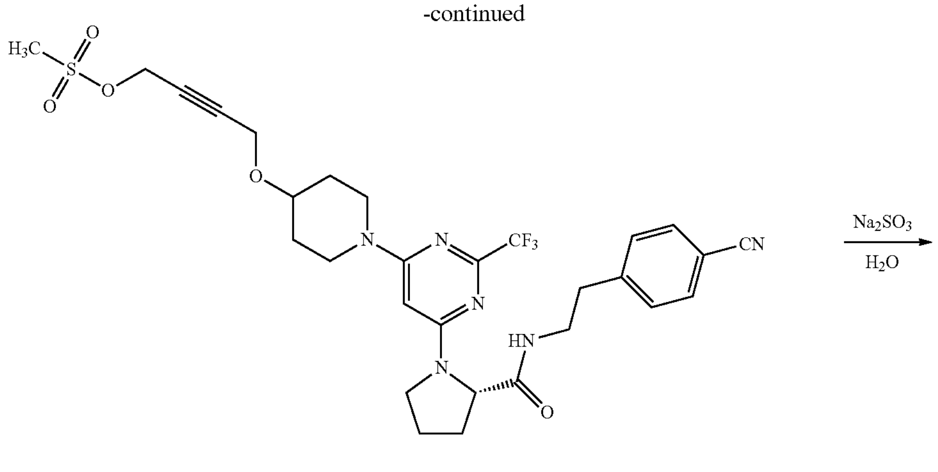

Compound 27A

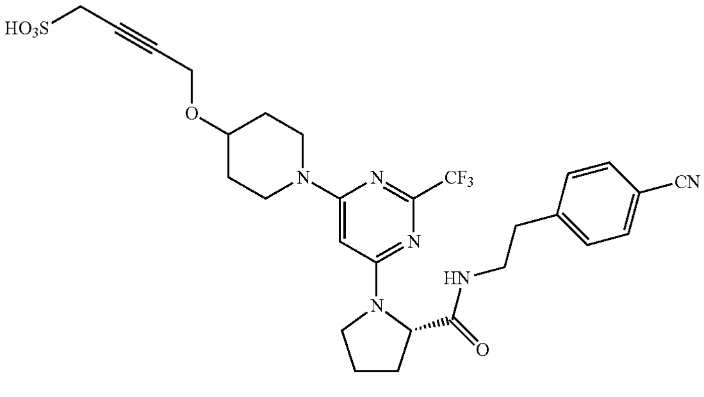

Compound 134

(S)-4-((1-(6-(2-((4-cyanophenethyl)carbamoyl)pyrrolidin-1-yl)-2-(trifluoromethyl) pyrimidin-4-yl) piperidin-4-yl)oxy)but-2-yn-1-yl methanesulfonate To a solution of Compound 26 (1.3 g, 2.3 mmol) and triethylamine (0.65 mL, 4.7 mmol) in DCM (20 mL) at 0° C. was added drop wise a solution of methanesulfonyl chloride (320 mg, 2.8 mmol) in DCM (10 mL). After stirring at room temperature for 0.5 hour, the reaction was poured into ice-water and extracted with DCM. The organic layer was washed with water and brine, dried over $Na_2SO_4$, and concentrated to give a crude oil, which was purified by silica gel chromatography (40-60% EtOAc/petroleum ether) to afford Compound 27A (1 g, 68%). LCMS (method A): m/z 635.4 $(M+H)^+$. $^1H$ NMR ($CDCl_3$): δ 7.66 (br s, 1H), 7.41 (d, 2H), 7.14 (d, 2H), 5.34 (s, 1H), 4.91 (m, 2H), 4.61 (br s, 1H), 4.29 (m, 2H), 4.03-3.91 (m, 2H), 3.81 (m, 1H), 3.59 (m, 1H), 3.41 (m, 4H), 3.22 (br, 1H), 3.12 (s, 3H), 2.86 (m, 1H), 2.77 (m, 1H), 2.44 (m, 1H), 2.22 (br, 1H), 2.08 (m, 1H), 1.96 (m, 2H), 1.84 (br, 1H), 1.67 (m, 2H).

(S)-4-((1-(6-(2-((4-cyanophenethyl)carbamoyl)pyrrolidin-1-yl)-2-(trifluoromethyl) pyrimidin-4-yl) piperidin-4-yl)oxy)but-2-yne-1-sulfonic acid Compound 27A (89 mg, 0.14 mmol) and $Na_2SO_3$ (54 mg, 0.42 mmol) were combined in $H_2O$ (1 mL), and $CH_3CN$ was added to aid solubility. After stirring overnight at room temperature, the reaction was heated to 50° C. for 72 hours, concentrated in vacuo, and purified by silica gel chromatography to afford Compound 134 (37 mg, 42%). LCMS (method A): m/z 621.5 $(M+H)^+$. $^1H$ NMR ($CD_3OD$): δ 7.58-7.56 (dd, 2H), 7.36-7.33 (m, 2H), 4.49-4.48 (b, 1H), 4.29-4.28 (m, 2H), 3.99-3.91 (m, 3H), 3.72 (s, 2H), 3.62 (b, 1H), 3.51-3.38 (m, 5H), 2.91-2.83 (m, 2H), 2.20-2.13 (m, 1H), 2.04-1.95 (m, 5H), 1.66-1.57 (m, 2H).

Example 28

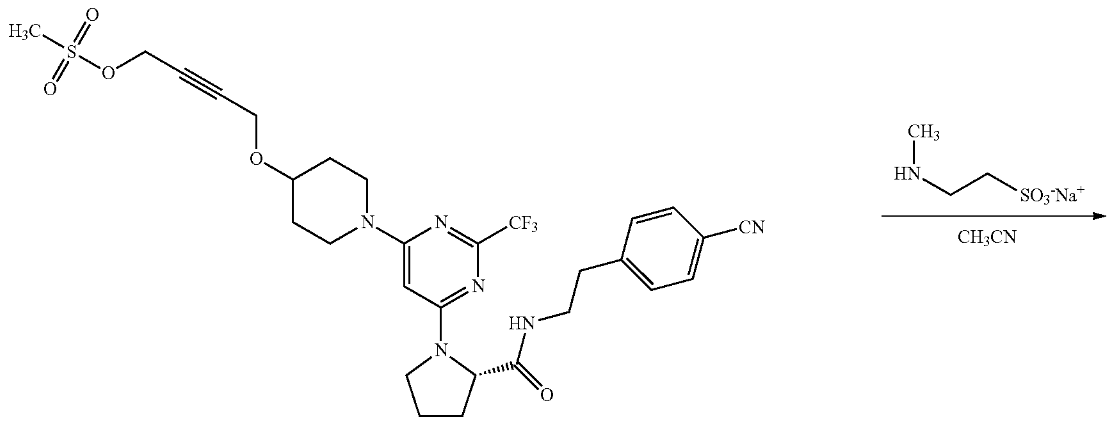

Compound 27A

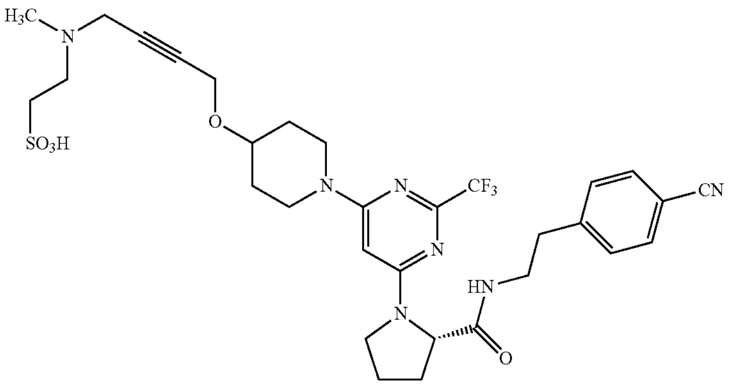

Compound 135

(S)-2-((4-((1-(6-(2-((4-cyanophenethyl)carbamoyl) pyrrolidin-1-yl)-2-(trifluoromethyl) pyrimidin-4-yl) piperidin-4-yl)oxy)but-2-yn-1-yl)(methyl)amino) ethanesulfonic acid To a solution of Compound 27A (52 mg, 0.08 mmol) in $CH_3CN$ (0.8 mL) was added sodium 2-(methylamino)ethanesulfonate (64-66% in $H_2O$) (93 mg, 0.38 mmol). The reaction was heated at 75° C. overnight. The reaction was concentrated in vacuo, and triturated with ethyl ether to provide a white solid which was further purified by reverse phase chromatography to afford Compound 135 (24 mg, 43%). LCMS (method A): m/z 678.5 $(M+H)^+$. $^1H$ NMR ($CD_3OD$) δ 8.05-8.02 (m, 1H), 7.55-7.53 (m, 2H), 7.32-7.30 (m, 2H), 5.62 (b, 1H), 4.47-4.37 (m, 3H), 4.25 (s, 2H), 4.01-4.00 (m, 2H), 3.88-3.83 (m, 1H), 3.66-3.63 (m, 3H), 3.49-3.22 (m, 7H), 3.01 (s, 3H), 2.88-2.80 (m, 2H), 2.15 (b, 1H), 2.01-1.94 (m, 5H), 1.62-1.53 (m, 2H).

Example 29
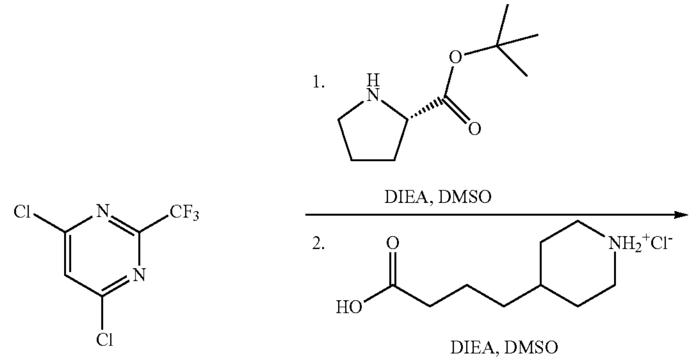
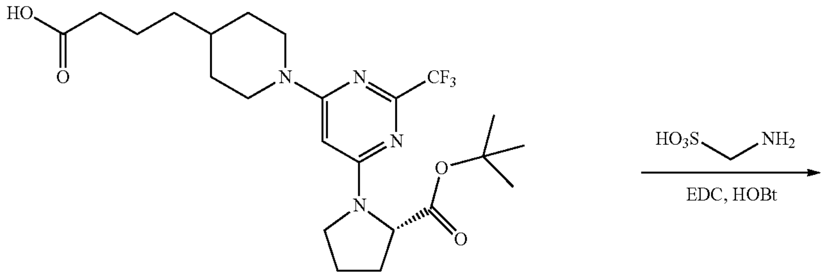
Compound 29A
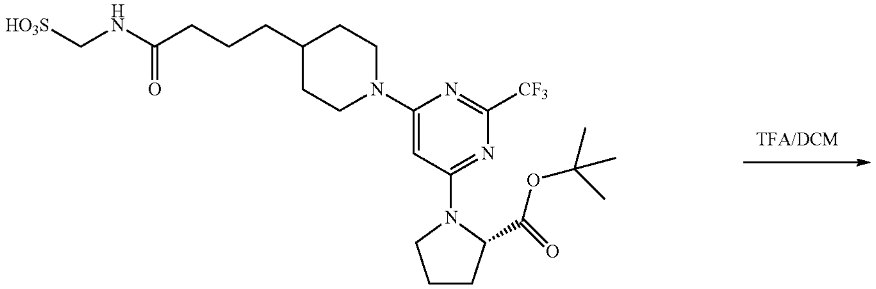
Compound 29B
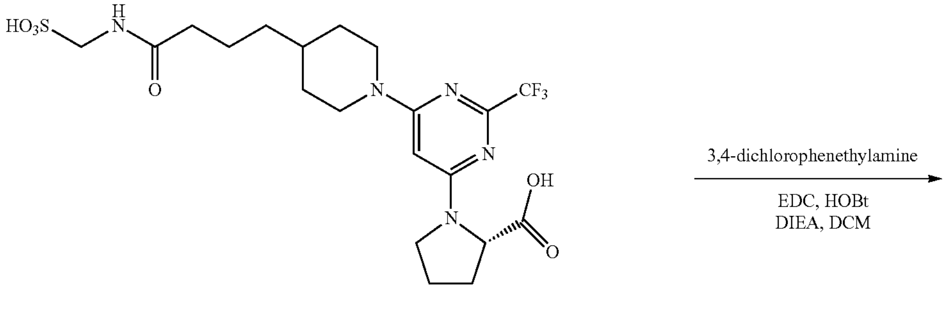
Compound 29C -continued

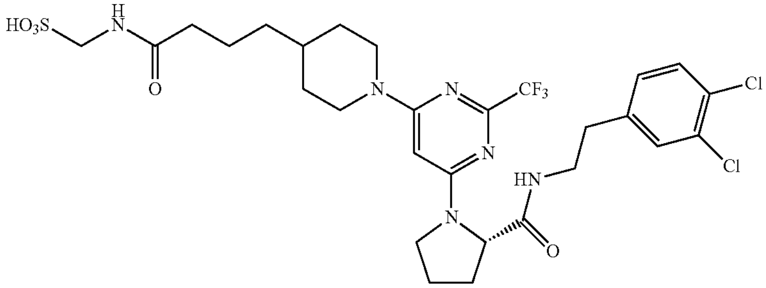

Compound 136

(S)-4-(1-(6-(2-(tert-butoxycarbonyl)pyrrolidin-1-yl)-2-(trifluoromethyl)pyrimidin-4-yl)piperidin-4-yl) butanoic acid To a solution of 4,6-dichloro-2-(trifluoromethyl)pyrimidine (800 mg, 3.7 mmol) in 2 mL of DMSO were added L-proline t-butylester (660 mg, 3.7 mmol) and DIEA (1.3 mL, 7.4 mmol). The mixture was heated at 90° C. in a microwave for one hour. After cooling, 4-(3-carboxypropyl) piperidine hydrochloride (770 mg, 3.7 mmol) and DIEA (650 μL, 3.7 mmol) were added, and the reaction was heated at 120° C. for three hours. EtOAc was added and the solution was washed with 1N HCl and brine, dried ($Na_2SO_4$), concentrated in vacuo, and purified via silica gel chromatography (0-5% MeOH/DCM) to afford Compound 29A (1.3 g, 72%). LCMS (method A): m/z 487.3 $(M+H)^+$.

(S)-(4-(1-(6-(2-(tert-butoxycarbonyl)pyrrolidin-1-yl)-2-(trifluoromethyl)pyrimidin-4-yl)piperidin-4-yl) butanamido)methanesulfonic acid Using a similar procedure as described in Example 7, Compound 29A (1.30 g, 2.67 mmol) was converted to Compound 29B. LCMS (method A): m/z 580.3 $(M+H)^+$.

(S)-1-(6-(4-(4-oxo-4-((sulfomethyl)amino)butyl) piperidin-1-yl)-2-(trifluoromethyl) pyrimidin-4-yl) pyrrolidine-2-carboxylic acid Compound 29B was stirred in a mixture of TFA (5 mL) and DCM (5 mL) for one hour and concentrated in vacuo to afford Compound 29C (1.25 g, 90% over two steps). LCMS (method A): m/z 524.2 $(M+H)^+$.

(S)-(4-(1-(6-(2-((3,4-dichlorophenethyl)carbamoyl) pyrrolidin-1-yl)-2-(trifluoromethyl) pyrimidin-4-yl) piperidin-4-yl)butanamido)methanesulfonic acid Using a similar procedure as described in Example 7, Compound 29C (120 mg, 0.23 mmol) was converted to Compound 136 (30 mg, 19%). LCMS (method A): m/z 695.2 $(M+H)^+$. $^1H$ NMR ($CD_3OD$) δ 7.33 (m, 2H), 7.08 (d, 1H), 4.49 (bs, 1H), 4.36 (m, 4H), 3.62 (bs, 1H), 3.42 (m, 3H), 2.94 (t, 2H), 2.76 (m, 2H), 2.18 (m, 3H), 2.05 (m, 3H), 1.81 (d, 2H), 1.70 (m, 2H), 1.60 (bs, 1H), 1.34 (m, 2H), 1.18 (m, 2H). Using the procedure described above for Example 29, the following compounds were prepared from Compound 32C and the reagents as indicated in Table 23.

TABLE 23

| No | Structure | Reagent | MS $(M + H)^+$ |
|---|---|---|---|
| 137 | 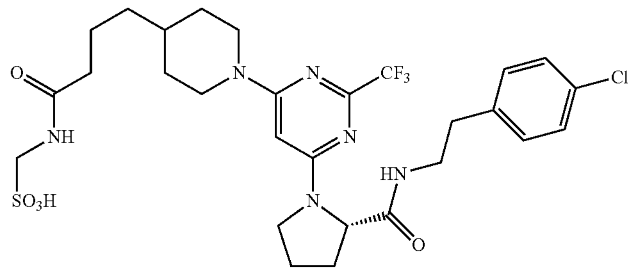 [SMILES: O=C(CCCC1CCN(c2cc(N3CCC[C@H]3C(=O)NCCc3ccc(Cl)cc3)nc(C(F)(F)F)n2)CC1)NCS(=O)(=O)O] (S)-(4-(1-(6-(2-((4-chlorophenethyl)-carbamoyl)pyrrolidin-1-yl)-2-(trifluoromethyl)pyrimidin-4-yl)-piperidin-4-yl)butanamido)-methanesulfonic acid | 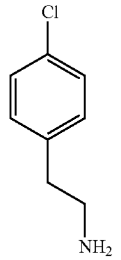 | 662.3 A |

TABLE 23-continued

| No | Structure | Reagent | MS (M + H)+ |
|---|---|---|---|
| 138 | 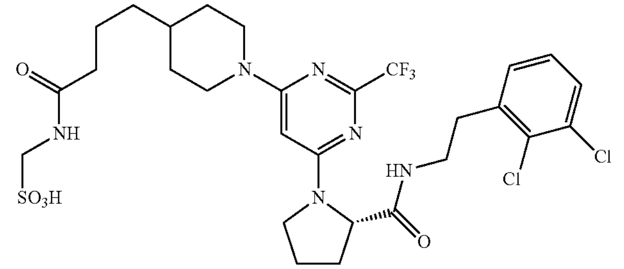 [SMILES: O=C(CCCC1CCN(c2cc(N3CCC[C@H]3C(=O)NCCc3cccc(Cl)c3Cl)nc(C(F)(F)F)n2)CC1)NCS(=O)(=O)O]<br>(S)-(4-(1-(6-(2-((2,3-dichlorophenethyl)carbamoyl)pyrrolidin-1-yl)-2-(trifluoromethyl)pyrimidin-4-yl)piperidin-4-yl)butanamido)-methanesulfonic acid | 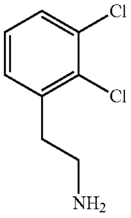 [SMILES: NCCc1cccc(Cl)c1Cl] | 695.4 |

Example 30

(S)—N-(4-cyanophenethyl)-1-(6-(5-hexylthiophen-2-yl)-2-(trifluoromethyl)pyrimidin-4-yl)pyrrolidine-2-carboxamide

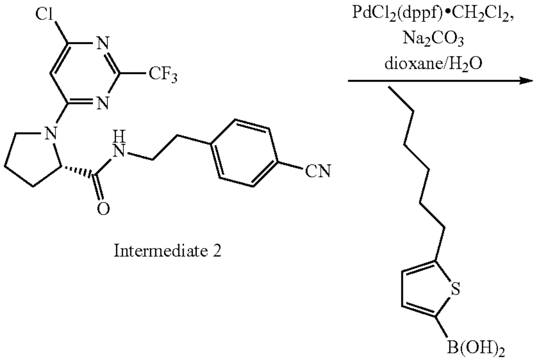

Intermediate 2

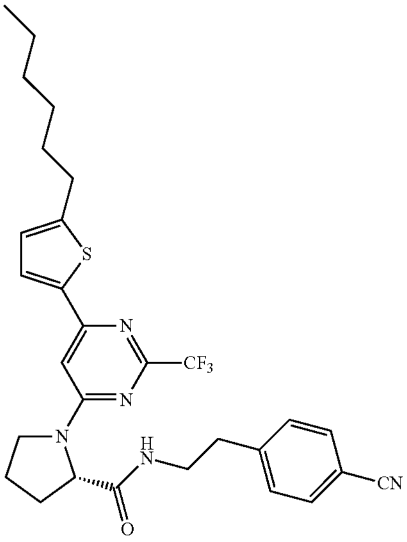

Compound 139

To a solution of Intermediate 2 (60 mg, 0.14 mmol) in dioxane/$H_2O$ (1.2 mL/0.3 mL) were added 2-(5-hexylthiophen-2-yl)-4,4,5,5-tetramethyl-1,3,2-dioxaborolane (84 mg, 0.28 mmol), $PdCl_2$(dppf).$CH_2Cl_2$ (23 mg, 0.03 mmol) and sodium carbonate (30 mg, 0.28 mmol). The reaction mixture was stirred at 100° C. overnight, and filtered through CELITE. The CELITE was washed with MeOH and the combined filtrate was concentrated in vacuo. The residue was purified by MS-HPLC to afford Compound 139 (67 mg, 85%). LCMS (method A): m/z 556.6 $(M+H)^+$. $^1$H NMR ($CDCl_3$) δ 7.63 (d, 1H), 7.44 (d, 2H), 7.28 (br s, 1H), 7.18 (d, 2H), 6.83 (s, 1H), 6.54 (br s, 1H), 4.68 (br s, 2H), 3.58-3.38 (m, 4H), 2.87-2.77 (m, 4H), 2.43 (br, 1H), 2.28 (br, 1H), 2.12 (br, 1H), 1.93 (br, 1H), 1.75-1.67 (m, 2H), 1.43-1.28 (m, 6H), 0.87 (m, 3H).

Using the procedure described above for Example 30, the following compounds were prepared from Intermediate 2 (except for compounds 172 and 194 in which intermediate 3 was used) and the reagents as indicated in Table 24.

TABLE 24
| No | Structure | Reagent | MS (M + H)+ |
|---|---|---|---|
| 140 | 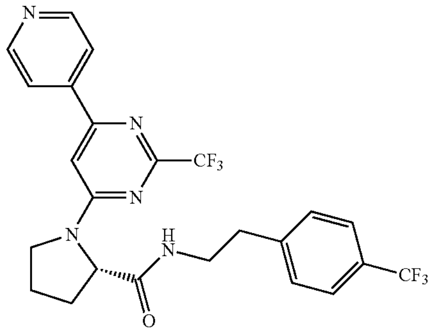 [SMILES: O=C(NCCc1ccc(C(F)(F)F)cc1)[C@@H]1CCCN1c1cc(-c2ccncc2)nc(C(F)(F)F)n1]<br>(S)-1-(6-(pyridin-4-yl)-2-(trifluoromethyl)pyrimidin-4-yl)-N-(4-(trifluoromethyl)phenethyl)pyrrolidine-2-carboxamide | 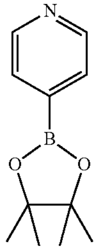<br>and Intermediate 3 | 510.4<br>A |
| 141 | 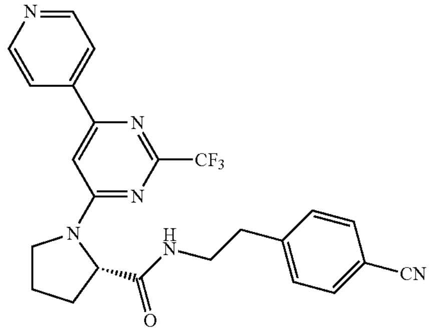 [SMILES: N#Cc1ccc(CCNC(=O)[C@@H]2CCCN2c2cc(-c3ccncc3)nc(C(F)(F)F)n2)cc1]<br>(S)-N-(4-cyanophenethyl)-1-(6-(pyridin-4-yl)-2-(trifluoromethyl)pyrimidin-4-yl)pyrrolidine-2-carboxamide | 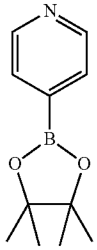 | 467.3<br>A |
| 142 | 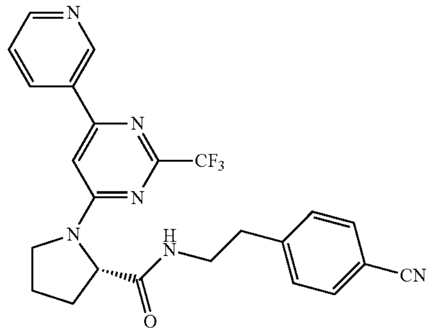 [SMILES: N#Cc1ccc(CCNC(=O)[C@@H]2CCCN2c2cc(-c3cccnc3)nc(C(F)(F)F)n2)cc1]<br>(S)-N-(4-cyanophenethyl)-1-(6-(pyridin-3-yl)-2-(trifluoromethyl)pyrimidin-4-yl)pyrrolidine-2-carboxamide | 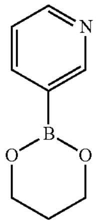 [SMILES: c1cncc(B2OCCCO2)c1] | 467.3<br>A |

TABLE 24-continued
| No | Structure | Reagent | MS (M + H)+ |
|---|---|---|---|
| 143 | 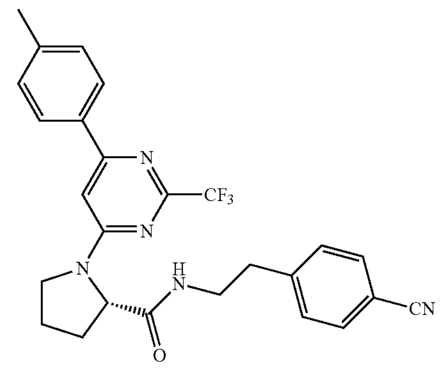 [SMILES: Cc1ccc(-c2cc(N3CCC[C@H]3C(=O)NCCc3ccc(C#N)cc3)nc(C(F)(F)F)n2)cc1] (S)-N-(4-cyanophenethyl)-1-(6-(p-tolyl)-2-(trifluoromethyl)pyrimidin-4-yl)pyrrolidine-2-carboxamide | 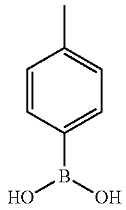 | 480.3 A |
| 144 | 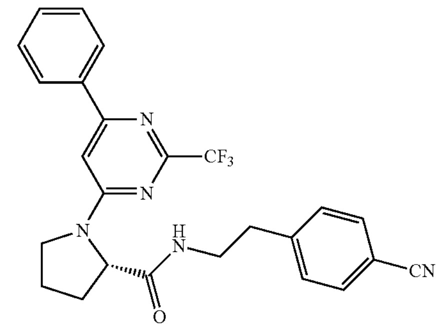 [SMILES: N#Cc1ccc(CCNC(=O)[C@@H]2CCCN2c2cc(-c3ccccc3)nc(C(F)(F)F)n2)cc1] (S)-N-(4-cyanophenethyl)-1-(6-phenyl-2-(trifluoromethyl)pyrimidin-4-yl)pyrrolidine-2-carboxamide | 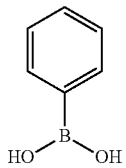 | 466.3 A |
| 145 | 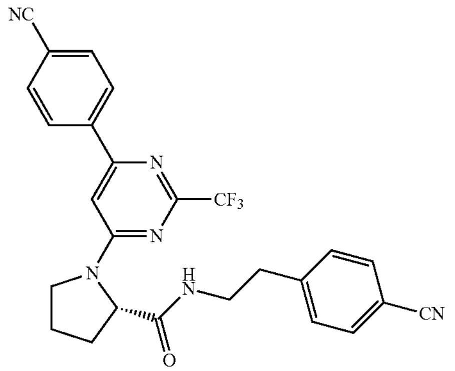 [SMILES: N#Cc1ccc(CCNC(=O)[C@@H]2CCCN2c2cc(-c3ccc(C#N)cc3)nc(C(F)(F)F)n2)cc1] (S)-N-(4-cyanophenethyl)-1-(6-(4-cyanophenyl)-2-(trifluoromethyl)pyrimidin-4-yl)pyrrolidine-2-carboxamide | 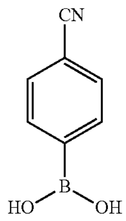 | 491.3 A |

TABLE 24-continued
| No | Structure | Reagent | MS (M + H)+ |
| --- | --- | --- | --- |
| 146 | 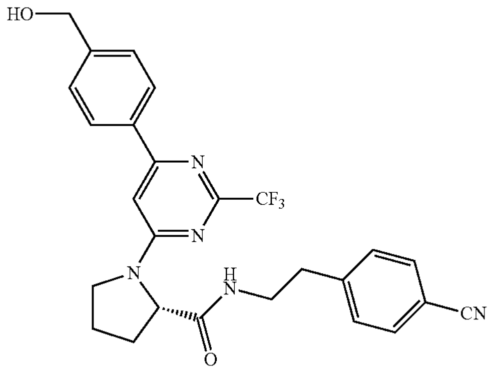 [SMILES: N#Cc1ccc(CCNC(=O)[C@@H]2CCCN2c2cc(-c3ccc(CO)cc3)nc(C(F)(F)F)n2)cc1] (S)-N-(4-cyanophenethyl)-1-(6-(4-(hydroxymethyl)phenyl)-2-(trifluoromethyl)pyrimidin-4-yl)pyrrolidine-2-carboxamide | 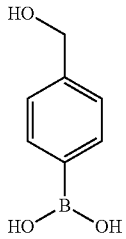 | 496.3 A |
| 147 | 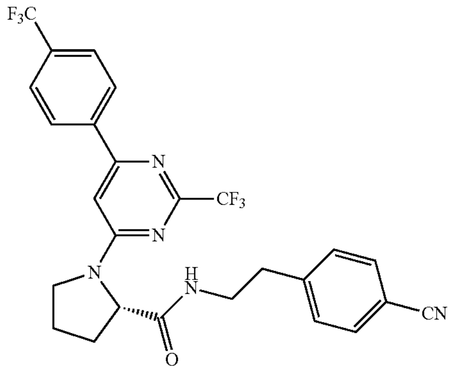 [SMILES: N#Cc1ccc(CCNC(=O)[C@@H]2CCCN2c2cc(-c3ccc(C(F)(F)F)cc3)nc(C(F)(F)F)n2)cc1] (S)-N-(4-cyanophenethyl)-1-(2-(trifluoromethyl)-6-(4-(trifluoromethyl)phenyl)pyrimidin-4-yl)pyrrolidine-2-carboxamide | 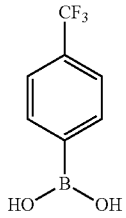 | 534.3 A |
| 148 | 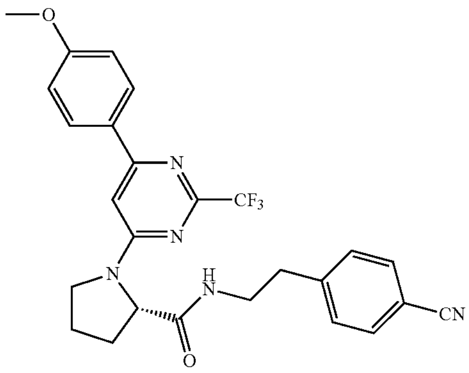 [SMILES: COc1ccc(-c2cc(N3CCC[C@H]3C(=O)NCCc3ccc(C#N)cc3)nc(C(F)(F)F)n2)cc1] (S)-N-(4-cyanophenethyl)-1-(6-(4-methoxyphenyl)-2-(trifluoromethyl)pyrimidin-4-yl)pyrrolidine-2-carboxamide | 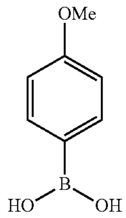 | 496.3 A |

TABLE 24-continued
| No | Structure | Reagent | MS (M + H)+ |
|---|---|---|---|
| 149 | 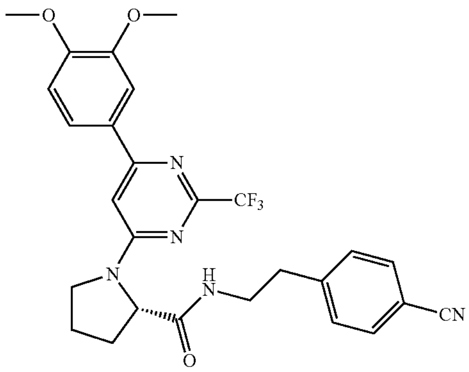 [SMILES: COc1ccc(-c2cc(N3CCC[C@H]3C(=O)NCCc3ccc(C#N)cc3)nc(C(F)(F)F)n2)cc1OC] (S)-N-(4-cyanophenethyl)-1-(6-(3,4-dimethoxyphenyl)-2-(trifluoromethyl)pyrimidin-4-yl)pyrrolidine-2-carboxamide | 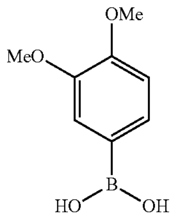 [SMILES: COc1ccc(B(O)O)cc1OC] | 526.4 A |
| 150 | 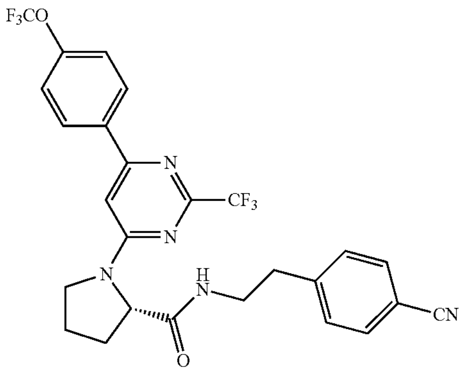 [SMILES: N#Cc1ccc(CCNC(=O)[C@@H]2CCCN2c2cc(-c3ccc(OC(F)(F)F)cc3)nc(C(F)(F)F)n2)cc1] (S)-N-(4-cyanophenethyl)-1-(6-(4-(trifluoromethoxy)phenyl)-2-(trifluoromethyl)pyrimidin-4-yl)pyrrolidine-2-carboxamide | 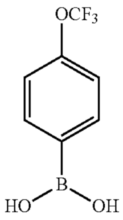 | 550.3 A |
| 151 | 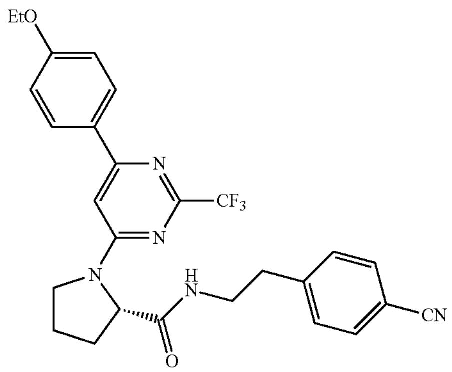 [SMILES: CCOc1ccc(-c2cc(N3CCC[C@H]3C(=O)NCCc3ccc(C#N)cc3)nc(C(F)(F)F)n2)cc1] (S)-N-(4-cyanophenethyl)-1-(6-(4-ethoxyphenyl)-2-(trifluoromethyl)pyrimidin-4-yl)pyrrolidine-2-carboxamide | 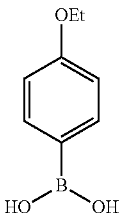 | 510.4 A |

TABLE 24-continued
| No | Structure | Reagent | MS (M + H)+ |
|---|---|---|---|
| 152 | 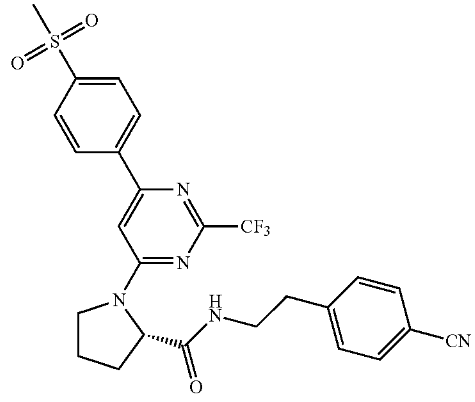 [SMILES: CS(=O)(=O)c1ccc(-c2cc(N3CCC[C@H]3C(=O)NCCc3ccc(C#N)cc3)nc(C(F)(F)F)n2)cc1] (S)-N-(4-cyanophenethyl)-1-(6-(4-(methylsulfonyl)phenyl)-2-(trifluoromethyl)pyrimidin-4-yl)pyrrolidine-2-carboxamide | 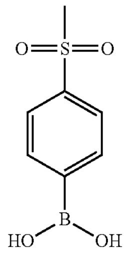 | 544.3 A |
| 153 | 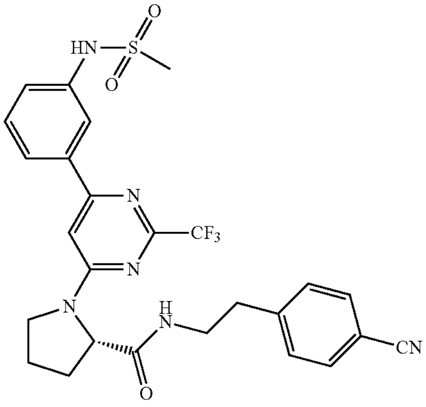 [SMILES: CS(=O)(=O)Nc1cccc(-c2cc(N3CCC[C@H]3C(=O)NCCc3ccc(C#N)cc3)nc(C(F)(F)F)n2)c1] (S)-N-(4-cyanophenethyl)-1-(6-(3-(methylsulfonamido)phenyl)-2-(trifluoromethyl)pyrimidin-4-yl)pyrrolidine-2-carboxamide | 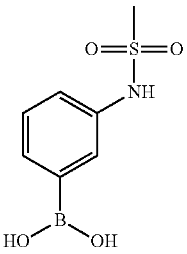 | 559.3 A |
| 154 | 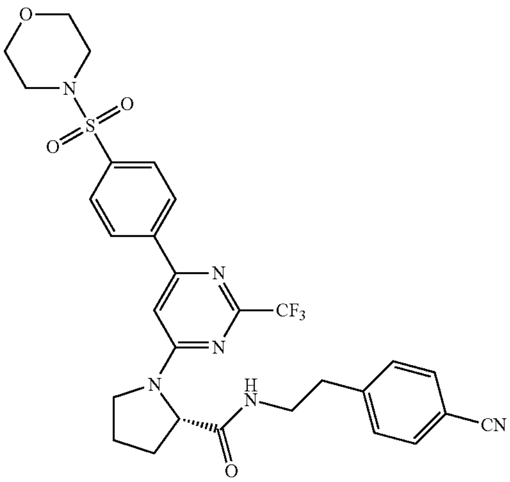 [SMILES: N#Cc1ccc(CCNC(=O)[C@@H]2CCCN2c2cc(-c3ccc(S(=O)(=O)N4CCOCC4)cc3)nc(C(F)(F)F)n2)cc1] (S)-N-(4-cyanophenethyl)-1-(6-(4-(morpholinosulfonyl)phenyl)-2- | 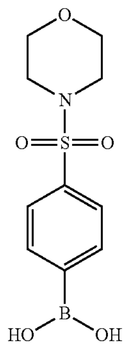 | 615.4 A |

TABLE 24-continued

| No | Structure | Reagent | MS (M + H)$^+$ |
|---|---|---|---|
| | (trifluoromethyl)pyrimidin-4-yl)pyrrolidine-2-carboxamide | | |
| 155 | 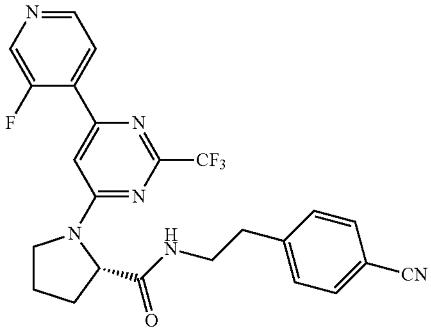 [SMILES: N#Cc1ccc(CCNC(=O)[C@@H]2CCCN2c2cc(-c3ccncc3F)nc(C(F)(F)F)n2)cc1] (S)-N-(4-cyanophenethyl)-1-(6-(3-fluoropyridin-4-yl)-2-(trifluoromethyl)pyrimidin-4-yl)pyrrolidine-2-carboxamide | 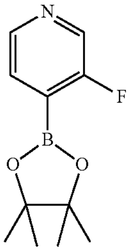 | 485.3 A |
| 156 | 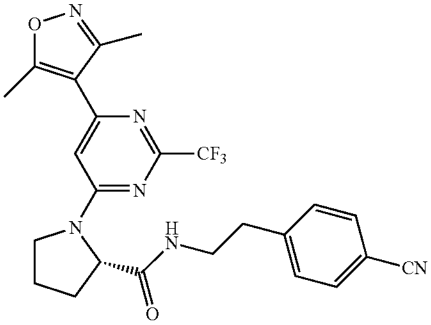 [SMILES: Cc1noc(C)c1-c1cc(N2CCC[C@H]2C(=O)NCCc2ccc(C#N)cc2)nc(C(F)(F)F)n1] (S)-N-(4-cyanophenethyl)-1-(6-(3,5-dimethylisoxazol-4-yl)-2-(trifluoromethyl)pyrimidin-4-yl)pyrrolidine-2-carboxamide | 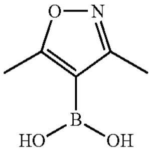 | 485.4 A |
| 157 | 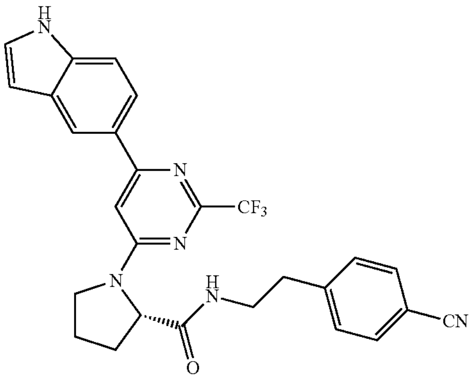 [SMILES: N#Cc1ccc(CCNC(=O)[C@@H]2CCCN2c2cc(-c3ccc4[nH]ccc4c3)nc(C(F)(F)F)n2)cc1] (S)-1-(6-(1H-indol-5-yl)-2-(trifluoromethyl)pyrimidin-4-yl)-N-(4-cyanophenethyl)pyrrolidine-2-carboxamide | 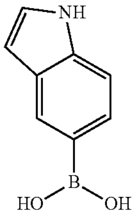 | 505.4 A |

TABLE 24-continued
| No | Structure | Reagent | MS (M + H)+ |
| --- | --- | --- | --- |
| 158 | 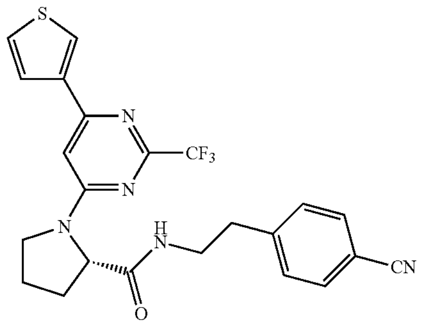 (S)-N-(4-cyanophenethyl)-1-(6-(thiophen-3-yl)-2-(trifluoromethyl)pyrimidin-4-yl)pyrrolidine-2-carboxamide | 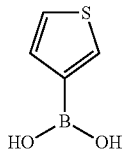 | 472.3 A |
| 159 | 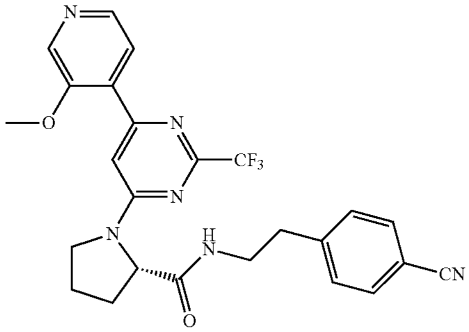 [SMILES: COc1cnccc1-c1cc(N2CCC[C@H]2C(=O)NCCc2ccc(C#N)cc2)nc(C(F)(F)F)n1] (S)-N-(4-cyanophenethyl)-1-(6-(3-methoxypyridin-4-yl)-2-(trifluoromethyl)pyrimidin-4-yl)pyrrolidine-2-carboxamide | 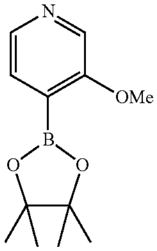 [SMILES: COc1cnccc1B1OC(C)(C)C(C)(C)O1] | 497.4 A |
| 160 | 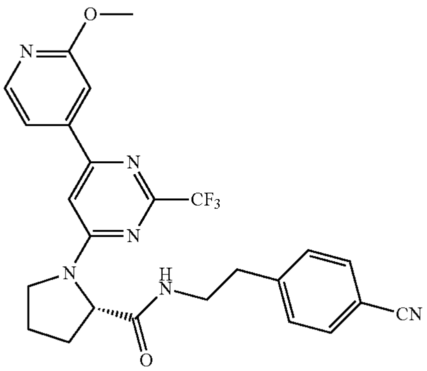 [SMILES: COc1cc(-c2cc(N3CCC[C@H]3C(=O)NCCc3ccc(C#N)cc3)nc(C(F)(F)F)n2)ccn1] (S)-N-(4-cyanophenethyl)-1-(6-(2-methoxypyridin-4-yl)-2-(trifluoromethyl)pyrimidin-4-yl)pyrrolidine-2-carboxamide | 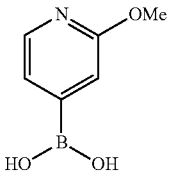 [SMILES: COc1cc(B(O)O)ccn1] | 497.3 A |

TABLE 24-continued

| No | Structure | Reagent | MS (M + H)+ |
|---|---|---|---|
| 161 | 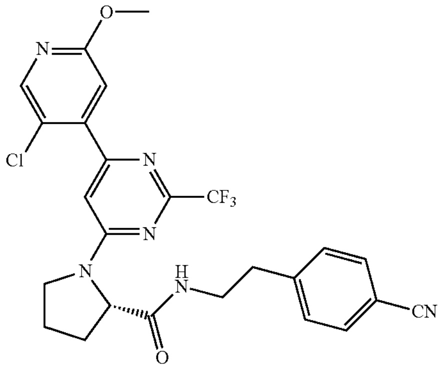 [SMILES: COc1cc(-c2cc(N3CCC[C@H]3C(=O)NCCc3ccc(C#N)cc3)nc(C(F)(F)F)n2)c(Cl)cn1]<br>(S)-1-(6-(5-chloro-2-methoxy-pyridin-4-yl)-2-(trifluoromethyl)pyrimidin-4-yl)-N-(4-cyanophenethyl)pyrrolidine-2-carboxamide | 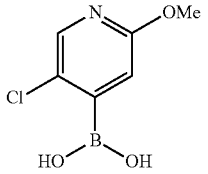 [SMILES: COc1cc(B(O)O)c(Cl)cn1] | 531.3 A |
| 162 | 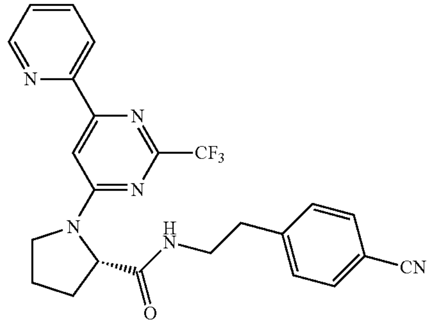 [SMILES: N#Cc1ccc(CCNC(=O)[C@@H]2CCCN2c2cc(-c3ccccn3)nc(C(F)(F)F)n2)cc1]<br>(S)-N-(4-cyanophenethyl)-1-(6-(pyridin-2-yl)-2-(trifluoromethyl)pyrimidin-4-yl)pyrrolidine-2-carboxamide | 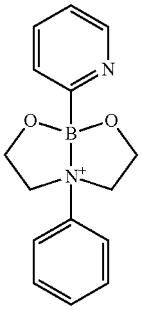 | 467.3 A |
| 163 | 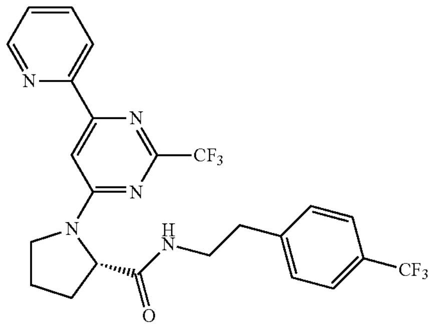 [SMILES: O=C(NCCc1ccc(C(F)(F)F)cc1)[C@@H]1CCCN1c1cc(-c2ccccn2)nc(C(F)(F)F)n1]<br>(S)-1-(6-(pyridin-2-yl)-2-(trifluoromethyl)pyrimidin-4-yl)-N-(4-(trifluoromethyl)phenethyl)-pyrrolidine-2-carboxamide | 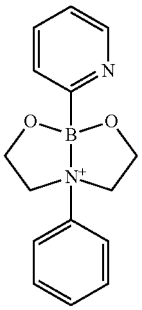<br>and Intermediate 3 | 510.3 A |

TABLE 24-continued
| No | Structure | Reagent | MS (M + H)+ |
|---|---|---|---|
| 164 | 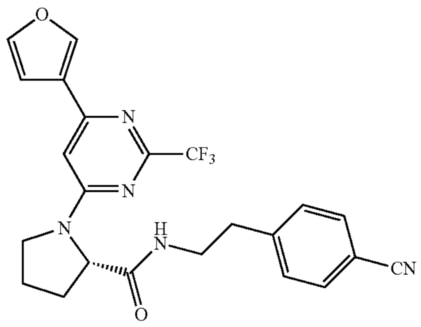 [SMILES: N#Cc1ccc(CCNC(=O)[C@@H]2CCCN2c2cc(-c3ccoc3)nc(C(F)(F)F)n2)cc1]<br>(S)-N-(4-cyanophenethyl)-1-(6-(furan-3-yl)-2-(trifluoromethyl)pyrimidin-4-yl)pyrrolidine-2-carboxamide | 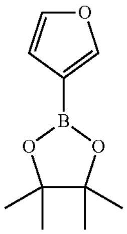 | 456.3 A |
| 165 | 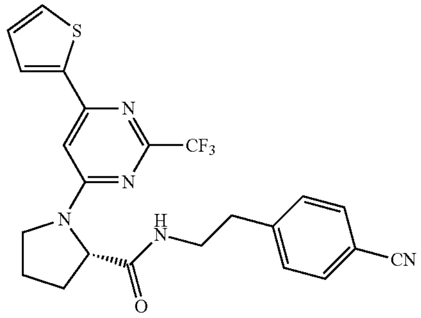 [SMILES: N#Cc1ccc(CCNC(=O)[C@@H]2CCCN2c2cc(-c3cccs3)nc(C(F)(F)F)n2)cc1]<br>(S)-N-(4-cyanophenthyl)-1-(6-(thiophene-2-yl)-2-(trifluoromethyl)pyrimidin-4-yl)pyrrolidine-2-carboxamide | 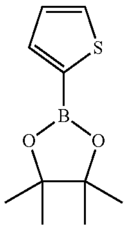 | 472.3 A |
| 166 | 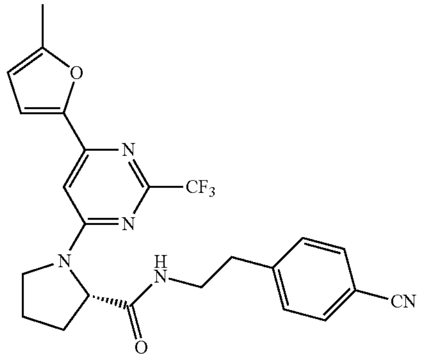 [SMILES: Cc1ccc(-c2cc(N3CCC[C@H]3C(=O)NCCc3ccc(C#N)cc3)nc(C(F)(F)F)n2)o1]<br>(S)-N-(4-cyanophenethyl)-1-(6-(5-methylfuran-2-yl)-2-(trifluoromethyl)pyrimidin-4-yl)pyrrolidine-2-carboxamide | 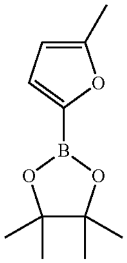 | 470.3 A |

TABLE 24-continued
| No | Structure | Reagent | MS (M + H)+ |
|---|---|---|---|
| 167 | 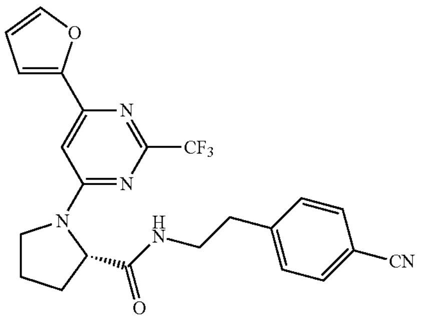 [SMILES: N#Cc1ccc(CCNC(=O)[C@@H]2CCCN2c2cc(-c3ccco3)nc(C(F)(F)F)n2)cc1] (S)-N-(4-cyanophenethyl)-1-(6-(furan-2-yl)-2-(trifluoromethyl)pyrimidin-4-yl)pyrrolidine-2-carboxamide | 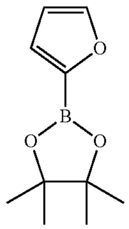 | 456.3 A |
| 168 | 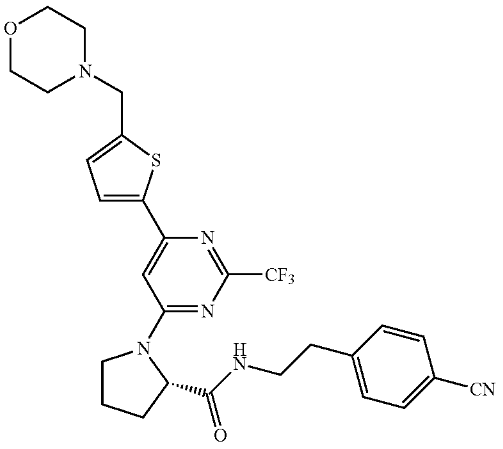 [SMILES: N#Cc1ccc(CCNC(=O)[C@@H]2CCCN2c2cc(-c3ccc(CN4CCOCC4)s3)nc(C(F)(F)F)n2)cc1] (S)-N-(4-cyanophenethyl)-1-(6-(5-(morpholinomethyl)thiophen-2-yl)-2-(trifluoromethyl)pyrimidin-4-yl)pyrrolidine-2-carboxamide | 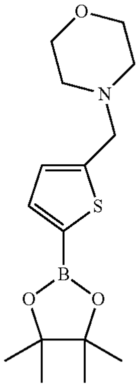 [SMILES: CC1(C)OB(c2ccc(CN3CCOCC3)s2)OC1(C)C] | 571.4 A |
| 169 | 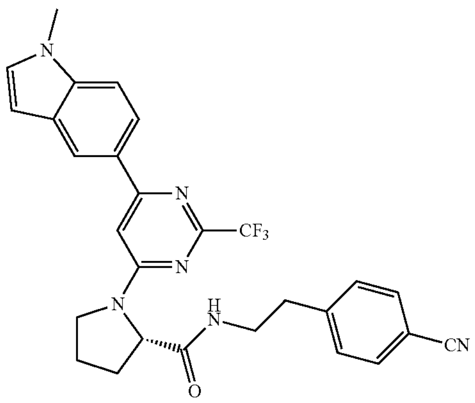 [SMILES: Cn1ccc2cc(-c3cc(N4CCC[C@H]4C(=O)NCCc4ccc(C#N)cc4)nc(C(F)(F)F)n3)ccc21] (S)-N-(4-cyanophenethyl)-1-(6-(1-methyl-1H-indol-5-yl)-2-(trifluoromethyl)pyrimidin-4-yl)pyrrolidine-2-carboxamide | 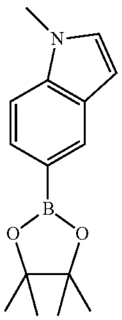 [SMILES: Cn1ccc2cc(B3OC(C)(C)C(C)(C)O3)ccc21] | 519.4 A |

TABLE 24-continued
| No | Structure | Reagent | MS (M + H)+ |
|---|---|---|---|
| 170 | 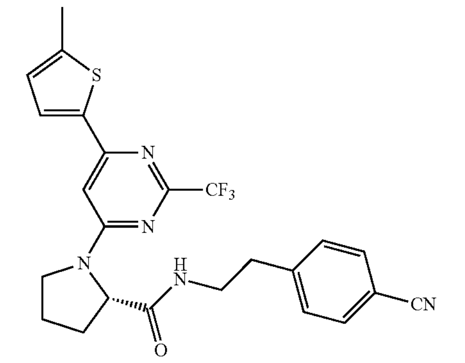 (S)-N-(4-cyanophenethyl)-1-(6-(5-methylthiophen-2-yl)-2-(trifluoromethyl)pyrimidin-4-yl)pyrrolidine-2-carboxamide | 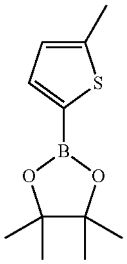 | 486.5 A |
| 171 | 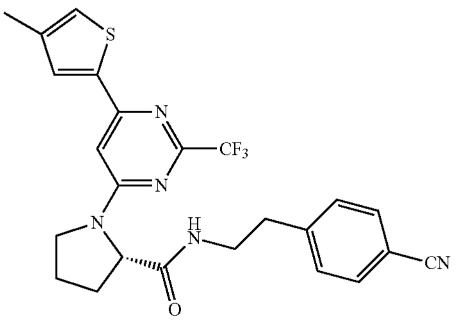 [SMILES: Cc1csc(-c2cc(N3CCC[C@H]3C(=O)NCCc3ccc(C#N)cc3)nc(C(F)(F)F)n2)c1] (S)-N-(4-cyanophenethyl)-1-(6-(4-methylthiophen-2-yl)-2-(trifluoromethyl)pyrimidin-4-yl)pyrrolidine-2-carboxamide | 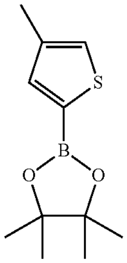 | 486.5 A |
| 172 | 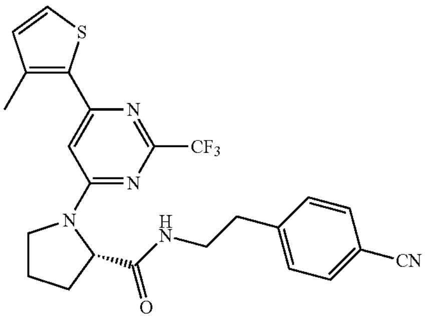 [SMILES: Cc1ccsc1-c1cc(N2CCC[C@H]2C(=O)NCCc2ccc(C#N)cc2)nc(C(F)(F)F)n1] (S)-N-(4-cyanophenethyl)-1-(6-(3-methylthiophen-2-yl)-2-(trifluoromethyl)pyrimidin-4-yl)pyrrolidine-2-carboxamide | 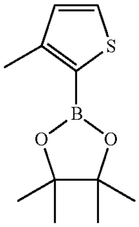 | 486.5 A |

TABLE 24-continued
| No | Structure | Reagent | MS (M + H)+ |
|---|---|---|---|
| 173 | 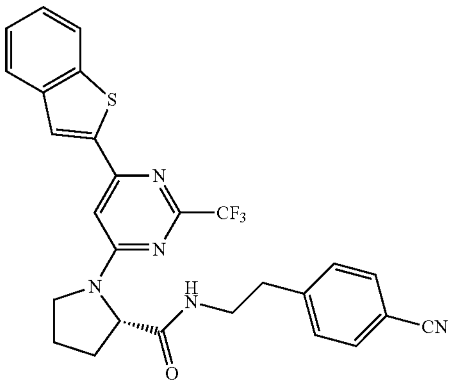 [SMILES: N#Cc1ccc(CCNC(=O)[C@@H]2CCCN2c2cc(-c3cc4ccccc4s3)nc(C(F)(F)F)n2)cc1] (S)-1-(6-(benzo[b]thiophen-2-yl)-2-(trifluoromethyl)pyrimidin-4-yl)-N-(4-cyanophenethyl)pyrrolidine-2-carboxamide | 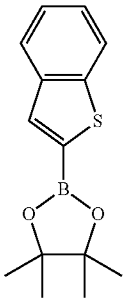 | 522.5 A |
| 174 | 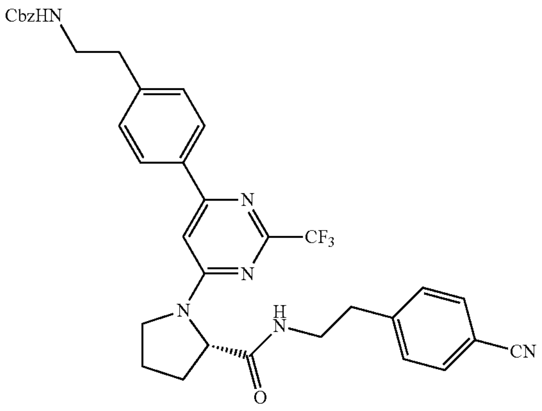 [SMILES: N#Cc1ccc(CCNC(=O)[C@@H]2CCCN2c2cc(-c3ccc(CCNC(=O)OCc4ccccc4)cc3)nc(C(F)(F)F)n2)cc1] (S)-benzyl 4-(6-(2-((4-cyanophenethyl)carbamoyl)pyrrolidin-1-yl)-2-(trifluoromethyl)pyrimidin-4-yl)phenethylcarbamate | 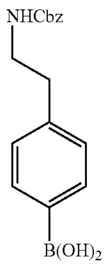 [SMILES: O=C(NCCc1ccc(B(O)O)cc1)OCc1ccccc1] | 643.5 A |
| 175 | 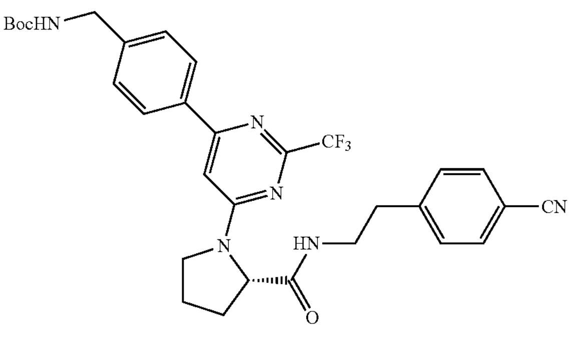 [SMILES: CC(C)(C)OC(=O)NCc1ccc(-c2cc(N3CCC[C@H]3C(=O)NCCc3ccc(C#N)cc3)nc(C(F)(F)F)n2)cc1] (S)-tert-butyl 4-(6-(2-((4-cyanophenethyl)carbamoyl)pyrrolidin-1-yl)-2-(trifluoromethyl)pyrimidin-4-yl)benzylcarbamate | 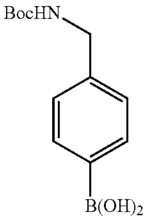 | 595.5 A |

TABLE 24-continued
| No | Structure | Reagent | MS (M + H)+ |
|---|---|---|---|
| 176 | 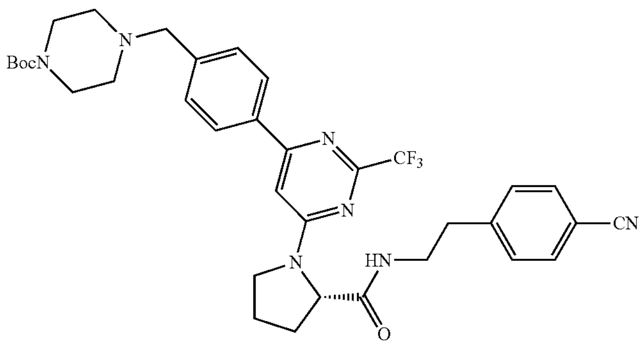 [SMILES: CC(C)(C)OC(=O)N1CCN(Cc2ccc(-c3cc(N4CCC[C@H]4C(=O)NCCc4ccc(C#N)cc4)nc(C(F)(F)F)n3)cc2)CC1] (S)-tert-butyl 4-(4-(6-(2-((4-cyanophenethyl)carbamoyl)pyrrolidin-1-yl)-2-(trifluoromethyl)pyrimidin-4-yl)benzyl)piperazine-1-carboxylate | 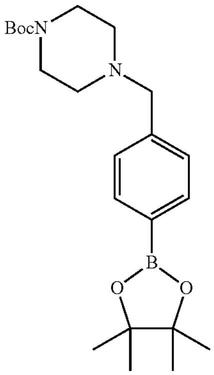 [SMILES: CC(C)(C)OC(=O)N1CCN(Cc2ccc(B3OC(C)(C)C(C)(C)O3)cc2)CC1] | 664.5 A |
| 177 | 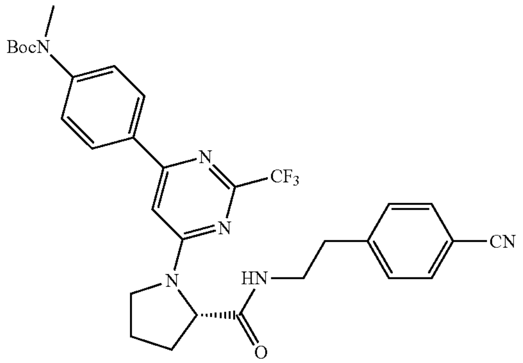 [SMILES: CN(C(=O)OC(C)(C)C)c1ccc(-c2cc(N3CCC[C@H]3C(=O)NCCc3ccc(C#N)cc3)nc(C(F)(F)F)n2)cc1] (S)-tert-butyl (4-(6-(2-((4-cyanophenethyl)carbamoyl)pyrrolidin-1-yl)-2-(trifluoromethyl)pyrimidin-4-yl)phenyl)(methyl)carbamate | 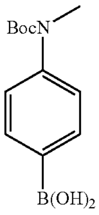 | 595.4 A |
Example 31
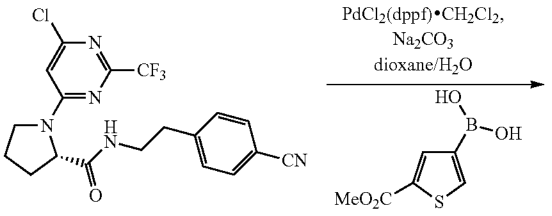
Intermediate 2
-continued
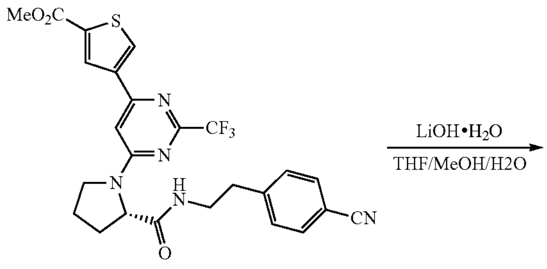
Compound 31A -continued

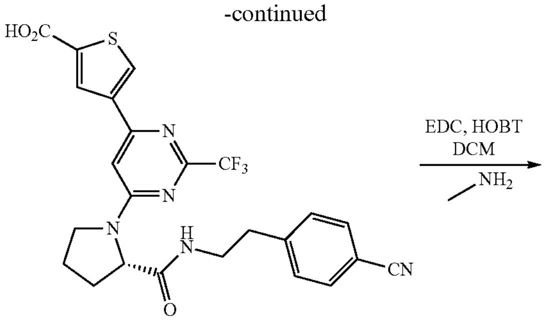

Compound 178

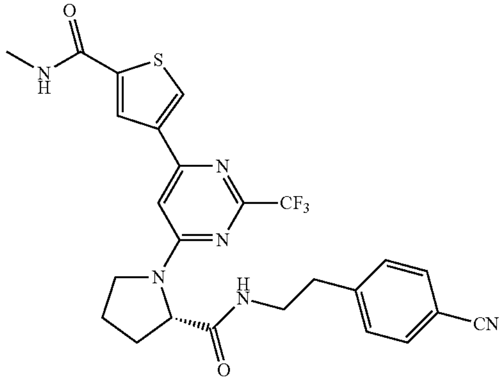

Compound 179

(S)-methyl 4-(6-(2-((4-cyanophenethyl)carbamoyl) pyrrolidin-1-yl)-2-(trifluoromethyl)pyrimidin-4-yl) thiophene-2-carboxylate Using the procedure as described in Example 30, Intermediate 2 (120 mg, 0.28 mmol) was converted to Compound 31A (70 mg, 47%). LCMS (method A): m/z 530.4 $(M+H)^+$.

(S)-4-(6-(2-((4-cyanophenethyl)carbamoyl)pyrrolidin-1-yl)-2-(trifluoromethyl)pyrimidin-4-yl)thiophene-2-carboxylic acid Using the procedure as described in Example 16, Compound 31A (67 mg, 0.13 mmol) was converted to Compound 178 (13 mg, 19%). LCMS (method A): m/z 516.3 $(M+H)^+$. $^1H$ NMR ($CD_3OD$) δ 8.51 (s, 1H), 8.38 (s, 1H), 8.21 (s, 1H), 7.59 (d, 2H), 7.37 (d, 2H), 7.03 (s, 1H), 4.59 (m, 1H), 3.74 (m, 1H), 3.60-3.45 (m, 3H), 2.87 (m, 2H), 2.26 (m, 1H), 2.09-1.99 (m, 3H).

(S)—N-(4-cyanophenethyl)-1-(6-(5-(methylcarbamoyl)thiophen-3-yl)-2-(trifluoromethyl) pyrimidin-4-yl)pyrrolidine-2-carboxamide Using the procedure as described in Example 7, Compound 178 (25 mg, 0.05 mmol) was converted to Compound 179 (5 mg, 21%). LCMS (method A): m/z 529.3 $(M+H)^+$. $^1H$ NMR ($CDCl_3$) δ 8.55 (br s, 1H), 7.30 (d, 2H), 7.08 (m, 2H), 6.78 (br s, 1H), 6.68 (br s, 1H), 4.67 (br s, 1H), 3.59-3.47 (m, 3H), 3.36 (br, 1H), 2.97-2.84 (m, 2H), 2.41 (br, 1H), 2.22-1.90 (m, 3H), 1.58 (s, 3H). Using the procedure described above for Example 31, the following compounds were prepared from Intermediate 2 and the reagents as indicated in Table 25.

TABLE 25

| No | Structure | Reagent | MS $(M + H)^+$ |
|---|---|---|---|
| 180 | 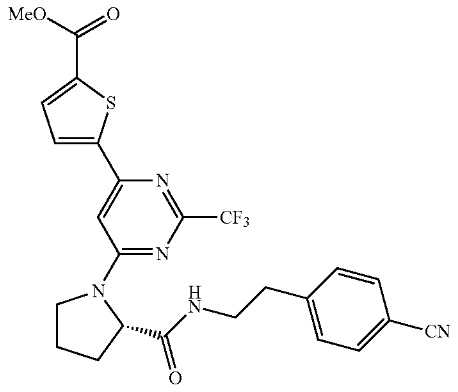 [SMILES: COC(=O)c1ccc(-c2cc(N3CCC[C@H]3C(=O)NCCc3ccc(C#N)cc3)nc(C(F)(F)F)n2)s1] (S)-methyl 5-(6-(2-((4-cyanophenethyl)carbamoyl)pyrrolidin-1-yl)-2-(trifluoromethyl)pyrimidin-4-yl)thiophene-2-carboxylate | 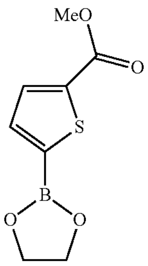 Step 1 of Example 31 | 530.5 A |

TABLE 25-continued
| No | Structure | Reagent | MS $(M + H)^+$ |
|---|---|---|---|
| 181 | 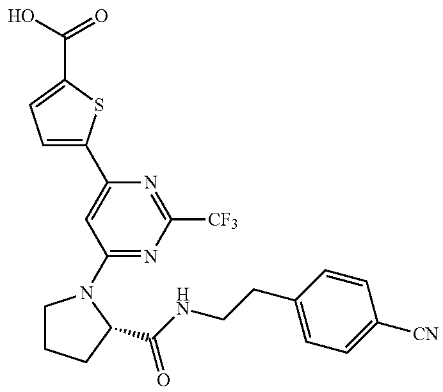 [SMILES: N#Cc1ccc(CCNC(=O)[C@@H]2CCCN2c2cc(-c3ccc(C(=O)O)s3)nc(C(F)(F)F)n2)cc1] (S)-5-(6-(2-((4-cyanophenethyl)carbamoyl)pyrrolidin-1-yl)-2-(trifluoromethyl)pyrimidin-4-yl)thiophene-2-carboxylic acid | Compound 180 and Step 2 of Example 31 | 516.4 A |
Example 32
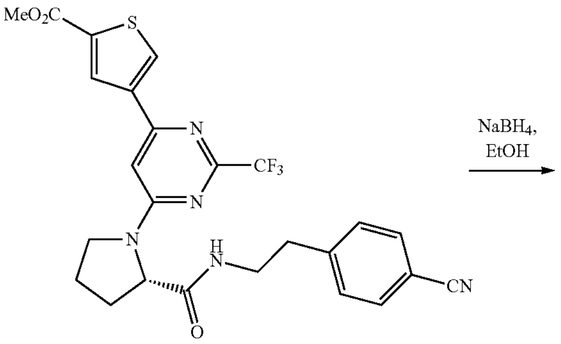
Compound 31A
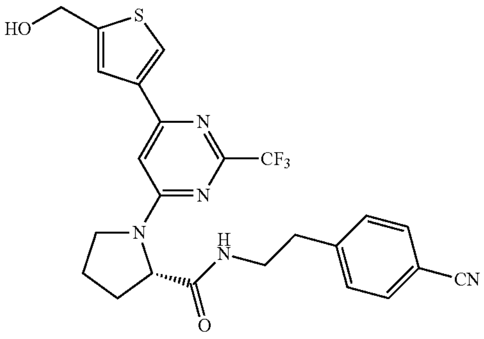
Compound 182

(S)—N-(4-cyanophenethyl)-1-(6-(5-(hydroxymethyl)thiophen-3-yl)-2-(trifluoromethyl)pyrimidin-4-yl)pyrrolidine-2-carboxamide To a solution of Compound 31A (53 mg, 0.10 mmol) in ethanol (2.5 mL) was added sodium borohydride (38 mg, 1 mmol). The reaction mixture was heated at 50° C. for three hours. Another portion of borohydride (38 mg, 1 mmol) was added, and the reaction mixture was heated at 50° C. for additional three hours. The reaction was quenched with water, and concentrated in vacuo. The residue was purified by MS-HPLC to afford Compound 182 (25 mg, 50%). LCMS (method A): m/z 502.5 $(M+H)^+$. $^1H$ NMR ($CD_3OD$) δ 8.24 (s, 1H), 7.61 (m, 3H), 7.37 (m, 2H), 7.02 (s, 1H), 4.79 (s, 2H), 4.63 (br s, 1H), 3.76 (br, 1H), 3.61 (br, 1H), 3.45 (m, 2H), 2.88 (m, 2H), 2.27 (br, 1H), 2.09-1.99 (m, 3H). Using the procedure described above for Example 32, the following compound was prepared indicated in Table 26.

TABLE 26

| No | Structure | Precursor | MS $(M + H)^+$ |
|---|---|---|---|
| 183 | 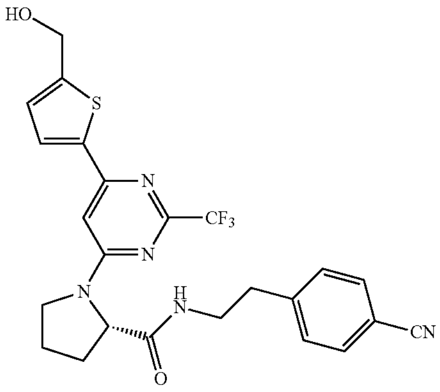 [SMILES: N#Cc1ccc(CCNC(=O)[C@@H]2CCCN2c2cc(-c3ccc(CO)s3)nc(C(F)(F)F)n2)cc1] (S)-N-(4-cyanophenethyl)-1-(6-(5-(hydroxymethyl)thiophen-2-yl)-2-(trifluoromethyl)pyrimidin-4-yl)pyrrolidine-2-carboxamide | 180 | 502.5 A |

Example 33

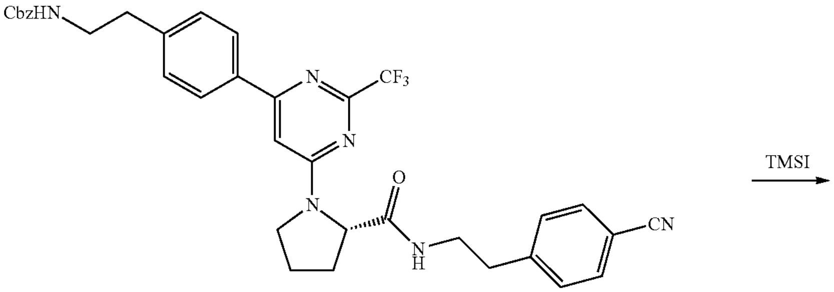

Compound 174

-continued

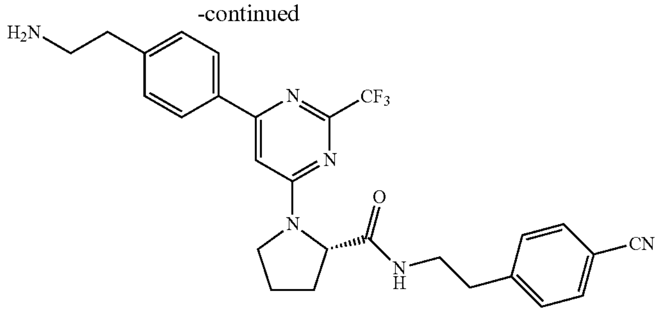

Compound 184

(S)-1-(6-(4-(2-aminoethyl)phenyl)-2-(trifluoromethyl)pyrimidin-4-yl)-N-(4-cyanophenethyl)pyrrolidine-2-carboxamide To a solution of Compound 174 in acetonitrile (1 mL) at 0° C. was added iodotrimethylsilane (31 uL, 0.23 mmol), and the mixture was warmed to room temperature and stirred for four hours. The solvent was removed in vacuo, and the residue purified by silica gel chromatography (0-5% 7 M $NH_3$ in MeOH/DCM) yielding Compound 184 (19 mg, 95% yield). LCMS (method A): m/z 509.4 $(M+H)^+$. $^1H$ NMR ($CDCl_3$) δ 8.00 (d, 1H), 7.44 (d, 1H), 7.35 (d, 1H), 7.31 (m, 1H), 7.18 (d, 1H), 6.76 (s, 1H), 4.72 (m, 1H), 3.58 (m, 2H), 3.45 (m, 2H), 3.01 (t, 2H), 2.83 (m, 4), 2.46 (m, 1H), 2.33 (m, 1H), 2.14 (m, 1H), 1.94 (m, 1H), 1.32 (m, 3H).

Example 34

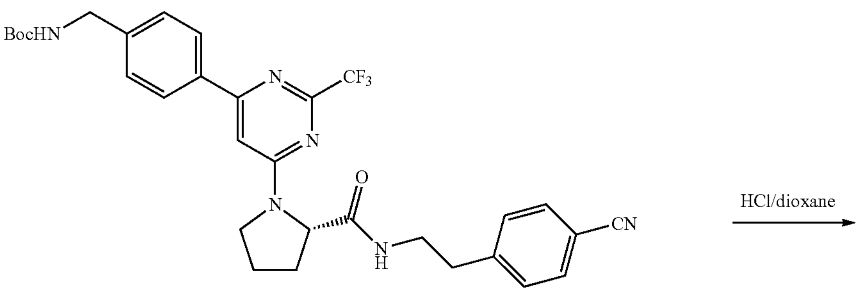

Compound 175

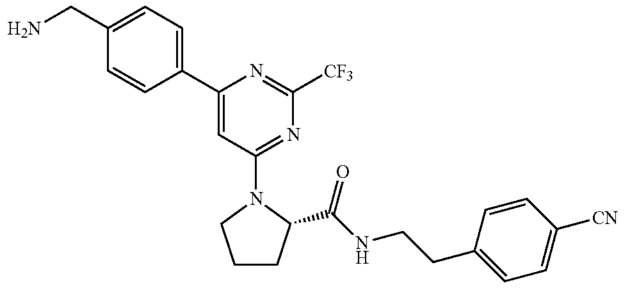

Compound 185

(S)-1-(6-(4-(aminomethyl)phenyl)-2-(trifluoromethyl)pyrimidin-4-yl)-N-(4-cyanophenethyl)pyrrolidine-2-carboxamide Using the procedure as described in Intermediate 9, step 3, Compound 175 (890 mg, 1.5 mmol) was converted to Compound 185 (830 mg). LCMS (Method A): m/z 495.4 $(M+H-)^+$. $^1H$ NMR ($CD_3OD$) δ 8.25 (d, 2H), 7.61 (m, 5H), 7.39 (d, 2H), 7.15 (s, 1H), 4.64 (m, 1H), 4.22 (s, 2H), 3.76 (m, 1H), 3.62 (m, 2H), 3.47 (m, 2H), 2.89 (t, 2H), 2.28 (m, 1H), 2.07 (m, 4H). Using the procedure described above for Example 34, the following compounds were prepared from the precursors as indicated in Table 27.

TABLE 27

| No | Structure | Pre-cursor | MS $(M + H)^+$ |
|---|---|---|---|
| 186 | 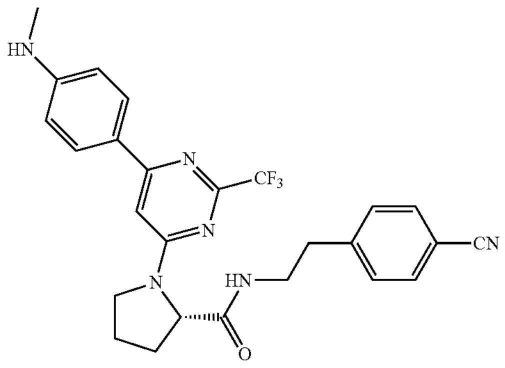 [SMILES: CNc1ccc(-c2cc(N3CCC[C@H]3C(=O)NCCc3ccc(C#N)cc3)nc(C(F)(F)F)n2)cc1]<br>(S)-N-(4-cyanophenethyl)-1-(6-(4-(methylamino)phenyl)-2-(trifluoromethyl)pyrimidin-4-yl)pyrrolidine-2-carboxamide | 177 | 495.4 A |
| 187 | 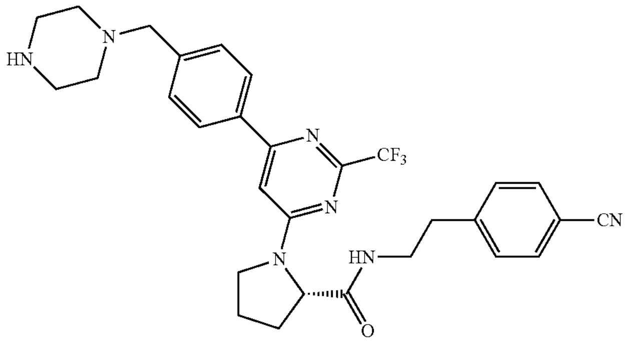 [SMILES: N#Cc1ccc(CCNC(=O)[C@@H]2CCCN2c2cc(-c3ccc(CN4CCNCC4)cc3)nc(C(F)(F)F)n2)cc1]<br>(S)-N-(4-cyanophenethyl)-1-(6-(4-(piperazin-1-ylmethyl)phenyl)-2-(trifluoromethyl)pyrimidin-4-yl)pyrrolidine-2-carboxamide | 176 | 564.5 A |

Example 35

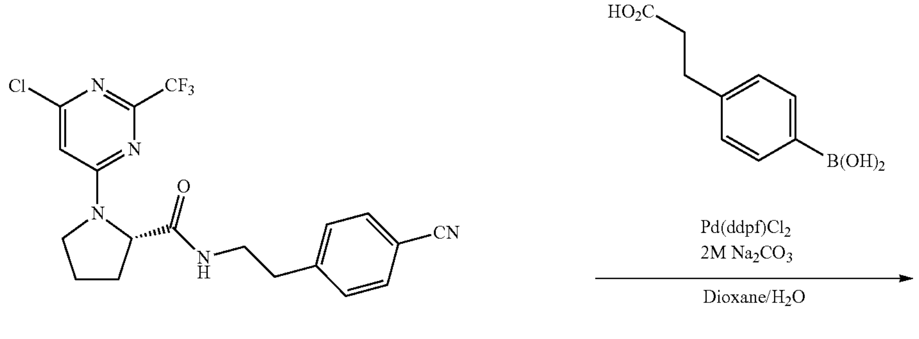

Intermediate 2

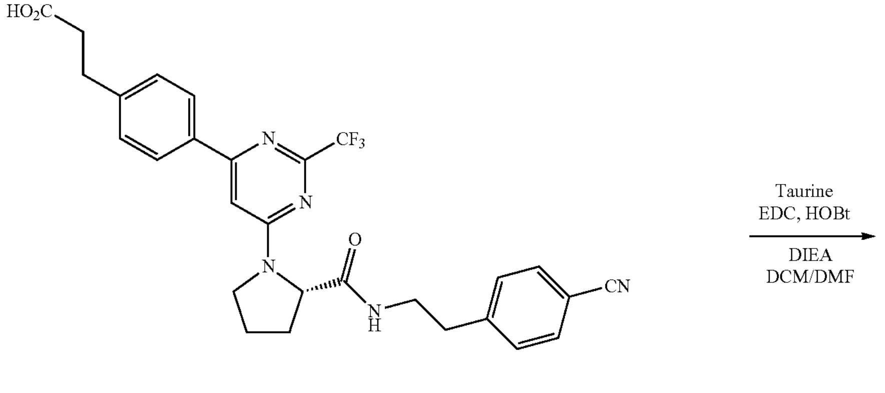

Compound 188

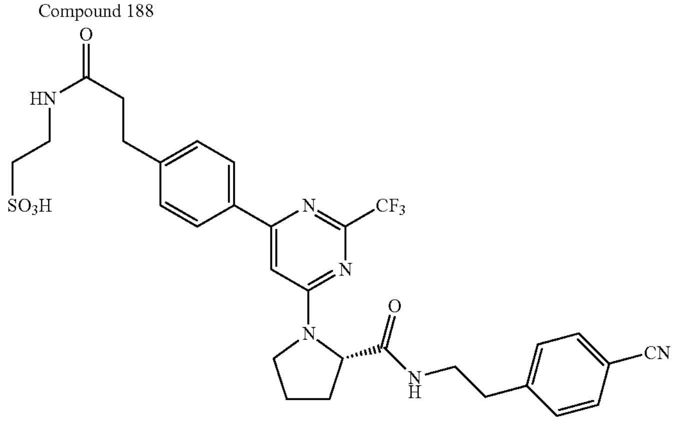

Compound 189

(S)-3-(4-(6-(2-((4-cyanophenethyl)carbamoyl)pyrrolidin-1-yl)-2-(trifluoromethyl) pyrimidin-4-yl)phenyl)propanoic acid Using the procedure as described in Example 30, Intermediate 2 (250 mg, 0.59 mmol) was converted to Compound 188 (188 mg, 59%). LCMS (method A): m/z 538.2 $(M+H)^+$. $^1H$ NMR ($CDCl_3$) δ 8.01-7.99 (dd, 2H), 7.45-7.43 (dd, 2H), 7.37-7.35 (m, 2H), 7.29 (m, 1H), 7.18-7.17 (m. 2H), 6.76 (s, 1H), 4.73-4.71 (m, 1H), 3.61-3.56 (m, 2H), 3.49-3.39 (m, 2H), 3.04 (t, 2H), 2.91-2.77 (m, 2H), 2.73 (t, 2H), 2.49-2.26 (m, 2H), 2.18-1.87 (m, 2H).

(S)-2-(3-(4-(6-(2-((4-cyanophenethyl)carbamoyl) pyrrolidin-1-yl)-2-(trifluoromethyl) pyrimidin-4-yl) phenyl)propanamido)ethanesulfonic acid Using the procedure as described in Example 7, Compound 188 (137 mg, 0.260 mmol) was converted to Compound 189 (76 mg, 46%). LCMS (Method D): m/z 645.1 $(M+H)^+$. $^1H$ NMR ($CDCl_3/CD_3OD$): δ 7.84-7.83 (m, 1H), 7.59-7.34 (m, 7H), 7.07-6.89 (b, 1H), 4.73-4.71 (m, 1H), 4.00-3.35 (m, 6H), 3.04 (t, 2H), 2.91-2.67 (m, 2H), 2.55 (t, 2H), 2.57-2.54 (m, 4H). Using the procedure described above for Example 35, the following compound was prepared from Intermediate 2 as indicated in Table 28.

TABLE 28
| No | Structure | Reagent | MS (M + H)+ |
|---|---|---|---|
| 190 | 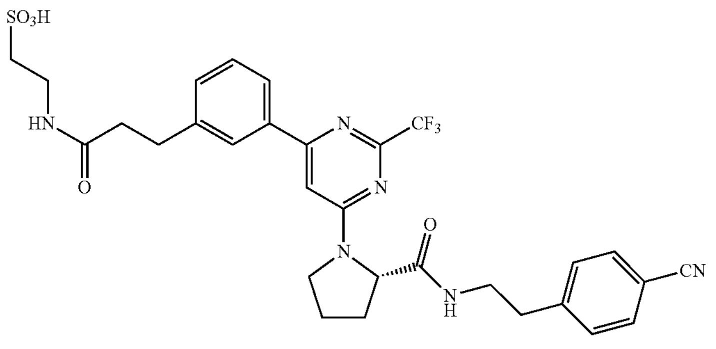 [SMILES: N#Cc1ccc(CCNC(=O)[C@@H]2CCCN2c2cc(-c3cccc(CCC(=O)NCCS(=O)(=O)O)c3)nc(C(F)(F)F)n2)cc1] (S)-2-(3-(3-(6-(2-((4-cyanophenethyl)-carbamoyl)pyrrolidin-1-yl)-2-(trifluoromethyl)pyrimidin-4-yl)phenyl)-propanamido)ethanesulfonic acid | 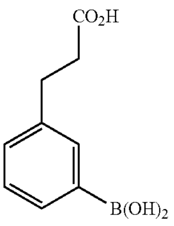 [SMILES: O=C(O)CCc1cccc(B(O)O)c1] | 645.3 A |
Example 36
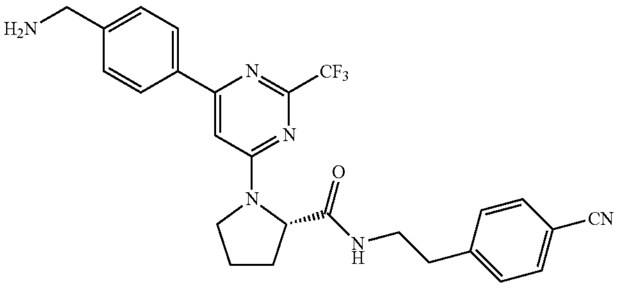
Compound 185
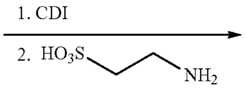
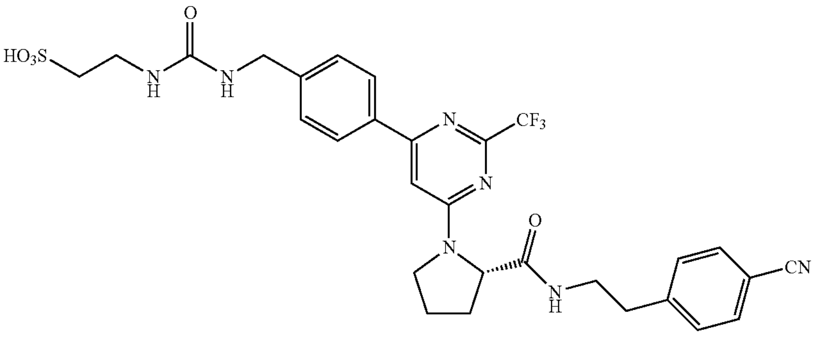
Compound 191

(S)-2-(3-(4-(6-(2-((4-cyanophenethyl)carbamoyl)pyrrolidin-1-yl)-2-(trifluoromethyl)pyrimidin-4-yl)benzyl)ureido)ethanesulfonic acid Using the procedure as described in Example 9, step 2, Compound 185 (135 mg, 0.270 mmol) was converted to Compound 191 (74 mg, 42%). LCMS (Method A): m/z 646.4 $(M+H)^+$. $^1H$ NMR ($CD_3OD$) δ 8.08 (d, 2H), 7.61 (d, 2H), 7.48 (d, 3H), 7.39 (d, 2H), 7.13 (s, 1H), 4.65 (m, 1H), 3.62 (m, 4H), 3.47 (m, 3H), 3.00 (m, 2H), 2.89 (m, 2H), 2.29 (m, 1H), 2.07 (m, 4H), 1.30 (m, 2H). Using the procedure described above for Example 36, the following compounds were prepared from the precursors as indicated in Table 29.

TABLE 29

| No | Structure | Pre-cursor | MS $(M + H)^+$ |
|---|---|---|---|
| 192 | 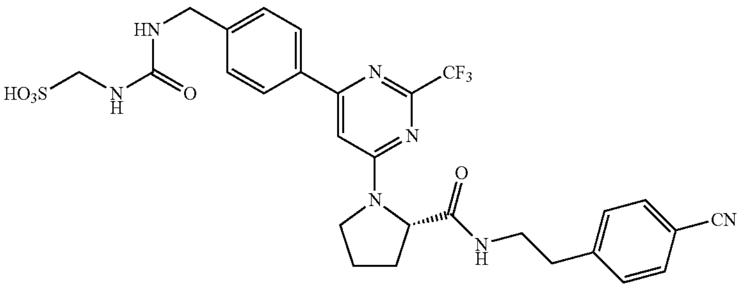 [SMILES: N#Cc1ccc(CCNC(=O)[C@@H]2CCCN2c2cc(-c3ccc(CNC(=O)NCS(=O)(=O)O)cc3)nc(C(F)(F)F)n2)cc1] (S)-(3-(4-(6-(2-((4-cyanophenethyl)carbamoyl)pyrrolidin-1-yl)-2-(trifluoromethyl)pyrimidin-4-yl)benzyl)ureido)methanesulfonic acid | 185 | 632.4 A |
| 193 | 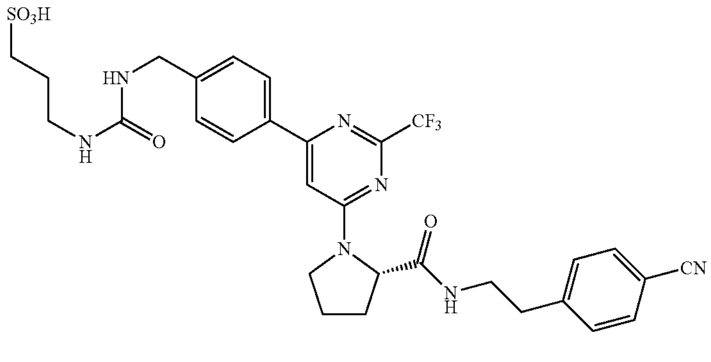 [SMILES: N#Cc1ccc(CCNC(=O)[C@@H]2CCCN2c2cc(-c3ccc(CNC(=O)NCCCS(=O)(=O)O)cc3)nc(C(F)(F)F)n2)cc1] (S)-3-(3-(4-(6-(2-((4-cyanophenethyl)carbamoyl)pyrrolidin-1-yl)-2-(trifluoromethyl)pyrimidin-4-yl)benzyl)ureido)propane-1-sulfonic acid | 185 | 660.4 A |
| 194 | 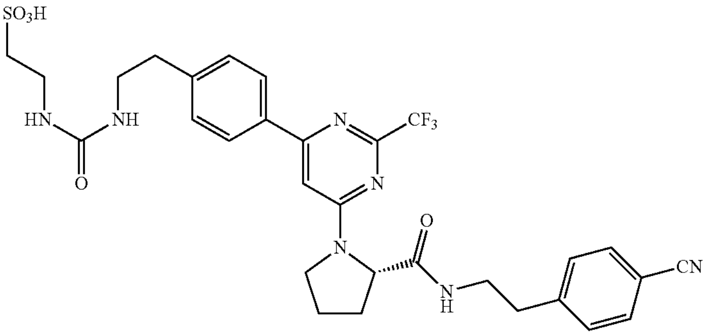 [SMILES: N#Cc1ccc(CCNC(=O)[C@@H]2CCCN2c2cc(-c3ccc(CCNC(=O)NCCS(=O)(=O)O)cc3)nc(C(F)(F)F)n2)cc1] (S)-2-(3-(4-(6-(2-((4-cyanophenethyl)carbamoyl)pyrrolidin-1-yl)-2-(trifluoromethyl)pyrimidin-4-yl)phenethyl)ureido)ethanesulfonic acid | 184 | 660.4 |

TABLE 29-continued
| No | Structure | Pre-cursor | MS (M + H)+ |
|---|---|---|---|
| 195 | 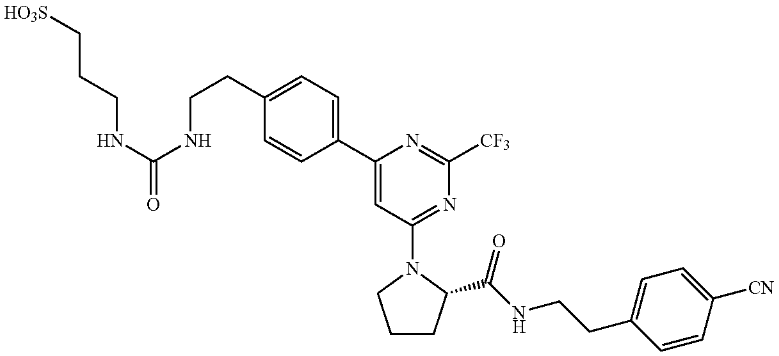 [SMILES: N#Cc1ccc(CCNC(=O)[C@@H]2CCCN2c2cc(-c3ccc(CCNC(=O)NCCCS(=O)(=O)O)cc3)nc(C(F)(F)F)n2)cc1] (S)-3-(3-(4-(6-(2-((4-cyanophenethyl)carbamoyl)pyrrolidin-1-yl)-2-(trifluoromethyl)pyrimidin-4-yl)phenethyl)ureido)propane-1-sulfonic acid | 184 | 674.5 A |
| 196 | 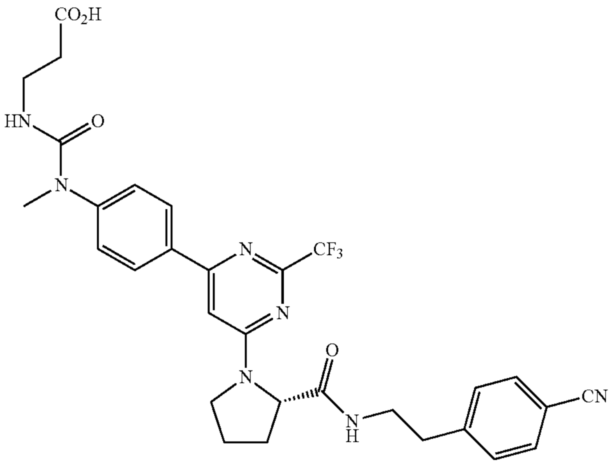 [SMILES: CN(C(=O)NCCC(=O)O)c1ccc(-c2cc(N3CCC[C@H]3C(=O)NCCc3ccc(C#N)cc3)nc(C(F)(F)F)n2)cc1] (S)-3-(3-(4-(6-(2-((4-cyanophenethyl)carbamoyl)pyrrolidin-1-yl)-2-(trifluoromethyl)pyrimidin-4-yl)phenyl)-3-methylureido)propanoic acid | 186 | 610.4 A |
Example 37
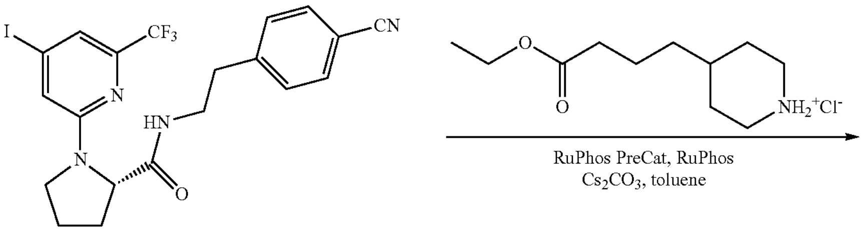
Intermediate 9

-continued

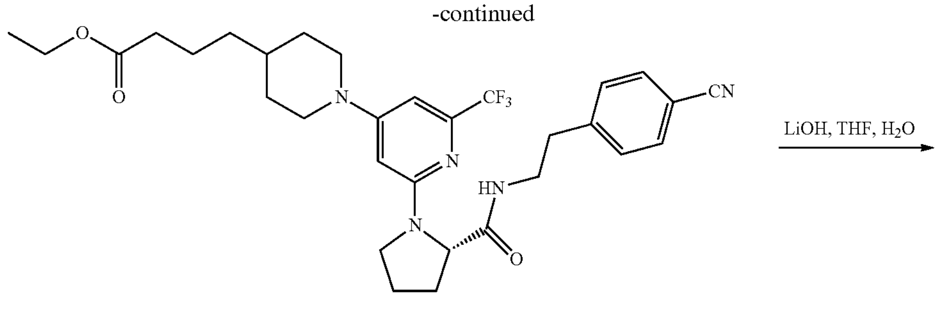

Compound 37A

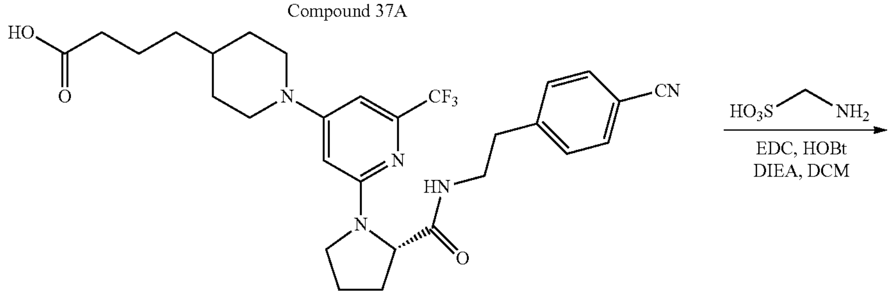

Compound 197

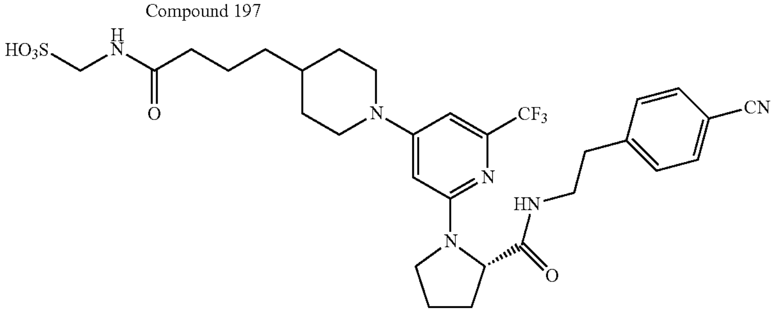

Compound 198

(S)-ethyl 4-(1-(2-(2-((4-cyanophenethyl)carbamoyl) pyrrolidin-1-yl)-6-(trifluoromethyl) pyridin-4-yl) piperidin-4-yl)butanoate To a nitrogen-sparged toluene solution (9 mL) of Intermediate 9 (700 mg, 1.36 mmol) were added ethyl 4-(piperidin-4-yl)butanoate hydrochloride, cesium carbonate (600 mg, 1.84 mmol), RuPhos (63 mg, 0.14 mmol) and RuPhos Precatalyst (99 mg, 0.14 mmol). The reaction tube was sealed and heated for 18 hours at 100° C. The resultant mixture was filtered through a CELITE plug. The filtrate was partitioned between EtOAc and $H_2O$. The EtOAc layer was washed with brine, dried ($Na_2SO_4$), concentrated in vacuo, and purified via silica gel chromatography (0-100% EtOAc/hexanes) to afford Compound 37A (0.7 g, 88%). LCMS (method A): m/z 586.5 $(M+H)^+$.

(S)-4-(1-(2-(2-((4-cyanophenethyl)carbamoyl)pyrrolidin-1-yl)-6-(trifluoromethyl)pyridin-4-yl)piperidin-4-yl)butanoic acid Using the procedure as described in Example 16, Compound 37A (0.70 g, 1.2 mmol) was converted to Compound 197 (0.42 g, 63%). LCMS (method A): m/z 558.5 $(M+H)^+$. $^1$H NMR ($CDCl_3$): δ 7.81 (bs, 1H), 7.18 (d, 2H), 6.92 (d, 2H), 6.34 (s, 1H). 5.51 (s, 1H), 4.41 (m, 1H), 3.69 (d, 2H), 3.41 (m, 1H), 3.20 (m, 2H), 3.40 (m, 1H), 2.71 (m, 3H), 2.56 (m, 1H), 2.29 (m, 1H), 2.20 (t, 2H), 1.91 (m, 2H), 1.64 (m, 3H), 1.52 (m, 2H), 1.38 (m, 1H), 1.13 (m, 4H).

(S)-(4-(1-(2-(2-((4-cyanophenethyl)carbamoyl)pyrrolidin-1-yl)-6-(trifluoromethyl)pyridin-4-yl)piperidin-4-yl)butanamido)methanesulfonic acid Using the procedure as described in Example 7, Compound 197 (123 mg, 0.220 mmol) was converted to Compound 198 (62 mg, 43%). LCMS (method A): m/z 651.6 $(M+H)^+$. $^1$H NMR ($CD_3OD$, 400 MHz) δ 7.58 (d, 2H), 7.37 (d, 2H), 6.99 (s, 1H), 5.77 (s, 1H), 4.45 m, 1H), 4.31 (s, 2H), 4.04 (m, 2H), 3.71 (m, 1H), 3.52 (m, 3H), 3.12 (q, 2H), 2.89 (t, 2H), 2.26 (t, 3H), 2.06 (m, 3H), 1.86 (m, 2H), 1.68 (m, 3H), 1.28 (m, 4H). Using the procedure described above for Example 37, the following compounds were prepared from Compound 197 and the reagents as indicated in Table 30.

TABLE 30

| No | Structure | Reagent | MS (M + H)+ |
|---|---|---|---|
| 199 | 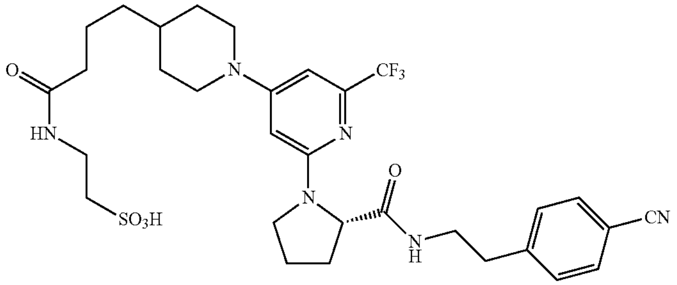 [SMILES: N#Cc1ccc(CCNC(=O)[C@@H]2CCCN2c2cc(N3CCC(CCCC(=O)NCCS(=O)(=O)O)CC3)cc(C(F)(F)F)n2)cc1]<br>(S)-2-(4-(1-(2-(2-((4-cyanophenethyl)carbamoyl)pyrrolidin-1-yl)-6-(trifluoromethyl)pyridin-4-yl)piperidin-4-yl)butanamido)ethanesulfonic acid | 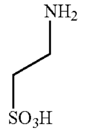 | 665.5 A |
| 200 | 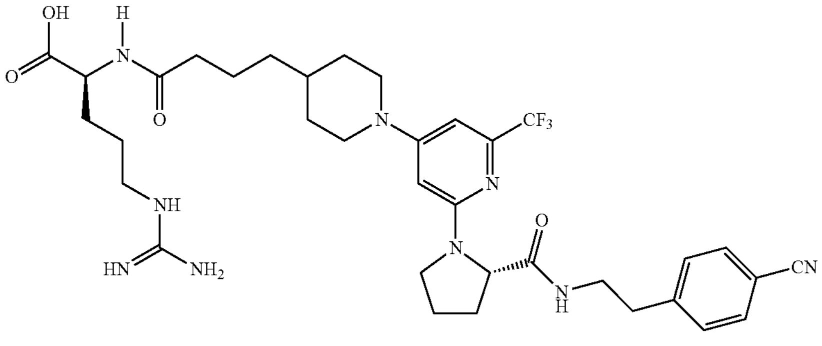 [SMILES: N#Cc1ccc(CCNC(=O)[C@@H]2CCCN2c2cc(N3CCC(CCCC(=O)N[C@@H](CCCNC(=N)N)C(=O)O)CC3)cc(C(F)(F)F)n2)cc1]<br>(S)-2-(4-(1-(2-((S)-2-((4-cyanophenethyl)carbamoyl)pyrrolidin-1-yl)-6-(trifluoromethyl)pyridin-4-yl)piperidin-4-yl)butanamido)-5-guanidinopentanoic acid | Coupling with<br>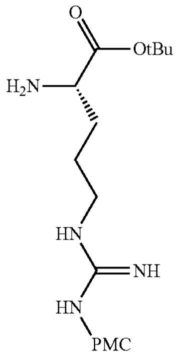<br>followed by deprotection with TFA as in Example 4 | 714.4 A |

Example 38

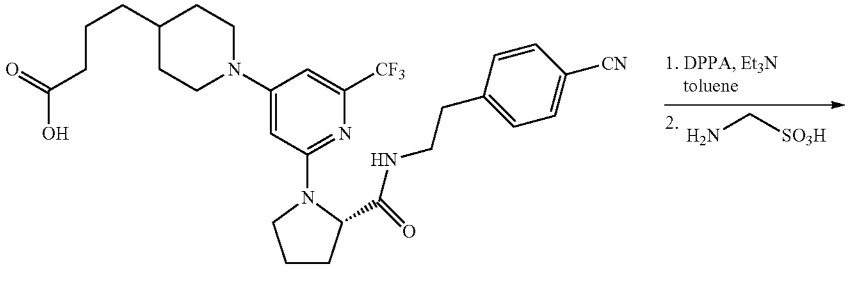

Compound 197

-continued
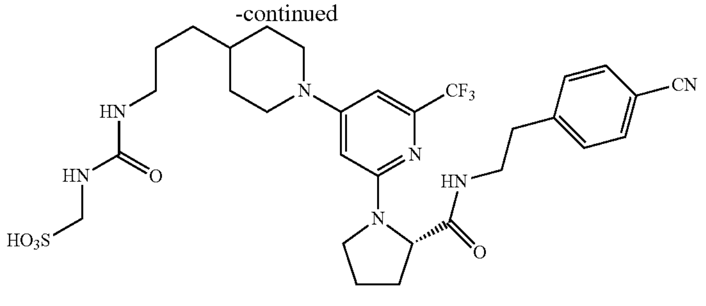
Compound 201
(S)-(3-(3-(1-(2-(2-((4-cyanophenethyl)carbamoyl) pyrrolidin-1-yl)-6-(trifluoromethyl) pyridin-4-yl) piperidin-4-yl)propyl)ureido)methanesulfonic acid
Using the procedure as described in Example 23, Compound 197 (75 mg, 0.13 mmol) was converted to Compound 201 (81 mg, 94%). LCMS (method A): m/z 666.5 $(M+H)^+$. $^1H$ NMR ($CD_3OD$, 400 MHz) δ 7.6 (d, 2H), 7.4 (d, 2H), 4.50 (bs, 1H), 4.22 (s, 2H), 4 (m, 2H), 3.58 (bs, 1H), 3.43 (m, 2H), 3.12 (m, 5H), 2.9 (t, 2H), 2.3 (m, 1H), 2. (m, 3H), 1.88 (d, 2H), 1.53 (m, 3H), 1.36 (m, 2H), 1.27 (m, 2H), 1.14 (m, 2H).
Example 39
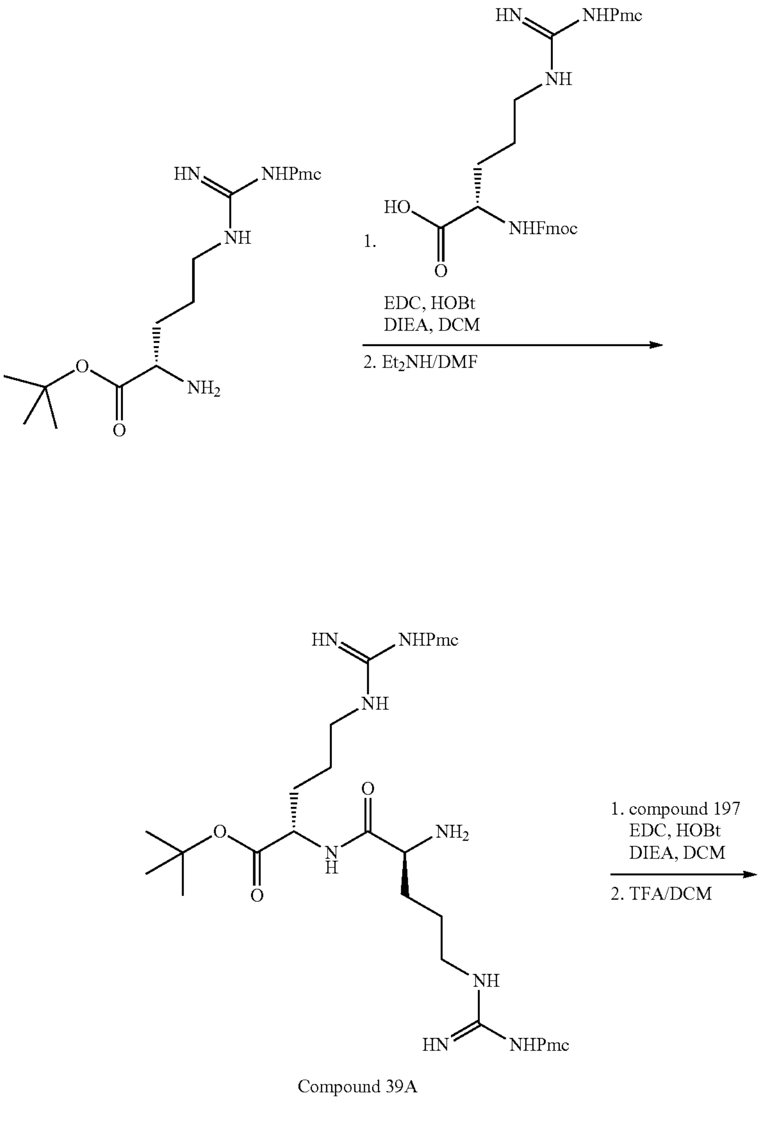
Compound 39A -continued

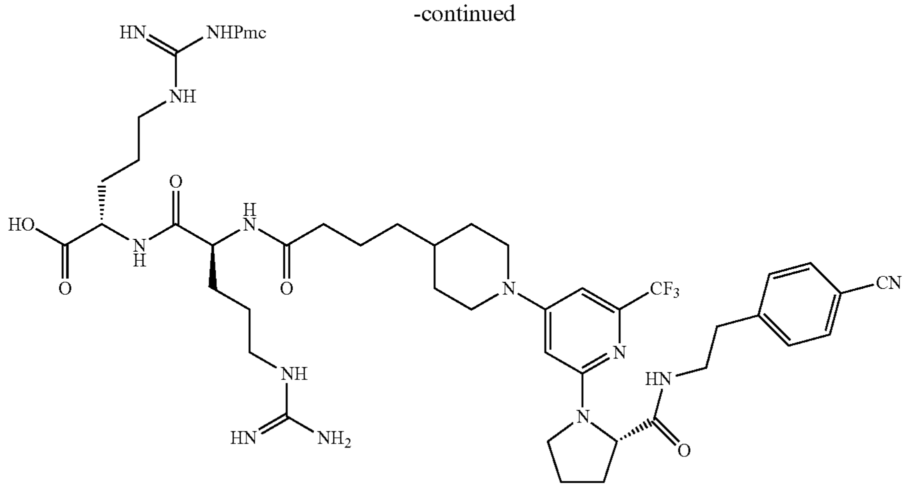

Compound 202

(S)-tert-butyl 2-((S)-2-amino-5-(3-((2,2,5,7,8-pentamethylchroman-6-yl)sulfonyl) guanidino)pentanamido)-5-(3-((2,2,5,7,8-pentamethylchroman-6-yl) sulfonyl) guanidino)pentanoate To a DCM solution (5 mL) of N-α-FMOC-N-ω-(2,2,5,7,8-pentamethylchromane-6-sulfonyl)-L-arginine (330 mg, 0.50 mmol) were added EDC (126 mg, 0.650 mmol), HOBt (88 mg, 0.65 mmol), DIEA (175 μL, 1.00 mmol) and $N^{\omega}$-(2,2,5,7,8-Pentamethylchroman-6-sulfonyl)-L-arginine t-butyl ester (250 mg, 0.50 mmol). After stirring overnight at room temperature, the solution was washed with saturated $NaHCO_3$ and brine, dried over $Na_2SO_4$, and concentrated in vacuo. Silica gel purification (0-10% MeOH/DCM) yielded the fully protected dipeptide. LCMS (method A): m/2z=571.5 $(M/2+H)^+$. The Fmoc protecting group was removed from the fully protected dipeptide by stirring in a solution of diethylamine (2 mL; 19.3 mmol) and DMF (10 mL) at room temperature. After four hrs, the diethylamine and DMF were removed in vacuo to yield crude Compound 39A. LCMS (method A): m/z 919.6 $(M+H)^+$.

(S)-2-((S)-2-(4-(1-(2-((S)-2-((4-cyanophenethyl) carbamoyl)pyrrolidin-1-yl)-6-(trifluoromethyl)pyridin-4-yl)piperidin-4-yl)butanamido)-5-guanidino-pentanamido)-5-guanidinopentanoic acid Using the procedure as described in Example 7, Compound 197 (89 mg, 0.16 mmol) was coupled with Compound 39A (0.25 mmol) and deprotected with TFA following Example 4 to afford Compound 202 (38 mg, 27%). LCMS (method A): m/z 870.5 $(M+H)^+$. $^1H$ NMR ($CD_3OD$, 400 MHz) δ 8.25 (b, 3H), 8.07 (bt, 1H), 7.46 (d, 2H), 7.24 (d, 2H), 6.59 (s, 1H), 5.83 (s, 1H), 4.38 (m, 3H), 3.90 (d, 2H), 3.60 (m, 1H), 3.43 (m, 2H), 3.20 (m, 4H), 2.85 (m, 4H), 2.26 (t, 2H), 2.13-1.53 (m, 18H), 2.47 (m, 4H). Using the procedure described above for Example 39, the following compound was prepared from the precursor and reagent as indicated in Table 31.

TABLE 31

| No | Structure | Pre-cursor | Reagent | MS (M + H)$^+$ |
|---|---|---|---|---|
| 203 | 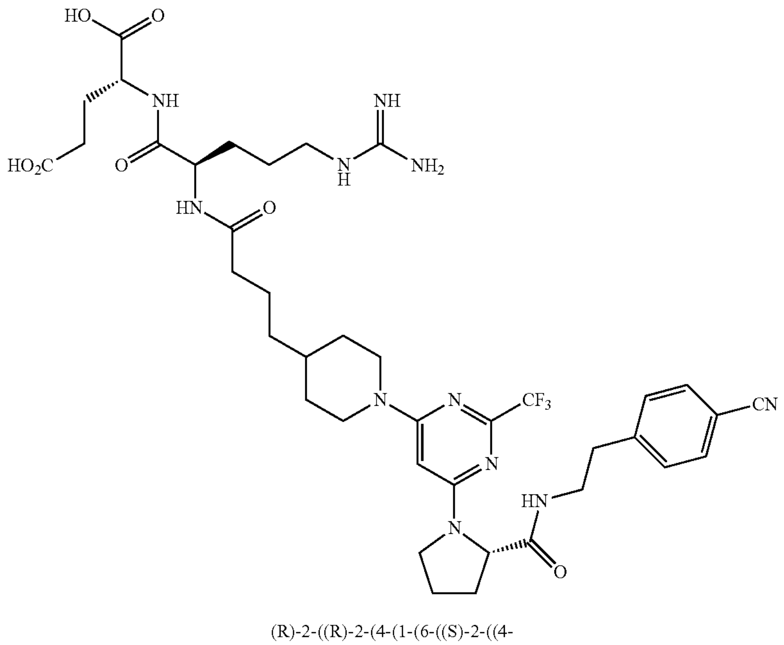 (R)-2-((R)-2-(4-(1-(6-((S)-2-((4-cyanophenethyl)carbamoyl)pyrrolidin-1-yl)-2-(trifluoromethyl)pyrimidin-4-yl)piperidin-4-yl)butanamido)-5-guanidino-pentanamido)pentanedioic acid | 29 | D-glu-D-Arg (prepared using the method of Example 31 step 1) | 844.6 A |

Example 40

(S)—N-(4-cyanophenethyl)-1-(4-(4-(hydroxymethyl)phenyl)-6-(trifluoromethyl) pyridin-2-yl)pyrrolidine-2-carboxamide

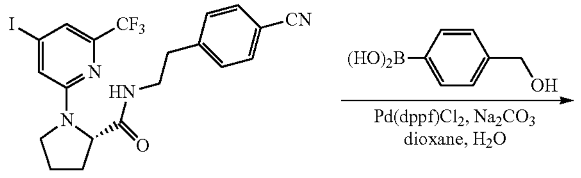

Intermediate 9

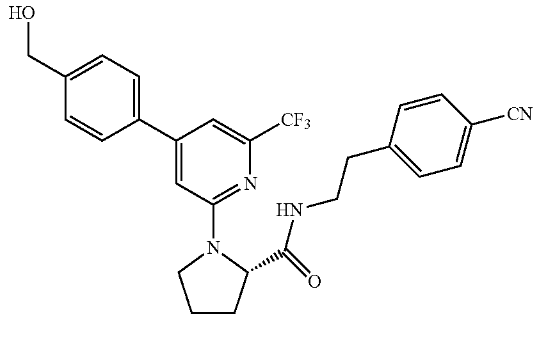

Compound 204

To a nitrogen-sparged dioxane solution (6 mL) of Intermediate 9 (300 mg, 0.58 mmol) were added water (1.0 mL), (4-(hydroxymethyl)phenyl)boronic acid (106 mg, 0.70 mmol), sodium carbonate (1.17 mL of a 2M aqueous solution, 2.34 mmol) and Pd(dppf)$Cl_2$ (47 mg, 0.058 mmol). The reaction tube was sealed and heated in a microwave for two hours at 100° C. The resultant mixture was filtered through a CELITE plug. The filtrate was partitioned between EtOAc and $H_2O$. The EtOAc layer was washed with brine, dried ($Na_2SO_4$), concentrated in vacuo, and purified via silica gel chromatography (0-5% MeOH/DCM) followed by a second silica gel chromatographic purification (0-100% EtOAC/hexanes) to afford Compound 204 (168 mg, 70%). LCMS (method A): m/z 495.5 (M+H)$^+$. $^1$H NMR ($CDCl_3$, 400 MHz) δ 7.65 (d, 2H), 7.53 (d, 2H), 7.46 (bs, 1H), 7.36 (d, 2H), 7.23 (s, 1H), 7.13 (d, 2H), 6.72 (s, 1H), 4.81 (s, 2H), 4.64 (d, 1H), 3.57 (m, 2H), 3.44 (m, 2H), 2.82 (m, 2H), 2.48 (m, 1H), 2.21 (m, 1H), 2.12 (m, 1H), 1.96 (m, 1H).

Example 41

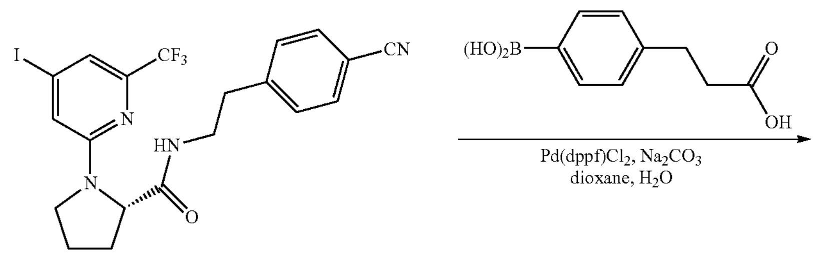

Intermediate 9

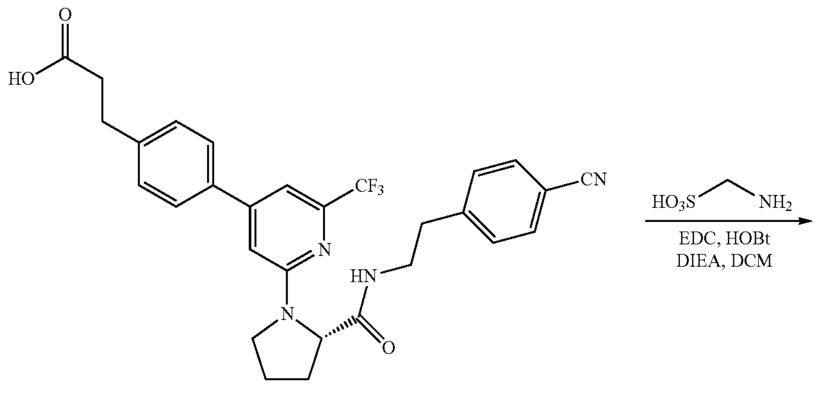

Compound 205

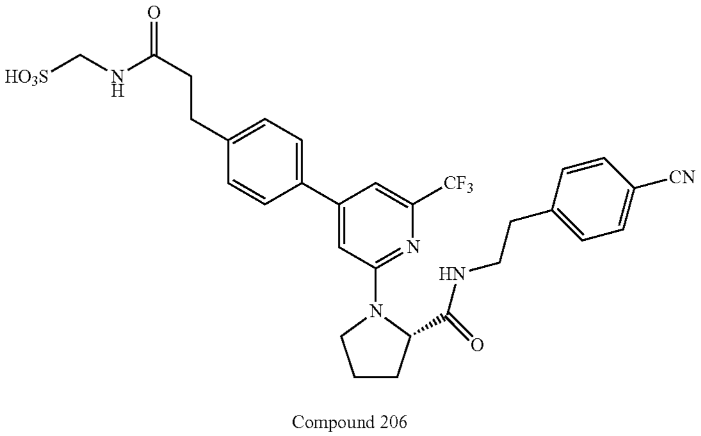

Compound 206

(S)-3-(4-(2-(2-((4-cyanophenethyl)carbamoyl)pyrrolidin-1-yl)-6-(trifluoromethyl)pyridin-4-yl)phenyl) propanoic acid Using the procedure as described in Example 30, Intermediate 9 (230 mg, 0.45 mmol) was converted to Compound 205 (168 mg, 70%). LCMS (method A): m/z 537.5 $(M+H)^+$. $^1H$ NMR ($CDCl_3$) δ 7.59 (d, 2H), 7.53 (bs, 1H), 7.37 (m, 4H), 7.20 (s, 1H), 7.12 (s, 2H), 6.72 (s, 1H), 4.65 (d, 1H), 3.57 (m, 2H), 3.40 (m, 2H), 3.05 (t, 2H), 2.82 (m, 4H), 2.47 (m, 1H), 2.21 (m, 1H), 2.11 (m, 1H), 1.98 (m, 1H).

(S)-(3-(4-(2-(2-((4-cyanophenethyl)carbamoyl)pyrrolidin-1-yl)-6-(trifluoromethyl)pyridin-4-yl)phenyl) propanamido)methanesulfonic acid Using the procedure as described in Example 7, Compound 205 (57 mg, 0.11 mmol) was converted to Compound 206 (31 mg, 46%). LCMS (method A): m/z 630.4 $(M+H)^+$. $^1H$ NMR ($CD_3OD$) δ 7.66 (d, 2H), 7.40 (d, 2H), 7.32 (s, 1H), 7.30 (d, 2H), 6.92 (s, 1H), 4.56 (d, 1H), 4.33 (s, 2H), 3.80 (bs, 1H), 3.45 (m, 4H), 3.01 (t, 2H), 2.87 (m, 2H), 2.63 (m, 2H), 2.27 (m, 1H), 2.05 (m, 3H). Using the procedure described above for Example 41, the following compound was prepared from Compound 205 and the reagent as indicated in Table 32.

TABLE 32
| No | Structure | Reagent | MS (M + H)+ |
|---|---|---|---|
| 207 | 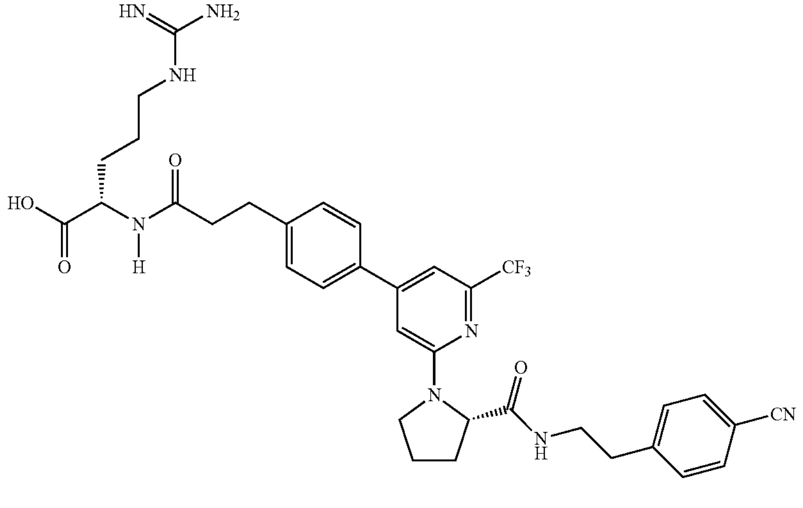 [SMILES: N#Cc1ccc(CCNC(=O)[C@@H]2CCCN2c2cc(-c3ccc(CCC(=O)N[C@@H](CCCNC(=N)N)C(=O)O)cc3)cc(C(F)(F)F)n2)cc1] (S)-2-(3-(4-(2-((S)-2-((4-cyanophenethyl)carbamoyl)pyrrolidin-1-yl)-6-(trifluoromethyl)pyridin-4-yl)phenyl)propanamido)-5-guanidino-pentanoic acid | Coupling with 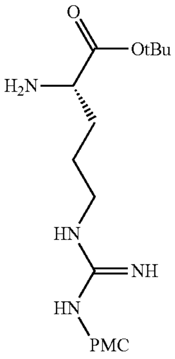 followed by deprotection with TFA as in Example 4 | 693.6 A |
Example 42
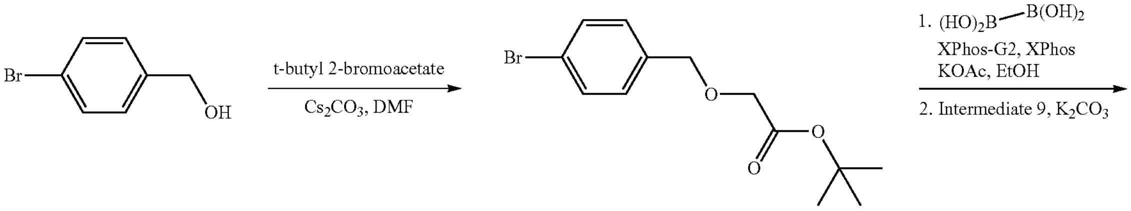
Compound 42A
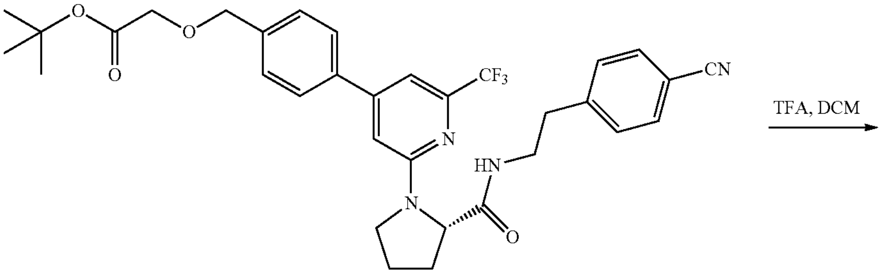
Compound 42B -continued

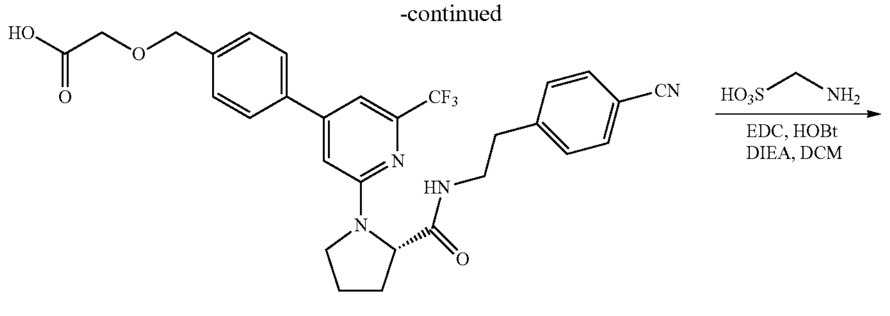

Compound 208

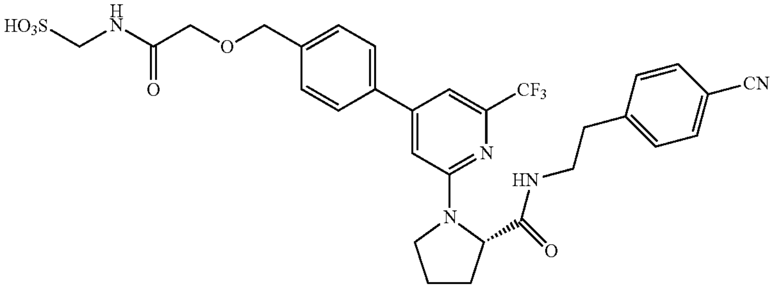

Compound 209 tert-butyl 2-((4-bromobenzyl)oxy)acetate

To a solution of 4-bromobenzylalcohol (2.0 g, 11 mmol) in DMF (20 mL) were added cesium carbonate (3.8 g, 12 mmol) and tert-butylbromoacetate (1.6 mL, 11 mmol). After stirring at room temperature for 18 hours, ethyl ether (25 mL) was added, and the mixture was washed with 1N HCl and brine, dried ($Na_2SO_4$), concentrated in vacuo, and purified by silica gel chromatography (0-50% EtOAc/hexanes) to afford Compound 42A (1.96 g; 61%). $^1$H NMR ($CDCl_3$): δ 7.41 (d, 2H), 7.19 (d, 2H), 4.50 (s, 2H), 3.91 (s, 2H), 1.41 (s, 9H).

(S)-tert-butyl 2-((4-(2-(2-((4-cyanophenethyl)carbamoyl)pyrrolidin-1-yl)-6-(trifluoromethyl) pyridin-4-yl)benzyl)oxy)acetate To a glass vessel were added tert-butyl 2-((4-bromobenzyl)oxy)acetate (Compound 42A) (84 mg, 0.28 mmol), tetrahydroxydiboron (75 mg, 0.84 mmol), potassium acetate (82 mg, 0.84 mmol) and ethanol (2.5 mL). After sparging with nitrogen for 10 min, XPhos (13 mg, 0.03 mmol) and XPhosG2 (11 mg, 0.01 mmol) were added and the septa-sealed tube was heated to 80° C. for three hours. A 1.8 M aqueous solution of potassium carbonate (560 μL, 1.0 mmol) and a preformed solution of Intermediate 9 (144 mg, 0.28 mmol dissolved in 600 mL THF and 300 mL ethanol) were added and the reaction was heated for 36 hours at 80° C. The resultant mixture was filtered through a CELITE plug. The filtrate was partitioned between EtOAc and $H_2O$. The EtOAc layer was washed with brine, dried ($Na_2SO_4$), concentrated in vacuo, and purified via silica gel chromatography (0-100% EtOAc/hexanes) to afford Compound 42B which was directly carried to the next step. LCMS (method A): m/z 609.5 $(M+H)^+$.

(S)-2-((4-(2-(2-((4-cyanophenethyl)carbamoyl)pyrrolidin-1-yl)-6-(trifluoromethyl)pyridin-4-yl)benzyl)oxy)acetic acid Compound 42B was dissolved in DCM (5 mL) and TFA (5 mL). The mixture was stirred for one hour. After concentrating in vacuo, the residue was purified via silica gel chromatography (0-5% MeOH/DCM) to afford Compound 208 (56 mg, 36% over two steps). LCMS (method A): m/z 553.4 $(M+H)^+$. $^1$H NMR ($CDCl_3$, 400 MHz) δ 7.62 (m, 2H), 7.50 (m, 3H), 7.34 (d, 2H), 7.19 (s, 1H), 7.11 (d, 2H), 6.71 (s, 1H), 4.70 (s, 2H), 4.64 (s, 1H), 4.18 (s, 2H), 3.48 (m, 4H), 2.80 (m, 2H), 2.45 (m, 1H), 2.14 (m, 2H), 1.96 (m, 1H).

(S)-(2-((4-(2-(2-((4-cyanophenethyl)carbamoyl)pyrrolidin-1-yl)-6-(trifluoromethyl)pyridin-4-yl)benzyl)oxy)acetamido)methanesulfonic acid Using the procedure as described in Example 7, Compound 208 (36 mg, 0.06 mmol) was converted to Compound 209 (4.4 mg, 11%). LCMS (method A): m/z 646.5 $(M+H)^+$. $^1$H NMR ($CD_3OD$, 400 MHz) δ 7.73 (d, 2H), 7.57 (d, 2H), 7.51 (d, 2H), 7.31 (d, 2H), 7.27 (s, 1H), 6.91 (s, 1H), 4.72 (s, 2H), 4.52 (d, 1H), 4.39 (s, 2H), 4.08 (s, 2H), 3.78 (m, 1H), 3.45 (m, 3H), 2.85 (m, 2H), 2.25 (m, 1H), 2.04 (m, 3H).

Example 43

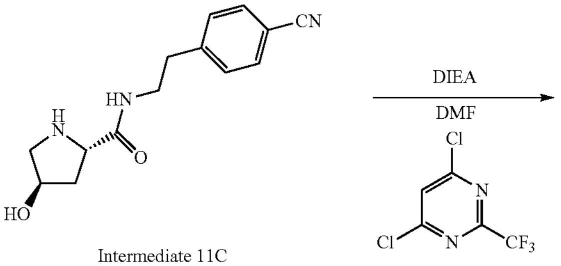

Intermediate 11C

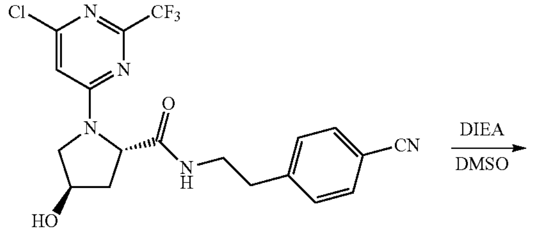

Compound 43A

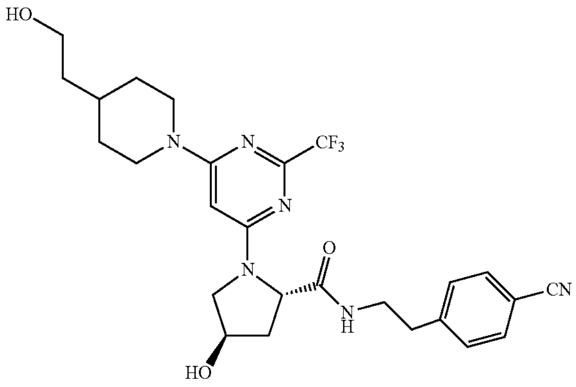

Compound 210

(2S,4R)-1-(6-chloro-2-(trifluoromethyl)pyrimidin-4-yl)-N-(4-cyanophenethyl)-4-hydroxypyrrolidine-2-carboxamide Using the procedure as described for Intermediate 1, step 3, Intermediate 11C (195 mg, 0.660 mmol) was converted to Compound 43A (39 mg, 48%). LCMS (method A): m/z 440.2 $(M+H)^+$. $^1H$ NMR ($CD_3OD$) δ 7.65-7.63 (d, 2H), 7.40-7.38 (d, 2H), 6.82 (s, 1H), 6.31 (s, 1H), 4.61 (t, 1H), 4.55 (br s, 1H), 3.75-3.71 (m, 1H), 3.53-3.34 (m, 3H), 2.94-2.84 (m, 2H), 2.27-2.23 (m, 1H), 2.06-1.99 (m, 1H).

(2S,4R)—N-(4-cyanophenethyl)-4-hydroxy-1-(6-(4-(2-hydroxyethyl)piperidin-1-yl)-2-(trifluoromethyl)pyrimidin-4-yl)pyrrolidine-2-carboxamide Using the procedure as described in Example 1, Compound 43A (47 mg, 0.11 mmol) was converted to Compound 210 (42 mg, 75%). LCMS (method A): m/z 533.5 $(M+H)^+$. $^1H$ NMR ($CD_3OD$) δ 7.60 (br s, 1H), 7.44-7.42 (d, 2H), 7.16-7.14 (m, 2H), 5.31 (s, 1H), 4.85-4.81 (m, 1H), 4.73-4.71 (m, 1H), 4.41-4.34 (m, 2H), 3.77-3.72 (m, 2H), 3.63-3.54 (m, 2H), 3.42-3.34 (m, 1H), 3.26-3.22 (m, 1H), 2.95-2.75 (m, 4H), 2.67-2.61 (M, 1H), 1.99-1.92 (m, 2H), 1.85-1.74 (m, 3H), 1.59-1.54 (m, 2H), 1.28-1.19 (m, 3H). Using the procedure described above for Example 43, the following compounds were prepared from Intermediates and reagents as indicated in Table 33.

TABLE 33

| No | Structure | Intermediate | Reagent In step 2 | MS $(M + H)^+$ |
|---|---|---|---|---|
| 211 | 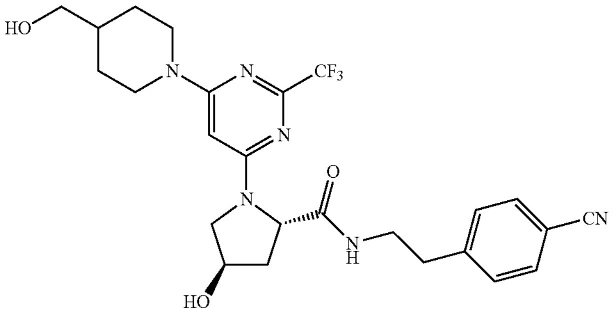 [SMILES: N#Cc1ccc(CCNC(=O)[C@@H]2C[C@@H](O)CN2c2cc(N3CCC(CO)CC3)nc(C(F)(F)F)n2)cc1] (2S,4R)-N-(4-cyanophenethyl)-4-hydroxy-1-(6-(4-(hydroxymethyl)piperidin-1-yl)-2-(trifluoromethyl)pyrimidin-4-yl)pyrrolidine-2-carboxamide | 11C | 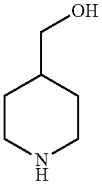 | 519.5 A |

TABLE 33-continued
| No | Structure | Inter-mediate | Reagent In step 2 | MS (M + H)+ |
|---|---|---|---|---|
| 212 | 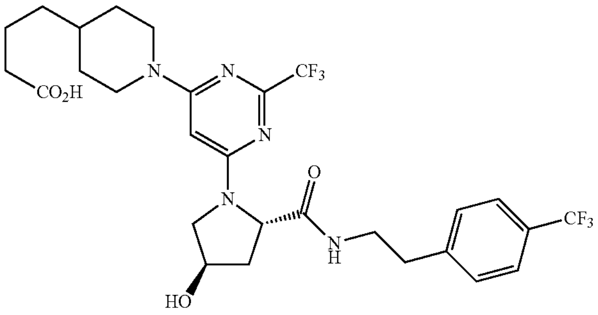 [SMILES: O=C(O)CCCC1CCN(c2cc(N3C[C@H](O)C[C@H]3C(=O)NCCc3ccc(C(F)(F)F)cc3)nc(C(F)(F)F)n2)CC1]<br>4-(1-(6-((2S,4R)-4-hydroxy-2-((4-(trifluoromethyl)phenethyl)carbamoyl) pyrrolidin-1-yl)-2-(trifluoromethyl)pyrimidin-4-yl)piperidin-4-yl)butanoic acid | 11B | 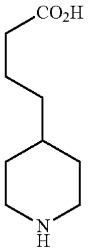 | 618.6 A |
| 213 | 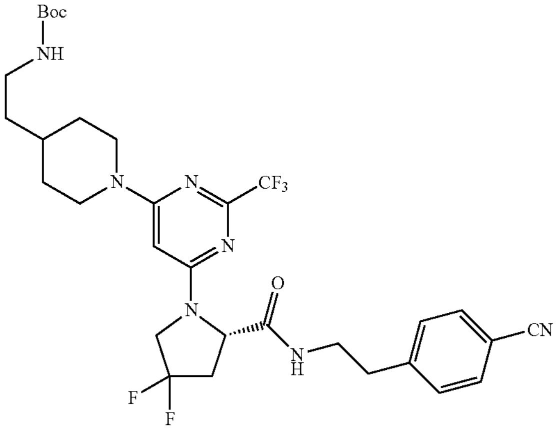 [SMILES: CC(C)(C)OC(=O)NCCC1CCN(c2cc(N3CC(F)(F)C[C@H]3C(=O)NCCc3ccc(C#N)cc3)nc(C(F)(F)F)n2)CC1]<br>(S)-tert-butyl (2-(1-(6-(2-((4-cyanophenethyl)carbamoyl)-4,4-difluoropyrrolidin-1-yl)-2-(trifluoromethyl)pyrimidin-4-yl)piperidin-4-yl)ethyl)carbamate | 11D | 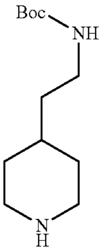 [SMILES: CC(C)(C)OC(=O)NCCC1CCNCC1] | 652.5 |
Example 44
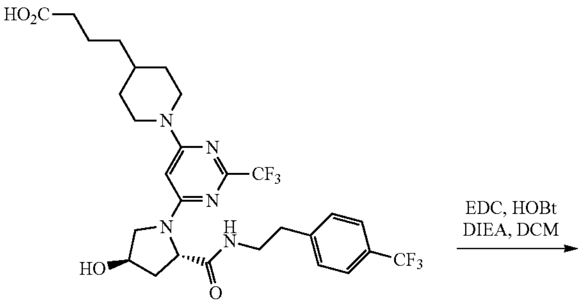
Compound 212

-continued

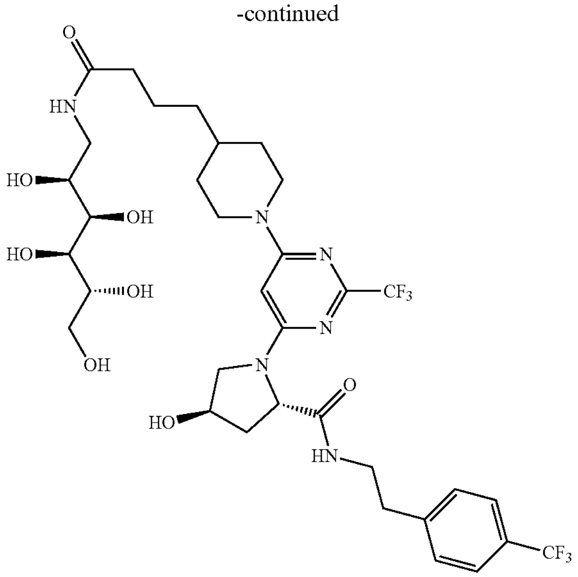

Compound 214

(2S,4R)-4-hydroxy-1-(6-(4-(4-oxo-4-(((2S,3R,4R,5R)-2,3,4,5,6-pentahydroxyhexyl)-amino)butyl)-piperidin-1-yl)-2-(trifluoromethyl)-pyrimidin-4-yl)-N-(4-(trifluoro-methyl)phenethyl)pyrrolidine-2-carboxamide Using the procedure as described in Example 7, Compound 212 was converted to Compound 214. LCMS (method A): m/z 534.4 $(M+H)^+$. $^1H$ NMR ($d_6$-DMSO) δ 8.37-7.99 (br s, 1H), 7.72 (br s, 1H), 7.59 (d, 2H), 7.37 (d, 2H), 5.75-5.37 (b, 1H), 5.11 (b, 1H), 4.75 (d, 1H), 4.36 (m, 8H), 3.57 (m, 4H), 3.41 (m, 4H), 3.25 (m, 3H), 3.01 (m, 1H), 2.97 (m, 4H), 2.07 (m, 3H), 1.89 (br, 1H), 1.71 (m, 2H), 1.51 (br, 3H), 1.81 (br, 2H), 1.00 (m, 2H).

Example 45

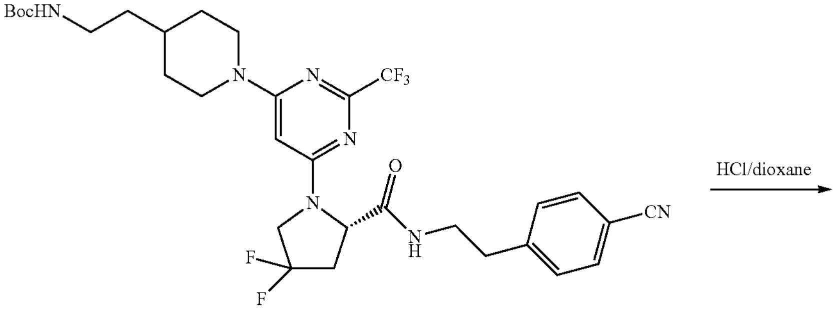

Compound 213

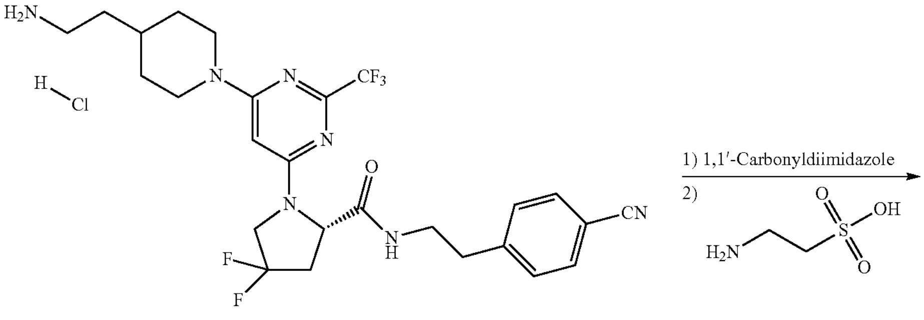

Compound 215

-continued

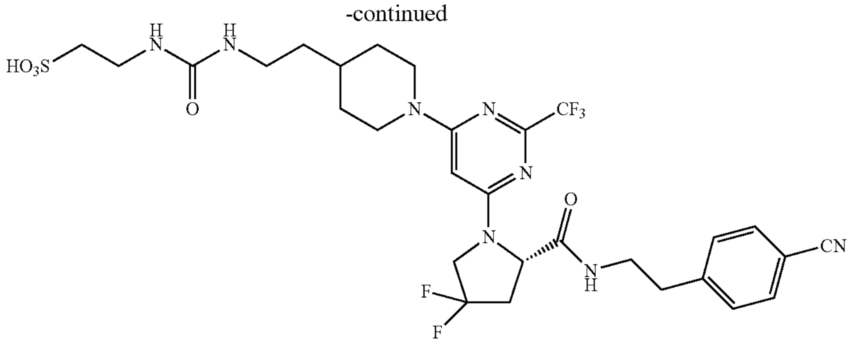

Compound 216

(S)-1-(6-(4-(2-aminoethyl)piperidin-1-yl)-2-(trifluoromethyl)pyrimidin-4-yl)-N-(4-cyanophenethyl)-4,4-difluoropyrrolidine-2-carboxamide Using the procedure as described in Intermediate 9, step 3, Compound 213 (0.56 g, 0.86 mmol) was converted to Compound 215 (0.53 g, Quantitative yield). LCMS (method A): m/z 552.5 $(M+H)^+$. $^1H$ NMR ($CD_3OD$) δ 8.24 (m, 1H), 7.58 (d, 2H), 7.35 (d, 2H), 5.65 (s, 1H), 4.73 (m, 1h), 4.48 (m, 2H), 3.93 (m, 2H), 3.46 (m, 2H), 3.01 (t, 2H), 2.89 (m, 4H), 2.77 (m, 1H), 2.47 (m, 1H), 1.83 (d, 2H), 1.72 (m, 1H), 1.63 (m, 2H), 1.23 (m, 2H).

(S)-2-(3-(2-(1-(6-(2-((4-cyanophenethyl)carbamoyl)-4,4-difluoropyrrolidin-1-yl)-2-(trifluoromethyl)pyrimidin-4-yl)piperidin-4-yl)ethyl)ureido)ethanesulfonic acid Using the procedure as described in Example 9, step 2, Compound 215 (0.13 g, 0.21 mmol) was converted to Compound 216 (34 mg, 23%). LCMS (method A): m/z 703.5 $(M+H)^+$. $^1H$ NMR ($CD_3OD$) δ 7.59 (d, 2H), 7.36 (d, 2H), 5.65 (s, 1H), 4.73 (m, 1H), 4.45 (t, 2H), 3.94 (m, 2H), 3.60 (t, 2H), 3.49 (m, 1H), 3.40 (m, 1H), 3.25 (t, 2H), 2.99 (t, 2H), 2.84 (m, 5H), 2.47 (m, 1H), 1.83 (d, 2H), 1.69 (m, 1H), 1.51 (m, 2H), 1.30 (s, 1H), 1.19 (m, 2H).

Example 46

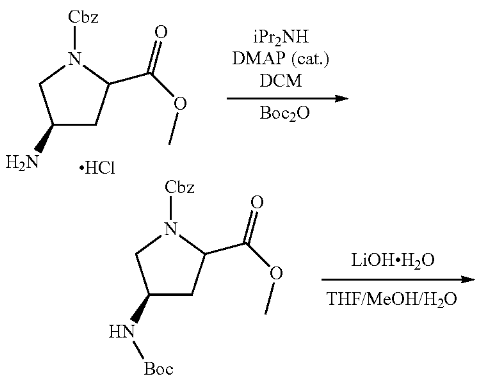

Compound 46A

-continued

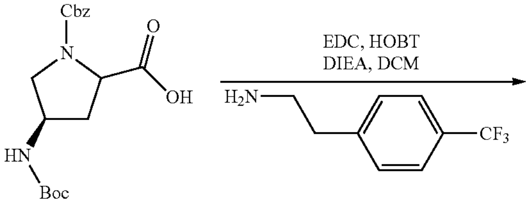

Compound 46B

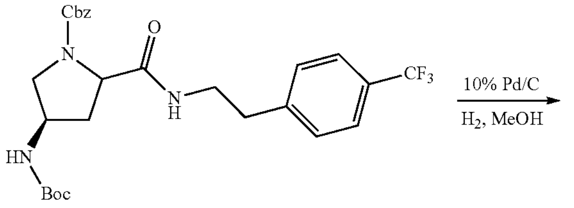

Compound 46C

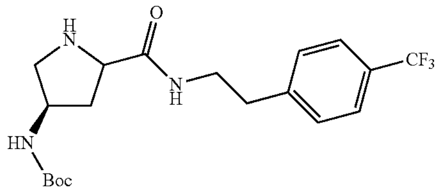

Compound 46D

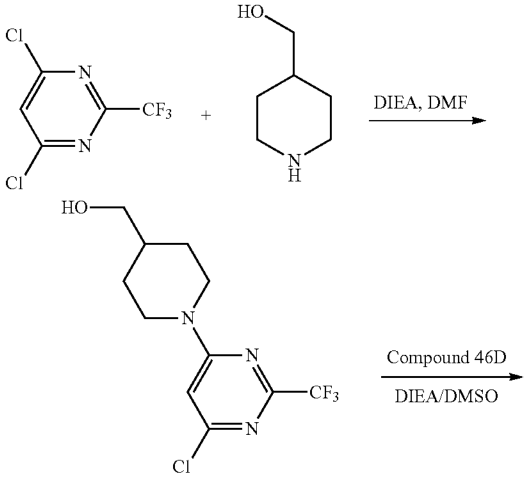

Compound 46E

-continued

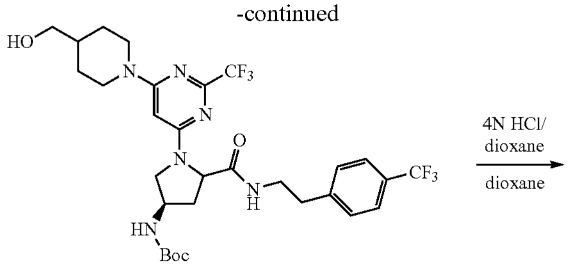

Compound 217

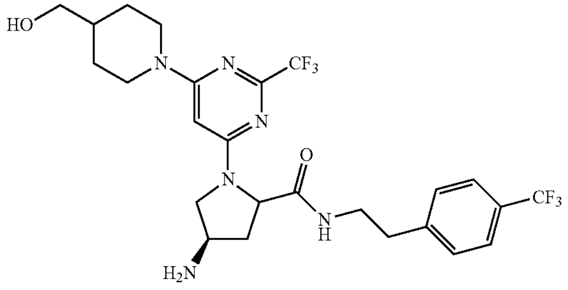

Compound 218

(4R)-1-benzyl 2-methyl 4-((tert-butoxycarbonyl) amino)pyrrolidine-1,2-dicarboxylate To a solution of (4R)-1-benzyl 2-methyl 4-aminopyrrolidine-1,2-dicarboxylate hydrochloride (1.58 g, 5 mmol) in DCM (7 mL) were added sequentially diisopropylamine (1.8 mL, 13 mmol), DMAP (61 mg, 0.50 mmol) and di-tert-butyl dicarbonate (1.1 g, 5.0 mmol). The reaction mixture was stirred at room temperature overnight. The reaction mixture was poured into water and extracted with DCM. The combined organic layers were dried over sodium sulfate, filtered, and concentrated in vacuo to afford Compound 46A (1.9 g, 100%) which was used in the next step without further purification. LCMS (method A): m/z 279.2 (M+H, loss of Boc group)$^+$.

(4R)-1-((benzyloxy)carbonyl)-4-((tert-butoxycarbonyl)amino)pyrrolidine-2-carboxylic acid Compound 46A (1.9 g, 5.0 mmol) was hydrolyzed as described in Example 16 to afford Compound 46B (1.8 g, 100%). LCMS (method A): m/z 265.2 (M+H, loss of Boc group)$^+$.

(4R)-benzyl 4-((tert-butoxycarbonyl)amino)-2-((4-(trifluoromethyl)phenethyl) carbamoyl)pyrrolidine-1-carboxylate Using the procedure as described in Example 7, Compound 46B (1.8 g, 5.0 mmol) was converted to Compound 46C (840 mg, 31%). LCMS (method A): m/z 536.4 (M+H)$^+$.

tert-butyl ((3R)-5-((4-(trifluoromethyl)phenethyl) carbamoyl)pyrrolidin-3-yl)carbamate To a solution of Compound 46C (834 mg, 1.56 mmol) in methanol (10 mL) was added 10% palladium on carbon (17 mg, 0.16 mmol). The reaction mixture was stirred at room temperature under a balloon of hydrogen gas for 90 minutes. The reaction mixture was filtered through CELITE and washed with methanol. The filtrate was concentrated in vacuo, and purified by silica gel chromatography (0-5% MeOH/DCM) to afford compound 46D (547 mg, 87%). LCMS (method A): m/z 402.4 (M+H)$^+$. $^1$H NMR ($CD_3OD$) δ 7.58 (d, 2H), 7.41 (d, 2H), 3.93 (br, 1H), 3.69 (m, 1H), 3.48 (m, 2H), 2.98 (m, 1H), 2.89 (m, 2H), 2.77 (m, 1H), 2.00 (m, 1H), 1.84 (m, 1H), 1.43 (s, 9H).

(1-(6-chloro-2-(trifluoromethyl)pyrimidin-4-yl)piperidin-4-yl)methanol

To a solution of 4,6-dichloro-2-(trifluoromethyl)pyrimidine (480 mg, 2.2 mmol) in DMF (2.8 mL) were added piperidin-4-ylmethanol (230 mg, 2.0 mmol) and diisopropylethylamine (0.4 mL, 2.3 mmol). The reaction mixture was stirred at room temperature for one hour. The reaction mixture was concentrated in vacuo, and purified by silica gel chromatography (0-70% EtOAc/hexanes) to afford compound 46E (571 mg, 97%). LCMS (method A): m/z 296.2 (M+H)$^+$.

tert-butyl ((3R)-1-(6-(4-(hydroxymethyl)piperidin-1-yl)-2-(trifluoromethyl)pyrimidin-4-yl)-5-((4-(trifluoromethyl)phenethyl)carbamoyl)pyrrolidin-3-yl)carbamate To a solution of Compound 46E (59 mg, 0.20 mmol) in DMSO (1.3 mL) were added Compound 50D (80 mg, 0.20 mmol) and diisopropylethylamine (0.17 mL, 1 mmol). The solution was heated in a microwave at 120° C. for five hours, and purified by MS-HPLC. A major portion of the desired product was used in the next step without further purification. A small portion of the desired product was re-purified by silica gel chromatography (0-5% MeOH/DCM) to afford Compound 217 (3 mg). LCMS (method A): m/z 661.4 (M+H)$^+$. $^1$H NMR ($CDCl_3$) δ 7.40 (d, 2H), 7.15 (d, 2H), 5.33 (s, 1H), 4.65 (m, 2H), 4.43 (m, 3H), 3.78 (br, 1H), 3.55 (m, 3H), 3.40 (m, 1H), 3.09 (br, 1H), 2.92-2.65 (m, 5H), 1.87-1.78 (m, 4H), 1.46 (s, 9H), 1.43-1.21 (m, 3H).

(4R)-4-amino-1-(6-(4-(hydroxymethyl)piperidin-1-yl)-2-(trifluoromethyl)pyrimidin-4-yl)-N-(4-(trifluoromethyl)phenethyl)pyrrolidine-2-carboxamide Using the procedure as described in Intermediate 9, step 3 but using dioxane as solvent instead of DCM, Compound 217 (50 mg, 0.08 mmol) was converted to Compound 218 (16 mg, 38%). LCMS (method A): m/z 561.4 (M+H)$^+$. $^1$H NMR ($CD_3OD$) δ 7.51 (d, 2H), 7.34 (d, 2H), 4.69 (br s, 1H), 4.43 (m, 2H), 4.06 (m, 1H), 3.97 (m, 1H), 3.62 (br, 1H), 3.50-3.39 (m, 4H), 3.00-2.85 (m, 4H), 2.38 (m, 2H), 1.84-1.75 (m, 3H), 1.23 (m, 2H).

Example 47

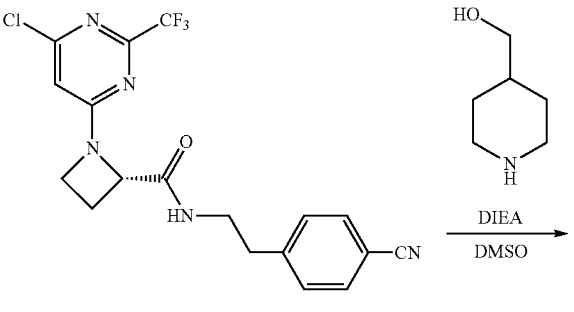

Intermediate 12

-continued

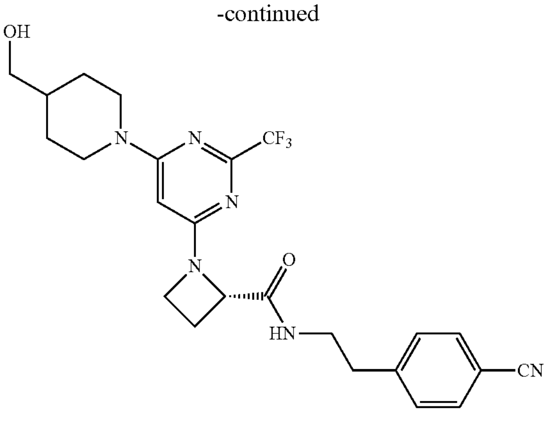

Compound 219

(S)—N-(4-cyanophenethyl)-1-(6-(4-(hydroxymethyl)piperidin-1-yl)-2-(trifluoromethyl)pyrimidin-4-yl)azetidine-2-carboxamide Using the procedure as described in Example 1, Intermediate 12 (35 mg, 0.09 mmol) was converted to Compound 219 (35 mg, 79%). LCMS (Method A): m/z 489.4 $(M+H)^+$. $^1H$ NMR ($CDCl_3$) δ 8.50 (br s, 1H), 6.47-6.45 (m, 2H), 7.25-7.22 (m, 2H), 5.26 (s, 1H), 4.80-4.76 (q, 1H), 4.42 (br, 2H), 3.95-3.89 (m, 1H), 3.81-3.75 (dd, 1H), 3.66-3.54 (m, 3H), 3.50-3.41 (m, 1H), 2.96-2.83 (m, 5H), 2.48-2.39 (m, 1H), 1.87-1.80 (m, 3H), 1.41 (t, 1H), 1.32-1.24 (m, 2H).

Using the procedure described above for Example 47, the following compounds were prepared from Intermediates and reagents as indicated in Table 34.

TABLE 34

| No | Compound | Intermediate | Reagent | MS $(M + H)^+$ |
|---|---|---|---|---|
| 220 | 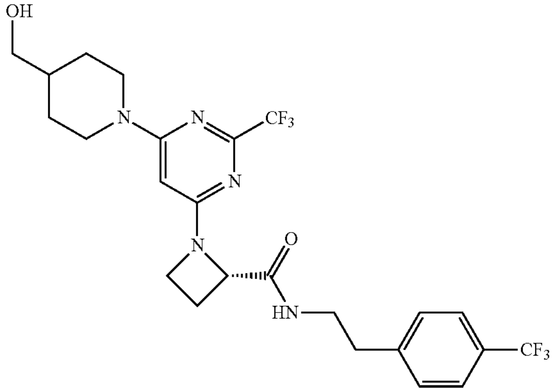 [SMILES: O=C(NCCc1ccc(C(F)(F)F)cc1)[C@@H]1CCN1c1cc(N2CCC(CO)CC2)nc(C(F)(F)F)n1] (S)-1-(6-(4-(hydroxymethyl)piperidin-1-yl)-2-(trifluoromethyl)pyrimidin-4-yl)-N-(4-(trifluoromethyl)-phenethyl)azetidine-2-carboxamide | 12A | 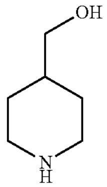 | 532.3 A |
| 221 | 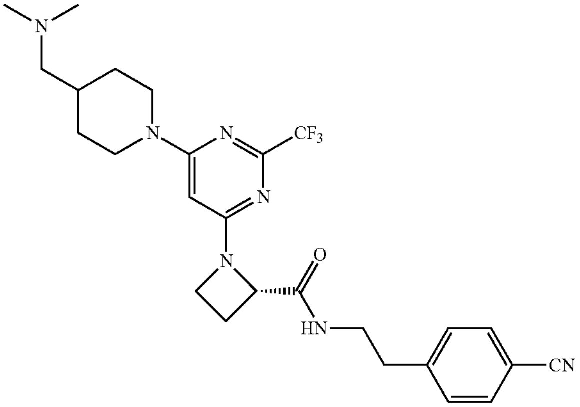 [SMILES: CN(C)CC1CCN(c2cc(N3CC[C@H]3C(=O)NCCc3ccc(C#N)cc3)nc(C(F)(F)F)n2)CC1] (S)-N-(4-cyanophenethyl)-1-(6-(4-((dimethylamino)methyl)piperidin-1-yl)-2-(trifluoromethyl)pyrimidin-4-yl)azetidine-2-carboxamide | 12 | 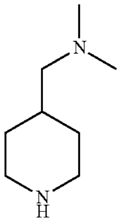 | 516.5 A |

TABLE 34-continued

| No | Compound | Inter-mediate | Reagent | MS (M + H)+ |
|---|---|---|---|---|
| 222 | 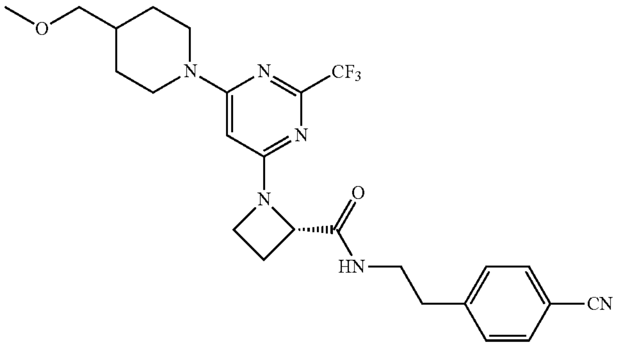 [SMILES: COCC1CCN(c2cc(N3CC[C@H]3C(=O)NCCc3ccc(C#N)cc3)nc(C(F)(F)F)n2)CC1] (S)-N-(4-cyanophenethyl)-1-(6-(4-(methoxymethyl)piperidin-1-yl)-2-(trifluoromethyl)pyrimidin-4-yl)azetidine-2-carboxamide | 12 | 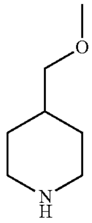 | 503.5 A |
| 223 | 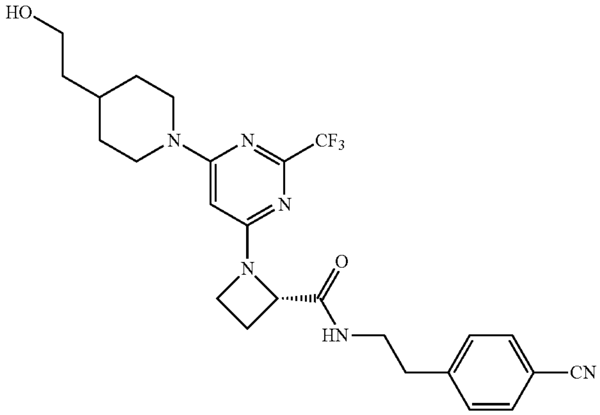 (S)-N-(4-cyanophenethyl)-1-(6-(4-(2-hydroxyethyl)piperidin-1-yl)-2-(trifluoromethyl)pyrimidin-4-yl)azetidine-2-carboxamide | 12 | 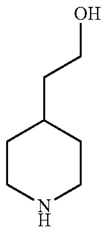 | 503.5 A |
| 224 | 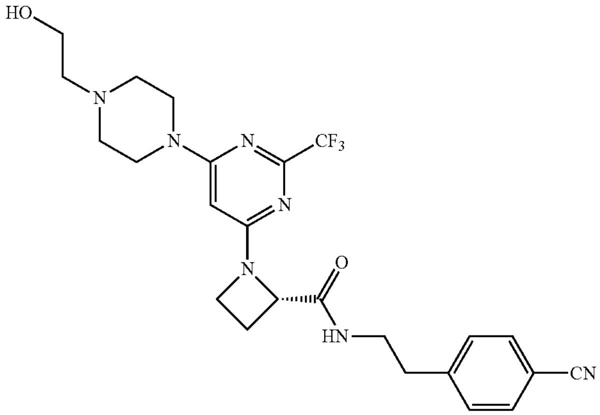 (S)-N-(4-cyanophenethyl)-1-(6-(4-(2-hydroxyethyl)piperazin-1-yl)-2-(trifluoromethyl)pyrimidin-4-yl)azetidine-2-carboxamide | 12 | 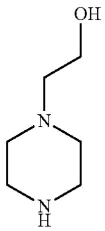 | 504.6 A |

TABLE 34-continued

| No | Compound | Inter-mediate | Reagent | MS (M + H)$^+$ |
|---|---|---|---|---|
| 225 | 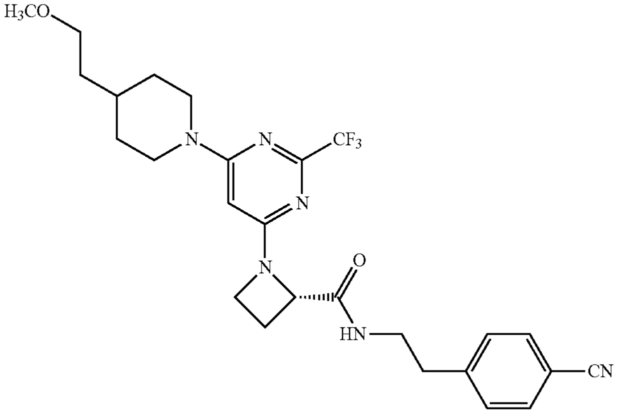<br>(S)-N-(4-cyanophenethyl)-1-(6-(4-(2-methoxyethyl)piperidin-1-yl)-2-(trifluoromethyl)pyrimidin-4-yl)azetidine-2-carboxamide | 12 | 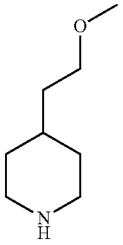 | 517.6<br>A |
| 226 | 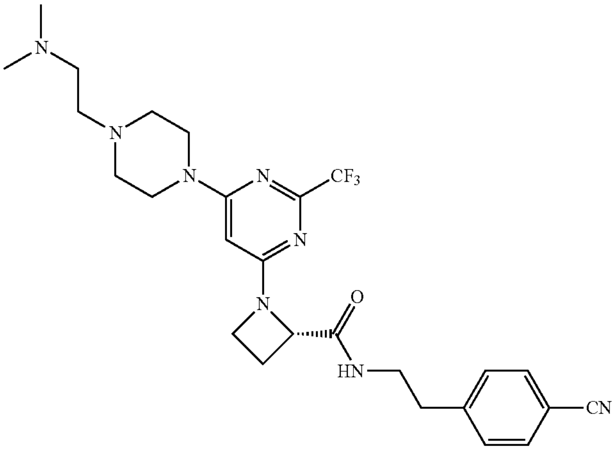<br>(S)-N-(4-cyanophenethyl)-1-(6-(4-(2-(dimethylamino)ethyl)piperazin-1-yl)-2-(trifluoromethyl)pyrimidin-4-yl)azetidine-2-carboxamide | 12 | 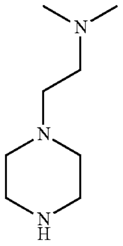 | 531.6<br>A |
| 227 | 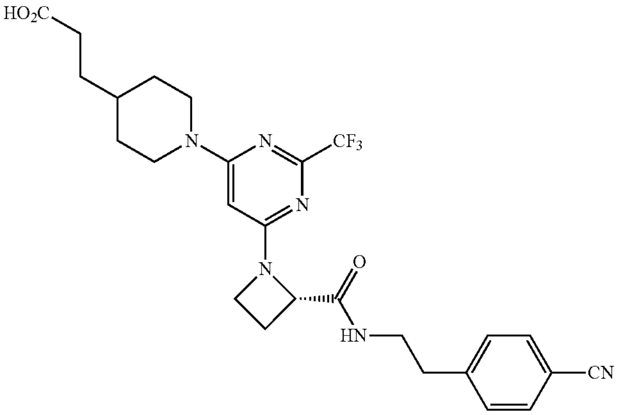 [SMILES: N#Cc1ccc(CCNC(=O)[C@@H]2CCN2c2cc(N3CCC(CCC(=O)O)CC3)nc(C(F)(F)F)n2)cc1]<br>(S)-3-(1 -(6-(2-((4-cyanophenethyl)carbamoyl)azetidin-1-yl)-2-(trifluoromethyl)pyrimidin-4-yl)piperidin-4-yl)propanoic acid | 12 | 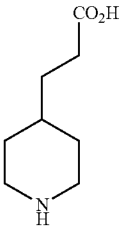 [SMILES: O=C(O)CCC1CCNCC1] | 530.5<br>A |

TABLE 34-continued
| No | Compound | Inter-mediate | Reagent | MS (M + H)+ |
|---|---|---|---|---|
| 228 | 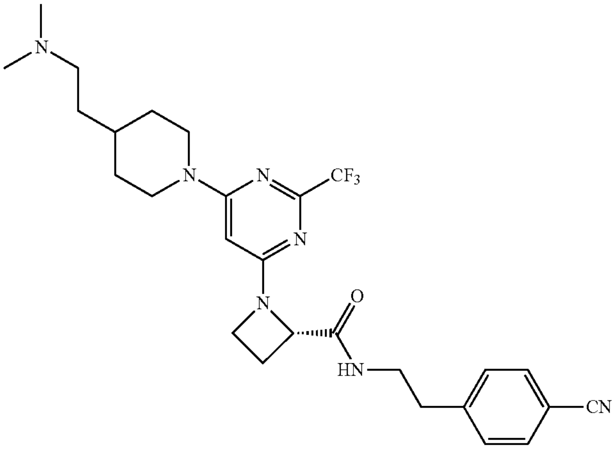 [SMILES: CN(C)CCC1CCN(c2cc(N3CC[C@H]3C(=O)NCCc3ccc(C#N)cc3)nc(C(F)(F)F)n2)CC1] (S)-N-(4-cyanophenethyl)-1-(6-(4-(2-(dimethylamino)ethyl)piperidin-1-yl)-2-(trifluoromethyl)pyrimidin-4-yl)azetidine-2-carboxamide | 12 | 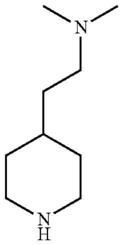 | 529.6 A |
| 229 | 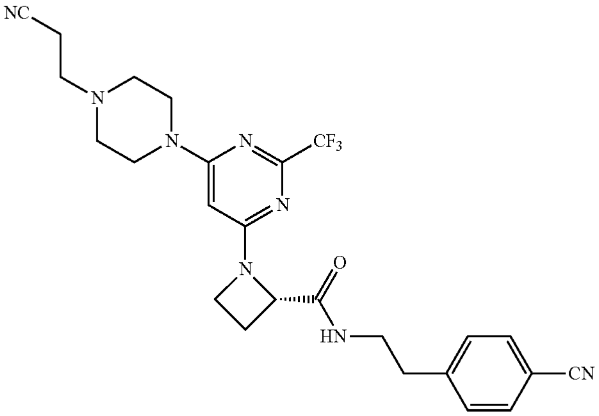 (S)-1-(6-(4-(2-cyanoethyl)piperazin-1-yl)-2-(trifluoromethyl)pyrimidin-4-yl)-N-(4-cyanophenethyl)azetidine-2-carboxamide | 12 | 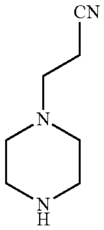 | 513.6 A |
| 230 | 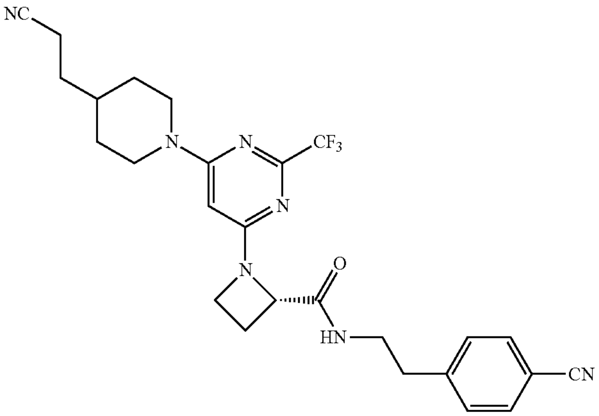 [SMILES: N#CCCC1CCN(c2cc(N3CC[C@H]3C(=O)NCCc3ccc(C#N)cc3)nc(C(F)(F)F)n2)CC1] (S)-1-(6-(4-(2-cyanoethyl)piperidin-1-yl)-2-(trifluoromethyl)pyrimidin-4-yl)- | 12 | 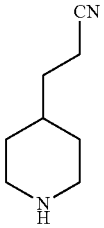 | 512.6 A |

TABLE 34-continued
| No | Compound | Inter-mediate | Reagent | MS (M + H)+ |
|---|---|---|---|---|
| | N-(4-cyanophenethyl)azetidine-2-carboxamide | | | |
| 231 | 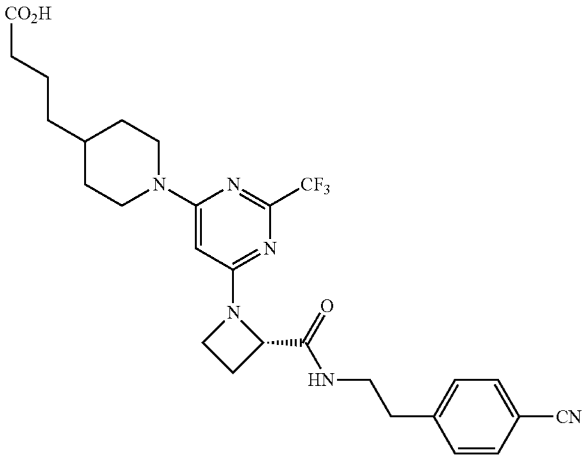 [SMILES: N#Cc1ccc(CCNC(=O)[C@@H]2CCN2c2cc(N3CCC(CCCC(=O)O)CC3)nc(C(F)(F)F)n2)cc1]<br>(S)-4-(1-(6-(2-((4-cyanophenethyl)carbamoyl)azetidin-1-yl)-2-(trifluoromethyl)pyrimidin-4-yl)piperidin-4-yl)butanoic acid | 12 | 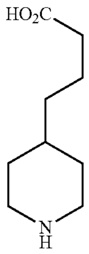 | 545.6 A |
| 232 | 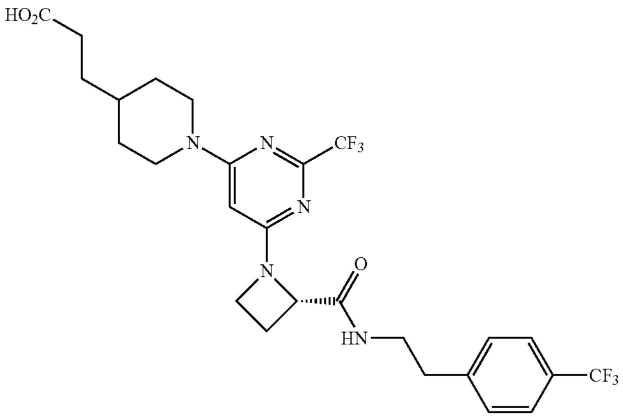 [SMILES: O=C(O)CCC1CCN(c2cc(N3CC[C@H]3C(=O)NCCc3ccc(C(F)(F)F)cc3)nc(C(F)(F)F)n2)CC1]<br>(S)-3-(1-(2-(trifluoromethyl)-6-(2-((4-(trifluoromethyl)phenethyl)carbamoyl)azetidin-1-yl)pyrimidin-4-yl)piperidin-4-yl)propanoic acid | 12A | 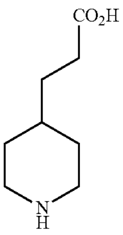 [SMILES: O=C(O)CCC1CCNCC1] | 574.5 B |

TABLE 34-continued
| No | Compound | Intermediate | Reagent | MS (M + H)+ |
|---|---|---|---|---|
| 233 | 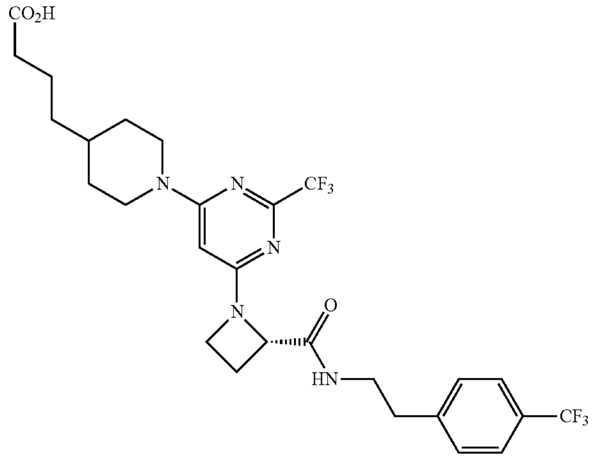 [SMILES: O=C(O)CCCC1CCN(c2cc(N3CC[C@H]3C(=O)NCCc3ccc(C(F)(F)F)cc3)nc(C(F)(F)F)n2)CC1] (S)-4-(1-(2-(trifluoromethyl)-6-(2-((4-(trifluoromethyl)phenethyl)carbamoyl)azetidin-1-yl)pyrimidin-4-yl)piperidin-4-yl)butanoic acid | 12A | 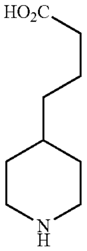 | 588.3 B |
| 234 | 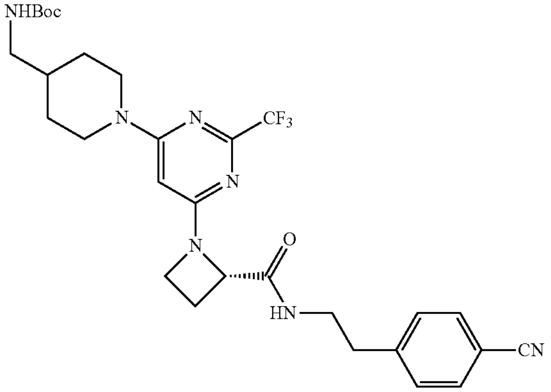 [SMILES: CC(C)(C)OC(=O)NCC1CCN(c2cc(N3CC[C@H]3C(=O)NCCc3ccc(C#N)cc3)nc(C(F)(F)F)n2)CC1] (S)-tert-butyl ((1-(6-(2-((4-cyanophenethyl)carbamoyl)azetidin-1-yl)-2-(trifluoromethyl)pyrimidin-4-yl)piperidin-4-yl)methyl)carbamate | 12 | 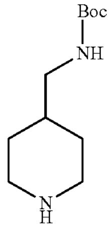 | 588.5 A |
| 235 | 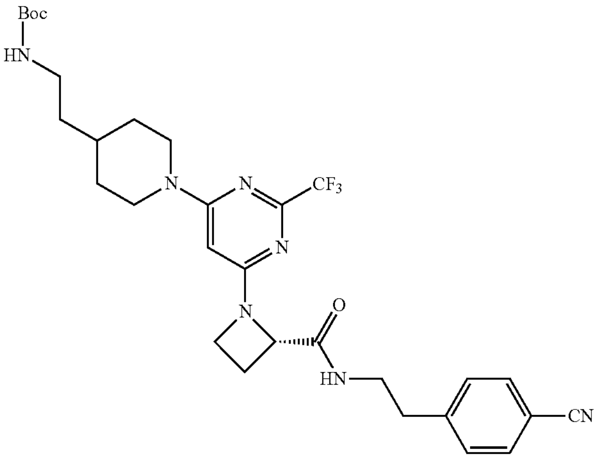 [SMILES: CC(C)(C)OC(=O)NCCC1CCN(c2cc(N3CC[C@H]3C(=O)NCCc3ccc(C#N)cc3)nc(C(F)(F)F)n2)CC1] (S)-tert-butyl (2-(1-(6-(2-((4-cyanophenethyl)carbamoyl)azetidin-1- | 12 | 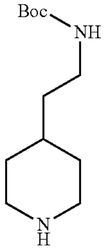 | 602.7 A |

TABLE 34-continued

| No | Compound | Inter-mediate | Reagent | MS (M + H)+ |
|---|---|---|---|---|
| | yl)-2-(trifluoromethyl)pyrimidin-4-yl)piperidin-4-yl)ethyl)carbamate | | | |
| 236 | 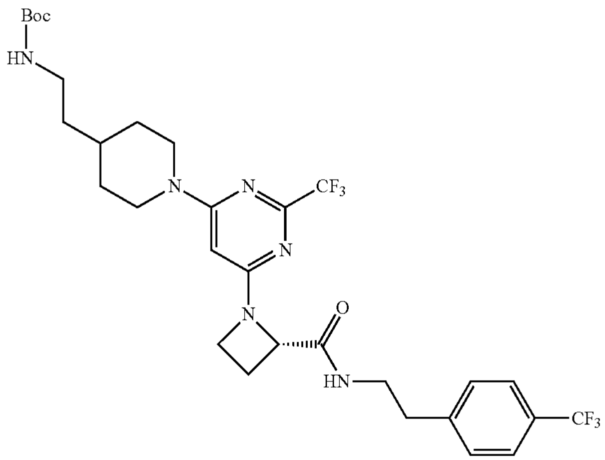 [SMILES: CC(C)(C)OC(=O)NCCC1CCN(c2cc(N3CC[C@H]3C(=O)NCCc3ccc(C(F)(F)F)cc3)nc(C(F)(F)F)n2)CC1] (S)-tert-butyl (2-(1-(2-(trifluoromethyl)-6-(2-((4-(trifluoromethyl)phenethyl)carbamoyl)azetidin-1-yl)pyrimidin-4-yl)piperidin-4-yl)ethyl)carbamate | 12A | 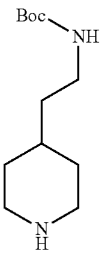 | 645.6 B |
| 237 | 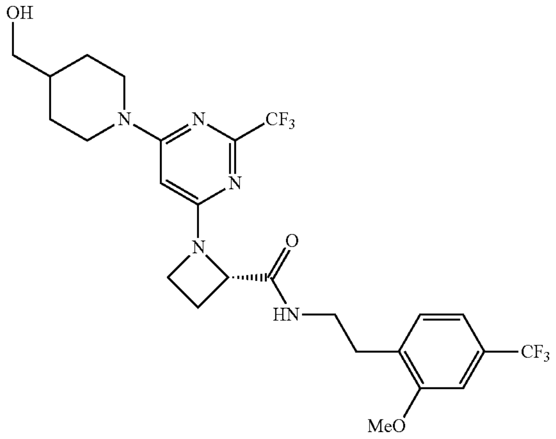 [SMILES: COc1cc(C(F)(F)F)ccc1CCNC(=O)[C@@H]1CCN1c1cc(N2CCC(CO)CC2)nc(C(F)(F)F)n1] (S)-1-(6-(4-(hydroxymethyl)piperidin-1-yl)-2-(trifluoromethyl)pyrimidin-4-yl)-N-(2-methoxy-4-(trifluoromethyl)phenethyl)azetidine-2-carboxamide | 12C | 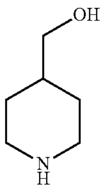 | 562.5 A |

TABLE 34-continued
| No | Compound | Inter-mediate | Reagent | MS (M + H)+ |
|---|---|---|---|---|
| 238 | 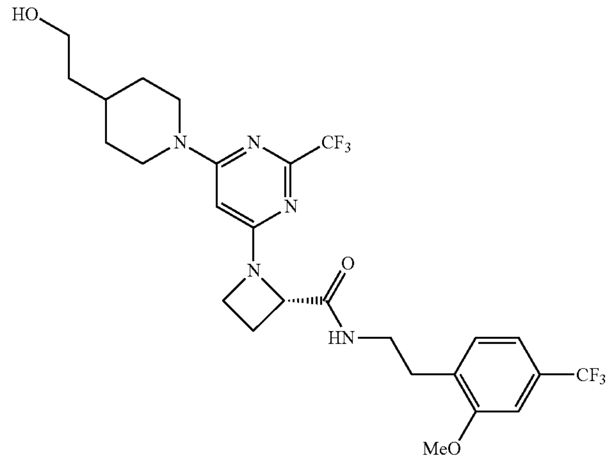 [SMILES: COc1cc(C(F)(F)F)ccc1CCNC(=O)[C@@H]1CCN1c1cc(N2CCC(CCO)CC2)nc(C(F)(F)F)n1]<br>(5)-1-(6-(4-(2-hydroxyethyl)piperidin-1-yl)-2-(trifluoromethyl)pyrimidin-4-yl)-N-(2-methoxy-4-(trifluoromethyl)phenethyl)azetidine-2-carboxamide | 12C | 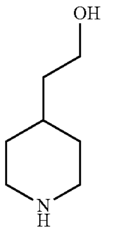 | 576.5 A |
| 239 | 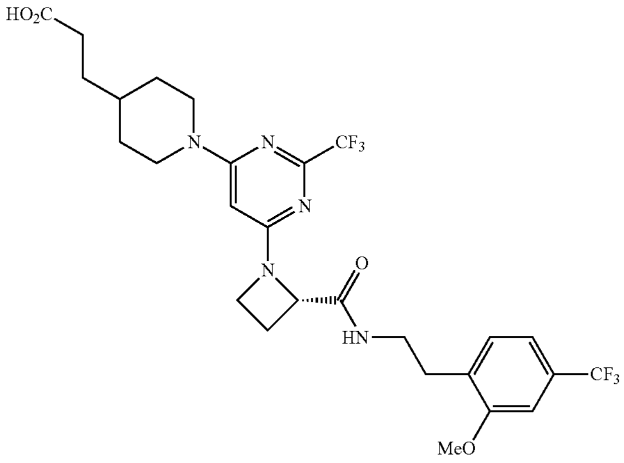 [SMILES: COc1cc(C(F)(F)F)ccc1CCNC(=O)[C@@H]1CCN1c1cc(N2CCC(CCC(=O)O)CC2)nc(C(F)(F)F)n1]<br>(S)-3-(1 -(6-(2-((2-methoxy-4-(trifluoromethyl)phenethyl)carbamoyl) azetidin-1-yl)-2-(trifluoromethyl)pyrimidin-4-yl)piperidin-4-yl)propanoic acid | 12C | 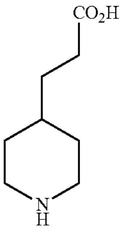 [SMILES: O=C(O)CCC1CCNCC1] | 603.2 A |

TABLE 34-continued
| No | Compound | Inter-mediate | Reagent | MS (M + H)$^+$ |
|---|---|---|---|---|
| 240 | 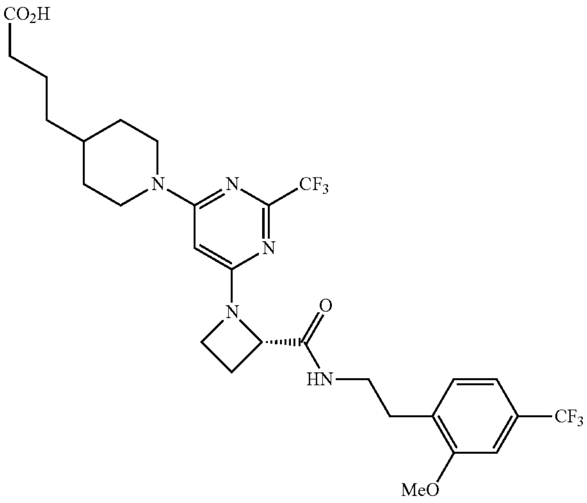 [SMILES: COc1cc(C(F)(F)F)ccc1CCNC(=O)[C@@H]1CCN1c1cc(N2CCC(CCCC(=O)O)CC2)nc(C(F)(F)F)n1] (S)-4-(1-(6-(2-((2-methoxy-4-(trifluoromethyl)phenethyl)carbamoyl) azetidin-1-yl)-2-(trifluoromethyl)pyrimidin-4-yl)piperidin-4-yl)butanoic acid | 12C | 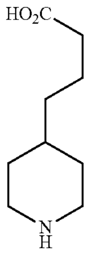 | 618.6 |
| 241 | 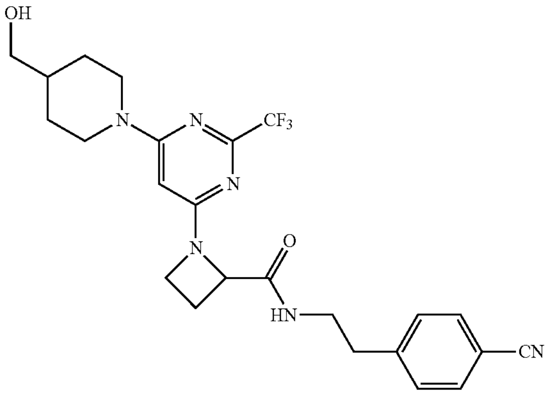 [SMILES: N#Cc1ccc(CCNC(=O)C2CCN2c2cc(N3CCC(CO)CC3)nc(C(F)(F)F)n2)cc1] N-(4-cyanophenethyl)-1-(6-(4-(hydroxymethyl)piperidin-1-yl)-2-(trifluoromethyl)pyrimidin-4-yl) azetidine-2-carboxamide | 12B | 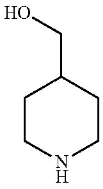 | 489.4 A |

Example 48

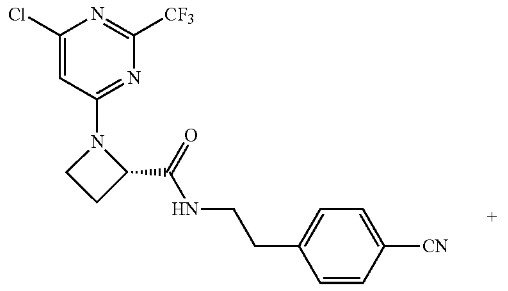

Intermediate 12

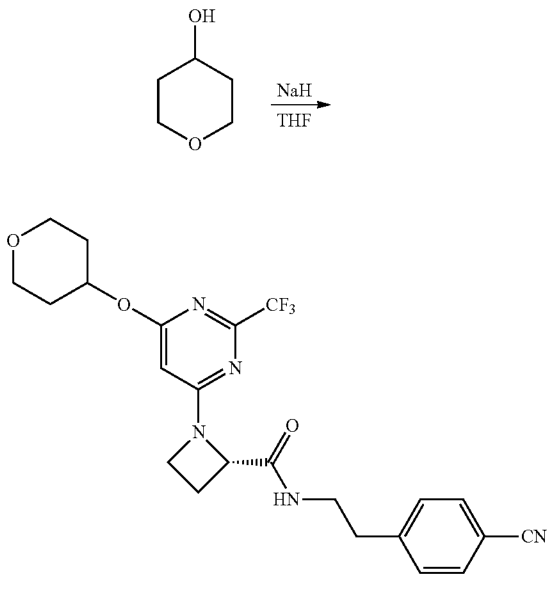

Compound 242

(S)—N-(4-cyanophenethyl)-1-(6-((tetrahydro-2H-pyran-4-yl)oxy)-2-(trifluoromethyl)pyrimidin-4-yl)azetidine-2-carboxamide Using the procedure as described in Example 3, Intermediate 12 (40 mg, 0.10 mmol) was converted to Compound 242 (6.3 mg, 14%). LCMS (Method A): m/z 476.4 $(M+H)^+$. $^1H$ NMR ($CDCl_3$) δ 8.03 (b, 1H), 7.47-7.45 (m, 2H), 7.25-7.23 (m, 2H), 5.63 (s, 1H), 5.36-5.30 (m, 1H), 4.84-4.80 (m, 1H), 3.88-3.82 (m, 3H), 3.88-3.82 (m, 1H), 3.66-3.58 (m, 3H), 3.52-3.43 (m, 1H), 2.94-2.84 (m, 3H), 2.55-2.47 (m, 1H), 2.11-2.03 (m, 2H), 1.85-1.72 (m, 2H). Using the procedure described above for Example 48, the following compounds were prepared from Intermediates and reagents as indicated in Table 35.

TABLE 35
| No | Structure | Inter-mediate | Reagent | MS (M + H)$^+$ |
|---|---|---|---|---|
| 243 | 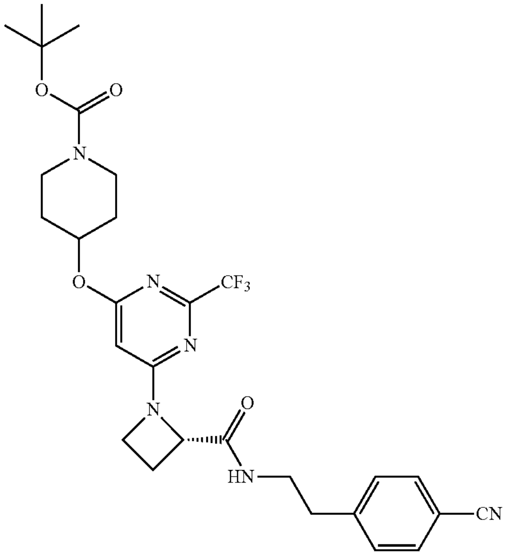 [SMILES: CC(C)(C)OC(=O)N1CCC(Oc2cc(N3CC[C@H]3C(=O)NCCc3ccc(C#N)cc3)nc(C(F)(F)F)n2)CC1] (S)-tert-butyl 4-((6-(2-((4-cyanophenethyl)carbamoyl)azetidin-1-yl)-2-(trifluoromethyl)pyrimidin-4-yl)oxy)piperidine-1-carboxylate | 12 | 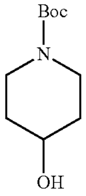 | 519.4 (loss of t-Butyl) A |
| 244 | 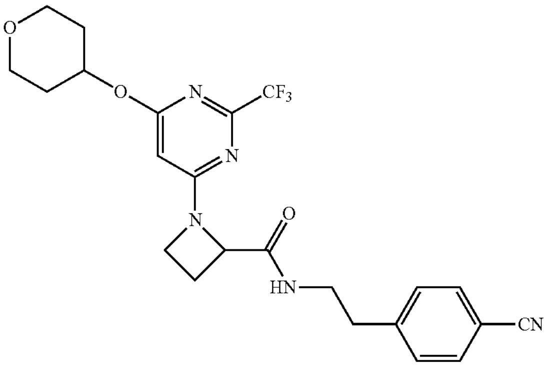 [SMILES: N#Cc1ccc(CCNC(=O)C2CCN2c2cc(OC3CCOCC3)nc(C(F)(F)F)n2)cc1] N-(4-cyanophenethyl)-1-(6-((tetra-hydro-2H-pyran-4-yl)oxy)-2-(trifluoromethyl)pyrimidin-4-yl)azetidine-2-carboxamide | 12B | 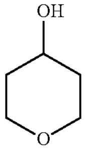 | 476.3 A |

Example 49

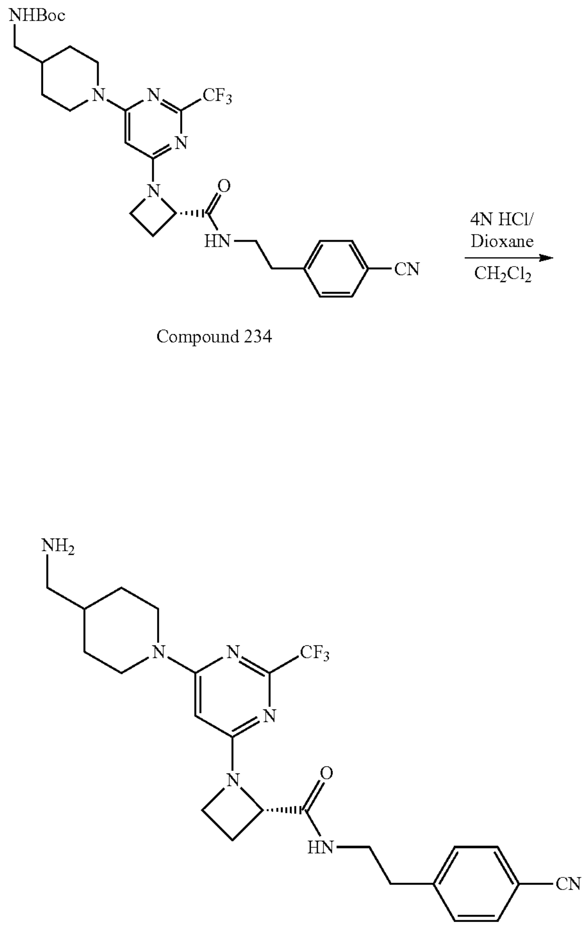

Compound 234

Compound 245

(S)-(1-(6-(4-aminomethylpiperidin-1-yl)-2-(trifluoromethyl)pyrimidin-4-yl)-N-(4-cyanophenethyl) azetidine-2-carboxamide hydrochloride Using the procedure as described for Intermediate 9, step 3, Compound 234 (69 mg, 0.12 mmol) was converted to Compound 245 (10 mg, 15%). LCMS (method A): m/z 489.4 $(M+H)^+$. $^1H$ NMR ($CD_3OD$) δ 7.53-7.50 (dd, 2H), 7.36-7.34 (m, 2H), 5.57 (s, 1H), 4.76-4.72 (dd, 1H), 4.50-4.45 (m, 2H), 4.06-4.00 (m, 1H), 3.94-3.88 (m, 1H), 3.62-3.55 (m, 1H), 3.47-3.40 (m, 1H), 3.00-2.87 (m, 6H), 2.60-2.43 (m, 2H), 2.03-1.92 (m, 1H), 1.88-1.85 (m, 2H), 1.35-1.22 (m, 2H). Using the procedure described above for Example 49, the following compounds were prepared from precursors as indicated in Table 36.

TABLE 36
| No | Structure | Pre-cursor | MS $(M + H)^+$ |
|---|---|---|---|
| 246 | 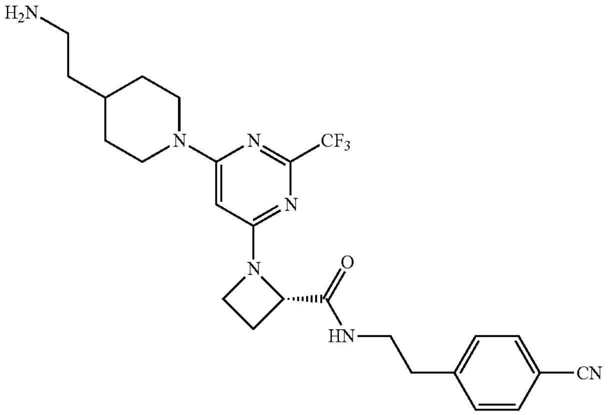 [SMILES: N#Cc1ccc(CCNC(=O)[C@@H]2CCN2c2cc(N3CCC(CCN)CC3)nc(C(F)(F)F)n2)cc1] (S)-1-(6-(4-(2-aminoethyl)piperidin-1-yl)-2-(trifluoromethyl)pyrimidin-4-yl)-N-(4-cyanophenethyl)azetidine-2-carboxamide | 235 | 502.6 A |
| 247 | 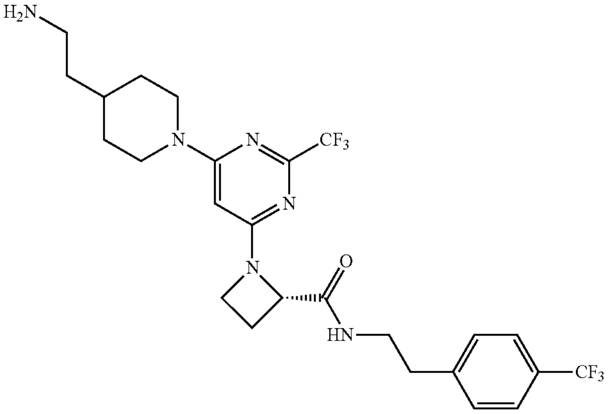 [SMILES: NCCC1CCN(c2cc(N3CC[C@H]3C(=O)NCCc3ccc(C(F)(F)F)cc3)nc(C(F)(F)F)n2)CC1] (S)-1-(6-(4-(2-aminoethyl)piperidin-1-yl)-2-(trifluoromethyl)pyrimidin-4-yl)-N-(4-(trifluoromethyl)phenethyl)-azetidine-2-carboxamide | 236 | 545.5 B |

Example 50

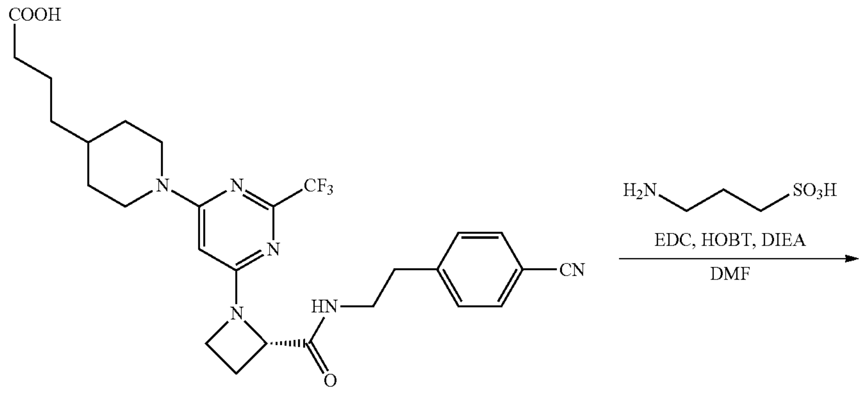

Compound 231

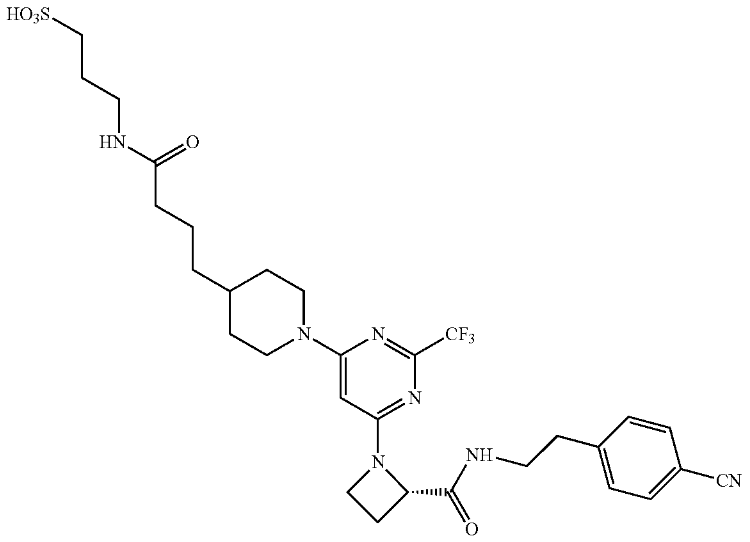

Compound 248

(S)-3-(4-(1-(6-(2-((4-cyanophenethyl)carbamoyl)azetidin-1-yl)-2-(trifluoromethyl) pyrimidin-4-yl)piperidin-4-yl)butanamido)propane-1-sulfonic acid Using the procedure as described in Example 7 and using DMF as solvent, Compound 231 (80 mg, 0.15 mmol) was converted to Compound 248 (20 mg, 20%). LCMS (Method A): m/z 666.7 $(M+H)^+$. $^1H$ NMR (DMSO-$d_6$) δ 8.20 (m, 1H), 7.83-7.80 (m, 1H), 7.70-7.68 (m, 2H), 7.40-7.38 (m, 2H), 5.57 (s, 1H), 4.60-4.57 (dd, 1H), 4.29-4.23 (m, 2H), 3.98-3.68 (m, 4H), 3.39-3.33 (m, 2H), 3.09-3.04 (m, 2H), 3.25-2.79 (m, 4H), 2.46-2.38 (m, 2H), 2.18-2.13 (m, 1H), 2.04-2.01 (m, 2H), 1.73-1.63 (m, 4H), 1.55-1.47 (m, 3H), 1.20-1.14 (m, 2H), 1.04-0.94 (m, 2H). Using the procedure described above for Example 50, the following compounds were prepared from precursors and reagents as indicated in Table 37.

TABLE 37
| No | Structure | Pre-cursor | Reagent | MS (M + H)+ |
|---|---|---|---|---|
| 249 | 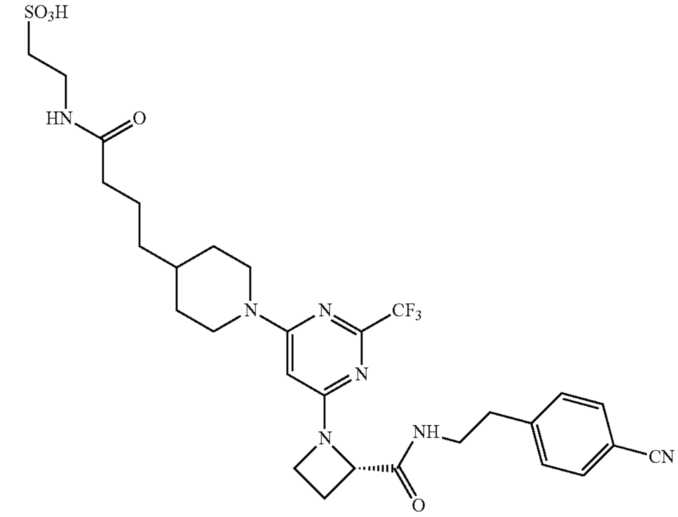 [SMILES: N#Cc1ccc(CCNC(=O)[C@@H]2CCN2c2cc(N3CCC(CCCC(=O)NCCS(=O)(=O)O)CC3)nc(C(F)(F)F)n2)cc1]<br>(S)-2-(4-(1-(6-(2-((4-cyanophenethyl)carbamoyl)azetidin-1-yl)-2-(trifluoromethyl)pyrimidin-4-yl)piperidin-4-yl)butanamido)ethanesulfonic acid | 231 | 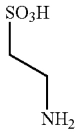 | 652.6<br>A |
| 250 | 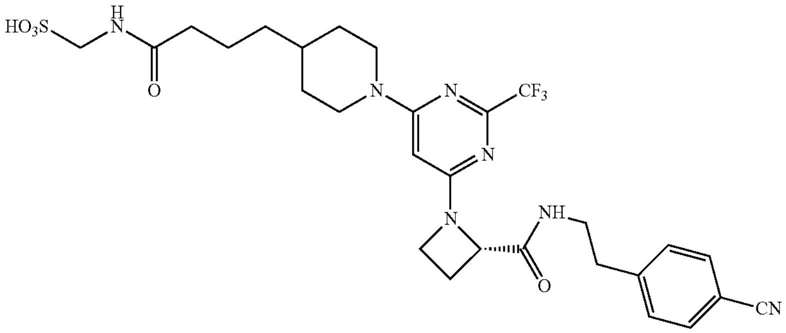 [SMILES: N#Cc1ccc(CCNC(=O)[C@@H]2CCN2c2cc(N3CCC(CCCC(=O)NCS(=O)(=O)O)CC3)nc(C(F)(F)F)n2)cc1]<br>(S)-(4-(1-(6-(2-((4-cyanophenethyl)carbamoyl)azetidin-1-yl)-2-(trifluoromethyl)pyrimidin-4-yl)piperidin-4-yl)butanamido)methanesulfonic acid | 231 | 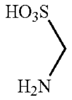 | 638.3<br>A |

TABLE 37-continued

| No | Structure | Pre-cursor | Reagent | MS (M + H)+ |
|---|---|---|---|---|
| 251 | 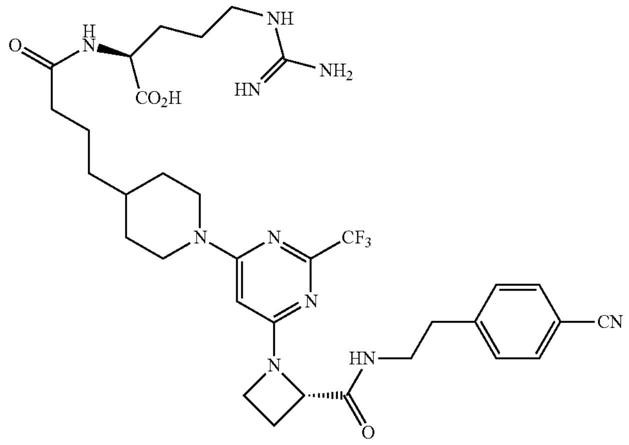 [SMILES: N#Cc1ccc(CCNC(=O)[C@@H]2CCN2c2cc(N3CCC(CCCC(=O)N[C@@H](CCCNC(=N)N)C(=O)O)CC3)nc(C(F)(F)F)n2)cc1]<br>(S)-2-(4-(1-(6-((S)-2-((4-cyanophenethyl)carbamoyl)azetidin-1-yl)-2-(trifluoromethyl)pyrimidin-4-yl)piperidin-4-yl)butanamido)-5-guanidinopentanoic acid | 231 | Coupling with<br>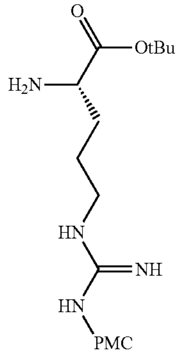<br>followed by de-protection with TFA as in Example 4 | 701.4<br>A |
| 252 | 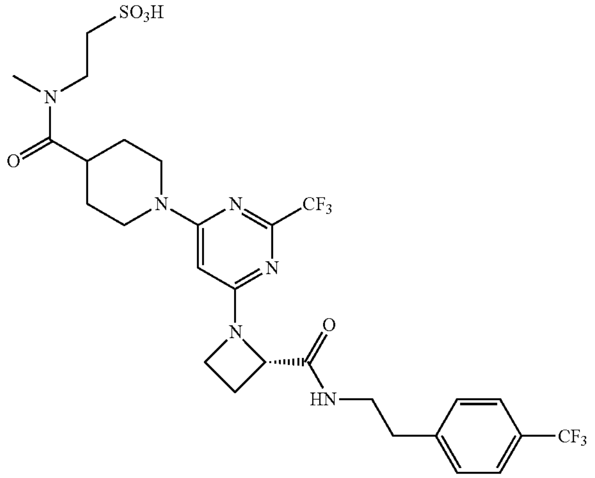 [SMILES: CN(CCS(=O)(=O)O)C(=O)C1CCN(c2cc(N3CC[C@H]3C(=O)NCCc3ccc(C(F)(F)F)cc3)nc(C(F)(F)F)n2)CC1]<br>(S)-2-(N-methyl-3-(1-(2-(trifluoromethyl)-6-(2-((4-(trifluoromethyl)phenethyl)carbamoyl)azetidin-1-yl)pyrimidin-4-yl)piperidin-4-yl)propanamido)ethanesulfonic acid | 232 | 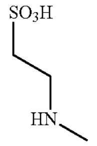 | 695.6<br>B |

TABLE 37-continued
| No | Structure | Pre-cursor | Reagent | MS (M + H)+ |
|---|---|---|---|---|
| 253 | 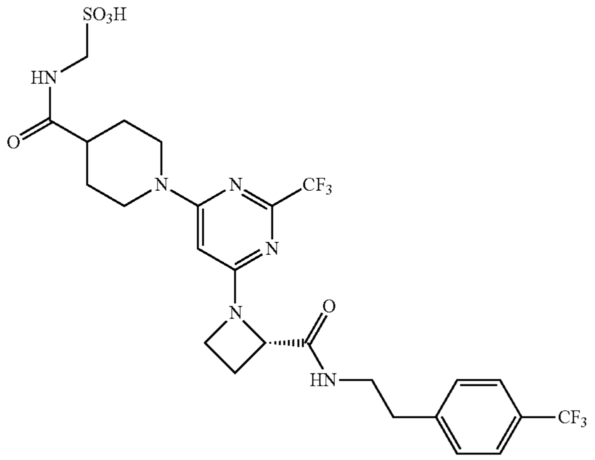 [SMILES: O=C(NCS(=O)(=O)O)C1CCN(c2cc(N3CC[C@H]3C(=O)NCCc3ccc(C(F)(F)F)cc3)nc(C(F)(F)F)n2)CC1] (S)-(3-(1-(2-(trifluoromethyl)-6-(2-((4-(trifluoromethyl)phenethyl)-carbamoyl)azetidin-1-yl)pyrimidin-4-yl)piperidin-4-yl)propanamido)-methanesulfonic acid | 232 | 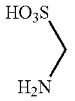 | 667.5 B |
| 254 | 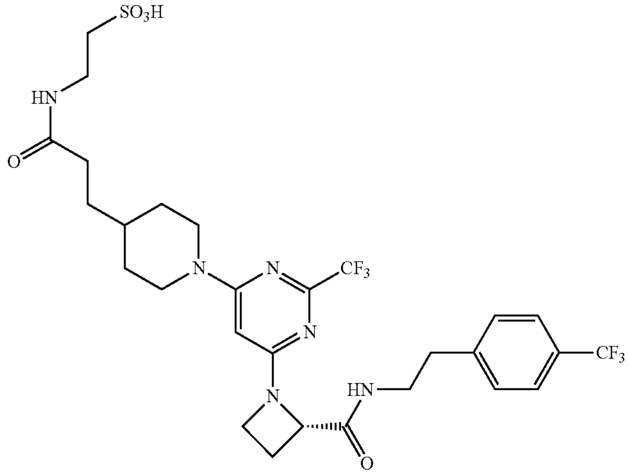 [SMILES: O=C(CCC1CCN(c2cc(N3CC[C@H]3C(=O)NCCc3ccc(C(F)(F)F)cc3)nc(C(F)(F)F)n2)CC1)NCCS(=O)(=O)O] (S)-2-(3-(1-(2-(trifluoromethyl)-6-(2-((4-(trifluoromethyl)-phenethyl)carbamoyl)azetidin-1-yl)pyrimidin-4-yl)piperidin-4-yl)propanamido)ethanesulfonic acid | 232 | 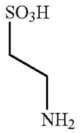 | 681.2 B |

TABLE 37-continued

| No | Structure | Pre-cursor | Reagent | MS (M + H)+ |
|---|---|---|---|---|
| 255 | 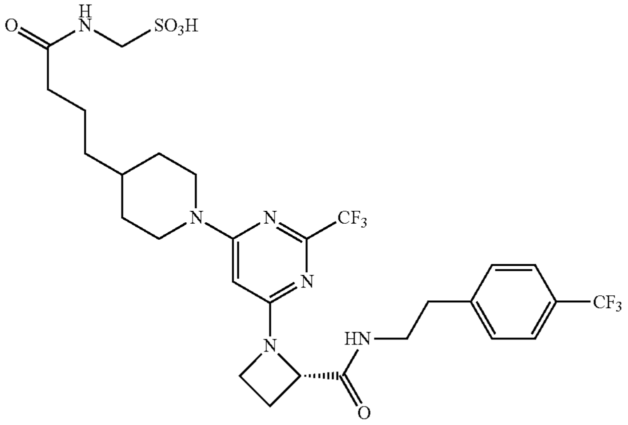 [SMILES: O=C(CCCC1CCN(c2cc(N3CC[C@H]3C(=O)NCCc3ccc(C(F)(F)F)cc3)nc(C(F)(F)F)n2)CC1)NCS(=O)(=O)O]<br>(S)-(4-(1-(2-(trifluoromethyl)-6-(2-((4-(trifluoromethyl)phenethyl)carbamoyl) azetidin-1-yl)pyrimidin-4-yl)piperidin-4-yl)butanamido)methanesulfonic acid | 233 | 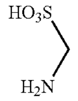 | 681.3 B |
| 256 | 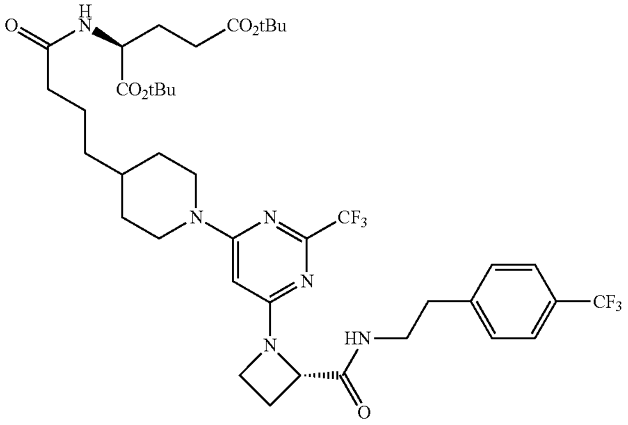 [SMILES: CC(C)(C)OC(=O)CC[C@H](NC(=O)CCCC1CCN(c2cc(N3CC[C@H]3C(=O)NCCc3ccc(C(F)(F)F)cc3)nc(C(F)(F)F)n2)CC1)C(=O)OC(C)(C)C]<br>(S)-di-tert-butyl 2-(4-(1-(2-(trifluoromethyl)-6-((S)-2-((4-(trifluoromethyl)phenethyl)carbamoyl) azetidin-1-yl)pyrimidin-4-yl)piperidin-4-yl)butanamido)pentanedioate | 233 | 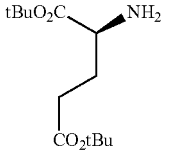 | 829.5 B |
| 257 | 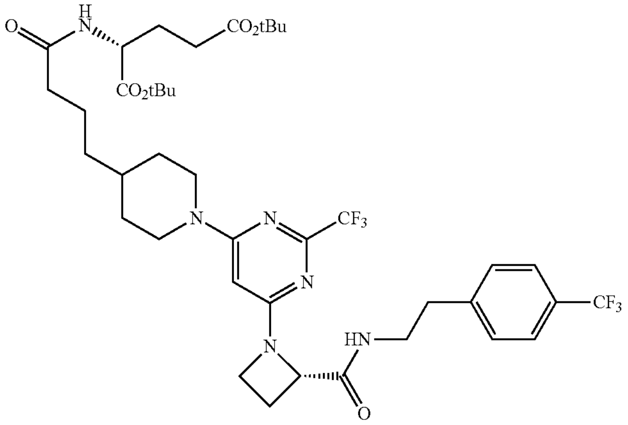 [SMILES: CC(C)(C)OC(=O)CC[C@@H](NC(=O)CCCC1CCN(c2cc(N3CC[C@H]3C(=O)NCCc3ccc(C(F)(F)F)cc3)nc(C(F)(F)F)n2)CC1)C(=O)OC(C)(C)C]<br>(R)-di-tert-butyl 2-(4-(1-(2-(trifluoromethyl)-6-((S)-2-((4-(trifluoromethyl)phenethyl)carbamoyl) | 233 | 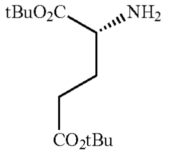 | 829.4 B |

TABLE 37-continued

| No | Structure | Pre-cursor | Reagent | MS (M + H)$^+$ |
|---|---|---|---|---|
| | azetidin-1-yl)pyrimidin-4-yl)piperidin-4-yl)butanamido)pentanedioate | | | |
| 258 | 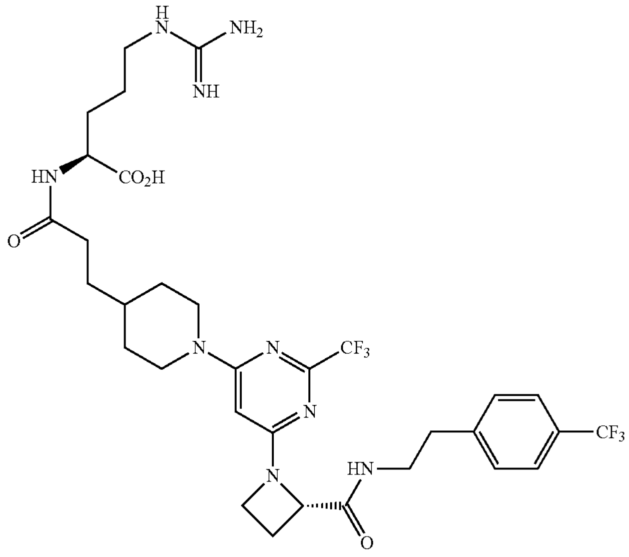 [SMILES: N=C(N)NCCC[C@H](NC(=O)CCC1CCN(c2cc(N3CC[C@H]3C(=O)NCCc3ccc(C(F)(F)F)cc3)nc(C(F)(F)F)n2)CC1)C(=O)O] (S)-5-guanidino-2-(3-(1-(2-(trifluoromethyl)-6-((S)-2-((4-(trifluoromethyl)phenethyl)carbamoyl) azetidin-1-yl)pyrimidin-4-yl)piperidin-4-yl)propanamido)pentanoic acid | 232 | Coupling with 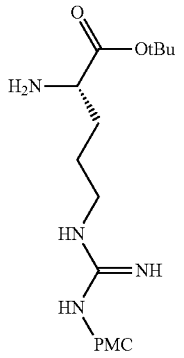 followed by deprotection with TFA as in Example 4 | 730.3 A |
| 259 | 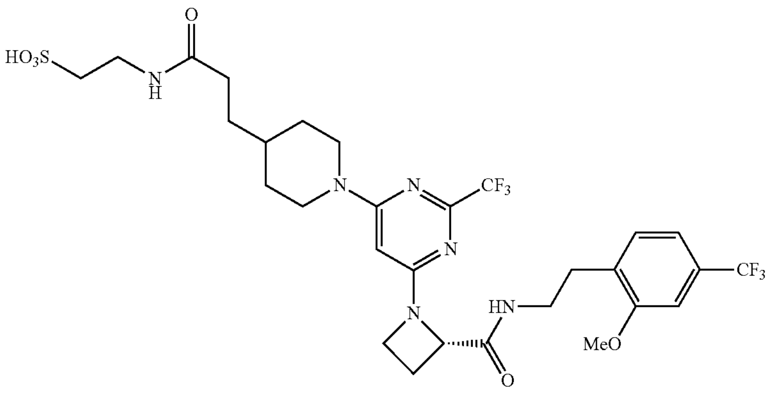 [SMILES: COc1cc(C(F)(F)F)ccc1CCNC(=O)[C@@H]1CCN1c1cc(N2CCC(CCC(=O)NCCS(=O)(=O)O)CC2)nc(C(F)(F)F)n1] (S)-2-(3-(1-(6-(2((2-methoxy-4-(trifluoromethyl)phenethyl)carbamoyl) azetidin-1-yl)-2-trifluoromethyl)-pyrimidin-4-yl)piperidin-4-yl)propanamido)ethanesulfonic acid | 239 | 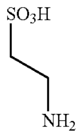 | 711.7 A |

Example 51

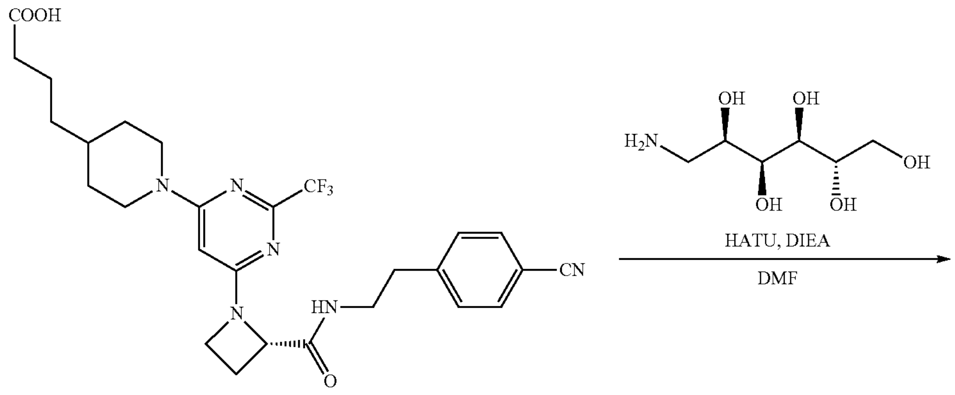

Compound 231

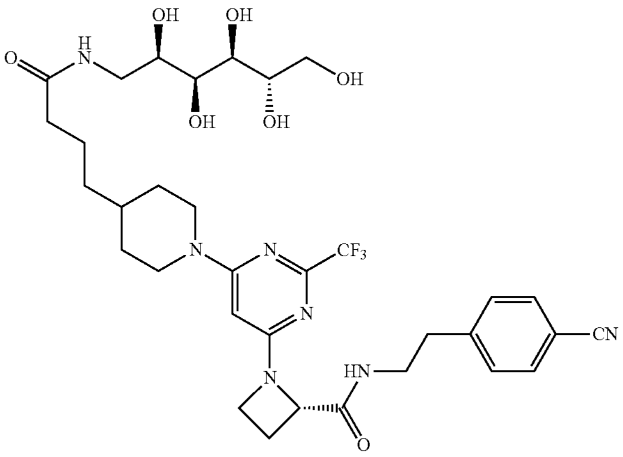

Compound 260

(S)—N-(4-cyanophenethyl)-1-(6-(4-(4-oxo-4-(((2R, 3S,4S,5S)-2,3,4,5,6-pentahydroxyhexyl) amino) butyl)piperidin-1-yl)-2-(trifluoromethyl)pyrimidin-4-yl)azetidine-2-carboxamide To a solution of Compound 231 (80 mg, 0.15 mmol) in DMF (2 mL) were added HATU (56 mg, 0.15 mmol) and N,N-diisopropylethylamine (51 μl, 0.29 mmol). The reaction was stirred for 20 minutes. D-Glucamine (40 mg, 0.22 mmol) was added. The reaction was stirred for two hours at room temperature. The reaction was purified by MS-HPLC to afford Compound 260 (72 mg, 69%). LCMS (Method A): m/z 708.8 $(M+H)^+$. $^1H$ NMR (DMSO-$d_6$) δ 8.20-8.18 (m, 1H), 7.74-7.68 (m, 3H), 7.40-7.38 (m, 2H), 5.56 (b, 1H), 4.61-5.59 (dd, 1H), 4.29-3.55 (m, 7H), 3.49-3.23 (m, 6H), 3.04-2.97 (m, 1H), 2.85-2.79 (m, 4H), 2.19-2.05 (m, 3H), 1.73-1.70 (m, 2H), 1.55-1.51 (m, 3H), 1.20-1.15 (m, 2H), 1.04-0.96 (m, 2H). Using the procedure described above for Example 51, the following compounds were prepared from precursors and reagents as indicated in Table 38.

TABLE 38
| No | Structure | Pre-cursor | Reagent | MS $(M + H)^+$ |
|---|---|---|---|---|
| 261 | 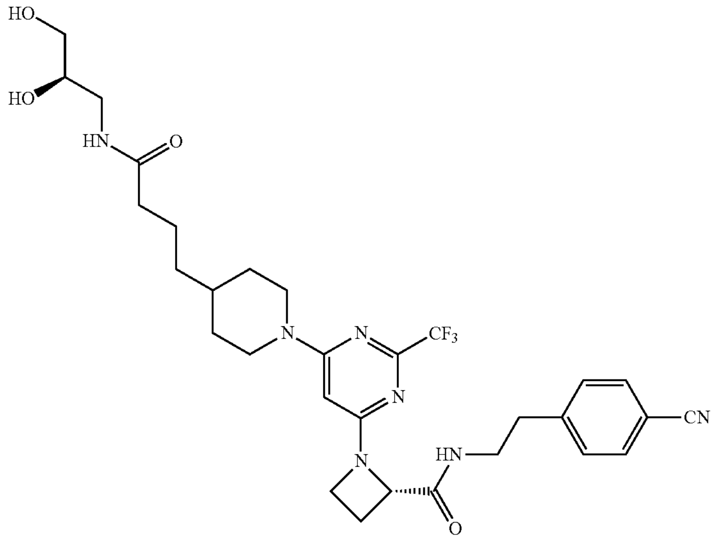 [SMILES: N#Cc1ccc(CCNC(=O)[C@@H]2CCN2c2cc(N3CCC(CCCC(=O)NC[C@@H](O)CO)CC3)nc(C(F)(F)F)n2)cc1] (S)-N-(4-cyanophenethyl)-1-(6-(4-(4-(((R)-2,3-dihydroxypropyl)amino)-4-oxobutyl)piperidin-1-yl)-2-(trifluoromethyl)pyrimidin-4-yl)azetidine-2-carboxamide | 231 | 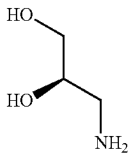 | 618.7 A |
| 262 | 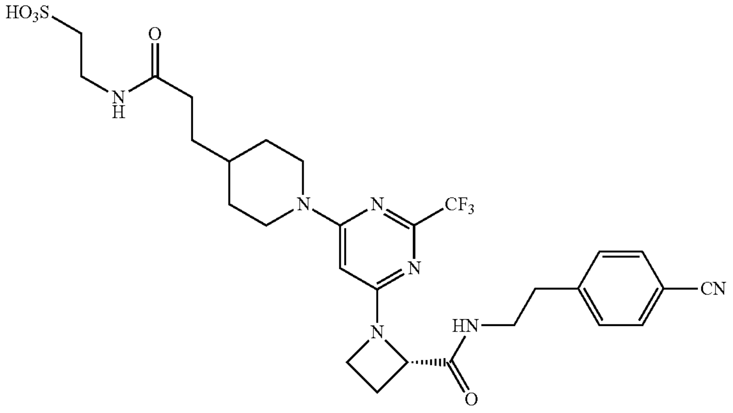 [SMILES: N#Cc1ccc(CCNC(=O)[C@@H]2CCN2c2cc(N3CCC(CCC(=O)NCCS(=O)(=O)O)CC3)nc(C(F)(F)F)n2)cc1] (S)-3-(3-(1-(6-(2((4-cyanophenethyl)carbamoyl)azetidin-1-yl)-2-trifluoromethyl)pyrimidin-4-yl)propanamido)propane-1-sulfonic acid | 227 | 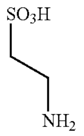 | 638.6 A |

TABLE 38-continued
| No | Structure | Pre-cursor | Reagent | MS (M + H)+ |
|---|---|---|---|---|
| 263 | 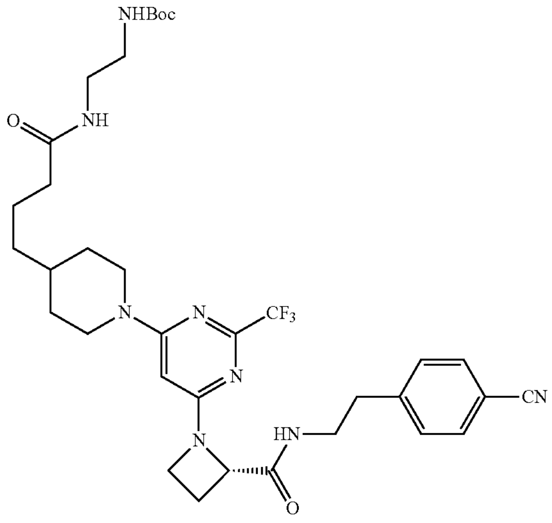 [SMILES: CC(C)(C)OC(=O)NCCNC(=O)CCCC1CCN(c2cc(N3CC[C@H]3C(=O)NCCc3ccc(C#N)cc3)nc(C(F)(F)F)n2)CC1] (S)-tert-butyl (2-(4-(1-(6-(2-((4-cyanophenethyl)carbamoyl)azetidin-1-yl)-2-(trifluoromethyl)pyrimidin-4-yl)piperidin-4-yl)butanamido)-ethyl)carbamate | 231 | 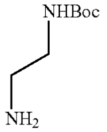 | 687.7 A |
| 264 | 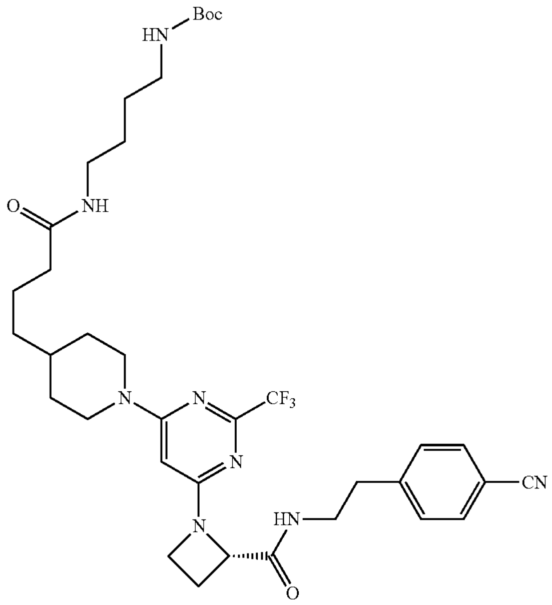 [SMILES: CC(C)(C)OC(=O)NCCCCNC(=O)CCCC1CCN(c2cc(N3CC[C@H]3C(=O)NCCc3ccc(C#N)cc3)nc(C(F)(F)F)n2)CC1] (S)-tert-butyl (4-(4-(1-(6-(2-((4-cyanophenethyl)carbamoyl)azetidin-1-yl)-2-(trifluoromethyl)pyrimidin-4-yl)piperidin-4-yl)butanamido)-butyl)carbamate | 231 | 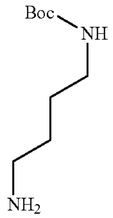 [SMILES: CC(C)(C)OC(=O)NCCCCN] | 579.9 A |

Example 52

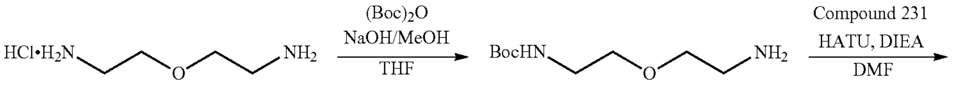

Compound 52A

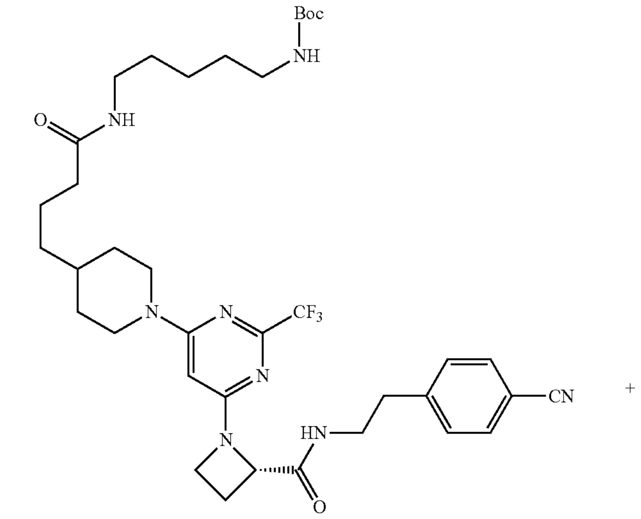

Compound 265

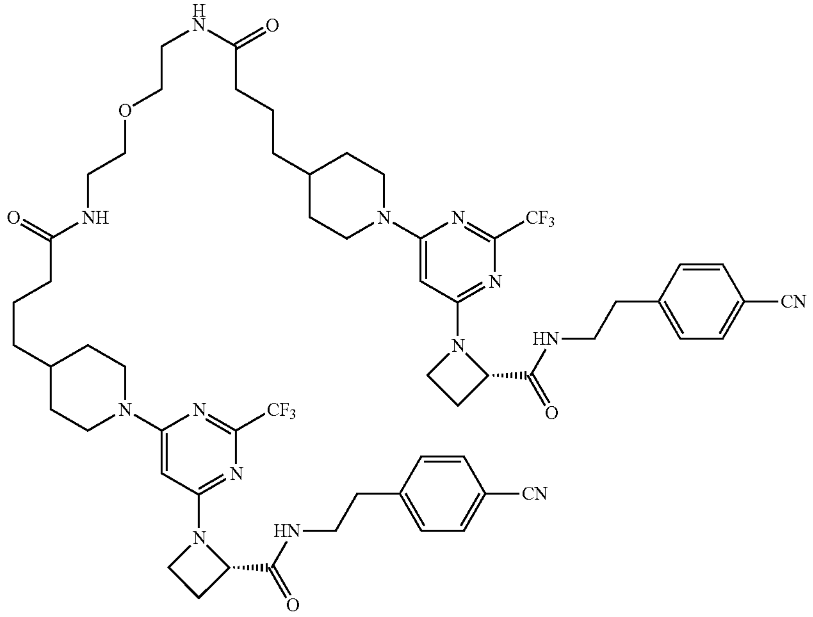

Compound 266 tert-butyl (2-(2-aminoethoxy)ethyl)carbamate

To a solution of NaOH (400 mg, 10 mmol) in anhydrous MeOH (70 mL) was added 2,2'-oxydiethanamine dihydrochloride (1.0 g, 5.7 mmol). The reaction mixture was stirred for 30 minutes at room temperature, and di-tert-butyl dicarbonate (740 mg, 3.40 mmol) in anhydrous THF (15 mL) was added drop wise at room temperature over 15 minutes. The reaction was stirred overnight. The mixture was concentrated in vacuo. The residue was taken up in $CH_2Cl_2$ (200 mL) and was stirred vigorously at room temperature for four hours. The mixture was filtered and the filtrate was concentrated in vacuo. The residue was used directly in the next reaction. The crude mixture can also be purified by silica gel chromatography to afford Compound 52A. LCMS (Method A): m/z 205.3 $(M+H)^+$.

(S)-tert-butyl (2-(2-(4-(1-(6-(2-((4-cyanophenethyl) carbamoyl)azetidin-1-yl)-2-(trifluoromethyl)pyrimidin-4-yl)piperidin-4-yl)butanamido)ethoxy)ethyl) carbamate Using the procedure as described in Example 51, Compound 231 (210 mg, 0.39 mmol) was coupled with crude 52A (88 mg, 0.43 mmol) to afford Compound 265 and Compound 266 (98 mg, 22%) (LCMS (Method A): m/z 731.7 $(M+H)^+$). Compound 265: LCMS (Method A): m/z 579.8 $(1/2M+H)^+$. $^1H$ NMR ($CDCl_3$) δ 8.50 (br s, 2H), 7.46-7.44 (m, 4H), 7.25-7.23 (m, 4H), 6.05-6.03 (m, 2H), 5.24 (s, 2H), 4.79-4.75 (dd, 2H), 4.35 (br s, 4H), 3.94-3.89 (m, 2H), 3.81-3.75 (m, 2H), 3.65-3.53 (m, 6H), 3.51-3.41 (m, 6H), 2.93-2.81 (m, 10H), 2.48-2.39 (m, 2H), 2.23-2.19 (t, 4H), 1.81-1.78 (m, 4H), 1.73-1.54 (m, 6H), 1.33-1.27 (m, 8H).

Example 53

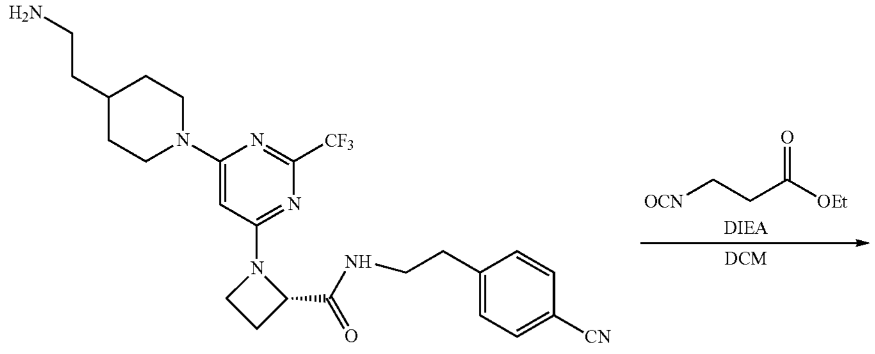

Compound 246

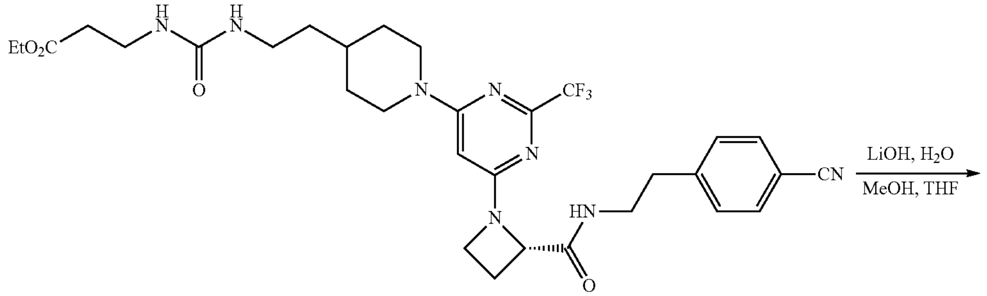

Compound 267

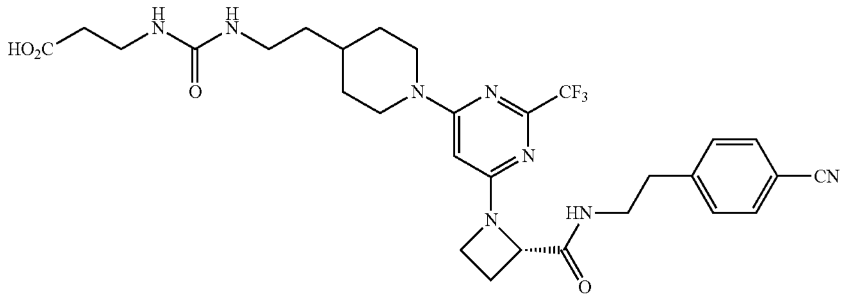

Compound 268

(S)-ethyl 3-(3-(2-(1-(6-(2-((4-cyanophenethyl)carbamoyl)azetidin-1-yl)-2-(trifluoromethyl) pyrimidin-4-yl)piperidin-4-yl)ethyl)ureido)propanoate Using the procedure as described in Example 6, Compound 246 (100 mg, 0.19 mmol) was converted to Compound 267 (110 mg, 91%). LCMS (method A): m/z 645.7 $(M+H)^+$.

(S)-3-(3-(2-(1-(6-(2-((4-cyanophenethyl)carbamoyl) azetidin-1-yl)-2-(trifluoromethyl) pyrimidin-4-yl) piperidin-4-yl)ethyl)ureido)propanoic acid Using the procedure as described in Example 16, Compound 267 (100 mg, 0.16 mmol) was converted to Compound 268 (49 mg, 51%). LCMS (method A): m/z 617.6 $(M+H)^+$. $^1H$ NMR ($CD_3OD$) δ 8.57 (t, 1H), 7.52-7.50 (dd, 2H), 7.33-7.31 (m, 2H), 5.44 (s, 1H), 4.75-4.73 (dd, 1H), 4.39 (b, 2H), 4.03-3.97 (m, 1H), 3.91-3.85 (m, 1H), 3.63-3.56 (m, 1H), 3.49-3.36 (m, 3H), 3.21-3.17 (t, 2H), 2.94-2.86 (m, 4H), 2.62-2.48 (m, 4H), 1.83-1.81 (m, 2H), 1.69-1.61 (m, 1H), 1.48-1.43 (m, 2H), 1.26-1.15 (m, 2H).

Example 54

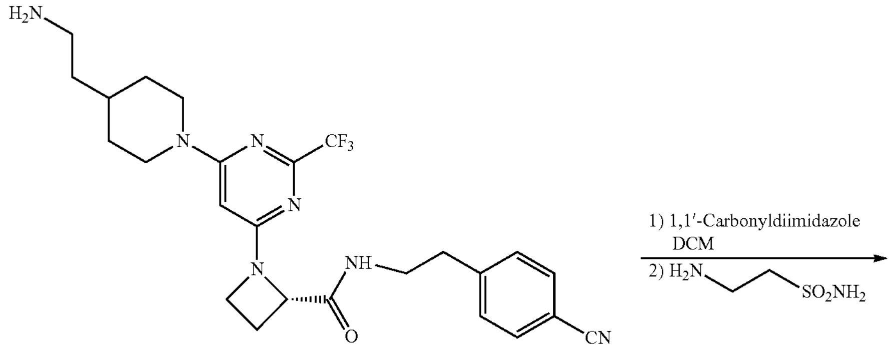

Compound 246

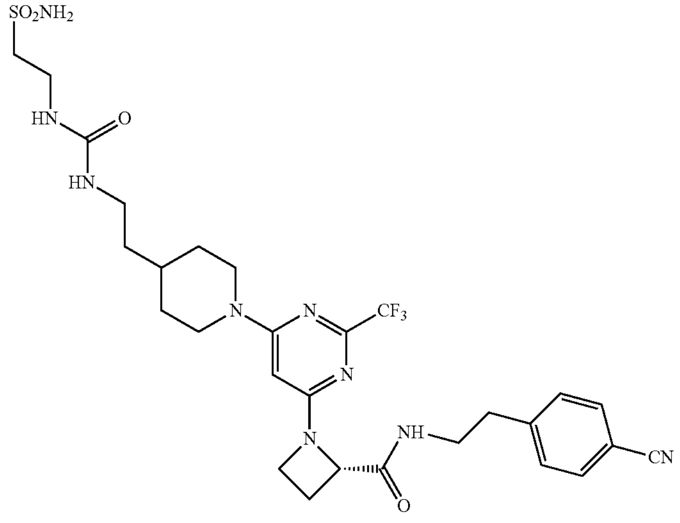

Compound 269

(S)—N-(4-cyanophenethyl)-1-(6-(4-(2-(3-(2-sulfamoylethyl)ureido)ethyl)piperidin-1-yl)-2-(trifluoromethyl)pyrimidin-4-yl)azetidine-2-carboxamide Using the procedure as described in Example 9, step 2, Compound 246 (100 mg, 0.19 mmol) was converted to Compound 269 (64 mg, 53%). LCMS (method A): m/z 652.6 $(M+H)^+$. $^1H$ NMR (DMSO-$d_6$) δ 8.19 (t, 1H), 7.70-7.68 (m, 2H), 7.40-7.38 (m, 2H), 6.86 (s, 2H), 6.11 (t, 1H), 5.94 (t, 1H), 5.57 (b, 1H), 4.61-4.57 (dd, 1H), 4.28-4.24 (b, 2H), 3.97-3.86 (m, 2H), 3.42-3.35 (m, 4H), 3.08-3.00 (m, 4H), 2.85-2.79 (m, 4H), 2.53-2.50 (m, 1H), 2.19-2.13 (m, 1H), 1.73-1.70 (m, 2H), 1.57-1.55 (m, 1H), 1.33-1.28 (m, 2H), 1.06-0.98 (m, 2H).

Using the procedure described above for Example 54, the following compounds were prepared from Compound 246 and reagents as indicated in Table 39.

TABLE 39

| No | Structure | reagent | MS $(M+H)^+$ |
|---|---|---|---|
| 270 | 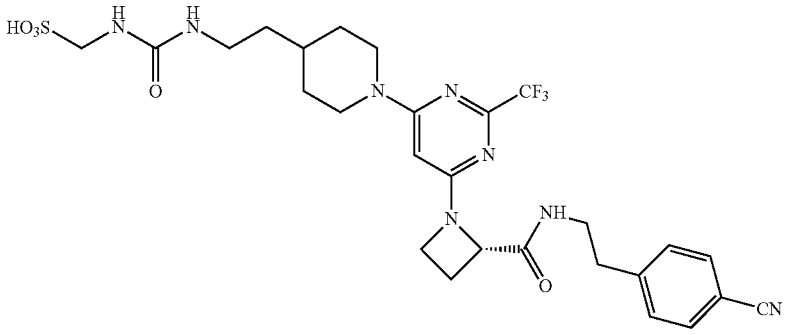 [SMILES: N#Cc1ccc(CCNC(=O)[C@@H]2CCN2c2cc(N3CCC(CCNC(=O)NCS(=O)(=O)O)CC3)nc(C(F)(F)F)n2)cc1] (S)-(3-(2-(1 -(6-(2-((4-cyanophenethyl)carbamoyl)azetidin-1-yl)-2-(trifluoromethyl)pyrimidin-4-yl)piperidin-4-yl)ethyl)ureido)-methanesulfonic acid | 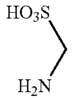 | 639.5 A |
| 271 | 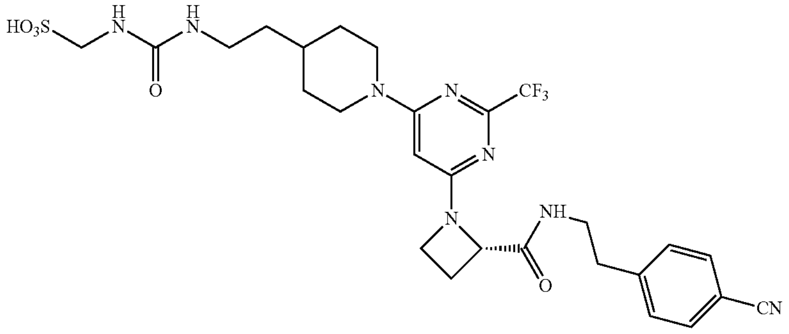 [SMILES: N#Cc1ccc(CCNC(=O)[C@@H]2CCN2c2cc(N3CCC(CCNC(=O)NCS(=O)(=O)O)CC3)nc(C(F)(F)F)n2)cc1] (S)-2-(3-(2-(1-(6-(2-((4-cyanophenethyl)carbamoyl)azetidin-1-yl)-2-(trifluoromethyl)pyrimidin-4-yl)piperidin-4-yl)ethyl)ureido)-ethanesulfonic acid | 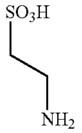 | 653.2 A |

TABLE 39-continued
| No | Structure | reagent | MS $(M + H)^+$ |
|---|---|---|---|
| 272 | 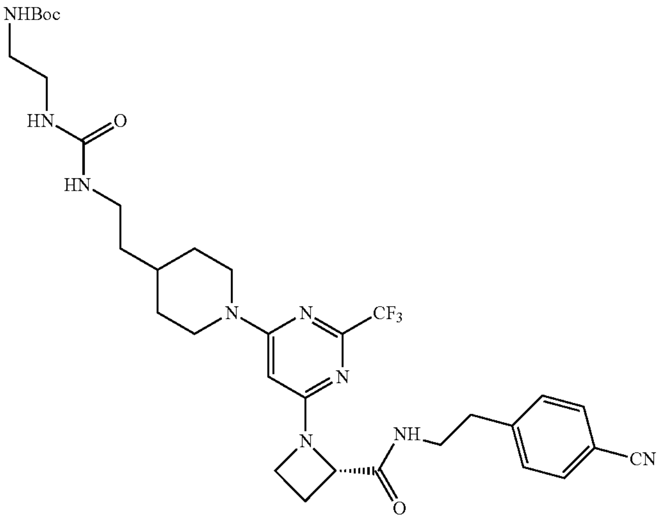 [SMILES: CC(C)(C)OC(=O)NCCNC(=O)NCCC1CCN(c2cc(N3CC[C@H]3C(=O)NCCc3ccc(C#N)cc3)nc(C(F)(F)F)n2)CC1]<br>(S)-tert-butyl (2-(3-(2-(1-(6-(2-((4-cyanophenethyl)carbamoyl)azetidin-1-yl)-2-(trifluoromethyl)pyrimidin-4-yl)-piperidin-4-yl)ethyl)ureido)ethyl)carbamate | 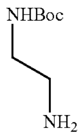 | 688.6<br>A |
| 273 | 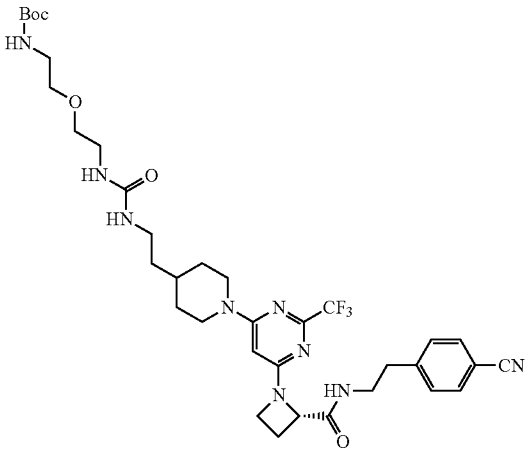 [SMILES: CC(C)(C)OC(=O)NCCOCCNC(=O)NCCC1CCN(c2cc(N3CC[C@H]3C(=O)NCCc3ccc(C#N)cc3)nc(C(F)(F)F)n2)CC1]<br>(S)-tert-butyl (2-(2-(3-(2-(1-(6-(2-((4-cyanophenethyl)carbamoyl)azetidin-1-yl)-2-(trifluoromethyl)pyrimidin-4-yl)piperidin-4-yl)ethyl)ureido)-ethoxy)ethyl)carbamate | 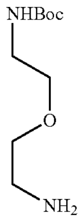 | 732.5<br>A |

TABLE 39-continued
| No | Structure | reagent | MS (M + H)$^+$ |
|---|---|---|---|
| 274 | 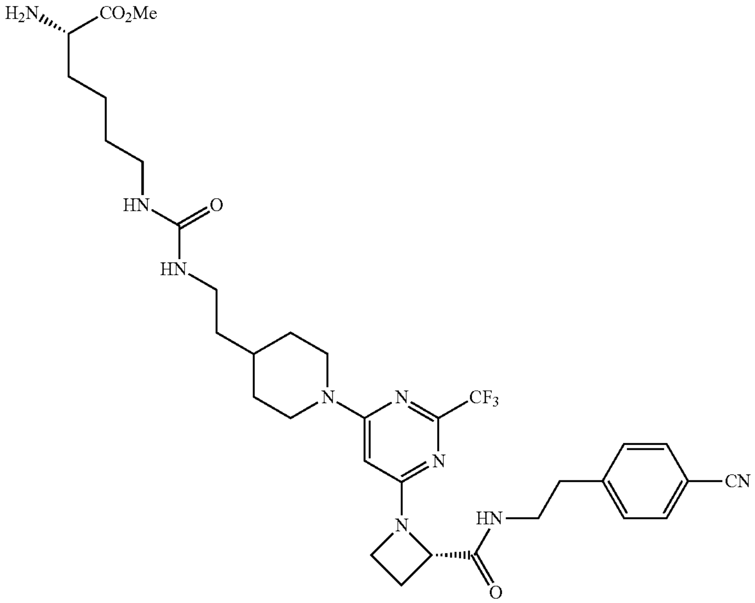 [SMILES: COC(=O)[C@@H](N)CCCCNC(=O)NCCC1CCN(c2cc(N3CC[C@H]3C(=O)NCCc3ccc(C#N)cc3)nc(C(F)(F)F)n2)CC1] (S)-methyl 2-amino-6-(3-(2-(1-(6-((S)-2-((4-cyanophenethyl)carbamoyl)azetidin-1-yl)-2-(trifluoromethyl)pyrimidin-4-yl)piperidin-4-yl)ethyl)ureido)hexanoate | 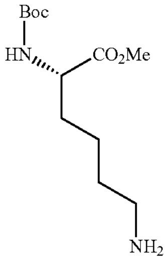 [SMILES: COC(=O)[C@H](CCCCN)NC(=O)OC(C)(C)C] followed by de-protection with TFA as in Example 4 | 688.6 A |
Example 55
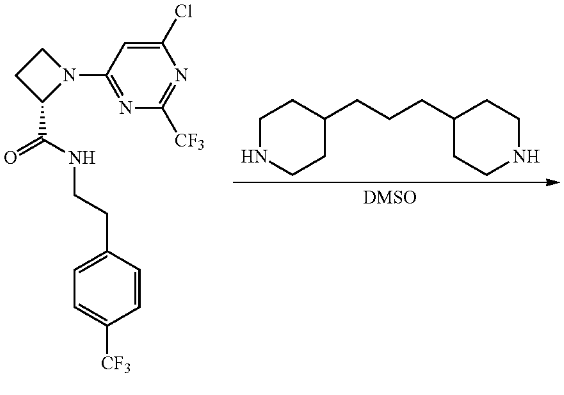
Intermediate 12A -continued

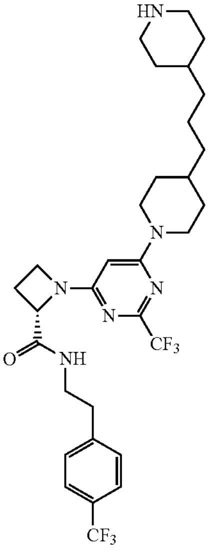

+

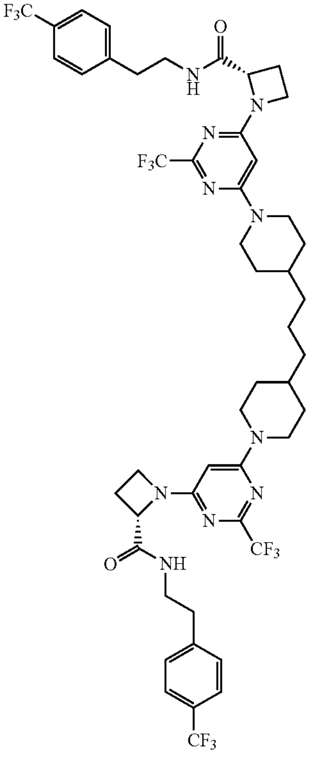

Compound 275

Compound 276

(S)-1-(6-(4-(3-(piperidin-4-yl)propyl)piperidin-1-yl)-2-(trifluoromethyl)pyrimidin-4-yl)-N-(4-(trifluoromethyl)phenethyl)azetidine-2-carboxamide A mixture of Intermediate 12A (1.4 g, 3.1 mmol), 1,3-di(piperidin-4-yl)propane (2.6 g, 12 mmol) and DMSO (5 mL) in a microwave vessel was capped and heated to 120° C. for four hours in a heating block. Upon cooling, the mixture was diluted with 80 mL of water and 80 mL of ethyl acetate. The layers were separated and the aqueous layer was extracted twice with 30 mL ethyl acetate. The combined organics were washed with water and brine, dried over sodium sulfate, and concentrated. The residue was purified by silica gel chromatography (3%-10% MeOH/DCM gradient) to afford 0.69 g of Compound 275 and 160 mg of Compound 276. Compound 275: LCMS (method B): m/z 627.7 $(M+H)^+$, $^1H$ NMR ($CDCl_3$) δ 8.49 (br s, 1H), 7.44 (2, 2H), 7.25 (d, 2H), 5.25 (s, 1H), 4.78 (t, 1H), 4.35 (m, 2H), 3.92 (m, 1H), 3.78 (m. 1H), 3.59 (m, 1H), 3.49 (m, 1H), 3.06 (m, 2H), 2.86 (m, 5H), 2.58 (m, 2H), 2.46 (m, 1H), 1.78 (m, 4H), 1.66 (m, 2H), 1.55 (m, 1H), 1.31-1.07 (m, 10H)). Compound 276: LCMS (method B): m/z 522.8 $(M/2+H)^+$, $^1H$ NMR ($CDCl_3$) δ 8.47 (br s, 2H), 7.44 (d, 4H), 7.25 (d, 4H), 5.25 (s, 2H), 4.79 (t, 2H), 4.36 (m, 4H), 3.92 (m, 2H), 3.78 (m, 2H), 3.60 (m, 2H), 3.49 (m, 2H), 2.93-2.83 (m, 10), 2.49 (m, 2H), 1.74 (m, 4H), 1.57 (m, 3H), 1.37 (m, 2H), 1.28 (m, 5H), 1.16 (m, 4H)).

Using the procedure described above for Example 55, the following compound was prepared from Intermediate 12A and the reagent as indicated in Table 40.

TABLE 40

| No | Structure | reagent | MS $(M + H)^+$ |
|---|---|---|---|
| 277 | 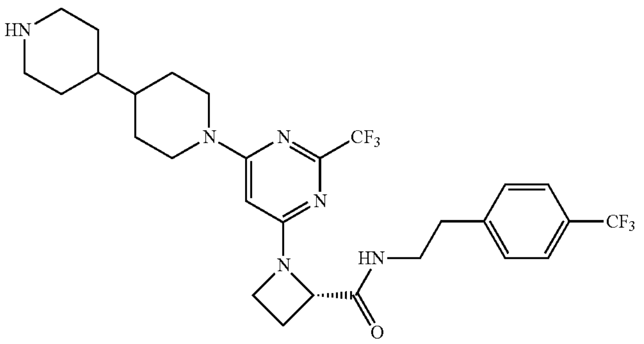 [SMILES: O=C(NCCc1ccc(C(F)(F)F)cc1)[C@@H]1CCN1c1cc(N2CCC(C3CCNCC3)CC2)nc(C(F)(F)F)n1] (S)-1-(6-([4,4'-bipiperidin]-1-yl)-2-(trifluoromethyl)pyrimidin-4-yl)-N-(4-(trifluoromethyl)phenethyl)-azetidine-2-carboxamide | 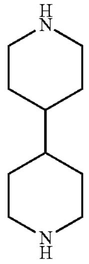 | 585.3 B |

Example 56

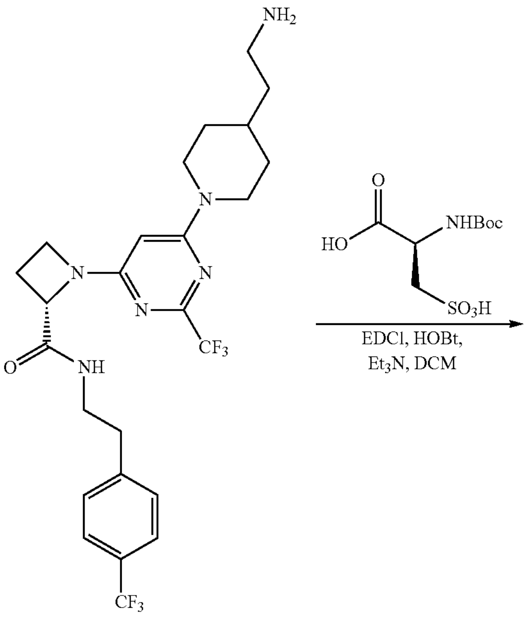

Compound 247

-continued

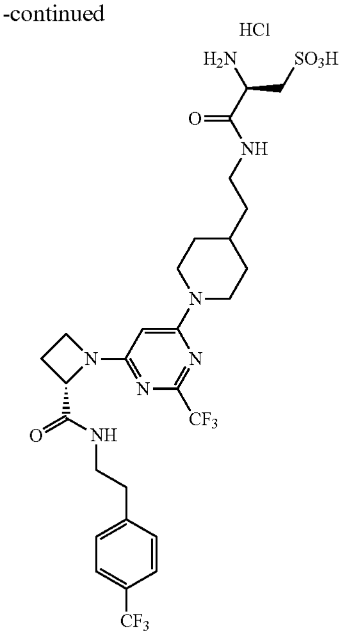

Compound 278

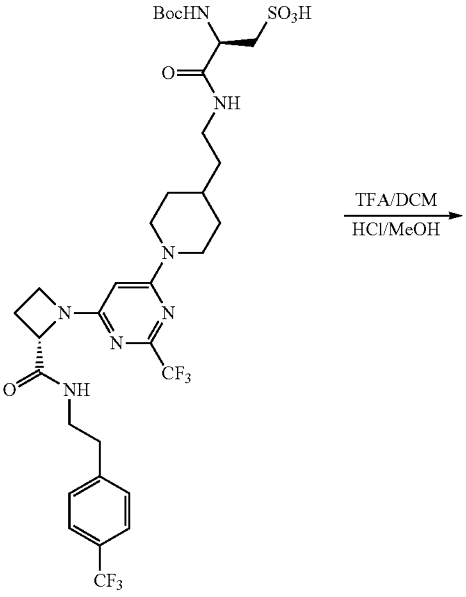

Compound 56A (R)-2-amino-3-oxo-3-((2-(1-(2-(trifluoromethyl)-6-((S)-2-((4-(trifluoromethyl)-phenethyl)carbamoyl)azetidin-1-yl)pyrimidin-4-yl)piperidin-4-yl)ethyl)amino)-propane-1-sulfonic acid Using the procedure as described in Example 7, Compound 247 (160 mg, 0.28 mmol) was converted to Compound 56A. The crude material was stirred with a 40% solution of TFA/DCM (6 mL) for 20 minutes. The mixture was concentrated. After the addition of MeCN and water, a white solid formed on standing (40 mg). The material was dissolved in 6 mL of anhydrous methanol. 1.25M HCl in methanol was added, and solvent was removed in vacuo. The material was recrystallized from MeCN/water to give Compound 278 (30 mg, 15% yield). LCMS (method B): m/z 696.3 $(M+H)^+$. $^1H$ NMR ($CD_3OD$) δ 8.51 (br m, 1H), 7.49 (d, 2H), 7.37 (d, 2H), 5.54 (s, 1H), 4.70 (t, 1H), 4.42 (m, 2H), 4.21 (m, 1H), 4.01 (m, 1H), 3.89 (m, 1H), 3.61-3.43 (m, 2H), 3.34 (m, 2H), 3.28 (m, 1H), 3.15 (m, 1H), 2.89 (m, 4H), 2.56 (m, 1H), 2.44 (m, 1H), 1.82 (m, 2H), 1.68 (m, 1H), 1.51 (m, 2H), 1.17 (m, 2H). Using the procedure described above for Example 56, step 1, the following compounds were prepared from precursors and the reagents as indicated in Table 41.

TABLE 41
| No | Structure | Pre-cursor | Reagent | MS (M + H)$^+$ |
|---|---|---|---|---|
| 279 | 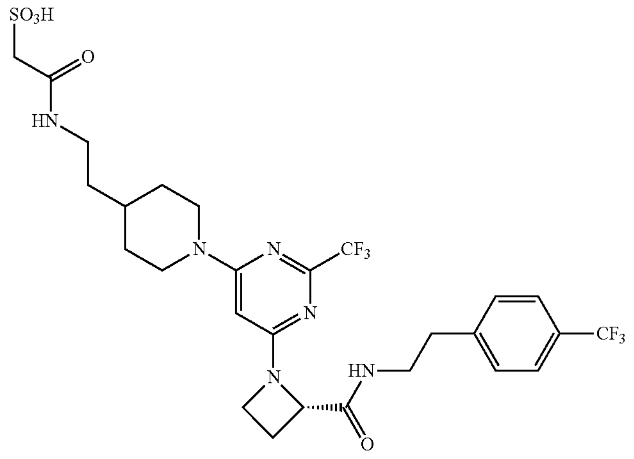 [SMILES: O=C(CS(=O)(=O)O)NCCC1CCN(c2cc(N3CC[C@H]3C(=O)NCCc3ccc(C(F)(F)F)cc3)nc(C(F)(F)F)n2)CC1] (S)-2-oxo-2-((2-(1-(2-(trifluoromethyl)-6-(2-((4-(trifluoromethyl)phenethyl)carbamoyl)azetidin-1-yl)pyrimidin-4-yl)piperidin-4-yl)ethyl)amino)-ethanesulfonic acid | 247 | 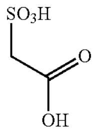 | 667.5 B |
| 280 | 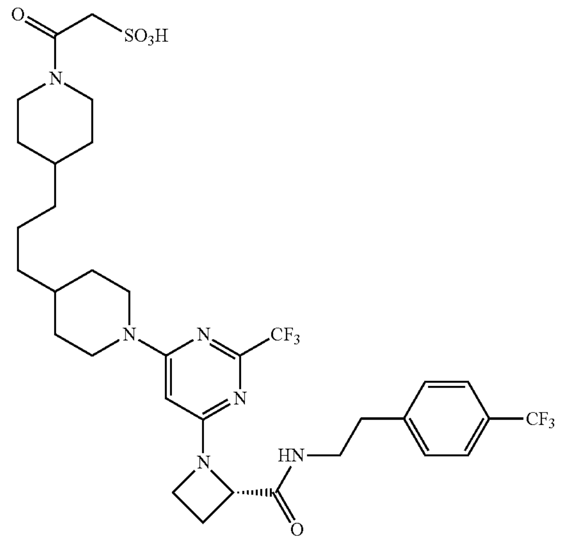 [SMILES: O=C(NCCc1ccc(C(F)(F)F)cc1)[C@@H]1CCN1c1cc(N2CCC(CCCC3CCN(C(=O)CS(=O)(=O)O)CC3)CC2)nc(C(F)(F)F)n1] (S)-2-oxo-2-(4-(3-(1-(2-(trifluoromethyl)-6-(2-((4-(trifluoromethyl)phenethyl)carbamoyl)azetidin-1-yl)pyrimidin-4-yl)piperidin-4-yl)propyl)piperidin-1-yl)ethanesulfonic acid | 275 | 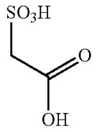 | 749.6 B |

Example 57

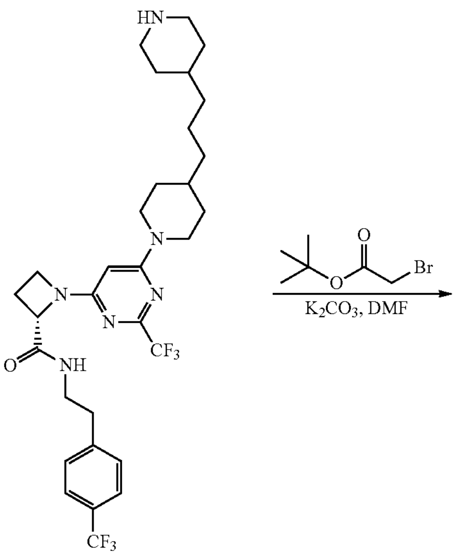

Compound 275

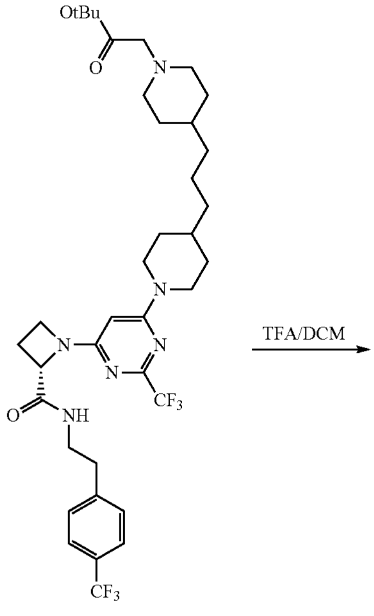

Compound 57A

-continued

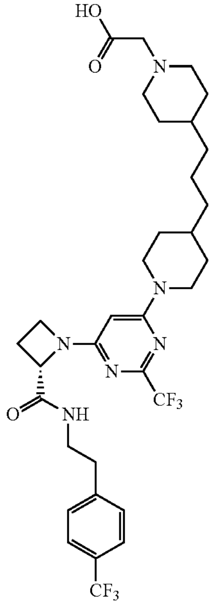

Compound 281

(S)-2-(4-(3-(1-(2-(trifluoromethyl)-6-(2-((4-(trifluoromethyl)phenethyl)carbamoyl)-azetidin-1-yl)pyrimidin-4-yl)piperidin-4-yl)propyl)piperidin-1-yl) acetic acid To a solution of Compound 275 (73 mg, 0.12 mmol) in DMF (0.75 mL) were added tert-butyl 2-bromoacetate (19 μL, 0.13 mmol) and potassium carbonate (24 mg, 0.18 mmol). After stirring for 16 hours at room temperature, the mixture was filtered through a cotton plug, and the plug washed with ethyl acetate. The combined filtrates were concentrated in vacuo, and purified by silica gel chromatography (45% to 100% EtOAc/hexanes) to give Compound 57A (68 mg, 79% yield). Compound 57A was treated with TFA as described in Example 56, step 2 to afford Compound 281 (18 mg, 29%). LCMS (method B): m/z 685.6 $(M+H)^+$. $^1H$ NMR ($CD_3OD$) δ 8.51 (br t, 1H), 8.11 (s, 1H), 7.49 (d, 2H), 7.37 (d, 2H), 5.52 (s, 1H), 4.71 (m, 1H), 4.41 (m, 1H), 4.00 (m, 1H), 3.90 (m, 1H), 3.62 (s, 2H), 3.66-3.45 (m, 4H), 3.08-2.82 (m, 6H), 2.54 (m, 1H), 2.44 (m, 1H), 1.95 (d, 2H), 1.79 (d, 1H), 1.66-1.26 (m, 10H), 1.14 (m, 2H).

Example 58

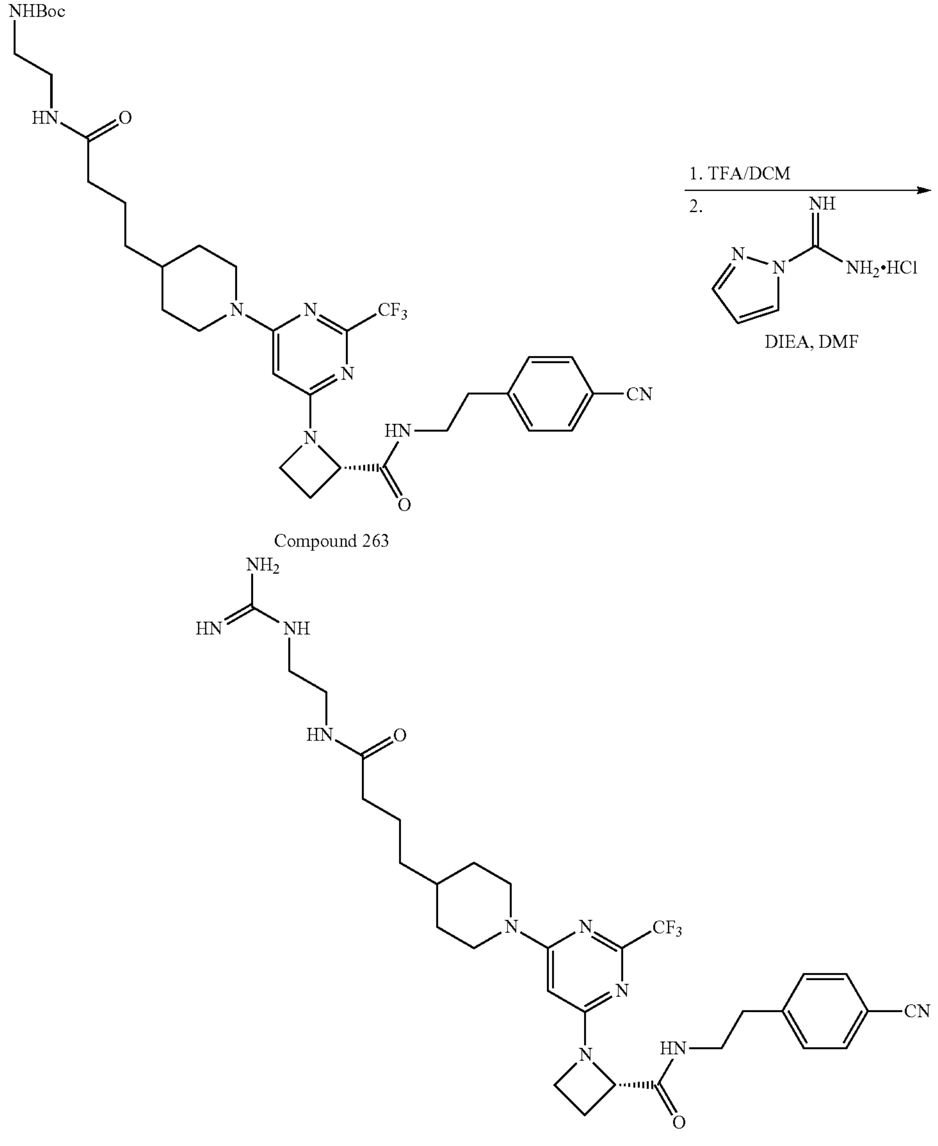

Compound 263

Compound 282

(S)—N-(4-cyanophenethyl)-1-(6-(4-(4-((2-guanidinoethyl)amino)-4-oxobutyl)piperidin-1-yl)-2-(trifluoromethyl)pyrimidin-4-yl)azetidine-2-carboxamide Compound 263 (105 mg, 0.150 mmol) was treated with TFA as described in example 4, followed by reaction with 1H-pyrazole-1-carboximidamide hydrochloride (90 mg, 0.61 mmol) as described in Example 26 to afford Compound 282 (63 mg, 65%). LCMS (method A): m/z 629.6 $(M+H)^+$. $^1H$ NMR ($CD_3OD$) δ 8.46 (s, 1H), 7.53-7.51 (m, 2H), 7.36-7.34 (m, 2H), 5.50 (s, 1H), 4.70-4.67 (dd, 1H), 4.43-4.36 (m, 2H), 4.03-3.97 (m, 1H), 3.91-3.85 (m, 1H), 3.61-3.39 (m, 2H), 3.34-3.26 (m, 4H), 2.91-2.84 (m, 4H), 2.55-2.43 (m, 2H), 2.22 (t, 2H), 1.81-1.77 (m, 2H), 1.71-1.55 (m, 3H), 1.32-1.26 (m, 2H), 1.19-1.09 (m, 2H). Using the procedure described above for Example 58, the following compounds were prepared from precursors as indicated in Table 42.

TABLE 42
| No | Structure | Precursor | MS (M + H)+ |
|---|---|---|---|
| 283 | 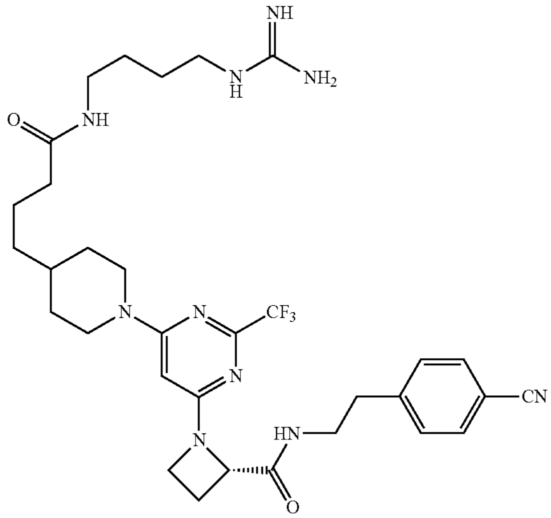 [SMILES: N#Cc1ccc(CCNC(=O)[C@@H]2CCN2c2cc(N3CCC(CCCC(=O)NCCCCNC(=N)N)CC3)nc(C(F)(F)F)n2)cc1] (S)-N-(4-cyanophenethyl)-1-(6-(4-(4-((4-guanidinobutyl)amino)-4-oxobutyl)piperidin-1-yl)-2-(trifluoromethyl)pyrimidin-4-yl)azetidine-2-carboxamide | 264 | 657.6 A |
| 284 | 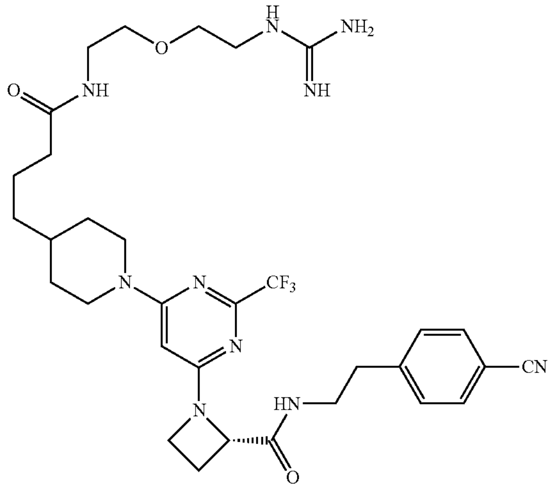 [SMILES: N#Cc1ccc(CCNC(=O)[C@@H]2CCN2c2cc(N3CCC(CCCC(=O)NCCOCCNC(=N)N)CC3)nc(C(F)(F)F)n2)cc1] (S)-N-(4-cyanophenethyl)-1-(6-(4-(4-((2-(2-guanidinoethoxy)-ethyl)amino)-4-oxobutyl)piperidin-1-yl)-2-(trifluoromethyl)pyrimidin-4-yl)azetidine-2-carboxamide | 265 | 673.5 A |

TABLE 42-continued
| No | Structure | Pre-cursor | MS (M + H)+ |
|---|---|---|---|
| 285 | 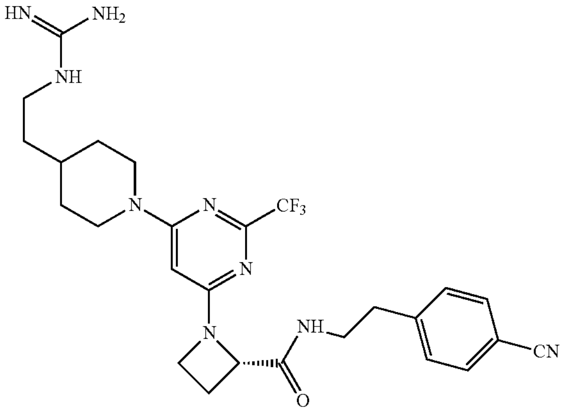 [SMILES: N#Cc1ccc(CCNC(=O)[C@@H]2CCN2c2cc(N3CCC(CCNC(=N)N)CC3)nc(C(F)(F)F)n2)cc1] (S)-N-(4-cyanophenethyl)-1-(6-(4-(2-guanidinoethyl)piperidin-1-yl)-2-(trifluoromethyl)pyrimidin-4-yl)azetidine-2-carboxamide | 246 and only step 2 | 544.5 A |
| 286 | 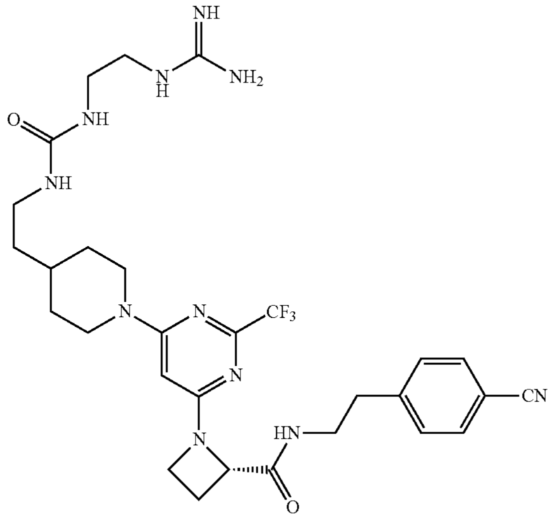 [SMILES: N#Cc1ccc(CCNC(=O)[C@@H]2CCN2c2cc(N3CCC(CCNC(=O)NCCNC(=N)N)CC3)nc(C(F)(F)F)n2)cc1] (S)-N-(4-cyanophenethyl)-1-(6-(4-(2-(3-(2-guanidinoethyl)-ureido)ethyl)piperidin-1-yl)-2-(trifluoromethyl)pyrimidin-4-yl)azetidine-2-carboxamide | 272 | 630.6 A |

TABLE 42-continued
| No | Structure | Pre-cursor | MS (M + H)+ |
|---|---|---|---|
| 287 | 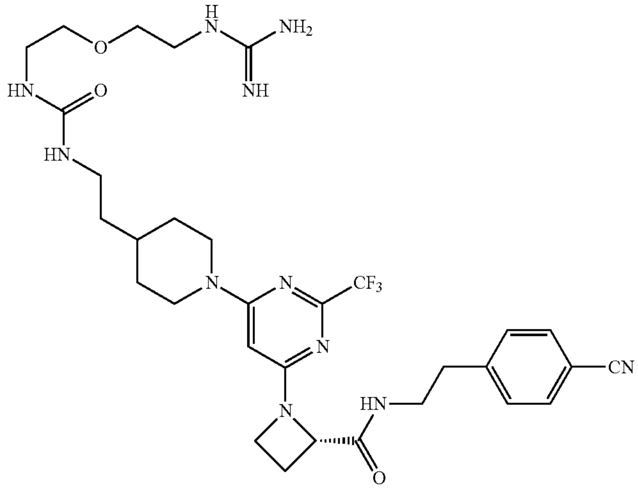 [SMILES: N#Cc1ccc(CCNC(=O)[C@@H]2CCN2c2cc(N3CCC(CCNC(=O)NCCOCCNC(=N)N)CC3)nc(C(F)(F)F)n2)cc1] (S)-1-(6-(4-(1-amino-1-imino-9-oxo-5-oxa-2,8,10-triazadodecan-12-yl)piperidin-1-yl)-2-(trifluoromethyl)pyrimidin-4-yl)-N-(4-cyanophenethyl)azetidine-2-carboxamid | 273 | 674.3 A |
| 288 | 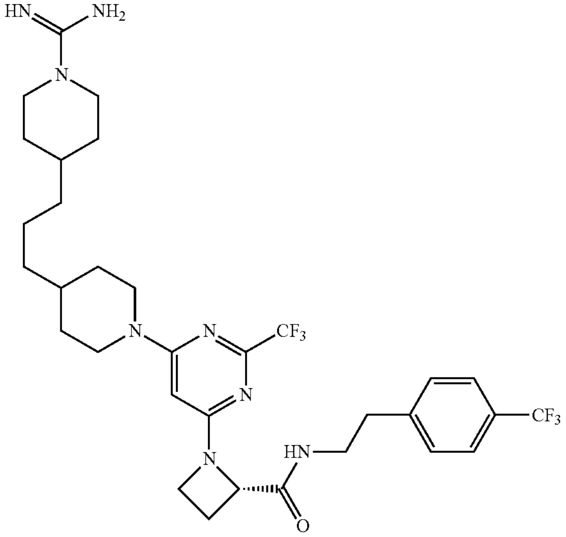 [SMILES: N=C(N)N1CCC(CCCC2CCN(c3cc(N4CC[C@H]4C(=O)NCCc4ccc(C(F)(F)F)cc4)nc(C(F)(F)F)n3)CC2)CC1] (S)-1-(6-(4-(3-(1-carbamimidoylpiperidin-4-yl)propyl)piperidin-1-yl)-2-(trifluoromethyl)pyrimidin-4-yl)-N-(4-(trifluoromethyl)phenethyl)-azetidine-2-carboxamide | 275 and only step 2 | 669.7 B |

TABLE 42-continued
| No | Structure | Pre-cursor | MS (M + H)$^+$ |
|---|---|---|---|
| 289 | 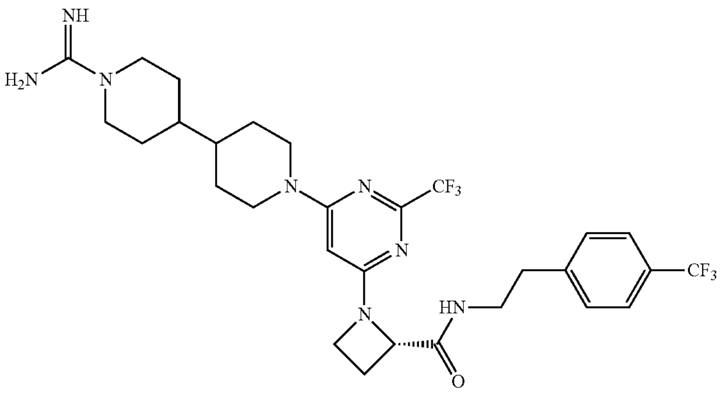 [SMILES: N=C(N)N1CCC(C2CCN(c3cc(N4CC[C@H]4C(=O)NCCc4ccc(C(F)(F)F)cc4)nc(C(F)(F)F)n3)CC2)CC1] (S)-1-(6-(1'-carbamimidoyl-[4,4'-bipiperidin]-1-yl)-2-(trifluoromethyl)pyrimidin-4-yl)-N-(4-(trifluoromethyl)phenethyl)-azetidine-2-carboxamide | 277 and only step 2 | 627.3 B |
Example 59
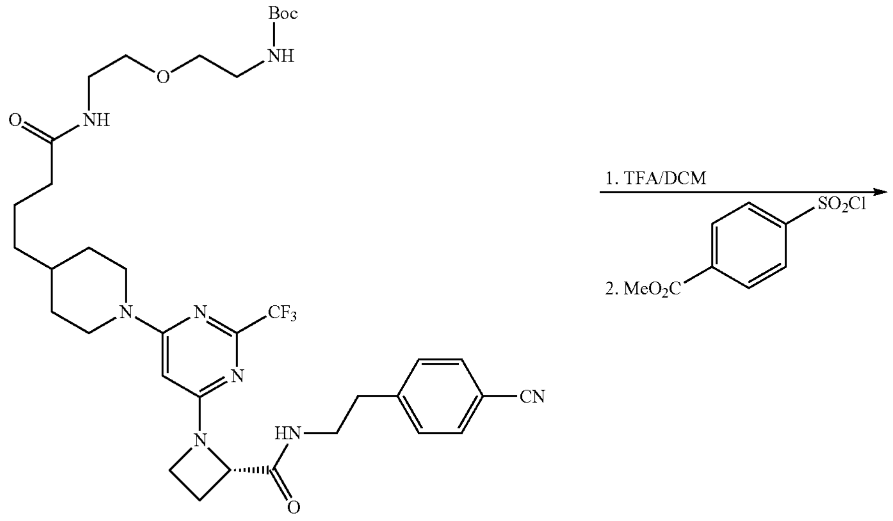
Compound 265

-continued

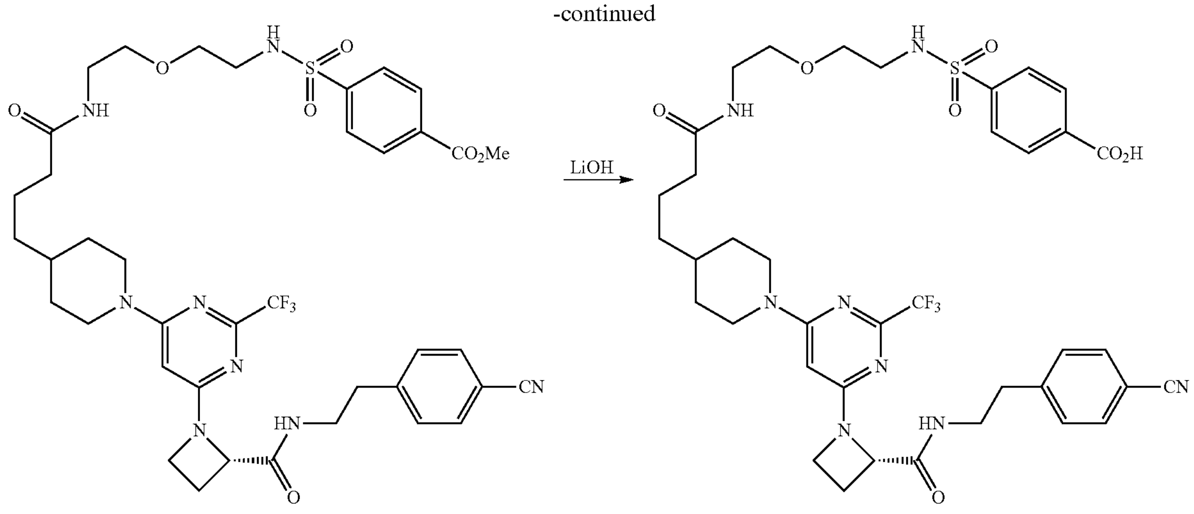

Compound 290 Compound 291

(S)-methyl 4-(N-(2-(2-(4-(1-(6-(2-((4-cyanophenethyl)carbamoyl)azetidin-1-yl)-2-(trifluoromethyl)pyrimidin-4-yl)piperidin-4-yl)butanamido)ethoxy)ethyl)-sulfamoyl)benzoate Using the procedure as described in Example 4 to remove the Boc group and the procedure as described in Example 11, step 3 for reaction with the sulfonyl chloride, Compound 265 was converted to Compound 290. LCMS (Method A): m/z 829.6 $(M+H)^+$.

(S)-4-(N-(2-(2-(4-(1-(6-(2-((4-cyanophenethyl)carbamoyl)azetidin-1-yl)-2-(trifluoromethyl)pyrimidin-4-yl)piperidin-4-yl)butanamido)ethoxy)ethyl)sulfamoyl)-benzoic acid Using the procedure as described in Example 16, Compound 290 was converted to Compound 291. LCMS (Method A): m/z 815.7 $(M+H)^+$. $^1$H NMR ($CD_3OD$) δ 8.49 (m, 0.5H), 8.18-8.16 (m, 2H), 7.95-7.88 (m, 2.5H), 7.53-7.51 (m, 2H), 7.35-7.33 (m, 2H), 5.50 (s, 1H), 4.71-4.67 (dd, 1H), 4.41-4.34 (m, 2H), 4.02-3.97 (m, 1H), 3.91-3.85 (m, 1H), 3.60-3.53 (m, 1H), 3.48-3.40 (m, 5H), 3.33-3.29 (m, 2H), 3.07 (t, 2H), 2.89-2.83 (m, 4H), 2.57-2.42 (m, 2H), 2.19 (t, 2H), 1.78-1.75 (m, 2H), 1.69-1.53 (m, 3H), 1.29-1.24 (m, 2H), 1.18-1.06 (m, 2H). Using the procedure described above for Example 59, the following compound was prepared from the precursor as indicated in Table 43.

TABLE 43
| No | Structure | Pre-cursor | MS (M + H)+ |
|---|---|---|---|
| 292 | 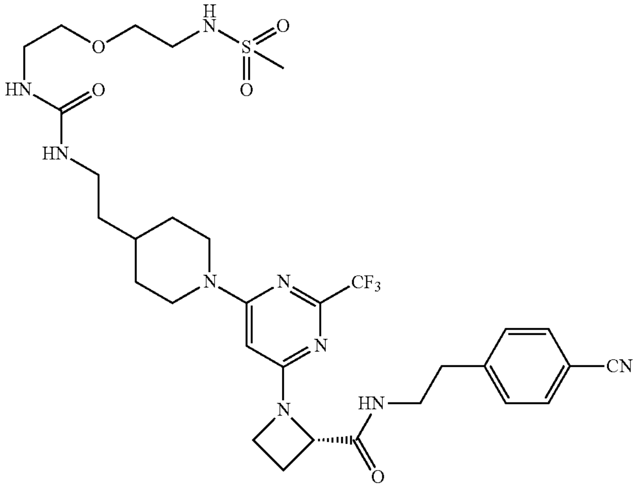 [SMILES: CS(=O)(=O)NCCOCCNC(=O)NCCC1CCN(c2cc(N3CC[C@H]3C(=O)NCCc3ccc(C#N)cc3)nc(C(F)(F)F)n2)CC1] (S)-N-(4-cyanophenethyl)-1-(6-(4-(2-(3-(2-(2-(methylsulfonylamino)-ethoxy)ethyl)ureido)ethyl)piperidin-1-yl)-2-(trifluoromethyl)pyrimidin-4-yl)azetidine-2-carboxamide | 273 and 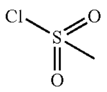 | 710.5 A |
Example 60
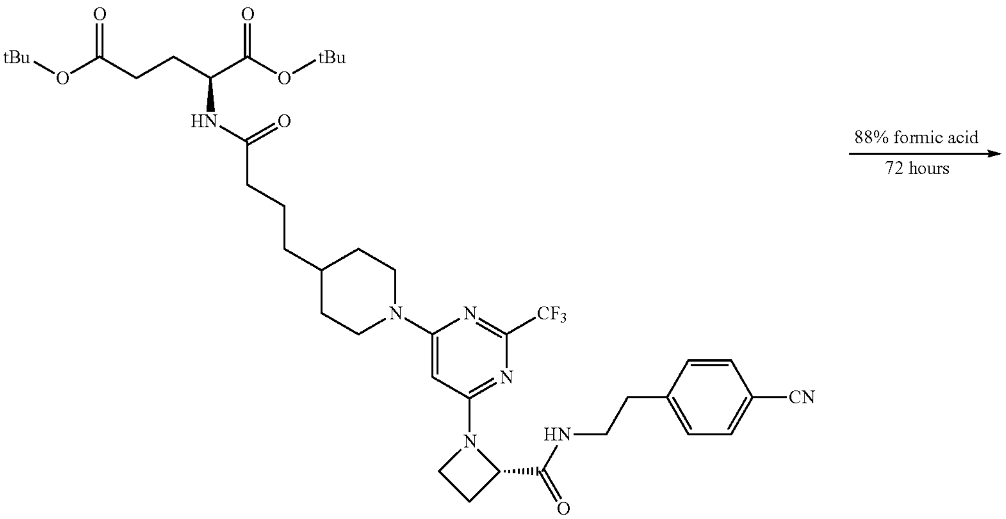
Compound 252

-continued

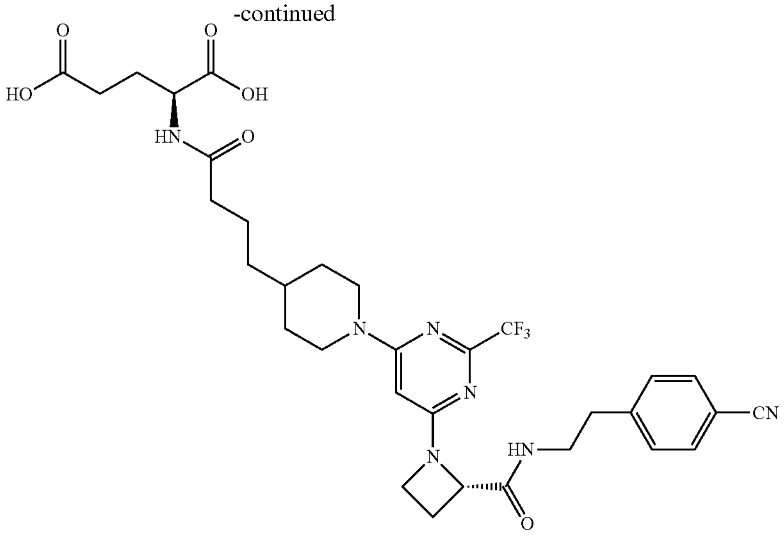

Compound 293

(S)-2-(3-(1-(2-(Trifluoromethyl)-6-((S)-2-((4-(trifluoromethyl)phenethyl)carbamoyl) azetidin-1-yl) pyrimidin-4-yl)piperidin-4-yl)propanamido)pentanedioic acid Compound 256 (168 mg, 0.200 mmol) was dissolved in formic acid (6 mL, 88%), and stirred overnight at room temperature. An additional portion of formic acid (1.5 mL) was added, and the mixture was stirred for 72 h at room temperature. The mixture was concentrated, and the compound was dried in vacuo to afford Compound 293 (140 mg, 98% yield). LCMS (Method B): m/z 717.3 $(M+H)^+$. $^1H$ NMR ($CD_3OD$) δ 8.50 (br t, 1H), 8.39 (br d, 1H), 7.49 (d, 2H), 7.37 (d, 2H), 5.53 (s, 1H), 4.71 (t, 1H), 4.44 (m, 3H), 4.04 (m, 1H), 3.89 (m, 1H), 3.61-3.41 (m, 2H), 2.90 (m, 4H), 2.55 (m, 1H), 2.41 (m, 3H), 2.27 (m, 3H), 1.95 (m, 1H), 1.81 (m, 2H), 1.75-1.55 (m, 3H), 1.33 (m, 2H), 1.13 (m, 2H). Using the procedure described above for Example 60, the following compound was prepared from the precursor as indicated in Table 44.

TABLE 44

| No | Structure | Precursor | MS $(M + H)^+$ |
|---|---|---|---|
| 294 | 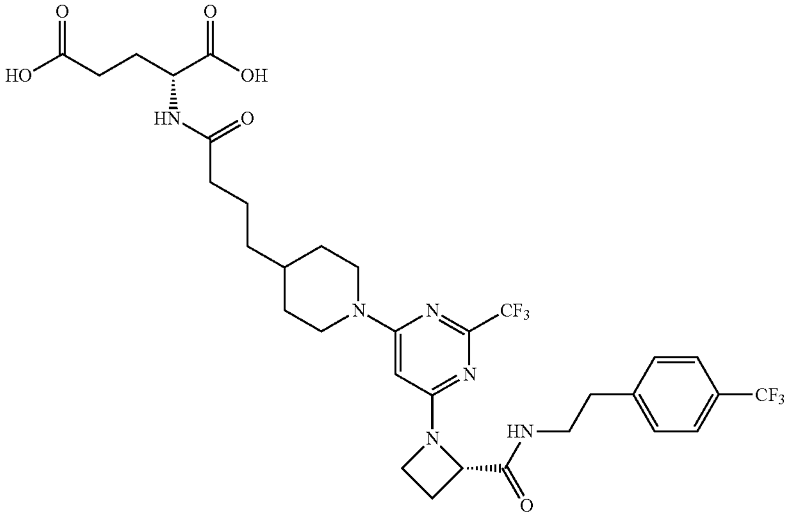 [SMILES: O=C(O)CC[C@@H](NC(=O)CCCC1CCN(c2cc(N3CC[C@H]3C(=O)NCCc3ccc(C(F)(F)F)cc3)nc(C(F)(F)F)n2)CC1)C(=O)O] (R)-2-(4-(1-(2-(trifluoromethyl)-6-((S)-2-((4-(trifluoromethyl)-phenethyl)carbamoyl)azetidin-1-yl)pyrimidin-4-yl)piperidin-4-yl)butanamido)pentanedioic acid | 257 | 717.3 B |

Example 61

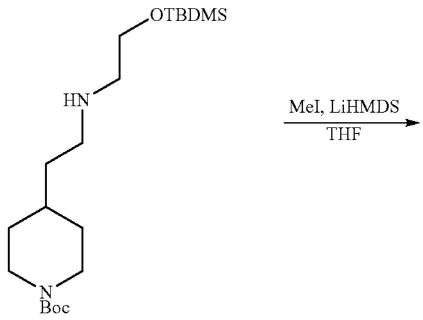

Intermediate 13

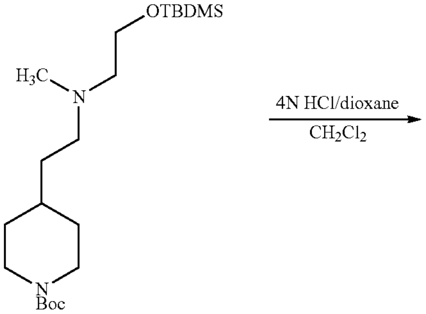

Compound 61A

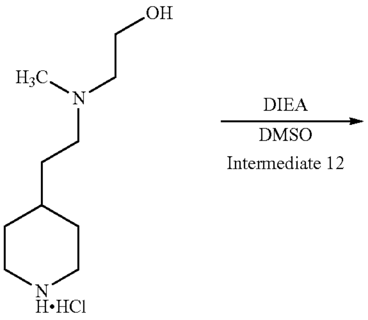

Compound 61B

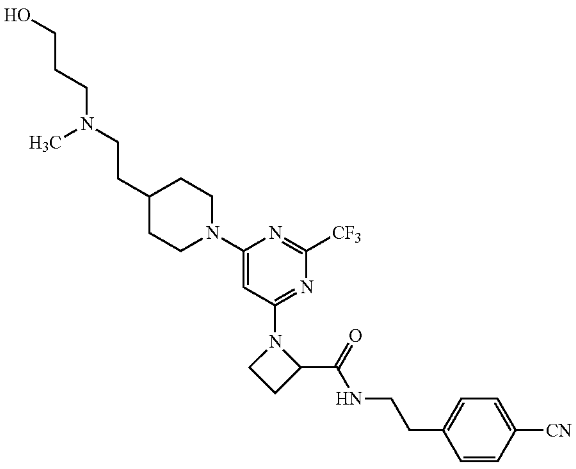

Compound 295 tert-butyl 4-(2-((tert-butyldimethlsilyl)oxy)ethyl)(methylamino)ethyl)piperidine-1-carboxylate To a solution of Intermediate 13 (53 mg, 0.14 mmol) in anhydrous THF (1 mL) under nitrogen at 0° C. was added methyl iodide (8.0 μL, 0.13 mmol), followed by addition of lithium bis(trimethylsilyl)amide (1M solution in THF, 130 μL, 0.13 mmol). The reaction was allowed to warm to room temperature, and was stirred overnight. The mixture was concentrated in vacuo to afford Compound 61A which was used directly in the next step. LCMS (Method A): m/z 401.6 $(M+H)^+$.

N-(4-cyanophenethyl)-1-(6-(4-(2-((3-hydroxypropyl)(methyl)amino)ethyl)piperidin-1-yl)-2-(trifluoromethyl)pyrimidin-4-yl)azetidine-2-carboxamide Using the procedure as described in Intermediate 9, step 3, Compound 61A was converted to Compound 61B which was reacted with intermediate 12 following the procedure as described in Example 1 to afford Compound 295. LCMS (method A): m/z 560.7 $(M+H)^+$. $^1H$ NMR ($CD_3OD$) δ 7.53-7.51 (m, 2H), 7.36-7.34 (m, 2H), 5.51 (s, 1H), 4.71-4.67 (dd, 1H), 4.43-4.37 (m, 2H), 4.03-3.98 (m, 1H), 3.91-3.85 (dd, 1H), 3.68-3.54 (m, 3H), 3.46-3.39 (m, 2H), 2.92-2.86 (m, 4H), 2.58-2.29 (m, 6H), 2.29 (s, 3H), 1.81-1.78 (m, 2H), 1.63-1.60 (m, 1H), 1.51-1.45 (m, 2H), 1.32-1.13 (m, 2H), 0.91-0.87 (m, 1H).

Example 62

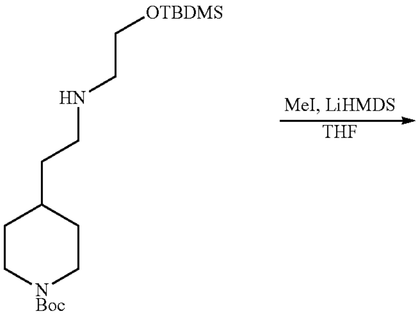

Intermediate 13

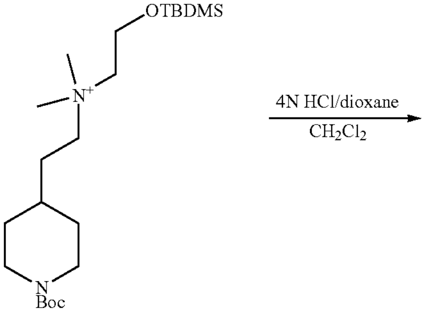

Compound 62A

-continued

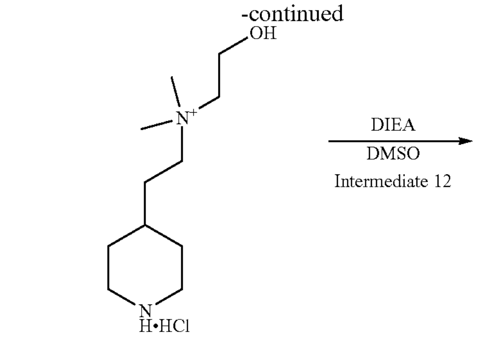

Compound 62B

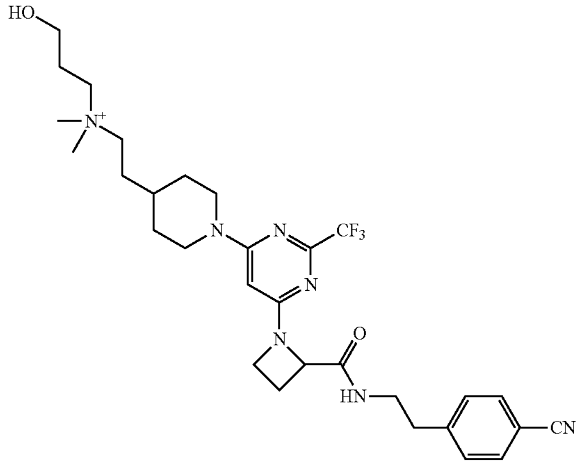

Compound 296

2-(1-(tert-butoxycarbonyl)piperidin-4-yl-N-(2-((tert-butyldimethlsilyl)oxy)ethyl)-N,N-dimethylethan-aminium To a solution of Intermediate 13 (61 mg, 0.16 mmol) in anhydrous THF (1 mL) under nitrogen at 0° C. was added methyl iodide (50 μL, 0.79 mmol) followed by addition of lithium bis(trimethylsilyl)amide (1M solution in THF, 0.24 ml, 0.24 mmol). The reaction was warmed to room temperature, stirred overnight, and purified by MS-HPLC to afford Compound 62A (20 mg, 30%). LCMS (Method A): m/z 416.6 $(M+H)^+$.

N-(2-(1-(6-(2-((4-cyanophenethyl)carbamoyl)azetidin-1-yl)-2-(trifluoromethyl)pyrimidin-4-yl)piperidin-4-yl)ethyl)-3-hydroxy-N,N-dimethylpropan-1-aminium To a solution of Compound 62A (20 mg, 0.05 mmol) in DCM (1 mL) was added 4 N HCl/dioxane (0.12 mL, 0.48 mmol). The reaction was stirred overnight at room temperature. The reaction was concentrated in vacuo to afford Compound 62B which was reacted with Intermediate 12 (8 mg, 0.02 mmol) following the procedure as described in Example 1 to afford Compound 296 (4 mg, 38%). LCMS (method A): m/z 547.7 $(M+H)^+$. $^1H$ NMR ($CD_3OD$): δ 8.49 (m, 1H), 7.52-7.50 (m, 2H), 7.35-7.33 (m, 2H), 5.53 (s, 1H), 4.71-4.68 (dd, 1H), 4.49-4.38 (m, 2H), 4.04-3.86 (m, 4H), 3.63-3.39 (m, 6H), 3.16 (s, 6H), 2.99-2.85 (m, 4H), 2.58-2.42 (m, 2H), 1.85-1.67 (m, 5H), 1.35-123 (m, 2H).

Example 63

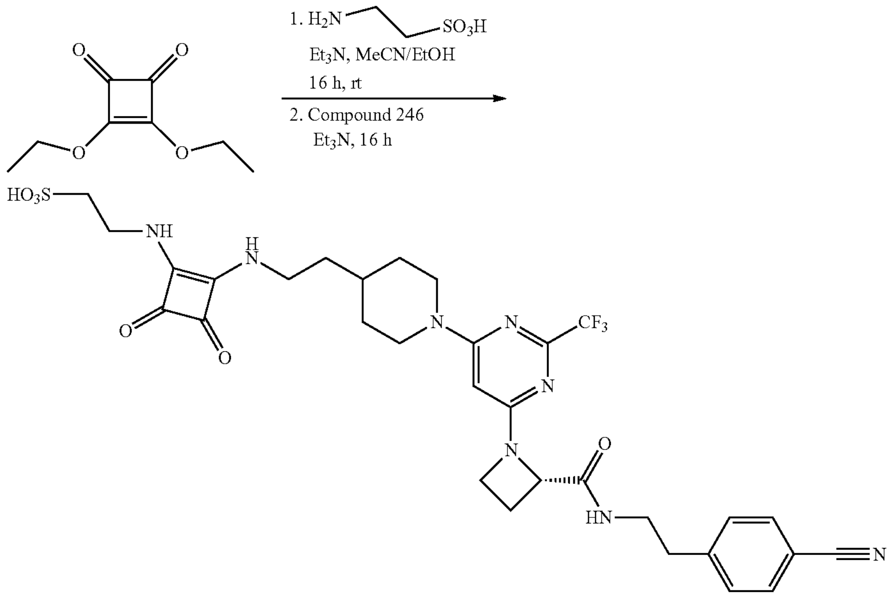

Compound 297

(S)-2-((2-((2-(1-(6-(2-((4-cyanophenethyl)carbamoyl)azetidin-1-yl)-2-(trifluoromethyl)pyrimidin-4-yl)piperidin-4-yl)ethyl)amino)-3,4-dioxocyclobut-1-en-1-yl)amino)ethanesulfonic acid Triethylamine (88 μL, 0.63 mmol) was added to a mixture of taurine (53 mg, 0.42 mmol) in acetonitrile (0.9 mL), and the mixture was cooled to 0° C. 3,4-diethoxycyclobut-3-ene-1,2-dione (62 μL, 0.42 mmol) was added in two portions, 10 minutes apart, and the mixture was allowed to warm to room temperature. After one hour, ethanol (0.3 mL) and triethylamine (20 μL) were added, and the reaction was allowed to stir for 16 hours. Compound 246 (150 mg, 0.28 mmol) and triethylamine (60 μL) were added, and the reaction was allowed to stir for 16 hours at room temperature. The volatiles were removed in vacuo, and the residue was purified by reverse phase medium pressure chromatography (C18 HP column, 5%-30% $MeCN/H_2O$/0.25% formic acid) to afford Compound 297 (64 mg, 32%). LCMS (method A): m/z 705.4 $(M+H)^+$. $^1H$ NMR ($CD_3OD$) δ 8.11 (s, 1H), 7.58 (d, 2H), 7.39 (d, 2H), 5.60 (s, 1H), 4.84 (m, 1H), 4.44 (m, 2H), 4.09-3.94 (m, 4H), 3.72 (m, 2H), 3.61-3.48 (m, 2H), 3.10 (m, 2H), 3.03-2.98 (m, 4H), 2.60 (m, 1H), 2.46 (m, 1H), 1.89 (m, 2H), 1.79 (m, 1H), 1.63 (m, 2H), 1.24 (m, 2H). Using the procedure described above for Example 63, the following compounds were prepared from Compound 246 and reagents as indicated in Table 45 with the exception that for Compound 340, Compound 247 was used as the starting material.

TABLE 45

| No | Compound | Reagent | MS (M + H) |
|---|---|---|---|
| 298 | 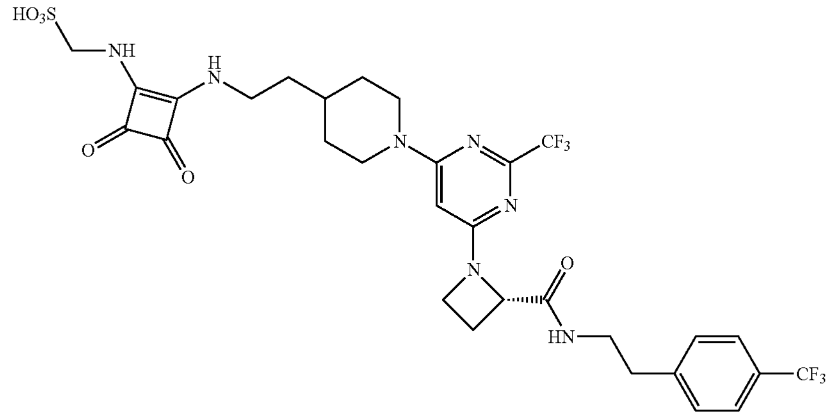 [SMILES: O=C(NCCc1ccc(C(F)(F)F)cc1)[C@@H]1CCN1c1cc(N2CCC(CCNc3c(NCS(=O)(=O)O)c(=O)c3=O)CC2)nc(C(F)(F)F)n1]<br>(S)-((2-((2-(1-(6-(2-((4-cyanophenethyl)carbamoyl)azetidin-1-yl)-2-(trifluoromethyl)pyrimidin-4-yl)piperidin-4-yl)ethyl)amino)-3,4-dioxocyclobut-1-en-1-yl)amino)methanesulfonic acid | 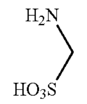<br>Reacted with Compound 247 | 734.4 A |
| 299 | 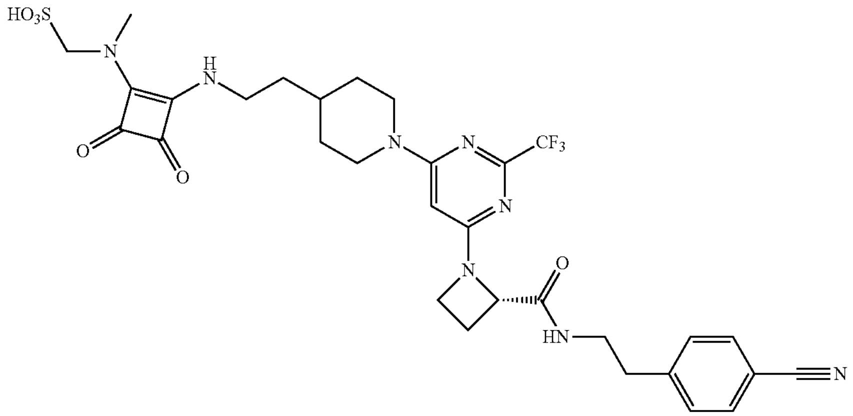 [SMILES: CN(CS(=O)(=O)O)c1c(NCCC2CCN(c3cc(N4CC[C@H]4C(=O)NCCc4ccc(C#N)cc4)nc(C(F)(F)F)n3)CC2)c(=O)c1=O]<br>(S)-2-((2-((2-(1-(6-(2-((4-cyanophenethyl)carbamoyl)azetidin-1-yl)-2-(trifluoromethyl)pyrimidin-4-yl)piperidin-4-yl)ethyl)amino)-3,4-dioxocyclobut-1-en-1-yl)(methyl)amino)ethanesulfonic acid | 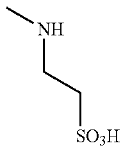 | 719.5 A |

TABLE 45-continued

| No | Compound | Reagent | MS (M + H) |
|---|---|---|---|
| 300 | 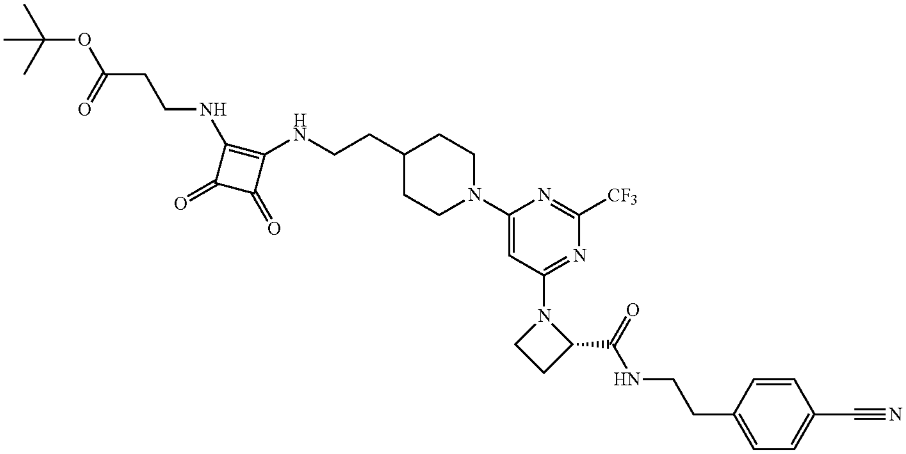 [SMILES: CC(C)(C)OC(=O)CCNc1c(NCCC2CCN(c3cc(N4CC[C@H]4C(=O)NCCc4ccc(C#N)cc4)nc(C(F)(F)F)n3)CC2)c(=O)c1=O] (S)-tert-butyl 3-((2-((2-(1-(6-(2-((4-cyanophenethyl)carbamoyl)azetidin-1-yl)-2-(trifluoromethyl)pyrimidin-4-yl)piperidin-4-yl)ethyl)amino)-3,4-dioxocyclobut-1-en-1-yl)amino)propanoate | 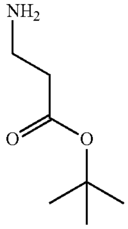 | 725.6 A |
| 301 | 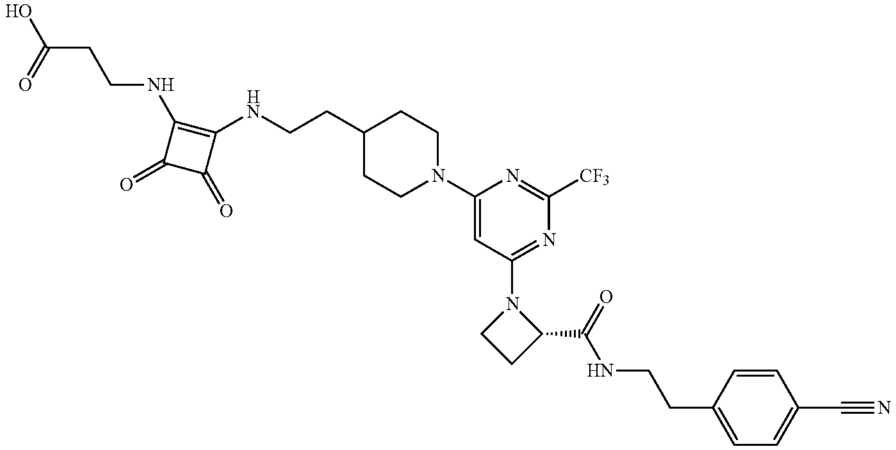 [SMILES: N#Cc1ccc(CCNC(=O)[C@@H]2CCN2c2cc(N3CCC(CCNc4c(NCCC(=O)O)c(=O)c4=O)CC3)nc(C(F)(F)F)n2)cc1] (S)-3-((2-((2-(1-(6-(2-((4-cyanophenethyl)carbamoyl)azetidin-1-yl)-2-(trifluoromethyl)pyrimidin-4-yl)piperidin-4-yl)ethyl)amino)-3,4-dioxocyclobut-1-en-1-yl)amino)propanoic acid | Reaction with 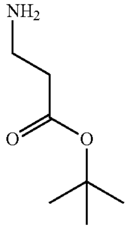 followed by deprotection with formic acid as in Example 60 | 669.5 A |

TABLE 45-continued

| No | Compound | Reagent | MS (M + H) |
|---|---|---|---|
| 302 | 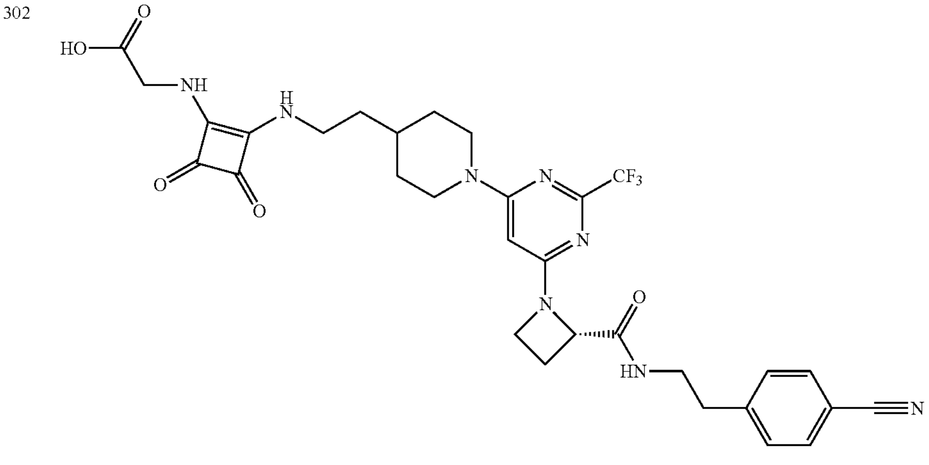 (S)-2-((2-((2-(1-(6-(2-((4-cyanophenethyl)carbamoyl)azetidin-1-yl)-2-(trifluoromethyl)pyrimidin-4-yl)piperidin-4-yl)ethyl)amino)-3,4-dioxocyclobut-1-en-1-yl)amino)acetic acid | Reaction with 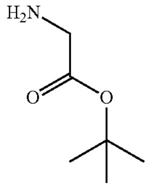 followed by deprotection with formic acid as in Example 60 | 655.5 A |

Example 64

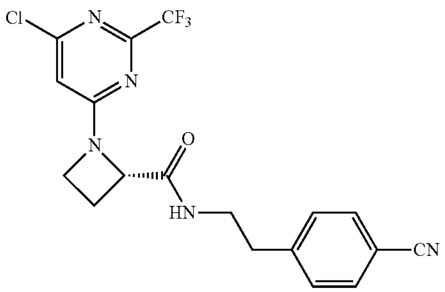

Intermediate 12

+

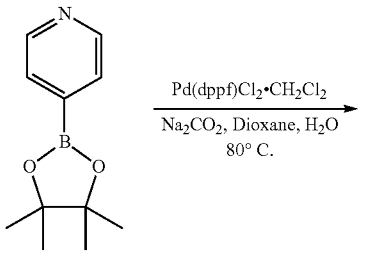

-continued

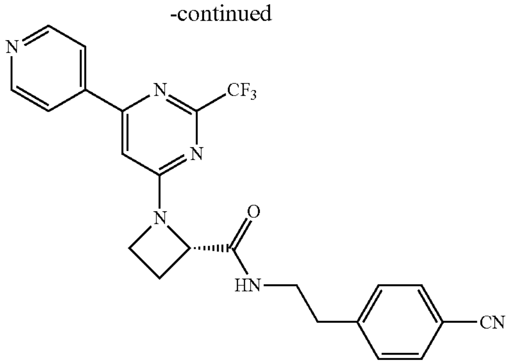

Compound 303

(S)—N-(4-cyanophenethyl)-1-(6-pyridin-4-yl)-2-(trifluoromethyl)pyrimidin-4-yl)azetidine-2-carboxamide Using the procedure as described in Example 30, Intermediate 12 (40 mg, 0.10 mmol), was converted to Compound 303 (20 mg, 44%). LCMS (method A): m/z 453.3 $(M+H)^+$. $^1$H NMR ($CDCl_3$): δ 8.81-8.79 (dd, 2H), 7.93-1.91 (m, 3H), 7.50-7.48 (dd, 2H), 7.27-7.25 (m, 2H), 6.74 (s, 1H), 4.99-4.95 (m, 1H), 4.21-4.16 (m, 1H), 4.10-4.04 (m, 1H), 3.63-3.53 (m, 2H), 3.04-2.87 (m, 3H), 2.62-2.60 (b, 1H). Using the procedure described above for Example 64, the following compounds were prepared from Intermediate 12 (unless otherwise specified) and reagents as indicated in Table 46.

TABLE 46
| No | Compound | reagent | MS (M + H) |
|---|---|---|---|
| 304 | 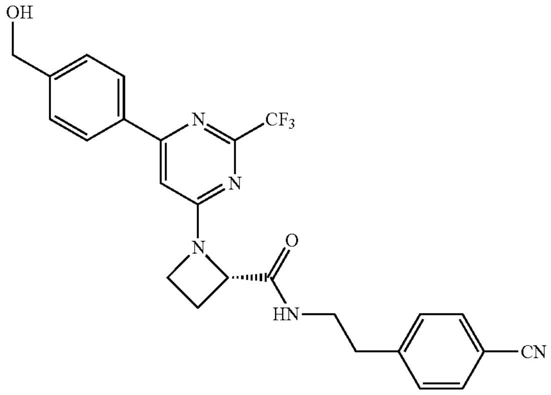 [SMILES: N#Cc1ccc(CCNC(=O)[C@@H]2CCN2c2cc(-c3ccc(CO)cc3)nc(C(F)(F)F)n2)cc1] (S)-N-(4-cyanophenethyl)-1-(6-(4-(hydroxymethyl)phenyl)-2-(trifluoromethyl)pyrimidin-4-yl)azetidine-2-carboxamide | 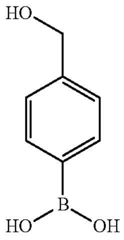 | 482.3 A |
| 305 | 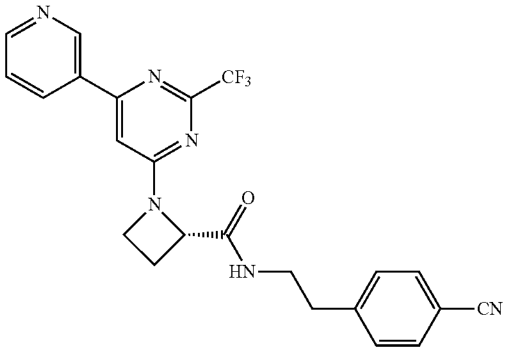 [SMILES: N#Cc1ccc(CCNC(=O)[C@@H]2CCN2c2cc(-c3cccnc3)nc(C(F)(F)F)n2)cc1] (S)-N-(4-cyanophenethyl)-1-(6-(pyridin-3-yl)-2-(trifluoromethyl)pyrimidin-4-yl)azetidine-2-carboxamide | 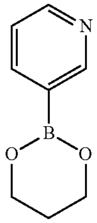 [SMILES: c1cncc(B2OCCCO2)c1] | 453.3 A |
| 306 | 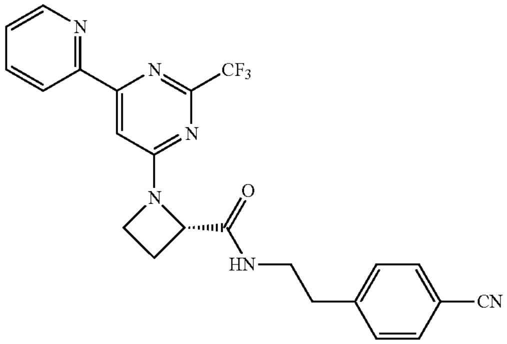 [SMILES: N#Cc1ccc(CCNC(=O)[C@@H]2CCN2c2cc(-c3ccccn3)nc(C(F)(F)F)n2)cc1] (S)-N-(4-cyanophenethyl)-1-(6-(pyridin-2-yl)-2-(trifluoromethyl)pyrimidin-4-yl)azetidine-2-carboxamide | 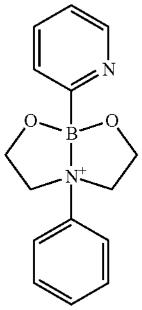 | 453.3 A |

TABLE 46-continued

| No | Compound | reagent | MS (M + H) |
|---|---|---|---|
| 307 | 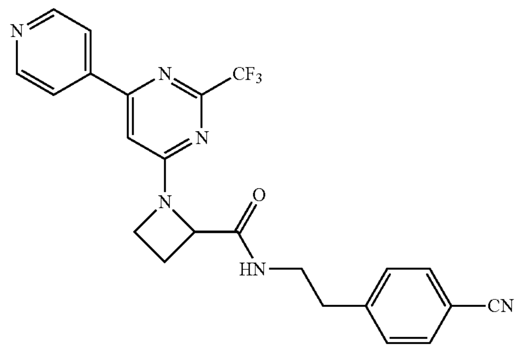 [SMILES: N#Cc1ccc(CCNC(=O)C2CCN2c2cc(-c3ccncc3)nc(C(F)(F)F)n2)cc1] N-(4-cyanophenethyl)-1-(6-(pyridin-4-yl)-2-(trifluoromethyl)pyrimidin-4-yl)azetidine-2-carboxamide | Inter-mediate 12B and 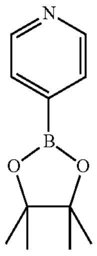 | 453.3 A |

Example 65

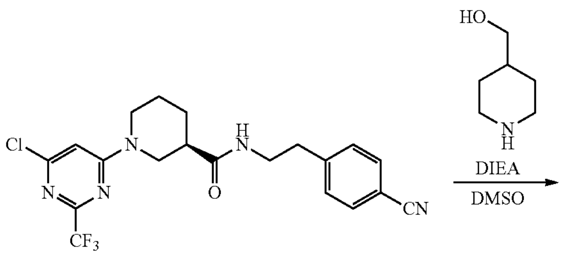

Intermediate 14

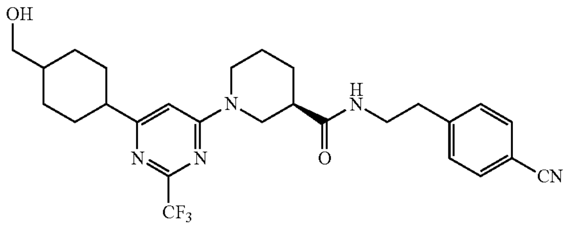

Compound 308

(R)—N-(4-cyanophenethyl)-1-(6-(4-(hydroxymethyl)piperidin-1-yl)-2-(trifluoromethyl)pyrimidin-4-yl)piperidine-3-carboxamide Using procedure as described in Example 1, Intermediate 14 (31 mg, 0.07 mmol) was converted to Compound 308 (18 mg, 49%). LCMS (Method A): m/z 517.4 $(M+H)^+$. $^1H$ NMR ($CD_3OD$) δ 7.63-7.61 (d, 2H), 7.38-7.36 (d, 2H), 5.81 (s, 1H), 4.45 (t, 2H), 4.28-4.24 (dd, 1H), 4.09-4.05 (m, 1H), 3.54-3.51 (m, 1H), 3.43-3.37 (m, 3H), 3.19-3.13 (dd, 1H), 3.02-2.64 (m, 5H), 2.37-2.30 (m, 1H), 1.88-1.68 (m, 6H), 1.56-1.48 (m, 1H), 1.23-1.14 (m, 2H). Using the procedure described above for Example 65, the following compounds were prepared from Intermediates and reagents as indicated in Table 47.

TABLE 47

| No | Compound | Inter-mediate | Reagent | MS (M + H)+ |
|---|---|---|---|---|
| 309 | 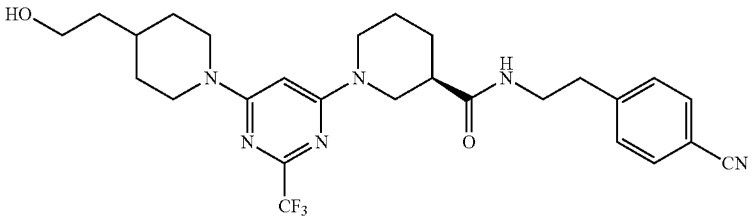 [SMILES: N#Cc1ccc(CCNC(=O)[C@@H]2CCCN(c3cc(N4CCC(CCO)CC4)nc(C(F)(F)F)n3)C2)cc1]<br>(R)-N-(4-cyanophenethyl)-1-(6-(4-(2-hydroxyethyl)piperidin-1-yl)-2-(trifluoromethyl)pyrimidin-4-yl)piperidine-3-carboxamide | 14 | 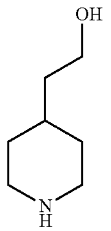 | 531.6<br>A |
| 310 | 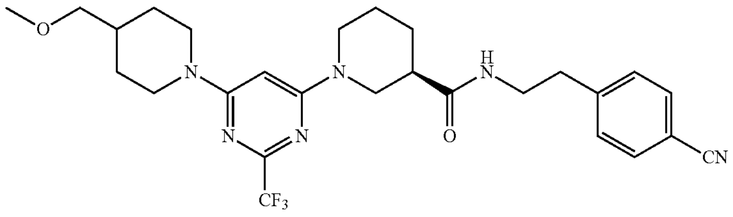 [SMILES: COCC1CCN(c2cc(N3CCC[C@@H](C(=O)NCCc4ccc(C#N)cc4)C3)nc(C(F)(F)F)n2)CC1]<br>(R)-N-(4-cyanophenethyl)-1-(6-(4-(methoxymethyl)piperidin-1-y1)-2-(trifluoromethyl)pyrimidin-4-yl)piperidine-3-carboxamide | 14 | 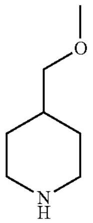 | 531.6<br>A |
| 311 | 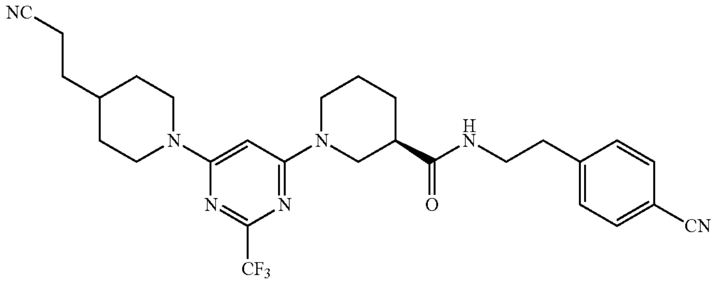<br>(R)-1-(6-(4-(2-cyanoethyl)piperidin-1-yl)-2-(trifluoromethyl)pyrimidin-4-yl)-N-(4-cyanophenethyl)piperidine-3-carboxamide | 14 | Inter-mediate 10 | 540.6<br>A |
| 312 | 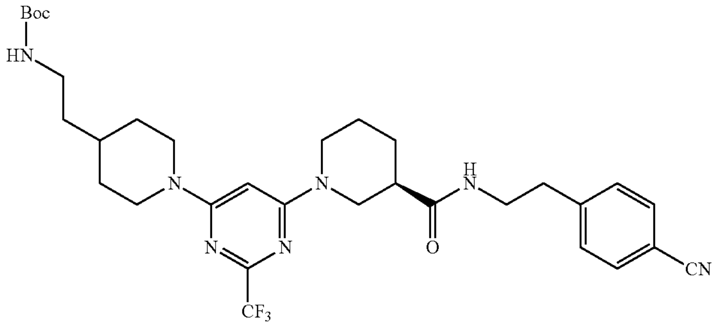 [SMILES: CC(C)(C)OC(=O)NCCC1CCN(c2cc(N3CCC[C@@H](C(=O)NCCc4ccc(C#N)cc4)C3)nc(C(F)(F)F)n2)CC1]<br>(R)-tert-butyl (2-(1-(6-(3-((4-cyanophenethyl)carbamoyl)piperidin-1-yl)-2-(trifluoromethyl)pyrimidin-4-yl)piperidin-4-yl)ethyl)carbamate | 14 | 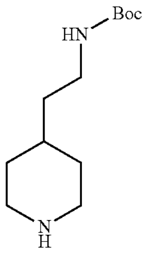 [SMILES: CC(C)(C)OC(=O)NCCC1CCNCC1] | 630.7<br>A |

TABLE 47-continued

| No | Compound | Inter-mediate | Reagent | MS (M + H)+ |
|---|---|---|---|---|
| 313 | 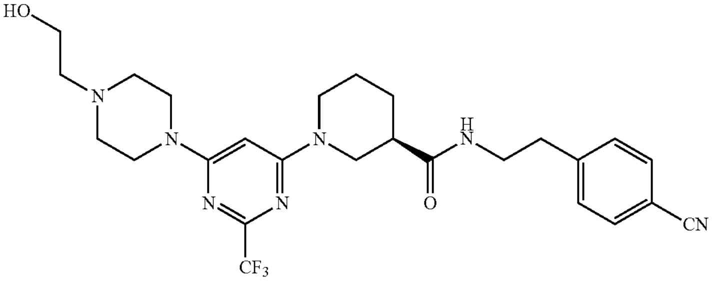<br>(R)-N-(4-cyanophenethyl)-1-(6-(4-(2-hydroxyethyl)piperazin-1-yl)-2-(trifluoromethyl)pyrimidin-4-yl)piperidine-3-carboxamide | 14 | 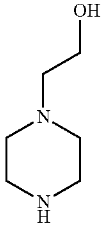 | 532.4<br>A |
| 314 | 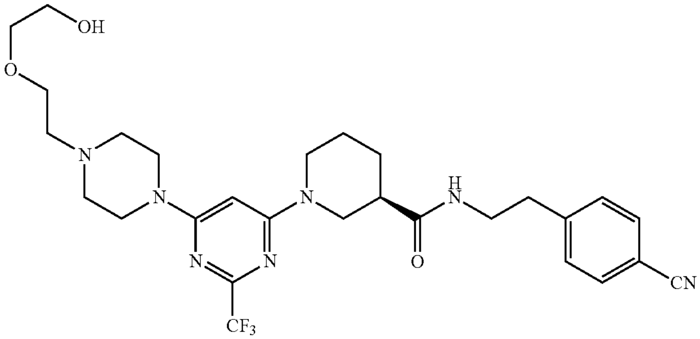 [SMILES: N#Cc1ccc(CCNC(=O)[C@@H]2CCCN(c3cc(N4CCN(CCOCCO)CC4)nc(C(F)(F)F)n3)C2)cc1]<br>(R)-N-(4-cyanophenethyl)-1-(6-(4-(2-(2-hydroxyethoxy)ethyl)piperazin-1-yl)-2-(trifluoromethyl)pyrimidin-4-yl)piperidine-3-carboxamide | 14 | 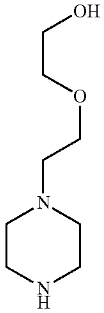 [SMILES: OCCOCCN1CCNCC1] | 576.7<br>A |
| 315 | 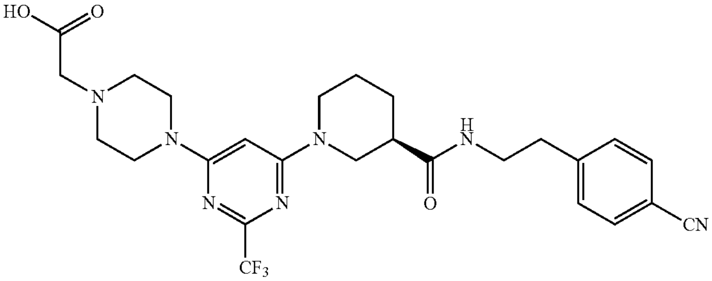 [SMILES: N#Cc1ccc(CCNC(=O)[C@@H]2CCCN(c3cc(N4CCN(CC(=O)O)CC4)nc(C(F)(F)F)n3)C2)cc1]<br>(R)-2-(4-(6-(3-((4-cyanophenethyl)carbamoyl)piperidin-1-yl)-2-(trifluoromethyl)pyrimidin-4-yl)piperazin-1-yl)acetic acid | 14 | 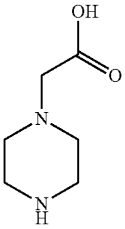 | 546.6<br>A |
| 316 | 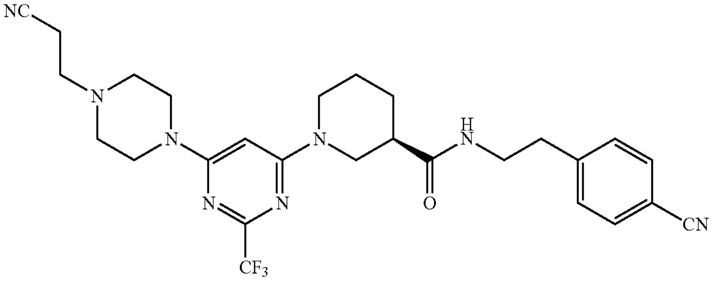 [SMILES: N#CCCN1CCN(c2cc(N3CCC[C@@H](C(=O)NCCc4ccc(C#N)cc4)C3)nc(C(F)(F)F)n2)CC1]<br>(R)-1-(6-(4-(2-cyanoethyl)piperazin-1-yl)-2-(trifluoromethyl)pyrimidin-4-yl)- | 14 | 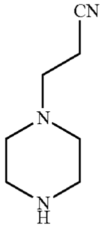 | 541.6<br>A |

TABLE 47-continued

| No | Compound | Inter-mediate | Reagent | MS (M + H)+ |
|---|---|---|---|---|
| | N-(4-cyanophenethyl)piperidine-3-carboxamide | | | |
| 317 | 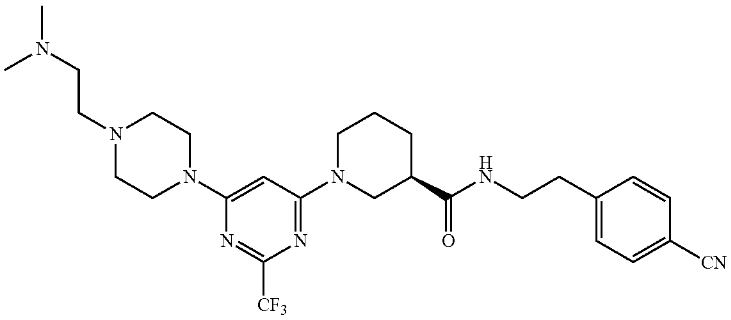 [SMILES: CN(C)CCN1CCN(c2cc(N3CCC[C@@H](C(=O)NCCc4ccc(C#N)cc4)C3)nc(C(F)(F)F)n2)CC1] (R)-N-(4-cyanophenethyl)-1-(6-(4-(2-(dimethylamino)ethyl)piperazin-1-yl)-2-(trifluoromethyl)pyrimidin-4-yl)piperidine-3-carboxamide | 14 | 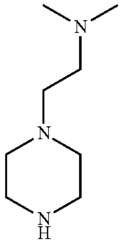 | 559.5 A |
| 318 | 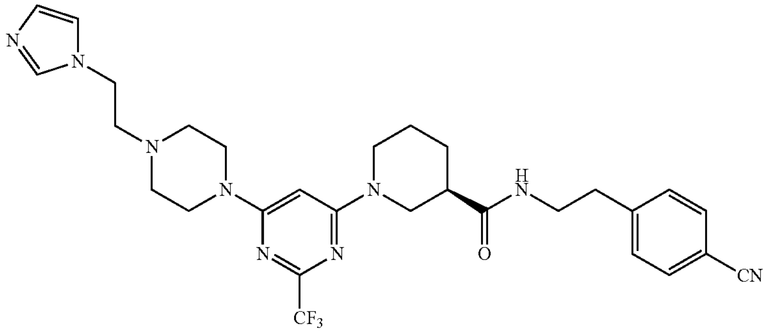 [SMILES: N#Cc1ccc(CCNC(=O)[C@@H]2CCCN(c3cc(N4CCN(CCn5ccnc5)CC4)nc(C(F)(F)F)n3)C2)cc1] (R)-1-(6-(4-(2-(1H-imidazol-1-yl)ethyl)piperazin-1-yl)-2-(trifluoromethyl)pyrimidin-4-yl)-N-(4-cyanophenethyl)piperidine-3-carboxamide | 14 | 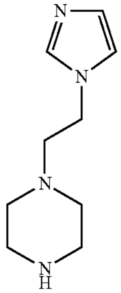 [SMILES: c1cn(CCN2CCNCC2)cn1] | 582.6 A |
| 319 | 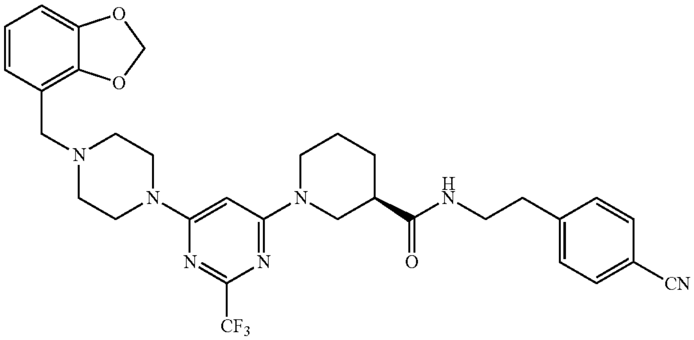 [SMILES: N#Cc1ccc(CCNC(=O)[C@@H]2CCCN(c3cc(N4CCN(Cc5cccc6c5OCO6)CC4)nc(C(F)(F)F)n3)C2)cc1] (R)-1-(6-(4-(benzo[d][1,3]dioxol-4-ylmethyl)piperazin-1-yl)-2-(trifluoromethyl)pyrimidin-4-yl)-N-(4-cyanophenethyl)piperidine-3-carboxamide | 14 | 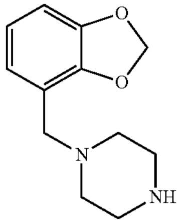 [SMILES: c1cc(CN2CCNCC2)c2c(c1)OCO2] | 622.5 A |

TABLE 47-continued

| No | Compound | Inter-mediate | Reagent | MS (M + H)$^+$ |
|---|---|---|---|---|
| 320 | 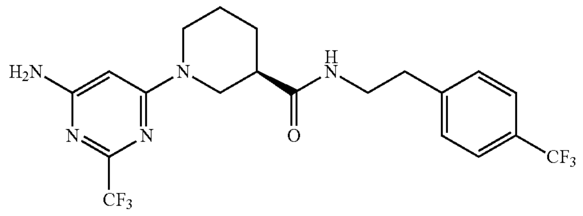 [SMILES: Nc1cc(N2CCC[C@@H](C(=O)NCCc3ccc(C(F)(F)F)cc3)C2)nc(C(F)(F)F)n1] (R)-1-(6-amino-2-(trifluoromethyl)pyrimidin-4-yl)-N-(4-(trifluoromethyl)phenethyl)piperidine-3-carboxamide | 14B | $NH_3$ | 462.3 A |
| 321 | 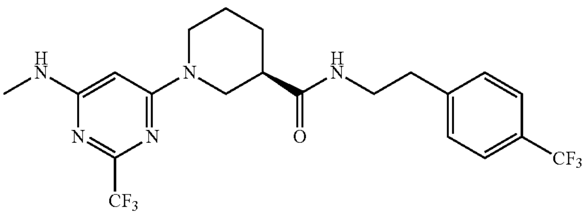 (R)-1-(6-(methylamino)-2-(trifluoromethyl)pyrimidin-4-yl)-N-(4-(trifluoromethyl)phenethyl)piperidine-3-carboxamide | 14B | $MeNH_2$ | 476.4 A |
| 322 | 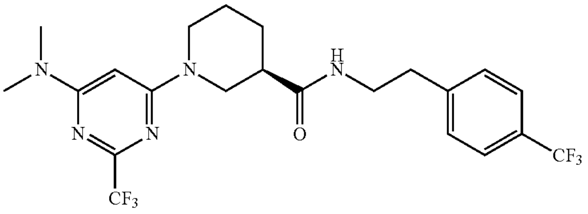 [SMILES: CN(C)c1cc(N2CCC[C@@H](C(=O)NCCc3ccc(C(F)(F)F)cc3)C2)nc(C(F)(F)F)n1] (R)-1-(6-(dimethylamino)-2-(trifluoromethyl)pyrimidin-4-yl)-N-(4-(trifluoromethyl)phenethyl)piperidine-3-carboxamide | 14B | $Me_2NH$ | 490.3 C |
| 323 | 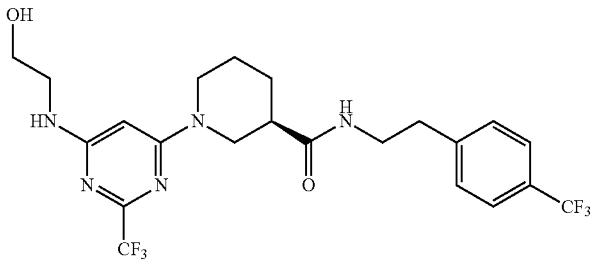 [SMILES: O=C(NCCc1ccc(C(F)(F)F)cc1)[C@@H]1CCCN(c2cc(NCCO)nc(C(F)(F)F)n2)C1] (R)-1-(6-((2-hydroxyethyl)amino)-2-(trifluoromethyl)pyrimidin-4-yl)-N-(4-(trifluoromethyl)phenethyl)piperidine-3-carboxamide | 14B | 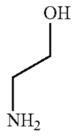 | 506.2 C |

TABLE 47-continued

| No | Compound | Inter-mediate | Reagent | MS (M + H)$^+$ |
|---|---|---|---|---|
| 324 | 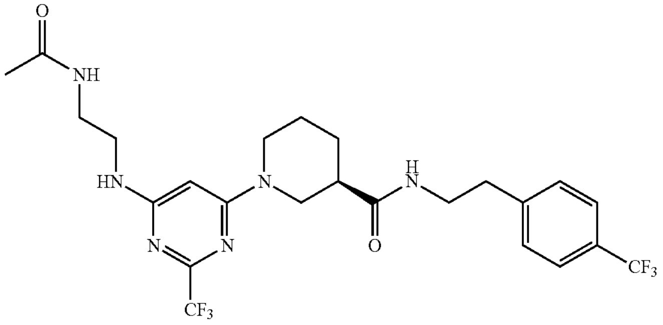 [SMILES: CC(=O)NCCNc1cc(N2CCC[C@@H](C(=O)NCCc3ccc(C(F)(F)F)cc3)C2)nc(C(F)(F)F)n1]<br>(R)-1-(6-((2-acetamidoethyl)amino)-2-(trifluoromethyl)pyrimidin-4-yl)-N-(4-(trifluoromethyl)phenethyl)piperidine-3-carboxamide | 14B | 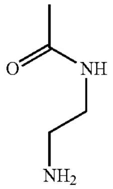 | 547.5<br>A |
| 325 | 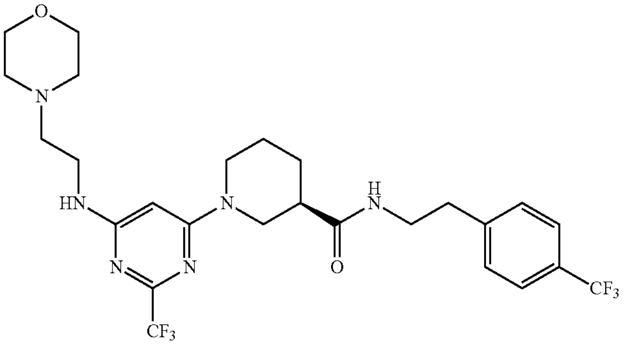 [SMILES: O=C(NCCc1ccc(C(F)(F)F)cc1)[C@@H]1CCCN(c2cc(NCCN3CCOCC3)nc(C(F)(F)F)n2)C1]<br>(R)-1-(6-((2-morpholinoethyl)amino)-2-(trifluoromethyl)pyrimidin-4-yl)-N-(4-(trifluoromethyl)phenethyl)-piperidine-3-carboxamide | 14B | 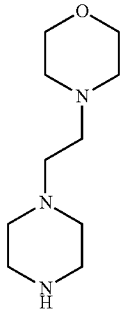 [SMILES: C1CN(CCN2CCOCC2)CCN1] | 575.5<br>A |
| 326 | 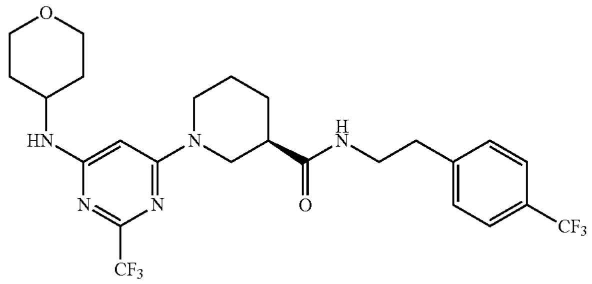 [SMILES: O=C(NCCc1ccc(C(F)(F)F)cc1)[C@@H]1CCCN(c2cc(NC3CCOCC3)nc(C(F)(F)F)n2)C1]<br>(R)-1-(6-((tetrahydro-2H-pyran-4-yl)amino)-2-(trifluoromethyl)-pyrimidin-4-yl)-N-(4-(trifluoromethyl)phenethyl)piperidine-3-carboxamide | 14B | 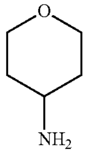 | 546.4<br>A |
| 327 | 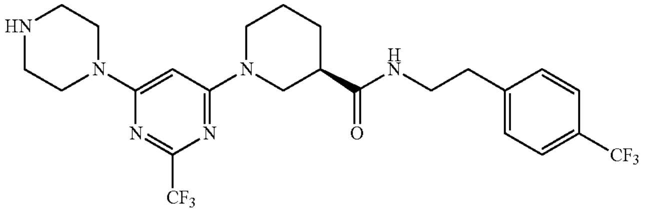 [SMILES: O=C(NCCc1ccc(C(F)(F)F)cc1)[C@@H]1CCCN(c2cc(N3CCNCC3)nc(C(F)(F)F)n2)C1]<br>(R)-1-(6-(piperazin-1-yl)-2-(trifluoromethyl)pyrimidin-4-yl)-N-(4- | 14B | 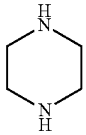 | 531.5<br>A |

TABLE 47-continued

| No | Compound | Inter-mediate | Reagent | MS (M + H)+ |
|---|---|---|---|---|
| | (trifluoromethyl)phenethyl)piperidine-3-carboxamide | | | |
| 328 | 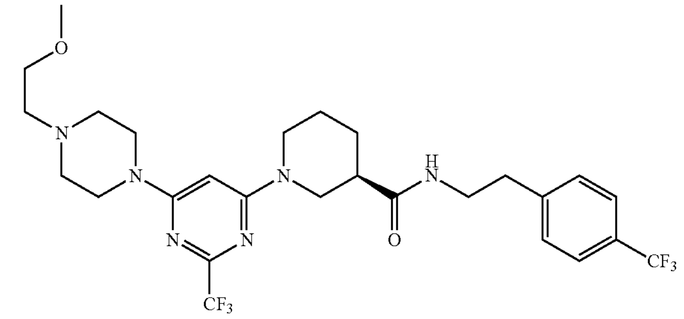 [SMILES: COCCN1CCN(c2cc(N3CCC[C@@H](C(=O)NCCc4ccc(C(F)(F)F)cc4)C3)nc(C(F)(F)F)n2)CC1] (R)-1-(6-(4-(2-methoxyethyl)piperazin-1-yl)-2-(trifluoromethyl)pyrimidin-4-yl)-N-(4-(trifluoromethyl)phenethyl)piperidine-3-carboxamide | 14B | 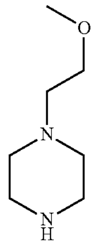 | 546.6 A |
| 329 | 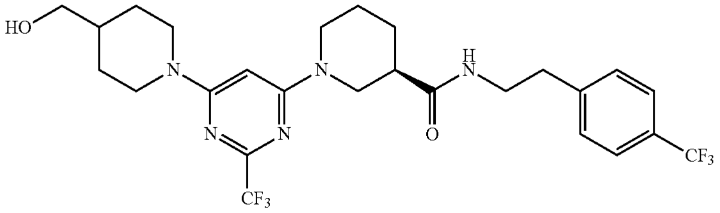 [SMILES: O=C(NCCc1ccc(C(F)(F)F)cc1)[C@@H]1CCCN(c2cc(N3CCC(CO)CC3)nc(C(F)(F)F)n2)C1] (R)-1-(6-(4-(hydroxymethyl)piperidin-1-yl)-2-(trifluoromethyl)pyrimidin-4-yl)-N-(4-(trifluoromethyl)-phenethyl)piperidine-3-carboxamide | 14B | 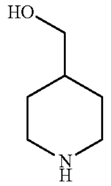 | 560.4 A |
| 330 | 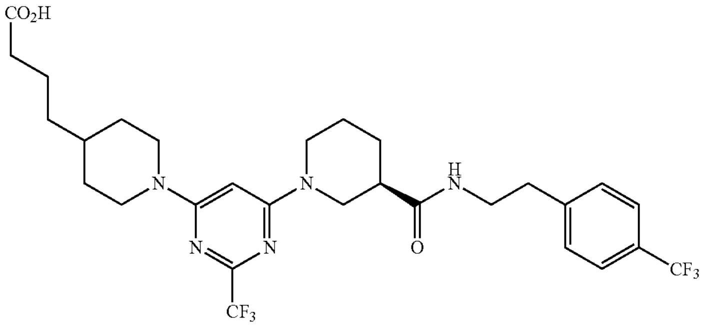 [SMILES: O=C(O)CCCC1CCN(c2cc(N3CCC[C@@H](C(=O)NCCc4ccc(C(F)(F)F)cc4)C3)nc(C(F)(F)F)n2)CC1] (R)-4-(1-(2-(trifluoromethyl)-6-(3-((4-(trifluoromethyl)phenethyl)carbamoyl) piperidin-1-yl)pyrimidin-4-yl)piperidin-4-yl)butanoic acid | 14B | 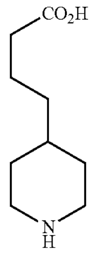 | 616.5 A |
| 331 | 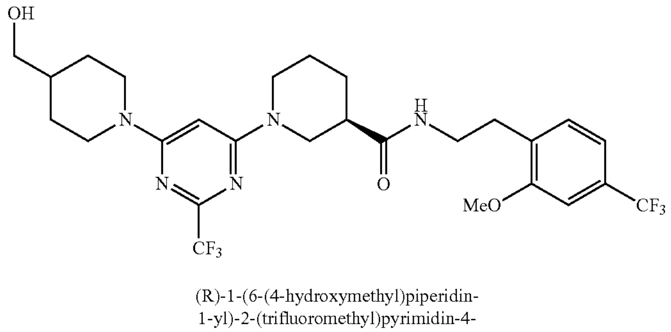 (R)-1-(6-(4-hydroxymethyl)piperidin-1-yl)-2-(trifluoromethyl)pyrimidin-4- | 14D | 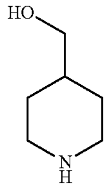 | 590.6 A |

TABLE 47-continued

| No | Compound | Inter-mediate | Reagent | MS (M + H)+ |
|---|---|---|---|---|
| | yl)-N-(2-methoxy-4-(trifluoromethyl)-phenethyl)piperidine-3-carboxamide | | | |
| 332 | 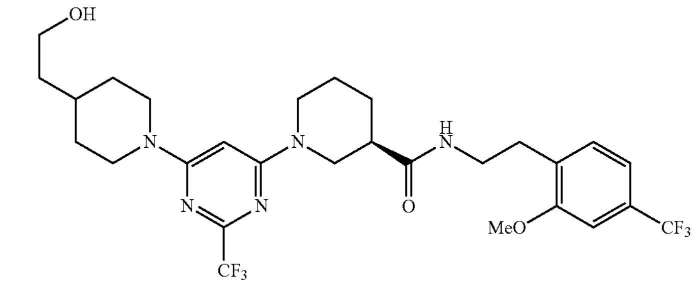 [SMILES: COc1cc(C(F)(F)F)ccc1CCNC(=O)[C@@H]1CCCN(c2cc(N3CCC(CCO)CC3)nc(C(F)(F)F)n2)C1] (R)-1-(6-(4-(2-hydroxyethyl)piperidin-1-yl)-2-(trifluoromethyl)pyrimidin-4-yl)-N-(2-methoxy-4-(trifluoromethyl)-phenethyl)piperidine-3-carboxamide | 14D | 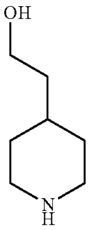 | 604.6 A |
| 333 | 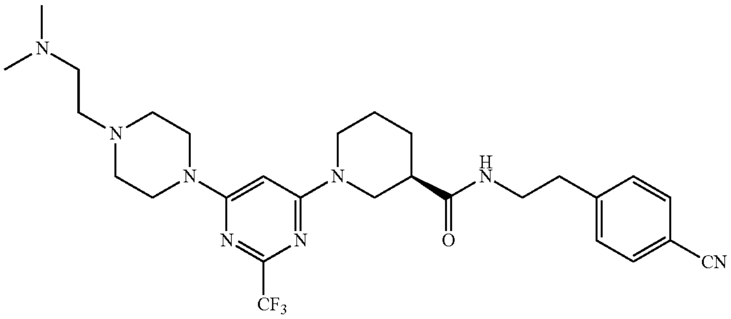 [SMILES: CN(C)CCN1CCN(c2cc(N3CCC[C@@H](C(=O)NCCc4ccc(C#N)cc4)C3)nc(C(F)(F)F)n2)CC1] (R)-N-(4-cyanophenethyl)-1-(6-(4-(2-(dimethylamino)ethyl)piperazin-1-yl)-2-(trifluoromethyl)pyrimidin-4-yl)piperidine-3-carboxamide | 14 | 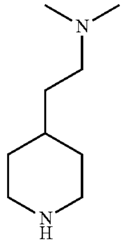 | 558.7 A |

Example 66

(R)—N-(cyanophenethyl)-1-(6-((tetrahydro-2H-pyran-4-yl)oxy-2-(trifluoromethyl) pyrimidin-4-yl) piperidine-3-carboxamide

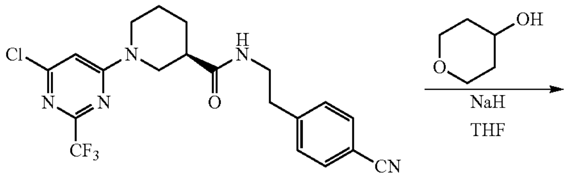

Intermediate 14

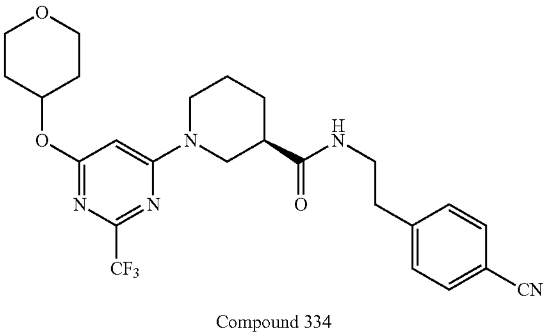

Compound 334

Using the procedure as described in Example 2, Intermediate 14 (44 mg, 0.10 mmol) was converted to Compound 334 (14 mg, 27%). LCMS (method A): m/z 504.3 $(M+H)^+$. $^1H$ NMR ($CDCl_3$) δ 7.54-7.51 (dd, 2H), 7.23-7.21 (m, 2H), 6.35 (b, 1H), 5.83 (s, 1H), 5.33-5.27 (m, 1H), 4.00-3.80 (m, 4H), 3.65-3.57 (m, 4H), 3.48-3.41 (m, 1H), 3.29-3.23 (m, 1H), 2.90-2.81 (m, 2H), 2.39-2.35 (m, 1H), 2.16-2.01 (m, 3H), 1.84-1.70 (m, 3H), 1.65-1.56 (m, 2H). Using the procedure described above for Example 66, the following compound was prepared from the Intermediate as indicated in Table 48.

TABLE 48

| No | Compound | Intermediate | MS (M + H) |
|---|---|---|---|
| 335 | 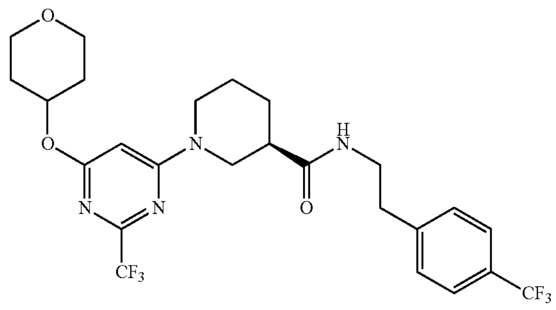 [SMILES: O=C(NCCc1ccc(C(F)(F)F)cc1)[C@@H]1CCCN(c2cc(OC3CCOCC3)nc(C(F)(F)F)n2)C1] (R)-1-(6-((tetrahydro-2H-pyran-4-yl)oxy)-2-(trifluoromethyl)pyrimidin-4-yl)-N-(4-(trifluoromethyl)-phenethyl)piperidine-3-carboxamide | 14B | 547.4 A |

Example 67

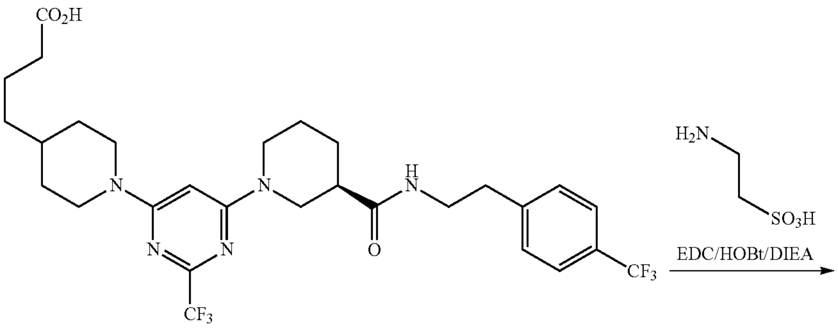

Compound 330

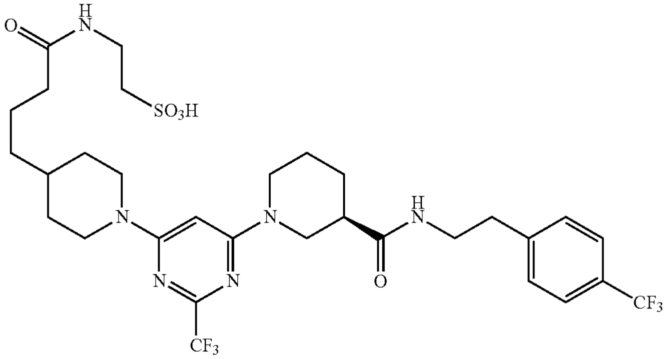

Compound 336

(R)-2-(4-(1-(2-(trifluoromethyl)-6-(3-((4-(trifluoromethyl)phenethyl)carbamoyl)-piperidin-1-yl)pyrimidin-4-yl)piperidin-4-yl)butanamido)ethanesulfonic acid Using the procedure as described in Example 7, Compound 330 (120 mg, 0.20 mmol) was converted to Compound 336. LCMS (method A): m/z 723.2 $(M+H)^+$. $^1H$ NMR ($CD_3OD$) δ 7.56 (d, 2H), 7.37 (d, 2H), 4.35 (d, 2H), 4.23 (d, 1H), 4.06 (d, 1H), 3.62 (br, 2H), 3.47 (t, 2H), 3.32-3.23 (m, 2H), 3.09 (t, 1H), 2.98-2.87 (m, 5H), 2.42 (m, 1H), 2.23 (t, 2H), 1.91-1.57 (m, 9H), 1.33-1.28 (m, 2H), 1.19 (m, 2H).

Example 68

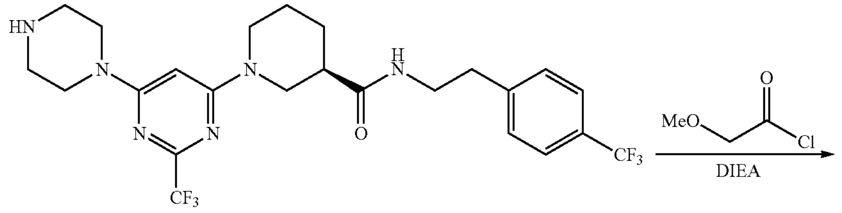

Compound 327

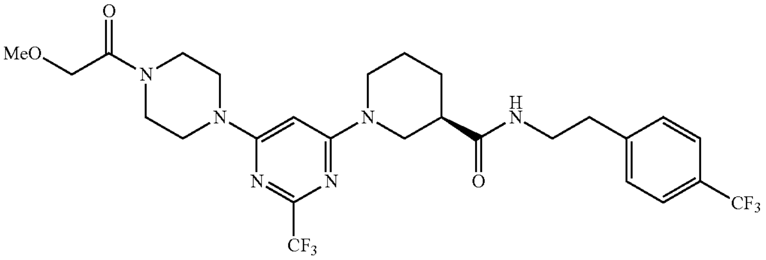

Compound 337

(R)-1-(6-(4-(2-methoxyacetyl)piperazin-1-yl)-2-(trifluoromethyl)pyrimidin-4-yl)-N-(4-(trifluoromethyl)phenethyl)piperidine-3-carboxamide Using the procedure as described in Example 5, replacing DIEA for TEA, Compound 327 (40 mg, 0.075 mmol) was converted to Compound 337 (23 mg). LCMS (method A): m/z 603.6 $(M+H)^+$. $^1H$ NMR ($CDCl_3$) δ 7.45 (d, 2H), 7.21 (d, 2H), 6.82 (br s, 1H), 5.50 (s, 1H), 4.14 (s, 2H), 4.06 (m, 1H), 3.73-3.58 (m, 10H), 3.49-3.41 (m, 5H), 3.27 (m, 1H), 2.91-2.81 (m, 2H), 2.43 (m, 1H), 2.17 (m, 1H), 1.81 (m, 1H), 1.56 (m, 2H). Using the procedure described above for Example 68, the following compounds were prepared from Compound 327 and the reagents as indicated in Table 49.

TABLE 49

| No | Structure | Reagent | MS (M + H) |
|---|---|---|---|
| 338 | 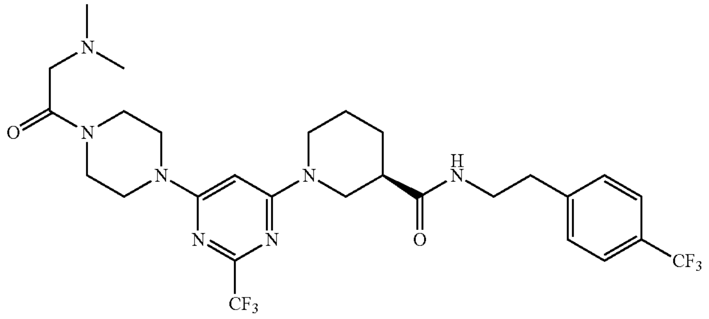 [SMILES: CN(C)CC(=O)N1CCN(c2cc(N3CCC[C@@H](C(=O)NCCc4ccc(C(F)(F)F)cc4)C3)nc(C(F)(F)F)n2)CC1] (R)-1-(6-(4-(2-(dimethylamino)-acetyl)piperazin-1-yl)-2-(trifluoromethyl)-pyrimidin-4-yl)-N-(4-(trifluoromethyl)phenethyl)-piperidine-3-carboxamide | 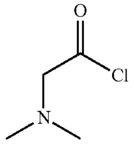 | 616.6 A |

TABLE 49-continued
| No | Structure | Reagent | MS (M + H) |
|---|---|---|---|
| 339 | 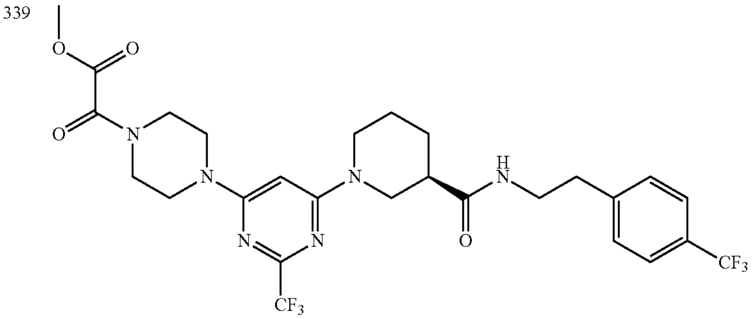 (R)-methyl 2-oxo-2-(4-(2-(trifluoromethyl)-6-(3-((4-(trifluoromethyl)phenethyl)-carbamoyl)piperidin-1-yl)pyrimidin-4-yl)piperazin-1-yl)acetate | 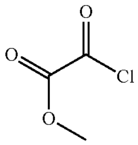 | 617.6 |
| 340 | 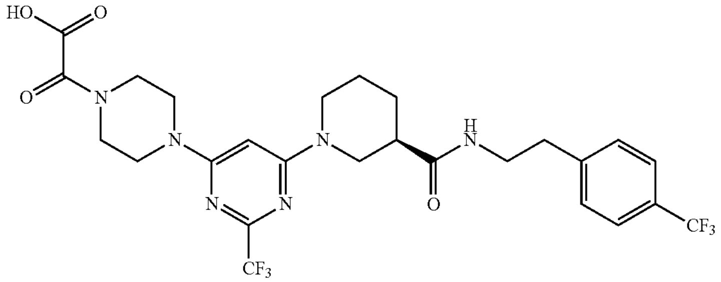 [SMILES: O=C(O)C(=O)N1CCN(c2cc(N3CCC[C@@H](C(=O)NCCc4ccc(C(F)(F)F)cc4)C3)nc(C(F)(F)F)n2)CC1] (R)-2-oxo-2-(4-(2-(trifluoromethyl)-6-(3-((4-(trifluoromethyl)phenethyl)-carbamoyl)piperidin-1-yl)pyrimidin-4-yl)piperazin-1-yl)acetic acid | Hydrolysis of Compound 339 by LiOH as in Example 16 | 603.5 A |
Example 69
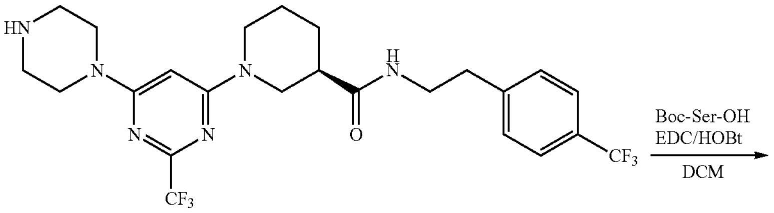
Compound 327
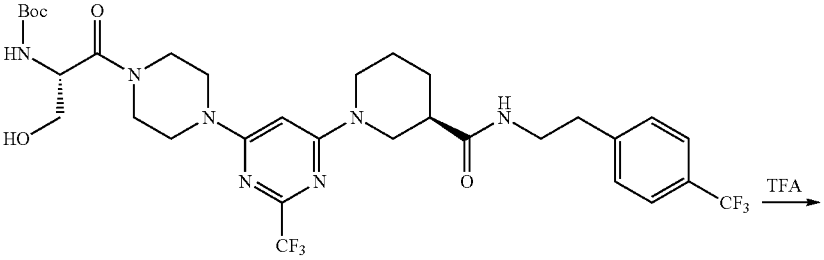
Compound 341

-continued

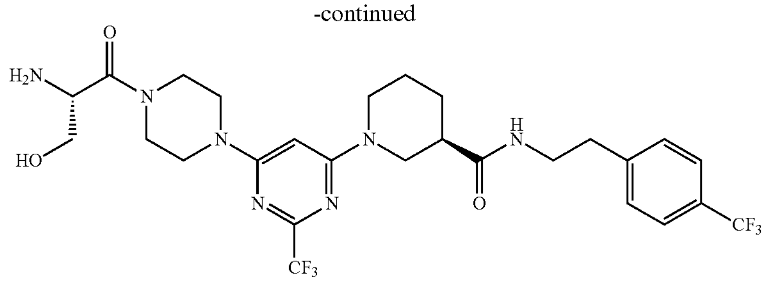

Compound 342 tert-butyl ((S)-3-hydroxy-t-oxo-1-(4-(2-(trifluoromethyl)-6-((R)-3-((4-(trifluoromethyl)phenethyl)carbamoyl)piperidin-1-yl)pyrimidin-4-yl)piperazin-1-yl)propan-2-yl)carbamate Using the procedure as described in Example 7, Compound 327 (53 mg, 0.10 mmol) was converted to Compound 341 (35 mg). LCMS (method A): m/z 718.7 $(M+H)^+$.

(R)-1-(6-(4-((S)-2-amino-3-hydroxypropanoyl)piperazin-1-yl)-2-(trifluoromethyl) pyrimidin-4-yl)-N-(4-(trifluoromethyl)phenethyl)piperidine-3-carboxamide Using the procedure as described in Example 4, Compound 341 (30 mg, 0.04 mmol) was converted to Compound 342 (12 mg). LCMS (method A): m/z 618.7 $(M+H)^+$. $^1H$ NMR ($CDCl_3$) δ 7.45 (d, 2H), 7.21 (d, 2H), 6.76 (br s, 1H), 5.49 (s, 1H), 4.11 (d, 1H), 3.81-3.54 (m, 13H), 3.47-3.41 (m, 2H), 3.27 (m, 1H), 2.92-2.79 (m, 2H), 2.43 (m, 1H), 2.19 (m, 1H), 1.86-1.56 (m, 6H).

Example 70

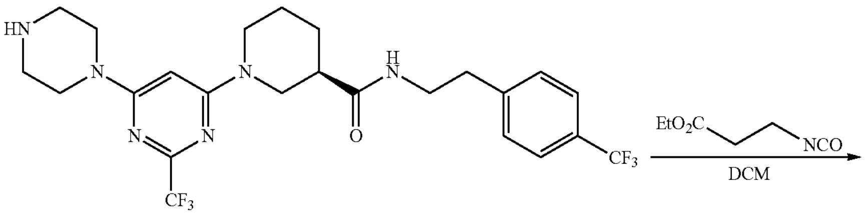

Compound 327

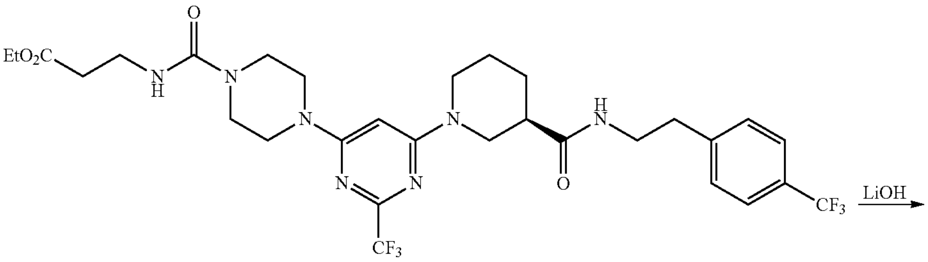

Compound 343

-continued

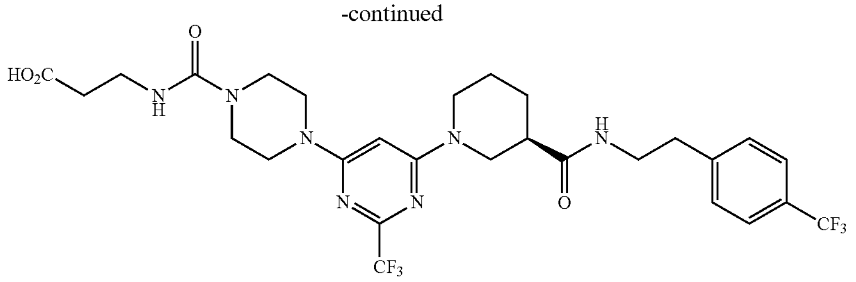

Compound 344

(R)-ethyl 3-(4-(2-(trifluoromethyl)-6-(3-((4-(trifluoromethyl)phenethyl)carbamoyl)-piperidin-1-yl)pyrimidin-4-yl)piperazine-1-carboxamido)propanoate Using the procedure as described in Example 6, Compound 327 (106 mg, 0.210 mmol) was converted to Compound 343 (115 mg). LCMS (method A): m/z 674.6 $(M+H)^+$.

(R)-3-(4-(2-(trifluoromethyl)-6-(3-((4-(trifluoromethyl)phenethyl)carbamoyl)-piperidin-1-yl)pyrimidin-4-yl)piperazine-1-carboxamido)propanoic acid Using the procedure as described in Example 16, Compound 343 (110 mg, 0.16 mmol) was converted to Compound 344 (20 mg). LCMS (method A): m/z 646.6 $(M+H)^+$. $^1H$ NMR ($CDCl_3$) δ 7.85 (t, 1H), 7.53 (d, 2H), 7.32 (d, 2H), 5.67 (s, 1H), 4.17 (dd, 1H), 3.94 (d, 1H), 3.68 (t, 4H), 3.57-3.38 (m, 8H), 3.37 (m, 1H), 3.08 (m, 1H), 2.88 (m, 2H), 1.89 (q, 2H), 1.69 (m, 1H), 1.56 (m, 1H).

Example 71

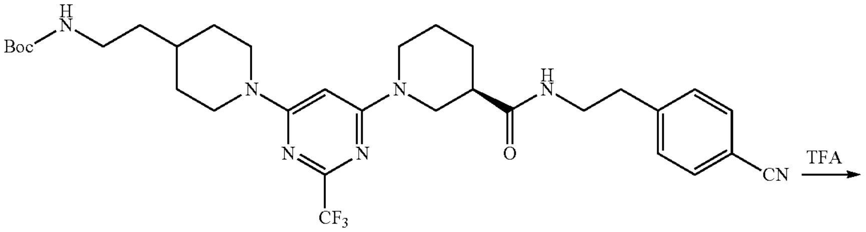

Compound 312

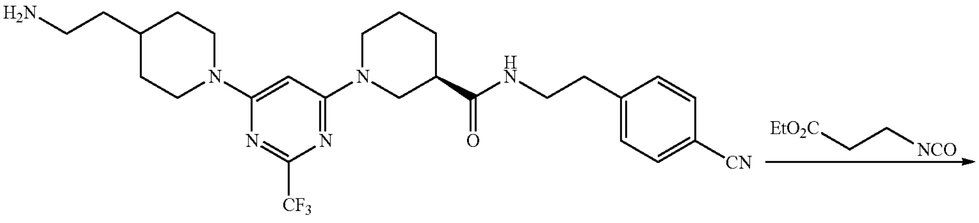

Compound 345

-continued

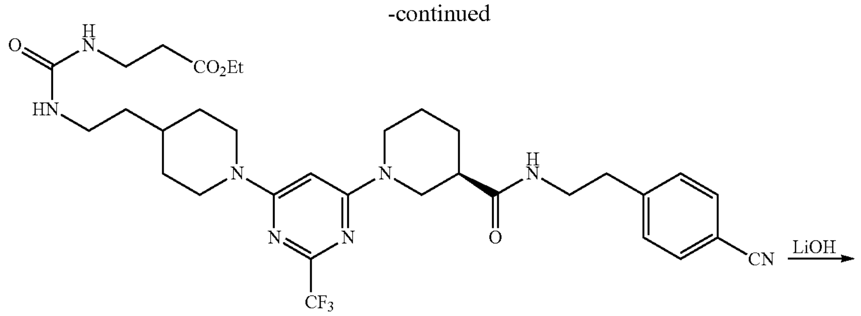

Compound 346

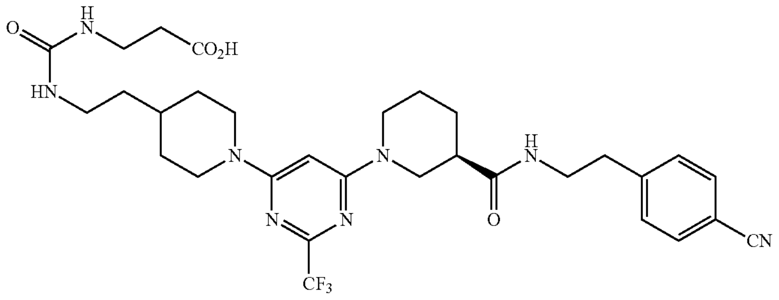

Compound 347

(R)-1-(6-(4-(2-aminoethyl)piperidin-1-yl)-2-(trifluoromethyl)pyrimidin-4-yl)-N-(4-cyanophenethyl) piperidine-3-carboxamide Using the procedure as described in Example 4, Compound 312 (74 mg, 0.12 mmol) was converted to Compound 345 (61 mg). LCMS (method A): m/z 530.6 $(M+H)^+$.

(R)-ethyl 3-(3-(2-(1-(6-(3-((4-cyanophenethyl)carbamoyl)piperidin-1-yl)-2-(trifluoromethyl) pyrimidin-4-yl)piperidin-4-yl)ethyl)ureido)propanoate Using the procedure as described in Example 6, Compound 345 (59 mg, 0.11 mmol) was converted to Compound 346 (71 mg). LCMS (method A): m/z 673.8 $(M+H)^+$.

(R)-3-(3-(2-(1-(6-(3-((4-cyanophenethyl)carbamoyl) piperidin-1-yl)-2-(trifluoromethyl) pyrimidin-4-yl) piperidin-4-yl)ethyl)ureido)propanoic acid Using the procedure as described in Example 16, Compound 346 (68 mg, 0.10 mmol) was converted to Compound 347 (16 mg). LCMS (method A): m/z 645.7 $(M+H)^+$. $^1H$ NMR ($CDCl_3$) δ 8.11 (t, 1H), 7.61 (d, 2H), 7.37 (d, 2H), 5.79 (s, 1H), 4.40 (t, 2H), 4.25 (d, 1H), 4.07 (d, 1H), 3.50 (m, 1H), 3.42-3.37 (m, 3H), 3.17 (m, 3H), 2.98 (m, 1H), 2.90-2.82 (m, 4H), 2.47 (t, 2H), 2.33 (t, 1H), 1.85-1.78 (m, 4H), 1.71-1.64 (m, 2H), 1.53-1.42 (m, 3H), 1.20 (q, 2H).

Example 72

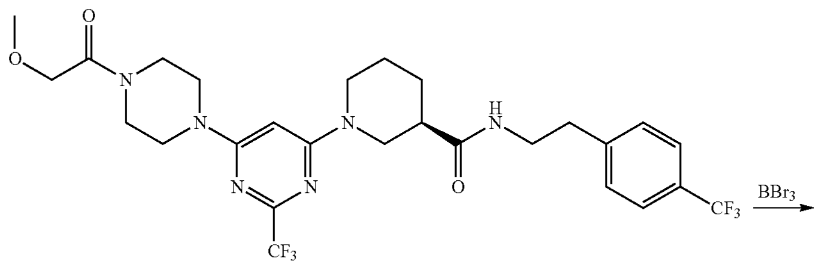

Compound 337

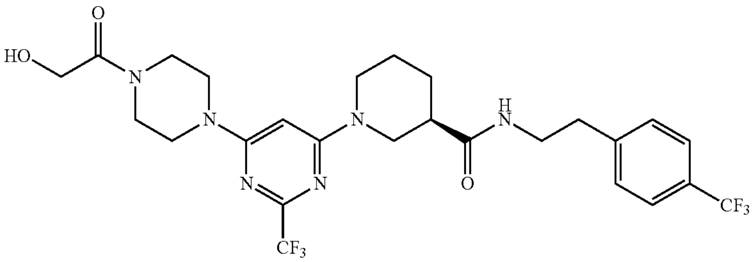

Compound 348

(R)-1-(6-(4-(2-hydroxyacetyl)piperazin-1-yl)-2-(trifluoromethyl)pyrimidin-4-yl)-N-(4-(trifluoromethyl)phenethyl)piperidine-3-carboxamide To a solution of Compound 337 (23 mg, 0.04 mmol) in DCM (1 mL) cooled at 0° C., $BBr_3$ (1M in DCM, 380 μL, 0.38 mmol) was added. The reaction was stirred at room temperature overnight. The solvent was removed in vacuo. The residue was purified by MS-HPLC to afford Compound 348 (6 mg). LCMS (method A): m/z 589.5 $(M+H)^+$. $^1H$ NMR ($CDCl_3$) δ 7.45 (d, 2H), 7.20 (d, 2H), 6.73 (s, 1H), 5.50 (s, 1H), 4.22 (s, 2H), 4.09 (d, 1H), 3.81-3.59 (m, 8H), 3.49-3.38 (m, 4H), 3.28 (m, 1H), 2.92-2.81 (m, 2H), 2.43 (d, 1H), 2.20 (t, 1H), 1.85-1.50 (m, 4H).

Example 73

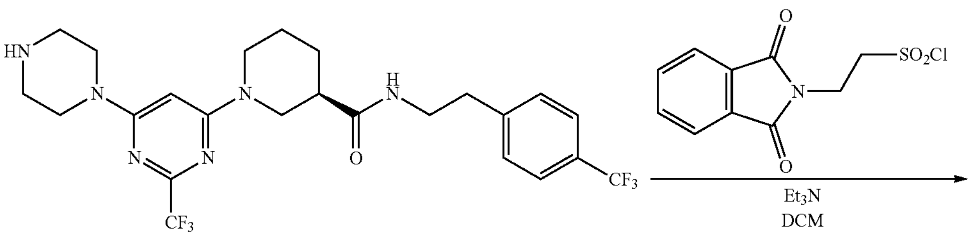

Compound 327

-continued

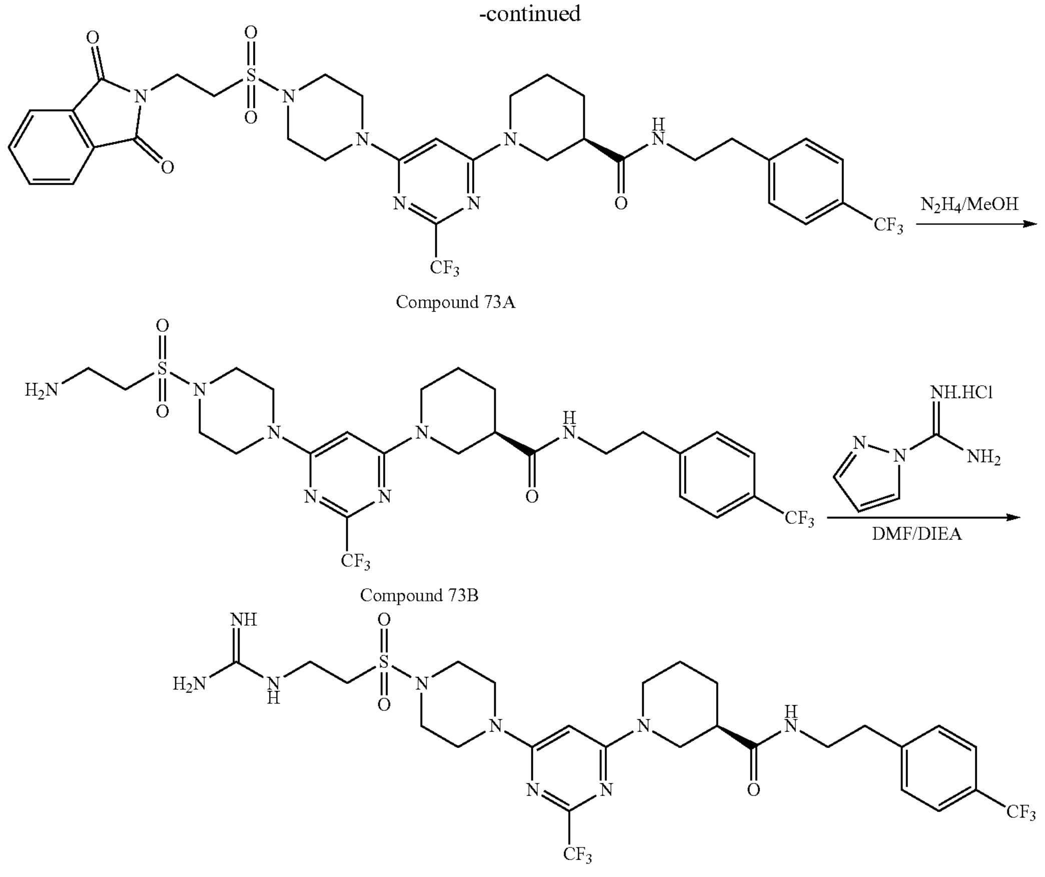

Compound 73A

Compound 73B

Compound 349

(R)-1-(6-(4-((2-(1,3-dioxoisoindolin-2-yl)ethyl)sulfonyl)piperazin-1-yl)-2-(trifluoromethyl)pyrimidin-4-yl)-N-(4-(trifluoromethyl)phenethyl)piperidine-3-carboxamide Using the procedure as described in Intermediate 21, step 1, Compound 327 (87 mg, 0.16 mmol) was converted to Compound 73A (80 mg, 65%). LCMS (method A): m/z 768.2 $(M+H)^+$.

(R)-1-(6-(4-((2-aminoethyl)sulfonyl)piperazin-1-yl)-2-(trifluoromethyl)pyrimidin-4-yl)-N-(4-(trifluoromethyl)phenethyl)piperidine-3-carboxamide Compound 73A (80 mg, 0.10 mmol) was deprotected using the procedure as described in Intermediate 21, step 2 to afford Compound 73B (31 mg, 47%). LCMS (method A): m/z 638.3 $(M+H)^+$.

(R)-1-(6-(4-((2-guanidinoethyl)sulfonyl)piperazin-1-yl)-2-(trifluoromethyl)-pyrimidin-4-yl)-N-(4-(trifluoromethyl)phenethyl)piperidine-3-carboxamide Using the procedure as described in Example 26, Compound 73B (31 mg, 0.05 mmol) was converted to Compound 349 (22 mg, 67%). LCMS (A): m/z 680.3 $(M+H)^+$. $^1$H NMR ($CD_3OD$) δ 8.56 (s, 1H), 7.64 (s, 1H), 7.54 (d, 2H), 7.34 (d, 2H), 5.80 (s, 1H), 4.27 (d, 1H), 4.05 (br s, 1H), 3.77 (m, 4H), 3.69 (t, 2H), 3.54-3.42 (m, 2H), 3.39-3.36 (m, 5H), 3.30-3.25 (m, 3H), 3.07-3.01 (m, 1H), 2.89 (m, 2H), 1.92-1.69 (m, 3H), 1.55 (m, 1H).

Example 74
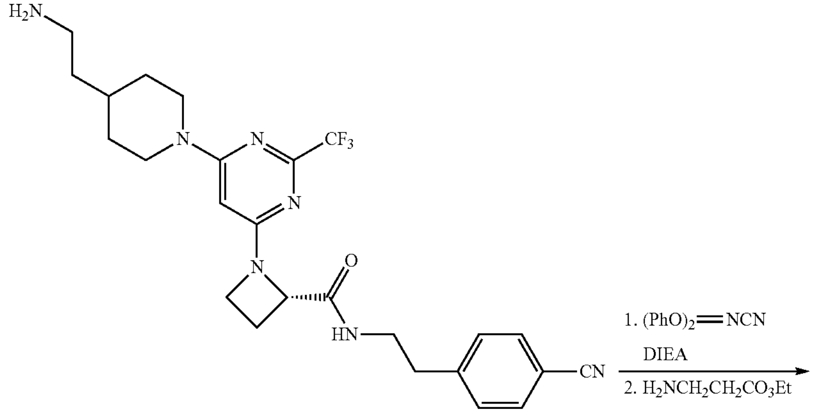
Compound 246
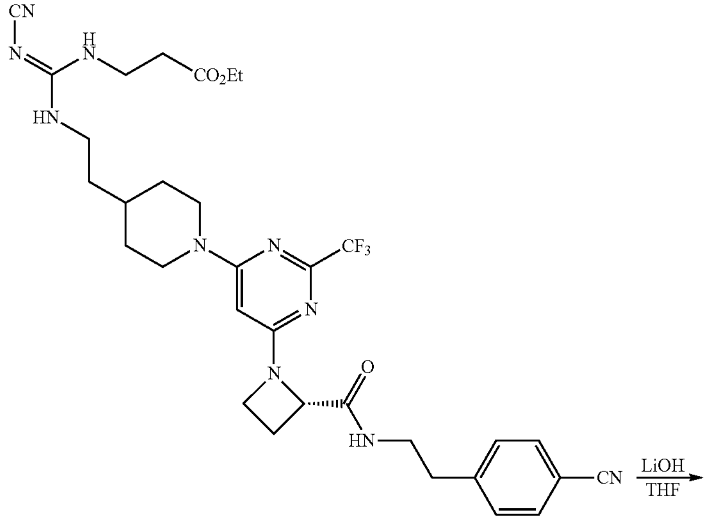
Compound 350
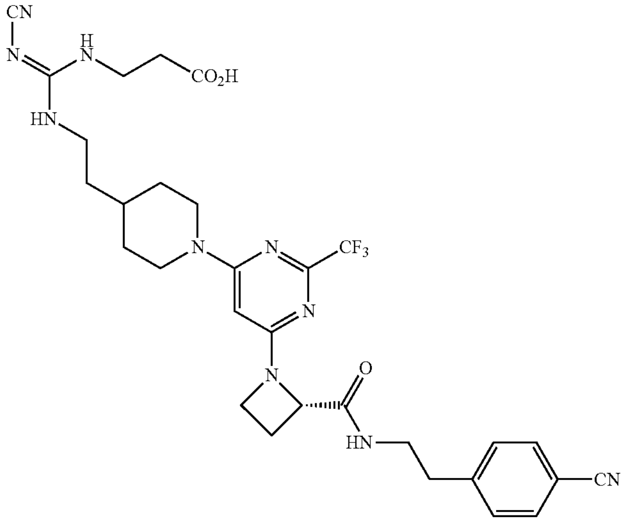
Compound 351

(S,Z)-ethyl 3-(2-cyano-3-(2-(1-(6-(2-((4-cyanophenethyl)carbamoyl)azetidin-1-yl)-2-(trifluoromethyl)pyrimidin-4-yl)piperidin-4-yl)ethyl)guanidino)propanoate To a stirred solution of Compound 246 (0.20 g, 0.37 mmol) in acetonitrile (3 mL) was added DIEA (0.26 mL, 1.49 mmol) and dibenzyl cyanocarbonimidate (98 mg, 0.41 mmol). The mixture was heated at 40° C. for 45 minutes, and more dibenzyl cyanocarbonimidate (33 mg) was added. The reaction was continued at 40° C. for 90 minutes. Then β-alanine ethyl ester (286 mg, 1.86 mmol) and DIEA (0.52 mL) were added. The reaction mixture was heated at 70° C. overnight. More β-alanine ethyl ester (57 mg) and DIEA (65 uL) were added and heating continued at 70° C. for three hours. The reaction was cooled and concentrated in vacuo. The residue was purified by reverse phase flash chromatography (0-100% ACN/$H_2O$) to afford Compound 350 (149 mg, 60%). LCMS (A): m/z 669.5 $(M+H)^+$. $^1H$ NMR ($CDCl_3$) δ 8.44 (br, 1H), 7.43 (d, 2H), 7.21 (d, 2H), 5.72 (br, 1H), 5.58 (t, 1H), 5.24 (s, 1H), 4.78 (t, 1H), 4.39 (br, 2H), 4.21 (q, 2H), 3.94 (m, 1H), 3.81 (m, 1H), 3.65-3.44 (m, 4H), 3.24 (m, 2H), 2.94-2.82 (m, 5H), 2.60 (m, 2H), 2.44 (m, 1H), 1.81 (d, 2H), 1.64 (m, 2H), 1.30-1.20 (m, 6H).

(S,Z)-3-(2-cyano-3-(2-(1-(6-(2-((4-cyanophenethyl)carbamoyl)azetidin-1-yl)-2-(trifluoromethyl)pyrimidin-4-yl)piperidin-4-yl)ethyl)guanidino)propanoic acid To a stirred solution of Compound 350 (149 mg, 0.22 mmol) in THF (1.3 mL) was added 1N LiOH solution (0.45 mL). The reaction was stirred at room temperature for three hours, and acidified with 2N HCl to pH~5. The mixture was concentrated in vacuo. The residue was purified by reverse phase flash chromatography (0-100% ACN/$H_2O$) to afford Compound 351 (110 mg, 77%). LCMS (A): m/z 641.5 $(M+H)^+$. $^1H$ NMR (DMSO-d6) δ 8.19 (t, 1H), 7.69 (d, 2H), 7.39 (d, 2H), 7.09 (br, 1H), 6.91 (t, 1H), 5.58 (br, 1H), 4.58 (m, 1H), 4.31 (br, 2H), 3.96-3.86 (m, 2H), 3.41-3.27 (m, 5H), 3.14 (m, 2H), 2.82 (m, 4H), 2.44 (t, 2H), 2.16 (m, 1H), 1.73 (d, 2H), 1.56 (br, 1H), 1.40 (m, 2H), 1.02 (m, 2H).

Example 75

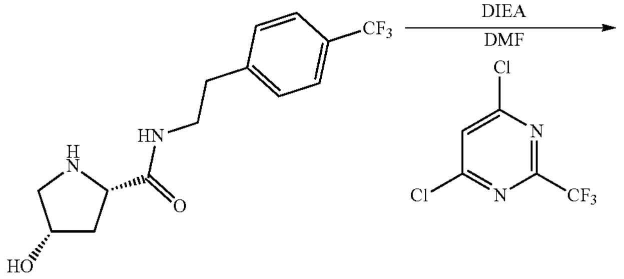

Intermediate 11

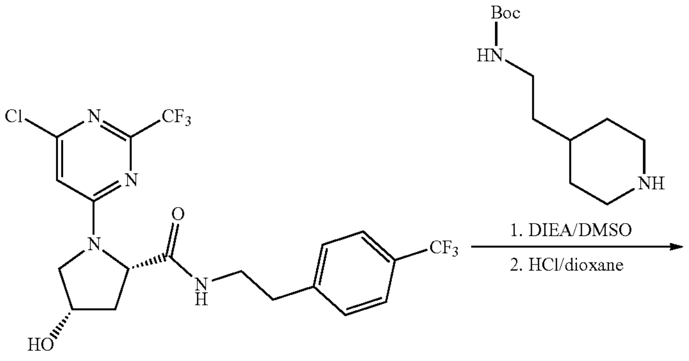

Compound 75A

-continued
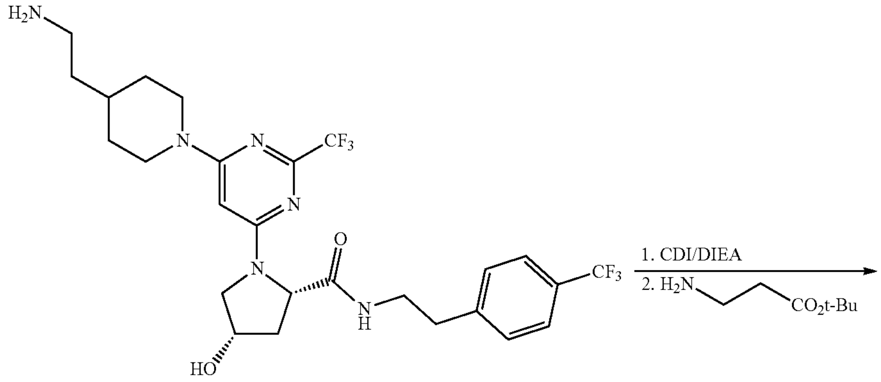
Compound 75B
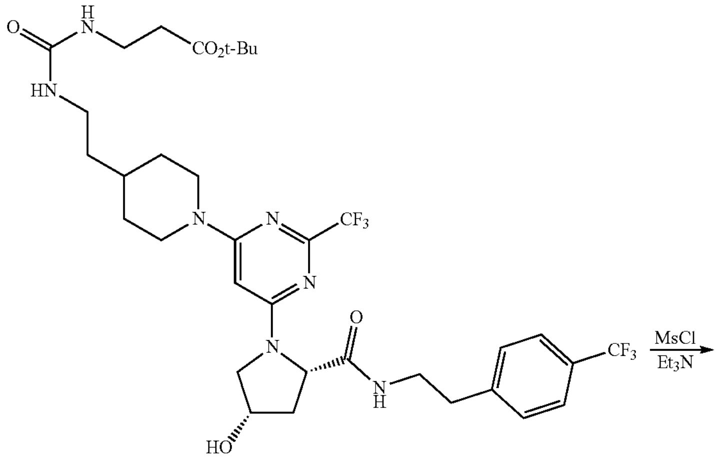
Compound 75C
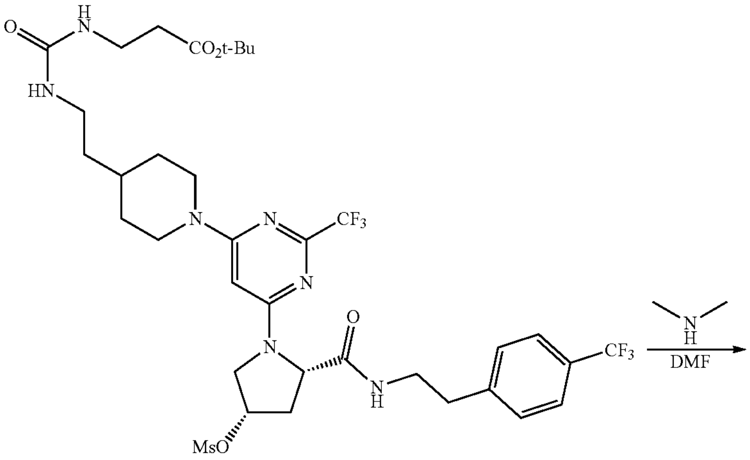
Compound 75D -continued

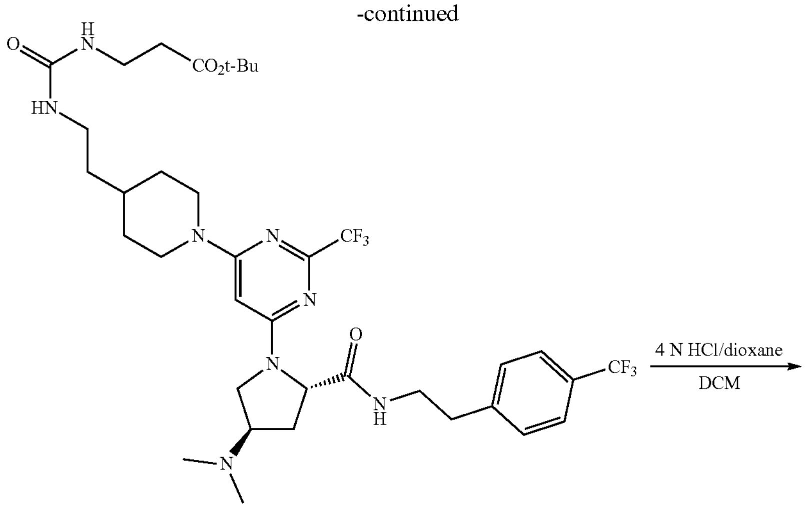

Compound 75E

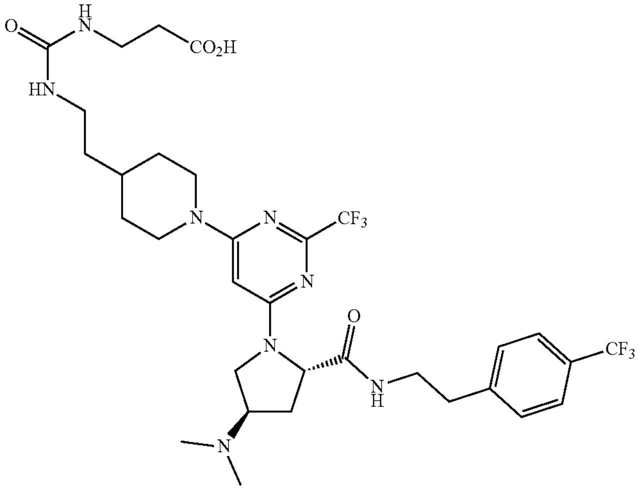

Compound 352

(2S,4S)-1-(6-chloro-2-(trifluoromethyl)pyrimidin-4-yl)-N-(4-cyanophenethyl)-4-hydroxypyrrolidine-2-carboxamide Using the procedure as described for Intermediate 1, step 3, Intermediate 11 was converted to Compound 75A. LCMS (method A): m/z 483.4/485.4 $(M+H)^+$. $^1H$ NMR ($CDCl_3$) δ 7.49 (d, 2H), 7.21 (m, 3H), 6.41 (s, 1H), 5.85 (d, 2H), 4.78 (d, 1H), 3.65 (br m, 1H), 3.52-3.42 (m, 3H), 2.94-2.80 (m, 2H), 2.41 (d, 1H), 2.30-2.20 (m, 1H).

(2S,4S)-1-(6-(4-(2-aminoethyl)piperidin-1-yl)-2-(trifluoromethyl)pyrimidin-4-yl)-4-hydroxy-N-(4-(trifluoromethyl)phenethyl)pyrrolidine-2-carboxamide Using the procedure as described in Example 1, Compound 75A (1.0 g, 2.07 mmol) was reacted with tert-butyl (2-(piperidin-4-yl)ethyl)carbamate, followed by removal of the Boc group with acid to afford Compound 75B (1.16 g, 92%). LCMS (method A): m/z 575.5 $(M+H)^+$. $^1H$ NMR ($CD_3OD$) δ 7.80 (br s, 0.5H), 7.50 (d, 2H), 7.36 (m, 2H), 5.61 (s, 1H), 4.45-4.40 (m, 4H), 3.59-3.42 (m, 3H), 3.38 (m, 1H), 2.99 (m, 2H), 2.92-2.82 (M, 4H), 2.40 (m, 1H), 2.08 (m, 1H), 1.82-1.78 (m, 2H), 1.72-1.58 (m, 3H), 1.24-1.18 (m, 2H).

tert-butyl 3-(3-(2-(1-(6-((2S,4S)-4-hydroxy-2-((4-(trifluoromethyl) phenethyl)carbamoyl) pyrrolidin-1-yl)-2-(trifluoromethyl)pyrimidin-4-yl)piperidin-4-yl)ethyl)ureido)propanoate Using the procedure as described in Example 9 step 2, Compound 75B (1.16 g, 1.90 mmol) was converted to Compound 75C (1.0 g, 71%). LCMS (method A): m/z 746.6 $(M+H)^+$. $^1H$ NMR ($CDCl_3$) δ 8.10 (br, 1H), 7.40 (d, 2H), 7.18 (d, 2H), 5.79 (br, 1H), 5.28 (s, 1H), 4.84 (m, 2H), 4.56 (m, 1H), 4.35 (br, 3H), 3.68 (m, 1H), 3.43-3.36 (m, 5H), 3.22 (q, 2H), 2.92-2.78 (m, 4H), 2.42 (m, 3H), 2.15 (m, 1H), 1.82 (d, 2H), 1.62 (br, 1H), 1.50-1.42 (m, 11H), 1.20 (m, 1H).

tert-butyl 3-(3-(2-(1-(6-((2S,4S)-4-((methylsulfonyl) oxy)-2-((4-(trifluoromethyl) phenethyl) carbamoyl) pyrrolidin-1-yl)-2-(trifluoromethyl)pyrimidin-4-yl) piperidin-4-yl)ethyl)ureido) propanoate To a stirred solution of Compound 75C (0.20 g, 0.27 mmol) in DCM (2 mL) at 0° C. under nitrogen was added methanesulfonyl chloride (34 mg, 0.30 mmol), followed by triethylamine (56 uL, 0.40 mmol). The mixture was stirred at 0° C. for 30 minutes, diluted with EtOAc and washed with water (×2) and brine (1×). The organic layer was dried ($MgSO_4$), filtered and concentrated in vacuo to afford Compound 75D (173 mg, 78%). LCMS (method A): m/z 824.5 $(M+H)^+$.

tert-butyl 3-(3-(2-(1-(6-((2S,4R)-4-(dimethylamino)-2-((4-(trifluoromethyl)phenethyl) carbamoyl)pyrrolidin-1-yl)-2-(trifluoromethyl)pyrimidin-4-yl)piperidin-4-yl)ethyl)ureido)propanoate To a solution of Compound 75D (80 mg, 0.097 mmol) in DMF (0.5 mL) in a microwave reaction vial under nitrogen was added dimethylamine (0.75 mL, 2 M in THF). The vial was capped and microwaved at 140° C. for 40 minutes. More dimethylamine (0.50 mL, 2 M in THF) was added and the vial was microwaved at 160° C. for two and half hours. Solvent was removed in vacuo. The residue was purified by flash column chromatography (0-20% MeOH/EtOAc), followed by semi-prep HPLC to afford Compound 75E (5.8 mg, 8%). LCMS (method A): m/z 773.6 $(M+H)^+$.

3-(3-(2-(1-(6-((2S,4R)-4-(dimethylamino)-2-((4-(trifluoromethyl)phenethyl) carbamoyl) pyrrolidin-1-yl)-2-(trifluoromethyl)pyrimidin-4-yl)piperidin-4-yl)ethyl)ureido)propanoic acid Using the procedure as described in Intermediate 9, step 3, Compound 75E (5.6 mg, 0.007 mmol) was converted to Compound 352 (2.2 mg, 43%). LCMS (method A): m/z 717.4 $(M+H)^+$. $^1H$ NMR ($CD_3OD$) δ 7.50 (d, 2H), 7.33 (d, 2H), 5.63 (br, 1H), 4.62 (br, 1H), 4.44 (br, 2H), 3.83 (br, 1H), 3.72-3.64 (m, 1H), 3.49-3.43 (m, 3H), 3.40-3.34 (m, 2H), 3.19-3.12 (m, 3H), 2.91-2.81 (m, 4H), 2.45 (br, 1H), 2.42 (s, 6H), 2.24-2.08 (m, 2H), 1.80 (d, 2H), 1.65 (br, 1H), 1.43 (m, 2H), 1.15 (m, 2H).

Example 76

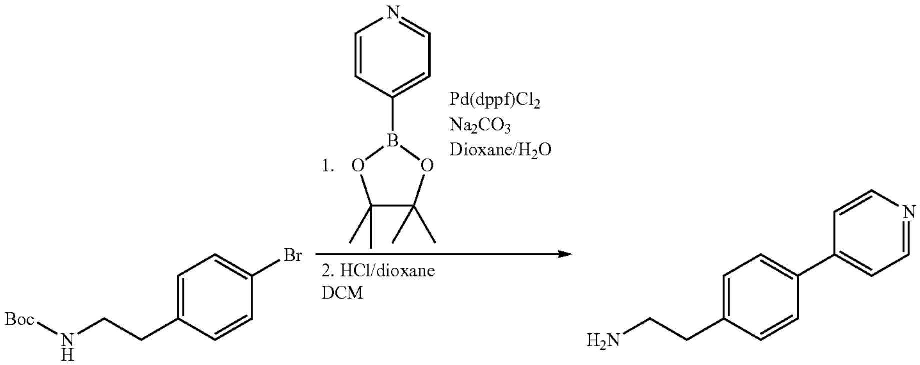

Compound 76A

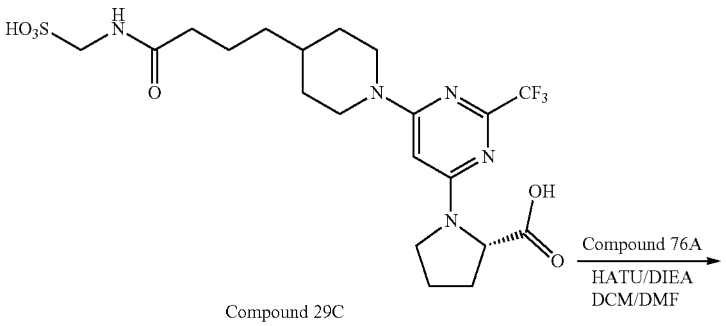

Compound 29C

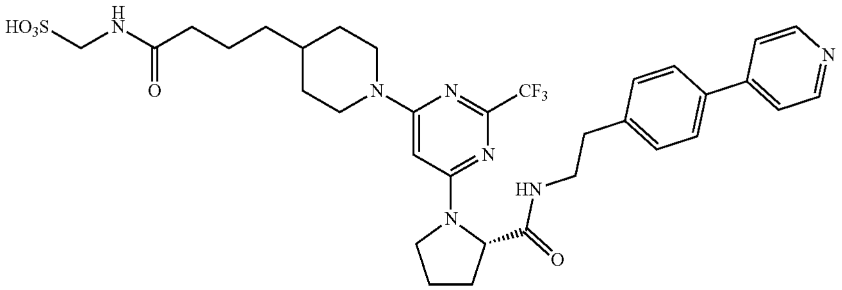

Compound 353 tert-butyl 4-(pyridin-4-yl)phenethylcarbamate

Using the procedure as described in Intermediate 19, step 2 and 3, tert-butyl 4-bromophenethylcarbamate (102 mg, 0.34 mmol) was converted to Compound 76A in 71% yield. LCMS (method A): m/z 199.3 $(M+H)^+$. $^1H$ NMR ($CD_3OD$) δ 8.86 (d, 2H), 8.41 (d, 2H), 8.01 (d, 2H), 7.59 (d, 2H), 3.26 (m, 2H), 3.09 (m, 2H).

(S)-(4-(1-(6-(2-((4-(pyridin-4-yl)phenethyl)carbamoyl)pyrrolidin-1-yl)-2-(trifluoromethyl)pyrimidin-4-yl)piperidin-4-yl)butanamido)methanesulfonic acid Using the procedure as described in Example 51, Compound 29C (64 mg, 0.12 mmol) was coupled with Compound 76A (30 mg, 0.13 mmol) to afford Compound 353 (41 mg, 47%). LCMS (method A): m/z 704.4 $(M+H)^+$. $^1H$ NMR ($CD_3OD$) δ 8.89 (d, 2H), 8.28 (m, 2H), 7.68 (m, 2H), 7.29 (m, 2H), 5.45 (br, 0.5H), 4.57 (br, 1H), 4.43-4.35 (m, 3H), 3.98 (m, 1H), 3.60-3.42 (m, 3H), 2.93-2.68 (m, 4H), 2.32-2.17 (m, 3H), 3.27 (br, 3H), 1.71-1.58 (m, 4H), 1.45 (br, 1H), 1.28-1.22 (m, 3H), 0.89-0.75 (m, 2H). Using the procedure described above for Example 76, the following compound was prepared from Compound 29C and the reagent as indicated in Table 50.

TABLE 50

| No | Structure | Reagent | MS $(M + H)^+$ |
|---|---|---|---|
| 354 | 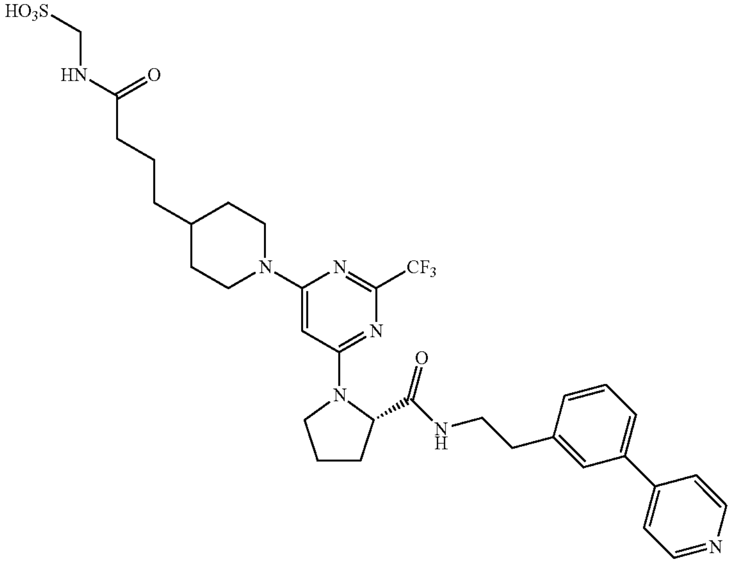 [SMILES: O=C(CCCC1CCN(c2cc(N3CCC[C@H]3C(=O)NCCc3cccc(-c4ccncc4)c3)nc(C(F)(F)F)n2)CC1)NCS(=O)(=O)O] (S)-(4-(1-(6-(2-((3-(pyridin-4-yl)phenethyl)carbamoyl)pyrrolidin-1-yl)-2-(trifluoromethyl)pyrimidin-4-yl)piperidin-4-yl)butanamido)methanesulfonic acid | 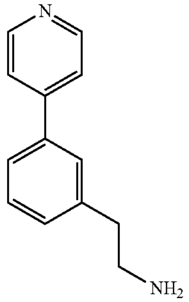 [SMILES: NCCc1cccc(-c2ccncc2)c1] | 704.4 A |

Example 77

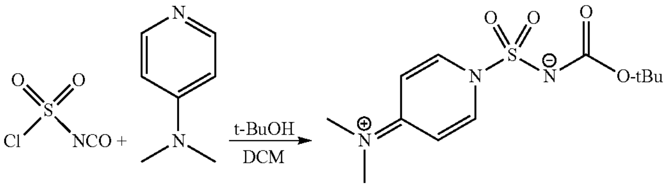

Compound 77A

-continued
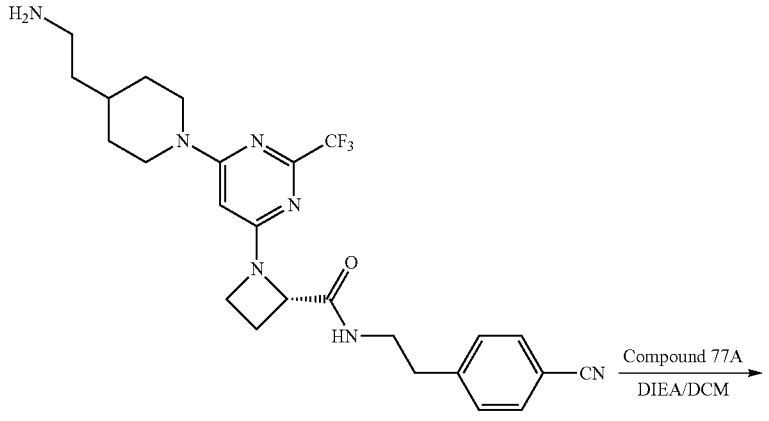
Compound 246
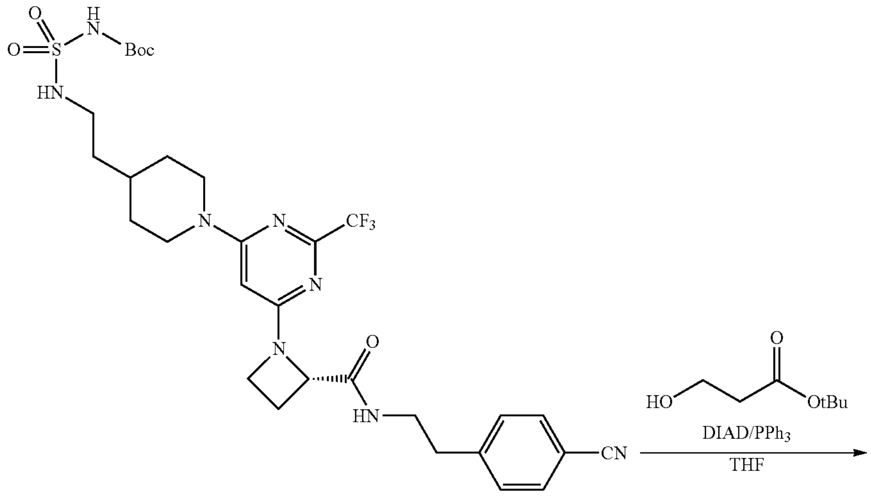
Compound 77B
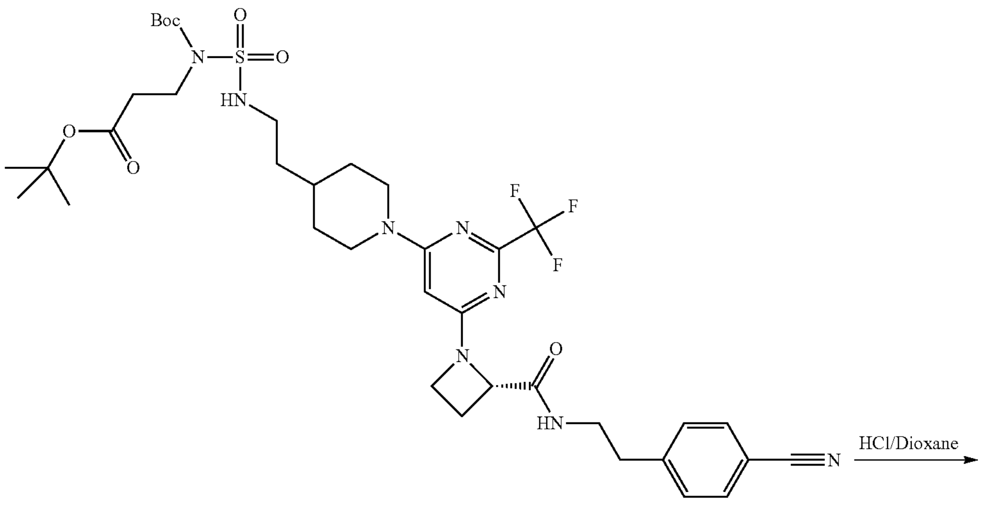
Compound 77C -continued

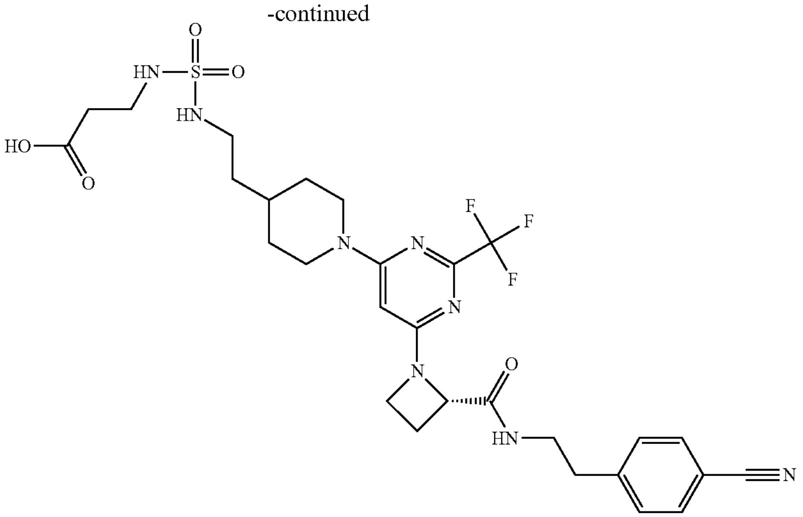

Compound 355

Pyridinium, 4-(dimethylamino)-1-[[[(1,1-dimethylethoxy)carbonyl]amino]sulfonyl], inner salt To a stirred solution of t-BuOH (1.3 mL, 13.5 mmol) in DCM (10 mL) at 0° C. was added chlorosulfonyl isocyanate (1.2 mL, 13.8 mmol) over 15 minutes. The mixture was stirred at 0° C. for 10 minutes and DMAP (3.45 g, 28.3 mmol) was added. The reaction was stirred at room temperature for one hour. The thick slurry was diluted with DCM (60 mL) and washed with water (3×). The organic layer was concentrated in vacuo and the residue was crystallized from DCM (30 mL) to afford Compound 77A (2.45 g, 59%). $^1$H NMR (DMSO-d6) δ 8.46 (d, 2H), 6.98 (d, 2H), 3.22 (s, 6H), 1.26 (s, (H).

(S)-tert-butyl N-(2-(1-(6-(2-((4-cyanophenethyl)carbamoyl)azetidin-1-yl)-2-(trifluoromethyl)pyrimidin-4-yl)piperidin-4-yl)ethyl)sulfamoylcarbamate To a stirred solution of Compound 246 (0.35 g, 0.65 mmol) in DCM (7 mL) was added DIEA (171 uL, 0.98 mmol) and Compound 77A (256 mg, 0.85 mmol). The reaction was stirred overnight at room temperature, diluted with EtOAc, and washed with $NH_4Cl_{(aq)}$, water, and brine. The organic layer was dried ($MgSO_4$), filtered and concentrated in vacuo. The residue was purified by flash column chromatography (0-100% EtOAc/hexanes) to afford Compound 77B (355 mg, 80%). LCMS (method A): m/z 681.5 $(M+H)^+$. $^1$H NMR ($CD_3OD$) δ 8.49 (br, 1H), 7.43 (d, 2H), 7.22 (d, 2H), 7.09 (s, 1H), 5.22 (s, 1H), 5.04 (m, 1H), 4.78 (m, 1H), 4.37 (br, 2H), 3.90 (m, 1H), 3.77 (m, 1H), 3.61 (m, 1H), 3.45 (m, 1H), 3.15 (m, 2H), 2.94-2.82 (m, 5H), 2.43 (m, 1H), 1.83-1.70 (m, 3H), 1.49 (br, 3H), 1.45 (s, 9H), 1.20 (m, 1H).

(S)-tert-butyl 3-((tert-butoxycarbonyl)(N-(2-(1-(6-(2-((4-cyanophenethyl)carbamoyl) azetidin-1-yl)-2-(trifluoromethyl)pyrimidin-4-yl)piperidin-4-yl)ethyl) sulfamoyl) amino)propanoate In an oven dried flask with a stir bar flushed with nitrogen was added Compound 77B (264 mg, 0.39 mmol), THF (3 mL) and DIAD (80 μL, 0.41 mmol). The mixture was stirred at room temperature. To this mixture was added a solution of tert-butyl 3-hydroxypropanoate (60 mg, 0.41 mmol) and triphenylphosphine (107 mg, 0.41 mmol) in THF (2 mL). The reaction was stirred at room temperature overnight. Solvent was removed in vacuo and the residue was purified by flash column chromatography (0-2% MeOH/DCM) to afford Compound 77C (120 mg, 38%). LCMS (method A): m/z 809.6 $(M+H)^+$.

(S)-3-4N-(2-(1-(6-(2-((4-cyanophenethyl)carbamoyl) azetidin-1-yl)-2-(trifluoromethyl) pyrimidin-4-yl) piperidin-4-yl)ethyl)sulfamoyl)amino)propanoic acid Using the procedure as described in Intermediate 9, step 3, Compound 77C (115 mg, 0.14 mmol) was converted to Compound 355 (49 mg, 53%). LCMS (method A): m/z 553.4 $(M+H)^+$. $^1$H NMR ($CD_3OD$) δ 8.49 (br, 0.4H), 7.53 (d, 2H), 7.36 (d, 2H), 5.52 (s, 1H), 4.69 (t, 1H), 4.40 (m, 2H), 4.00 (m, 1H), 3.86 (m, 1H), 3.60-3.40 (m, 2H), 3.22 (t, 2H), 3.03 (t, 2H), 2.88 (m, 4H), 2.57-2.42 (m, 4H), 1.85-1.70 (m, 3H), 1.50 (m, 2H), 1.26-1.12 (m, 2H). Using previously described examples, the following compounds in Table 51 were prepared:

TABLE 51
| No | Structure | Example | MS (M + H)+ |
|---|---|---|---|
| 356 | 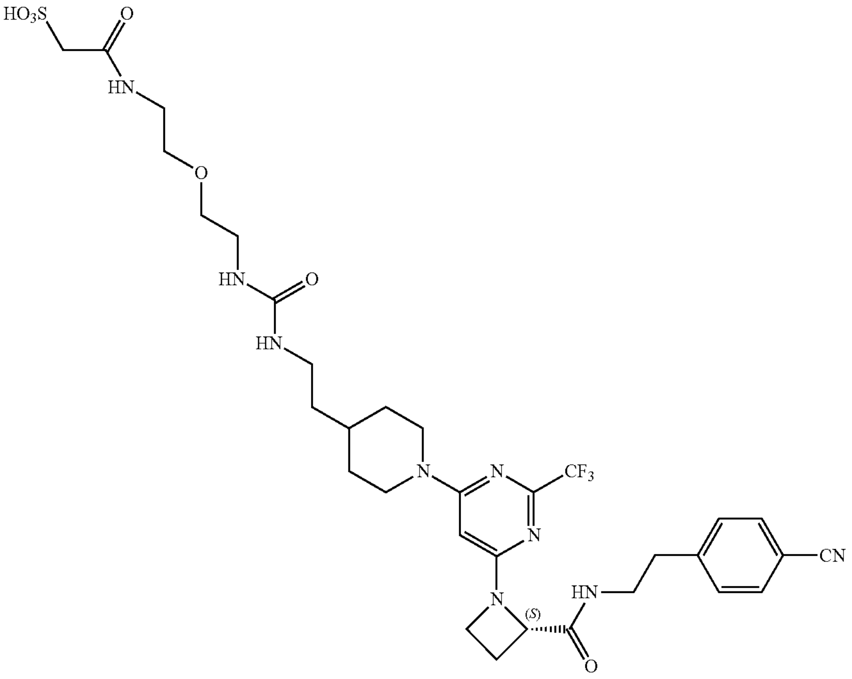 (S)-1-(1-(6-(2-((4-cyanophenethyl)carbamoyl)azetidin-1-yl)-2-(trifluoromethyl)pyrimidin-4-yl)piperidin-4-yl)-4,12-dioxo-8-oxa-3,5,11-triazatridecane-13-sulfonic acid | 54 | 754.7 A |
| 357 | 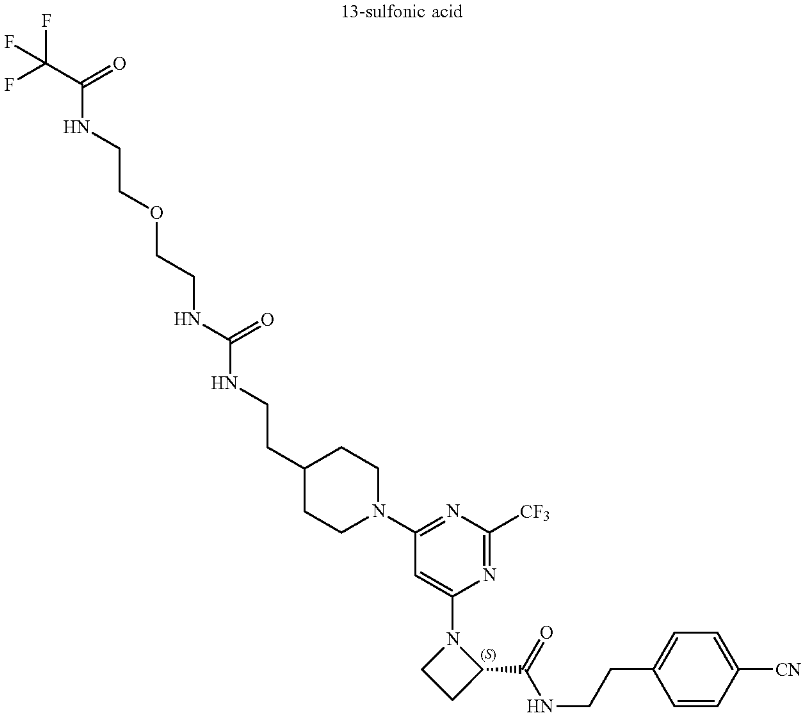 (S)-N-(4-cyanophenethyl)-1-(6-(4-(13,13,13-trifluoro-4,12-dioxo-8-oxa-3,5,11-triazatridecyl)piperidin-1-yl)-2-(trifluoromethyl)pyrimidin-4-yl)azetidine-2-carboxamide | 54 | 728.7 A |

TABLE 51-continued
| No | Structure | Example | MS (M + H)$^+$ |
|---|---|---|---|
| 358 | 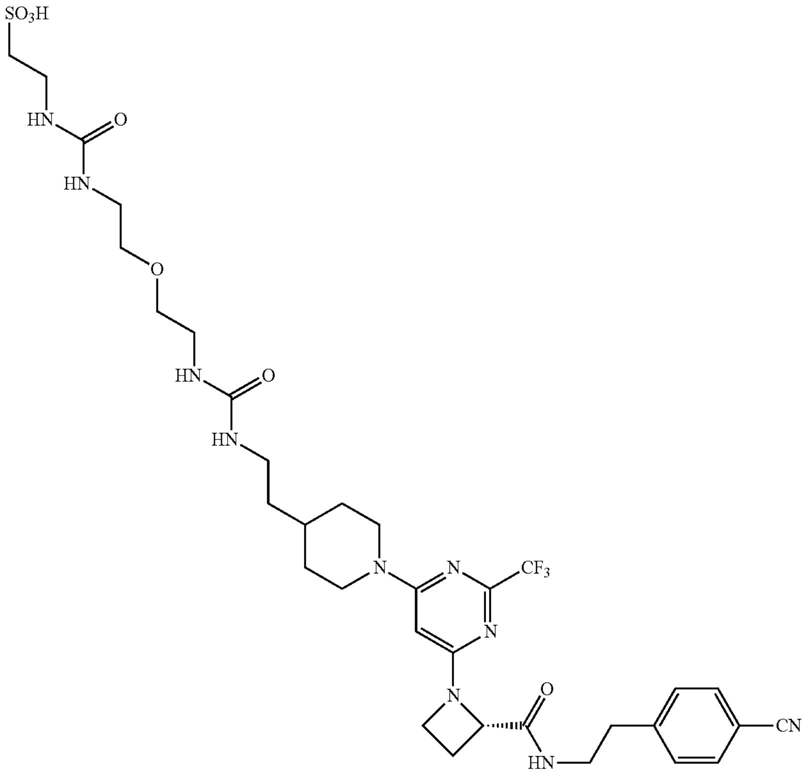 [SMILES: N#Cc1ccc(CCNC(=O)[C@@H]2CCN2c2cc(N3CCC(CCNC(=O)NCCOCCNC(=O)NCCS(=O)(=O)O)CC3)nc(C(F)(F)F)n2)cc1] (S)-15-(1-(6-(2-((4-cyanophenethyl)carbamoyl)azetidin-1-yl)-2-(trifluoromethyl)pyrimidin-4-yl)piperidin-4-yl)-4,12-dioxo-8-oxa-3,5,11,13-tetraazapentadecane-1-sulfonic acid | 54 | 783.7 A |

TABLE 51-continued
| No | Structure | Example | MS (M + H)+ |
|---|---|---|---|
| 359 | 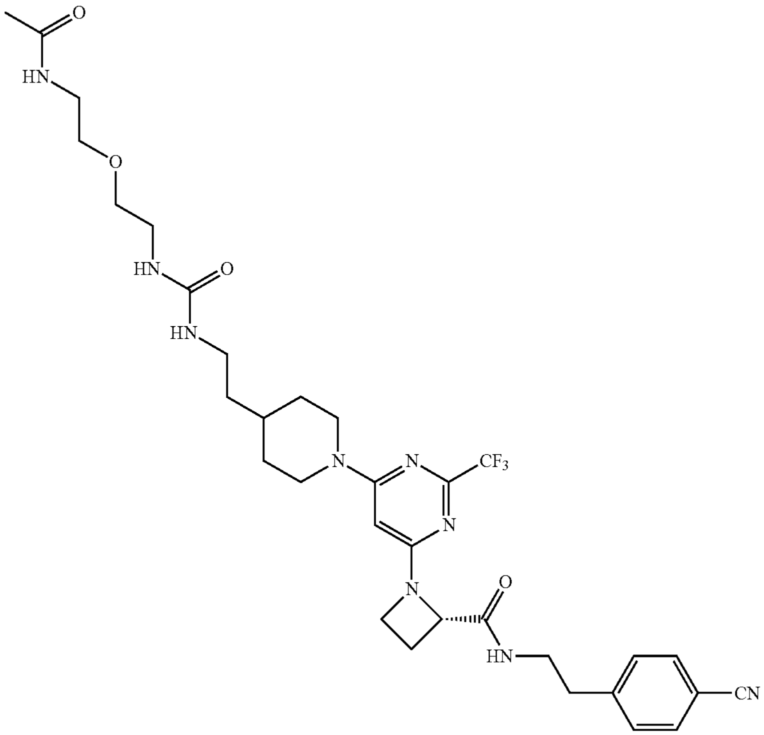 [SMILES: CC(=O)NCCOCCNC(=O)NCCC1CCN(c2cc(N3CC[C@H]3C(=O)NCCc3ccc(C#N)cc3)nc(C(F)(F)F)n2)CC1]<br>(S)-N-(4-cyanophenethyl)-1-(6-(4-(4,12-dioxo-8-oxa-3,5,11-triazatridecyl)piperidin-1-yl)-2-(trifluoromethyl)pyrimidin-4-yl)azetidine-2-carboxamide | 54 | 674.7<br>A |

TABLE 51-continued
| No | Structure | Example | MS (M + H)+ |
|---|---|---|---|
| 360 | 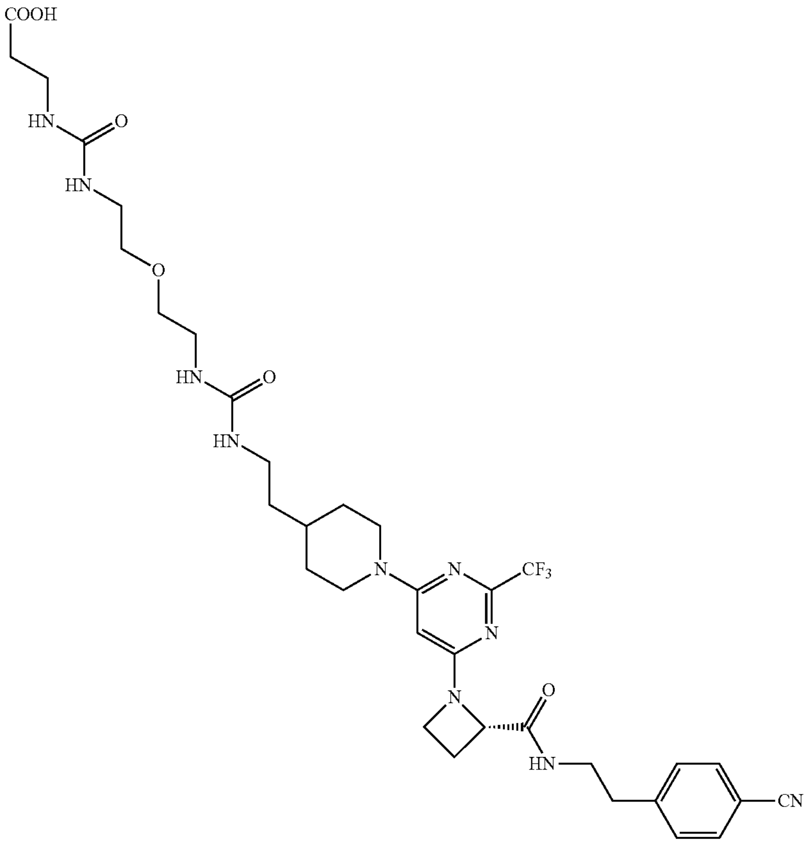 [SMILES: N#Cc1ccc(CCNC(=O)[C@@H]2CCN2c2cc(N3CCC(CCNC(=O)NCCOCCNC(=O)NCCC(=O)O)CC3)nc(C(F)(F)F)n2)cc1] (S)-1-(1-(6-(2-((4-cyanophenethyl)carbamoyl)azetidin-1-yl)-2-(trifluoromethyl)pyrimidin-4-yl)piperidin-4-yl)-4,12-dioxo-8-oxa-3,5,11,13-tetraazahexadecan-16-oic acid | 54 | 747.7 A |
| 361 | 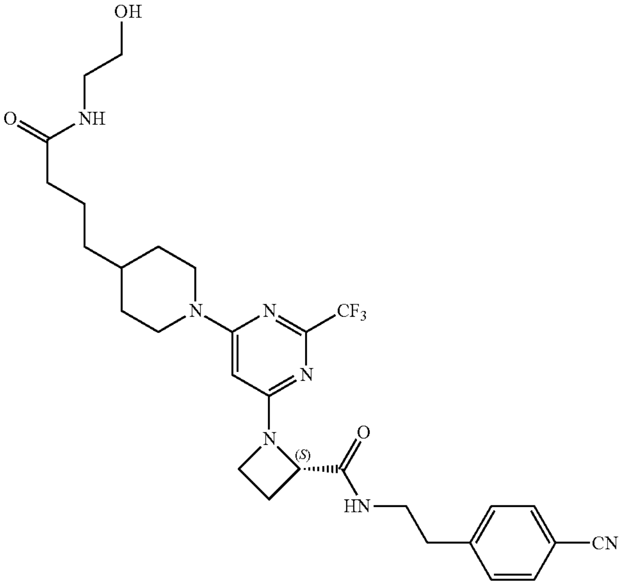 (S)-N-(4-cyanophenethyl)-1-(6-(4-(4-((2-hydroxyethyl)amino)-4-oxobutyl)piperidin- | 50 | 588.6 A |

TABLE 51-continued

| No | Structure | Example | MS (M + H)+ |
|---|---|---|---|
| | 1-yl)-2-(trifluoromethyl)pyrimidin-4-yl)azetidine-2-carboxamide | | |
| 362 | 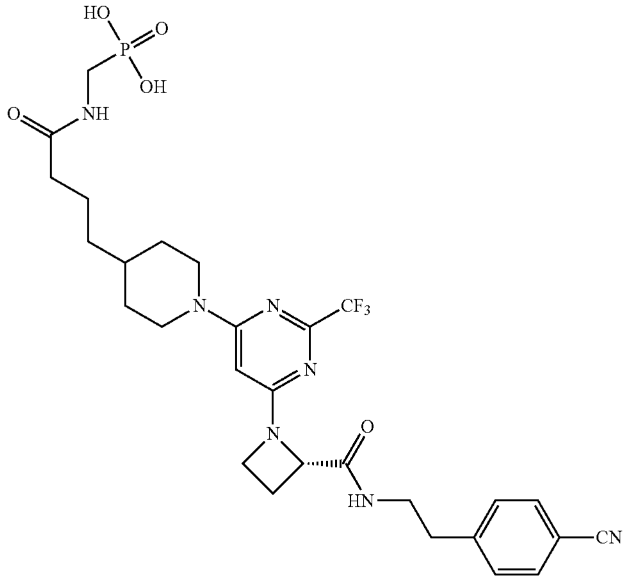 [SMILES: N#Cc1ccc(CCNC(=O)[C@@H]2CCN2c2cc(N3CCC(CCCC(=O)NCP(=O)(O)O)CC3)nc(C(F)(F)F)n2)cc1] (S)-((4-(1-(6-(2-((4-cyanophenethyl)carbamoyl)azetidin-1-yl)-2-(trifluoromethyl)pyrimidin-4-yl)piperidin-4-yl)butanamido)methyl)phosphonic acid | 50 | 636.2 (M − H+) |
| 363 | 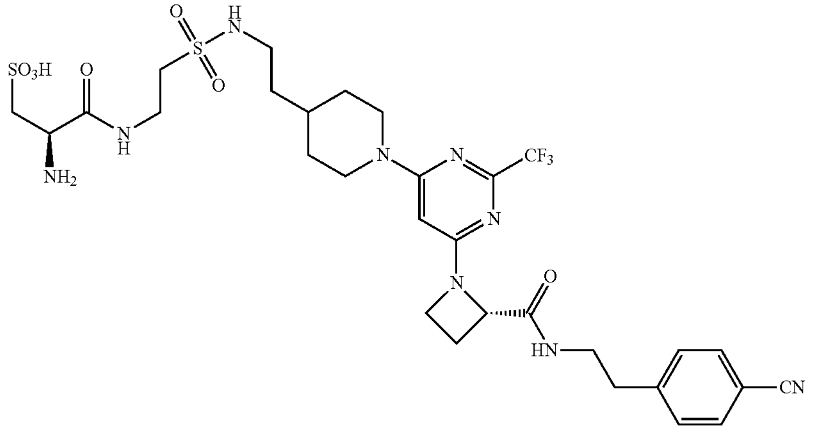 [SMILES: N#Cc1ccc(CCNC(=O)[C@@H]2CCN2c2cc(N3CCC(CCNS(=O)(=O)CCNC(=O)[C@@H](N)CS(=O)(=O)O)CC3)nc(C(F)(F)F)n2)cc1] (R)-2-amino-3-((2-(N-(2-(1-(6-((S)-2-((4-cyanophenethyl)carbamoyl)azetidin-1-yl)-2-(trifluoromethyl)pyrimidin-4-yl)piperidin-4-yl)ethyl)sulfamoyl)ethyl)amino)-3-oxopropane-1-sulfonic acid | 59 & 56 | 760.3 A |

TABLE 51-continued
| No | Structure | Example | MS (M + H)+ |
|---|---|---|---|
| 364 | 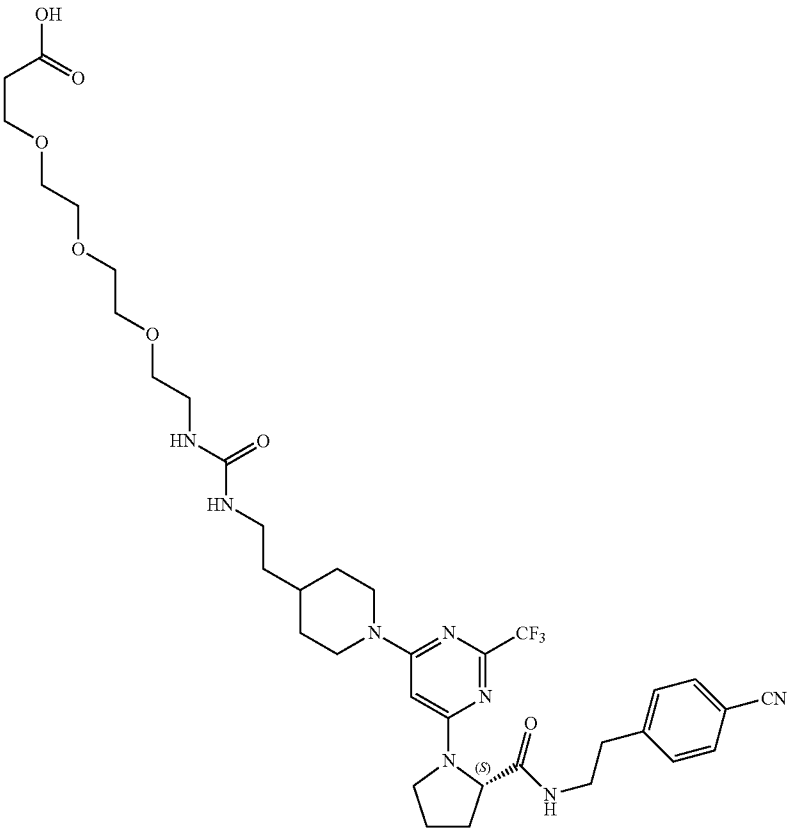 (S)-1-(1-(6-(2-((4-cyanophenethyl)carbamoyl)pyrrolidin-1-yl)-2-(trifluoromethyl)pyrimidin-4-yl)piperidin-4-yl)-4-oxo-8,11,14-trioxa-3,5-diazaheptadecan-17-oic acid | 9 | 763.8 A |
| 365 | 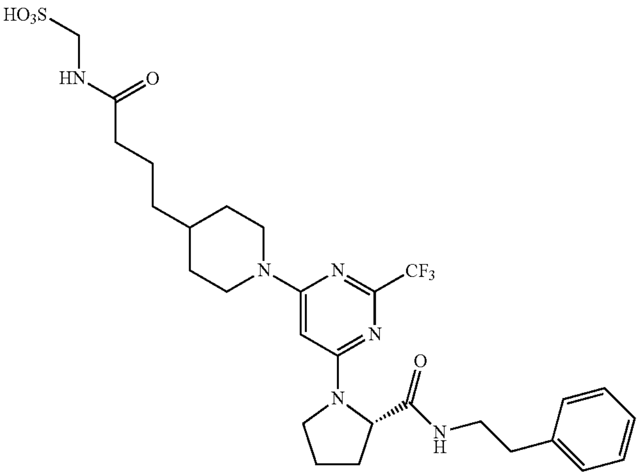 [SMILES: O=C(CCCC1CCN(c2cc(N3CCC[C@H]3C(=O)NCCc3ccccc3)nc(C(F)(F)F)n2)CC1)NCS(=O)(=O)O] (S)-(4-(1-(6-(2-(phenethylcarbamoyl)pyrrolidin-1-yl)-2-(trifluoromethyl)pyrimidin-4-yl)piperidin-4-yl)butanamido)methanesulfonic acid | 29 | 627.5 A |

TABLE 51-continued
| No | Structure | Example | MS (M + H)+ |
|---|---|---|---|
| 366 | 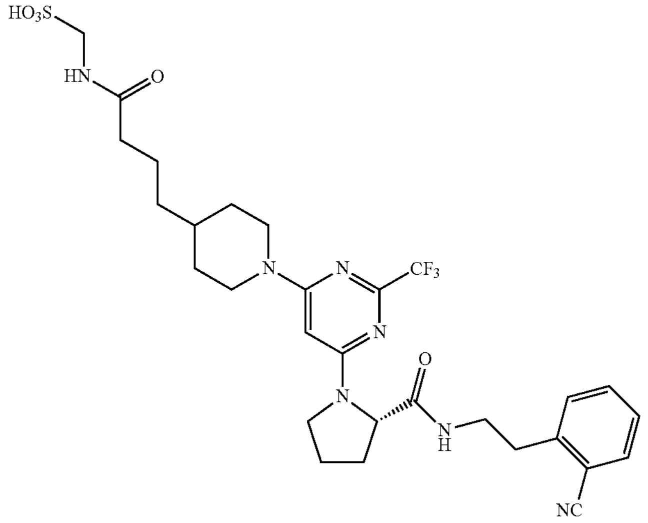 [SMILES: N#Cc1ccccc1CCNC(=O)[C@@H]1CCCN1c1cc(N2CCC(CCCC(=O)NCS(=O)(=O)O)CC2)nc(C(F)(F)F)n1] (S)-(4-(1-(6-(2-((2-cyanophenethyl)carbamoyl)pyrrolidin-1-yl)-2-(trifluoromethyl)pyrimidin-4-yl)piperidin-4-yl)butanamido)methanesulfonic acid | 29 | 652.5 A |
| 367 | 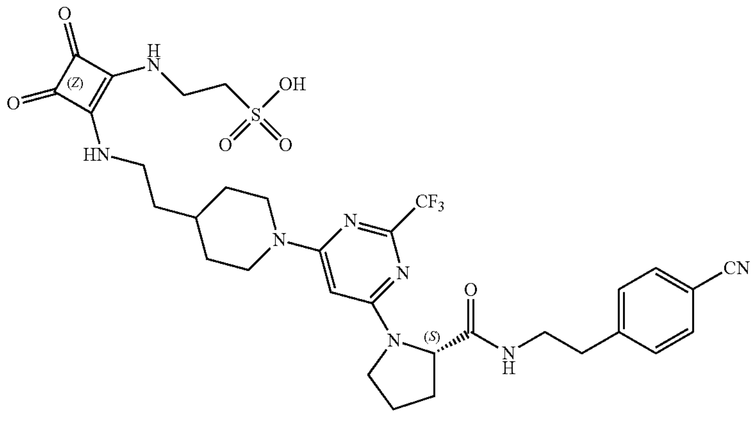 (S)-2-((2-((2-(1-(6-(2-((4-cyanophenethyl)carbamoyl)pyrrolidin-1-yl)-2-(trifluoromethyl)pyrimidin-4-yl)piperidin-4-yl)ethyl)amino)-3,4-dioxocyclobut-1-en-1-yl)amino)ethanesulfonic acid | 9 & 63 | 719.5 |

TABLE 51-continued
| No | Structure | Example | MS (M + H)+ |
|---|---|---|---|
| 368 | 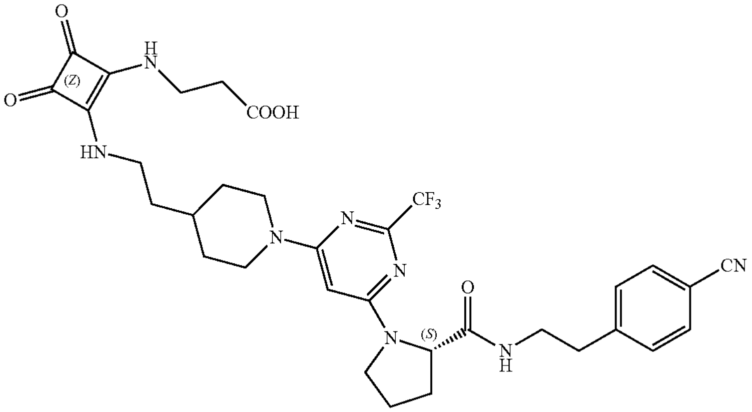 (S)-3-((2-((2-(1-(6-(2-((4-cyanophenethyl)carbamoyl)pyrrolidin-1-yl)-2-(trifluoromethyl)pyrimidin-4-yl)piperidin-4-yl)ethyl)amino)-3,4-dioxocyclobut-1-en-1-yl)amino)propanoic acid | 9 & 63 | 683.4 A |
| 369 | 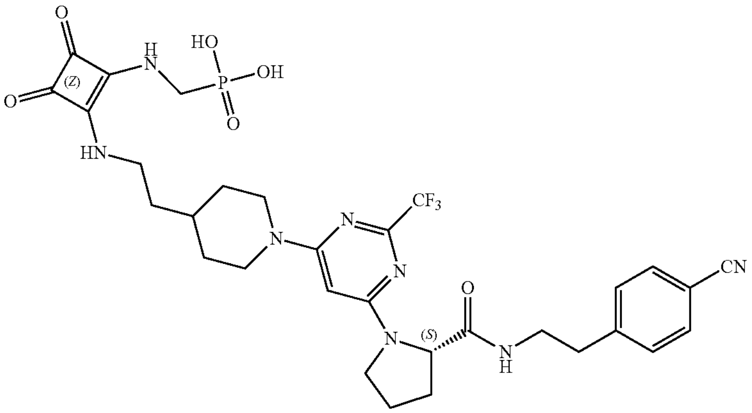 (S)-(((2-((2-(1-(6-(2-((4-cyanophenethyl)carbamoyl)pyrrolidin-1-yl)-2-(trifluoromethyl)pyrimidin-4-yl)piperidin-4-yl)ethyl)amino)-3,4-dioxocyclobut-1-en-1-yl)amino)methyl)phosphonic acid | 9 & 63 | 703.2 (M − H+) |

TABLE 51-continued
| No | Structure | Example | MS (M + H)+ |
| --- | --- | --- | --- |
| 370 | 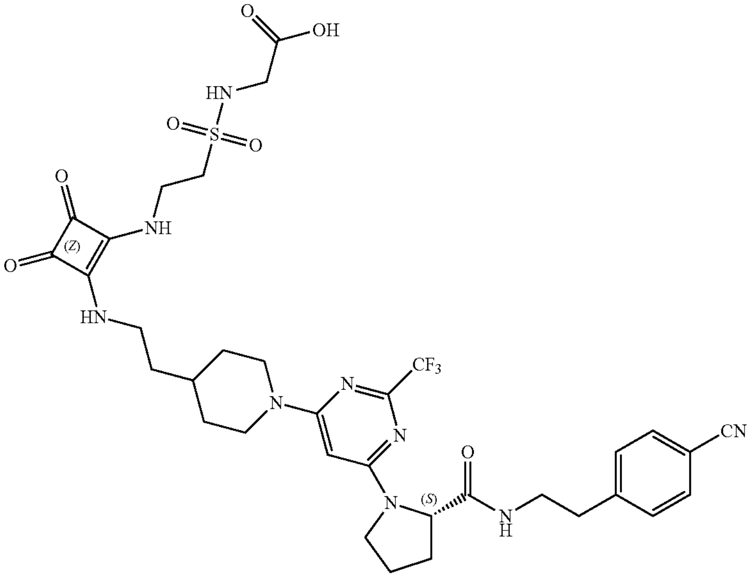 (S)-2-(2-((2-((2-(1-(6-(2-((4-cyanophenethyl)carbamoyl)pyrrolidin-1-yl)-2-(trifluoromethyl)pyrimidin-4-yl)piperidin-4-yl)ethyl)amino)-3,4-dioxocyclobut-1-en-1-yl)amino)ethylsulfonamido)acetic acid | 9 & 63 | 776.4 A |
| 371 | 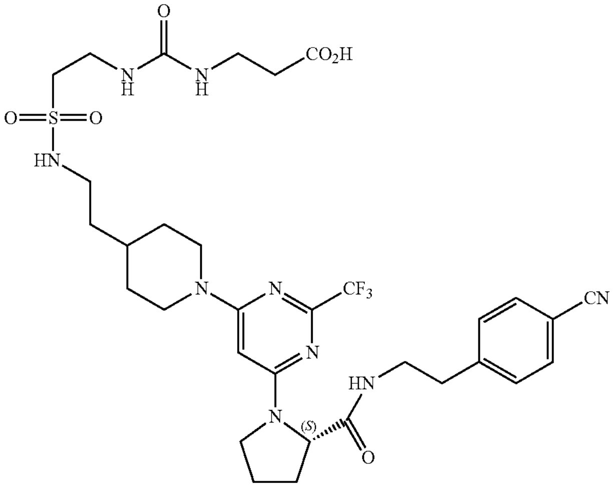 (S)-3-(3-(3-((2-(1-(6-(2-((4-cyanophenethyl)carbamoyl)pyrrolidin-1-yl)-2-(trifluoromethyl)pyrimidin-4-yl)piperidin-4-yl)ethyl)amino)-2-sulfonyl)ethylureido)propanoic acid | 22 & 9 | 738.5 A |

TABLE 51-continued
| No | Structure | Example | MS (M + H)+ |
|---|---|---|---|
| 372 | 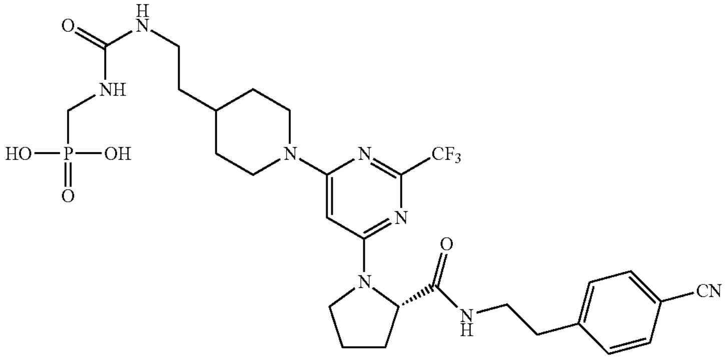 [SMILES: N#Cc1ccc(CCNC(=O)[C@@H]2CCCN2c2cc(N3CCC(CCNC(=O)NCP(=O)(O)O)CC3)nc(C(F)(F)F)n2)cc1]<br>(S)-((3-(2-(1-(6-(2-((4-cyanophenethyl)carbamoyl)pyrrolidin-1-yl)-2-(trifluoromethyl)pyrimidin-4-yl)piperidin-4-yl)ethyl)ureido)methyl)phosphonic acid | 9 | 651.2 (M − H+) |
| 373 | 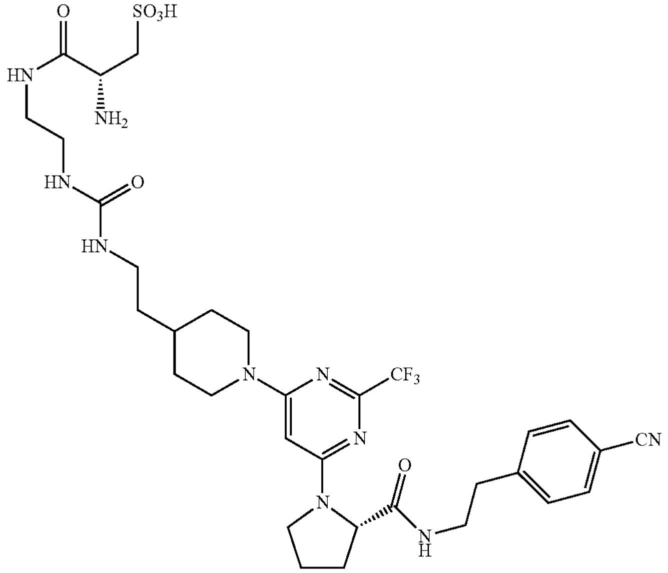 [SMILES: N#Cc1ccc(CCNC(=O)[C@@H]2CCCN2c2cc(N3CCC(CCNC(=O)NCCNC(=O)[C@@H](N)CS(=O)(=O)O)CC3)nc(C(F)(F)F)n2)cc1]<br>(R)-2-amino-3-((2-(3-(2-(1-(6-((S)-2-((4-cyanophenethyl)carbamoyl)pyrrolidin-1-yl)-2-(trifluoromethyl)pyrimidin-4-yl)piperidin-4-yl)ethyl)ureido)ethyl)amino)-3-oxopropane-1-sulfonic acid | 9 & 25 | 753.5 A |

TABLE 51-continued
| No | Structure | Example | MS (M + H)+ |
|---|---|---|---|
| 374 | 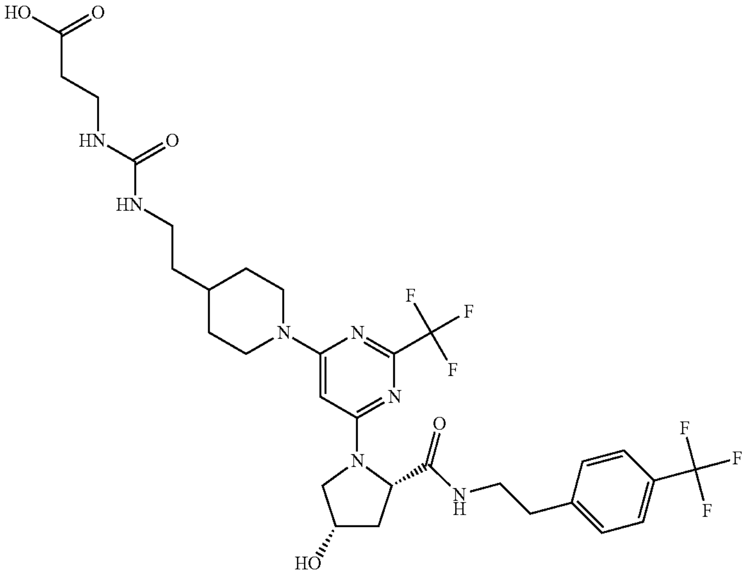 [SMILES: O=C(O)CCNC(=O)NCCC1CCN(c2cc(N3C[C@@H](O)C[C@H]3C(=O)NCCc3ccc(C(F)(F)F)cc3)nc(C(F)(F)F)n2)CC1]<br>3-(3-(2-(1-(6-((2S,4S)-4-hydroxy-2-((4-(trifluoromethyl)phenethyl)carbamoyl) pyrrolidin-1-yl)-2-(trifluoromethyl)pyrimidin-4-yl)piperidin-4-yl)ethyl)ureido)propanoic acid | 9 & 43 | 690.6 As |
| 375 | 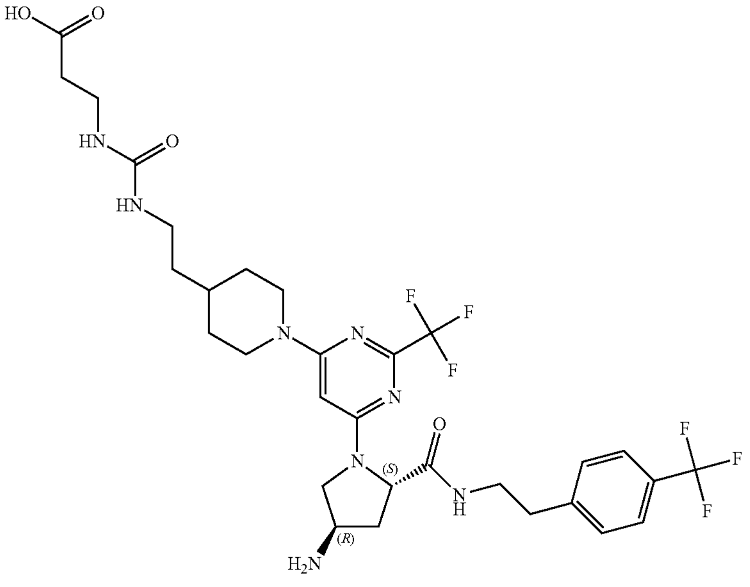<br>3-(3-(2-(1-(6-((2S,4R)-4-amino-2-((4-(trifluoromethyl)phenethyl)carbamoyl) pyrrolidin-1-yl)-2-(trifluoromethyl)pyrimidin-4-yl)piperidin-4-yl)ethyl)ureido)propanoic acid | 9 & 46 | 689.6 A |

TABLE 51-continued
| No | Structure | Example | MS (M + H)+ |
|---|---|---|---|
| 376 | 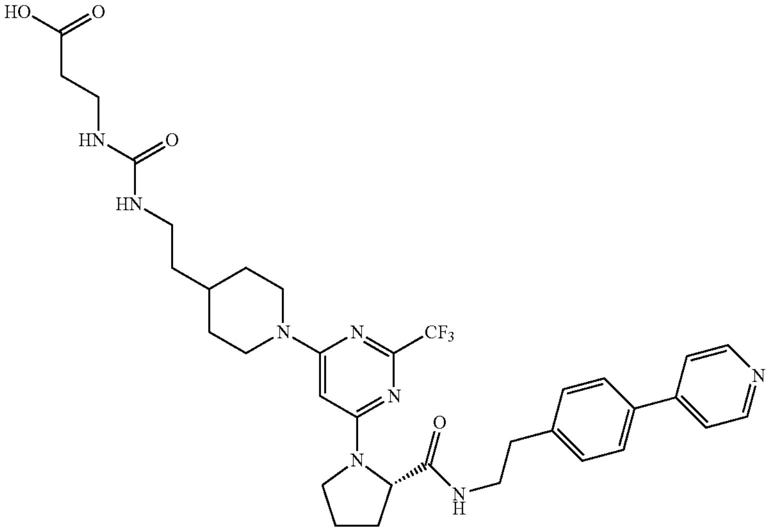 [SMILES: O=C(O)CCNC(=O)NCCC1CCN(c2cc(N3CCC[C@H]3C(=O)NCCc3ccc(-c4ccncc4)cc3)nc(C(F)(F)F)n2)CC1]<br>(S)-3-(3-(2-(1-(6-(2-((4-(pyridin-4-yl)phenethyl)carbamoyl)pyrrolidin-1-yl)-2-(trifluoromethyl)pyrimidin-4-yl)piperidin-4-yl)ethyl)ureido)propanoic acid | 9 & 76 | 683.4 A |
| 377 | 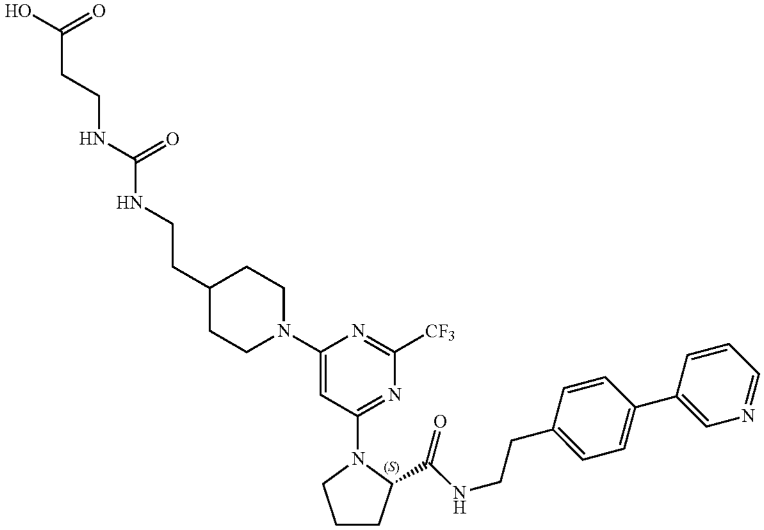<br>(S)-3-(3-(2-(1-(6-(2-((4-(pyridin-3-yl)phenethyl)carbamoyl)pyrrolidin-1-yl)-2-(trifluoromethyl)pyrimidin-4-yl)piperidin-4-yl)ethyl)ureido)propanoic acid | 9 & 76 | 683.4 A |

TABLE 51-continued

| No | Structure | Example | MS (M + H)+ |
|---|---|---|---|
| 378 | 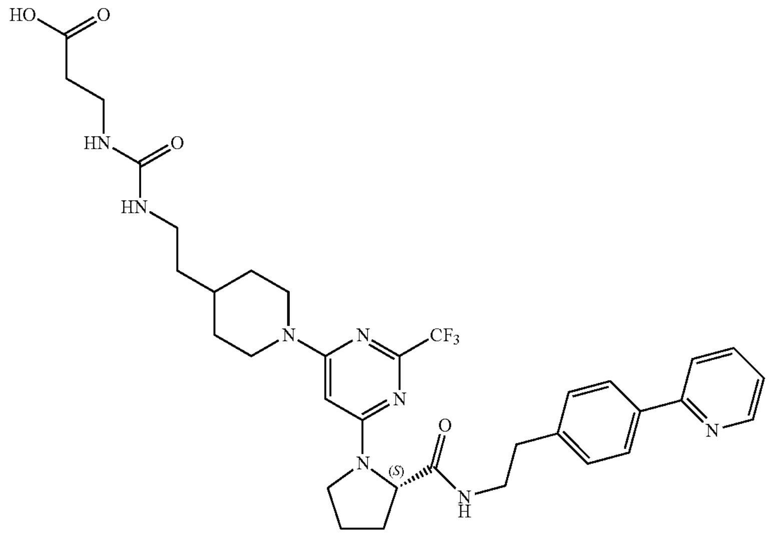 (S)-3-(3-(2-(1-(6-(2-((4-(pyridin-2-yl)phenethyl)carbamoyl)pyrrolidin-1-yl)-2-(trifluoromethyl)pyrimidin-4-yl)piperidin-4-yl)ethyl)ureido)propanoic acid | 9 & 76 | 683.5 A |

In Vitro and In Vivo Experimental Studies

Example 78

Human TGR5 cAMP Production Assay

Compounds of the present invention were evaluated for their ability to induce cAMP production using CHO-K1 cells overexpressing the human TGR5 receptor.

CHO-K1 cells stably expressing human TGR5 receptor (accession number NM_001077194.1) (hTGR5) (i.e., hTGR5-CHO cells) were purchased from DiscoveRx Corporation (Fremont, Calif.). hTGR5-CHO cells were grown in Ham's F-12 media supplemented with 10% Fetal Bovine Serum, 1% Penicillin-Streptomycin, 2 mM L-Alanine L-Glutamine (Glutamax), and 800 μg/mL Geneticin selection. The cAMP production assay was performed using DiscoveRx's cAMP XS+ kit (Catalog No. 90-0075XL) following the manufacturer's recommended protocol. Briefly, hTGR5-CHO cells were harvested using non-enzymatic cell dissociation buffer (Sigma-Aldrich, St. Louis, Mo.) and $1\times10^6$ cells were combined in Phosphate-Buffered Saline (PBS) to a final volume of 496 μL to which 4 μL of 125 mM IBMX (Sigma-Aldrich, St. Louis, Mo.) was added. 500 μL of cAMP antibody solution was added to the harvested cells and incubated at room temperature for 20 min.

Test compounds were serially diluted (half-log dilutions) in DMSO and then further diluted 1:50 in PBS, 10 mM HEPES buffer. 2 μL of serially diluted compound was added to a 384-well low volume plate (Greiner; cat #784075) and centrifuged briefly. 2 μl of the cell/cAMP antibody mixture was then added to each compound-containing well and allowed to incubate at room temperature for one hour. Following incubation, the XS+ kits' ED/Lysis/CL Substrate Working Solution was prepared following the manufacturer's recommended protocol and 4 μL was added to each well of the plate. The plate was then incubated for one hour at room temperature. Following incubation, 4 μL of Enzyme Acceptor reagent was added to the plate and allowed to incubate overnight at room temperature. Luminescent signal was then detected using the Viewlux instrument (Perkin-Elmer, Waltham, Mass.). $EC_{50}$ values were determined using GraphPad Prism analysis (GraphPad Software, Inc.) and the results are shown in Table 52 (below).

Example 79

Mouse TGR5 cAMP Production Assay

Compounds of the present invention were evaluated for their ability to induce cAMP production in HEK-EBNA cells overexpressing the mouse TGR5 receptor. Human embryonic kidney cells (HEK293-EBNA) stably expressing mouse TGR5 receptor were established using the following procedure. Specifically, a commercially obtained gene encoding mouse TGR5 (accession number BC116914) from Thermo Scientific (Waltham, Mass.) was cloned into an episomal expression vector. The resulting expression plasmid was then transfected into 293 c18 (ATCC® CRL10852™) cells, which express the Epstein-Barr virus nuclear antigen EBNA1 and can support the replication of episomal vectors. Selection for the plasmid was maintained with Hygromycin B. Cells were cultured and maintained in DMEM (Sigma; cat #6429) supplemented with 10% Fetal Bovine Serum, 1% penicillin/streptomycin, 2 mM L-alanine L-glutamine (GlutaMax), and 250 μg/mL Hygromycin.

We developed two cAMP production assays.

(i) Luminescent cAMP Production Assay

In this first cAMP production assay, the cAMP production was measured using DiscoveRx's cAMP XS+ kit following the manufacturer's recommended protocol. Briefly, HEK293-EBNA cells stably overexpressing mouse TGR5 were harvested using non-enzymatic cell dissociation buffer (Sigma-Aldrich, St. Louis, Mo.), spun down, then resuspended in serum-free DMEM with 500 μM IBMX at a density of $1.25\times10^6$ cells/mL. 500 μL of cAMP antibody solution was added to 500 μL of cell suspension and incubated at room temperature for 20 min.

Test compounds were serially diluted (half-log dilutions) in DMSO and then further diluted 1:50 in PBS, 10 mM HEPES buffer. 2 μL of serially diluted compound was added to a 384-well low volume plate (Greiner cat #784075) and centrifuged briefly. 2 μl of the cell/cAMP antibody mixture was then added to each compound-containing well and allowed to incubate at room temperature for one (1) hour. Following incubation, the XS+ kits' ED/Lysis/CL Substrate Working Solution was prepared following the manufacturer's recommended protocol and 4 μL was added to each well of the plate. The plate was then incubated for one (1) hour at room temperature. Following incubation, 4 μL of (Enzyme Acceptor) EA reagent was added to the plate and allowed to incubate overnight at room temperature. Luminescent signal was then detected using the Viewlux instrument (PerkinElmer, Waltham, Mass.). $EC_{50}$ values were determined using GraphPad Prism analysis (GraphPad Software, Inc.) and the results are shown in Table 52 (below).

(ii) HTRF cAMP Production Assay

In this second cAMP production assay, the cAMP production was measured in 384-well low volume plates (Greiner; cat #784075) using the Cisbio™ cAMP HiRange HTRF Assay Kit (CisBio) according to the manufacturer's protocol.

Briefly, compounds were initially diluted in 100% DMSO (12-point serial dilution by half logs) in a 96-well plate and then were further diluted 1:50 in PBS containing 10 mM HEPES. 5 μL were transferred to the 384-well assay plate in duplicate. HEK293-EBNA cells stably overexpressing mouse TGR5 were harvested using non-enzymatic cell dissociation buffer (Sigma), spun down, then resuspended in serum-free DMEM with 500 μM IBMX at a density of 500,000 cells/mL. 5 μL of cell suspension was transferred to each well of the 384-well assay plate already containing compound. The plate was covered and incubated at room temperature for 1 hour. The d2-cAMP and anti-cAMP Ab-cryptate stock solutions were prepared as per kit instructions. Then 5 μL of each conjugate (d2 and cryptate) were added to each well of the assay plate. The plate was covered and incubated at room temperature for one (1) hour. The plate was read on an Envision™ plate reader (PerkinElmer). $EC_{50}$ values were determined using GraphPad Prism (GraphPad Software, Inc.) and the results are shown in Table 52 (below).

Human and Mouse TGR5 cAMP

In Table 52, $EC_{50}$ values for both human and mouse cells were determined according to the TGR5 cAMP assays described above. The $EC_{50}$ values are coded as A, B, C or D: A<100° nM; B=100-999 nM; C=1,000-30,000 nM; D>30,000 nM. The $EC_{50}$ results are summarized as follows:

TABLE 52

| Compound No. | Human TGR5 Lum. cAMP Activity | Mouse TGR5 Lum. cAMP Activity | Mouse TGR5 HTRF cAMP Activity |
|---|---|---|---|
| 1 | A | A | |
| 2 | A | A | |
| 3 | C | B | |
| 4 | C | B | |
| 5 | A | | A |
| 7 | A | A | |
| 8 | A | B | |
| 9 | A | | A |
| 10 | A | | A |
| 11 | A | | A |
| 12 | C | | C |
| 13 | B | A | |
| 14 | C | C | |
| 15 | C | A | |
| 16 | B | A | |
| 17 | B | B | |
| 18 | B | B | |
| 19 | B | A | |
| 20 | C | C | |
| 21 | A | | B |
| 22 | A | A | |
| 23 | A | | A |
| 24 | A | A | |
| 25 | A | | A |
| 26 | A | | A |
| 27 | B | | A |
| 28 | B | | A |
| 29 | A | | A |
| 30 | B | | B |
| 31 | B | | A |
| 32 | A | | A |
| 33 | A | | A |
| 34 | A | | A |
| 35 | C | | B |
| 36 | B | | C |
| 37 | C | | D |
| 38 | A | | A |
| 39 | B | A | |
| 40 | A | A | |
| 41 | A | A | |
| 42 | B | B | |
| 43 | B | B | |
| 44 | C | B | |
| 45 | B | A | |
| 46 | B | | B |
| 47 | A | B | |
| 49 | B | B | |
| 50 | A | A | |
| 51 | C | B | |
| 52 | B | A | |
| 53 | C | A | |
| 54 | B | A | |
| 55 | A | | A |
| 56 | A | | A |
| 57 | A | | A |
| 58 | A | | A |
| 59 | A | | A |
| 60 | A | | A |
| 61 | A | | A |
| 62 | A | | A |
| 63 | A | | A |
| 64 | A | | A |
| 65 | A | | A |
| 66 | A | | A |
| 68 | A | | A |
| 71 | A | | A |
| 72 | A | | A |
| 73 | A | | A |
| 74 | A | | A |
| 75 | A | | A |
| 76 | A | | A |
| 77 | A | | A |
| 78 | A | | A |
| 79 | A | | A |
| 80 | A | | A |
| 81 | A | | A |
| 82 | A | | A |
| 83 | A | | A |
| 84 | A | | A |
| 86 | A | | A |
| 87 | A | | A |
| 88 | B | | A |

TABLE 52-continued

| Compound No. | Human TGR5 Lum. cAMP Activity | Mouse TGR5 Lum. cAMP Activity | Mouse TGR5 HTRF cAMP Activity |
|---|---|---|---|
| 89 | A | | A |
| 90 | A | | A |
| 91 | A | | A |
| 92 | A | | A |
| 93 | A | | A |
| 94 | A | | A |
| 95 | A | | A |
| 96 | A | | A |
| 97 | A | | A |
| 98 | A | | A |
| 100 | B | | A |
| 101 | A | | A |
| 102 | A | | A |
| 103 | A | | A |
| 104 | A | | A |
| 105 | A | | A |
| 107 | A | | A |
| 108 | A | | A |
| 109 | A | | A |
| 110 | A | | A |
| 111 | A | | A |
| 112 | A | | A |
| 113 | A | | A |
| 114 | A | | A |
| 115 | A | | A |
| 116 | A | | A |
| 117 | A | | A |
| 118 | A | | A |
| 119 | A | | A |
| 120 | A | | A |
| 121 | B | | A |
| 122 | A | | A |
| 123 | A | | A |
| 124 | A | | A |
| 125 | A | | A |
| 126 | A | | A |
| 127 | A | | A |
| 128 | A | | A |
| 129 | A | | A |
| 130 | A | | A |
| 131 | A | | A |
| 132 | A | | A |
| 133 | A | | A |
| 134 | A | | A |
| 135 | B | | A |
| 136 | A | | A |
| 137 | A | | A |
| 138 | A | | A |
| 139 | C | C | |
| 140 | B | B | |
| 141 | B | B | |
| 142 | C | B | |
| 143 | B | B | |
| 144 | B | B | |
| 145 | B | A | |
| 146 | A | A | |
| 147 | B | B | |
| 148 | B | A | |
| 149 | B | B | |
| 150 | B | B | |
| 151 | B | B | |
| 152 | B | A | |
| 153 | C | B | |
| 154 | C | B | |
| 155 | B | B | |
| 156 | C | C | |
| 157 | B | A | |
| 158 | B | A | |
| 159 | C | A | |
| 160 | C | A | |
| 161 | C | A | |
| 162 | B | B | |
| 163 | B | C | |
| 164 | C | B | |
| 165 | B | B | |
| 166 | B | B | |
| 167 | C | B | |
| 168 | C | B | |
| 169 | C | B | |
| 170 | B | B | B |
| 171 | B | B | A |
| 172 | B | | B |
| 173 | B | B | B |
| 178 | C | A | |
| 179 | C | C | |
| 181 | B | | A |
| 182 | B | | A |
| 183 | B | | A |
| 184 | B | | B |
| 185 | B | B | |
| 187 | C | | B |
| 188 | B | | A |
| 189 | A | | A |
| 190 | C | | A |
| 191 | B | | A |
| 192 | B | | A |
| 193 | B | | A |
| 194 | B | | A |
| 195 | B | | A |
| 196 | C | | B |
| 197 | A | | A |
| 198 | A | | A |
| 199 | A | | A |
| 200 | A | | A |
| 201 | B | | A |
| 202 | A | | A |
| 203 | A | | A |
| 204 | A | | A |
| 205 | A | | A |
| 206 | A | | A |
| 207 | B | | A |
| 208 | B | | A |
| 209 | A | | A |
| 210 | B | B | |
| 211 | B | B | |
| 212 | B | | A |
| 214 | B | | A |
| 216 | B | | B |
| 218 | C | B | |
| 219 | A | A | |
| 220 | A | A | |
| 221 | B | A | |
| 222 | A | B | |
| 223 | A | A | A |
| 224 | B | | A |
| 225 | A | | A |
| 226 | B | | B |
| 227 | A | | A |
| 228 | A | | A |
| 229 | A | | A |
| 230 | A | | A |
| 231 | A | | A |
| 232 | A | | A |
| 233 | A | | A |
| 237 | A | | A |
| 238 | A | | A |
| 239 | A | | A |
| 240 | A | | A |
| 241 | A | A | |
| 242 | B | A | |
| 243 | B | B | |
| 244 | B | A | |
| 245 | B | B | |
| 246 | A | | A |
| 248 | A | | A |
| 249 | A | | A |
| 250 | A | | A |
| 251 | A | | A |
| 252 | A | | A |
| 253 | A | | A |
| 254 | B | | A |
| 255 | A | | A |

TABLE 52-continued

| Compound No. | Human TGR5 Lum. cAMP Activity | Mouse TGR5 Lum. cAMP Activity | Mouse TGR5 HTRF cAMP Activity |
|---|---|---|---|
| 258 | A | | A |
| 259 | A | | A |
| 260 | A | | A |
| 261 | A | | A |
| 262 | A | | A |
| 266 | B | | A |
| 267 | A | | A |
| 268 | A | | A |
| 269 | A | | A |
| 270 | A | | A |
| 271 | A | | A |
| 274 | A | | A |
| 275 | A | | B |
| 276 | C | | C |
| 278 | A | | A |
| 279 | A | | A |
| 280 | B | | A |
| 281 | A | | A |
| 282 | A | | A |
| 283 | A | | A |
| 284 | A | | A |
| 285 | A | | A |
| 286 | A | | A |
| 287 | A | | A |
| 288 | B | | A |
| 289 | A | | A |
| 290 | B | | A |
| 291 | B | | A |
| 292 | A | | A |
| 293 | A | | A |
| 294 | A | | A |
| 295 | B | | A |
| 296 | B | | B |
| 297 | A | | A |
| 298 | A | | A |
| 299 | A | | A |
| 300 | B | | A |
| 301 | A | | A |
| 302 | A | | A |
| 303 | B | B | |
| 304 | B | B | |
| 305 | C | B | |
| 306 | B | B | |
| 307 | B | A | |
| 308 | A | A | |
| 309 | A | A | |
| 310 | A | B | |
| 311 | A | | A |
| 312 | B | | B |
| 313 | B | B | |
| 314 | B | | A |
| 315 | C | | A |
| 316 | A | | A |
| 317 | B | B | |
| 318 | B | | A |
| 319 | B | B | |
| 320 | B | B | |
| 321 | B | B | |
| 322 | B | C | |
| 323 | B | B | |
| 324 | C | B | |
| 325 | B | A | |
| 326 | B | A | |
| 327 | C | B | |
| 328 | A | | A |
| 329 | A | A | |
| 330 | A | | A |
| 331 | A | | B |
| 332 | A | | A |
| 333 | A | | A |
| 334 | A | A | |
| 335 | B | B | |
| 336 | B | | A |
| 337 | B | A | |
| 338 | B | | B |
| 339 | C | | B |
| 340 | B | | A |
| 341 | C | | B |
| 342 | B | | A |
| 343 | B | | A |
| 344 | B | | A |
| 345 | A | | A |
| 346 | A | | A |
| 347 | A | | A |
| 348 | B | | A |
| 349 | A | | A |
| 350 | A | | A |
| 351 | A | | A |
| 352 | C | | C |
| 353 | A | | A |
| 354 | C | | B |
| 355 | A | | A |
| 356 | A | | A |
| 357 | A | | A |
| 358 | A | | A |
| 359 | A | | A |
| 360 | A | | A |
| 361 | A | | A |
| 362 | A | | A |
| 363 | A | | A |
| 364 | A | | A |
| 365 | B | | B |
| 366 | A | | A |
| 367 | A | | A |
| 368 | A | | A |
| 369 | A | | A |
| 370 | A | | A |
| 371 | A | | A |
| 372 | A | | A |
| 373 | A | | A |
| 374 | A | | A |
| 375 | C | | B |
| 376 | B | | A |
| 377 | B | | B |
| 378 | C | | C |

Example 80

STC-1 GLP-1 Assay

Compounds of the present invention were evaluated for their ability to induce GLP-1 production in mouse intestinal neuroendocrine tumor cells.

Mouse STC-1 cells were cultured and maintained in high glucose DMEM (Sigma #5796) supplemented with 15% horse serum, 5% Fetal Bovine Serum (FBS), 1%° penicillin/streptomycin, and 2 mM L-alanine L-glutamine (GlutaMax). Two days prior to analysis of GLP-1 secretion cells were harvested using Accutase (Sigma), spun down then resuspended in high glucose DMEM media containing 2 mM L-alanine L-glutamine (GlutaMax), 10% charcoal-dextran stripped FBS, and 50 μg/mL Gentamicin, at a density of 100,000° cells/mL. 100 μL of cell suspension was added to each well of a 96-well Poly-D-Lysine coated culture plate (Sigma; cat #2382493) and was incubated at 37° C. with 5% $CO_2$.

Compounds were initially diluted in 100% DMSO (12-point serial dilution by half logs) in a 96-well plate and then were further diluted 1:500 in Hanks' Balanced Salt Solution (HBSS) containing protease inhibitor cocktail, DPP-IV inhibitor, and 0.1% fatty acid free bovine serum albumin. On the day of the experiment cells were washed once with HBSS. After wash, 100 μL of test compound was added to each well. The plate was incubated at 37° C. with 5% $CO_2$ for 2° h. Supernatants were collected and GLP-1 secretion was measured using the Cisbio™ Active GLP-1 HTRF Assay Kit (CisBio). Briefly, Anti-GLP-1-d2 conjugate and Anti-GLP-1 Terbium Cryptate conjugate stock solutions were prepared as per kit instructions. The two solutions were pre-mixed and 10 μL were transferred to a 384-well low volume plate (Greiner; cat #784075). 10 μL of collected supernatants were added to wells already containing the conjugate solution. The plate was covered and incubated at room temperature overnight. The plate was read on an Envision™ plate reader (PerkinElmer). $EC_{50}$ values were determined using GraphPad Prism (GraphPad Software, Inc.) and the results are shown in Table 53.

STC-1 GLP-1

In Table 53, $EC_{50}$ values were obtained from the STC-1 GLP-1 production assay for compounds of the present invention are summarized. The $EC_{50}$ values were coded as A, B, or C: A<100 nM; B=100-999 nM; and C=1,000-30,000 nM.

TABLE 53

| Compound No. | Mouse STC-1 HTRF GLP-1 Activity |
|---|---|
| 1 | B |
| 2 | B |
| 5 | B |
| 9 | A |
| 10 | B |
| 19 | C |
| 22 | A |
| 24 | B |
| 28 | B |
| 29 | B |
| 32 | B |
| 33 | A |
| 34 | A |
| 38 | B |
| 40 | B |
| 41 | B |
| 47 | C |
| 50 | C |
| 56 | B |
| 57 | A |
| 58 | A |
| 59 | A |
| 60 | A |
| 61 | A |
| 62 | A |
| 63 | A |
| 64 | B |
| 66 | A |
| 68 | B |
| 72 | B |
| 76 | B |
| 78 | A |
| 80 | B |
| 81 | B |
| 86 | A |
| 88 | B |
| 91 | A |
| 93 | A |
| 96 | A |
| 101 | A |
| 103 | A |
| 104 | B |
| 107 | B |
| 109 | B |
| 112 | A |
| 113 | B |
| 114 | A |
| 115 | A |
| 120 | A |
| 121 | B |
| 123 | A |
| 125 | B |
| 126 | B |
| 128 | B |
| 129 | B |
| 130 | A |
| 133 | A |
| 134 | B |
| 146 | C |
| 152 | B |
| 197 | A |
| 198 | B |
| 199 | A |
| 202 | A |
| 204 | B |
| 206 | B |
| 219 | A |
| 220 | A |
| 223 | A |
| 227 | B |
| 228 | B |
| 229 | B |
| 230 | B |
| 231 | B |
| 232 | A |
| 238 | B |
| 239 | A |
| 240 | A |
| 248 | B |
| 249 | A |
| 250 | A |
| 253 | A |
| 259 | B |
| 260 | B |
| 261 | B |
| 262 | B |
| 268 | A |
| 269 | A |
| 270 | A |
| 271 | A |
| 278 | A |
| 282 | B |
| 283 | B |
| 284 | B |
| 285 | A |
| 286 | B |
| 287 | A |
| 292 | B |
| 293 | A |
| 294 | A |
| 297 | B |
| 302 | A |
| 308 | B |
| 309 | B |
| 328 | B |
| 329 | B |
| 330 | B |
| 333 | B |
| 342 | B |
| 346 | A |
| 347 | B |
| 351 | A |
| 356 | B |
| 358 | A |
| 360 | A |
| 362 | A |
| 363 | A |
| 367 | B |
| 368 | B |
| 369 | B |
| 371 | B |
| 372 | A |

Example 81

Pharmacokinetic Profile in Mice

In this series of studies, the pharmacokinetic profile characteristics of compounds of the present invention were evaluated. The plasma concentration levels of the compounds were monitored in the blood stream (i.e., plasma) after oral gavage using $C_{max}$, and area under the curve (AUC).

8 week old male Hilltop mice were fasted overnight. Animals were randomized into groups (n=9) by body weight. Mice were dosed with 10 mg/kg compound (in 20% PEG400/80% 0.5% carboxymethylcellulose (medium viscosity)+0.25% Tween-80) at a volume of 10° mL/kg through oral gavage. Blood was collected via orbital bleeding at 0, 0.25, 0.5, 1, 2, and 4 h post-dose, with no one mouse having more than 3 blood draws. Blood was collected in EDTA coated tubes. Samples were stored at −20° C. until analysis.

Quantitation of compound levels in plasma was accomplished by LC-MS/MS analysis. Standard curve and quality control samples were prepared in male CD-1 mouse plasma containing EDTA $K^{2+}$ as an anticoagulant at final concentrations ranging from 500 to 0.1 ng/mL. The plasma samples, calibration curve standards, and quality control samples were prepared in an identical method in a 96-well deep plate (1 mL) with a quenching solution (1:1 mixed acetonitrile:methanol containing the internal standard Reserpine @ 400 ng/mL). Low volume samples were supplemented with CD-1 mouse plasma. The plate was mixed on multi-tube vortexer for 1 min and centrifuged at 4000 rpm for 30 min at 4° C. (Sorvall® Super T21) before LC-MS/MS analysis. LC conditions were developed and optimized based on each compound as needed. The outlet of the column was coupled to AB Sciex 4000 QTrap Mass Spectrometer (AB Sciex, Brugg Switzerland). Detection was carried out using multiple reaction monitoring mode with positive-ion detection focusing. The pharmacokinetic parameters were derived from the plasma-time data and calculated using the standard non-compartmental method with WinNonlin (Pharsight, Mountain View, Calif.) or PK Solver (*Comp. Meth. Prog. Biomed.* (2010), 99, 306-314).

The $C_{max}$ (ng/mL) of compounds studied are listed in Table 54. Values reported are the mean plasma concentration of three mice. Values reported are the mean plasma concentration of three mice. In summary, the data show that most of the compounds of the present invention exhibit low plasma exposure ($C_{max}$<200 ng/mL). In other words, the compounds of the present invention do not substantially appear in the blood stream after oral gavage.

TABLE 54

| Compound No. | Cmax (ng/mL) |
|---|---|
| 1 | 233 |
| 5 | 338 |
| 9 | 48 |
| 22 | 171 |
| 24 | 970 |
| 26 | 55 |
| 28 | 75 |
| 29 | 55 |
| 32 | 1,347 |
| 33 | 88 |
| 34 | 31 |
| 50 | 214 |
| 56 | 14 |
| 57 | 13 |
| 58 | 29 |
| 59 | 43 |
| 60 | 4.3 |
| 61 | 3.3 |
| 62 | 33 |
| 63 | 1.3 |
| 64 | 2.9 |

TABLE 54-continued

| Compound No. | Cmax (ng/mL) |
|---|---|
| 66 | 7.3 |
| 68 | 15 |
| 72 | 1.6 |
| 73 | 2.8 |
| 74 | 3.6 |
| 75 | 22 |
| 76 | 3.0 |
| 78 | 1.3 |
| 79 | 15 |
| 80 | 1.2 |
| 81 | 60 |
| 83 | 2.5 |
| 86 | 13 |
| 87 | 35 |
| 88 | 630 |
| 89 | 2.1 |
| 91 | 10 |
| 93 | 5.0 |
| 94 | 26 |
| 95 | 2.0 |
| 96 | 1.1 |
| 98 | 12 |
| 101 | 0.7 |
| 103 | 9.3 |
| 104 | 8.9 |
| 105 | 51 |
| 107 | 0.4 |
| 109 | 3.2 |
| 111 | 5.3 |
| 112 | 1.1 |
| 113 | 0.13 |
| 114 | 4.8 |
| 115 | 2.7 |
| 116 | 15 |
| 117 | 6.5 |
| 118 | 7.9 |
| 119 | 16 |
| 120 | 2.6 |
| 121 | 235 |
| 123 | 1.4 |
| 125 | 0.14 |
| 126 | 2.0 |
| 127 | 11 |
| 128 | 670 |
| 129 | 0.6 |
| 130 | 2.8 |
| 131 | 12 |
| 133 | 4.1 |
| 134 | 22 |
| 136 | 59 |
| 137 | 22 |
| 138 | 69 |
| 197 | 143 |
| 198 | 6.8 |
| 199 | 1.0 |
| 202 | <0.1 |
| 204 | 4.4 |
| 206 | 3.8 |
| 210 | 54 |
| 219 | 75 |
| 223 | 44 |
| 231 | 28 |
| 232 | 64 |
| 239 | 53 |
| 248 | 6.2 |
| 249 | 3.4 |
| 250 | 7.6 |
| 253 | 48 |
| 255 | 64 |
| 258 | 42 |
| 259 | 27 |
| 260 | 3.2 |
| 261 | 48 |
| 266 | 73 |
| 268 | 7.7 |
| 269 | 3.2 |
| 270 | 5.4 |

TABLE 54-continued

| Compound No. | Cmax (ng/mL) |
|---|---|
| 271 | <1.0 |
| 276 | 2.1 |
| 278 | 3.7 |
| 281 | 92 |
| 282 | 4.2 |
| 283 | 2.7 |
| 284 | 13 |
| 285 | 0.9 |
| 286 | 5.2 |
| 287 | 5.0 |
| 292 | 1.3 |
| 293 | 5.5 |
| 294 | 1.7 |
| 297 | 11 |
| 298 | 16 |
| 301 | 2.6 |
| 302 | 3.7 |
| 308 | 18 |
| 330 | 20 |
| 332 | 37 |
| 347 | 30 |
| 349 | 1.7 |
| 351 | 301 |
| 355 | 48 |
| 356 | 8.4 |
| 358 | 3.4 |
| 360 | 0.5 |
| 362 | 36 |
| 363 | 0.5 |
| 364 | 8.0 |
| 367 | 1.5 |
| 368 | 2.5 |
| 369 | 1.7 |
| 372 | 105 |

Example 82

In vivo Mouse GLP-1 Study

After establishing that the compounds of the present invention exhibit low $C_{max}$ values after single dose oral administration (i.e., they do not substantially appear in the blood stream), an evaluation was made whether the compounds produce a biological effect in a live animal consistent with the activation of the TGR5 receptor. To that end, we measured GLP-1 levels in the blood of male C57BL/6NTac mice after oral administration of the compounds.

12-14 week old male C57BL/6NTac (Taconic) mice were divided into experimental groups (n=6) by randomizing mice based on pre-fasting body weight and then were fasted overnight. On experiment day, all mice were dosed with 3 mg/kg sitagliptin via oral gavage exactly 1 hour before oral gavage dosing of vehicle [0.5% carboxymethylcellulose (medium viscosity)+0.25% Tween-80] or 10 mg/kg compound in vehicle. Four (4) hours following the administration of compound, blood was collected via cardiac puncture. For the GLP-1 assay, 200-250 μL of blood was placed in an EDTA $K^{2+}$ tube containing 5 μL of 40 mg/mL aprotinin (Sigma A1153) and 1 μL of 10 mM sitagliptin (Sigma 58576) and plasma was separated by centrifugation. Plasma samples were stored at −20° C. until analysis. The active form of GLP-1 (GLP-1 (7-36) amide) was analyzed using Meso Scale Discovery System according to the manufacturer's directions (item number K150HYC). Values of $p<0.05$ are considered statistically significant.

The active GLP-1 assay results from the mice in vivo study are shown in Table 55 (below), expressed as fold change over vehicle (sitagliptin only). These results indicate that the compounds increase GLP-1 level in the circulating blood of experimental mice four (4) hours after the compound administration.

TABLE 55

| Compound No. | GLP-1 Fold Increase |
|---|---|
| 56 | 4.1 |
| 58 | 3.1 |
| 60 | 2.3 |
| 61 | 3.6 |
| 62 | 1.5 |
| 63 | 2.3 |
| 66 | 3.8 |
| 72 | 1.3 |
| 93 | 1.3 |
| 96 | 1.1 |
| 114 | 3.1 |
| 126 | 1.7 |
| 129 | 1.1 |
| 199 | 3.8 |
| 202 | 1.2 |
| 206 | 2.6 |
| 248 | 2.2 |
| 249 | 4.3 |
| 250 | 2.7 |
| 268 | 2.9 |
| 269 | 1.8 |
| 271 | 2.7 |
| 278 | 2.4 |
| 282 | 1.5 |
| 283 | 1.5 |
| 286 | 2.3 |
| 287 | 1.5 |
| 292 | 0.9 |
| 360 | 3.6 |
| 367 | 3.5 |

Example 83

Oral Glucose Tolerance Test (OGTT)

Compounds of the present invention were tested to determine if they could decrease blood glucose levels in mice after glucose administration (i.e., effective in glycemic control). In this study, we orally administered a standard dose of glucose to mice and measured glucose levels in circulating blood at several defined time points after the glucose administration.

Figure 2:
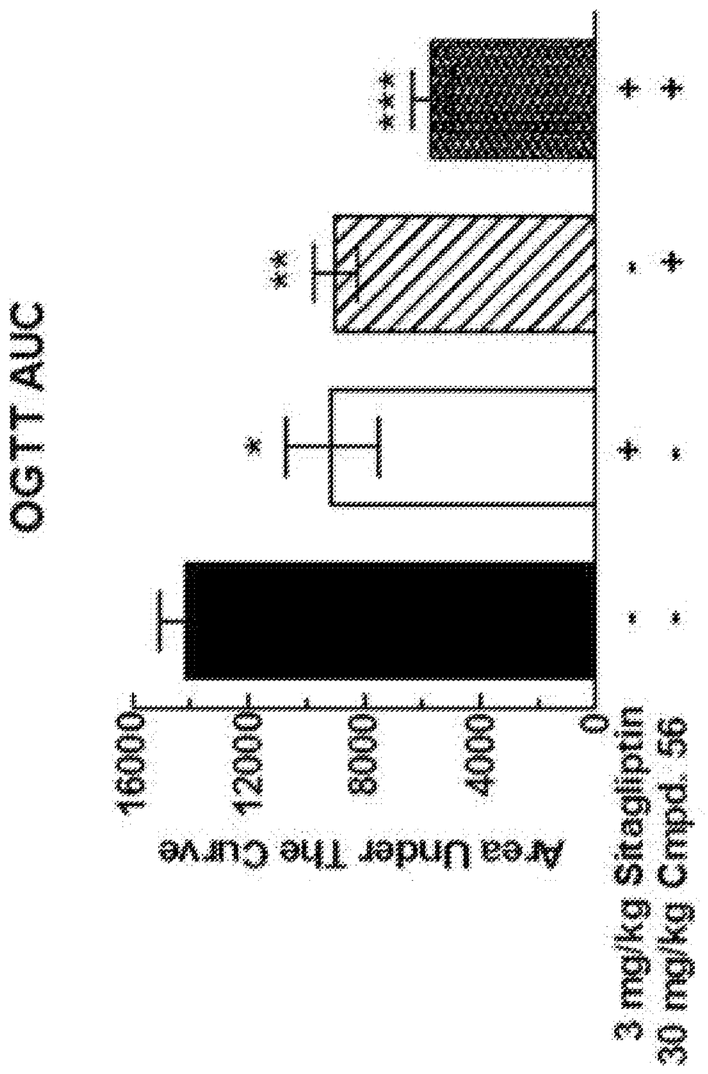
FIG. 2 depicts the area under the curve (AUC) of plasma glucose level in an Oral Glucose Tolerance Test (OGTT) in C57BL/6NT mice treated with vehicle, sitagliptin (3 mg/kg), Compound 56 (30 mg/kg), or Compound 56 (30 mg/kg)+ sitagliptin (3 mg/kg).

8-12 week old male C57BL/6NTac (Taconic) mice were fasted overnight. On the morning of the experiment, the mice were weighed and divided into experimental groups (n=8) assigned by randomizing mice based on baseline blood glucose levels. Following group assignments, mice were dosed with 3 mg/kg sitagliptin or PBS as vehicle control via oral gavage (5 mL/kg) exactly 1 hour before oral gavage dosing of compound (30 mg/kg) or vehicle (0.5% carboxymethylcellulose (medium viscosity)+0.25% Tween −80) at a volume of 10 mL/kg. Time zero blood glucose levels were measured 4 hours after compound or vehicle dosing. Immediately following time zero blood glucose level measurement, mice were gavaged with 2 g/kg of glucose. Blood glucose measurements were subsequently conducted at 15, 30, 60, 90, and 120 min following glucose gavage via tail tip by hand-held glucometer (One-touch Ultra II, Johnson & Johnson) (FIG. 1). AUC were calculated and data analyzed using one-way ANOVA followed by Dunnett's post-test in GraphPad Prism (FIG. 2). Values of $p<0.05$ are considered statistically significant.

Figure 3:
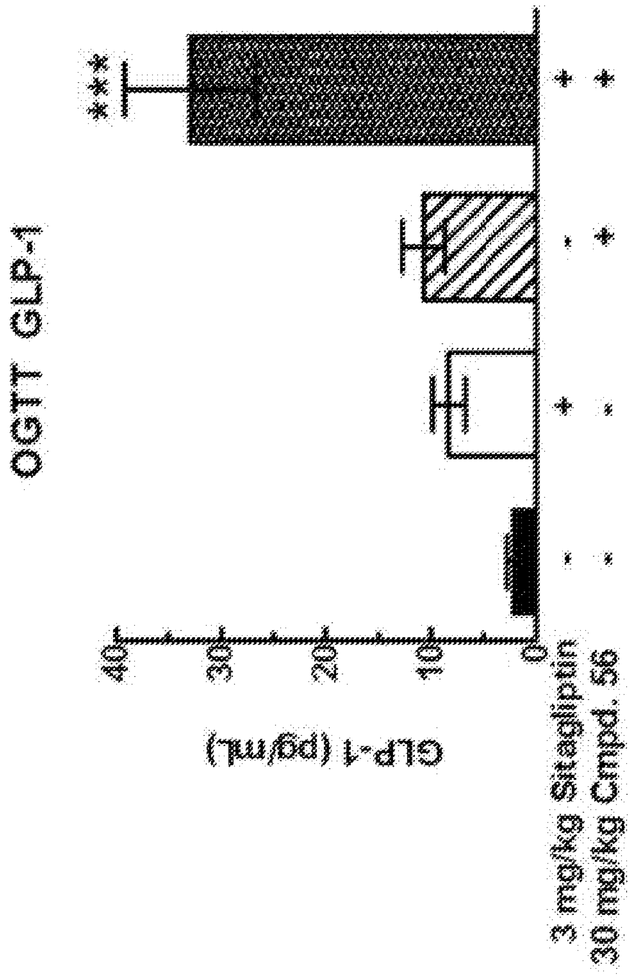
FIG. 3 depicts the GLP-1 elevation in C57BL/6NT mice treated with vehicle, sitagliptin (3 mg/kg), Compound 56 (30 mg/kg), or Compound 56 (30 mg/kg)+sitagliptin (3 mg/kg).

Immediately after the last blood glucose measurement (i.e., 120 minutes after the glucose administration), the blood was collected via cardiac puncture for GLP-1 measurements. The collected blood (200-250 μL) was placed in an EDTA $K^{2+}$ tube containing 5 μL of 40 mg/mL aprotinin (Sigma A1153) and 1 μL of 10 mM sitagliptin (Sigma S8576) and plasma was separated by centrifugation. Plasma samples were stored at −20° C. until analysis. The active form of GLP-1 [GLP-1 (7-36) amide] was analyzed using Meso Scale Discovery System according to the manufacturer's directions (item number K150HYC). There is an increased GLP-1 level when Compound 56 is orally administered. A synergy between the Compound 56 and sitagliptin is also observed (FIG. 3). Values of $p<0.01$ and $<0.001$ are considered statistically significant.

As shown in FIGS. 1, 2, and 3, the Compound 56 (i.e., (S)-2-(3-(1-(6-(2-((4-cyanophenethyl)carbamoyl)pyrrolidin-1-yl)-2-(trifluoromethyl)pyrimidin-4-yl)piperidin-4-yl) propanamido)ethanesulfonic acid) of the present invention effectively reduced blood glucose levels throughout the time period measured and elevated blood GLP-1 levels, indicating the effectiveness of the compound in glycemic control.

Example 84

Oral Glucose Tolerance Test (OGTT)

In this study, we continued to test the compounds of the present invention with respect to their effectiveness in glycemic control. To do so, we tested a different compound (i.e., Compound 268; (S)-3-(3-(2-(1-(6-(2-((4-cyanophenethyl)carbamoyl)azetidin-1-yl)-2-(trifluoromethyl)pyrimidin-4-yl)piperidin-4-yl)ethyl)ureido)propanoic acid) in the oral glucose tolerance test as described in Example 83 (above).

Figure 4:
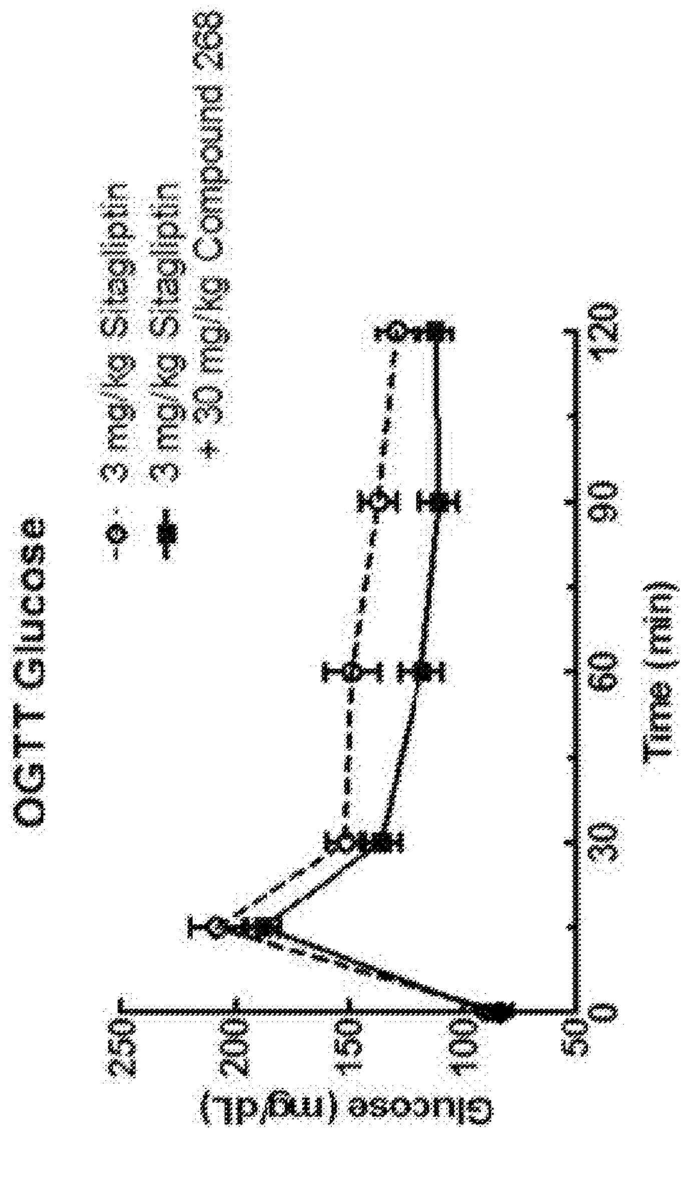
FIG. 4 depicts the plasma glucose level in an Oral Glucose Tolerance Test (OGTT) in C57BL/6NT mice treated with Compound 268 (30 mg/kg)+sitagliptin (3 mg/kg) or sitagliptin (3 mg/kg).
Figure 5:
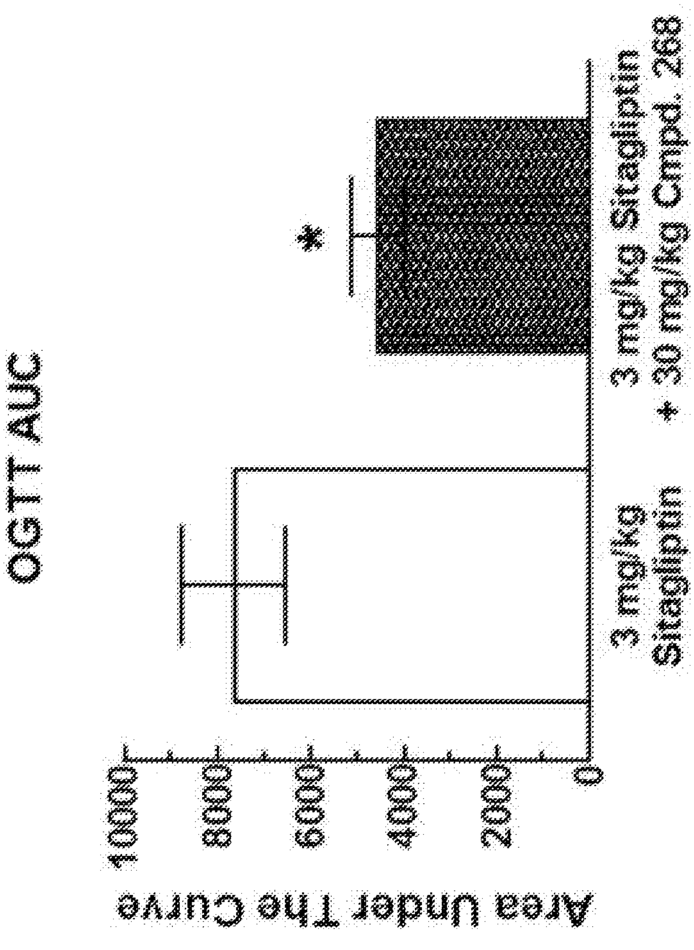
FIG. 5 depicts the area under the curve (AUC) of plasma glucose level in an Oral Glucose Tolerance Test (OGTT) in C57BL/6NT mice treated with Compound 268 (30 mg/kg)+ sitagliptin (3 mg/kg) or sitagliptin (3 mg/kg).
Figure 6:
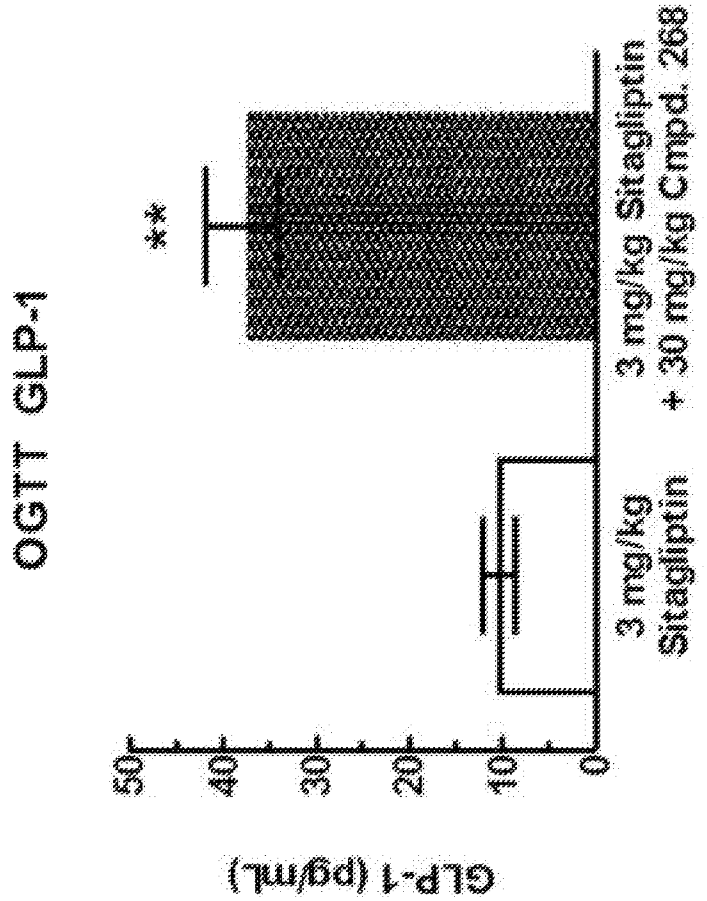
FIG. 6 depicts the GLP-1 elevation in C57BL/6NT mice treated with treated with Compound 268 (30 mg/kg)+sitagliptin (3 mg/kg) or sitagliptin (3 mg/kg).

FIG. 4 depicts blood glucose measurements at 15, 30, 60, 90, and 120 min following glucose gavage. FIG. 5 depicts AUC data after glucose gavage. FIG. 6 depicts the blood GLP-1 levels comparing mice treated with a DPP-4 inhibitor (i.e., sitagliptin) to mice treated with Compound 268+a DPP-4 inhibitor (i.e., sitagliptin).

As shown in FIGS. 4 and 5, Compound 268 of the present invention effectively reduced blood glucose levels throughout the time period measured and induced GLP-1 production (FIG. 6), indicating the effectiveness of the compound in glycemic control. Note that mice treated with Compound 268+a DPP-4 inhibitor (i.e., sitagliptin) showed statistically significant effect as compared to mice treated with a DPP-4 inhibitor (i.e., sitagliptin) alone, which itself is known to be effective in glycemic control. Thus, the results are consistent with a synergy in glycemic control between Compound 268 and sitagliptin.

Example 85

Bile Weight after a Single Oral Administration of the Compound

Figure 9:
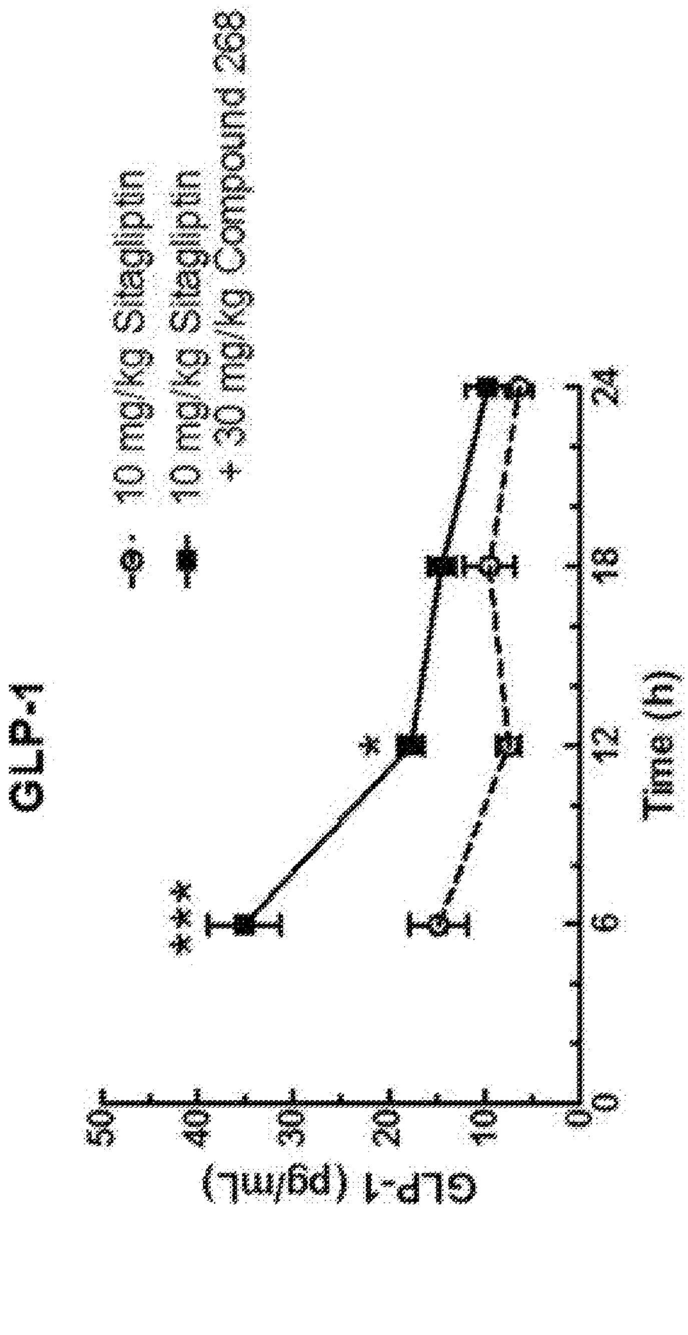
FIG. 9 depicts the time course (i.e., 6, 12, 18, and 24 hours) increases in GLP-1 in DIO male mice treated with Compound 268 (30 mg/kg)+sitagliptin (10 mg/kg) or sitagliptin (10 mg/kg).

In this study, we evaluated if the observed GLP-1 elevation (induced by the compounds of the present invention) may be associated with gallbladder filling. We treated mice with Compound 268 and monitored the bile weight (a measure that indicated gallbladder filling) to determine if the compound retained more bile in the gallbladder as compared to the control mice (i.e., vehicle alone). A time course study was performed to measure weight of the bile aspirated from the gallbladder after oral administration of Compound 268 (30 mg/kg) in high fat diet induced obese (DIO) mice. In this study, GLP-1 levels were also measured at each time point (FIG. 9).

Approximately 12 week old DIO male mice (obtained from Taconic) were acclimated in the testing facility for over two weeks. The mice were provided a high fat diet [Research Diet D12492 (60% Fat kcal)] while in the testing facility. On the day of the experiment, the mice were administered with 10 mg/kg sitagliptin or with 10 mg/kg sitagliptin+30 mg/kg Compound 268 by oral gavage (5 mL/kg). Following the treatment, the blood was collected via cardiac puncture at 6, 12, 18, and 24 hours after the dosing. The blood samples were distributed as follows: 150-200 μL of blood were placed in an EDTA $K^{2+}$ tube containing 5 μL of 40 mg/mL aprotinin (Sigma A1153) and 1 μL of 10 mM sitagliptin (Sigma 58576) to be used for GLP-1 measurements; the remaining blood (≥250 μL) was placed in an EDTA $K^{2+}$ tube and plasma was processed for analytical chemistry and analyzed by LCMS/MS method as described in Example 81. Bile was removed from the gallbladder and weighed to approximate volume of bile contained within the bladder.

In addition, bile weight was determined in the OGTT study on lean mice described in Example 84 above. At the end of that study, bile was removed from the gallbladder and weighed to approximate volume of bile contained within the gallbladder.

Figure 7:
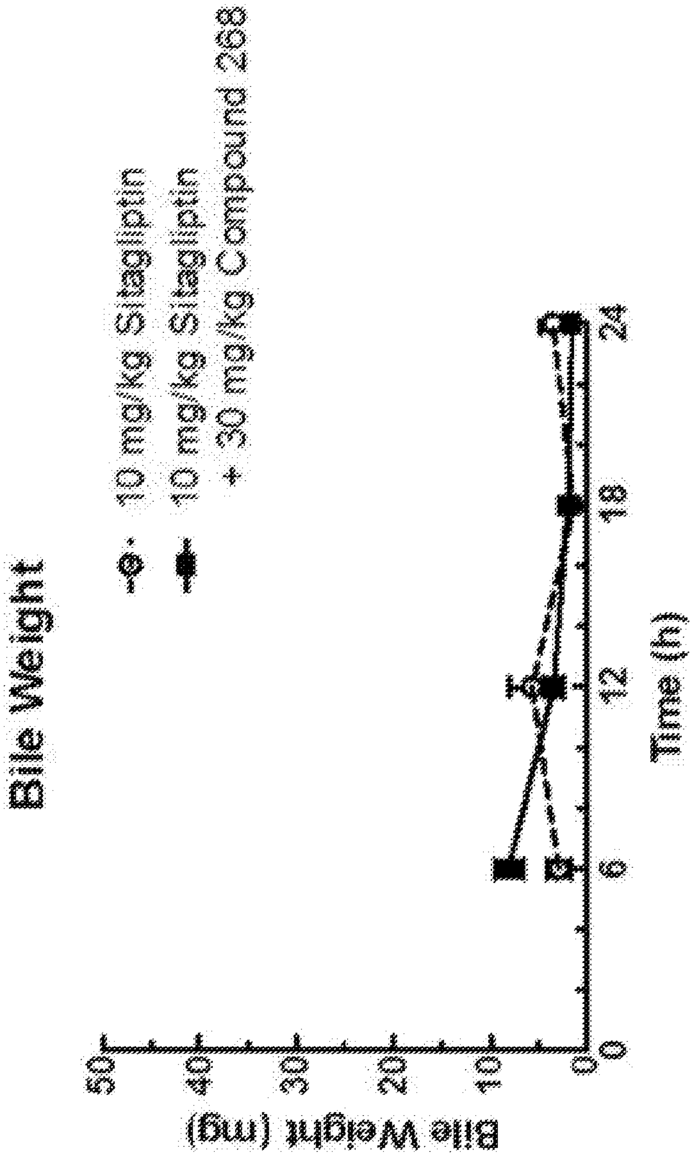
FIG. 7 depicts the time course (i.e., 6, 12, 18, and 24 hours) of the changes in bile weights in DIO male mice treated with Compound 268 (30 mg/kg)+sitagliptin (10 mg/kg), or sitagliptin (10 mg/kg).
Figure 8:
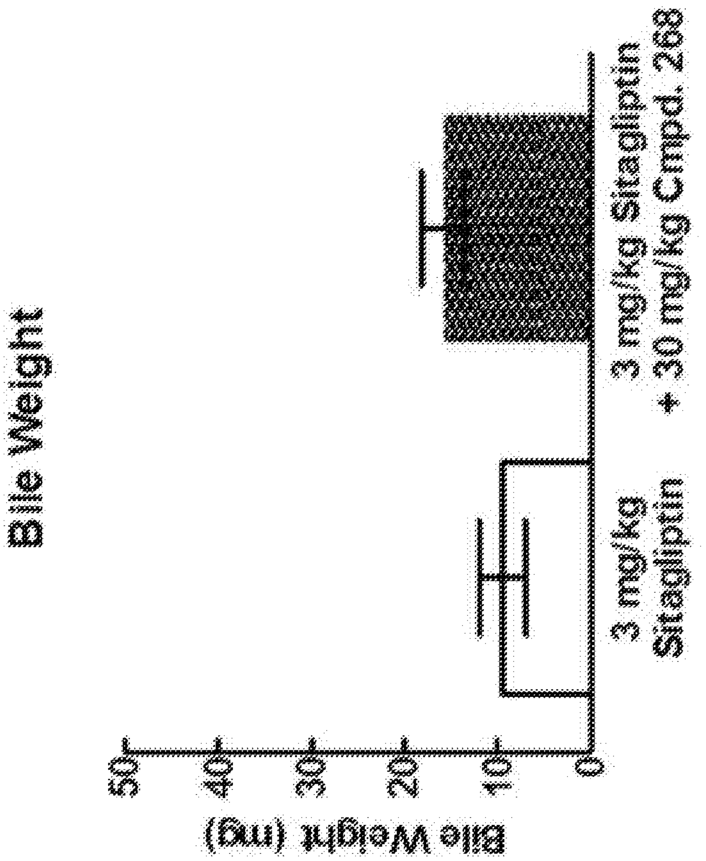
FIG. 8 depicts the bile weights in C57BL/6N lean mice treated with Compound 268 (30 mg/kg)+sitagliptin (10 mg/kg) or sitagliptin (10 mg/kg).

FIG. 7 depicts bile weight in DIO mice at 6, 12, 18, and 24 hours after oral administration of 10 mg/kg sitagliptin alone or 10 mg/kg sitagliptin+30 mg/kg Compound 268. FIG. 8 depicts the comparison in bile weight between sitagliptin (3 mg/kg, p.o.) and Compound 268 (30 mg/kg, p.o.)+sitagliptin (3 mg/kg, p.o.) following an OGTT assay in lean C57BL/6N mice, 6 hours after treatment. FIG. 9 illustrates plasma GLP-1 levels from the DIO mice at the same time points.

Note that Compound 268 did not cause any significant increase in bile weight in DIO mice throughout the time periods studied. In contrast, significant elevation of GLP-1 levels was observed in mice treated with 3 mg/kg sitagliptin+30 mg/kg Compound 268 over the levels from mice treated with sitagliptin alone. In addition, no significant differences in bile weight between sitagliptin+Compound 268 and sitagliptin alone were observed suggesting, that no bile accumulation in response to treatment with the compounds of the present invention when used in combination with DPP-4 inhibitor sitagliptin.

Example 86

Plasma Concentration of Compound in Mice

In these studies, the plasma concentration of the compounds of the present invention was measured in DIO mice as well as lean C57BL/6N mice.

Figure 10:
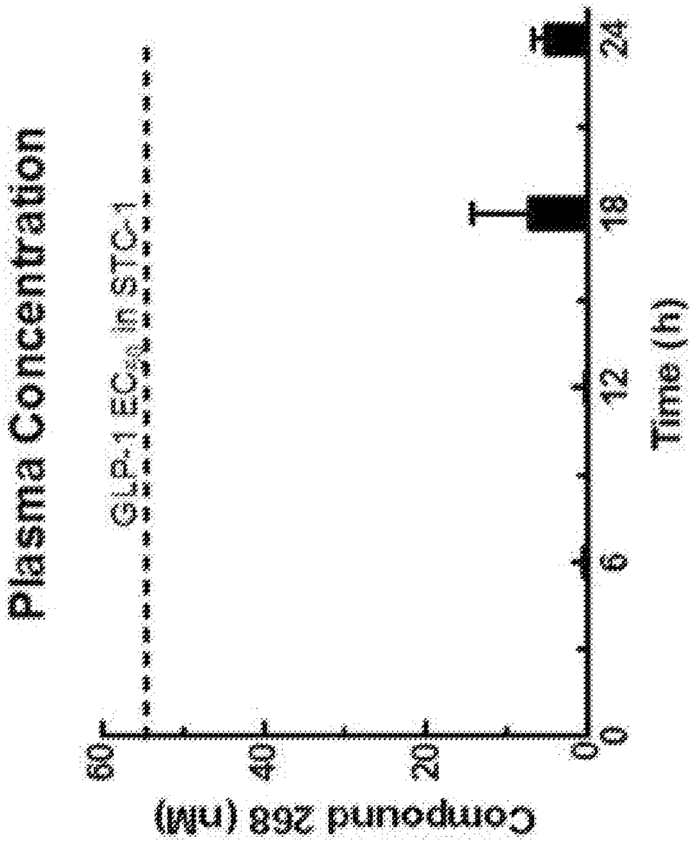
FIG. 10 depicts the time course (i.e., 6, 12, 18, and 24 hours) of plasma concentration of Compound 268 in DIO male mice.

In the first study, (data represented in FIG. 10), plasma concentration levels were measured over a 24 hour time period in DIO mice. Following the treatment with the compound, the blood was collected via cardiac puncture at 6, 12, 18, and 24 hours. The blood samples (>250 μL) were placed in an EDTA $K^{2+}$ tube and plasma was processed for analytical chemistry and analyzed by LCMS/MS method as described in Example 81. FIG. 10 depicts the plasma concentrations of Compound 268 after oral administration at 30 mg/kg in combination with 10° mg/kg sitagliptin. The plasma concentrations of Compound 268 were below 10 nM at every tested time points.

Figure 11:
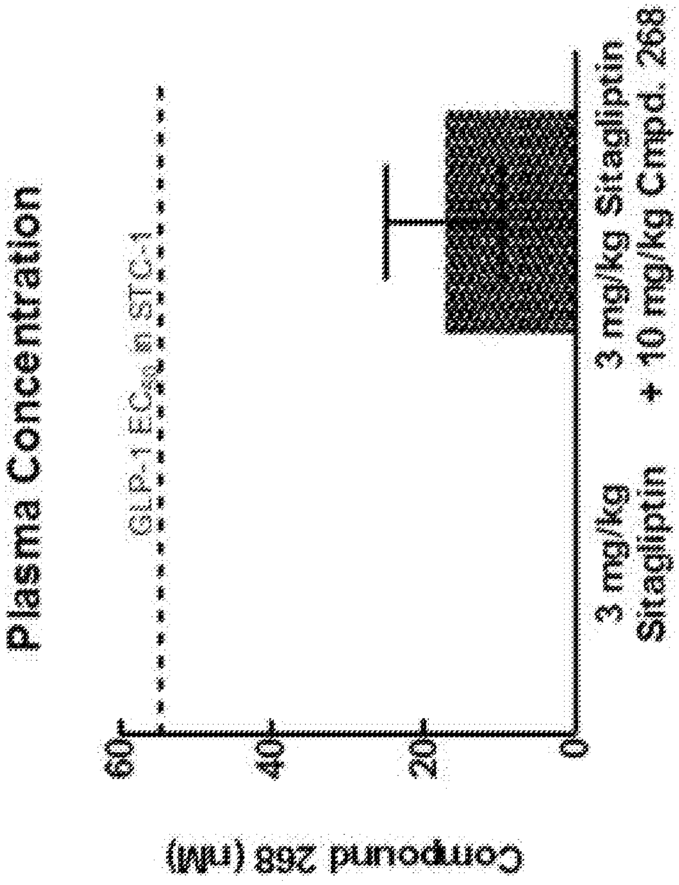
FIG. 11 depicts the plasma concentration of Compound 268 in the Compound 268 (10 mg/kg)+sitagliptin (3 mg/kg) or sitagliptin (3 mg/kg) in C57BL/5N mice after oral dosing. Note that there is a minimal level change in plasma Compound 268 at 6 hour post-dose.

In the second study (data represented in FIG. 11), plasma concentration levels were measured in lean mice after an OGTT experiment described in Example 84. The blood was collected via cardiac puncture 6 hours post compound dosing (and 2 hours after the 2 g/kg glucose bolus). The blood samples (?250 μL) were placed in an EDTA $K^{2+}$ tube and plasma was processed for analytical chemistry and analyzed by LCMS/MS method as described in Example 81. FIG. 11 depicts low levels of Compound 268 following OGTT in lean C57BL/6N mice, 6 hours after treatment with 30 mg/kg in combination with 3 mg/kg sitagliptin.

Note that the mean plasma concentrations of Compound 268 in both studies were well below the $EC_{50}$ concentration of GLP-1 stimulation in STC-1 cells (~55 nM) as described in Example 80. These results indicate the compounds of the present invention are not found in the circulating blood. Overall, the results indicate that the compounds of the present invention are non-systemic TGR5 agonists.

Example 87

GLP-1 Levels after Chronic Dosing of Compounds

The chronic dosing of compounds of the present invention was evaluated to determine if they produce sustained GLP-1 levels.

Male DIO mice were received at 12 weeks of age (from Taconic), and were single-housed at the testing facility and acclimated for at least 2 weeks. The mice were provided a high fat diet [Research Diet D12492 (60% Fat kcal)] while in the testing facility. Before the study initiation, the animals were randomized into 18 experimental groups by body weight. The first 10 groups were administered with sitagliptin alone at 10 mg/kg or sitagliptin (10 mg/kg)+Compound 268 at 30 mg/kg by oral gavage and then again 14 hours later (except for one sitagliptin treated and one sitagliptin+Compound 268 treated groups that were euthanized 14° hours after the first dose). The remaining mice were euthanized at 3, 6, or 9 hours after the second dose to collect blood for GLP-1 measurements and bile weights. The remaining 8 groups were administered by oral gavage with sitagliptin alone at 10 mg/kg or sitagliptin (10 mg/kg)+Compound 268 at 30 mg/kg every 10 or 14 hours for 5 days. On day 5, following the tenth injection, one sitagliptin treated and one sitagliptin+Compound 268 treated groups were euthanized every 3 hours (at 3, 6, 9, and 12 hours after the last compound administration) for bile weights and blood collection. The collected blood (200-250 μL) was placed in an EDTA $K^{2+}$ tube containing 5 μL of 40 mg/mL aprotinin (Sigma A1153) and 1 μL of 10 mM sitagliptin (Sigma 58576) and plasma was separated by centrifugation. Plasma samples were stored at −20° C. until analysis. The active form of GLP-1 [GLP-1 (7-36) amide] was analyzed using Meso Scale Discovery System according to the manufacturer's instruction.

Figure 12:
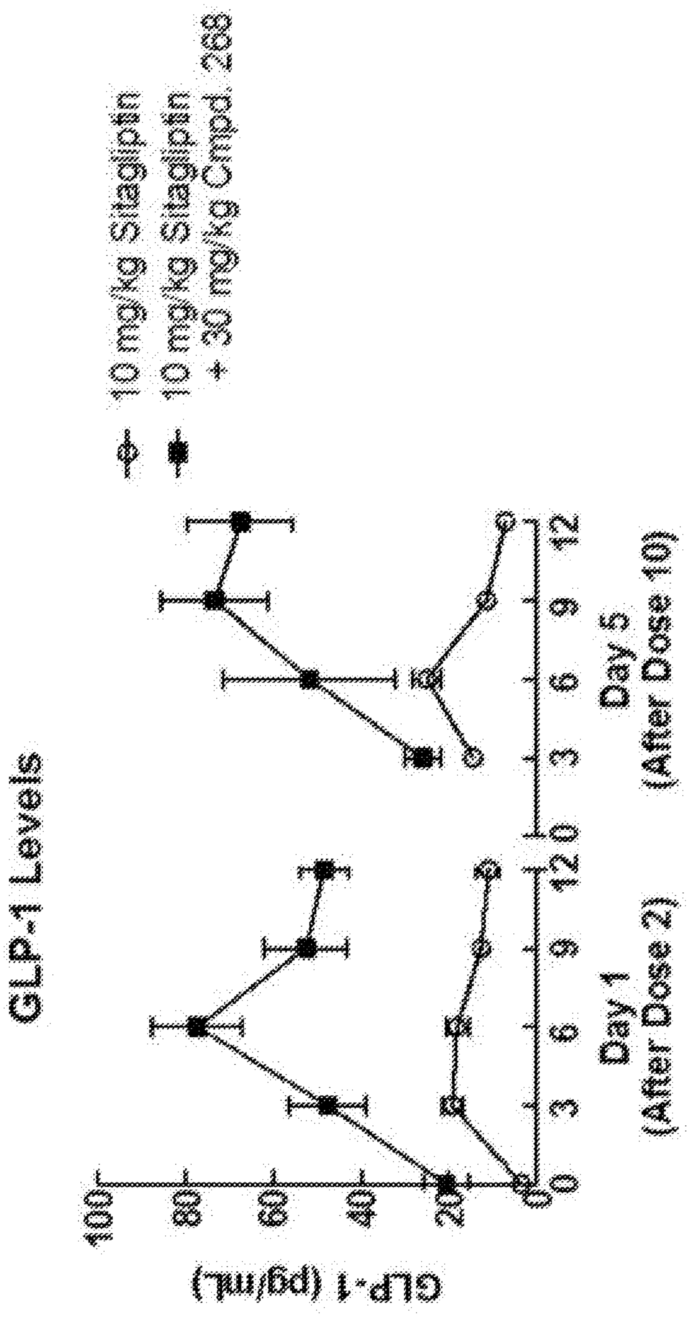
FIG. 12 depicts the sustained GLP-1 increase in plasma following oral administration of Compound 268 (30 mg/kg)+sitagliptin (10 mg/mkg) or sitagliptin (10 mg/kg) in DIO mice at 0, 3, 6, 9, and 12 hours of day 1 (after dose 2) and day 5 (after dose 10).

FIG. 12 depicts the sustained GLP-1 plasma level increase following oral administration of Compound 268 in DIO mice. Mice treated with Compound 268 (+sitagliptin) exhibited a significantly increased level of GLP-1 as compared to the mice treated with sitagliptin alone. Note that similar GLP-1 levels were observed after the second and the tenth treatment. These data indicate that chronic dosing of compounds stably increases GLP-1 levels over 5 days of treatment.

Example 88

Bile Weight after Chronic Dosing of Compounds

In this study, chronic dosing of compounds of the present invention was examined to determine if they lead to an increase in bile weight.

Figure 13:
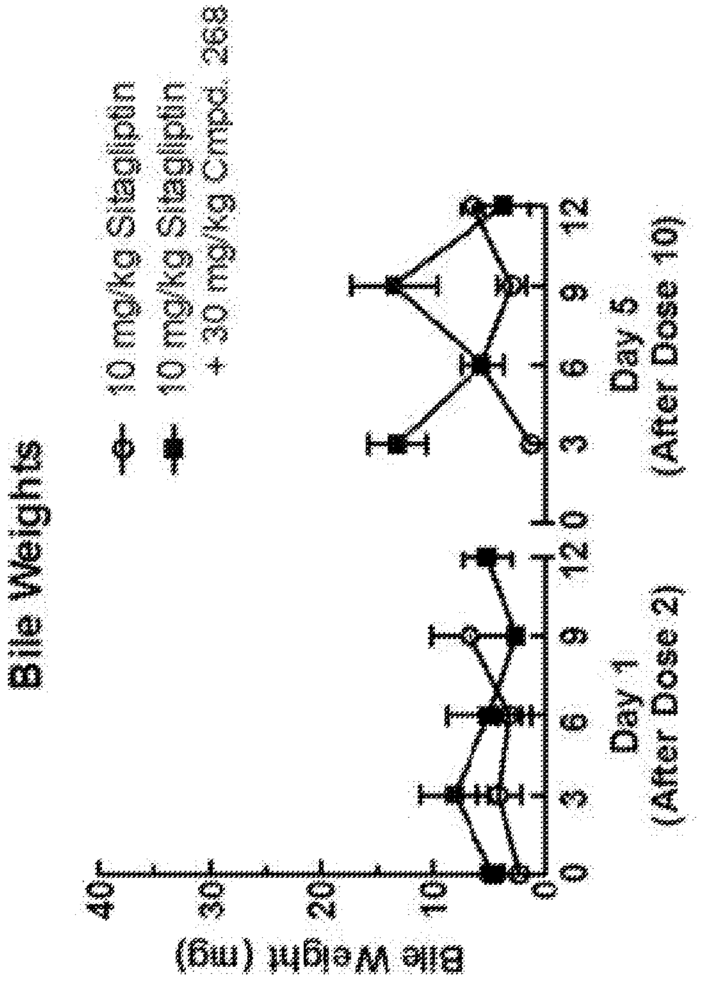
FIG. 13 depicts the time course of bile weight changes over times in DIO mice receiving Compound 268 (30 mg/kg)+sitagliptin (10 mg/kg) or sitagliptin (10 mg/kg).

FIG. 13 depicts the time course of bile weight changes over time (i.e., 0, 3, 6, 9, and 12 hours) after the second and the tenth treatment with Compound 268 using the protocol in Example 87. As shown in FIG. 13, no significant changes in bile weight were observed between mice treated with Compound 268 (+sitagliptin) and sitagliptin alone.

Example 89

Plasma Concentrations after Chronic Dosing of Compound

In the study, the plasma level of compounds of the present invention (i.e., Compound 268) was monitored at day 1 and day 5. The same animal protocol as described in Examples 87 and 88 was utilized.

Figure 14:
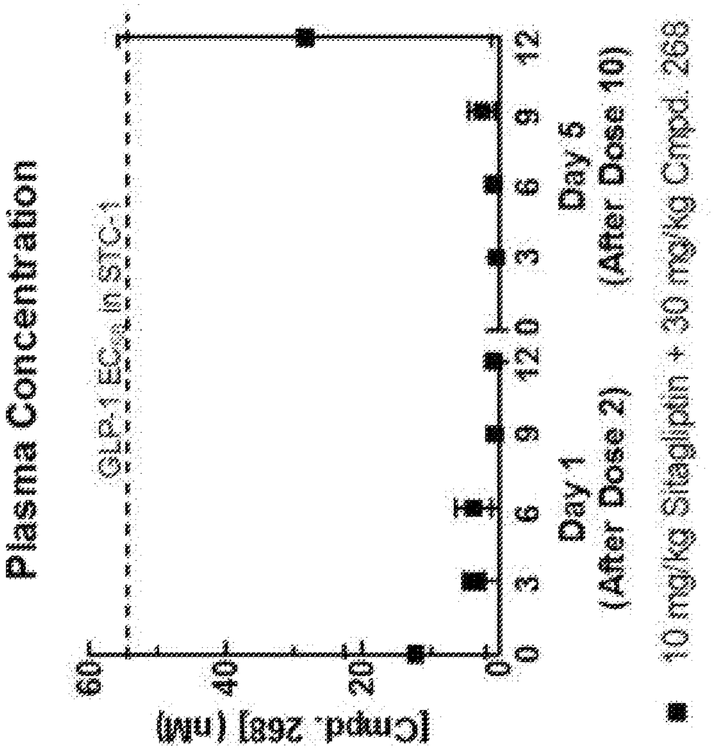
FIG. 14 depicts the plasma concentration of Compound 268 at 0, 3, 6, 9, and 12 hours after the $2^{nd}$ dose and 3, 6, 9, and 12 hours after the $10^{th}$ dose.

FIG. 14 depicts the plasma concentration of Compound 268 at 0, 3, 6, 9, and 12 hours after the second and at 3, 6, 9, and 12 hours after the tenth dose. Note that the plasma level of Compound 268 maintained at a low concentration level. No significant increases were observed over time.

Altogether these data indicate that chronic oral dosing of Compound 268 increases GLP-1 production in sustained manner (FIG. 12), without any alternations in bile weight (FIG. 13), and the plasma levels of the compound remain low at all time points tested (FIG. 14).

Example 90

Low Level of Compounds is Attributed to Low Intestinal Absorption

In this study, we determined if low plasma level of the compounds of the present invention is due to low absorption in the gut, or due to the first pass effect (i.e., absorption followed by a rapid degradation of compounds by liver). Hepatic portal vein cannulated male CD(SD) rats obtained from Charles River Laboratory were utilized. In brief, Compound 268 was administered orally at 10 mg/kg, and the blood was obtained simultaneously from the portal vein and systemic circulation (retro-orbital sinus) at predose, 0.25, 0.5, 1, 2, and 4 hours post-dose, in EDTA coated tubes. The samples were processed into plasma and quantification of compound levels in the plasma was accomplished by means of LC-MS/MS analysis as described in Example 81. The pharmacokinetic characteristics were determined and summarized in Table 56 below.

TABLE 56

| | $C_{max}$ (ng/mL) | $T_{max}$ (h) | AUC (0→7 h) (ng/mL*h) |
|---|---|---|---|
| Portal Vein bleed | 15.7 ± 6.7 | 0.25-1 | 49.1 ± 47.3 |
| Peripheral bleed | 43.9 ± 50.2 | 0.25-1 | 76.2 ± 84.3 |

The pharmacokinetic characteristics of Compound 268 in the portal vein were similar to that of the systemic circulation (retro-orbital sinus). $C_{max}$, $T_{max}$, and AUC were not significantly different between the portal vein and systemic circulation, the observation is consistent with low absorption of the compound in the intestine, rather than fast first pass hepatic metabolism.

Example 91

Absorption Vs. First Pass Metabolism

In this study, we further examined the absorption as compared to first pass metabolism of the compounds of the present invention. ICR mice (Hilltop) were pre-treated with 1-aminobenzotriazole (ABT), a nonselective inhibitor of cytochrome P450 enzymes, to inhibit Cyp450-mediated degradation of the compounds in liver.

ABT was administered at 150 mg/kg in 5 mL/kg of 0.04% ethanol in 0.5% methyl cellulose (w/v) by oral gavage, 2 hours prior to test compound administration. The compounds (i.e., Compounds 56, 268, 249, 61, 126, and 199) were administered by oral gavage at 10 mg/kg in 10 mL/kg of 20% PEG400/80% (0.5% (w/v) CMC containing 0.25% (v/v) Tween 80) (v/v), 2 hours after the ABT treatment. Blood was collected via orbital bleeding at predose, 0.25, 0.5, 1, 2, and 4 hours post-dose and the quantification of compound levels in plasma was accomplished by means of LC-MS/MS analysis as described in Example 81. Reference compound "Propranolol" that is known to be metabolized by Cyp450 was used as a positive control.

Figure 15:
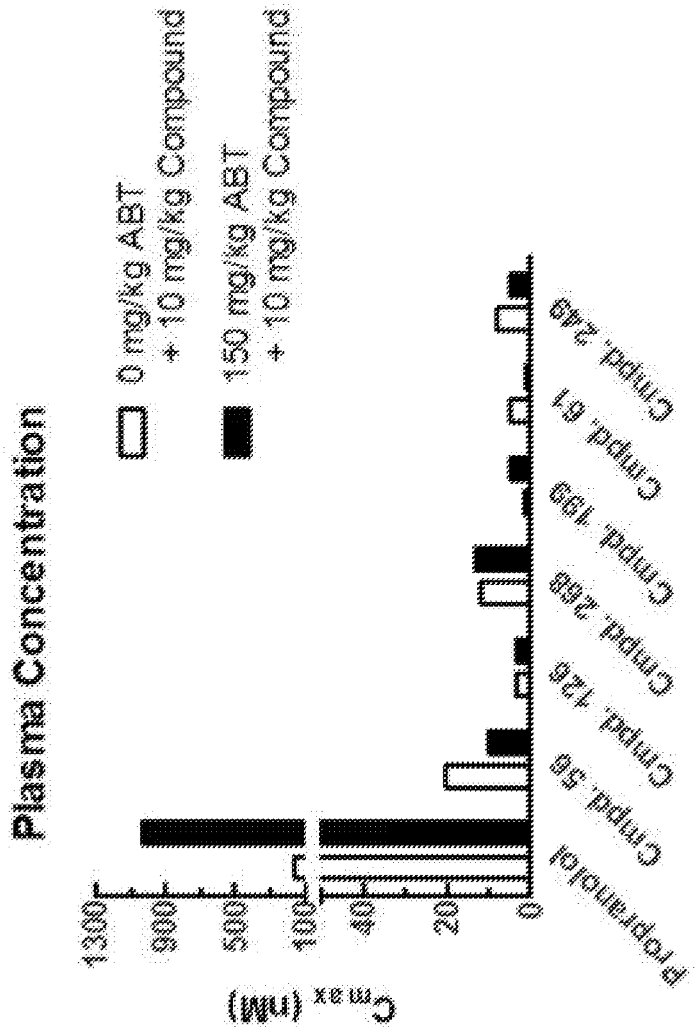
FIG. 15 depicts the $C_{max}$ (nM) of Compounds 56, 126, 268, 199, 61, and 249 (10 mg/kg) in ICR mice with and without 1-aminobenzotriazole pretreatment (150 mg/kg). Propranolol serves as a positive control.

FIG. 15 depicts the $C_{max}$ (nM) of the compounds of the present invention with and without ABT pre-treatment. As shown in FIG. 15, similar $C_{max}$ values were observed for the compounds of the present invention with or without ABT pre-treatment, indicating the lack of rapid Cyp450-mediated degradation of the compounds. In contrast, the $C_{max}$ value of the positive control propranolol was significantly higher in ABT pre-treated mice, as expected. All together, our data are consistent with the hypothesis that lower $C_{max}$ values exhibited by the compounds of the present invention are due to poor absorption in the intestine, rather than rapid degradation in the first pass metabolism.

Example 92

Comparison of PK in DIO Mice and Lean Mice

The PK characteristics of Compound 268 were examined in non-fasted lean C57BL/6N and DIO mice (Taconic). Compound 268 was orally administered to both groups at 10 mg/kg by oral gavage and plasma concentration of the compound was determined as described in Example 81. The data are summarized in Table 57.

TABLE 57

| DIO mice, Non-fasted PK (10 mg/kg, p.o.) | | Lean mice, Non-fasted PK (10 mg/kg, p.o.) | |
|---|---|---|---|
| $C_{max}$ (nM) | $T_{max}$ (h) | $C_{max}$ (nM) | $T_{max}$ (h) |
| 0.6 | 1 | 2.1 | 1.0 |

The data show similar low $C_{max}$ values for Compound 268 orally administered to lean mice as well as DIO mice. The results suggest the phenomenon of low plasma concentration of the compound does not depend on diet composition and animal adiposity.

In addition, PK parameters were determined for Compound 268 (i.e., $C_{max}$, $T_{max}$, and AUC) following oral administration in four groups of mice: (i) fasted lean mice; (ii) non-fasted lean mice; (iii) non-fasted DIO mice; and (iv) lean mice receiving ABT.

TABLE 58

| Study | Cmax (nM) | Tmax (h) | AUC (0→4 h) (ng/mL*h) |
|---|---|---|---|
| Fasted Lean | 12 | 0.25 | 18 |
| Non-fasted Lean | 2.1 | 1.0 | 2.9 |
| Non-fasted DIO | 0.57 | 1.0 | 0.76 |
| ABT (150 mg/kg) | 4.2 | 0.5 | 5.1 |

The data in Table 58 clearly show that Compound 268 has a low $C_{max}$ profile in lean and DIO mice, regardless the status of fasting or non-fasting. The ABT treatment confirms that the low $C_{max}$ value of Compound 268 is attributed to low absorption.

Example 93

Monitoring of Weight Loss after Multiple Weeks of Dosing Compounds

Compounds of the present invention were dosed for multiple weeks and were evaluated for their ability to cause mice to lose weight.

In the next series of studies (Examples 93-99), Male DIO mice were received at 12 weeks of age (from Taconic), and were single-housed at the testing facility and acclimated for at least 2 weeks. The mice were provided a high fat diet [Research Diet D12492 (60% Fat kcal)] while in the testing facility. Before the study initiation, the animals were randomized into 5 experimental groups by body weight. The vehicle group contained only 0.5% carboxymethylcellulose (medium viscosity)+0.25% Tween-80. The second group contained 10 mg/kg of the DPP-IV inhibitor Sitagliptin while the third group contained 30 mg/kg Compound 268. The fourth group contained the combination of 10 mg/kg Sitagliptin and 30 mg/kg Compound 268. The fifth group was the positive control for weight loss, Rimonabant. All mice were dosed BID at approximately 6:00 am and again at approximately 4:00 pm. The positive control rimonabant was administered at a dose of 10 mg/kg in the afternoon and the morning dosing was vehicle (no compound).

Figure 16:
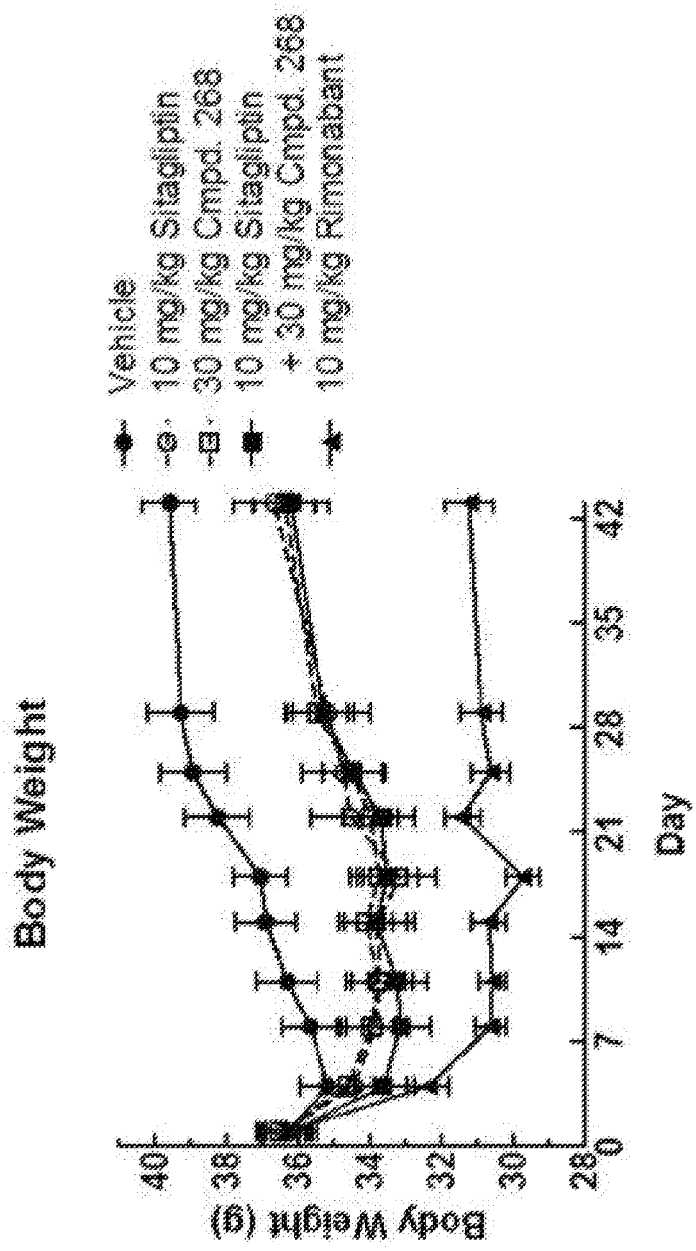
FIG. 16 depicts the body weight changes over 42 days in DIO mice receiving twice a day oral administration of vehicle, Compound 268 (30 mg/kg), sitagliptin (10 mg/kg), or Compound 268 (30 mg/kg)+sitagliptin (10 mg/kg). Rimonabant (10 mg/kg once a day) serves at the positive control.

Compounds of the present invention were evaluated for their ability to cause mice to lose weight. Mice were dosed compounds for 6 weeks and body weights were recorded twice a week. FIG. 16 shows that Compound 268 was able to produce a modest weight loss in the mice.

Example 94

Monitoring of Food Intake after Multiple Weeks of Dosing Compounds

Compounds of the present invention were dosed for multiple weeks and were evaluated for their ability to cause mice to have a lower food intake. Mice were dosed with compounds for 6 weeks as per the protocol in Example 93.

Figure 17:
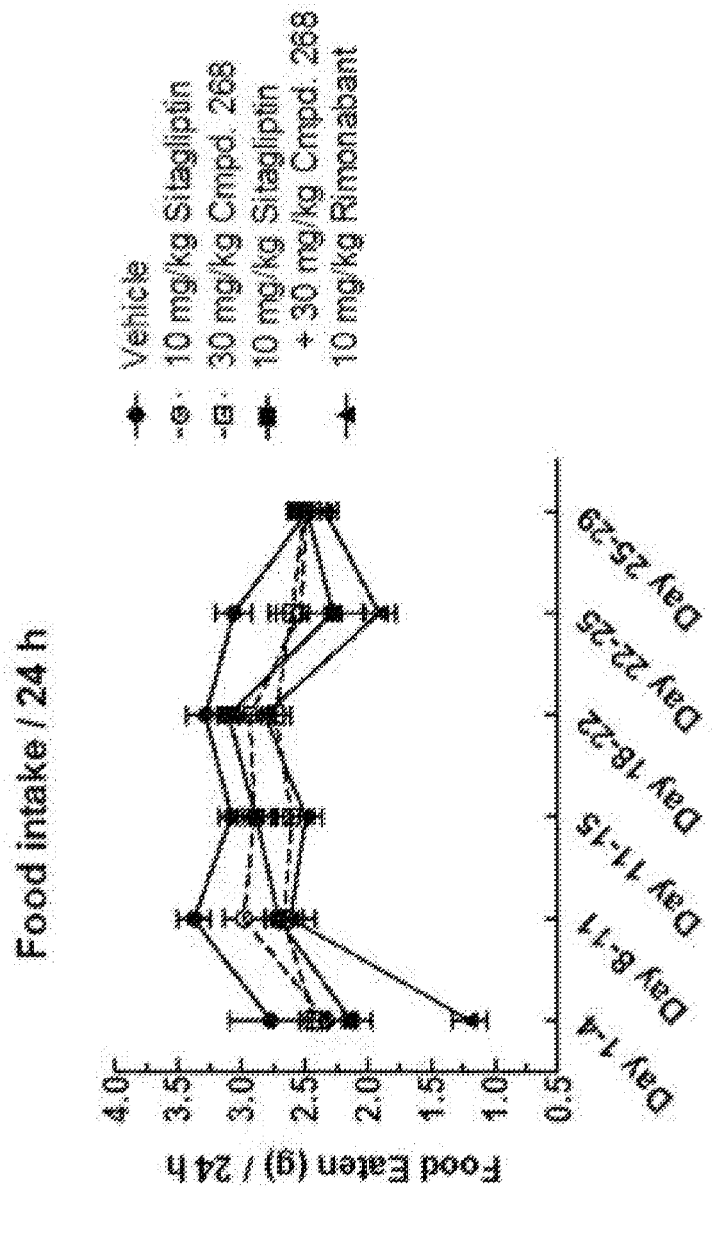
FIG. 17 depicts the food intake over multiple weeks in DIO mice receiving twice a day oral administration of vehicle, Compound 268 (30 mg/kg), sitagliptin (10 mg/kg), or Compound 268 (30 mg/kg)+sitagliptin (10 mg/kg). Rimonabant (10 mg/kg once a day) serves at the positive control.

The HFD (Research Diets, D12492, 60% fat kcal) was placed at the bottom of the cage on a singly-housed animal. The remaining food in each cage was recovered and weighed again at the same time of day 3 or 4 days later. The difference in the starting and ending food weight represents the amount of food consumed. Daily food intake is calculated by averaging over a 3 or 4 day period every week. FIG. 17 shows that Compound 268 had a minor, but steady effect on food intake similar to that seen in sitagliptin.

Example 95

OGTT and Insulin Measurements after Multiple Weeks of Dosing Compounds

Compounds of the present invention were dosed for multiple weeks and were evaluated for their effectiveness in glycemic control. Utilizing the protocol from Example 93, an OGTT experiment was conducted after 5 weeks of dosing compounds. Following an overnight fast, a baseline blood glucose measurement was taken (time=0). Immediately following this, mice were gavaged with 2 g/kg of glucose. Blood glucose measurements were subsequently conducted at 15, 30, 60, and 120 min following glucose gavage via tail tip by hand-held glucometer (One-touch Ultra II, Johnson & Johnson). OGTT was conducted over 3 days to test all mice with groups being tested evenly distributed over those days. The OGTT experiments began 4 hours after most recent dose. Plasma was also collected at each time point and prepared for insulin measurements. Insulin is also analyzed using Meso Scale Discovery according to the manufacturer's directions (item number K152BZC). Plasma samples (104) were loaded in duplicate onto the assay plate and measured against internal standards.

Figure 18:
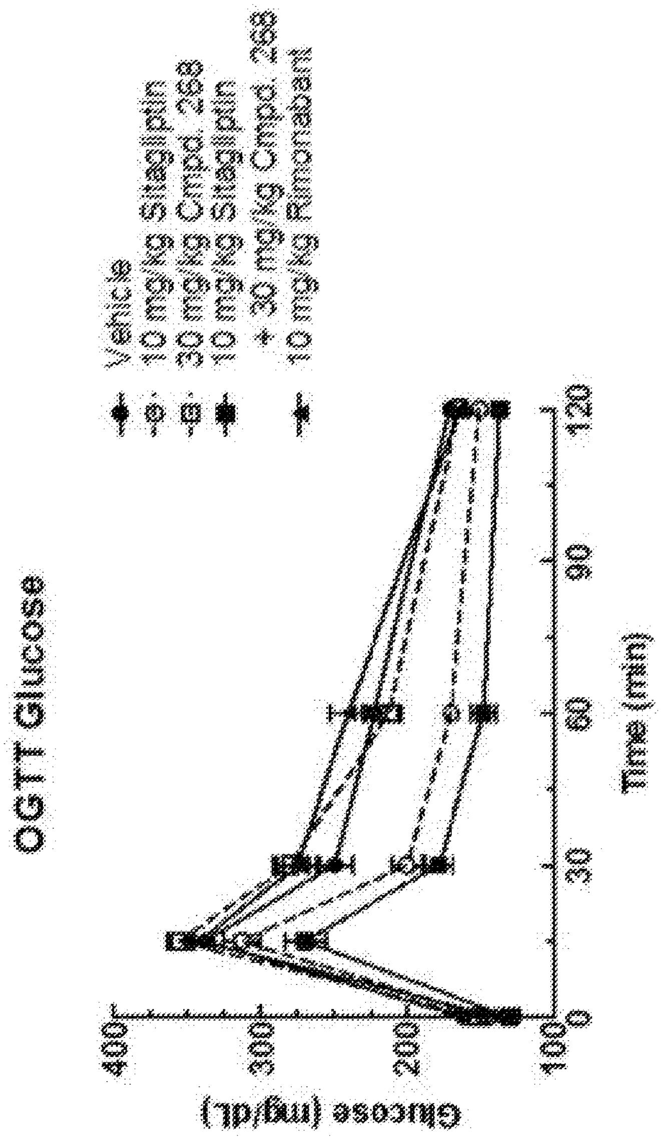
FIG. 18 depicts the glucose levels in an OGTT experiment in DIO mice conducted after 5 weeks receiving twice a day oral administration of vehicle, Compound 268 (30 mg/kg), sitagliptin (10 mg/kg), or Compound 268 (30 mg/kg)+ sitagliptin (10 mg/kg). Rimonabant (10 mg/kg once a day) serves at the positive control.
Figure 19:
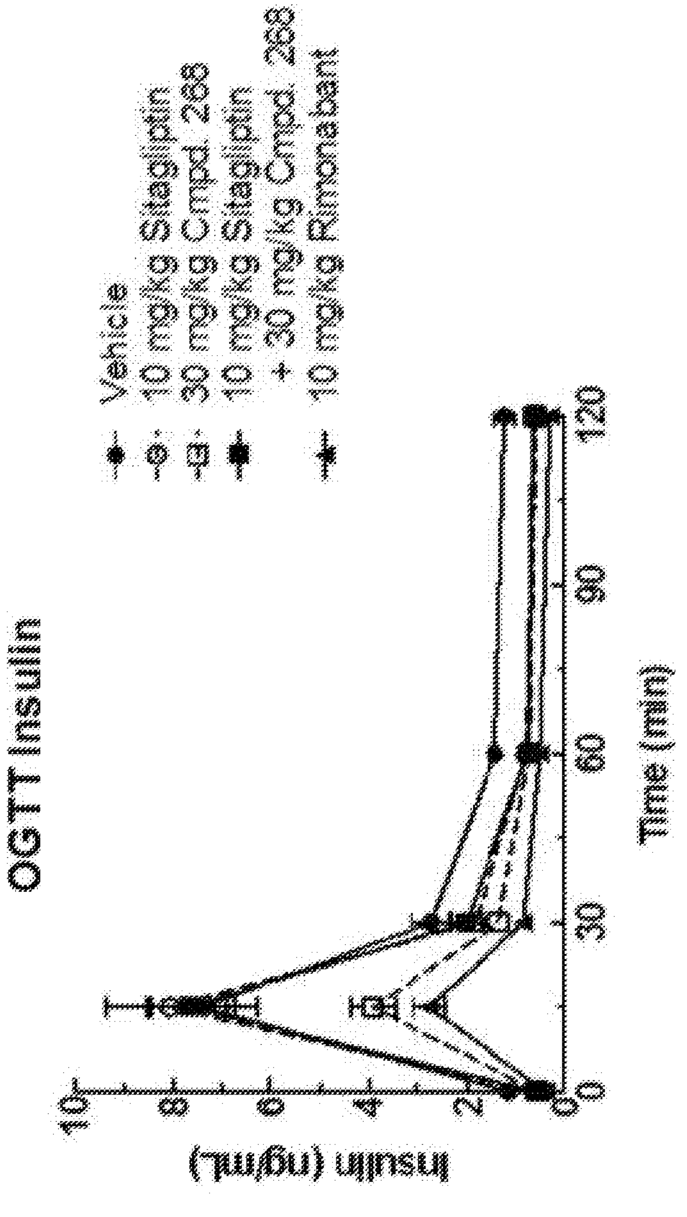
FIG. 19 depicts the insulin levels in an OGTT experiment in DIO mice conducted after 5 weeks receiving twice a day oral administration of vehicle, Compound 268 (30 mg/kg), sitagliptin (10 mg/kg), or Compound 268 (30 mg/kg)+ sitagliptin (10 mg/kg). Rimonabant (10 mg/kg once a day) serves at the positive control.

FIG. 18 shows that Compound 268 of the present invention in the presence of the DPP-IV inhibitor sitagliptin reduced the glucose levels relative to vehicle after 5 weeks of dosing compounds. FIG. 19 shows that the Compound 268 has an increased the sensitivity of the mice to insulin in that a much lower amount of insulin was required to handle the glucose load in the body.

Example 96

6-Week Dexa Analysis after Multiple Weeks of Dosing Compounds

Compounds of the present invention were dosed for multiple weeks and the mice were analyzed to determine whether weight loss seen in Example 93 was due to a loss in fat or lean mass.

In this example, the protocol from Example 93 was utilized. The day of experiment, the mice were anesthetized using 2.5% avertin [tert-amyl alcohol (Aldrich #15,256-3) and 2,2,2-tribromoethanol (Aldrich # T4, 840-2)]. Their body composition was assessed using the PIXImus2 X-ray unit (GE Lunar Corporation, Madison, Wis.) connected to a computer equipped with LUNAR PIXImus2 software. The head region of each mouse was excluded from the analysis. The following measurements were automatically measured or calculated by the PIXImus2 software: bone mineral density (BMD), bone mineral content (BMC), bone area (B Area), tissue area (T Area), percent fat, and total tissue mass (TTM). Fat mass, the percentage of lean mass, and lean mass, were calculated manually as follows:

% Lean=100−% Fat

Lean Mass=TTM×(100−% Fat)

Fat Mass=TTM×% Fat

Figure 20:
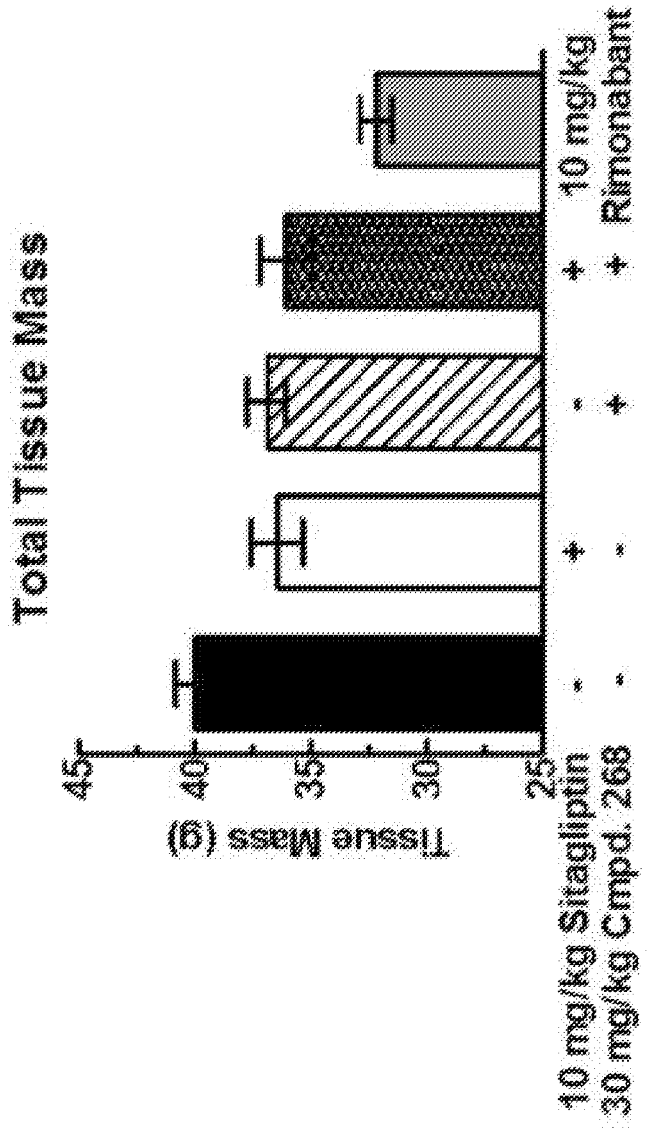
FIG. 20 depicts the total tissue mass of DIO mice after 6 weeks of receiving twice a day oral administration of vehicle, Compound 268 (30 mg/kg), sitagliptin (10 mg/kg), or Compound 268 (30 mg/kg)+sitagliptin (10 mg/kg). Rimonabant (10 mg/kg once a day) serves at the positive control.
Figure 21:
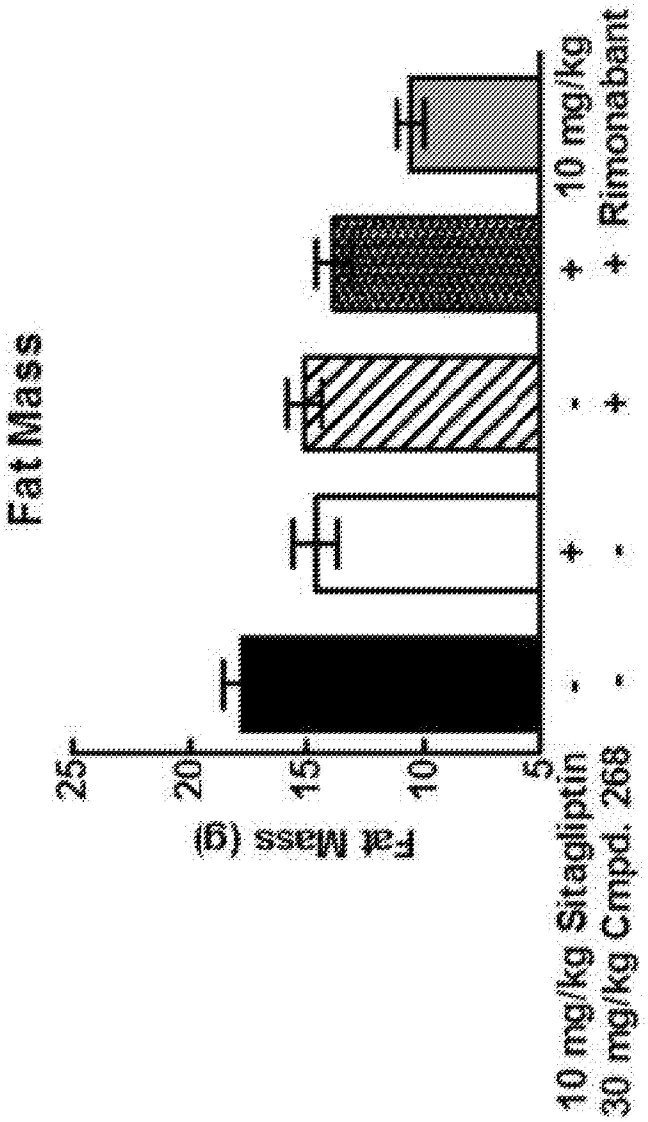
FIG. 21 depicts the fat mass of DIO mice after 6 weeks of receiving twice a day oral administration of vehicle, Compound 268 (30 mg/kg), sitagliptin (10 mg/kg), or Compound 268 (30 mg/kg)+sitagliptin (10 mg/kg). Rimonabant (10 mg/kg once a day) serves at the positive control.
Figure 22:
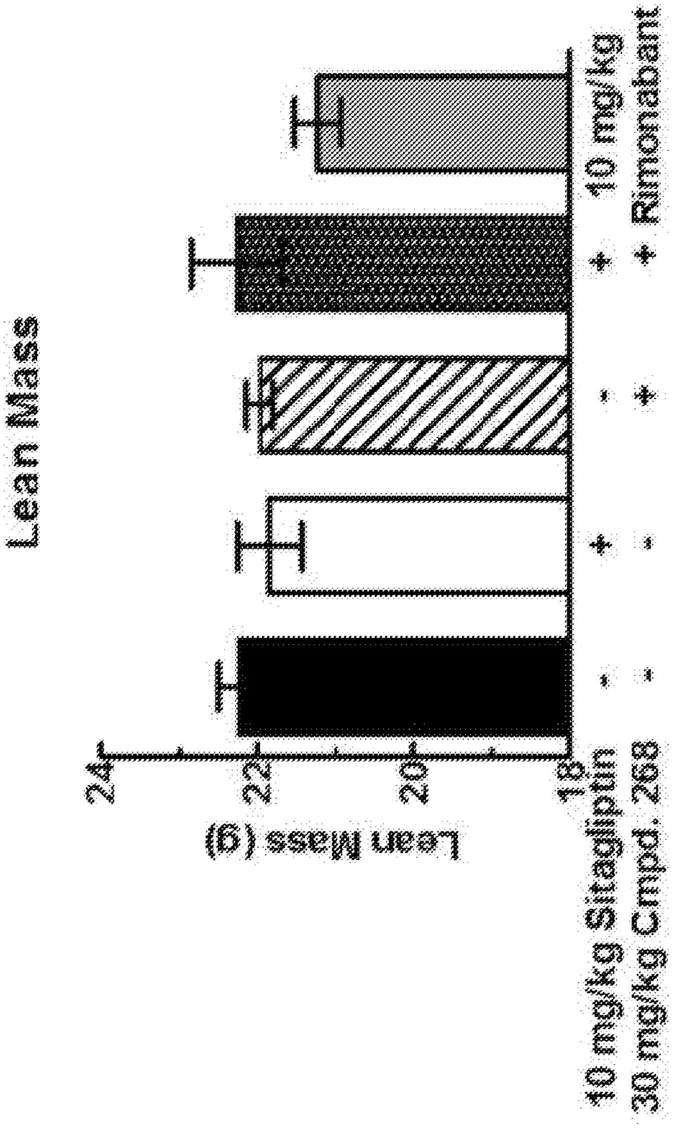
FIG. 22 depicts the lean mass of DIO mice after 6 weeks of receiving twice a day oral administration of vehicle, Compound 268 (30 mg/kg), sitagliptin (10 mg/kg), or Compound 268 (30 mg/kg)+sitagliptin (10 mg/kg). Rimonabant (10 mg/kg once a day) serves at the positive control.

The DPP-IV inhibitor sitagliptin and Compound 268 of the present invention produced about the same loss in weight at the time of experiment (FIG. 16) as also observed in the total tissue mass FIG. 20. FIGS. 21 and 22 demonstrate that the observed weight loss was due to a loss in the Fat Mass.

Example 97

GLP-1 Levels after Multiple Weeks of Dosing Compounds

Compounds of the present invention were dosed for multiple weeks and were evaluated to determine if they produce sustained GLP-1 levels.

In this example, the protocol from Example 93 was utilized. In week 6 of the study, mice were euthanized and blood was collected 6 hours after the final dose of compound. For the GLP-1 assay, 200-250 μL of blood was placed in an EDTA $K^{2+}$ tube containing 5 μL of 40 mg/mL aprotinin (Sigma A1153) and 1 μL of 10 mM sitagliptin (Sigma 58576) and plasma was separated by centrifugation. Plasma samples were stored at −20° C. until analysis. The active form of GLP-1 [GLP-1 (7-36) amide] was analyzed using Meso Scale Discovery System according to the manufacturer's directions (item number K150HYC). Values of $p<0.05$ are considered statistically significant.

Figure 23:
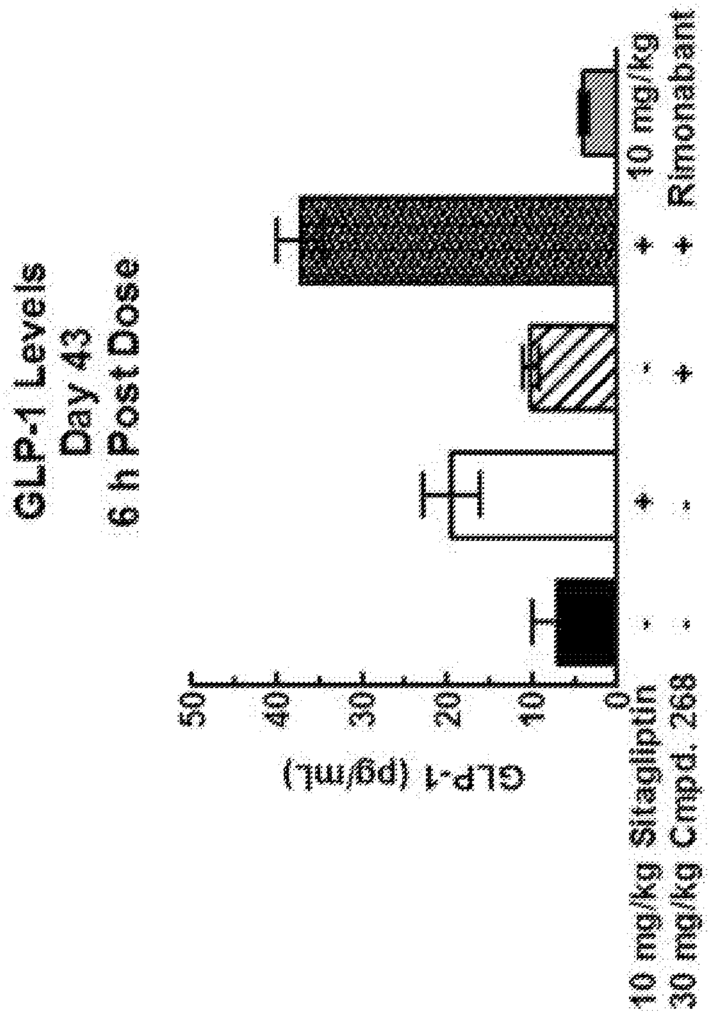
FIG. 23 depicts the GLP-1 elevation in DIO mice after 43 days of receiving twice a day oral administration of vehicle, Compound 268 (30 mg/kg), sitagliptin (10 mg/kg), or Compound 268 (30 mg/kg)+sitagliptin (10 mg/kg). Rimonabant (10 mg/kg once a day) serves at the positive control.

FIG. 23 depicts the GLP-1 plasma level increase following oral administration of Compound 268 in DIO mice. Mice treated with Compound 268 (in combination with sitagliptin) exhibited a significantly increased level of GLP-1 as compared to the mice treated with sitagliptin alone. Note that similar GLP-1 levels were observed after the second and the tenth treatment. These data indicate that chronic dosing of compounds increases GLP-1 levels and shows no evidence of desensitization after 6 weeks of dosing compounds.

Example 98

Low Compound Concentration Levels in Plasma after Multiple Weeks of Dosing Compounds Compounds of the present invention were dosed for multiple weeks and evaluated for plasma concentration of the compounds at the time mice were euthanized.

In this example, the protocol from Example 93 was utilized. In week 6 of the study, mice were euthanized and blood was collected 6 hours after the final dose of compound. The collected blood (200-250 μL) was placed in an EDTA $K^{2+}$ tube containing 5 μL of 40 mg/mL aprotinin (Sigma A1153) and 1 μL of 10 mM sitagliptin (Sigma S8576) and plasma was separated by centrifugation. Plasma samples were stored at −20° C. until analysis. The plasma measurements were performed as described in Example 81.

Figure 24:
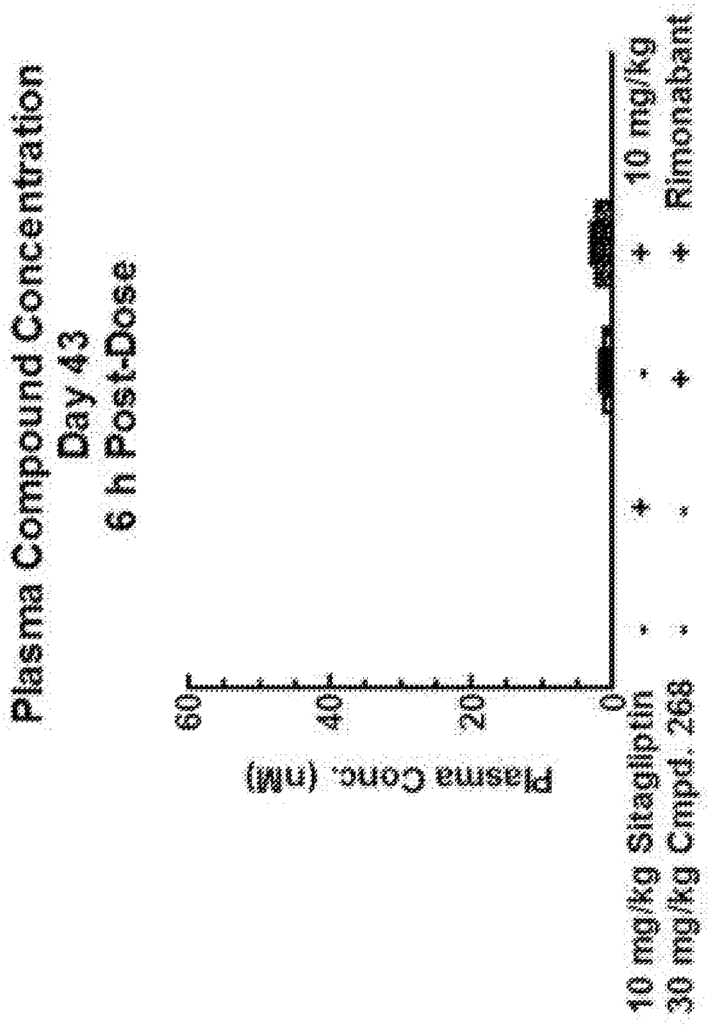
FIG. 24 depicts the plasma concentration of Compound 268 in DIO mice after 43 days of receiving twice a day oral administration of vehicle, Compound 268 (30 mg/kg), sitagliptin (10 mg/kg), or Compound 268 (30 mg/kg)+sitagliptin (10 mg/kg). Rimonabant (10 mg/kg once a day) serves at the positive control.

FIG. 24 shows the results and that the compound concentration in the blood is low. Overall, the results indicate that the compounds of the present invention are consistent with non-systemic TGR5 agonists.

Example 99

No Bile Weight Increase after 6 Weeks of Dosing Compounds

Compounds of the present invention were dosed for multiple weeks and were evaluated to determine if they lead to an increase in bile weight.

In this example, the protocol from Example 93 was utilized. In week 6 of the study, mice were euthanized and bile was removed from the gallbladder about 6 hours after the final dose and the bile was weighed to approximate volume of bile contained within the bladder.

Figure 25:
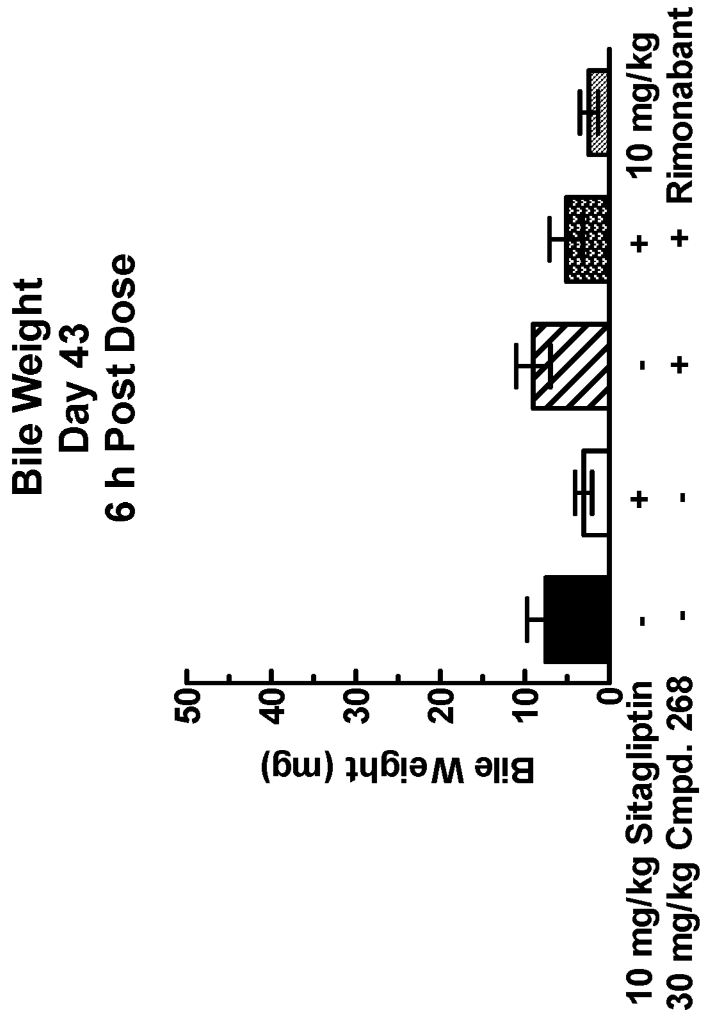
FIG. 25 depicts the bile weight change in DIO mice after 43 days of receiving twice a day oral administration of vehicle, Compound 268 (30 mg/kg), sitagliptin (10 mg/kg), or Compound 268 (30 mg/kg)+sitagliptin (10 mg/kg). Rimonabant (10 mg/kg once a day) serves at the positive control.

FIG. 25 depicts that the gallbladder does not show an increase in size even after 6 weeks of dosing Compound 268. These results indicate that the compounds of the present invention are consistent with non-systemic TGR5 agonists.

All references to the literature and all patents mentioned in this specification are incorporated herein by reference in their entirety. The present invention is not to be limited in terms of the particular embodiments described in this application, which are intended as single illustrations of individual aspects of the present invention. Functionally equivalent pharmaceutical compositions and methods of treatment within the scope of the present invention, in addition to those enumerated herein, will be apparent to those skilled in the art from the foregoing description. Such modifications and variations are intended to fall within the scope of the appended claims.

What is claimed is:

1. A compound of formula (I)

(I)

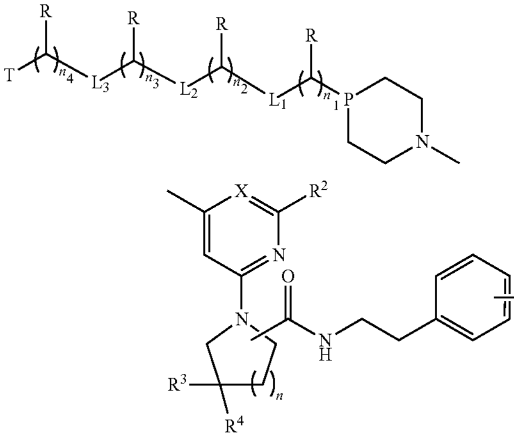

or a pharmaceutically acceptable salt thereof, wherein:

each $R^1$ is independently CN, $C_{1-6}$alkyl, pyridyl, or $C_{1-6}$alkoxy, wherein alkyl group is optionally further substituted with 1-4 halogen;

m is 0, 1, 2 or 3;

$R^2$ is $C_{1-6}$alkyl or H, wherein alkyl group is optionally further substituted with 1-4 halogen;

X is CH or N;

P is CH or N;

$L_1$, $L_2$ and $L_3$ are each independently absent,

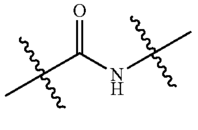, 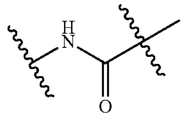,

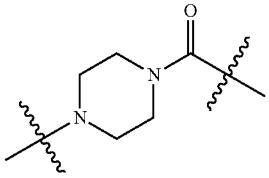,

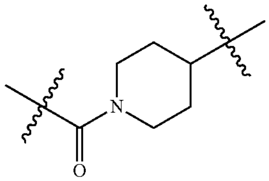,

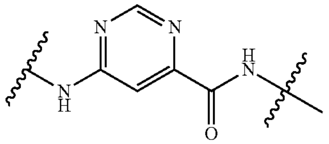,

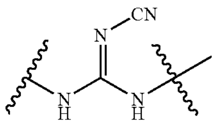,

-continued

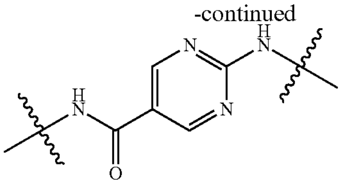,

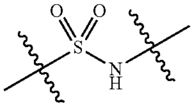, 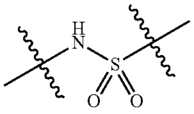,

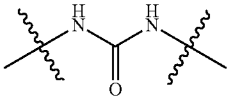,

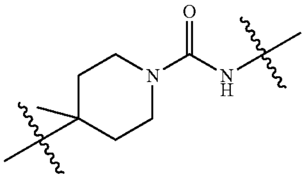,

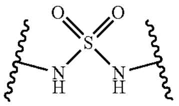, 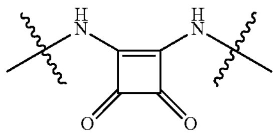,

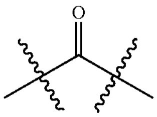, 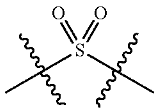,

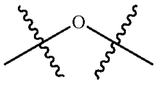, 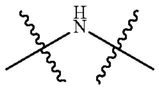,

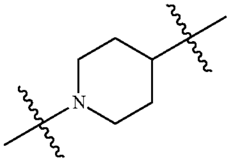, or 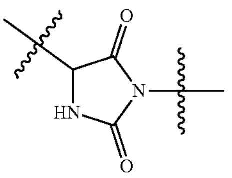, wherein N is optionally further substituted with $C_{1-3}$alkyl;

$n_1$, $n_2$, $n_3$ and $n_4$ are each independently 0, 1, 2, 3, 4 or 5, and when $L_1$ is absent, $n_2$ is 0, when $L_2$ is absent, $n_3$ is 0, when $L_3$ is absent, $n_4$ is 0, with the proviso that when $L_1$, $L_2$ and $L_3$ are all absent, $n_1$ cannot be 0;

each R is independently H, OH, $NH_2$, COOH, $C_{1-6}$alkylCOOH, $COOC_{1-6}$alkyl, $C_{1-6}$ alkylOH or $C_{1-6}$ alkylNHC(NH)$NH_2$;

T is

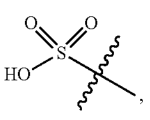, 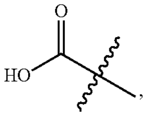, 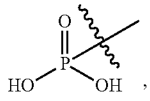,

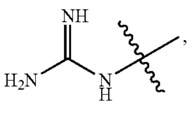, 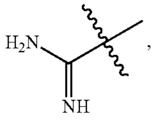,

-continued
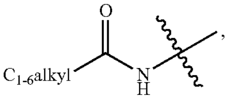
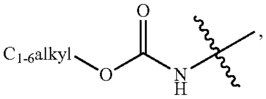
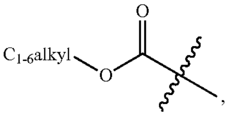
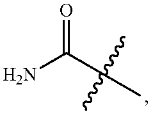
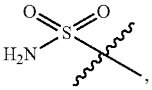
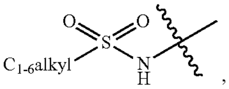
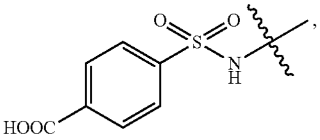
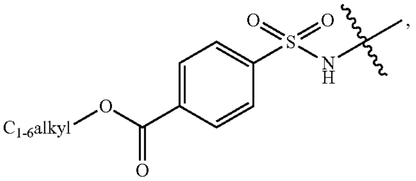
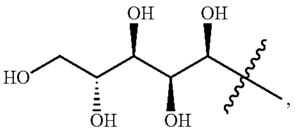
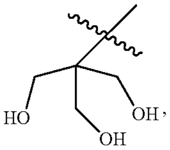
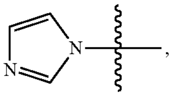
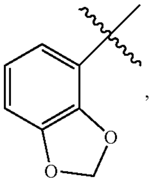
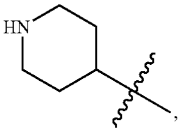
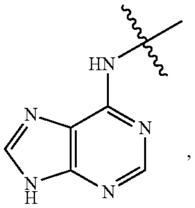
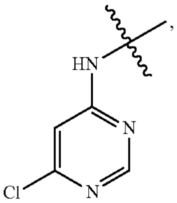
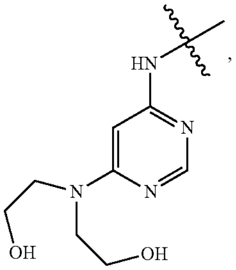
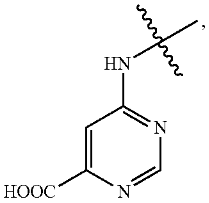
-continued
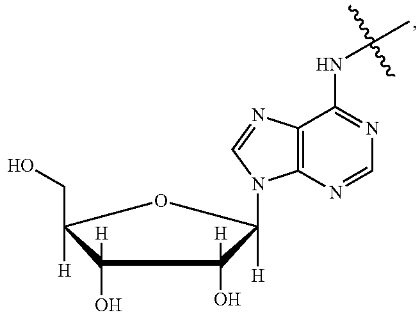
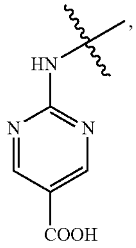
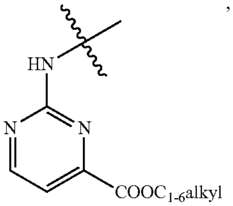
CN, OH, $NH_2$ or $OCH_3$, wherein N is optionally further substituted with $C_{1-3}$ alkyl;
$R^3$ and $R^4$ are each independently H, OH, halogen, $N(CH_3)_2$ or $NH_2$; and
n is 0, 1 or 2.
2. The compound of claim 1, or a pharmaceutically acceptable salt thereof, wherein:
$L_3$ is absent, and $L_1$ and $L_2$ are each independently
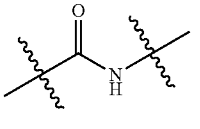
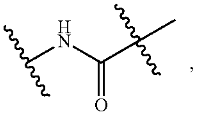
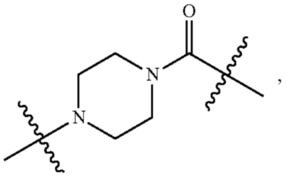
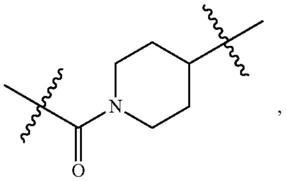
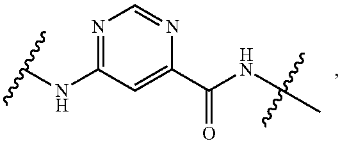
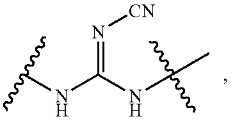

-continued
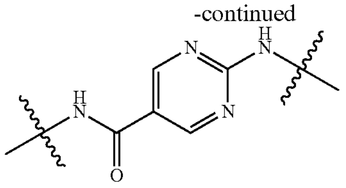,
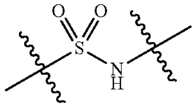, 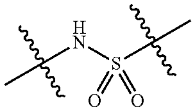,
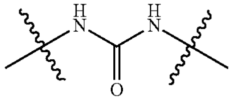,
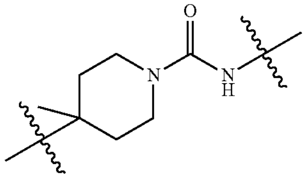,
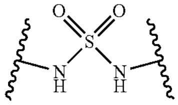, 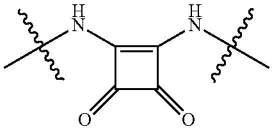,
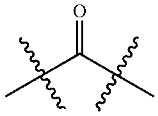, 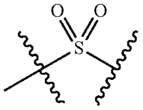,
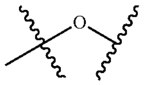, 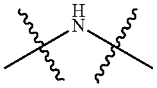,
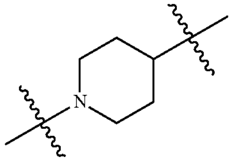, or 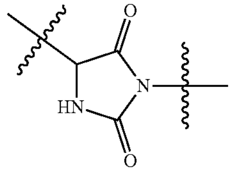.
3. The compound of claim 1, or a pharmaceutically acceptable salt thereof, wherein:
$L_3$ is absent, and $L_1$ and $L_2$ are each independently
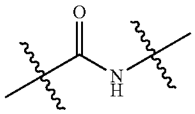, 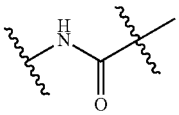,
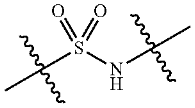, 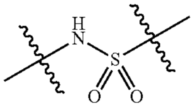,
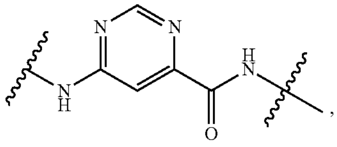,
-continued
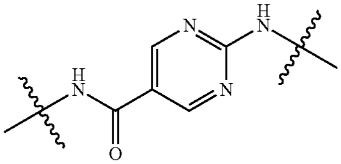,
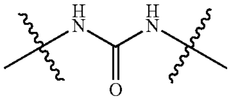, or 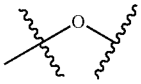.
4. The compound of claim 1, or a pharmaceutically acceptable salt thereof, wherein:
$L_2$ and $L_3$ are absent, and $L_1$ is
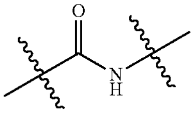, 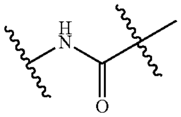,
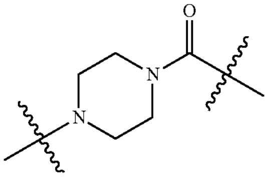,
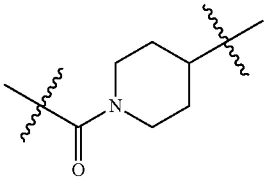,
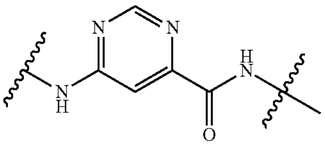,
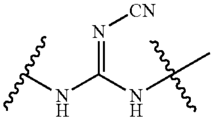,
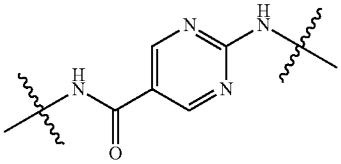,
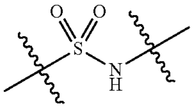, 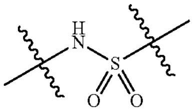,
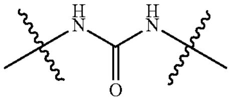, -continued
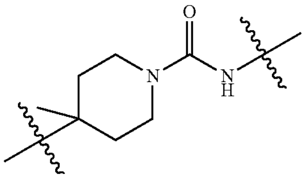,
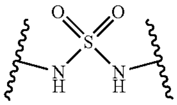, 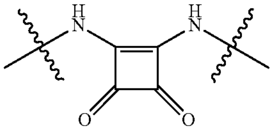,
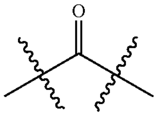, 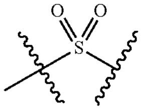,
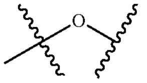, 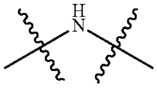,
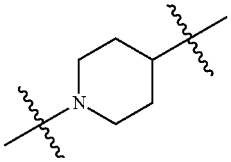, or 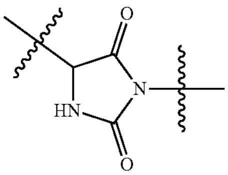.
5. The compound of claim 1, or a pharmaceutically acceptable salt thereof, wherein:
$L_2$ and $L_3$ are absent, and $L_1$ is
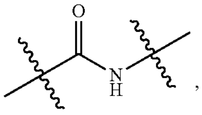, 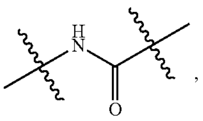,
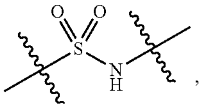, 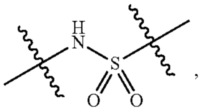,
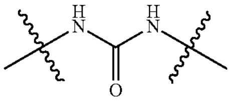,
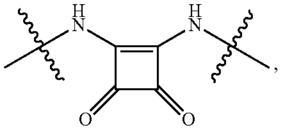, or
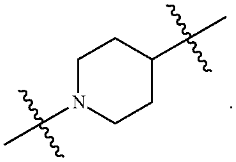.
6. The compound of claim 1, or a pharmaceutically acceptable salt thereof, wherein:
T is
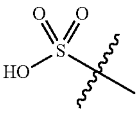, 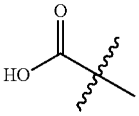, 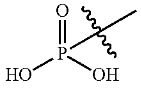,
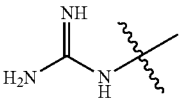, 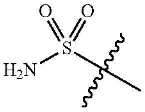,
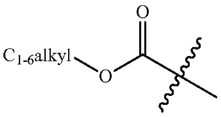,
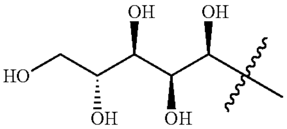, 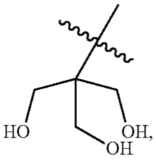,
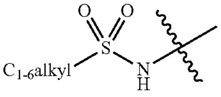, 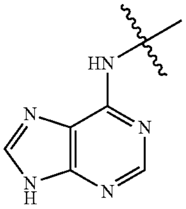,
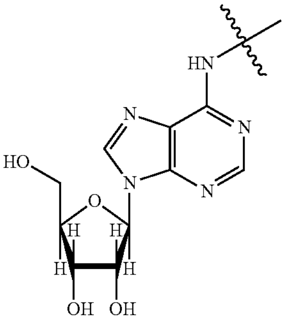, 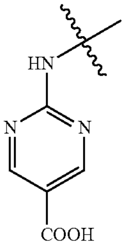,
or $NH_2$.
7. The compound of claim 1, or a pharmaceutically acceptable salt thereof, wherein:
T is
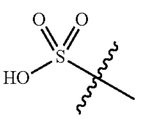, 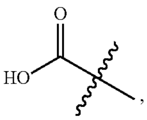, 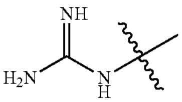,
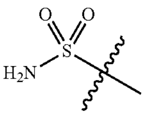, 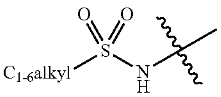, -continued

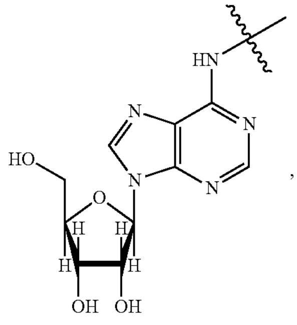

, or $NH_2$.

8. The compound of claim 1, or a pharmaceutically acceptable salt thereof, wherein n is 0, and phenethylcarboxamide is substituted in the two position of N in the azetidinyl ring.

9. The compound of claim 1, or a pharmaceutically acceptable salt thereof, wherein n is 1, and phenethylcarboxamide is substituted in the two position of N in the pyrrolidinyl ring.

10. The compound of claim 1, or a pharmaceutically acceptable salt thereof, wherein n is 2, and phenethylcarboxamide is substituted in the three position of N in the piperidinyl ring.

11. The compound of claim 1, or a pharmaceutically acceptable salt thereof, wherein $R^1$ is $CF_3$ or CN, and it is substituted in the para position of phenethyl ring.

12. A compound selected from:

1) (S)—N-(4-cyanophenethyl)-1-(6-(4-(hydroxymethyl) piperidin-1-yl)-2-(trifluoromethyl)pyrimidin-4-yl)pyrrolidine-2-carboxamide;

2) (S)-1-(6-(4-(hydroxymethyl)piperidin-1-yl)-2-(trifluoromethyl) pyrimidin-4-yl)-N-(4-(trifluoromethyl)-phenethyl)pyrrolidine-2-carboxamide;

3) (S)-1-(6-(4-(2-(dimethylamino)ethyl)piperidin-1-yl)-2-(trifluoromethyl) pyrimidin-4-yl)-N-(4-(trifluoromethyl)phenethyl)-pyrrolidine-2-carboxamide;

4) (S)-tert-butyl (2-(1-(2-(trifluoromethyl)-6-(2-((4-(trifluoromethyl)phenethyl) carbamoyl)pyrrolidin-1-yl)pyrimidin-4-yl)piperidin-4-yl)ethyl)carbamate;

5) (S)-1-(6-(4-(2-hydroxyethyl)piperidin-1-yl)-2-(trifluoromethyl)pyrimidin-4-yl)-N-(4-(trifluoromethyl)phenethyl)-pyrrolidine-2-carboxamide;

6) (S)-1-(6-(4-(methoxymethyl)piperidin-1-yl)-2-(trifluoromethyl)pyrimidin-4-yl)-N-(4-(trifluoromethyl)phenethyl)-pyrrolidine-2-carboxamide;

7) (S)-4-(1-(2-(trifluoromethyl)-6-(2-((4-(trifluoromethyl)phenethyl)carbamoyl) pyrrolidin-1-yl)pyrimidin-4-yl)piperidin-4-yl)butanoic acid;

8) (S)-1-(6-(4-(2-cyanoethyl)piperazin-1-yl)-2-(trifluoromethyl)pyrimidin-4-yl)-N-(4-(trifluoromethyl)-phenethyl)pyrrolidine-2-carboxamide;

9) (S)-1-(6-(4-(2-cyanoethyl)piperidin-1-yl)-2-(trifluoromethyl)pyrimidin-4-yl)-N-(4-(trifluoromethyl)phenethyl)-pyrrolidine-2-carboxamide;

10) (S)-tert-butyl ((1-(6-(2-((4-cyanophenethyl)carbamoyl)pyrrolidin-1-yl)-2-(trifluoromethyl)pyrimidin-4-yl)piperidin-4-yl)methyl)carbamate;

11) (S)-tert-butyl (2-(1-(6-(2-((4-cyanophenethyl)carbamoyl)pyrrolidin-1-yl)-2-(trifluoromethyl)pyrimidin-4-yl)piperidin-4-yl)ethyl)carbamate;

12) (S)—N-(4-cyanophenethyl)-1-(6-(4-((dimethyl amino)methyl)piperidin-1-yl)-2-(trifluoromethyl)pyrimidin-4-yl)pyrrolidine-2-carboxamide;

13) (S)-tert-butyl ((1-(6-(2-((4-cyanophenethyl)carbamoyl)pyrrolidin-1-yl)-2-(trifluoromethyl)pyrimidin-4-yl)piperidin-4-yl)methyl)(methyl)carbamate;

14) (S)—N-(4-cyanophenethyl)-1-(6-(4-(2-(dimethylamino)ethyl)piperidin-1-yl)-2-(trifluoromethyl)pyrimidin-4-yl)pyrrolidine-2-carboxamide;

15) (S)—N-(4-cyanophenethyl)-1-(6-(4-(2-hydroxyethyl) piperidin-1-yl)-2-(trifluoromethyl)pyrimidin-4-yl)pyrrolidine-2-carboxamide;

16) (S)—N-(4-cyanophenethyl)-1-(6-(4-(3-hydroxypropyl)piperidin-1-yl)-2-(trifluoromethyl)pyrimidin-4-yl) pyrrolidine-2-carboxamide;

17) (S)—N-(4-cyanophenethyl)-1-(6-(4-(methoxymethyl)piperidin-1-yl)-2-(trifluoromethyl)pyrimidin-4-yl)pyrrolidine-2-carboxamide;

18) (S)—N-(4-cyanophenethyl)-1-(6-(4-(2-methoxyethyl)piperidin-1-yl)-2-(trifluoromethyl)pyrimidin-4-yl)pyrrolidine-2-carboxamide;

19) (S)-2-(1-(6-(2-((4-cyanophenethyl)carbamoyl)pyrrolidin-1-yl)-2-(trifluoromethyl)pyrimidin-4-yl)piperidin-4-yl)acetic acid;

20) (S)-3-(1-(6-(2-((4-cyanophenethyl)carbamoyl)pyrrolidin-1-yl)-2-(trifluoromethyl)pyrimidin-4-yl)piperidin-4-yl)propanoic acid;

21) (S)-4-(1-(6-(2-((4-cyanophenethyl)carbamoyl)pyrrolidin-1-yl)-2-(trifluoromethyl)pyrimidin-4-yl)piperidin-4-yl)butanoic acid;

22) (S)—N-(4-cyanophenethyl)-1-(6-(4-(2-(dimethylamino)ethyl)piperazin-1-yl)-2-(trifluoromethyl)pyrimidin-4-yl)pyrrolidine-2-carboxamide;

23) (S)—N-(4-cyanophenethyl)-1-(6-(4-(2-hydroxyethyl) piperazin-1-yl)-2-(trifluoromethyl)pyrimidin-4-yl)pyrrolidine-2-carboxamide;

24) (S)-1-(6-(4-(2-cyanoethyl)piperazin-1-yl)-2-(trifluoromethyl)pyrimidin-4-yl)-N-(4-cyanophenethyl)pyrrolidine-2-carboxamide;

25) (S)-1-(6-(4-(2-cyanoethyl)piperidin-1-yl)-2-(trifluoromethyl)pyrimidin-4-yl)-N-(4-cyanophenethyl)pyrrolidine-2-carboxamide;

26) (S)-4-(1-(6-(2-((2-methoxy-4-(trifluoromethyl)phenethyl)carbamoy)pyrrolidin-1-yl)-2-(trifluoromethyl)-pyrimidin-4-yl)piperidin-4-yl)butanoic acid;

27) (S)-4-(1-(6-(2-((2,4-dichlorophenethyl)carbamoyl) pyrrolidin-1-yl)pyrimidin-4-yl)piperidin-4-yl)butanoic acid;

28) (S)—N-(4-cyanophenethyl)-1-(6-(4-(hydroxymethyl) piperidin-1-yl)-2-methylpyrimidin-4-yl)pyrrolidine-2-carboxamide;

29) (S)—N-(4-cyanophenethyl)-1-(4-(4-(hydroxymethyl) piperidin-1-yl)-6-(trifluoromethyl)pyridine-2-yl)pyrrolidine-2-carboxamide;

30) (S)-1-(6-(4-(aminomethyl)piperidin-1-yl)-2-(trifluoromethyl)pyrimidin-4-yl)-N-(4-cyanophenethyl)pyrrolidine-2-carboxamide;

31) (S)—N-(4-cyanophenethyl)-1-(6-(3-oxopiperazin-1-yl)-2-(trifluoromethyl) pyrimidin-4-yl)pyrrolidine-2-carboxamide;

32) (S)-1-(6-(4-(2-aminoethyl)piperidin-1-yl)-2-(trifluoromethyl)pyrimidin-4-yl)-N-(4-cyanophenethyl)pyrrolidine-2-carboxamide;

33) (S)-1-(6-(4-(acetamidomethyl)piperidin-1-yl)-2-(trifluoromethyl)pyrimidin-4-yl)-N-(4-cyanophenethyl) pyrrolidine-2-carboxamide;

34) (S)—N-(4-cyanophenethyl)-1-(6-(4-((N-methylacetamido)methyl)piperidin-1-yl)-2-(trifluoromethyl)pyrimidin-4-yl)pyrrolidine-2-carboxamide;

35) (S)-ethyl 3-(3-(2-(1-(6-(2-((4-cyanophenethyl)carbamoyl)pyrrolidin-1-yl)-2-(trifluoromethyl)pyrimidin-4-yl)piperidin-4-yl)ethyl)ureido)propanoate;

36) (S)-2-(3-(1-(6-(2-((4-cyanophenethyl)carbamoyl)pyrrolidin-1-yl)-2-(trifluoromethyl)pyrimidin-4-yl)piperidin-4-yl)propanamido)ethanesulfonic acid;

37) (S)-2-(4-(1-(6-(2-((2-methoxy-4-(trifluoromethyl)phenethyl)carbamoyl)-pyrrolidin-1-yl)-2-(trifluoromethyl)-pyrimidin-4-yl)piperidin-4-yl) butanamido)ethanesulfonic acid;

38) (S)-2-(4-(1-(2-(trifluoromethyl)-6-(2-((4-(trifluoromethyl)phenethyl)-carbamoyl)-pyrrolidin-1-yl)-pyrimidin-4-yl)piperidin-4-yl) butanamido)ethanesulfonic acid;

39) (S)-1-(6-(4-(4-oxo-4-((2-sulfamoylethyl)amino)butyl)piperidin-1-yl)-2-(trifluoromethyl)pyrimidin-4-yl)-N-(4-(trifluoromethyl)phenethyl)-pyrrolidine-2-carboxamide;

40) (S)-3-(4-(1-(2-(trifluoromethyl)-6-(2-((4-(trifluoromethyl)phenethyl) carbamoyl)pyrrolidin-1-yl)pyrimidin-4-yl)piperidin-4-yl)butanamido)propane-1-sulfonic acid;

41) (S)-2-(4-(1-(6-(2-((4-cyanophenethyl)carbamoyl)pyrrolidin-1-yl)-2-(trifluoromethyl)pyrimidin-4-yl)-piperidin-4-yl)butanamido)ethanesulfonic acid;

42) (S)—N-(4-cyanophenethyl)-1-(6-(4-(4-oxo-4-((2-sulfamoylethyl)amino) butyl)piperidin-1-yl)-2-(trifluoromethyl)pyrimidin-4-yl)pyrrolidine-2-carboxamide;

43) (S)-3-(4-(1-(6-(2-((4-cyanophenethyl)carbamoyl)pyrrolidin-1-yl)-2-(trifluoromethyl)pyrimidin-4-yl)-piperidin-4-yl)butanamido)propane-1-sulfonic acid;

44) (S)-((4-(1-(6-(2-((4-cyanophenethyl)carbamoyl)pyrrolidin-1-yl)-2-(trifluoromethyl)pyrimidin-4-yl)piperidin-4-yl)butanamido)methyl)-phosphonic acid;

45) (S)-4-(4-(1-(6-((S)-2-((4-cyanophenethyl)carbamoyl) pyrrolidin-1-yl)-2-(trifluoromethyl)pyrimidin-4-yl)piperidin-4-yl)butanamido)-5-methoxy-N,N,N-trimethyl-5-oxopentan-1-aminium;

46) (S)-(4-(1-(6-(2-((4-cyanophenethyl)carbamoyl)pyrrolidin-1-yl)-2-(trifluoromethyl)pyrimidin-4-yl)piperidin-4-yl)butanamido)-methanesulfonic acid;

47) (S)-1-(6-(4-(4-((2-(2-(2-aminoethoxy)ethoxy)ethyl) amino)-4-oxobutyl)piperidin-1-yl)-2-(trifluoromethyl) pyrimidin-4-yl)-N-(4-cyanophenethyl)pyrrolidine-2-carboxamide;

48) (S)-1-(6-(4-(4-((2-amino-2-oxoethyl)amino)-4-oxobutyl)piperidin-1-yl)-2-(trifluoromethyl)pyrimidin-4-yl)-N-(4-cyanophenethyl)pyrrolidine-2-carboxamide;

49) (S)-methyl 2-(4-(1-(6-(2-((4-cyanophenethyl)carbamoyl)pyrrolidin-1-yl)-2-(trifluoromethyl)pyrimidin-4-yl)piperidin-4-yl)butanamido)acetate;

50) (S)-methyl 3-(4-(1-(6-(2-((4-cyanophenethyl)carbamoyl)pyrrolidin-1-yl)-2-(trifluoromethyl)pyrimidin-4-yl)piperidin-4-yl)butanamido)-propanoate;

51) (S)-methyl 2-amino-6-(4-(1-(6-((S)-2-((4-cyanophenethyl)carbamoyl)-pyrrolidin-1-yl)-2-(trifluoromethyl)-pyrimidin-4-yl)piperidin-4-yl)butanamido)hexanoate;

52) (S)-2-(4-(1-(6-((S)-2-((4-cyanophenethyl)carbamoyl) pyrrolidin-1-yl)-2-(trifluoromethyl)pyrimidin-4-yl)piperidin-4-yl)butanamido)-5-guanidinopentanoic acid;

53) (R)-2-(4-(1-(6-((S)-2-((4-cyanophenethyl)carbamoyl) pyrrolidin-1-yl)-2-(trifluoromethyl)pyrimidin-4-yl)piperidin-4-yl)butanamido)-5-guanidinopentanoic acid;

54) (S)-5-guanidino-2-(4-(1-(2-(trifluoromethyl)-6-((S)-2-((4-(trifluoromethyl)phenethyl)carbamoyl)pyrrolidin-1-yl)pyrimidin-4-yl)piperidin-4-yl)butanamido) pentanoic acid;

55) (R)-2-(4-(1-(6-((S)-2-((4-cyanophenethyl)carbamoyl) pyrrolidin-1-yl)-2-(trifluoromethyl)pyrimidin-4-yl)piperidin-4-yl)butanamido)succinic acid;

56) (S)-2-(4-(1-(6-((S)-2-((4-cyanophenethyl)carbamoyl) pyrrolidin-1-yl)-2-(trifluoromethyl)pyrimidin-4-yl)piperidin-4-yl)butanamido)-pentanedioic acid;

57) (S)-2-amino-5-oxo-5-((3-(1-(2-(trifluoromethyl)-6-((S)-2-((4-(trifluoromethyl)phenethyl)carbamoyl)pyrrolidin-1-yl)pyrimidin-4-yl)piperidin-4-yl)propyl) amino)pentanoic acid;

58) (S)-2-(3-(2-(1-(6-(2-((4-cyanophenethyl)carbamoyl) pyrrolidin-1-yl)-2-(trifluoromethyl)pyrimidin-4-yl)piperidin-4-yl)ethyl)ureido)ethanesulfonic acid;

59) (S)-(3-(2-(1-(6-(2-((4-cyanophenethyl)carbamoyl) pyrrolidin-1-yl)-2-(trifluoromethyl)pyrimidin-4-yl)piperidin-4-yl)ethyl)ureido)methanesulfonic acid;

60) (S)—N-(4-cyanophenethyl)-1-(6-(4-(2-(3-(2-sulfamoyl ethyl)ureido)-ethyl)piperidin-1-yl)-2-(trifluoromethyl)pyrimidin-4-yl)pyrrolidine-2-carboxamide;

61) (S)-3-(3-(2-(1-(6-(2-((4-cyanophenethyl)carbamoyl) pyrrolidin-1-yl)-2-(trifluoromethyl)pyrimidin-4-yl)piperidin-4-yl)ethyl)ureido)-propanoic acid;

62) (R)-2-(3-(2-(1-(6-((S)-2-((4-cyanophenethyl)carbamoyl)pyrrolidin-1-yl)-2-(trifluoromethyl)pyrimidin-4-yl)piperidin-4-yl)ethyl)ureido)succinic acid;

63) (S)-2-(3-(2-(1-(6-((S)-2-((4-cyanophenethyl)carbamoyl)pyrrolidin-1-yl)-2-(trifluoromethyl)pyrimidin-4-yl)piperidin-4-yl)ethyl)ureido)-5-guanidinopentanoic acid;

64) (S)—N-(2-(1-(6-(2-((4-cyanophenethyl)carbamoyl) pyrrolidin-1-yl)-2-(trifluoromethyl)pyrimidin-4-yl)piperidin-4-yl)ethyl)-4-(hydroxymethyl)-4-methylpiperidine-1-carboxamide;

65) (S)—N-(2-(1-(6-(2-((4-cyanophenethyl)-carbamoyl) pyrrolidin-1-yl)-2-(trifluoromethyl)pyrimidin-4-yl)piperidin-4-yl)ethyl)-2-(2-aminoethylsulfonamido)acetate methyl ester;

66) (S)-2-(3-(2-(1-(2-(trifluoromethyl)-6-(2-((4-(trifluoromethyl)phenethyl)-carbamoyl)pyrrolidin-1-yl)pyrimidin-4-yl)piperidin-4-yl)ethyl)ureido)-ethanesulfonic acid;

67) (S)-2-(3-(3-(1-(2-(trifluoromethyl)-6-(2-((4-(trifluoromethyl)phenethyl)-carbamoyl)-pyrrolidin-1-yl)pyrimidin-4-yl)piperidin-4-yl)propyl)ureido)-ethanesulfonic acid;

68) (S)-2-((1-(6-(2-((4-cyanophenethyl)carbamoyl)pyrrolidin-1-yl)-2-(trifluoromethyl)pyrimidin-4-yl)piperidin-4-yl)methoxy)acetic acid;

69) (S)-2-(2-((1-(6-(2-((4-cyanophenethyl)carbamoyl) pyrrolidin-1-yl)-2-(trifluoromethyl)pyrimidin-4-yl)piperidin-4-yl)methoxy)acetamido)-ethanesulfonic acid;

70) (S)-1-(6-(4-(4-(2-aminoethyl)amino)-4-oxobutyl)piperidin-1-yl)-2-(trifluoromethyl)pyrimidin-4-yl)-N-(4-(trifluoromethyl)phenethyl)pyrrolidine-2-carboxamide;

71) (S)-1-(6-(4-(4-((2-(methylsulfonamido)ethyl)amino)-4-oxobutyl)piperidin-1-yl)-2-(trifluoromethyl)pyrimidin-4-yl)-N-(4-(trifluoromethyl)phenethyl)pyrrolidine-2-carboxamide;

72) (S)-1-(6-(4-(4-(2-aminoethyl)amino)-4-oxobutyl)piperidin-1-yl)-2-(trifluoromethyl)pyrimidin-4-yl)-N-(4-cyanophenethyl)pyrrolidine-2-carboxamide;

73) (S)—N-(4-cyanophenethyl)-1-(6-(4-(4-((2-(methylsulfonamido)ethyl)amino)-4-oxobutyl)piperidin-1-yl)-2-(trifluoromethyl)pyrimidin-4-yl)pyrrolidine-2-carboxamide;
74) (S)-4-(N-(2-(4-(1-(2-(trifluoromethyl)-6-(2-((4-(trifluoromethyl)phenethyl)-carbamoyl)-pyrrolidin-1-yl)pyrimidin-4-yl)piperidin-4-yl)butanamido)ethyl)-sulfamoyl)benzoic acid;
75) (S)-1-(6-(4-(4-((2-((9H-purin-6-yl)amino)ethyl)amino)-4-oxobutyl)piperidin-1-yl)-2-(trifluoromethyl)pyrimidin-4-yl)-N-(4-(trifluoromethyl)phenethyl)pyrrolidine-2-carboxamide;
76) (2S)-1-(6-(4-(4-((2-((9-((2R,5R)-3,4-dihydroxy-5-(hydroxymethyl)-tetrahydrofuran-2-yl)-9H-purin-6-yl)amino)ethyl)amino)-4-oxobutyl)piperidin-1-yl)-2-(trifluoromethyl)-pyrimidin-4-yl)-N-(4-(trifluoromethyl)-phenethyl)-pyrrolidine-2-carboxamide;
77) (2S)—N-(4-cyanophenethyl)-1-(6-(4-(4-((2-((9-((2R,5R)-3,4-dihydroxy-5-(hydroxymethyl)tetrahydrofuran-2-yl)-9H-purin-6-yl)amino)ethyl)amino)-4-oxobutyl)piperidin-1-yl)-2-(trifluoromethyl)-pyrimidin-4-yl)pyrrolidine-2-carboxamide;
78) (S)-2-((2-(4-(1-(6-(2-((4-cyanophenethyl)carbamoyl)pyrrolidin-1-yl)-2-(trifluoromethyl)pyrimidin-4-yl)piperidin-4-yl)butanamido)ethyl)-amino)pyrimidine-5-carboxylic acid;
79) (S)-methyl-2-((2-(4-(1-(6-(2-((4-cyanophenethyl)carbamoyl)pyrrolidin-1-yl)-2-(trifluoromethyl)pyrimidin-4-yl)-piperidin-4-yl)butanamido)ethyl)amino)-pyrimidine-4-carboxylate;
80) N-(2-(4-(1-(6-((S)-2-((4-cyanophenethyl)carbamoyl)pyrrolidin-1-yl)-2-(trifluoromethyl)pyrimidin-4-yl)piperidin-4-yl)butanamido)ethyl)-6-(((2S,3R,4R,5R)-2,3,4,5,6-pentahydroxyhexyl)amino)-pyrimidine-4-carboxamide;
81) (S)-6-((2-(4-(1-(6-(2-((4-cyanophenethyl)carbamoyl)pyrrolidin-1-yl)-2-(trifluoromethyl)pyrimidin-4-yl)piperidin-4-yl)butanamido)ethyl)amino)-pyrimidine-4-carboxylic acid;
82) (S)-2-((2-(4-(1-(6-(2-((4-cyanophenethyl)carbamoyl)pyrrolidin-1-yl)-2-(trifluoromethyl)pyrimidin-4-yl)piperidin-4-yl)butanamido)ethyl)amino) pyrimidine-4-carboxylic acid;
83) (S)-2-(4-(1-(6-(2-((4-cyanophenethyl)carbamoyl)pyrrolidin-1-yl)-2-(trifluoromethyl)pyrimidin-4-yl)piperidin-4-yl)butanamido)acetic acid;
84) (S)-3-(4-(1-(6-(2-((4-cyanophenethyl)carbamoyl)pyrrolidin-1-yl)-2-(trifluoromethyl)pyrimidin-4-yl)-piperidin-4-yl)butanamido)-propanoic acid;
85) (S)-4-carboxy-4-(4-(1-(6-((S)-2-((4-cyanophenethyl)carbamoyl)pyrrolidin-1-yl)-2-(trifluoromethyl)pyrimidin-4-yl)piperidin-4-yl)butanamido)-N,N,N-trimethylbutan-1-aminium;
86) (S)-2-amino-6-(4-(1-(6-((S)-2-((4-cyanophenethyl)carbamoyl)pyrrolidin-1-yl)-2-(trifluoromethyl)pyrimidin-4-yl)-piperidin-4-yl)butanamido)hexanoic acid;
87) (S)—N-(2-(1-(6-(2-((4-cyanophenethyl)-carbamoyl)pyrrolidin-1-yl)-2-(trifluoromethyl)pyrimidin-4-yl)piperidin-4-yl)ethyl)-2-(2-aminoethylsulfonamido)-acetic acid;
88) (S)-2-(4-(4-(1-(6-(2-((4-cyanophenethyl)carbamoyl)pyrrolidin-1-yl)-2-(trifluoromethyl)pyrimidin-4-yl)piperidin-4-yl)butanoyl)piperazin-1-yl)acetic acid;
89) (S)—N-(4-cyanophenethyl)-1-(6-(4-(4-((3-((1,3-dihydroxy-2-(hydroxymethyl)propan-2-yl)amino)-3-oxopropyl)amino)-4-oxobutyl)piperidin-1-yl)-2-(trifluoromethyl)-pyrimidin-4-yl)pyrrolidine-2-carboxamide;
90) (S)-1-(6-(4-(4-((2-((6-chloropyrimidin-4-yl)amino)ethyl)amino)-4-oxobutyl)piperidin-1-yl)-2-(trifluoromethyl)pyrimidin-4-yl)-N-(4-cyanophenethyl)pyrrolidine-2-carboxamide;
91) (S)-1-(6-(4-(4-((2-((6-(bis(2-hydroxyethyl)amino)pyrimidin-4-yl)amino)ethyl)amino)-4-oxobutyl)piperidin-1-yl)-2-(trifluoromethyl)pyrimidin-4-yl)-N-(4-cyanophenethyl)pyrrolidine-2-carboxamide;
92) (S)-2-(2-((2-(4-(1-(6-(2-((4-cyanophenethyl)carbamoyl)pyrrolidin-1-yl)-2-(trifluoromethyl)pyrimidin-4-yl)piperidin-4-yl)butanamido)ethyl)amino)-pyrimidine-5-carboxamido)ethanesulfonic acid;
93) (S)-2-(3-(3-(2-(1-(6-(2-((4-cyanophenethyl)carbamoyl)pyrrolidin-1-yl)-2-(trifluoromethyl)pyrimidin-4-yl)piperidin-4-yl)ethyl)ureido)-propanamido)-ethanesulfonic acid;
94) (S)-2-(2-(4-(1-(2-(trifluoromethyl)-6-(2-((4-(trifluoromethyl)phenethyl)-carbamoyl)-pyrrolidin-1-yl)pyrimidin-4-yl)piperidin-4-yl)butanamido)ethyl-sulfonamido)acetic acid;
95) (S)-2-(2-(4-(1-(6-(2-((4-cyanophenethyl)carbamoyl)pyrrolidin-1-yl)-2-(trifluoromethyl)pyrimidin-4-yl)piperidin-4-yl)butanamido)-ethylsulfonamido)acetic acid;
96) (S)-1-(6-(4-(2-(2-aminoethylsulfonamido)ethyl)piperidin-1-yl)-2-(trifluoromethyl)-pyrimidin-4-yl)-N-(4-cyanophenethyl)pyrrolidine-2-carboxamide;
97) (S)-2-((2-(N-(2-(1-(6-(2-((4-cyanophenethyl)carbamoyl)pyrrolidin-1-yl)-2-(trifluoromethyl)pyrimidin-4-yl)piperidin-4-yl)ethyl)sulfamoyl)ethyl)amino)-pyrimidine-5-carboxylic acid;
98) (S)-(3-(3-(1-(6-(2-((4-cyanophenethyl)carbamoyl)pyrrolidin-1-yl)-2-(trifluoromethyl)pyrimidin-4-yl)piperidin-4-yl)propyl)ureido)methanesulfonic acid;
99) (S)-2-(3-(3-(1-(6-(2-((4-cyanophenethyl)carbamoyl)pyrrolidin-1-yl)-2-(trifluoromethyl)pyrimidin-4-yl)piperidin-4-yl)propyl)ureido)-ethanesulfonic acid;
100) (S)—N-(4-cyanophenethyl)-1-(6-(4-(3-(3-(2-sulfamoylethyl)ureido) propyl)piperidin-1-yl)-2-(trifluoromethyl)pyrimidin-4-yl)pyrrolidine-2-carboxamide;
101) (S)-2-(3-(3-(1-(6-(2-(4-cyanophenethyl)carbamoyl)pyrrolidin-1-yl)-2-(trifluoromethyl)pyrimidin-4-yl)piperidin-4-yl)propyl)ureido)acetic acid;
102) ((R)-1-(2-(1-(6-((S)-2-((4-cyanophenethyl)carbamoyl)pyrrolidin-1-yl)-2-(trifluoromethyl)pyrimidin-4-yl)piperidin-4-yl)ethyl)-2,5-dioxoimidazolidin-4-yl)methanesulfonic acid;
103) (R)-2-amino-3-((2-(1-(6-((S)-2-((4-cyanophenethyl)carbamoyl)pyrrolidin-1-yl)-2-(trifluoromethyl)pyrimidin-4-yl)piperidin-4-yl)ethyl)amino)-3-oxopropane-1-sulfonic acid;
104) (S)-2-((2-(4-(1-(6-(2-(4-cyanophenethyl)carbamoyl)pyrrolidin-1-yl)-2-(trifluoromethyl)pyrimidin-4-yl)piperidin-4-yl)butanamido)-ethyl)amino)-2-oxoethanesulfonic acid;
105) (R)-2-amino-3-((2-(N-(2-(1-(6-((S)-2-(4-cyanophenethyl)carbamoyl)-pyrrolidin-1-yl)-2-(trifluoromethyl)-pyrimidin-4-yl)piperidin-4-yl)ethyl)sulfamoyl)ethyl)amino)-3-oxopropane-1-sulfonic acid;
106) (S)—N-(4-cyanophenethyl)-1-(6-(4-(2-guanidinoethyl)piperidin-1-yl)-2-(trifluoromethyl)pyrimidin-4-yl)pyrrolidine-2-carboxamide;

107) (S)-1-(6-(4-(1-amino-1-imino-12-oxo-5,8-dioxa-2,11-diazapentadecan-15-yl)piperidin-1-yl)-2-(trifluoromethyl)-pyrimidin-4-yl)-N-(4-cyanophenethyl)-pyrrolidine-2-carboxamide;

108) (S)—N-(4-cyanophenethyl)-1-(6-(4-(4-((2-guanidinoethyl)amino)-4-oxobutyl)piperidin-1-yl)-2-(trifluoromethyl)pyrimidin-4-yl)pyrrolidine-2-carboxamide;

109) (S)-6-(4-(1-(6-((S)-2-(4-cyanophenethyl)carbamoyl)pyrrolidin-1-yl)-2-(trifluoromethyl)pyrimidin-4-yl)piperidin-4-yl)butanamido)-2-guanidinohexanoic acid;

110) (S)—N-(4-cyanophenethyl)-1-(6-(4-(2-(2-guanidinoethylsulfonamido) ethyl)piperidin-1-yl)-2-(trifluoromethyppyrimidin-4-yl)pyrrolidine-2-carboxamide;

111) (S)-1-(6-(4-(4-((2-guanidinoethyl)-amino)-4-oxobutyl)piperidin-1-yl)-2-(trifluoromethyl)pyrimidin-4-yl)-N-(4-(trifluoromethyl)phenethyl)pyrrolidine-2-carboxamide;

112) (S)-1-(6-(4-(3-guanidinopropyl)piperidin-1-yl)-2-(trifluoromethyl)pyrimidin-4-yl)-N-(4-(trifluoromethyl)phenethyl)-pyrrolidine-2-carboxamide;

113) (S)-2-guanidino-5-oxo-5-((3-(1-(2-(trifluoromethyl)-6-((S)-2-((4-(trifluoromethyl)phenethyl)carbamoyl)pyrrolidin-1-yl)pyrimidin-4-yl)piperidin-4-yl)propyl)amino)pentanoic acid;

114) (S)-(4-(1-(6-(2-((3,4-dichlorophenethyl)carbamoyl)pyrrolidin-1-yl)-2-(trifluoromethyl)pyrimidin-4-yl)piperidin-4-yl)butanamido)methanesulfonic acid;

115) (S)-(4-(1-(6-(2-(4-chlorophenethyl)-carbamoyl)pyrrolidin-1-yl)-2-(trifluoromethyl)pyrimidin-4-yl)-piperidin-4-yl)butanamido)-methanesulfonic acid;

116) (S)-(4-(1-(6-(2-((2,3-dichlorophenethyl)carbamoyl)pyrrolidin-1-yl)-2-(trifluoromethyl)pyrimidin-4-yl)piperidin-4-yl)butanamido)-methanesulfonic acid;

117) (S)-4-(1-(2-(2-((4-cyanophenethyl)carbamoyl)pyrrolidin-1-yl)-6-(trifluoromethyl)pyridin-4-yl)piperidin-4-yl)butanoic acid;

118) (S)-(4-(1-(2-(2-((4-cyanophenethyl)carbamoyl)pyrrolidin-1-yl)-6-(trifluoromethyl)pyridin-4-yl)piperidin-4-yl)butanamido)methanesulfonic acid;

119) (S)-2-(4-(1-(2-(2-(4-cyanophenethyl)carbamoyl)pyrrolidin-1-yl)-6-(trifluoromethyl)pyridin-4-yl)piperidin-4-yl)butanamido)ethanesulfonic acid;

120) (S)-2-(4-(1-(2-((S)-2-(4-cyanophenethyl)carbamoyl)pyrrolidin-1-yl)-6-(trifluoromethyl)pyridin-4-yl)piperidin-4-yl)butanamido)-5-guanidinopentanoic acid;

121) (S)-(3-(3-(1-(2-(2-((4-cyanophenethyl)carbamoyl)pyrrolidin-1-yl)-6-(trifluoromethyl)pyridin-4-yl)piperidin-4-yl)propyl)ureido)methanesulfonic acid;

122) (S)-2-((S)-2-(4-(1-(2-((S)-2-((4-cyanophenethyl)carbamoyl)pyrrolidin-1-yl)-6-(trifluoromethyl)pyridin-4-yl)piperidin-4-yl)butanamido)-5-guanidinopentanamido)-5-guanidinopentanoic acid;

123) (R)-2-((R)-2-(4-(1-(6-((S)-2-((4-cyanophenethyl)carbamoyl)pyrrolidin-1-yl)-2-(trifluoromethyl)pyrimidin-4-yl)piperidin-4-yl)butanamido)-5-guanidino-pentanamido)pentanedioic acid;

124) (2S,4R)—N-(4-cyanophenethyl)-4-hydroxy-1-(6-(4-(2-hydroxyethyl)piperidin-1-yl)-2-(trifluoromethyppyrimidin-4-yl)pyrrolidine-2-carboxamide;

125) (2S,4R)—N-(4-cyanophenethyl)-4-hydroxy-1-(6-(4-(hydroxymethyl)piperidin-1-yl)-2-(trifluoromethyl)pyrimidin-4-yl)pyrrolidine-2-carboxamide;

126) 4-(1-(6-((2S,4R)-4-hydroxy-2-((4-(trifluoromethyl)phenethyl)carbamoyl)pyrrolidin-1-yl)-2-(trifluoromethyl)pyrimidin-4-yl)piperidin-4-yl)butanoic acid;

127) (S)-tert-butyl (2-(1-(6-(2-(4-cyanophenethyl)carbamoyl)-4,4-difluoropyrrolidin-1-yl)-2-(trifluoromethyl)pyrimidin-4-yl)piperidin-4-yl)ethyl)carbamate;

128) (2S,4R)-4-hydroxy-1-(6-(4-(4-oxo-4-(((2S,3R,4R,5R)-2,3,4,5,6-pentahydroxyhexyl)-amino)butyl)-piperidin-1-yl)-2-(trifluoromethyl)-pyrimidin-4-yl)-N-(4-(trifluoro-methyl)phenethyl)pyrrolidine-2-carboxamide;

129) (S)-1-(6-(4-(2-aminoethyl)piperidin-1-yl)-2-(trifluoromethyl)pyrimidin-4-yl)-N-(4-cyanophenethyl)-4,4-difluoropyrrolidine-2-carboxamide;

130) (S)-2-(3-(2-(1-(6-(2-((4-cyanophenethyl)carbamoyl)-4,4-difluoropyrrolidin-1-yl)-2-(trifluoromethyl)pyrimidin-4-yl)piperidin-4-yl)ethyl)ureido)ethanesulfonic acid;

131) (4R)-4-amino-1-(6-(4-(hydroxymethyl)piperidin-1-yl)-2-(trifluoromethyl)pyrimidin-4-yl)-N-(4-(trifluoromethyl)phenethyl)pyrrolidine-2-carboxamide;

132) (S)—N-(4-cyanophenethyl)-1-(6-(4-(hydroxymethyl)piperidin-1-yl)-2-(trifluoromethyl)pyrimidin-4-yl)azetidine-2-carboxamide;

133) (S)-1-(6-(4-(hydroxymethyl)piperidin-1-yl)-2-(trifluoromethyl)pyrimidin-4-yl)-N-(4-(trifluoromethyl)-phenethyl)azetidine-2-carboxamide;

134) (S)—N-(4-cyanophenethyl)-1-(6-(4-((dimethyl amino)methyl)piperidin-1-yl)-2-(trifluoromethyl)pyrimidin-4-yl)azetidine-2-carboxamide;

135) (S)—N-(4-cyanophenethyl)-1-(6-(4-(methoxymethyl)piperidin-1-yl)-2-(trifluoromethyl)pyrimidin-4-yl)azetidine-2-carboxamide;

136) (S)—N-(4-cyanophenethyl)-1-(6-(4-(2-hydroxyethyl)piperidin-1-yl)-2-(trifluoromethyl)pyrimidin-4-yl)azetidine-2-carboxamide;

137) (S)—N-(4-cyanophenethyl)-1-(6-(4-(2-hydroxyethyl)piperazin-1-yl)-2-(trifluoromethyl)pyrimidin-4-yl)azetidine-2-carboxamide;

138) (S)—N-(4-cyanophenethyl)-1-(6-(4-(2-methoxyethyl)piperidin-1-yl)-2-(trifluoromethyl)pyrimidin-4-yl)azetidine-2-carboxamide;

139) (S)—N-(4-cyanophenethyl)-1-(6-(4-(2-(dimethylamino)ethyl)piperazin-1-yl)-2-(trifluoromethyl)pyrimidin-4-yl)azetidine-2-carboxamide;

140) (S)-3-(1-(6-(2-(4-cyanophenethyl)carbamoyl)azetidin-1-yl)-2-(trifluoromethyl)pyrimidin-4-yl)piperidin-4-yl)propanoic acid;

141) (S)—N-(4-cyanophenethyl)-1-(6-(4-(2-(dimethylamino)ethyl)piperidin-1-yl)-2-(trifluoromethyl)pyrimidin-4-yl)azetidine-2-carboxamide;

142) (S)-1-(6-(4-(2-cyanoethyl)piperazin-1-yl)-2-(trifluoromethyl)pyrimidin-4-yl)-N-(4-cyanophenethyl)azetidine-2-carboxamide;

143) (S)-1-(6-(4-(2-cyanoethyl)piperidin-1-yl)-2-(trifluoromethyl)pyrimidin-4-yl)-N-(4-cyanophenethyl)azetidine-2-carboxamide;

144) (S)-4-(1-(6-(2-(4-cyanophenethyl)carbamoyl)azetidin-1-yl)-2-(trifluoromethyl)pyrimidin-4-yl)piperidin-4-yl)butanoic acid;

145) (S)-3-(1-(2-(trifluoromethyl)-6-(2-((4-(trifluoromethyl)phenethyl) carbamoyl)azetidin-1-yl)pyrimidin-4-yl)piperidin-4-yl)propanoic acid;

146) (S)-4-(1-(2-(trifluoromethyl)-6-(2-((4-(trifluoromethyl)phenethyl) carbamoyl)azetidin-1-yl)pyrimidin-4-yl)piperidin-4-yl)butanoic acid;

147) (S)-tert-butyl ((1-(6-(2-(4-cyanophenethyl)carbamoyl)azetidin-1-yl)-2-(trifluoromethyl)pyrimidin-4-yl)piperidin-4-yl)methyl)carbamate;

148) (S)-tert-butyl (2-(1-(6-(2-(4-cyanophenethyl)carbamoyl)azetidin-1-yl)-2-(trifluoromethyl)pyrimidin-4-yl)piperidin-4-yl)ethyl)carbamate;
149) (S)-tert-butyl (2-(1-(2-(trifluoromethyl)-6-(2((4-(trifluoromethyl)phenethyl) carbamoyl)azetidin-1-yl)pyrimidin-4-yl)piperidin-4-yl)ethyl)carbamate;
150) (S)-1-(6-(4-(hydroxymethyl)piperidin-1-yl)-2-(trifluoromethyl)pyrimidin-4-yl)-N-(2-methoxy-4-(trifluoromethyl)phenethyl)azetidine-2-carboxamide;
151) (S)-1-(6-(4-(2-hydroxyethyl)piperidin-1-yl)-2-(trifluoromethyl)pyrimidin-4-yl)-N-(2-methoxy-4-(trifluoromethyl)phenethyl)azetidine-2-carboxamide;
152) (S)-3-(1-(6-(2-((2-methoxy-4-(trifluoromethyl) phenethyl)carbamoyl)azetidin-1-yl)-2-(trifluoromethyl)pyrimidin-4-yl)piperidin-4-yl)propanoic acid;
153) (S)-4-(1-(6-(2-((2-methoxy-4-(trifluoromethyl) phenethyl)carbamoyl)azetidin-1-yl)-2-(trifluoromethyl)pyrimidin-4-yl)piperidin-4-yl)butanoic acid;
154) N-(4-cyanophenethyl)-1-(6-(4-(hydroxymethyl)piperidin-1-yl)-2-(trifluoromethyl)pyrimidin-4-yl)azetidine-2-carboxamide;
155) (S)-(1-(6-(4-aminomethylpiperidin-1-yl)-2-(trifluoromethyl)pyrimidin-4-yl)-N-(4-cyanophenethyl)azetidine-2-carboxamide hydrochloride;
156) (S)-1-(6-(4-(2-aminoethyl)piperidin-1-yl)-2-(trifluoromethyl)pyrimidin-4-yl)-N-(4-cyanophenethyl)azetidine-2-carboxamide;
157) (S)-1-(6-(4-(2-aminoethyl)piperidin-1-yl)-2-(trifluoromethyl)pyrimidin-4-yl)-N-(4-(trifluoromethyl)phenethyl)-azetidine-2-carboxamide;
158) (S)-3-(4-(1-(6-(2-(4-cyanophenethyl)carbamoyl) azetidin-1-yl)-2-(trifluoromethyl)pyrimidin-4-yl)piperidin-4-yl)butanamido)propane-1-sulfonic acid;
159) (S)-2-(4-(1-(6-(2-(4-cyanophenethyl)carbamoyl) azetidin-1-yl)-2-(trifluoromethyl)pyrimidin-4-yl)piperidin-4-yl)butanamido)ethanesulfonic acid;
160) (S)-(4-(1-(6-(2-(4-cyanophenethyl)carbamoyl)azetidin-1-yl)-2-(trifluoromethyl)pyrimidin-4-yl)piperidin-4-yl)butanamido)methanesulfonic acid;
161) (S)-2-(4-(1-(6-((S)-2-(4-cyanophenethyl)carbamoyl)azetidin-1-yl)-2-(trifluoromethyl)pyrimidin-4-yl) piperidin-4-yl)butanamido)-5-guanidinopentanoic acid;
162) (S)-2-(N-methyl-3-(1-(2-(trifluoromethyl)-6-(2-((4-(trifluoromethyl) phenethyl)carbamoyl)azetidin-1-yl) pyrimidin-4-yl)piperidin-4-yl)propanamido)ethanesulfonic acid;
163) (S)-(3-(1-(2-(trifluoromethyl)-6-(2-((4-(trifluoromethyl)phenethyl)-carbamoyl)azetidin-1-yl)pyrimidin-4-yl)piperidin-4-yl)propanamido)-methanesulfonic acid;
164) (S)-2-(3-(1-(2-(trifluoromethyl)-6-(2-((4-(trifluoromethyl)phenethyl) carbamoyl)-azetidin-1-yl)pyrimidin-4-yl)piperidin-4-yl)propanamido)ethanesulfonic acid;
165) (S)-(4-(1-(2-(trifluoromethyl)-6-(2-((4-(trifluoromethyl)phenethyl)-carbamoyl)azetidin-1-yl)pyrimidin-4-yl)piperidin-4-yl)butanamido)methanesulfonic acid;
166) (S)-di-tert-butyl 2-(4-(1-(2-(trifluoromethyl)-6-((S)-2-((4-(trifluoromethyl) phenethyl)carbamoyl)azetidin-1-yl)pyrimidin-4-yl)piperidin-4-yl)butanamido)pentanedioate;
167) (R)-di-tert-butyl 2-(4-(1-(2-(trifluoromethyl)-6-((S)-2-((4-(trifluoromethyl) phenethyl)carbamoyl)azetidin-1-yl)pyrimidin-4-yl)piperidin-4-yl)butanamido)pentanedioate;
168) (S)-5-guanidino-2-(3-(1-(2-(trifluoromethyl)-6-((S)-2-((4-(trifluoromethyl) phenethyl)carbamoyl)azetidin-1-yl)pyrimidin-4-yl)piperidin-4-yl)propanamido)pentanoic acid;
169) (S)-2-(3-(1-(6-(2((2-methoxy-4-(trifluoromethyl) phenethyl)carbamoyl) azetidin-1-yl)-2-trifluoromethyl)-pyrimidin-4-yl)piperidin-4-yl)propanamido)ethanesulfonic acid;
170) (S)—N-(4-cyanophenethyl)-1-(6-(4-(4-oxo-4-((2R,3S,4S,5S)-2,3,4,5,6-pentahydroxyhexyl)amino)butyl) piperidin-1-yl)-2-(trifluoromethyl)pyrimidin-4-yl)azetidine-2-carboxamide;
171) (S)—N-(4-cyanophenethyl)-1-(6-(4-(4-(((R)-2,3-dihydroxypropyl)amino)-4-oxobutyl)piperidin-1-yl)-2-(trifluoromethyl)pyrimidin-4-yl)azetidine-2-carboxamide;
172) (S)-3-(3-(1-(6-(2((4-cyanophenethyl)carbamoyl) azetidin-1-yl)-2-trifluoromethyl)pyrimidin-4-yl)propanamido)propane-1-sulfonic acid;
173) (S)-tert-butyl (2-(4-(1-(6-(2-((4-cyanophenethyl) carbamoyl)azetidin-1-yl)-2-(trifluoromethyl)pyrimidin-4-yl)piperidin-4-yl)butanamido)-ethyl)carbamate;
174) (S)-tert-butyl (4-(4-(1-(6-(2-((4-cyanophenethyl) carbamoyl)azetidin-1-yl)-2-(trifluoromethyl)pyrimidin-4-yl)piperidin-4-yl)butanamido)-butyl)carbamate;
175) (S)-tert-butyl (2-(2-(4-(1-(6-(2-((4-cyanophenethyl) carbamoyl)azetidin-1-yl)-2-(trifluoromethyl)pyrimidin-4-yl)piperidin-4-yl)butanamido)ethoxy) ethyl)carbamate;
176) (S)-ethyl 3-(3-(2-(1-(6-(2-((4-cyanophenethyl)carbamoyl)azetidin-1-yl)-2-(trifluoromethyl)pyrimidin-4-yl)piperidin-4-yl)ethyl)ureido)propanoate;
177) (S)-3-(3-(2-(1-(6-(2-((4-cyanophenethyl)carbamoyl) azetidin-1-yl)-2-(trifluoromethyl)pyrimidin-4-yl)piperidin-4-yl)ethyl)ureido)propanoic acid;
178) (S)—N-(4-cyanophenethyl)-1-(6-(4-(2-(3-(2-sulfamoyl ethyl)ureido) ethyl)piperidin-1-yl)-2-(trifluoromethyppyrimidin-4-yl)azetidine-2-carboxamide;
179) (S)-(3-(2-(1-(6-(2-(4-cyanophenethyl)carbamoyl) azetidin-1-yl)-2-(trifluoromethyl)pyrimidin-4-yl)piperidin-4-yl)ethyl)ureido)-methanesulfonic acid;
180) (S)-2-(3-(2-(1-(6-(2-((4-cyanophenethyl)carbamoyl) azetidin-1-yl)-2-(trifluoromethyl)pyrimidin-4-yl)piperidin-4-yl)ethyl)ureido)-ethanesulfonic acid;
181) (S)-tert-butyl (2-(3-(2-(1-(6-(2-((4-cyanophenethyl) carbamoyl)azetidin-1-yl)-2-(trifluoromethyl)pyrimidin-4-yl)-piperidin-4-yl)ethyl)ureido)ethyl)carbamate;
182) (S)-tert-butyl (2-(2-(3-(2-(1-(6-(2-((4-cyanophenethyl)carbamoyl)azetidin-1-yl)-2-(trifluoromethyl)pyrimidin-4-yl)piperidin-4-yl)ethyl)ureido)-ethoxy) ethyl)carbamate;
183) (S)-methyl-2-amino-6-(3-(2-(1-(6-((S)-2-((4-cyanophenethyl)carbamoyl) azetidin-1-yl)-2-(trifluoromethyl)pyrimidin-4-yl)piperidin-4-yl)ethyl)ureido) hexanoate;
184) (S)-1-(6-(4-(3-(piperidin-4-yl)propyl)piperidin-1-yl)-2-(trifluoromethyl) pyrimidin-4-yl)-N-(4-(trifluoromethyl)phenethyl)azetidine-2-carboxamide;
185) (R)-2-amino-3-oxo-3-((2-(1-(2-(trifluoromethyl)-6-((S)-2-((4-(trifluoromethyl)-phenethyl)carbamoyl)azetidin-1-yl)pyrimidin-4-yl)piperidin-4-yl)ethyl)amino)-propane-1-sulfonic acid;
186) (S)-2-oxo-2-((2-(1-(2-(trifluoromethyl)-6-(2-((4-(trifluoromethyl)phenethyl) carbamoyl)azetidin-1-yl) pyrimidin-4-yl)piperidin-4-yl)ethyl)amino)-ethanesulfonic acid;

187) (S)-2-oxo-2-(4-(3-(1-(2-(trifluoromethyl)-6-(2-((4-(trifluoromethyl)phenethyl) carbamoyl)azetidin-1-yl) pyrimidin-4-yl)piperidin-4-yl)propyl)piperidin-1-yl) ethanesulfonic acid;

188) (S)-2-(4-(3-(1-(2-(trifluoromethyl)-6-(2-((4-(trifluoromethyl)phenethyl) carbamoyl)-azetidin-1-yl)pyrimidin-4-yl)piperidin-4-yl)propyl)piperidin-1-yl)acetic acid;

189) (S)—N-(4-cyanophenethyl)-1-(6-(4-(4-((2-guanidinoethyl)amino)-4-oxobutyl)piperidin-1-yl)-2-(trifluoromethyl)pyrimidin-4-yl)azetidine-2-carboxamide;

190) (S)—N-(4-cyanophenethyl)-1-(6-(4-(4-((4-guanidinobutyl)amino)-4-oxobutyl)piperidin-1-yl)-2-(trifluoromethyl)pyrimidin-4-yl)azetidine-2-carboxamide;

191) (S)—N-(4-cyanophenethyl)-1-(6-(4-(4-((2-(2-guanidinoethoxy)-ethyl)amino)-4-oxobutyl)piperidin-1-yl)-2-(trifluoromethyl)pyrimidin-4-yl)azetidine-2-carboxamide;

192) (S)—N-(4-cyanophenethyl)-1-(6-(4-(2-guanidinoethyl)piperidin-1-yl)-2-(trifluoromethyl)pyrimidin-4-yl)azetidine-2-carboxamide;

193) (S)—N-(4-cyanophenethyl)-1-(6-(4-(2-(3-(2-guanidinoethyl)-ureido)ethyl)piperidin-1-yl)-2-(trifluoromethyl)pyrimidin-4-yl)azetidine-2-carboxamide;

194) (S)-1-(6-(4-(1-amino-1-imino-9-oxo-5-oxa-2,8,10-triazadodecan-12-yl)piperidin-1-yl)-2-(trifluoromethyl)pyrimidin-4-yl)-N-(4-cyanophenethyl)azetidine-2-carboxamid;

195) (S)-1-(6-(4-(3-(1-carbamimidoylpiperidin-4-yl)propyl)piperidin-1-yl)-2-(trifluoromethyl)pyrimidin-4-yl)-N-(4-(trifluoromethyl)phenethyl)-azetidine-2-carboxamide;

196) (S)-methyl-4-(N-(2-(2-(4-(1-(6-(2-((4-cyanophenethyl)carbamoyl)azetidin-1-yl)-2-(trifluoromethyl)pyrimidin-4-yl)piperidin-4-yl)butanamido)ethoxy)ethyl)-sulfamoyl)benzoate;

197) (S)-4-(N-(2-(2-(4-(1-(6-(2-((4-cyanophenethyl)carbamoyl)azetidin-1-yl)-2-(trifluoromethyl)pyrimidin-4-yl)piperidin-4-yl)butanamido) ethoxy) ethyl)sulfamoyl)-benzoic acid;

198) (S)—N-(4-cyanophenethyl)-1-(6-(4-(2-(3-(2-(2-(methylsulfonylamino)-ethoxy)ethyl)ureido)ethyl)piperidin-1-yl)-2-(trifluoromethyl)pyrimidin-4-yl)azetidine-2-carboxamide;

199) (S)-2-(3-(1-(2-(Trifluoromethyl)-6-((S)-2-((4-(trifluoromethyl)phenethyl) carbamoyl)azetidin-1-yl)pyrimidin-4-yl)piperidin-4-yl)propanamido)pentanedioic acid;

200) (R)-2-(4-(1-(2-(trifluoromethyl)-6-((S)-2-((4-(trifluoromethyl)-phenethyl)carbamoyl)azetidin-1-yl)pyrimidin-4-yl)piperidin-4-yl)butanamido)pentanedioic acid;

201) N-(4-cyanophenethyl)-1-(6-(4-(2-((3-hydroxypropyl)(methyl)amino)ethyl)-piperidin-1-yl)-2-(trifluoromethyl)pyrimidin-4-yl)azetidine-2-carboxamide;

202) N-(2-(1-(6-(2-((4-cyanophenethyl)carbamoyl)azetidin-1-yl)-2-(trifluoromethyl)pyrimidin-4-yl)piperidin-4-yl)ethyl)-3-hydroxy-N,N-dimethylpropan-1-aminium;

203) (S)-2-((2-((2-(1-(6-(2-((4-cyanophenethyl)carbamoyl)azetidin-1-yl)-2-(trifluoromethyl)pyrimidin-4-yl) piperidin-4-yl)ethyl)amino)-3,4-dioxocyclobut-1-en-1-yl)amino)ethanesulfonic acid;

204) (S)-((2-((2-(1-(6-(2-((4-cyanophenethyl)carbamoyl) azetidin-1-yl)-2-(trifluoromethyl)pyrimidin-4-yl)piperidin-4-yl)ethyl)amino)-3,4-dioxocyclobut-1-en-1-yl) amino)methanesulfonic acid;

205) (S)-2-((2-((2-(1-(6-(2-((4-cyanophenethyl)carbamoyl)azetidin-1-yl)-2-(trifluoromethyl)pyrimidin-4-yl) piperidin-4-yl)ethyl)amino)-3,4-dioxocyclobut-1-en-1-yl)(methyl)amino)ethanesulfonic acid;

206) (S)-tert-butyl 3-((2-((2-(1-(6-(2-((4-cyanophenethyl) carbamoyl)azetidin-1-yl)-2-(trifluoromethyl)pyrimidin-4-yl)piperidin-4-yl)ethyl)amino)-3,4-dioxocyclobut-1-en-1-yl)amino)propanoate;

207) (S)-3-((2-((2-(1-(6-(2-((4-cyanophenethyl)carbamoyl)azetidin-1-yl)-2-(trifluoromethyl)pyrimidin-4-yl) piperidin-4-yl)ethyl)amino)-3,4-dioxocyclobut-1-en-1-yl)amino)propanoic acid;

208) (S)-2-((2-((2-(1-(6-(2-((4-cyanophenethyl)carbamoyl)azetidin-1-yl)-2-(trifluoromethyl)pyrimidin-4-yl) piperidin-4-yl)ethyl)amino)-3,4-dioxocyclobut-1-en-1-yl)amino)acetic acid;

209) (R)—N-(4-cyanophenethyl)-1-(6-(4-(hydroxymethyl)piperidin-1-yl)-2-(trifluoromethyl)pyrimidin-4-yl)piperidine-3-carboxamide;

210) (R)—N-(4-cyanophenethyl)-1-(6-(4-(2-hydroxyethyl)piperidin-1-yl)-2-(trifluoromethyl)pyrimidin-4-yl)piperidine-3-carboxamide;

211) (R)—N-(4-cyanophenethyl)-1-(6-(4-(methoxymethyl)piperidin-1-yl)-2-(trifluoromethyl)pyrimidin-4-yl)piperidine-3-carboxamide;

212) (R)-1-(6-(4-(2-cyanoethyl)piperidin-1-yl)-2-(trifluoromethyl)pyrimidin-4-yl)-N-(4-cyanophenethyl)piperidine-3-carboxamide;

213) (R)-tert-butyl (2-(1-(6-(3-((4-cyanophenethyl)carbamoyl)piperidin-1-yl)-2-(trifluoromethyl)pyrimidin-4-yl)piperidin-4-yl)ethyl)carbamate;

214) (R)—N-(4-cyanophenethyl)-1-(6-(4-(2-hydroxyethyl)piperazin-1-yl)-2-(trifluoromethyl)pyrimidin-4-yl)piperidine-3-carboxamide;

215) (R)—N-(4-cyanophenethyl)-1-(6-(4-(2-(2-hydroxyethoxy)ethyl)piperazin-1-yl)-2-(trifluoromethyl)pyrimidin-4-yl)piperidine-3-carboxamide;

216) (R)-2-(4-(6-(3-((4-cyanophenethyl)carbamoyl)piperidin-1-yl)-2-(trifluoromethyl)pyrimidin-4-yl)piperazin-1-yl)acetic acid;

217) (R)-1-(6-(4-(2-cyanoethyl)piperazin-1-yl)-2-(trifluoromethyl)pyrimidin-4-yl)-N-(4-cyanophenethyl)piperidine-3-carboxamide;

218) (R)—N-(4-cyanophenethyl)-1-(6-(4-(2-(dimethylamino)ethyl)piperazin-1-yl)-2-(trifluoromethyl)pyrimidin-4-yl)piperidine-3-carboxamide;

219) (R)-1-(6-(4-(2-(1H-imidazol-1-yl)ethyl)piperazin-1-yl)-2-(trifluoromethyl) pyrimidin-4-yl)-N-(4-cyanophenethyl)piperidine-3-carboxamide;

220) (R)-1-(6-(4-(benzo[d][1,3]dioxol-4-ylmethyl)piperazin-1-yl)-2-(trifluoromethyl)pyrimidin-4-yl)-N-(4-cyanophenethyl)piperidine-3-carboxamide;

221) (R)-1-(6-(4-(2-methoxyethyl)piperazin-1-yl)-2-(trifluoromethyl)pyrimidin-4-yl)-N-(4-(trifluoromethyl) phenethyl)piperidine-3-carboxamide;

222) (R)-1-(6-(4-(hydroxymethyl)piperidin-1-yl)-2-(trifluoromethyl)pyrimidin-4-yl)-N-(4-(trifluoromethyl)-phenethyl)piperidine-3-carboxamide;

223) (R)-4-(1-(2-(trifluoromethyl)-6-(3-((4-(trifluoromethyl)phenethyl)carbamoyl) piperidin-1-yl)pyrimidin-4-yl)piperidin-4-yl)butanoic acid;

224) (R)-1-(6-(4-hydroxymethyl)piperidin-1-yl)-2-(trifluoromethyl)pyrimidin-4-yl)-N-(2-methoxy-4-(trifluoromethyl)-phenethyl)piperidine-3-carboxamide;

225) (R)-1-(6-(4-(2-hydroxyethyl)piperidin-1-yl)-2-(trifluoromethyl)pyrimidin-4-yl)-N-(2-methoxy-4-(trifluoromethyl)-phenethyl)piperidine-3-carboxamide;

226) (R)—N-(4-cyanophenethyl)-1-(6-(4-(2-(dimethylamino)ethyl)piperazin-1-yl)-2-(trifluoromethyl)pyrimidin-4-yl)piperidine-3-carboxamide;

227) (R)-2-(4-(1-(2-(trifluoromethyl)-6-(3-((4-(trifluoromethyl)phenethyl) carbamoyl)-piperidin-1-yl)pyrimidin-4-yl)piperidin-4-yl)butanamido)ethanesulfonic acid;

228) (R)-1-(6-(4-(2-methoxyacetyl)piperazin-1-yl)-2-(trifluoromethyl)pyrimidin-4-yl)-N-(4-(trifluoromethyl) phenethyl)piperidine-3-carboxamide;

229) (R)-1-(6-(4-(2-(dimethylamino)-acetyl)piperazin-1-yl)-2-(trifluoromethyl)-pyrimidin-4-yl)-N-(4-(trifluoromethyl)phenethyl)-piperidine-3-carboxamide;

230) (R)-methyl 2-oxo-2-(4-(2-(trifluoromethyl)-6-(3-((4-(trifluoromethyl) phenethyl)-carbamoyl)piperidin-1-yl)pyrimidin-4-yl)piperazin-1-yl)acetate;

231) (R)-2-oxo-2-(4-(2-(trifluoromethyl)-6-(3-((4-(trifluoromethyl)phenethyl)-carbamoyl)piperidin-1-yl)pyrimidin-4-yl)piperazin-1-yl)acetic acid;

232) tert-butyl-((S)-3-hydroxy-1-oxo-1-(4-(2-(trifluoromethyl)-6-((R)-3-((4-(trifluoromethyl)phenethyl) carbamoyl)piperidin-1-yl)pyrimidin-4-yl)piperazin-1-yl)propan-2-yl)carbamate;

233) (R)-1-(6-(4-((S)-2-amino-3-hydroxypropanoyl)piperazin-1-yl)-2-(trifluoromethyl)pyrimidin-4-yl)-N-(4-(trifluoromethyl)phenethyl)piperidine-3-carboxamide;

234) (R)-ethyl 3-(4-(2-(trifluoromethyl)-6-(3-((4-(trifluoromethyl)phenethyl) carbamoyl)-piperidin-1-yl)pyrimidin-4-yl)piperazine-1-carboxamido)propanoate;

235) (R)-3-(4-(2-(trifluoromethyl)-6-(3-((4-(trifluoromethyl)phenethyl)carbamoyl)-piperidin-1-yl)pyrimidin-4-yl)piperazine-1-carboxamido)propanoic acid;

236) (R)-1-(6-(4-(2-aminoethyl)piperidin-1-yl)-2-(trifluoromethyl)pyrimidin-4-yl)-N-(4-cyanophenethyl)piperidine-3-carboxamide;

237) (R)-ethyl 3-(3-(2-(1-(6-(3-((4-cyanophenethyl)carbamoyl)piperidin-1-yl)-2-(trifluoromethyl)pyrimidin-4-yl)piperidin-4-yl)ethyl)ureido)propanoate;

238) (R)-3-(3-(2-(1-(6-(3-(4-cyanophenethyl)carbamoyl) piperidin-1-yl)-2-(trifluoromethyl)pyrimidin-4-yl)piperidin-4-yl)ethyl)ureido)propanoic acid;

239) (R)-1-(6-(4-(2-hydroxyacetyl)piperazin-1-yl)-2-(trifluoromethyl)pyrimidin-4-yl)-N-(4-(trifluoromethyl) phenethyl)piperidine-3-carboxamide; and 240) (R)-1-(6-(4-((2-guanidinoethyl)sulfonyl)piperazin-1-yl)-2-(trifluoromethyl)-pyrimidin-4-yl)-N-(4-(trifluoromethyl)phenethyl)piperidine-3-carboxamide, or a pharmaceutically acceptable salt thereof.

13. The compound of claim 12, which is selected from:

1) (S)-2-(3-(1-(6-(2-((4-cyanophenethyl)carbamoyl)pyrrolidin-1-yl)-2-(trifluoromethyl)pyrimidin-4-yl)piperidin-4-yl)propanamido)-ethanesulfonic acid;

2) (S)-3-(4-(1-(2-(trifluoromethyl)-6-(2-((4-(trifluoromethyl)phenethyl)-carbamoyl)pyrrolidin-1-yl)pyrimidin-4-yl)piperidin-4-yl)butanamido)propane-1-sulfonic acid;

3) (S)-2-(4-(1-(6-(2-((4-cyanophenethyl)carbamoyl)pyrrolidin-1-yl)-2-(trifluoromethyl)pyrimidin-4-yl)-piperidin-4-yl)butanamido)ethanesulfonic acid;

4) (S)-3-(4-(1-(6-(2-((4-cyanophenethyl)carbamoyl)pyrrolidin-1-yl)-2-(trifluoromethyl)pyrimidin-4-yl)-piperidin-4-yl)butanamido)propane-1-sulfonic acid;

5) (S)-(4-(1-(6-(2-((4-cyanophenethyl)carbamoyl)pyrrolidin-1-yl)-2-(trifluoromethyl)pyrimidin-4-yl)piperidin-4-yl)butanamido)-methanesulfonic acid;

6) (S)-5-guanidino-2-(4-(1-(2-(trifluoromethyl)-6-((S)-2-((4-(trifluoromethyl)phenethyl)carbamoyl)pyrrolidin-1-yl)pyrimidin-4-yl)piperidin-4-yl)butanamido)pentanoic acid;

7) (S)-2-(4-(1-(6-((S)-2-((4-cyanophenethyl)carbamoyl) pyrrolidin-1-yl)-2-(trifluoromethyl)pyrimidin-4-yl)piperidin-4-yl)butanamido)-pentanedioic acid;

8) (S)-2-(3-(2-(1-(6-(2-((4-cyanophenethyl)carbamoyl) pyrrolidin-1-yl)-2-(trifluoromethyl)pyrimidin-4-yl)piperidin-4-yl)ethyl)ureido)ethanesulfonic acid;

9) (S)—N-(4-cyanophenethyl)-1-(6-(4-(2-(3-(2-sulfamoyl ethyl)ureido)-ethyl)piperidin-1-yl)-2-(trifluoromethyl)pyrimidin-4-yl)pyrrolidine-2-carboxamide;

10) (S)-3-(3-(2-(1-(6-(2-((4-cyanophenethyl)carbamoyl) pyrrolidin-1-yl)-2-(trifluoromethyl)pyrimidin-4-yl)piperidin-4-yl)ethyl)ureido)-propanoic acid;

11) (S)—N-(2-(1-(6-(2-((4-cyanophenethyl)-carbamoyl) pyrrolidin-1-yl)-2-(trifluoromethyl)pyrimidin-4-yl)piperidin-4-yl)ethyl)-2-(2-aminoethylsulfonamido)acetate methyl ester;

12) (S)-2-(2-((2-(4-(1-(6-(2-((4-cyanophenethyl)carbamoyl)pyrrolidin-1-yl)-2-(trifluoromethyl)pyrimidin-4-yl)piperidin-4-yl)butanamido)ethyl)amino)-pyrimidine-5-carboxamido)ethanesulfonic acid;

13) (S)-2-(2-(4-(1-(2-(trifluoromethyl)-6-(2-((4-(trifluoromethyl)phenethyl)-carbamoyl)-pyrrolidin-1-yl)pyrimidin-4-yl)piperidin-4-yl)butanamido)ethyl-sulfonamido)acetic acid;

14) (S)-2-(2-(4-(1-(6-(2-((4-cyanophenethyl)carbamoyl) pyrrolidin-1-yl)-2-(trifluoromethyl)pyrimidin-4-yl)piperidin-4-yl)butanamido)-ethylsulfonamido)acetic acid;

15) (S)-2-((2-(N-(2-(1-(6-(2-((4-cyanophenethyl)carbamoyl)pyrrolidin-1-yl)-2-(trifluoromethyl)pyrimidin-4-yl)piperidin-4-yl)ethyl)sulfamoyl)ethyl)-amino)-pyrimidine-5-carboxylic acid;

16) (S)-(3-(3-(1-(6-(2-((4-cyanophenethyl)carbamoyl) pyrrolidin-1-yl)-2-(trifluoromethyl)pyrimidin-4-yl)piperidin-4-yl)propyl)ureido)-methanesulfonic acid;

17) (R)-2-amino-3-((2-(N-(2-(1-(6-((S)-2-((4-cyanophenethyl)carbamoyl)-pyrrolidin-1-yl)-2-(trifluoromethyl)-pyrimidin-4-yl)piperidin-4-yl)ethyl)sulfamoyl)ethyl) amino)-3-oxopropane-1-sulfonic acid;

18) (S)—N-(4-cyanophenethyl)-1-(6-(4-(2-(2-guanidinoethylsulfonamido)ethyl)-piperidin-1-yl)-2-(trifluoromethyl)pyrimidin-4-yl)pyrrolidine-2-carboxamide;

19) (S)-2-guanidino-5-oxo-5-((3-(1-(2-(trifluoromethyl)-6-((S)-2-((4-(trifluoromethyl)phenethyl)carbamoyl) pyrrolidin-1-yl)pyrimidin-4-yl)piperidin-4-yl)propyl) amino)pentanoic acid;

20) (S)-2-(4-(1-(2-(2-((4-cyanophenethyl)carbamoyl)pyrrolidin-1-yl)-6-(trifluoromethyl)pyridin-4-yl)piperidin-4-yl)butanamido)ethanesulfonic acid;

21) (S)-(3-(4-(2-(2-((4-cyanophenethyl)carbamoyl)pyrrolidin-1-yl)-6-(trifluoromethyl)pyridin-4-yl)phenyl)propanamido)methanesulfonic acid;

22) (S)-3-(4-(1-(6-(2-((4-cyanophenethyl)carbamoyl)azetidin-1-yl)-2-(trifluoromethyl)pyrimidin-4-yl)piperidin-4-yl)butanamido)propane-1-sulfonic acid;

23) (S)-2-(4-(1-(6-(2-((4-cyanophenethyl)carbamoyl)azetidin-1-yl)-2-(trifluoromethyl)pyrimidin-4-yl)piperidin-4-yl)butanamido)ethanesulfonic acid;

24) (S)-(4-(1-(6-(2-((4-cyanophenethyl)carbamoyl)azetidin-1-yl)-2-(trifluoromethyl)pyrimidin-4-yl)piperidin-4-yl)butanamido)methanesulfonic acid;

25) (S)-3-(3-(2-(1-(6-(2-((4-cyanophenethyl)carbamoyl)azetidin-1-yl)-2-(trifluoromethyl)pyrimidin-4-yl)piperidin-4-yl)ethyl)ureido)propanoic acid;
26) (S)—N-(4-cyanophenethyl)-1-(6-(4-(2-(3-(2-sulfamoyl ethyl)ureido)ethyl)-piperidin-1-yl)-2-(trifluoromethyl)pyrimidin-4-yl)azetidine-2-carboxamide;
27) (S)-2-(3-(2-(1-(6-(2-((4-cyanophenethyl)carbamoyl)azetidin-1-yl)-2-(trifluoromethyl)pyrimidin-4-yl)piperidin-4-yl)ethyl)ureido)-ethanesulfonic acid;
28) (R)-2-amino-3-oxo-3-((2-(1-(2-(trifluoromethyl)-6-((S)-2-((4-(trifluoromethyl)-phenethyl)carbamoyl)azetidin-1-yl)pyrimidin-4-yl)piperidin-4-yl)ethyl)amino)-propane-1-sulfonic acid;
29) (S)—N-(4-cyanophenethyl)-1-(6-(4-(4-((4-guanidinobutyl)amino)-4-oxobutyl)piperidin-1-yl)-2-(trifluoromethyl)pyrimidin-4-yl)azetidine-2-carboxamide;
30) (S)—N-(4-cyanophenethyl)-1-(6-(4-(2-guanidinoethyl)piperidin-1-yl)-2-(trifluoromethyl)pyrimidin-4-yl)azetidine-2-carboxamide; and
31) (S)-2-(3-(1-(2-(Trifluoromethyl)-6-((S)-2-((4-(trifluoromethyl)phenethyl)-carbamoyl)azetidin-1-yl)pyrimidin-4-yl)piperidin-4-yl)propanamido)-pentanedioic acid, or a pharmaceutically acceptable salt thereof.

14. A pharmaceutical composition comprising the compound of claim 1, or a pharmaceutical acceptable salt thereof, and a pharmaceutically acceptable carrier.

15. A pharmaceutical composition comprising the compound of claim 12, or a pharmaceutical acceptable salt thereof, and a pharmaceutically acceptable carrier.

16. A pharmaceutical composition comprising the compound of claim 13, or a pharmaceutical acceptable salt thereof, and a pharmaceutically acceptable carrier.

17. A method of treating a human inflicted with a TGR5-related metabolic disorder, comprising the step of administering a pharmaceutically effective amount of the compound of claim 1 to a human in need thereof.

18. A method of treating a human inflicted with a TGR5-related metabolic disorder, comprising the step of administering a pharmaceutically effective amount of the compound of claim 12 to a human in need thereof.

19. A method of treating a human inflicted with a TGR5-related metabolic disorder, comprising the steps of:

(a) administering a pharmaceutically effective amount of the compound of claim 1; and (b) administering an agent selected from the group consisting of metformin, gliclazide, glimepiride, glipizide, nateglinide and repaglinide, linagliptin, saxagliptin, sitagliptin and vildagliptin, glitazones, pioglitazone, acarbose, pramlintide, insulin, exenatide, liraglutide, dapagliflozin, and canagliflozin to a human in need thereof.

20. A method of treating a human inflicted with a TGR5-related metabolic disorder, comprising the steps of:

(a) administering a pharmaceutically effective amount of the compound of claim 12; and (b) administering an agent selected from the group consisting of metformin, gliclazide, glimepiride, glipizide, nateglinide and repaglinide, linagliptin, saxagliptin, sitagliptin and vildagliptin, glitazones, pioglitazone, acarbose, pramlintide, insulin, exenatide, liraglutide, dapagliflozin, and canagliflozin to a human in need thereof.

* * * * *